United States Patent
Ferreira et al.

(10) Patent No.: US 11,767,518 B2
(45) Date of Patent: Sep. 26, 2023

(54) ENGINEERED ARYL SULFATE-DEPENDENT ENZYMES

(71) Applicant: OPTIMVIA, LLC, Batavia, OH (US)

(72) Inventors: Tarsis Gesteira Ferreira, Pearland, TX (US); Daniel H. Lajiness, Fairfield, OH (US)

(73) Assignee: OPTIMVIA, LLC, Batavia, OH (US)

( * ) Notice: Subject to any disclaimer, the term of this patent is extended or adjusted under 35 U.S.C. 154(b) by 0 days.

(21) Appl. No.: 17/894,932

(22) Filed: Aug. 24, 2022

(65) Prior Publication Data

US 2023/0051957 A1 Feb. 16, 2023

Related U.S. Application Data

(60) Division of application No. 17/376,332, filed on Jul. 15, 2021, now Pat. No. 11,572,550, which is a continuation-in-part of application No. PCT/US2020/013677, filed on Jan. 15, 2020.

(60) Provisional application No. 62/792,440, filed on Jan. 15, 2019, provisional application No. 62/797,466, filed on Jan. 28, 2019, provisional application No. 62/808,074, filed on Feb. 20, 2019, provisional application No. 62/853,261, filed on May 28, 2019.

(51) Int. Cl.
*C12N 9/10* (2006.01)
*C12N 15/63* (2006.01)
*C12P 19/64* (2006.01)

(52) U.S. Cl.
CPC ............ *C12N 9/13* (2013.01); *C12N 15/63* (2013.01); *C12P 19/64* (2013.01); *C12Y 208/02008* (2013.01)

(58) Field of Classification Search
CPC C12N 9/13; C12N 15/63; C12P 19/64; C12Y 208/02008
See application file for complete search history.

(56) References Cited

FOREIGN PATENT DOCUMENTS

WO WO 2002079258 A2 * 10/2002

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*

* cited by examiner

*Primary Examiner* — Iqbal H Chowdhury
(74) *Attorney, Agent, or Firm* — Daniel H. Lajiness; Daniel F. Nesbitt; Nesbitt IP LLC

(57) ABSTRACT

The present invention provides several non-naturally occurring sulfotransferase enzymes that have been engineered to react with aryl sulfate compounds as sulfo group donors, instead of the natural substrate 3'-phosphoadenosine 5'-phosphosulfate (PAPS), and with heparosan-based polysaccharides, particularly heparan sulfate, as sulfo group acceptors. Each of the engineered sulfotransferase enzymes have a biological activity characterized by the position within the heparosan-based polysaccharide that receives the sulfo group, including glucosaminyl N-sulfotransferase activity, hexuronyl 2-O sulfotransferase activity, glucosaminyl 6-O sulfotransferase activity, or glucosaminyl 3-O sulfotransferase activity. Methods of using the engineered sulfotransferases to produce sulfated heparosan-based polysaccharides, including polysaccharides having anticoagulant activity, are also provided.

16 Claims, 60 Drawing Sheets

Specification includes a Sequence Listing.

Reaction

Transition State

Figure 6C

Reaction

Transition State

Reaction

Transition State

Products

Reaction

Transition State

Products

ENGINEERED ARYL SULFATE-DEPENDENT ENZYMES

CROSS-REFERENCE TO RELATED APPLICATIONS

The instant application is a divisional of U.S. patent application Ser. No. 17/376,332, filed on Jul. 15, 2021, which is a continuation-in-part of International Application No. PCT/US2020/013677, filed on Jan. 15, 2020, which claims of the benefit of U.S. Provisional Applications 62/792,440, filed on Jan. 15, 2019; 62/797,466, filed on Jan. 28, 2019; 62/808,074, filed on Feb. 20, 2019; and 62/853,261, filed May 28, 2019, the disclosures of which are hereby incorporated by reference in their entireties.

FIELD OF THE INVENTION

The present invention relates to non-natural sulfotransferase enzymes that are engineered to react with an aryl sulfate compound, instead of 3'-phosphoadenosine 5'-phosphosulfate, as a sulfo group donor.

REFERENCE TO SEQUENCE LISTING

The present application is being filed along with a sequence listing in electronic format. The sequence listing is provided as a file entitled "OPT-001XRT-3DT_Sequence_Listing.xml" created on Aug. 23, 2022, and which is 555,098 bytes in size. The information in electronic format of the sequence listing is incorporated by reference in its entirety.

BACKGROUND OF THE INVENTION

Sulfotransferases are a vital class of enzymes that catalyze the transfer of a sulfo group from a sulfo group donor to a sulfo group acceptor. Sulfotransferases are nearly ubiquitous in nature, and they exist in nearly all types of organisms, including bacteria, yeast, and animals, including humans. Similarly, sulfotransferase enzymes play an integral role in the sulfation of a wide array of sulfo group acceptors, including many types of steroids, polysaccharides, proteins, xenobiotics, and other molecules.

There are several polysaccharides that can be utilized as sulfo group acceptors, including, for example, dermatan, keratan, heparosan, and chondroitin. In particular, heparosan comprises repeating disaccharide units of 1→4 glycosidically-linked, glucuronic acid and N-acetylated glucosamine ($[\beta(1,4)GlcA-\alpha(1,4)GlcNAc]_n$) residues, any of which can be further modified by one or more enzyme-catalyzed deacetylation, sulfation, or epimerization reactions. Sulfation of heparosan-based polysaccharides can be catalyzed by up to four sulfotransferase enzymes to form heparan sulfate (HS), and when performed in a particular order along with deacetylation of one or more glucosamine residues and epimerization of one or more glucuronic acid residues, can be utilized to form heparin.

However, as wide-ranging and voluminous as the set of sulfo group acceptors can be, there are only a couple of molecules that can be utilized by sulfotransferase enzymes as sulfo group donors. The nearly ubiquitous sulfo group donor, including for each of the four HS sulfotransferases, is 3'-phosphoadenosine 5'-phosphosulfate (PAPS). These in vivo systems have evolved to exclusively utilize PAPS because it has a short half-life and can readily be synthesized and metabolized, as needed, by the organism. However, that same short half-life renders PAPS to be unsuitable for most in vitro syntheses, particularly in large scale syntheses, that utilize sulfotransferases because it can readily decompose into adenosine 3',5'-diphosphate, which actively inhibits the sulfotransferases' biological activity.

Aryl sulfate compounds, such asp-nitrophenyl sulfate (PNS) and 4-methylumbelliferyl sulfate (MUS) have been identified as cheap, widely-available compounds that can be useful as sulfo donors with a very limited number of sulfotransferases to synthesize certain small molecule products (see Malojcic, G., et al. (2008) *Proc. Nat. Acad. Sci.* 105 (49):19217-19222 and Kaysser, L., et al., (2010) *J. Biol. Chem.* 285 (17):12684-12694, the disclosures of which are incorporated by reference in their entireties). Yet, only a small number of bacterial sulfotransferases have been shown to react with aryl sulfate compounds as sulfo group donors, and none of these react with polysaccharides, let alone heparosan-based polysaccharides, as sulfo group acceptors. As a result, when sulfotransferases are used in the in vitro synthesis of sulfated polysaccharides, PAPS must be included in the reaction mixture to effectively catalyze sulfo group transfer, and aryl sulfate compounds can only be used indirectly, to repopulate the system with PAPS (see U.S. Pat. No. 6,255,088, the disclosure of which is incorporated by reference in its entirety).

Consequently, there is a need to develop sulfotransferase enzymes that react with aryl sulfate compounds as sulfo group donors, as well as polysaccharides as sulfo group acceptors. In particular, the development of sulfotransferase enzymes that are capable of both reacting with aryl sulfate compounds as sulfo group donors and with heparosan-based polysaccharides as sulfo group acceptors would present a large step forward toward the development of large-scale syntheses of heparin in vitro.

SUMMARY OF THE INVENTION

The present invention provides several engineered, biologically-active enzymes that are capable of recognizing, binding to, and reacting with aryl sulfate compounds as substrates. According to the present invention, the engineered enzyme can have sulfatase activity. According to the present invention, the engineered enzyme can have sulfotransferase activity.

According to the present invention, an engineered enzyme having sulfatase and/or sulfotransferase activity can react with an aryl sulfate compound, preferably selected from the group consisting of p-nitrophenyl sulfate (PNS), 4-methylumbelliferyl sulfate, 7-hydroxycoumarin sulfate, phenyl sulfate, 4-acetylphenyl sulfate, indoxyl sulfate, 1-naphthyl sulfate, 2-naphthyl sulfate (2NapS), and 4-nitrocatechol sulfate (NCS). According to the present invention, an engineered sulfotransferase can recognize, bind, and react with PNS as the sulfo group donor. According to the present invention, an engineered sulfotransferase can recognize, bind, and react with NCS as the sulfo group donor. According to the present invention, an engineered sulfotransferase can recognize, bind, and react with either PNS or NCS as the sulfo group donor.

In an aspect of the invention, an engineered enzyme of the present invention can have sulfatase biological activity. According to the present invention, sulfatase activity comprises the nucleophilic attack of a sulfur atom within an aryl sulfate compound, causing hydrolysis of a sulfate group and releasing the aromatic moiety from the active site. According to the present invention, the nucleophilic attack of the sulfur atom can be initiated by an amino acid residue within the active site of the engineered enzyme, particularly a histidine residue. According to the present invention, the reaction with the aryl sulfate compound can result in a sulfohistidine intermediate, in which a sulfate group is covalently bound to the amino acid nucleophile, particularly a histidine residue.

According to the present invention, an engineered enzyme of the present invention having sulfatase activity differs from other known sulfatases, which typically comprise greater than 500 amino acid residues, at least one cysteine or serine residue that is post-translationally modified to become α-formylglycine, and one or more characteristic signature sequences, C/S-X-P-S/X-R-X-X-X-L/X-T/X-G/X-R/X or G-Y/V-X-S/T-X-X-X-G-K-X-X-H (SEQ ID NO: 272), which direct the post-translational modification of the cysteine or serine into α-formylglycine. Thus, according to the present invention, engineered enzymes having sulfatase activity can comprise less than 500 amino acid residues. According to the present invention, engineered enzymes having sulfatase activity can have zero α-formylglycine residues. According to the present invention, engineered enzymes having sulfatase activity can have no sulfatase signature sequences.

According to the present invention, engineered enzymes of the present invention that have sulfatase activity can comprise any amino acid sequence, so long as nucleophilic attack of the aryl sulfate compound is initiated by an active site amino acid residue, preferably a histidine residue. According to the present invention, an engineered enzyme having sulfatase activity can have an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, and SEQ ID NO: 151. According to the present invention, an engineered enzyme having sulfatase activity can have an amino acid sequence selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 68, SEQ ID NO: 69, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. According to the present invention, an engineered enzyme having sulfatase activity can have comprise any amino acid sequence that is a biological equivalent of any of the amino acid sequences above.

In another aspect of the present invention, an engineered enzyme of the present invention can have sulfotransferase biological activity. According to the present invention, sulfotransferase activity comprises the enzymatic transfer of a sulfo group from an aryl sulfate compound to a sulfo group acceptor. According to the present invention, the sulfo group acceptor can be a polysaccharide. According to the present invention, the sulfo group acceptor polysaccharide can be a heparosan-based polysaccharide. According to the present invention, the heparosan-based polysaccharide can be N-deacetylated heparosan. According to the present invention, the heparosan-based polysaccharide can be N-sulfated heparosan. According to the present invention, the heparosan-based polysaccharide can be N-sulfated, 2-O sulfated heparan sulfate (N,2O-HS). According to the present invention, the heparosan-based polysaccharide can be N-sulfated, 2-O sulfated, 6-O sulfated heparan sulfate (N,2O,6O-HS). According to the present invention, the heparosan-based polysaccharide can be N-sulfated, 2-O sulfated, 3-O sulfated, 6-O sulfated heparan sulfate (N,2O,3O,6O-HS). According the present invention, and as described below, the N,2O,3O,6O-HS product can have one or more molecular weight properties and/or anticoagulant activity that are similar or equivalent to heparin. According to the present invention, the heparosan-based polysaccharide can be sulfated at any of the N-, 2-O, 3-O, and/or 6-O positions, within any of the disaccharide units comprising the heparosan-based polysaccharide. According to the present invention, the heparosan-based polysaccharide can comprise one or more iduronic acid residues substituted in place of a glucuronic acid residue. According to the present invention, one or more of the iduronic acid residues can be 2-O sulfated.

According to the present invention, the sulfotransfer reaction catalyzed by an engineered sulfotransferase enzyme can proceed via a reaction mechanism in which a sulfohistidine intermediate is first formed upon the reaction between the enzyme and an aryl sulfate compound, followed by the binding of a heparosan-based polysaccharide within the active site, and subsequent transfer of the sulfo group from the sulfohistidine intermediate to the polysaccharide. Alternatively, according to the present invention, the sulfotransfer reaction catalyzed by an engineered sulfotransferase enzyme can proceed via a reaction mechanism in which both an aryl sulfate compound and a heparosan-based polysaccharide are bound within the active site, and the enzyme catalyzes the direct transfer of the sulfo group from the aryl sulfate compound to the polysaccharide.

According to the present invention, an engineered sulfotransferase enzyme can have a biological activity based on the position within the heparosan-based polysaccharide that receives the sulfo group, including glucosaminyl N-sulfotransferase activity, hexuronyl 2-O sulfotransferase activity, glucosaminyl 6-O sulfotransferase activity, or glucosaminyl 3-O sulfotransferase activity. Each biological activity is described in further detail, below.

In an aspect of the invention, an engineered sulfotransferase enzyme can have glucosaminyl N-sulfotransferase activity, comprising the transfer of a sulfo group from an aryl sulfate compound to the N-position of an unsubstituted glucosamine residue within a heparosan-based polysaccharide. According to the present invention, an engineered glucosaminyl N-sulfotransferase (NST) enzyme can comprise any amino acid sequence, so long as the sulfo group donor is an aryl sulfate compound and the sulfo group acceptor is a heparosan-based polysaccharide.

According to the present invention, engineered NST enzymes can be mutants of the N-sulfotransferase domain of natural N-deacetylase/N-sulfotransferase (NDST) enzymes, which are members of enzyme class (EC) 2.8.2.8. In contrast to the engineered NST enzymes of the present invention, natural enzymes within EC 2.8.2.8 do not react with aryl sulfate compounds, and only react with 3'-phosphoadenosine 5'-phosphosulfate (PAPS) as a sulfo group donor. However, the engineered NST enzymes can retain the same biological activity as the natural enzymes within EC 2.8.2.8 with heparosan-based polysaccharides as sulfo group acceptors. According to the present invention, heparosan-based polysaccharides that can be utilized as sulfo acceptors with any of the engineered NST enzymes can comprise one or more disaccharide units having the structure of Formula II, below:

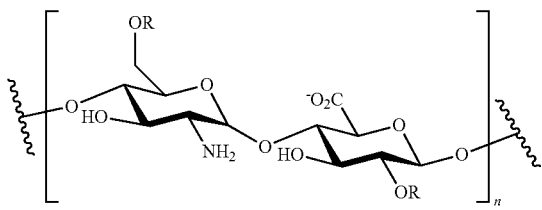

wherein n is an integer and R is selected from the group consisting of a hydrogen atom or a sulfo group. According to the present invention, both R groups within the disaccharide unit can be a hydrogen atom. According to the present invention, all of the R groups within the same polysaccharide molecule can be hydrogen atoms. When the sulfo acceptor polysaccharide comprises the structure of Formula II, upon transfer of the sulfo group from an aryl sulfate compound, the sulfated polysaccharide product comprises the structure of Formula III, below:

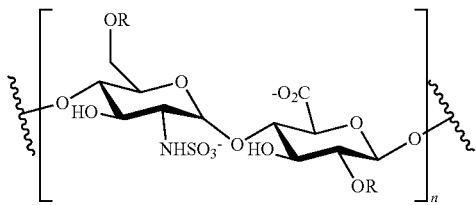

wherein n is an integer and R is selected from the group consisting of a hydrogen atom or a sulfo group.

According to the present invention, although the glucosamine residue that receives the sulfo group is N-unsubstituted, as illustrated in Formula II and Formula III above, other glucosamine residues within the same polysaccharide molecule can be N-acetylated, N-sulfated, or N-unsubstituted, 3-O sulfated, and/or 6-O sulfated. Similarly, hexuronic acid residues in other positions within the polysaccharide that are not adjacent to the glucosamine residue receiving the sulfo group can be glucuronic acid or iduronic acid residues, any of which can be optionally 2-O sulfated. According to the present invention, and in some preferred embodiments, the heparosan-based polysaccharide can be N-deacetylated heparosan, in which all of the glucosamine residues are N-unsubstituted, or are present as a mixture of N-acetylglucosamine and N-unsubstituted glucosamine.

According to the present invention, an engineered NST enzyme can consist of a single N-sulfotransferase domain that is capable of binding and reacting with an aryl sulfate compound as a sulfo group donor. However, most natural NDST enzymes within EC 2.8.2.8 have dual N-deacetylase/N-sulfotransferase activity, with one domain structurally configured for N-deacetylase activity and another domain structurally configured for N-sulfotransferase activity. Therefore, according to the present invention, the engineered NST enzyme can also comprise an N-deacetylase domain having either an identical or mutated amino acid sequence to the N-deacetylase domain of any of the NDST enzymes in EC 2.8.2.8.

To facilitate its exclusive reactivity with PAPS as the sulfo group donor, natural NDST enzymes typically comprise highly-conserved or identical amino acid sequences that define the active site and govern the enzyme's recognition, binding, and reactivity with PAPS. According to the present invention, the amino acid sequence of an engineered NST enzyme can comprise one or more mutations relative to the N-sulfotransferase domain of a natural NDST enzyme, in order to facilitate binding of an aryl sulfate compound instead of PAPS. According to the present invention, an engineered NST enzyme can comprise an amino acid sequence having at least one amino acid mutation relative to the N-sulfotransferase domain of a natural NDST enzyme, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered NST enzyme can comprise at least one amino acid mutation relative to the amino acid sequence of any of the NDST enzymes, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered NST enzyme can be expressed as a "percent identity" or "% identity" relative to the amino acid sequence of one or more of the natural NDST enzymes within EC 2.8.2.8, particularly relative to their N-sulfotransferase domains, and including biological functional fragments thereof. According to the present invention, an engineered NST enzyme can have at least 50% sequence identity, and up to at least 97% sequence identity, with the N-sulfotransferase domain of any of the enzymes within EC 2.8.2.8. In a non-limiting example, the amino acid sequence of the non-natural NST enzyme can have at least 80% sequence identity with the amino acid sequence of the N-sulfotransferase domain of a natural NDST enzyme, the natural NDST enzyme selected from the group consisting of: the human NDST1 enzyme (SEQ ID NO: 164, UniProtKB Accession No. P52848); the human NDST2 enzyme (SEQ ID NO: 177, UniProtKB Accession No. P52849); the human NDST3 enzyme (SEQ ID NO: 174, UniProtKB Accession No. O95803); and the human NDST4 enzyme (SEQ ID NO: 173, UniProtKB Accession No. Q9H3R1). According to the present invention, such engineered NST enzymes can also have an N-deacetylase domain that is either identical to, or contains one or more amino acid mutations relative to, any of the enzymes within EC 2.8.2.8.

According to the present invention, an engineered NST enzyme can comprise one or more mutated amino acid sequence motifs relative to conserved amino acid sequence motifs found in one or more natural NDST enzymes within EC 2.8.2.8. Each mutated amino acid sequence motif, when present, can have at least one amino acid mutation relative to the corresponding conserved amino acid sequence motif within the natural NDSTs. According to the present invention, an engineered NST enzyme can comprise one, two, three, four, or five mutated amino acid sequence motifs relative to the following conserved NST amino acid sequence motifs: (Q-K-T-G-T-T-A), (T-F-E-E), (F-E-K-S-A), (S-W-Y-Q-H), and (C-L-G-K/R-S-K-G-R), which correspond to SEQ ID NO: 221, SEQ ID NO: 222, SEQ ID NO: 223, SEQ ID NO: 224, and SEQ ID NO: 225 in the sequence listing, respectively. In some embodiments, within the amino acid sequence of the engineered NST enzyme, the conserved Q-K-T-G-T-T-A amino acid sequence motif (SEQ ID NO: 221) is mutated to an amino acid sequence motif selected from the group consisting of: H-$X_1$-T-G-$X_2$-H-A (SEQ ID NO: 226), wherein $X_1$ and $X_2$ are either both glycine (as indicated in SEQ ID NO: 227), or wherein $X_1$ is lysine and $X_2$ is valine (as indicated in SEQ ID NO: 228); and $X_3$-K-T-G-A-W/F-A/L (SEQ ID NO: 234), wherein $X_3$ can optionally be mutated to a serine (as indicated in SEQ ID NO: 235) or alanine (as indicated in SEQ ID NO: 236). In some embodiments, when the mutated amino acid sequence motif H-$X_1$-T-G-$X_2$-H-A (SEQ ID NO: 226) is selected, the C-terminal lysine residue within the conserved C-L-G-K/R-S-K-G-R amino acid sequence motif (SEQ ID NO: 225) is mutated to either a leucine (as indicated in SEQ ID NO: 229) or valine (as indicated in SEQ ID NO: 230) residue, and the amino acid sequence of the non-natural NST enzyme contains at least one additional mutation to a histidine residue, at a position selected from the group consisting of: the C-terminal glutamic acid residue in the conserved T-F-E-E amino acid sequence (as illustrated in SEQ ID NO: 231); the lysine residue in the conserved F-E-K-S-A amino acid sequence (as illustrated in SEQ ID NO: 232); and the serine residue in the conserved C-L-G-K/R-S-K-G-R amino acid sequence (as illustrated in SEQ ID NO: 233). In some embodiments, when the mutated amino acid sequence motif $X_3$-K-T-G-A-W/F-A/L (SEQ ID NO: 234) is selected, the final three residues in the conserved T-F-E-E amino acid sequence motif are mutated such that the C-terminal glutamic acid residue in SEQ ID NO: 222 is mutated to a serine residue, and the mutated amino acid sequence motif is selected from the group consisting of: T-H-G-S(SEQ ID NO: 237); T-G-H-S(SEQ ID NO: 238); the conserved C-L-G-K/R-S-K-G-R amino acid sequence motif (SEQ ID NO: 225) is mutated to include a histidine residue, at a position selected from the group consisting of the leucine residue, the serine residue, or the C-terminal lysine residue (as illustrated in SEQ ID NO: 239, SEQ ID NO: 240, or SEQ ID NO: 243, respectively), and if the histidine is substituted within the conserved C-L-G-K/R-S-K-G-R amino acid sequence motif at the leucine or serine residue, the C-terminal lysine residue is mutated to either a leucine (as illustrated in SEQ ID NO: 239 or SEQ ID NO: 240) or a tryptophan residue (as illustrated in SEQ ID NO: 241 or SEQ ID NO: 242). Additional non-limiting examples of mutated amino acid sequence motifs are described in further detail, below.

According to the present invention, an engineered NST enzyme can comprise an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, each of which contains several amino acid mutations made relative to highly conserved amino acid sequences that define the N-sulfotransferase domain of natural enzymes within EC 2.8.2.8. According to the present invention, engineered NST enzymes utilized in accordance with any of the methods described herein can also comprise any amino acid sequence that is a biological equivalent, and/or a functional fragment, of an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

According to the present invention, any of the engineered NST enzymes described above can possess one or more residue differences or mutations as compared to the amino acid sequences disclosed by an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 can comprise non-conservative substitutions, conservative substitutions, as well as combinations of conservative and non-conservative amino acid substitutions. According to the present invention, an amino acid mutation can be made at any position within SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, so long as the mutated enzyme retains its NST activity with an aryl sulfate compound as a sulfo group donor and a heparosan-based polysaccharide comprising the structure of Formula II as the sulfo group acceptor.

According to the present invention, an engineered NST enzyme can comprise the amino acid sequence of SEQ ID NO: 18. Within SEQ ID NO: 18, residues having the designation, "X," illustrate known instances in which there is a lack of identity at a particular position within the amino acid sequences of SEQ ID NO: 5, SEQ ID NO: 7, and SEQ ID NO: 15. Thus, an "X" designation indicates the amino acid at that position can be selected from a group of two or more amino acids, as defined by SEQ ID NO: 18.

According to the present invention, an engineered NST enzyme can comprise the amino acid sequence of SEQ ID NO: 19. Within SEQ ID NO: 19, residues having the designation, "X," illustrate known instances in which there is a lack of identity at a particular position within the amino acid sequences of SEQ ID NO: 9, SEQ ID NO: 11, and SEQ ID NO: 13. Thus, an "X" designation indicates the amino acid at that position can be selected from a group of two or more amino acids, as defined by SEQ ID NO: 19.

Additionally, and according to the present invention, amino acid mutations can be made at one or more positions within SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 so long as the mutated enzyme retains its glucosaminyl N-sulfotransferase activity with an aryl sulfate compound as a sulfo group donor. According to the present invention, an aryl sulfate-dependent enzyme comprising the amino acid sequence of SEQ ID NO: 18 or SEQ ID NO: 19 can optionally comprise one or more amino acid mutations at positions not designated as "X," while still retaining its glucosaminyl N-sulfotransferase activity with an aryl sulfate compound as a sulfo group donor.

In an aspect of the invention, an engineered sulfotransferase enzyme can have hexuronyl 2-O sulfotransferase activity, comprising the transfer of a sulfo group from an aryl sulfate compound to the 2-O position of a hexuronic acid residue within a heparosan-based polysaccharide. According to the present invention, an engineered 2OST can comprise any amino acid sequence, so long as the sulfo group donor is an aryl sulfate compound and the sulfo group acceptor is a heparosan-based polysaccharide.

According to the present invention, engineered 2OST enzymes can be mutants of natural sulfotransferases that have 2OST activity, which are members of enzyme class (EC) 2.8.2.-. In contrast to the engineered 2OST enzymes of the present invention, natural 2OST enzymes within EC 2.8.2.- do not react with aryl sulfate compounds, and only react with PAPS as a sulfo group donor. However, the engineered 2OST enzymes can retain the same biological activity as the natural 2OST enzymes within EC 2.8.2.- with heparosan-based polysaccharides as sulfo group acceptors. According to the present invention, heparosan-based polysaccharides that can be utilized as sulfo acceptors with any of the engineered 2OST enzymes can comprise one or more structural motifs having the structure of Formula IV, below:

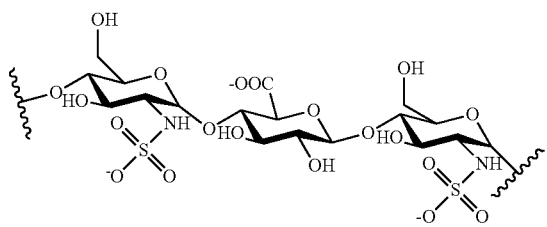

As indicated in Formula IV, the hexuronic acid residue is glucuronic acid. According to the present invention, and in another non-limiting example, when the hexuronic acid residue is iduronic acid, the heparosan-based polysaccharide comprises the structure of Formula V, below:

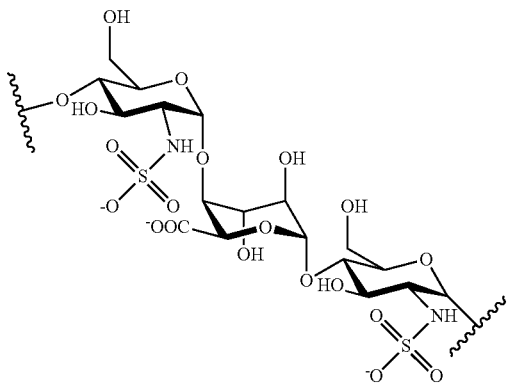

According to the present invention, when the heparosan-based polysaccharide comprises the structure of Formula IV, the 2-O sulfated polysaccharide product comprises the structure of Formula VI, below:

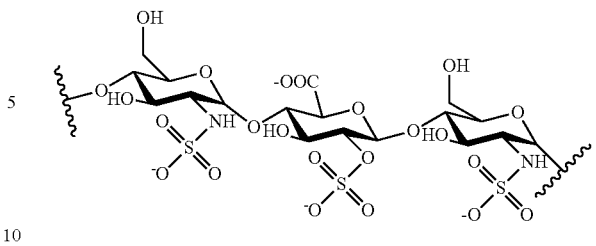

According to the present invention, when the heparosan-based polysaccharide comprises the structure of Formula V, the 2-O sulfated polysaccharide product comprises the structure of Formula VII, below:

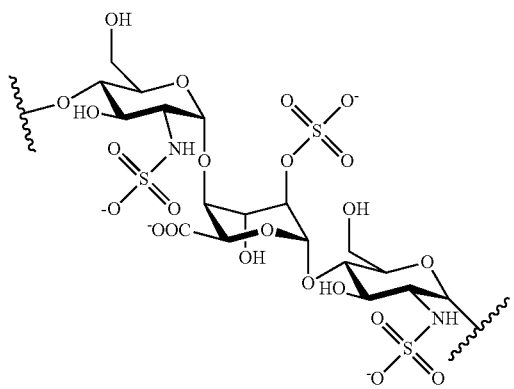

According to the present invention, the heparosan-based polysaccharide comprising the structure of Formula IV or Formula V can be N-sulfated heparosan. According to the present invention, a sulfo group acceptor for an engineered 2OST enzyme can comprise multiple motifs comprising the structure of Formula IV and/or Formula V, any or all of which can be sulfated by the enzyme. According to the present invention, and as illustrated in Formula IV and Formula V above, both of the glucosamine residues adjacent to the hexuronic acid residue that receives the sulfo group are N-sulfated. According to the present invention, a sulfo group acceptor for an engineered 2OST enzyme can be the sulfated polysaccharide product of an engineered NST enzyme, described above. According to the present invention, a sulfated polysaccharide product formed by an engineered 2OST enzyme, and comprising the structure(s) of Formula VI and/or Formula VII, is an N,2O-HS product.

According to the present invention, glucosamine residues within the polysaccharide that are not adjacent to the hexuronic acid residue receiving the sulfo group can optionally be N-, 3-O, and/or 6-O sulfated, N-acetylated, or N-unsubstituted. Similarly, hexuronic acid residues in other positions within the polysaccharide that are not adjacent to the glucosamine residue receiving the sulfo group can be glucuronic acid or iduronic acid residues, any of which can be optionally 2-O sulfated.

According to the present invention, polysaccharides comprising the structures of Formula IV and/or Formula V can be reacted with a glucuronyl $C_5$-epimerase enzyme to reversibly invert the stereochemistry of the $C_5$-carbon to form iduronic acid from glucuronic acid, and vice versa. However, once a hexuronic acid residue has been 2-O sulfated, it can no longer react with the glucuronyl $C_5$-epimerase. In some preferred embodiments, a glucuronyl $C_5$-epimerase enzyme can be used to invert the stereochemistry of hexuronic acid residues within N-sulfated heparosan polysaccharides comprising the structure of Formula III and form a structural motif comprising the structure of Formula V, prior to reacting with a 2OST enzyme. According to the present invention, the glucuronyl $C_5$-epimerase enzyme can comprise the amino acid sequence of SEQ ID NO: 67, preferably residues 34-617 of SEQ ID NO: 67. According to the present invention, the glucuronyl $C_5$-epimerase enzyme can be used to catalyze the conversion of one or more glucuronic acid residues within N-sulfated heparosan to iduronic acid residues, prior to reacting with an engineered 2OST enzyme.

To facilitate its exclusive reactivity with PAPS as the sulfo group donor, natural 2OST enzymes within EC 2.8.2.- typically comprise highly-conserved or identical amino acid sequences that define the active site and govern the enzyme's recognition, binding, and reactivity with PAPS. According to the present invention, the amino acid sequence of an engineered 2OST enzyme can comprise one or more mutations relative to one or more natural 2OST enzymes within EC 2.8.2.-, in order to facilitate binding of an aryl sulfate compound instead of PAPS. According to the present invention, an engineered 2OST enzyme can comprise an amino acid sequence having at least one amino acid mutation relative to any of the natural 2OST enzymes within EC 2.8.2.-, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 2OST enzyme can comprise at least one amino acid mutation relative to the amino acid sequence of any of the natural 2OST enzymes within EC 2.8.2.-, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 2OST enzyme can be expressed as a "percent identity" or "% identity" relative to the amino acid sequence of one or more of the natural 2OST enzymes within EC 2.8.2.-, including biological functional fragments thereof. According to the present invention, an engineered 2OST enzyme can have at least 50% sequence identity, and up to at least 97% sequence identity, with any of the 2OST enzymes within EC 2.8.2.-. In a non-limiting example, the amino acid sequence of the engineered 2OST enzyme can have at least 80% sequence identity with the amino acid sequence of the chicken 2OST1 enzyme (SEQ ID NO: 179, UniProtKB Accession No. Q76KB1).

According to the present invention, an engineered 2OST enzyme can comprise one or more mutated amino acid sequence motifs relative to conserved amino acid sequence motifs found in one or more natural 2OST enzymes within EC 2.8.2.-. Each mutated amino acid sequence motif, when present, can have at least one amino acid mutation relative to the corresponding conserved amino acid sequence motif within the natural 2OST enzymes within EC 2.8.2.-. According to the present invention, an engineered 2OST enzyme can comprise one, two, three, four, five, or six mutated amino acid sequence motifs relative to the following conserved 2OST amino acid sequence motifs: (R-V-P-K-T-A/G-S-T), (N-T-S/T-K-N), (Y-H-G-H), (F-L-R-F/H-G-D-D/N-F/Y), (R-R-K/R-Q-G), and (S-H-L-R-K/R-T), which correspond to SEQ ID NO: 244, SEQ ID NO: 273, SEQ ID NO: 274, SEQ ID NO: 245, SEQ ID NO: 246, and SEQ ID NO: 247 in the sequence listing, respectively. In some embodiments, within the amino acid sequence of the engineered 2OST enzyme, the conserved R-V-P-K-T-A/G-S-T amino acid sequence motif (SEQ ID NO: 244) is mutated to the amino acid sequence motif R-V-$X_1$-$X_2$-T-A-S-$X_3$, wherein the amino acid sequence motif R-V-$X_1$-$X_2$-T-A-S-$X_3$ is selected from the group consisting of R-V-P-H-T-A-S-T and R-V-H-R-T-A-S-H (corresponding to SEQ ID NO: 248 and SEQ ID NO: 249 in the sequence listing, respectively), and the conserved S-H-L-R-K/R-T amino acid sequence motif (SEQ ID NO: 247) is mutated to S-H-L-H-K-T (SEQ ID NO: 250). In a further embodiment, when the amino acid sequence R-V-P-H-T-A-S-T (SEQ ID NO: 248) is selected, the conserved F-L-R-F/H-G-D-D/N-F/Y sequence motif (SEQ ID NO: 245) can be mutated to H-L-R-F-G-D-D-Y (SEQ ID NO: 251). Additional non-limiting examples of mutated amino acid sequence motifs are described in further detail, below.

According to the present invention, an engineered 2OST enzyme can comprise an amino acid sequence selected from the group consisting of SEQ ID NO: 63, SEQ ID NO: 65, SEQ ID NO: 68, and SEQ ID NO: 69, each of which contains several amino acid mutations made relative to highly conserved amino acid sequences that define the natural 2OST enzymes within EC 2.8.2.-. According to the present invention, engineered 2OST enzymes utilized in accordance with any of the methods described herein can also comprise any amino acid sequence that is a biological equivalent, and/or a functional fragment, of an amino acid sequence selected from the group consisting of SEQ ID NO: 63, SEQ ID NO: 65, SEQ ID NO: 68, and SEQ ID NO: 69.

According to the present invention, any of the engineered 2OST enzymes described above can possess one or more residue differences or mutations as compared to the amino acid sequences disclosed by an amino acid sequence selected from the group consisting of SEQ ID NO: 63, SEQ ID NO: 65, SEQ ID NO: 68, and SEQ ID NO: 69. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 63, SEQ ID NO: 65, SEQ ID NO: 68, and SEQ ID NO: 69 can comprise non-conservative substitutions, conservative substitutions, as well as combinations of conservative and non-conservative amino acid substitutions. According to the present invention, an amino acid mutation can be made at any position within SEQ ID NO: 63, SEQ ID NO: 65, SEQ ID NO: 68, or SEQ ID NO: 69, so long as the mutated enzyme retains its hexuronyl 2-O sulfotransferase activity with an aryl sulfate compound as a sulfo group donor and a heparosan-based polysaccharide comprising the structure of Formula IV and/or Formula V as the sulfo group acceptor.

In an aspect of the invention, an engineered sulfotransferase enzyme can have glucosaminyl 6-O sulfotransferase activity, comprising the transfer of a sulfo group from an aryl sulfate compound to the 6-O position of a glucosamine residue within a heparosan-based polysaccharide. According to the present invention, an engineered 6OST enzyme can comprise any amino acid sequence, so long as the sulfo group donor is an aryl sulfate compound and the sulfo group acceptor is a heparosan-based polysaccharide.

According to the present invention, engineered 6OST enzymes can be mutants of natural sulfotransferases that have glucosaminyl 6-O sulfotransferase activity, which are members of EC 2.8.2.-. In contrast to the engineered 6OST enzymes of the present invention, natural 6OST enzymes within EC 2.8.2.- do not react with aryl sulfate compounds, and only react with PAPS as a sulfo group donor. However, the engineered 6OST enzymes can retain the same biological activity as the natural 6OST enzymes within EC 2.8.2.- with heparosan-based polysaccharides as sulfo group acceptors.

According to the present invention, the glucosamine residue receiving the sulfo group at the 6-O position can be N-sulfated, N-unsubstituted, and/or 3-O sulfated, prior to reacting with the enzyme. According to the present invention, any other glucosamine residue within the sulfo acceptor polysaccharide can be optionally be N-, 3-O, and/or 6-O sulfated, N-acetylated, or N-unsubstituted. According to the present invention, any of the hexuronic acid residues within the heparosan-based polysaccharide, including hexuronic acid residues adjacent to the glucosamine residue receiving the sulfo group, can optionally be iduronic acid or glucuronic acid, and can optionally be 2-O sulfated, prior to reacting with the 6OST enzyme.

One non-limiting example of a heparosan-based polysaccharide that can be utilized as a sulfo acceptor with any of the engineered 6OST enzymes is a heparosan-based polysaccharide comprising one or more structural motifs having the structure of Formula VIII, below:

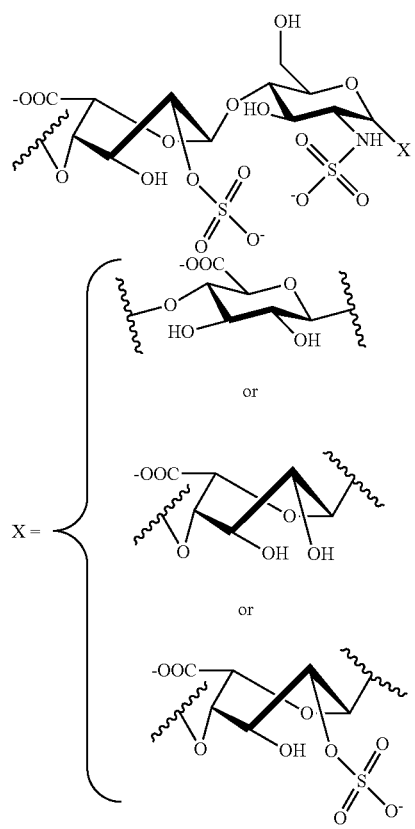

wherein X comprises any of the hexuronic acid residues depicted in Formula VIII above. When the sulfo acceptor polysaccharide comprises the structure of Formula VIII, upon transfer of the sulfo group from an aryl sulfate compound, the sulfated polysaccharide product comprises the structure of Formula IX, below:

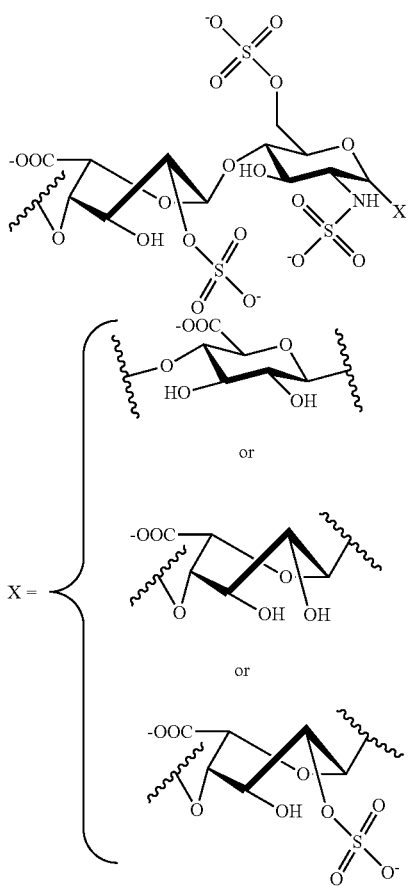

wherein X comprises any of the hexuronic acid residues depicted in Formula IX, above.

According to the present invention, the sulfo group acceptor for the engineered 6OST enzyme can comprise multiple structural motifs comprising the structure of Formula VIII, any or all of which can be sulfated by an engineered 6OST enzyme. According to the present invention, the sulfo group acceptor can be N-deacetylated heparosan. According to the present invention, the sulfo group acceptor can be N-sulfated heparosan. According to the present invention, the sulfo group acceptor for the engineered 6OST can be N,2O-HS. According to the present invention, the sulfo group acceptor for the engineered 6OST enzyme can be a sulfated polysaccharide product formed by an engineered NST enzyme, described above. According to the present invention, the sulfo group acceptor for the engineered 6OST enzyme can be a sulfated polysaccharide product formed by an engineered 2OST enzyme, as described above. According to the present invention, the sulfated polysaccharide product of an engineered 6OST enzyme is an N,2O,6O-HS product.

To facilitate its exclusive reactivity with PAPS as the sulfo group donor, natural 6OST enzymes within EC 2.8.2.- typically comprise highly-conserved or identical amino acid sequences that define the active site and govern the enzyme's recognition, binding, and reactivity with PAPS. According to the present invention, the amino acid sequence of an engineered 6OST enzyme can comprise one or more mutations relative to natural 6OST enzymes within EC 2.8.2.-, in order to facilitate binding of an aryl sulfate compound instead of PAPS. According to the present invention, an engineered 6OST enzyme can comprise an amino acid sequence having at least one amino acid mutation relative to any of the natural 6OST enzymes within EC 2.8.2.-, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 6OST enzyme can comprise at least one amino acid mutation relative to the amino acid sequence of any of the natural 6OST enzymes within EC 2.8.2.-, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 6OST enzyme can be expressed as a "percent identity" or "% identity" relative to the amino acid sequence of one or more of the natural 6OST enzymes within EC 2.8.2.-, particularly relative to one or more of the natural 6OST enzymes within EC 2.8.2.-, and including biological functional fragments thereof. According to the present invention, an engineered 6OST enzyme can have at least 50% sequence identity, and up to at least 97% sequence identity, with any of the natural 6OST enzymes within EC 2.8.2.-. In a non-limiting example, the amino acid sequence of the non-natural 6OST enzyme can have at least 80% sequence identity with the amino acid sequence of a natural 6OST enzyme, the natural 6OST enzyme selected from the group consisting of the mouse 6OST1 enzyme (SEQ ID NO: 191, UniProtKB Accession No. Q9QYK5), the mouse 6OST2 enzyme (SEQ ID NO: 199, UniProtKB Accession No. Q80UW0), and the mouse 6OST3 enzyme (SEQ ID NO: 201, UniProtKB Accession No. Q9QYK4).

According to the present invention, an engineered 6OST enzyme can comprise one or more mutated amino acid sequence motifs relative to conserved amino acid sequence motifs found in one or more natural 6OST enzymes within EC 2.8.2.-. Each mutated amino acid sequence motif, when present, can have at least one amino acid mutation relative to the corresponding conserved amino acid sequence motif within the natural 6OST enzymes within EC 2.8.2.-. According to the present invention, an engineered 6OST enzyme can comprise one, two, three, four, or five mutated amino acid sequence motifs relative to the following conserved 6OST amino acid sequence motifs: (Q-K-T-G-G-T), (C-G-L-H-A-D), (L-R-D-V-P-S), (S-E-W-R/K-H-V-Q-R-G-A-T-W-K), or (L-T-E-F/Y-Q), which correspond to SEQ ID NO: 254, SEQ ID NO: 255, SEQ ID NO: 275, SEQ ID NO: 256, and SEQ ID NO: 276 in the sequence listing, respectively. In some embodiments, the conserved Q-K-T-G-G-T amino acid sequence motif (SEQ ID NO: 254) is mutated to G-H-T-G-G-T (SEQ ID NO: 257); the leucine residue within the conserved C-G-L-H-A-D amino acid sequence motif (SEQ ID NO: 255) is mutated to a alcohol residue selected from the group consisting of a threonine and a serine (as indicated in SEQ ID NO: 258 or SEQ ID NO: 259, respectively), and the conserved S-E-W-R/K-H-V-Q-R-G-A-T-W-K amino acid sequence motif (SEQ ID NO: 256) is mutated to the amino acid sequence motif $X_1$-$X_2$-W-R-H-$X_3$-Q-R-G-G-$X_4$-N-K (SEQ ID NO: 260), wherein: $X_1$ can be selected from the group consisting of serine or glycine; $X_2$ can be selected from the group consisting of glycine and histidine; $X_3$ can be selected from the group consisting of threonine and histidine; and $X_4$ can be selected from the group consisting of threonine and alanine. In some further embodiments, the identity of $X_1$ and $X_4$ are dependent on each other such that when $X_1$ is glycine, $X_4$ is threonine (as illustrated in SEQ ID NO: 261), and when $X_1$ is serine, $X_4$ is alanine (as illustrated in SEQ ID NO: 262). In other further embodiments, the identity of $X_2$ and $X_3$ are dependent on each other such that when $X_2$ is glycine, $X_3$ is histidine (as illustrated in SEQ ID NO: 263), and when $X_2$ is histidine, $X_3$ is threonine (as illustrated in SEQ ID NO: 264). Additional non-limiting examples of mutated amino acid sequence motifs are described in further detail, below.

According to the present invention, an engineered 6OST enzyme can comprise an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, each of which contains several amino acid mutations made relative to highly conserved amino acid sequences of natural 6OST enzymes within EC 2.8.2.-. According to the present invention, engineered 6OST enzymes utilized in accordance with any of the methods described herein can also comprise any amino acid sequence that is a biological equivalent, and/or a functional fragment, of an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

According to the present invention, any of the engineered 6OST enzymes described above can possess one or more residue differences or mutations as compared to the amino acid sequences disclosed by an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122 can comprise non-conservative substitutions, conservative substitutions, as well as combinations of conservative and non-conservative amino acid substitutions. According to the present invention, an amino acid mutation can be made at any position within SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, so long as the mutated enzyme retains its 6OST activity with an aryl sulfate compound as a sulfo group donor and any of the heparosan-based polysaccharides described above as a sulfo group acceptor.

According to the present invention, an engineered 6OST enzyme can comprise the amino acid sequence of SEQ ID NO: 112. Within SEQ ID NO: 112, residues having the designation, "X," illustrate known instances in which there is a lack of identity at a particular position within the amino acid sequences of SEQ ID NO: 104, SEQ ID NO: 106, and SEQ ID NO: 108. Thus, an "X" designation indicates the amino acid at that position can be selected from a group of two or more amino acids, as defined by SEQ ID NO: 112.

According to the present invention, an engineered 6OST enzyme can comprise the amino acid sequence of SEQ ID NO: 113. According to the present invention, within SEQ ID NO: 113, residues having the designation, "X," illustrate known instances in which there is a lack of identity at a particular position within the amino acid sequences of SEQ ID NO: 104, SEQ ID NO: 106, and SEQ ID NO: 108. According to the present invention, SEQ ID NO: 113 also comprises N-terminal residues 1-66, and C-terminal residues 378-411, of several full-length 6OST enzymes within EC 2.8.2.-, including, as non-limiting examples, the mouse, human, and pig 6OST enzymes. Thus, an "X" designation indicates the amino acid at that position can be selected from a group of two or more amino acids, as defined by SEQ ID NO: 113.

Additionally, and according to the present invention, amino acid mutations can be made at one or more positions within SEQ ID NO: 104, SEQ ID NO: 106, SEQ ID NO: 108, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122 so long as the mutated enzyme retains its glucosaminyl 6-O sulfotransferase activity with an aryl sulfate compound as a sulfo group donor. According to the present invention, an aryl sulfate-dependent enzyme comprising the amino acid sequence of SEQ ID NO: 132 or SEQ ID NO: 133 can optionally comprise one or more amino acid mutations at positions not designated as "X," while still retaining its glucosaminyl 6-O sulfotransferase activity with an aryl sulfate compound as a sulfo group donor.

In an aspect of the invention, an engineered sulfotransferase enzyme can have glucosaminyl 3-O sulfotransferase activity, comprising the transfer of a sulfo group from an aryl sulfate compound to the 3-O position of a glucosamine residue within a heparosan-based polysaccharide. According to the present invention, an engineered 3OST can comprise any amino acid sequence, so long as the sulfo group donor is an aryl sulfate compound and the sulfo group acceptor is a heparosan-based polysaccharide.

According to the present invention, engineered 3OST enzymes can be mutants of natural sulfotransferases that have 3OST activity, which are members of EC 2.8.2.23. In contrast to the engineered 3OST enzymes of the present invention, natural 3OST enzymes within EC 2.8.2.23 do not react with aryl sulfate compounds, and only react with PAPS as a sulfo group donor. However, the engineered 3OST enzymes can retain the same biological activity as the natural 3OST enzymes within EC 2.8.2.23 with heparosan-based polysaccharides as sulfo group acceptors.

According to the present invention, glucosamine residues within the heparosan-based polysaccharide that can receive a sulfo group at the 3-O position are N-sulfated, and can optionally comprise a 6-O sulfo group as well. According to the present invention, any other glucosamine residue within the sulfo acceptor polysaccharide can be optionally be N-, 3-O, and/or 6-O sulfated, N-acetylated, or N-unsubstituted. According to the present invention, one or more of the glucosamine residues within the heparosan-based polysaccharide, including the glucosamine residue being 3-O sulfated, can be both N-sulfated and 6-O sulfated. According to the present invention, the glucosamine residue being 3-O sulfated can be adjacent to an unsulfated glucuronic acid residue at the non-reducing end and an iduronic acid residue at the reducing end. According to the present invention, the iduronic acid residue at the reducing end of the glucosamine residue being 3-O sulfated can optionally be 2-O sulfated. According to the present invention, any of the other hexuronic acid residues within the heparosan-based polysaccharide acting as the sulfo group acceptor for the 3OST can optionally be iduronic acid or glucuronic acid, and can optionally be 2-O sulfated. One non-limiting example of a heparosan-based polysaccharide that can be utilized as a sulfo acceptor with any of the engineered 3OST enzymes is a heparosan-based polysaccharide comprising one or more structural motifs having the structure of Formula X, below:

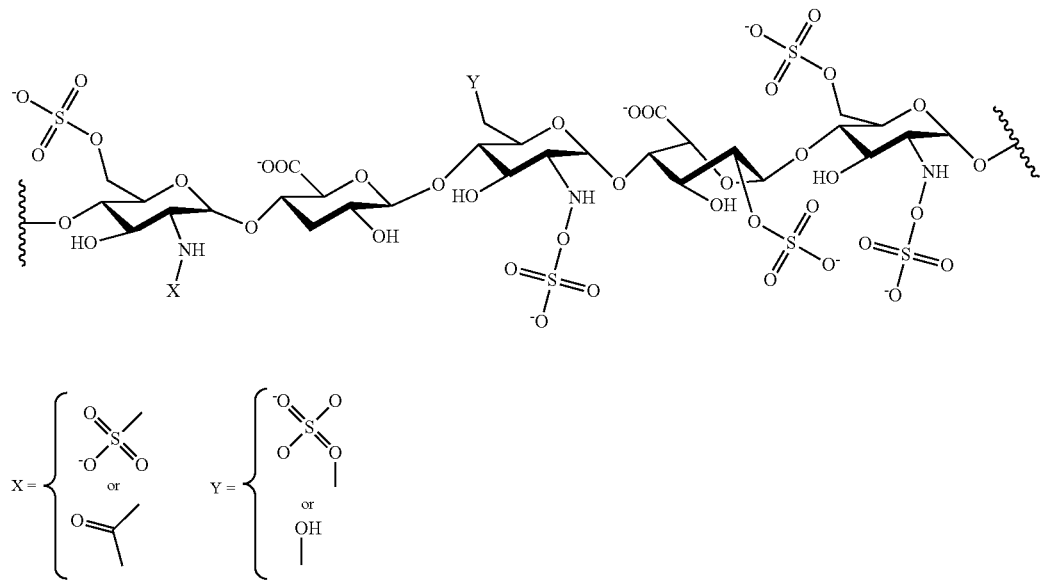

wherein X is either a sulfo group or an acetate group and Y is either a sulfo group or a hydroxyl group. According to the present invention, in some preferred embodiments, X can be a sulfo group and Y can be a sulfo group. When the heparosan-based polysaccharide comprises the structure of Formula X, the 3-O sulfated polysaccharide product comprises the structure of Formula I, below:

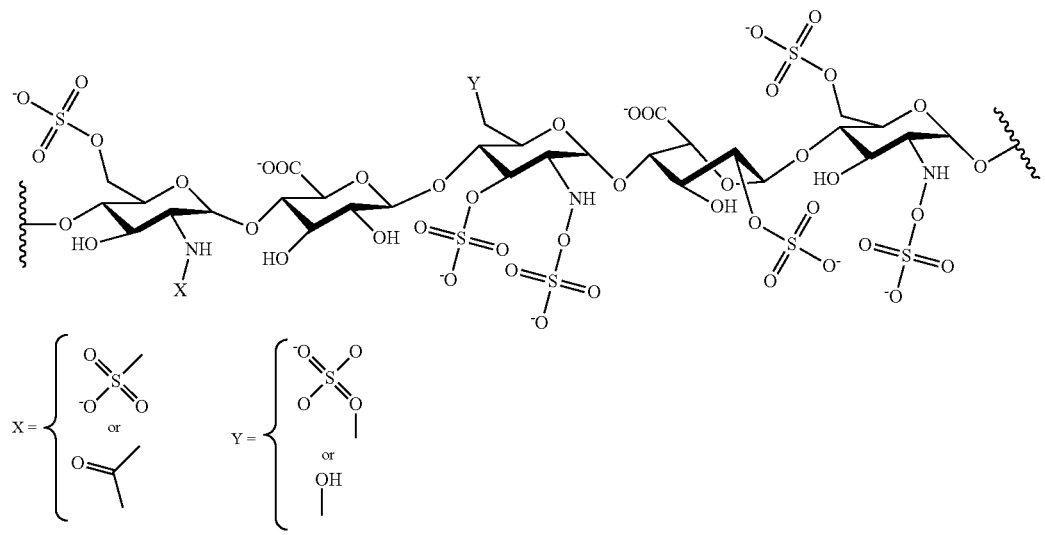

wherein X is either a sulfo group or an acetate group and Y is either a sulfo group or a hydroxyl group. According to the present invention, in some preferred embodiments, X can be a sulfo group and Y can be a sulfo group. According to the present invention, an N,2O,3O,6O-HS products comprising the structure of Formula I and which are formed upon reacting with an engineered 3OST enzyme can have anti-coagulant activity and have similar or equivalent physical properties to heparin. The anticoagulant activity of heparin and other N,2O,3O,6O-HS polysaccharides is described in further detail, below.

According to the present invention, the sulfo group acceptor for the engineered 3OST enzyme can comprise multiple structural motifs comprising the structure of Formula X, any or all of which can be sulfated by an engineered 3OST enzyme. According to the present invention, the sulfo group acceptor for the engineered 3OST can be N,2O,6O-HS. According to the present invention, the sulfo group acceptor for the engineered 3OST enzyme can be a sulfated polysaccharide product formed by an engineered 6OST enzyme, described above.

To facilitate its exclusive reactivity with PAPS as the sulfo group donor, natural 3OST enzymes within EC 2.8.2.23 typically comprise highly-conserved or identical amino acid sequences that define the active site and govern the enzyme's recognition, binding, and reactivity with PAPS. According to the present invention, the amino acid sequence of an engineered 3OST enzyme can comprise one or more mutations relative to natural 3OST enzymes within EC 2.8.2.23, in order to facilitate binding of an aryl sulfate compound instead of PAPS. According to the present invention, an engineered 3OST enzyme can comprise an amino acid sequence having at least one amino acid mutation relative to any of the natural 3OST enzymes within EC 2.8.2.23, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 3OST enzyme can comprise at least one amino acid mutation relative to the amino acid sequence of any of the natural 3OST enzymes within EC 2.8.2.23, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 3OST enzyme can be expressed as a "percent identity" or "% identity" relative to the amino acid sequence of one or more of the natural 3OST enzymes within EC 2.8.2.23, particularly relative to one or more of the natural 3OST enzymes within EC 2.8.2.23, and including biological functional fragments thereof. According to the present invention, an engineered 3OST enzyme can have at least 50% sequence identity, and up to at least 97% sequence identity, with any of the natural 3OST enzymes within EC 2.8.2.23. In a non-limiting example, the amino acid sequence of the engineered 3OST enzyme can have at least 80% sequence identity with the amino acid sequence of a natural 3OST enzyme, the natural 3OST enzyme selected from the group consisting of the human 3OST1 enzyme (SEQ ID NO: 206, UniProtKB Accession No. O14792) and the human 3OST5 enzyme (SEQ ID NO: 220, UniProtKB Accession No. Q8IZT8).

According to the present invention, an engineered 3OST enzyme can comprise one or more mutated amino acid sequence motifs relative to conserved amino acid sequence motifs found in one or more natural 3OST enzymes within EC 2.8.2.23. Each mutated amino acid sequence motif, when present, can have at least one amino acid mutation relative to the corresponding conserved amino acid sequence motif within the natural 3OST enzymes within EC 2.8.2.23. According to the present invention, an engineered 3OST enzyme can comprise one, two, three, or four mutated amino acid sequence motifs relative to the following conserved 3OST amino acid sequence motifs: (G-V-R-K-G-G), (P-A/G-Y-F), (S-D-Y-T-Q-V), or (Y-K-A). The conserved amino acid sequence motifs G-V-R-K-G-G, and S-D-Y-T-Q-V correspond to SEQ ID NO: 265 and SEQ ID NO: 267 in the sequence listing, respectively. In some embodiments, within the amino acid sequence of the engineered 3OST enzyme, the conserved G-V-R-K-G-G amino acid sequence motif (SEQ ID NO: 265) is mutated to G-V-G-H-G-G (SEQ ID NO: 268), the conserved P-A/G-Y-F amino acid sequence motif is mutated to H-S-Y-F (SEQ ID NO: 269), and the conserved Y-K-A amino acid sequence motif is mutated to Y-V/T-G. Additional non-limiting examples of mutated amino acid sequence motifs are described in further detail, below.

According to the present invention, an engineered 3OST enzyme can comprise an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160, each of which contains several amino acid mutations made relative to highly conserved amino acid sequences of natural 3OST enzymes within EC 2.8.2.23. According to the present invention, engineered 3OST enzymes utilized in accordance with any of the methods described herein can also comprise any amino acid sequence that is a biological equivalent, and/or a functional fragment, of an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

According to the present invention, any of the engineered 3OST enzymes described above can possess one or more residue differences or mutations as compared to the amino acid sequence disclosed by an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160 can comprise non-conservative substitutions, conservative substitutions, as well as combinations of conservative and non-conservative amino acid substitutions. According to the present invention, an amino acid mutation can be made at any position within SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160, so long as the mutated enzyme retains its glucosaminyl 3-O sulfotransferase activity with an aryl sulfate compound as a sulfo group donor and any of the heparosan-based polysaccharides described above as a sulfo group acceptor.

According to the present invention, an engineered 3OST enzyme can comprise the amino acid sequence of SEQ ID NO: 154. Within SEQ ID NO: 154, residues having the designation, "X," illustrate known instances in which there is a lack of identity at a particular position within the amino acid sequences of SEQ ID NO: 147, SEQ ID NO: 149, and SEQ ID NO: 151. Thus, an "X" designation indicates the amino acid at that position can be selected from a group of two or more amino acids, as defined by SEQ ID NO: 154.

Additionally, and according to the present invention, amino acid mutations can be made at one or more positions within SEQ ID NO: 147, SEQ ID NO: 149, SEQ ID NO: 151, SEQ ID NO: 155, SEQ ID NO: 156, SEQ ID NO: 157, SEQ ID NO: 158, SEQ ID NO: 159, and SEQ ID NO: 160 so long as the mutated enzyme retains its glucosaminyl 3-O sulfotransferase activity with an aryl sulfate compound as a sulfo group donor. According to the present invention, an aryl sulfate-dependent enzyme comprising the amino acid sequence of SEQ ID NO: 154 can optionally comprise one or more amino acid mutations at positions not designated as "X," while still retaining its glucosaminyl 3-O sulfotransferase activity with an aryl sulfate compound as a sulfo group donor.

In another aspect, the invention provides methods for enzymatically transferring a sulfo group from an aryl sulfate compound to a polysaccharide to form a sulfated polysaccharide product. According to the present invention, the polysaccharide can be a heparosan-based polysaccharide. According to the present invention, a method for enzymatically transferring a sulfo group from an aryl sulfate compound to a heparosan-based polysaccharide can comprise the following steps: (a) providing an aryl sulfate compound; (b) providing any of the engineered sulfotransferase enzymes described above, wherein the engineered sulfotransferase enzyme has biological activity with an aryl sulfate compound as a sulfo group donor; (c) providing a heparosan-based polysaccharide; (d) combining the aryl sulfate compound, the sulfotransferase enzyme, and the heparosan-based polysaccharide into a reaction mixture; and (e) transferring the sulfo group from the aryl sulfate compound to the heparosan-based polysaccharide, using the sulfotransferase enzyme, thereby forming the sulfated polysaccharide product. According to the present invention, the aryl sulfate compound can be selected from the consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. According to the present invention, the aryl sulfate compound can be PNS. According to the present invention, the aryl sulfate compound can be NCS.

According to the present invention, the engineered sulfotransferase can be any of the engineered NST enzymes described above, preferably an engineered NST enzyme comprising an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. According to the present invention, and useful in combination with any one or more of the above aspects and embodiments, the heparosan-based polysaccharide can be N-deacetylated heparosan. According to the present invention, and useful in combination with any one or more of the above aspects and embodiments, the heparosan-based polysaccharide can comprise one or more disaccharide units comprising the structure of Formula II. According to the present invention, and useful in combination with any one or more of the above aspects and embodiments, the sulfated polysaccharide product comprises the structure of Formula III.

According to the present invention, the engineered sulfotransferase can be any of the engineered 2OST enzymes described above, preferably an engineered 2OST enzyme comprising an amino acid sequence selected from the group consisting of SEQ ID NO: 65, SEQ ID NO: 66, SEQ ID NO: 67, and SEQ ID NO: 69. According to the present invention, and useful in combination with any one or more of the above aspects and embodiments, the heparosan-based polysaccharide can be N-sulfated heparosan. According to the present invention, and useful in combination with any one or more of the above aspects and embodiments, the heparosan-based polysaccharide can comprise one or more structural motifs comprising the structure of Formula IV and/or Formula V, and preferably at least one structural motif comprising the structure of Formula V. According to the present invention, and useful in combination with any one or more of the above aspects and embodiments, the method can further comprise the step of providing a glucuronyl $C_5$-epimerase, preferably a glucuronyl $C_5$-epimerase comprising the amino acid sequence of SEQ ID NO: 67, and more preferably residues 34-617 of SEQ ID NO: 67. According to the present invention, and useful in combination with any one or more of the above aspects and embodiments, the sulfated polysaccharide product comprises the structure of Formula VI and/or Formula VII.

According to the present invention, the engineered sulfotransferase can be any of the engineered 6OST enzymes described above, preferably an engineered 6OST enzyme comprising an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. According to the present invention, and useful in combination with any one or more of the above aspects and embodiments, the heparosan-based polysaccharide can be any of the heparosan-based polysaccharides described above that are suitable sulfo acceptors for an engineered 6OST enzyme. According to the present invention, and useful in combination with any one or more of the above aspects and embodiments, the heparosan-based polysaccharide can be N,2O-HS. According to the present invention, and useful in combination with any one or more of the above aspects and embodiments, the heparosan-based polysaccharide can comprise one or more structural motifs comprising the structure of Formula VIII. According to the present invention, and useful in combination with any one or more of the above aspects and embodiments, the sulfated polysaccharide product comprises the structure of Formula IX.

According to the present invention, the engineered sulfotransferase can be any of the engineered 3OST enzymes described above, preferably an engineered 3OST enzyme comprising an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. According to the present invention, and useful in combination with any one or more of the above aspects and embodiments, the heparosan-based polysaccharide can be N,2O,6O-HS. According to the present invention, and useful in combination with any one or more of the above aspects and embodiments, the heparosan-based polysaccharide can comprise one or more structural motifs comprising the structure of Formula X. According to the present invention, and useful in combination with any one or more of the above aspects and embodiments, the sulfated polysaccharide product comprises the structure of Formula I. According to the present invention, and useful in combination with any one or more of the above aspects and embodiments, the sulfated polysaccharide product comprising the structure of Formula I can have anticoagulant activity. According to the present invention, and useful in combination with any one or more of the above aspects and embodiments, the sulfated polysaccharide product comprising the structure of Formula I can have one or more similar or equivalent molecular weight properties and/or anticoagulant activity relative to heparin.

According to the present invention, and useful in combination with any one or more of the above aspects and embodiments, within any reaction mixture or composition comprising a heparosan-based polysaccharide used as a starting material or a sulfated polysaccharide product, the polysaccharides can be present as a polydisperse mixture of polysaccharides having variable chain lengths, molecular weights, N-acetylation, and/or N-, 2-O, 6-O, or 3-O sulfation. Alternatively, according to the present invention, any of the polysaccharides described above can be present as a homogeneous composition comprised of polysaccharides having identical chain lengths, molecular weights, N-acetylation, and/or N-, 2-O, 6-O, or 3-O sulfation.

According to the present invention, and useful in combination with one or more of the above aspects and embodiments, an engineered enzyme of the present invention having sulfatase and/or sulfotransferase activity with an aryl sulfate compounds as a substrate can be expressed from a nucleic acid comprising any nucleotide sequence that encodes for a polypeptide having the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160. According to the present invention, such nucleotide sequences can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, and SEQ ID NO: 152, which encode for the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively. Persons skilled in the art can determine appropriate nucleotide sequences that encode for polypeptides having the amino acid sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, based on the nucleotide sequences listed above and the identity of the desired engineered enzyme.

According to the present invention, and useful in combination with one or more of the above aspects and embodiments, a nucleic acid comprising a nucleotide sequence encoding for any of the engineered enzymes described above can be inserted into an expression vector that is engineered to be inserted into biological host cells configured to retain the expression vector and overexpress the desired enzyme. According to the present invention, the nucleic acid inserted into an expression vector can comprise any nucleotide sequence encoding for any of the engineered enzymes described above, particularly those comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. According to the present invention, the nucleic acid inserted into an expression vector can comprise any nucleotide sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, and SEQ ID NO: 152.

According to the present invention, and useful in combination with one or more of the above aspects and embodiments, the expression vector can optionally further comprise one or more nucleic acid sequences or genes encoding for proteins or host recognition sites that supplement the production of engineered enzymes of the present invention. Non-limiting examples include promoter sequences, antibiotic resistance genes, and genes encoding for fusion proteins that assist in the folding and stability of the engineered sulfotransferase enzyme. According to the present invention, any of the expression vectors described above can further comprise the malE gene from Escherichia coli, which encodes for maltose binding protein (MBP). According to the present invention, any of the expression vectors described above can further comprise a gene encoding for a small ubiquitin-related modifier (SUMO) protein, preferably the SUMO1 gene, which encodes for the SUMO1 protein. As a result, and according to the present invention, once protein expression is initiated, a fusion protein can be formed that comprises either MBP or SUMO, as well as an engineered enzyme having an amino acid sequence selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO:

120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160.

Expression vectors are typically transformed into host cells from which the enzyme can be overexpressed and extracted. According to the present invention, and useful in combination with one or more of the above aspects and embodiments, host cells can be transformed with expression vectors containing a nucleic acid sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, or any sequence that encodes for an enzyme having the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. According to the present invention, any of the above expression vectors transformed into the host cell can further comprise the malE or SUMO1 gene. According to the present invention, the transformed host cells can be bacterial, yeast, insect, or mammalian cells. According to the present invention, the host cells can be bacterial cells. According to the present invention, the bacterial cells can be from a non-pathogenic strain of Escherichia coli (E. coli).

In another aspect of the invention, kits for forming a sulfated polysaccharide product, particularly N,2O,3O,6O-HS products having anticoagulant activity similar or equivalent to heparin, according to any of the methods described above, are provided. According to the present invention, the kit can comprise at least one engineered aryl sulfate-dependent sulfotransferase and at least one aryl sulfate compound, preferably PNS or NCS. According to the present invention, and useful in combination with any one or more of the above aspects and embodiments, the kit can comprise an engineered NST, an engineered 2OST, an engineered 6OST, and/or an engineered 3OST, each of which is dependent on reacting with an aryl sulfate compound as a sulfo group donor to catalyze a transfer of the sulfo group to a polysaccharide, preferably a heparosan-based polysaccharide. According to the present invention, and useful in combination with any one or more of the above aspects and embodiments, the kit can further comprise any of the heparosan-based polysaccharides described above as sulfo group donor. According to the present invention, and useful in combination with any one or more of the above aspects and embodiments, the kit can further comprise a glucuronyl $C_5$-epimerase, preferably an epimerase comprising the amino acid sequence of SEQ ID NO: 67, and more preferably an epimerase comprising amino acid residues 34-617 of SEQ ID NO: 67.

According to the present invention, and useful in combination with any one or more of the above aspects and embodiments, any of the sulfated polysaccharide products, including anticoagulant N,2O,3O,6O-HS products, prepared according to any of the methods described above can be prepared as pharmaceutically-acceptable salts, particularly alkali or alkali earth salts including, but not limited to, sodium, lithium, or calcium salts.

These and other embodiments of the present invention will be apparent to one of ordinary skill in the art from the following detailed description.

BRIEF DESCRIPTION OF THE FIGURES

FIG. 6A, FIG. 6B, and FIG. 6C show a multiple sequence alignment for the N-sulfotransferase domains of fifteen wild type EC 2.8.2.8 enzymes, illustrating conserved amino acid sequence motifs that are present regardless of overall sequence identity.

DEFINITIONS

Figure 1:
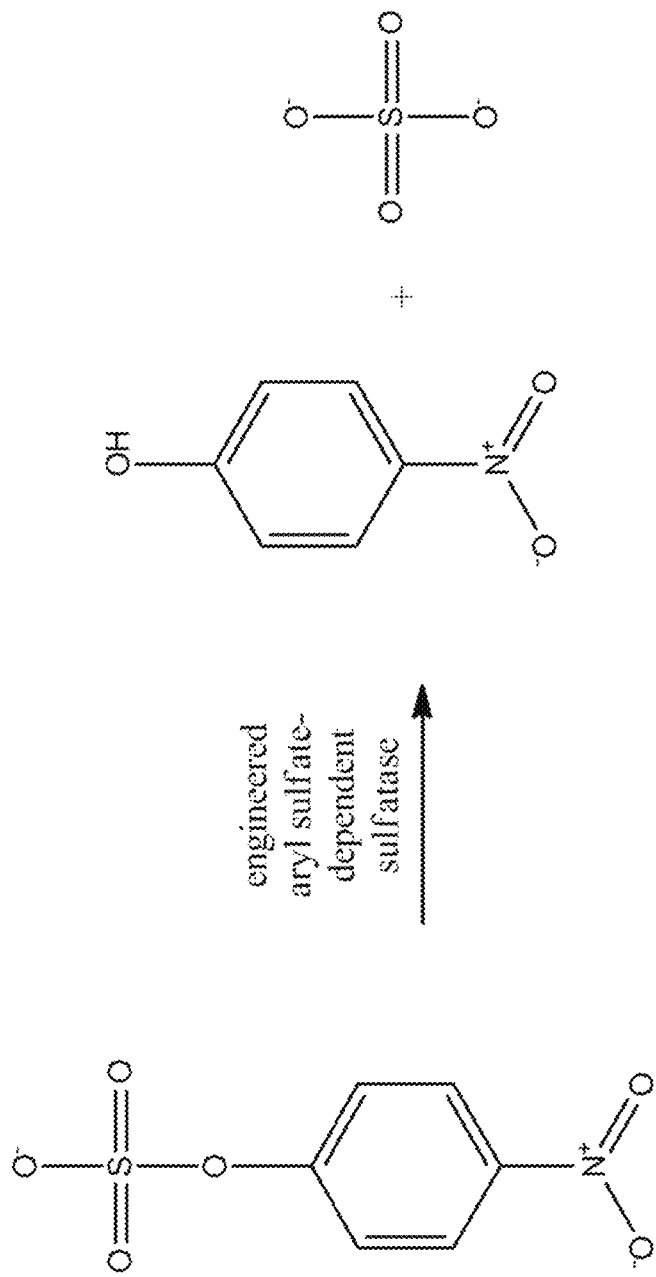
FIG. 1 shows the sulfatase activity catalyzed by one of the engineered enzymes of the present invention, when PNS is the substrate.

The term, "active site," refers to sites in catalytic proteins, in which catalysis occurs, and can include one or more substrate binding sites. Active sites are of significant utility in the identification of compounds that specifically interact with, and modulate the activity of, a particular polypeptide. The association of natural ligands or substrates with the active sites of their corresponding receptors or enzymes is the basis of many biological mechanisms of action. Similarly, many compounds exert their biological effects through association with the active sites of receptors and enzymes. Such associations may occur with all or any parts of the active site. An understanding of such associations helps lead to the design of engineered active sites within sulfotransferases that are capable of binding to and reacting with aryl sulfate compounds instead of PAPS.

The term, "amino acid," refers to a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino and carboxylic groups in the dehydration reaction that links one amino acid to another. As a result, when incorporated into a protein, an amino acid is referred to as an "amino acid residue." In the case of naturally occurring proteins, an amino acid residue's R group differentiates the 20 amino acids from which proteins are synthesized, although one or more amino acid residues in a protein may be derivatized or modified following incorporation into protein in biological systems (e.g., by glycosylation and/or by the formation of cysteine through the oxidation of the thiol side chains of two non-adjacent cysteine amino acid residues, resulting in a disulfide covalent bond that frequently plays an important role in stabilizing the folded conformation of a protein, etc.). Additionally, when an alpha-carbon atom has four different groups (as is the case with the 20 amino acids used by biological systems to synthesize proteins, except for glycine, which has two hydrogen atoms bonded to the carbon atom), two different enantiomeric forms of each amino acid exist, designated D and L. In mammals, only L-amino acids are incorporated into naturally occurring polypeptides. Engineered enzymes utilized of the present invention can incorporate one or more D- and L-amino acids, or can be comprised solely of D- or L-amino acid residues.

Non-naturally occurring amino acids can also be incorporated into any of the engineered enzymes of the present invention, particularly engineered sulfotransferase enzymes having aryl sulfate-dependent activity. Non-limiting examples of such amino acids include: alpha-amino isobutyric acid, 4-amino butyric acid, L-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butyl glycine, t-butyl alanine, phenylglycine, cyclohexyl alanine, beta-alanine, fluoro-amino acids, designer amino acids (e.g., beta-methyl amino acids, alpha-methyl amino acids, alpha-methyl amino acids) and amino acid analogs in general.

The term, "and/or," when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The terms, "aryl sulfate" or "aryl sulfate compound," refer to any compound, functional group, or substituent derived from an aromatic ring in which one or more of the hydrogen atoms directly bonded to the aromatic ring is replaced by a sulfate functional group. Typically, the sulfate functional group is covalently bound to the aromatic moiety of an aryl sulfate compound through a sulfate ester linkage. Non-limiting examples of aryl sulfate compounds that can be used as substrates with any of the engineered enzymes of the present invention include, but are not limited to, PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS.

The term, "aryl sulfate-dependent sulfotransferase," refers to the collective group of engineered sulfotransferases that possess biological or catalytic activity with aryl sulfate compounds as sulfo donors. Non-limiting examples of aryl sulfate compounds upon which the biological activity of the sulfotransferase can be dependent include PNS and NCS. As described herein, engineered sulfotransferases having biological activity with aryl sulfate compounds as sulfo group donors can possess biological activity with polysaccharides, particularly heparosan-based polysaccharides, as sulfo group acceptors. "Aryl sulfate-dependent sulfotransferase" also includes both nucleic acids and polypeptides encoding for any aryl sulfate-dependent sulfotransferase, including mutants derived from the sequences disclosed herein.

The term, "average molecular weight," with respect to any of the polysaccharide starting materials, intermediates, and/or products used or generated according to any of the methods of the present invention, and unless otherwise indicated, can refer to any accepted measure of determining the molar mass distribution or molar mass average of a mixture of polymers having varying degrees of polymerization, functionalization, and molar mass, including but not limited to "number-average molecular weight," "mass-average molecular weight," "weight-average molecular weight," "Z (centrifugation) average molar mass," or "viscosity average molar mass."

The term, "weight-average molecular weight," refers to a method of reporting the average molecular weight of polysaccharides in a mixture, calculated using the mole fraction distribution of the polysaccharides within the sample, using the equation $$\bar{M}_w = \frac{\sum_i N_i M_i^2}{\sum_i N_i M_i},$$

wherein $N_i$ is the number of polysaccharides of molecular mass $M_i$.

The term, "number-average molecular weight," refers to a method of reporting the average molecular weight of polysaccharides in a mixture, calculated by dividing the total weight of all of the polysaccharides in the sample divided by the number of polysaccharides in a sample, using the equation, $$\bar{M}_N = \frac{\sum_i N_i M_i}{\sum_i N_i},$$

wherein $N_i$ is the number of polysaccharides of molecular mass $M_i$. Accordingly, the weight-average molecular weight, $\bar{M}_w$, is necessarily skewed toward higher values corresponding to polysaccharides within the sample that are larger than other polysaccharides within the same mixture, and will always be larger than the number-average molecular weight, $\bar{M}_n$, except when the sample is monodisperse, and $\bar{M}_w$ equals $\bar{M}_n$. If a particular sample of polysaccharides within the sample has a large dispersion of actual weights, then $\bar{M}_w$ will be much larger than $\bar{M}_n$. Conversely, as the weight dispersion of polysaccharides in a sample narrows, $\bar{M}_w$ approaches $\bar{M}_n$.

The terms, "relative molecular weight" or "relative molar mass" ($M_r$), refers to another method of reporting the average molecular weight of polysaccharides in a mixture as a unitless quantity, most broadly determined by dividing the average mass of the molecule by an atomic mass constant, such as 1 atomic mass unit (amu) or 1 Dalton (Da). With respect to polysaccharides, $M_r$ does not take into account the different chain-lengths, functionalization, and/or weight distribution of the polysaccharides in the sample, and instead simply represents the true average mass of the polysaccharides in the sample in a manner similar to small molecules.

The terms, "biological activity" or "catalytic activity," refer to the ability of an enzyme to catalyze a particular chemical reaction by specific recognition of a particular substrate or substrates to generate a particular product or products. In some embodiments, the engineered enzymes of the present invention possess a biological or catalytic activity that is dependent on binding and reacting with aryl sulfate compounds, particularly PNS or NCS, as substrates. Additionally, some engineered enzymes are capable of having promiscuous catalytic activity with one or more alternate aryl sulfate compounds in addition to PNS, including but not limited to MUS, 7-hydroxycoumarin sulfate, phenyl sulfate, 4-acetylphenyl sulfate, indoxyl sulfate, 1-naphthyl sulfate, and 2NapS.

The term, "coding sequence," refers to that portion of a nucleic acid, for example, a gene, that encodes an amino acid sequence of a protein.

The term, "codon-optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, it is well known that codon usage by particular organisms is non-random and biased toward particular codon triplets. In some embodiments of the invention, the polynucleotide encoding for an engineered enzyme may be codon optimized for optimal production from the host organism selected for expression.

The terms, "corresponding to," "reference to," or "relative to," when used in the context of the numbering of a given amino acid or polynucleotide sequence, refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence.

The term, "deletion," refers to modification of a polypeptide by removal of one or more amino acids from the reference polypeptide. Deletions can comprise removal of 1 or more amino acids, the net result of which is retaining the catalytic activity of the reference polypeptide. Deletions can be directed to the internal portions and/or terminal portions of a polypeptide. Additionally, deletions can comprise continuous segments or they can be discontinuous.

The term, "disaccharide unit," refers to the smallest repeating backbone unit within many polysaccharides, including linear polysaccharides, in which the smallest repeating unit consists of two sugar residues. With respect to a heparosan-based polysaccharide, the disaccharide unit consists of a hexuronic acid residue and a glucosamine residue, either of which can be functionalized and in which the hexuronic acid residue can either be glucuronic acid or iduronic acid. Each disaccharide unit within the heparosan-based polysaccharide can be described by its backbone structure and by the number and position of sulfo groups that are present. Further, the relative abundance of disaccharide units having the same structure within the same polysaccharide, and/or within the same sample of polysaccharides, can be characterized to determine the amount of sulfation at a particular position as a result of reacting with any of the sulfotransferases described herein.

The terms, "fragment" or "segment," refer to a polypeptide that has an amino- or carboxy-terminal deletion, but where the remaining amino acid sequence is identical to the corresponding positions in a reference sequence. Fragments can be at least 50 amino acids or longer, and comprise up to 70%, 80%, 90%, 95%, 98%, and 99% of the amino acid sequence of an enzyme.

The terms, "functional site" or "functional domain," generally refer to any site in a protein that confers a function on the protein. Representative examples include active sites (i.e., those sites in catalytic proteins where catalysis occurs) and ligand binding sites. Ligand binding sites include, but are not limited to, metal binding sites, co-factor binding sites, antigen binding sites, substrate channels and tunnels, and substrate binding domains. In an enzyme, a ligand binding site that is a substrate binding domain may also be an active site. Functional sites may also be composites of multiple functional sites, wherein the absence of one or more sites comprising the composite results in a loss of function. As a non-limiting example, the active site of a particular sulfotransferase enzyme may include multiple binding sites or clefts, including one site for the sulfo donor and one site for the sulfo acceptor.

The terms, "gene," "gene sequence," and "gene segment," refer to a functional unit of nucleic acid unit encoding for a functional protein, polypeptide, or peptide. As would be understood by those skilled in the art, this functional term includes both genomic sequences and cDNA sequences. The terms, "gene," "gene sequence," and "gene segment," additionally refer to any DNA sequence that is substantially identical to a polynucleotide sequence disclosed herein encoding for engineered enzyme gene product, protein, or polysaccharide, and can comprise any combination of associated control sequence. The terms also refer to RNA, or antisense sequences, complementary to such DNA sequences. As used herein, the term "DNA segment" includes isolated DNA molecules that have been isolated free of recombinant vectors, including but not limited to plasmids, cosmids, phages, and viruses.

The term, "glycosaminoglycan," refers to long, linear polysaccharides consisting of repeating disaccharide units. Examples of glycosaminoglycans (GAGs) include chondroitin, dermatan, heparosan, hyaluronic acid, and keratan. GAGs are generally heterogeneous with respect to mass, length, disaccharide unit structure and functionalization, degree of sulfation.

The term, "heparosan," refers to a particular GAG having repeating $[\beta(1,4)GlcA-\alpha(1,4)GlcNAc]_n$ disaccharide units, in which GlcA is glucuronic acid and GlcNAc is N-acetyl glucosamine.

The term, "heparosan-based polysaccharide," refers to polysaccharides having the same backbone structure as heparosan, in which the disaccharide unit contains 1→4 glycosidically-linked hexuronic acid and glucosamine residues. The hexuronic acid residue can either be glucuronic acid, as in heparosan, or iduronic acid, and can optionally have a sulfo group at the 2-O position. The glucosamine residue can either be N-acetylated, as in heparosan, N-sulfated, or N-unsubstituted, and can optionally be sulfated at the N-, 3-O, or 6-O position. As used herein, the term "N-unsubstituted," with respect to a glucosamine residue, is equivalent to an "N-deacetylated" glucosamine residue, and refers to an amine functional group that is capable of receiving a sulfo group either chemically, or enzymatically using a NST. According to the present invention, heparosan-based polysaccharides can be utilized as starting materials, formed as intermediates, acting as sulfo group acceptors and/or synthesized as products according to any of the methods described herein.

The term, "insertion," refers to modifications to the polypeptide by addition of one or more amino acids to the reference polypeptide. Insertions can be in the internal portions of the polypeptide, or to the C- or N-termini of the polypeptide. Insertions can include fusion proteins as is known in the art and described below. The insertions can comprise a continuous segment of amino acids or multiple insertions separated by one or more of the amino acids in the reference polypeptide.

The term, "isolated nucleic acid" as used herein with respect to nucleic acids derived from naturally-occurring sequences, means a ribonucleic or deoxyribonucleic acid which comprises a naturally-occurring nucleotide sequence and which can be manipulated by standard recombinant DNA techniques, but which is not covalently joined to the nucleotide sequences that are immediately contiguous on its 5' and 3' ends in the naturally-occurring genome of the organism from which it is derived. As used herein with respect to synthetic nucleic acids, the term "isolated nucleic acid" means a ribonucleic or deoxyribonucleic acid which comprises a nucleotide sequence which does not occur in nature and which can be manipulated by standard recombinant DNA techniques. An isolated nucleic acid can be manipulated by standard recombinant DNA techniques when it may be used in, for example, amplification by polymerase chain reaction (PCR), in vitro translation, ligation to other nucleic acids (e.g., cloning or expression vectors), restriction from other nucleic acids (e.g., cloning or expression vectors), transformation of cells, hybridization screening assays, or the like.

The terms, "naturally occurring" or "wild-type," refer to forms of an enzyme found in nature. For example, a naturally occurring or wild-type polypeptide or polynucleotide sequence is a sequence present in an organism that can be isolated from a source in nature and which has not been intentionally modified by human manipulation. A wild-type polypeptide or polynucleotide sequence can also refer to recombinant proteins or nucleic acids that can be synthesized, amplified, and/or expressed in vitro, and which have the same sequence and biological activity as an enzyme produced in vivo. In contrast to naturally occurring or wild-type sulfotransferase enzymes, the engineered sulfotransferase enzymes utilized in accordance with methods of the present invention have unique amino acid and nucleic acid sequences, have biological activity with aryl sulfate compounds as sulfo group donors instead of PAPS, and cannot be found in nature.

The term, "oligosaccharide," refers to saccharide polymers containing a small number, typically three to nine, sugar residues within each molecule.

The term, "percent identity," refers to a quantitative measurement of the similarity between two or more nucleic acid or amino acid sequences. As a non-limiting example, the percent identity can be assessed between two or more engineered enzymes of the present invention, two or more naturally occurring enzymes, or between one or more engineered enzymes and one or more naturally occurring enzymes. Percent identity can be assessed relative to two or more full-length sequences, two or more truncated sequences, or a combination of full-length sequences and truncated sequences.

The term, "polysaccharide," refers to polymeric carbohydrate structures formed of repeating units, typically monosaccharide or disaccharide units, joined together by glycosidic bonds, and which can range in structure from a linear chain to a highly-branched three-dimensional structure. Although the term "polysaccharide," as used in the art, can refer to saccharide polymers having more than ten sugar residues per molecule, "polysaccharide" is used within this application to describe saccharide polymers having more than one sugar residue, including saccharide polymers that have three to nine sugar residues that may be defined in the art as an "oligosaccharide." According to the present invention, the term "polysaccharide," is also used to generally describe GAGs and GAG-based compounds, including chondroitin, dermatan, heparosan, hyaluronic acid, and keratan compounds.

The terms, "protein," "gene product," "polypeptide," and "peptide" can be used interchangeably to describe a biomolecule consisting of one or more chains of amino acid residues. In addition, proteins comprising multiple polypeptide subunits (e.g., dimers, trimers or tetramers), as well as other non-proteinaceous catalytic molecules will also be understood to be included within the meaning of "protein" as used herein. Similarly, "protein fragments," i.e., stretches of amino acid residues that comprise fewer than all of the amino acid residues of a protein, are also within the scope of the invention and may be referred to herein as "proteins." Additionally, "protein domains" are also included within the term "protein." A "protein domain" represents a portion of a protein comprised of its own semi-independent folded region having its own characteristic spherical geometry with hydrophobic core and polar exterior.

The term, "recombinant," when used with reference to, for example, a cell, nucleic acid, or polypeptide, refers to a material that has been modified in a manner that would not otherwise exist in nature. Non-limiting examples include, among others, recombinant cells expressing genes that are not found within the native (non-recombinant) form of the cell or express native genes that are otherwise expressed at a different level.

The term, "reference sequence," refers to a disclosed or defined sequence used as a basis for sequence comparison. A reference sequence may be a subset of a larger sequence, for example, a segment of a full-length gene or polypeptide sequence. Generally, a reference sequence refers to at least a portion of a full-length sequence, typically at least 20 amino acids, or the full-length sequence of the nucleic acid or polypeptide.

The term, "saccharide," refers to a carbohydrate, also known as a sugar, which is a broad term for a chemical compound comprised of carbon, hydrogen, and oxygen, wherein the number of hydrogen atoms is essentially twice that of the number of oxygen atoms. Often, the number of repeating units may vary in a saccharide. Thus, disaccharides, oligosaccharides, and polysaccharides are all examples of chains composed of saccharide units that are recognized by the engineered sulfotransferase enzymes of the present invention as sulfo group acceptors.

The term, "substantially equivalent," with respect to polysaccharides utilized as starting materials, formed as intermediates, acting as sulfo group acceptors, and/or synthesized as products according to any of the methods described herein, refers to one or more properties of a polysaccharide sample that are identical to those found in a polysaccharide sample characterized in the prior art. Such properties may include, but are not limited to, chemical structure, sulfation frequency and location, disaccharide unit composition, molecular weight profile, and/or anticoagulant activity. Even if the two polysaccharide samples have additional properties that may be different, such differences do not significantly affect their substantial equivalence. In a non-limiting example, anticoagulant N,2O,3O,6O-HS products synthesized using engineered 3OSTs according to methods of the present invention can be substantially equivalent to the United States Pharmacopeia (USP) reference standard (CAS No: 9041-08-1) with respect to chemical structure, molecular weight profile, and/or anticoagulant activity, but can be produced at a different purity than the USP reference standard, which is isolated from natural sources and can contain non-trace amounts of other GAGs in the same sample.

The term, "substantially pure," with respect to protein preparations, refers to a preparation which contains at least 60% (by dry weight) the protein of interest, exclusive of the weight of other intentionally included compounds. Particularly the preparation is at least 75%, more particularly at least 90%, and most particularly at least 99%, by dry weight the protein of interest, exclusive of the weight of other intentionally included compounds. Purity can be measured by any appropriate method, e.g., column chromatography, gel electrophoresis, or high-performance liquid chromatography (HPLC) analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. Particularly, for such preparations containing two or more proteins of the invention, the total weight of the proteins of the invention can be at least 75%, more particularly at least 90%, and most particularly at least 99%, of the total dry weight of the preparation, exclusive of the weight of other intentionally included compounds.

The terms, "sulfo" or "sulfuryl" refer to a functional group, substituent, or moiety having the chemical formula $SO_3H$- that can be removed from an aryl sulfate compound and/or be transferred from a donor compound to an acceptor compound. In some embodiments, the engineered sulfotransferases of the present invention catalyze the transfer of sulfo groups from aryl sulfate compounds to a polysaccharide, particularly heparosan and/or heparosan-based polysaccharides.

The term, "sulfotransferase," refers to any enzyme in an in vivo or in vitro process that is used to catalyze the transfer of a sulfo group from a sulfo donor compound to a sulfo acceptor compound. "Sulfotransferase" can be used interchangeably to describe enzymes that catalyze sulfotransfer reactions in vivo or to describe engineered enzymes of the present invention that catalyze sulfotransfer reactions in vitro.

The term, "transformation," refers to any method of introducing exogenous a nucleic acid into a cell including, but not limited to, transformation, transfection, electroporation, microinjection, direct injection of naked nucleic acid, particle-mediated delivery, viral-mediated transduction or any other means of delivering a nucleic acid into a host cell which results in transient or stable expression of said nucleic acid or integration of said nucleic acid into the genome of said host cell or descendant thereof.

DETAILED DESCRIPTION OF THE INVENTION

The present disclosure describes engineered enzymes that are configured to recognize, bind, and react with aryl sulfate compounds as substrates. The enzymes of the present invention are especially useful because many sulfate-containing compounds that are common substrates for bacterial and eukaryotic enzymes in vivo, including sulfatases and sulfotransferases, are often impractical to use as substrates for those same reactions in vitro. Aryl sulfate compounds are ubiquitous, cheap, stable, and comparatively easy to work with in a laboratory setting, but they are can react with very few enzymes in vivo. In particular, eukaryotic sulfotransferases cannot bind or react with aryl sulfate compounds as sulfo group donors, and instead can only react with 3'-phosphoadenosine 5'-phosphosulfate (PAPS) as a sulfo group donor. As a result, the sulfotransferases' nearly universal reliance on PAPS has been an insurmountable roadblock to the large-scale chemoenzymatic or enzymatic in vitro synthesis of sulfated products, particularly sulfated polysaccharide products.

The engineered enzymes of the present invention, disclosed below, are mutants of natural sulfotransferase enzymes that exclusively recognize, bind, and react with PAPS, but instead are engineered to bind and react with aryl sulfate compounds as substrates. In an embodiment of the invention, many of the engineered enzymes possess sulfatase activity, in which the enzyme catalyzes hydrolysis of a sulfo group from an aryl sulfate compound. Without being limited by a particular theory, it is believed that the reaction mechanism for the sulfatase is unique relative to known natural sulfatases, which possess conserved signal sequences and post-translationally modified amino acids.

The sulfatase activity of both natural enzymes and the engineered enzymes of the present invention is described in further detail below.

In another embodiment of the invention, several of the engineered enzymes possess sulfotransferase activity, in which the enzyme catalyzes the transfer of a sulfo group from an aryl sulfate compound to a sulfo group acceptor. In another embodiment, the sulfo group acceptor is a polysaccharide, particularly a heparosan-based polysaccharide. Without being limited by a particular theory, it is believed that sulfotransferase enzymes that recognize polysaccharides as sulfo group acceptors, but also bind and react with aryl sulfate compounds as sulfo donors, have neither been observed in nature nor described previously. Those skilled in the art will appreciate that the engineered aryl sulfate-dependent sulfotransferase enzymes of the present invention have several advantages over in vitro and in vivo reaction mechanisms that are unable to bind and react with aryl sulfate compounds in order to catalyze sulfo transfer.

It should be understood that while reference is made to exemplary embodiments and specific language is used to describe them, no limitation of the scope of the invention is intended. Further modifications of the methods described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such. Headings are provided for convenience only and are not to be construed to limit the invention in any way. Additionally, throughout the specification and claims, a given chemical formula or name shall encompass all optical isomers and stereoisomers, as well as racemic mixtures where such isomers and mixtures exist.

Aryl Sulfate-Dependent Sulfatases

In an embodiment of the invention, several of the engineered enzymes disclosed herein have sulfatase activity, and are capable of hydrolyzing the sulfate ester within an aryl sulfate compound (see Recksiek, et al., (1998) *J. Biol. Chem.* 273 (11):6096-6103, the disclosure of which is incorporated by reference in its entirety). Upon binding with an aryl sulfate compound in an aqueous solution, engineered enzymes having sulfatase activity can catalyze the hydrolysis of the aryl sulfate compound to produce an aromatic compound and a sulfate ion. Non-limiting examples of aryl sulfate compounds include p-nitrophenyl sulfate (PNS), 4-methylumbelliferyl sulfate, 7-hydroxycoumarin sulfate, phenyl sulfate, 4-acetylphenyl sulfate, indoxyl sulfate, 1-naphthyl sulfate, 2-naphthyl sulfate (2NapS), and 4-nitrocatechol sulfate (NCS). As a non-limiting example and as illustrated in FIG. 1, when the aryl sulfate compound is PNS, the products are p-nitrophenol and a sulfate ion. In reactions conducted at a pH greater than the pKa of p-nitrophenol, the aromatic product is the p-nitrophenolate ion.

Figure 2:
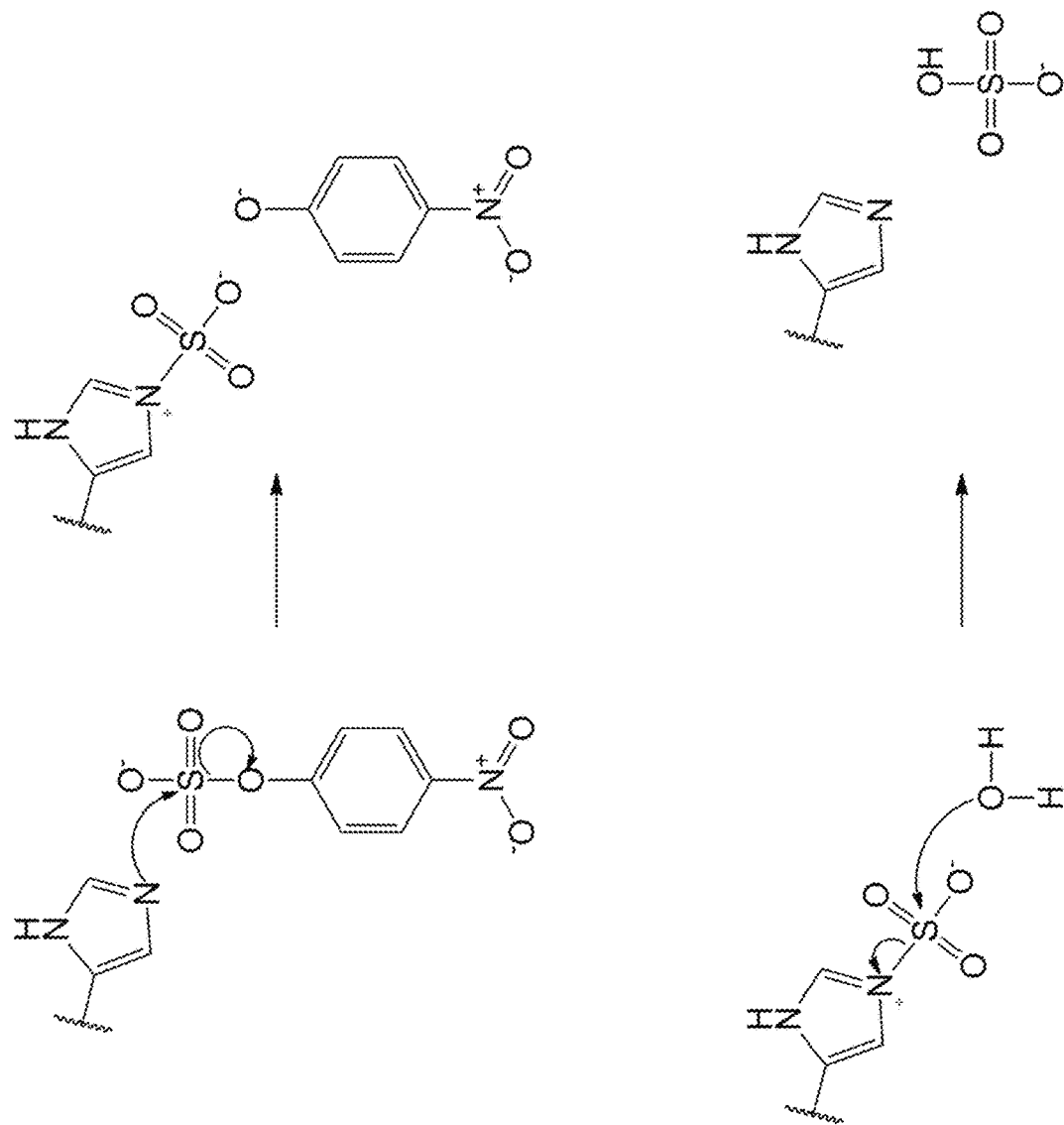
FIG. 2 shows a theoretical reaction mechanism for the hydrolysis of the sulfate ester linkage and formation of a sulfohistidine intermediate.

Without being limited by any particular theory, the hydrolysis of the sulfate ester catalyzed by an engineered enzyme of the present invention can occur upon binding of an aryl sulfate compound within the active site of the enzyme. As illustrated in FIG. 2, the lone pair of the basic nitrogen atom within the imidazole ring of an active site histidine residue initiates a nucleophilic attack of the sulfur atom within PNS, causing hydrolysis of the adjacent C-O bond and formation of a sulfohistidine intermediate. In a second step, the sulfohistidine intermediate itself can be nucleophilically attacked by a water molecule within the active site to cause a release of the sulfo group from the histidine side chain and restore the enzyme to its pre-reaction state.

Proceeding through a reaction mechanism that utilizes a histidine residue within the active site to hydrolyze the sulfate ester creates a unique niche for the engineered enzymes of the present invention relative to other known sulfatases. In nature, sulfatases comprise a class of enzymes (EC 3.1.5.6) that are highly conserved sequentially, structurally, and mechanistically across both prokaryotic and eukaryotic species, having functions such as cell development and detoxification, sulfur scavenging, degradation of compounds, and osmoprotection. Such similarities among natural sulfatases include a highly conserved N-terminal sequence region containing consensus sequence motifs, as well as unique, post-translationally modified active-site aldehyde residue, α-formylglycine, which is necessary for natural sulfatase activity (see Hanson, S. R., et al., (2004) *Agnew. Chem. Int. Ed.* 43:5736-5763, the disclosure of which is incorporated by reference in its entirety). Additionally, natural sulfatases are typically large proteins that often comprise more than 500 amino acid residues, including up to about 800 amino acid residues for some eukaryotic sulfatases.

Without being limited by a particular theory, it is believed that all known natural hydrolytic sulfatases contain two highly homologous amino acid motifs that have been previously identified as sulfatase signature sequences I and II, both of which are found in the N-terminal sequence region (see Hanson, S. R., et al., above). Signature sequence I comprises the amino acids C/S-X-P-S/X-R-X-X-X-L/X-T/X-G/X-R/X, whereas signature sequence II comprises the amino acids G-Y/V-X-S/T-X-X-X-G-K-X-X-H (SEQ ID NO: 272). Both signature sequences play a vital role in the natural sulfatase enzyme activity. Signature sequence I is necessary for directing the post-translational modification of the active site to contain an α-formylglycine residue (described in further detail below) and signature sequence II contains important binding contacts that are important for optimizing sulfate ester catalysis within the α-formylglycine-containing active site.

In particular, the presence of α-formylglycine within the active site is the most salient feature within natural sulfatases, having been found in every characterized prokaryotic and eukaryotic sulfatase to date (see Uhlhorn-Dierls, G., et al., (1998) *Agnew. Chem.* 37:2453, and Uhlhorn-Dierls, G., et al., (1998) *Agnew. Chem.* 110:2591, the disclosures of which are incorporated by reference in their entireties). α-formylglycine residues can be formed from cysteine (most common) or serine residues within the active site, the modification of which has been determined to be directed by signature sequence I.

Figure 3A:
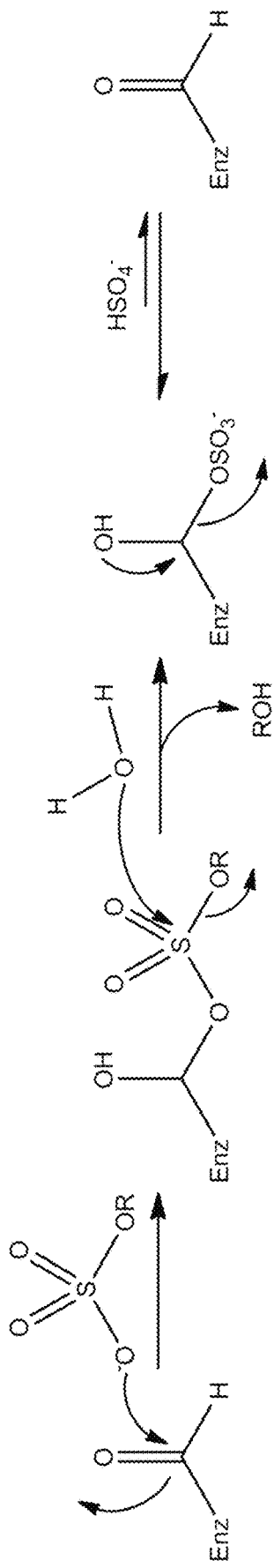
FIG. 3A and FIG. 3B show two proposed reaction mechanisms for natural sulfatase enzymes, catalyzed using an α-formylglycine residue.

Based on the crystal structures of several natural sulfatases, two reaction mechanisms that prominently utilize the α-formylglycine residue for catalysis have been proposed. A first mechanism, illustrated in FIG. 3A, has been proposed in which the α-formylglycine residue, in its aldehyde form, is nucleophilically attacked by one of the sulfate group oxygen atoms within the substrate to form a sulfate diester. The alcohol conjugate is then released through the action of a nucleophile, such as an activated water molecule to form a sulfate hemiacetal. Subsequent attack by the alcohol of the nucleophilic center within the sulfate hemiacetal causes the release of the sulfate molecule from the active site, regenerating the enzyme for future catalysis. A second mechanism, illustrated in FIG. 3B, the α-formylglycine in its hydrated form can nucleophilically attack the sulfate atom via an $S_N^2$ reaction to form the sulfate hemiacetal, and ultimately release the sulfate group from the active site, similar to the mechanism in FIG. 3A. Subsequent addition of water rehydrates the a-formylglycine aldehyde to reform the hydrated α-formylglycine residue.

However, and in another embodiment, the engineered enzymes of the present invention can be synthesized without signature sequence I, signature sequence IL, and/or any α-formylglycine residues being present. In another embodiment, an enzyme that does not contain signature sequence I, signature sequence IL, and/or any α-formylglycine residues, and which has been shown to have sulfatase activity (see the Examples, below) can be selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151. In another embodiment, an engineered enzyme having sulfatase activity can comprise an amino acid sequence that is substantially identical, or is a biological equivalent, to the amino acid sequence of any of the above polypeptides having sulfatase activity, as defined in the "Nucleic Acid and Polypeptide Preparation" section, below.

Accordingly, in another embodiment, the invention provides a method for enzymatically hydrolyzing an aryl sulfate compound, comprising the steps of: providing an aryl sulfate compound; providing an engineered enzyme having an active site configured to bind with an aryl sulfate compound and a polysaccharide, preferably a heparosan-based polysaccharide; combining the aryl sulfate compound and the engineered enzyme into a reaction mixture; and catalyzing the hydrolysis of the aryl sulfate compound using the engineered enzyme. In another embodiment, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In another embodiment, the aryl sulfate compound is PNS. In another embodiment, the aryl sulfate compound is NCS. In another embodiment, the aryl sulfate compound is 2NapS. In another embodiment, hydrolysis of the aryl sulfate compound proceeds by a mechanism comprising the nucleophilic attack of the sulfur atom within the aryl sulfate compound, causing hydrolysis of the adjacent C—O bond and formation of a sulfohistidine intermediate. In another embodiment, the nucleophilic attack is initiated by a histidine residue.

Aryl Sulfate-Dependent Sulfotransferases

In another embodiment, and as described above, several of the engineered enzymes of the present invention have sulfotransferase activity with aryl sulfate compounds as sulfo group donors. In another embodiment, the sulfo group donor is a polysaccharide, preferably a heparosan-based polysaccharide. In each sulfotransfer reaction, the aryl sulfate compound participates as a sulfo group donor, while the polysaccharide participates as a sulfo group acceptor. Sulfotransferase enzymes that recognize polysaccharides as sulfo group acceptors, but also bind and react with aryl sulfate compounds as sulfo group donors, have neither been observed in nature nor described previously.

One particular polysaccharide, heparosan, is a starting material in the synthesis of a multitude of sulfated polysaccharides in vivo, particularly within eukaryotic organisms. Typically, heparosan is synthesized as a glycosaminoglycan (GAG) by the organism within the Golgi apparatus, and comprises repeating co-polymers of [β(1,4)GlcA-α(1,4) GlcNAc]n disaccharide units, in which GlcA is glucuronic acid and GlcNAc is N-acetyl glucosamine. Heparosan GAGs can then be modified, particularly by one or more heparan sulfate (HS)-sulfotransferase enzymes, to form functionalized heparosan-based polysaccharide products, particularly HS and heparin. Such modifications to heparosan includes N-deacetylation and N-sulfation of glucosamine, $C_5$-epimerization of glucuronic acid to form iduronic acid, 2-O-sulfation of iduronic and/or glucuronic acid, as well as 6-O-sulfation and 3-O-sulfation of glucosamine residues. The natural sulfotransferases that catalyze N-acetylation and N-sulfation, 2-O-sulfation, 6-O-sulfation, and 3-O-sulfation of heparosan and heparosan-based polysaccharides in vivo exclusively recognize and bind with PAPS as the sulfo group donor. Without being limited by a particular theory, it is believed that none of the four natural HS sulfotransferase enzymes—NDST, 2OST, 6OST, and 3OST—are active with any aryl sulfate compounds as a sulfo group donor.

Figure 4A:
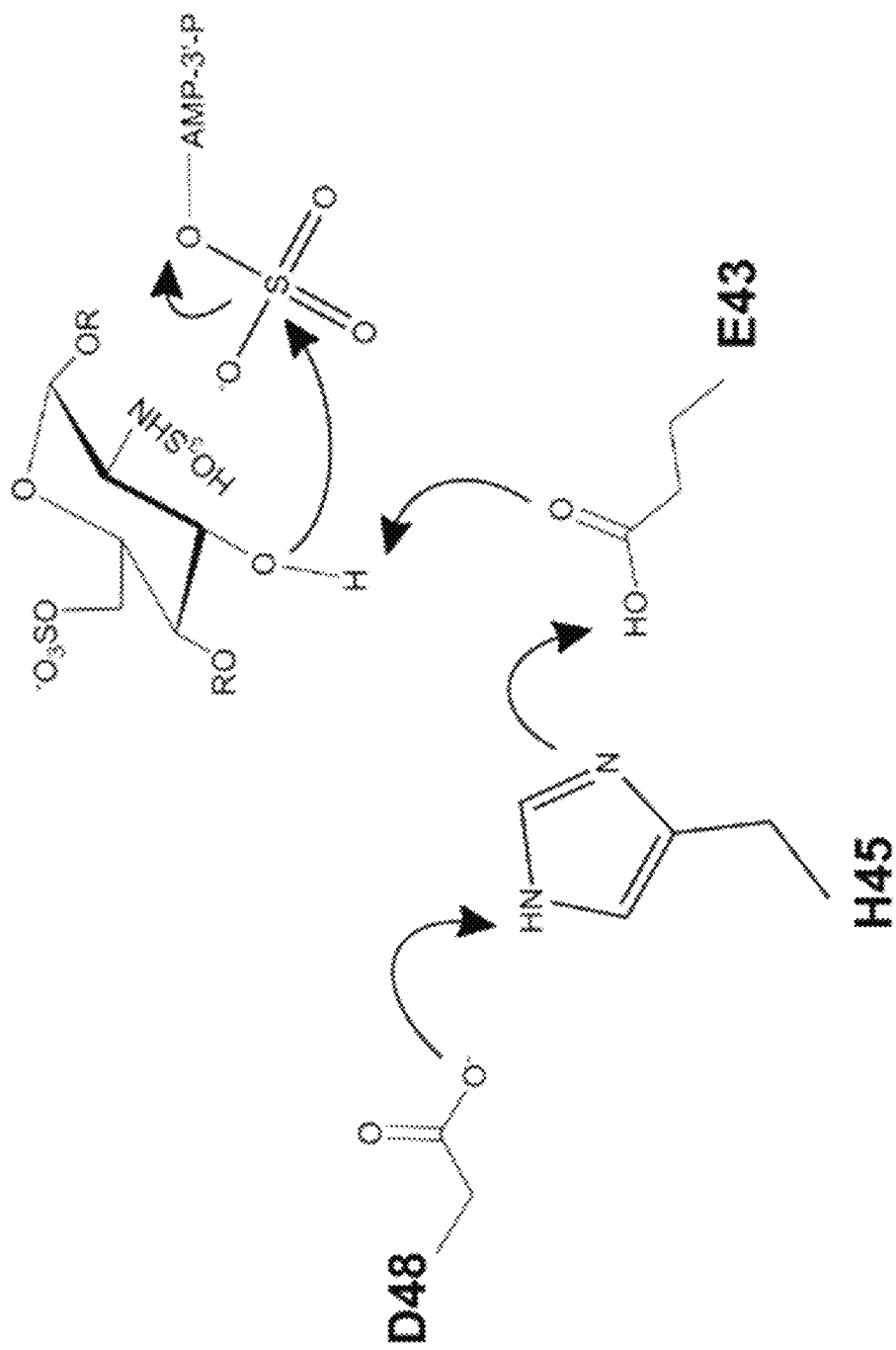
FIG. 4A, FIG. 4B, and FIG. 4C show a proposed reaction mechanism, transition state, and products formed as a result of a sulfotransfer reaction between the natural human 3OST enzyme, PAPS, and a heparosan-based polysaccharide.
Figure 4B:
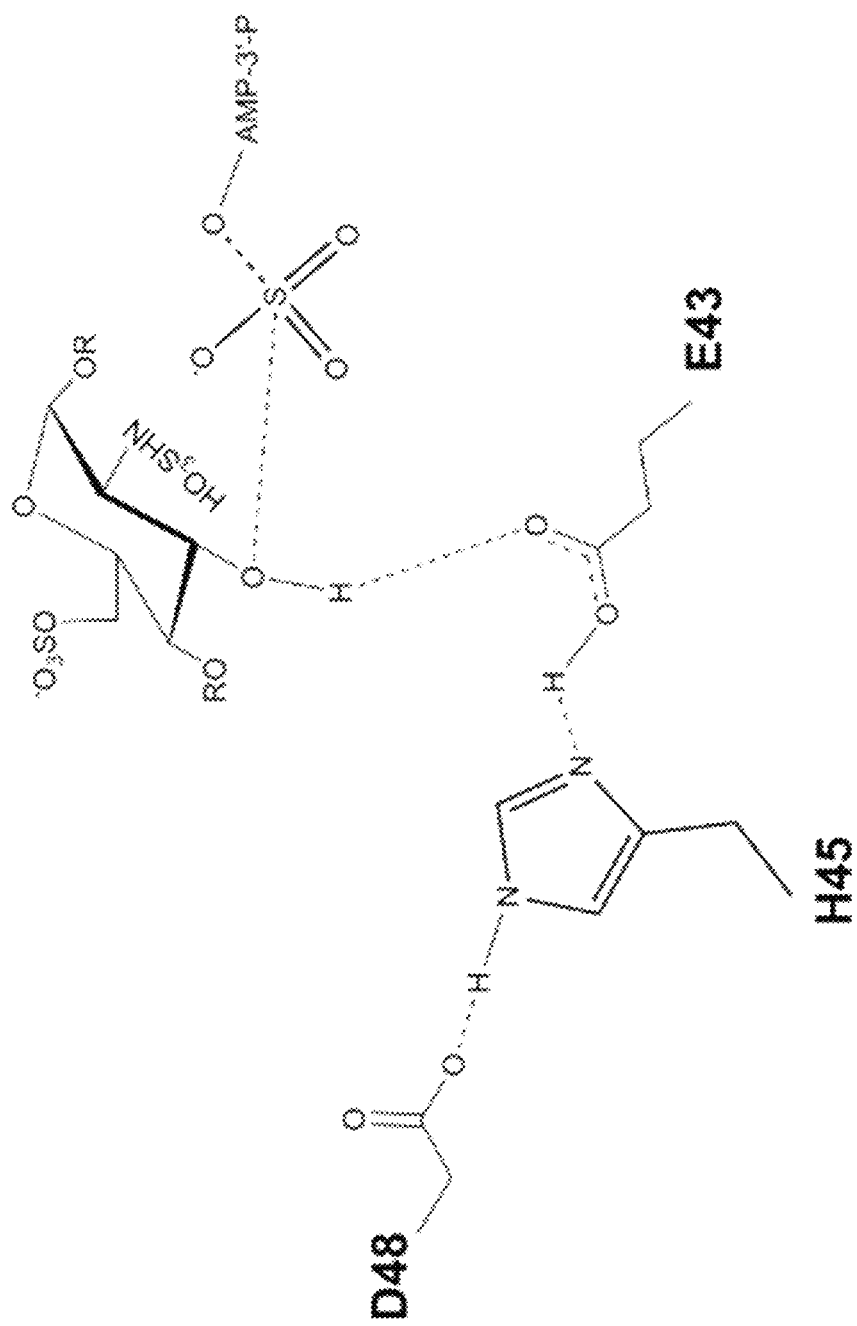
Figure 4C:
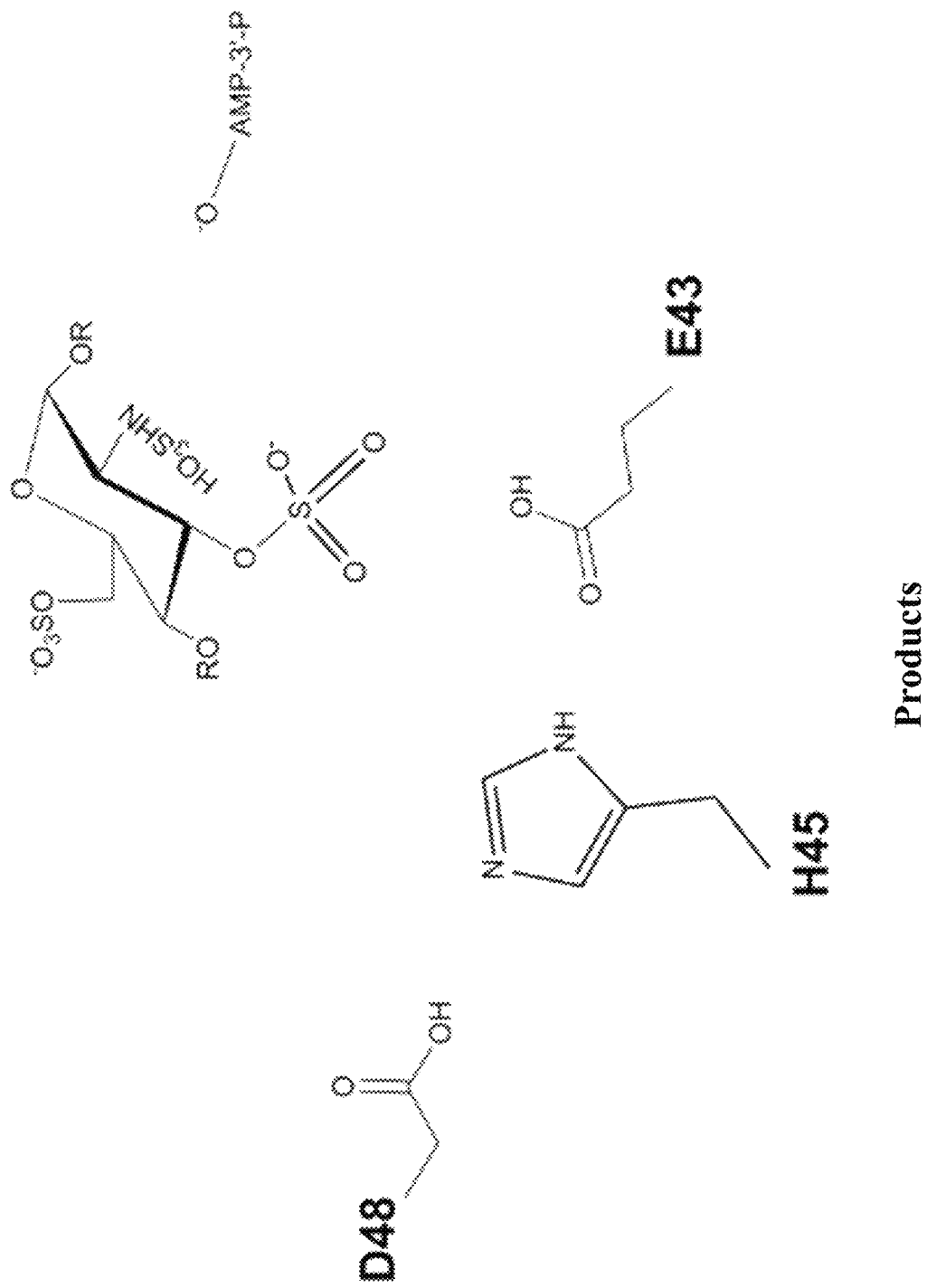

Each of the four natural HS sulfotransferase enzymes generally catalyze the direct transfer of a sulfo group from PAPS to a heparosan-based polysaccharide in a single step. An example of a typical sulfotransfer reaction mechanism catalyzed by an HS sulfotransferase enzyme is illustrated in FIG. 4A, FIG. 4B, and FIG. 4C, which collectively show a proposed mechanism, transition state, and products formed in a reaction between the human 3OST enzyme, PAPS, and a heparosan-based polysaccharide. In particular, the glutamic acid residue at position 43 abstracts the proton from the 3-O position of an N-, 6-O sulfated sulfoglucosamine residue within the heparosan-based polysaccharide, enabling the nucleophilic attack and removal of the sulfo group from PAPS, whereas His-45 and Asp-48 coordinate to stabilize the transition state of the enzyme before the sulfated polysaccharide product is released from the active site.

However, although PAPS is the exclusive sulfo donor in eukaryotes, it has a short half-life and can readily decompose into adenosine 3',5'-diphosphate, which acts as a competitive inhibitor during sulfotransfer reactions. Animals can efficiently utilize PAPS because they can metabolize adenosine 3',5'-diphosphate to prevent competitive inhibition and also replenish PAPS for each sulfotransfer reaction, as needed. On the other hand, aryl sulfate compounds, which can be utilized as sulfo donors in a limited number of bacterial systems (see Malojcic, G., et al., above), cannot react with any of the known native sulfotransferase enzymes in eukaryotes, including those that are involved in synthesizing HS and other heparosan-based polysaccharides in vivo. Without being limited by a particular theory, it is believed that the binding pockets for PAPS within the active sites of eukaryotic sulfotransferases either do not have a high enough affinity for aryl sulfate compounds to facilitate binding, and/or that the aryl sulfate compounds are sterically hindered from entering the active site at all.

Heparin, HS, and other heparosan-based polysaccharides play critical roles in a variety of important biological processes in vivo, including assisting viral infection, regulating blood coagulation and embryonic development, suppressing tumor growth, and controlling the eating behavior of test subjects by interacting with specific regulatory proteins. Depending on their role, heparosan polysaccharides can contain one or more unique patterns or motifs recognized by specific protein(s) involved in the particular biological process. In particular, heparin and other heparan sulfate polysaccharides, as well as routes to synthesizing such polysaccharides in vitro, are topics of extreme interest within the pharmaceutical industry.

The present disclosure includes engineered sulfotransferase enzymes, described in further detail below, which have activity with aryl sulfate compounds as sulfo group donors and heparosan-based polysaccharides as sulfo group acceptors. Each of the engineered sulfotransferase enzymes is designed to be a mutant of a corresponding natural HS sulfotransferase: glucosaminyl N-deacetylase/N-sulfotransferase (NDST) (via its N-sulfotransferase (NST) domain), hexuronyl 2-O sulfotransferase (2OST), glucosaminyl 6-O sulfotransferase (6OST), and glucosaminyl 3-O sulfotransferase (3OST). In each instance, the engineered sulfotransferase enzyme has activity with one or more aryl sulfate compounds (instead of PAPS) as a sulfo group donor, but retains the affinity of the native HS-sulfotransferase enzyme for a particular heparosan-based polysaccharide as a sulfo group acceptor. As a non-limiting example, an engineered 2OST enzyme has sulfotransferase activity with an aryl sulfate compound as a sulfo group donor and N-sulfated heparosan as a sulfo group acceptor. In contrast, natural 2OST enzymes have sulfotransferase activity with PAPS as the sole sulfo group donor and N-sulfated heparosan as a sulfo group acceptor. Each of the engineered sulfotransferase enzymes, including their sequences, structures, and biological activities, are described in further detail below. Methods of synthesizing sulfated heparosan-based polysaccharides in vitro using an engineered sulfotransferase enzyme and an aryl sulfate compound are also described below. In some embodiments of the invention, HS polysaccharides having anticoagulant activity, including those having anticoagulant activity similar or equivalent to heparin, can be synthesized in vitro.

Engineered NSTs

In nature, HS NDST enzymes have dual N-deacetylase and N-sulfotransferase activity, in which the same enzyme first catalyzes the removal of an N-acetyl group from a glucosamine residue within heparosan, and then catalyzes the transfer of a sulfo group from PAPS to the same glucosamine residue that was N-deacetylated in the first step. The dual N-deacetylase and N-sulfotransferase activity of the enzymes is achieved via two separate structural domains—an N-deacetylase domain and an N-sulfotransferase domain. However, the activity of one of the domains is not a pre-requisite for the activity of the other domain, and recombinant single-domain enzymes comprising either N-deacetylase or N-sulfotransferase activity can be expressed and purified. Similarly, and in an embodiment of the invention, engineered enzymes with NST activity can be expressed and purified as a single N-sulfotransferase domain, without additionally comprising an N-deacetylase domain.

Naturally-occurring NDST enzymes that utilize PAPS as the sulfo group donor are members of the EC 2.8.2.8 enzyme class. Generally, the N-deacetylase domain of an NDST enzyme can deacetylate one or more of the N-acetyl glucosamine residues within heparosan to form N-deacetylated heparosan, which can then be recognized as a sulfo group acceptor by the enzyme's N-sulfotransferase domain. However, the N-sulfotransferase domains of NDST enzymes have been shown to have sulfotransferase activity with N-deacetylated heparosan having one or more disaccharide units comprising the structure of Formula II, below:

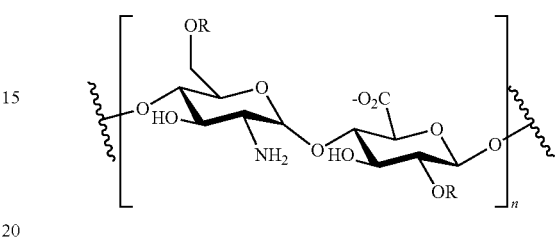

wherein n is an integer and R is selected from the group consisting of a hydrogen atom or a sulfo group. Further, although the portion of the N-deacetylated heparosan that reacts with the enzyme comprises the structure of Formula II, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Typically, N-deacetylated heparosan and other heparosan-based polysaccharides comprising the structure of Formula II comprise at least four disaccharide units, or at least eight sugar residues total. Sulfotransfer reactions in which N-deacetylated heparosan is utilized as the sulfo group acceptor for NDST enzymes are discussed in Sheng, J., et al., (2011) *J. Biol. Chem.* 286 (22):19768-76, as well as Gesteira, T. F., et al., (2013)*PLoS One* 8 (8):e70880, the disclosures of which are incorporated by reference in their entireties.

Upon successfully binding PAPS and N-deacetylated heparosan, the N-sulfotransferase domain of natural NDST enzymes can catalyze transfer of the sulfo group to an unsubstituted glucosamine residue, forming an N-sulfated heparosan product comprising the structure of Formula III, below:

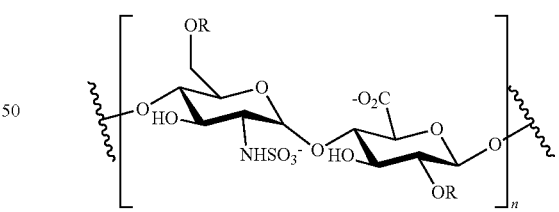

wherein n is an integer and R is selected from the group consisting of a hydrogen atom or a sulfo group.

Figure 5:
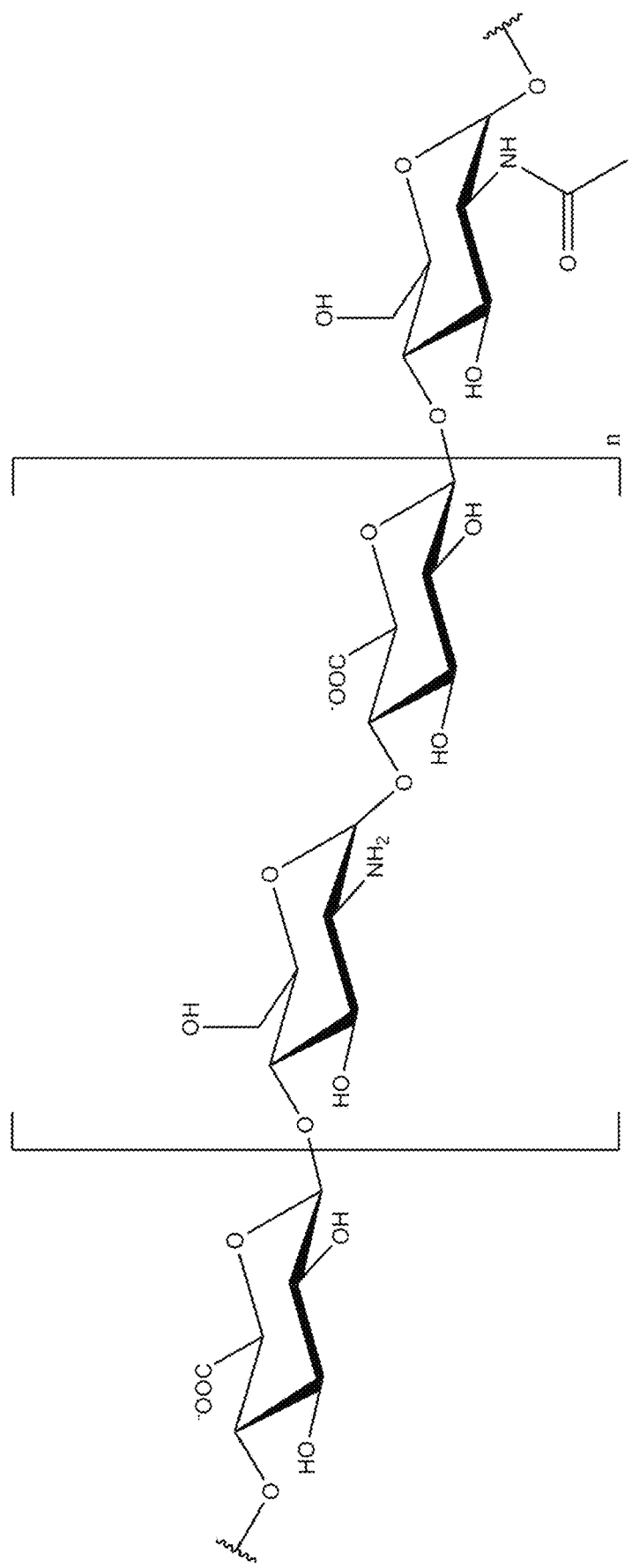
FIG. 5 shows a non-limiting example of a heparosan-based polysaccharide that can be used as a sulfo group acceptor with engineered NST enzymes of the present invention.

In another embodiment, each of the repeating disaccharide units within the N-deacetylated heparosan comprises the structure of Formula II. In another embodiment, both of the R groups at the 6-O position of the glucosaminyl residues and the 2-O position of the glucuronic acid residues are hydrogen atoms, in one or more, including all, of the disaccharide units within the polysaccharide. In another embodiment, in some locations within the polysaccharide, at least a portion of the glucosamine residues are still N-acetylated, as shown in FIG. 5, although glucosaminyl residues within the polymer that are N-acetylated cannot directly participate as sulfo group acceptors with the engineered sulfotransferases of the present invention. However, the presence of N-acetylated residues within the polysaccharide does not affect the binding affinity that the engineered sulfotransferases have for non-acetylated glucosamine residues within the same polysaccharide. In another embodiment, regardless of the structure of the heparosan-based polysaccharide, a disaccharide unit comprising the structure of Formula II can be recognized as a sulfo acceptor by an engineered NST enzyme and an aryl sulfate compound to generated an N-sulfated product comprising the structure of Formula III.

In another embodiment, when there are multiple disaccharide units within the N-deacetylated heparosan that comprise the structure of Formula II, the glucosamine residue within any of those disaccharide units can be N-sulfated. Similarly, and in another embodiment, within a polysaccharide comprising multiple disaccharide units having the structure of Formula II, a plurality of glucosamine residues can be N-sulfated, including and up to all of the available glucosamine residues within the polysaccharide.

The N-sulfotransferase domains of natural NDST enzymes typically comprise approximately 300 to 350 amino acid residues that can vary greatly in their sequence, yet ultimately have the exact same function, namely, to catalyze the N-sulfation of unsubstituted glucosamine residues within N-deacetylated heparosan. Without being limited by a particular theory, it is believed that each of the natural NDST enzymes can catalyze the same chemical reaction because there are multiple amino acid sequence motifs and secondary structures that are either identical or highly conserved across all species.

Figure 6A:
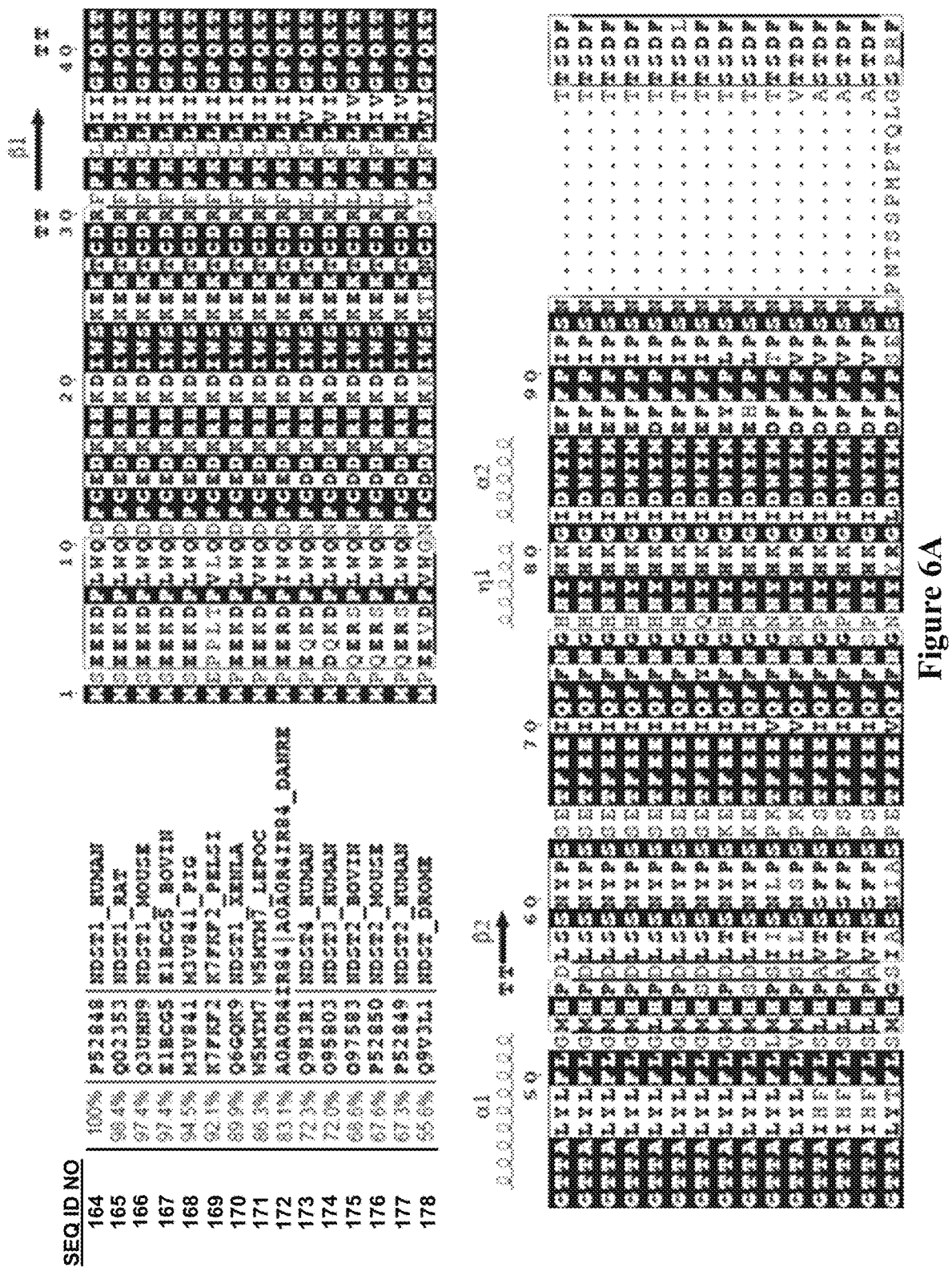
Figure 6B:
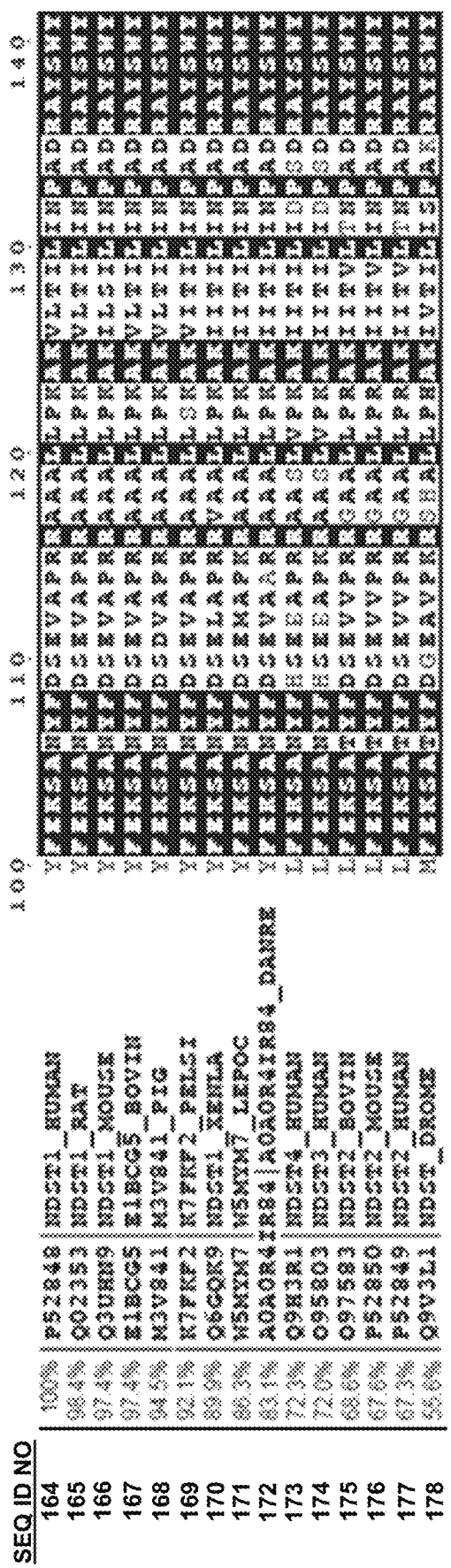
Figure 6B:
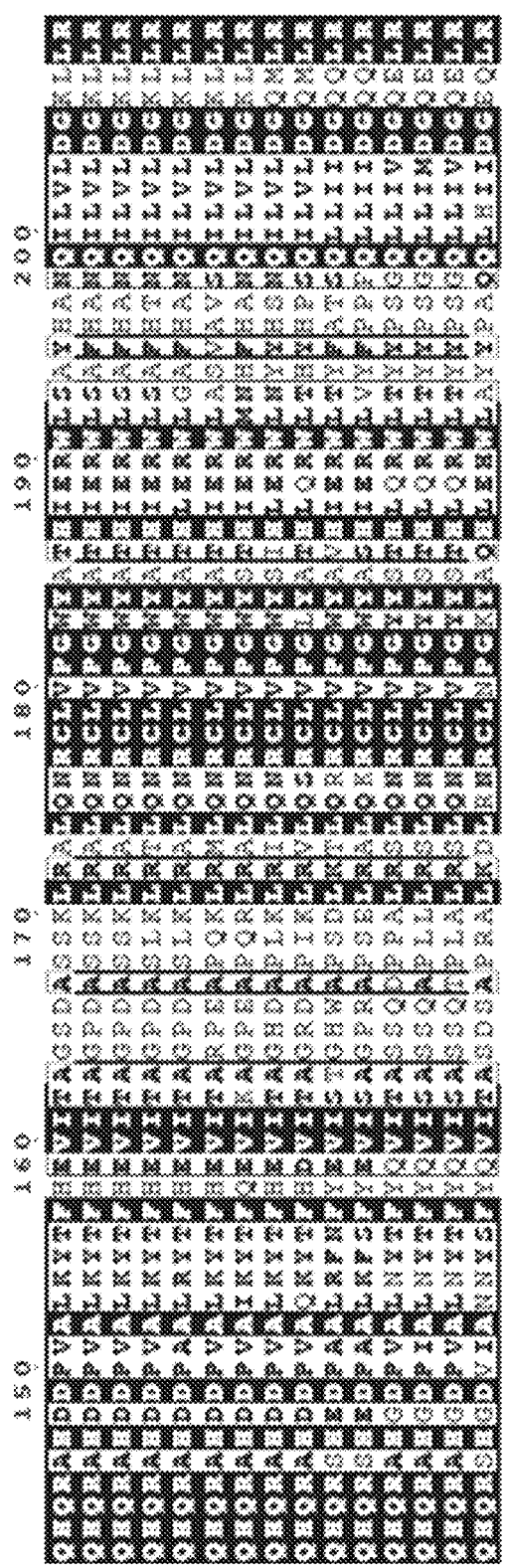
Figure 6C:
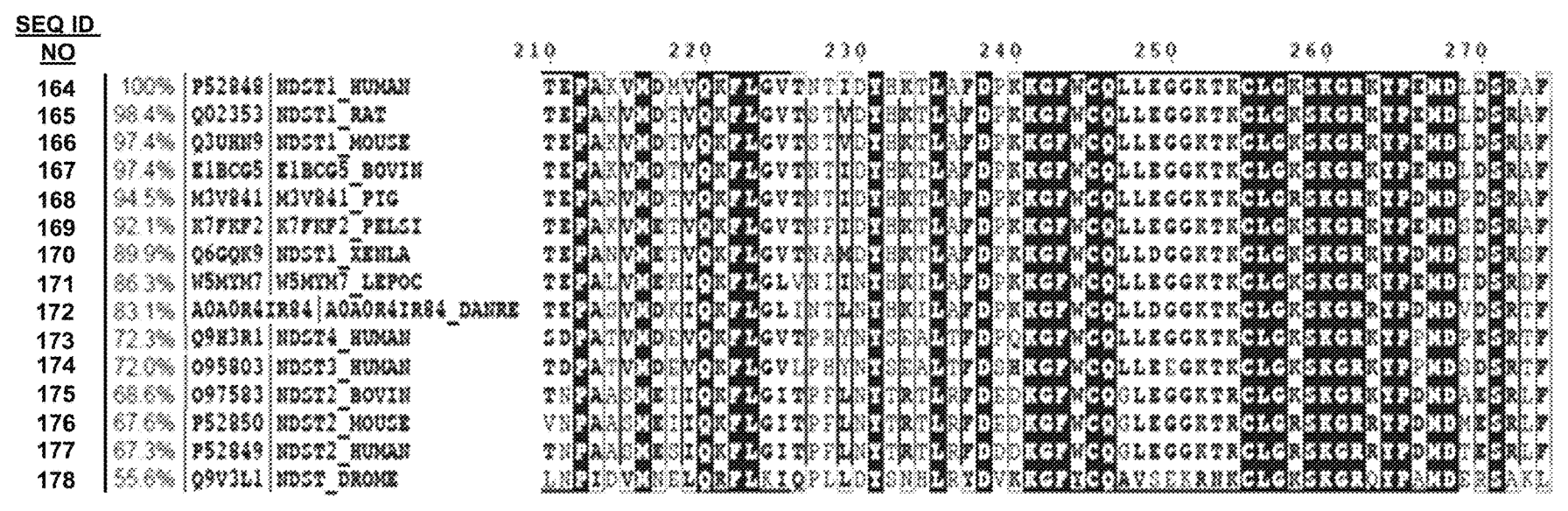

Further, it is believed that several of the conserved amino acid sequence motifs within the natural N-sulfotransferase domains are directly involved in binding of either PAPS and/or the polysaccharide, or participate in the chemical reaction itself. The identity of conserved amino acid sequence motifs can be demonstrated by comparing the amino acid sequence of the N-sulfotransferase domain (SEQ ID NO: 164) of the human NDST enzyme, which has a known crystal structure (PDB code: 1NST) in which amino acid residues within the active site have been identified, alongside the amino acid sequences of the N-sulfotransferase domains of other natural NDST enzymes. A multiple sequence alignment of the amino acid sequences of the N-sulfotransferase domains of fifteen NDST enzymes, including several eukaryotic organisms and several isoforms of the human NDST enzyme, is shown in FIG. 6A, FIG. 6B, and FIG. 6C, along with percent identity relative to the N-sulfotransferase domain of human NDST1 (UniProtKB Accession No. P52848). As illustrated in FIG. 6A, FIG. 6B, and FIG. 6C, each amino acid sequence, corresponding to SEQ ID NOs: 164-178, ranges from having 98.4% sequence identity with the P52848 reference sequence (SEQ ID NO: 165, entry sp|Q02353|NDST1_RAT) for the rat N-sulfotransferase domain down to 55.6% sequence identity (SEQ ID NO: 178, entry sp|Q9V3L1|NDST_DROME) for the fruit fly N-sulfotransferase domain. Those skilled in the art would appreciate that the multiple sequence alignment was limited to fifteen sequences for clarity, and that there are hundreds of amino acid sequences encoding for the N-sulfotransferase domains of other wild-type NDST enzymes that have been identified and that have highly conserved active site and/or binding regions as well.

Within FIG. 6A, FIG. 6B, and FIG. 6C, amino acids that are depicted in white with a black background at a particular position, are 100% identical across all sequences. Amino acids that are highly conserved at a particular position, meaning that the amino acids are either identical or chemically or structurally similar, are enclosed with a black outline. Within highly conserved regions, consensus amino acids that are present in a majority of the sequences are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the N-sulfotransferase domain of the human NDST1 enzyme as a reference. The β symbol adjacent to an arrow refers to a β-sheet, whereas a coil adjacent to an α symbol or a η symbol refers to a helix secondary structure.

Within the fifteen aligned sequences in FIG. 6A, FIG. 6B, and FIG. 6C, there are several conserved amino acid motifs that include one or more amino acids that comprise the active site, based on the crystal structure of the N-sulfotransferase domain of human NDST1. These conserved amino acid sequence motifs, based on the numbering of the amino acid residues within FIG. 6A, FIG. 6B, and FIG. 6C include residues 40-46 (Q-K-T-G-T-T-A); residues 66-69 (T-F-E-E); residues 101-105 (F-E-K-S-A); residues 139-143 (S-W-Y-Q-H); and residues 255-262 (C-L-G-K/R-S-K-G-R) which correspond to SEQ ID NO: 221, SEQ ID NO: 222, SEQ ID NO: 223, SEQ ID NO: 224, and SEQ ID NO: 225 in the sequence listing, respectively. In further embodiments, some NDST enzymes that comprise the conserved amino acid sequence motif Q-K-T-G-T-T-A (SEQ ID NO: 221) further comprise the conserved amino acids L-Y-L, from residues 47-49.

Figure 7A:
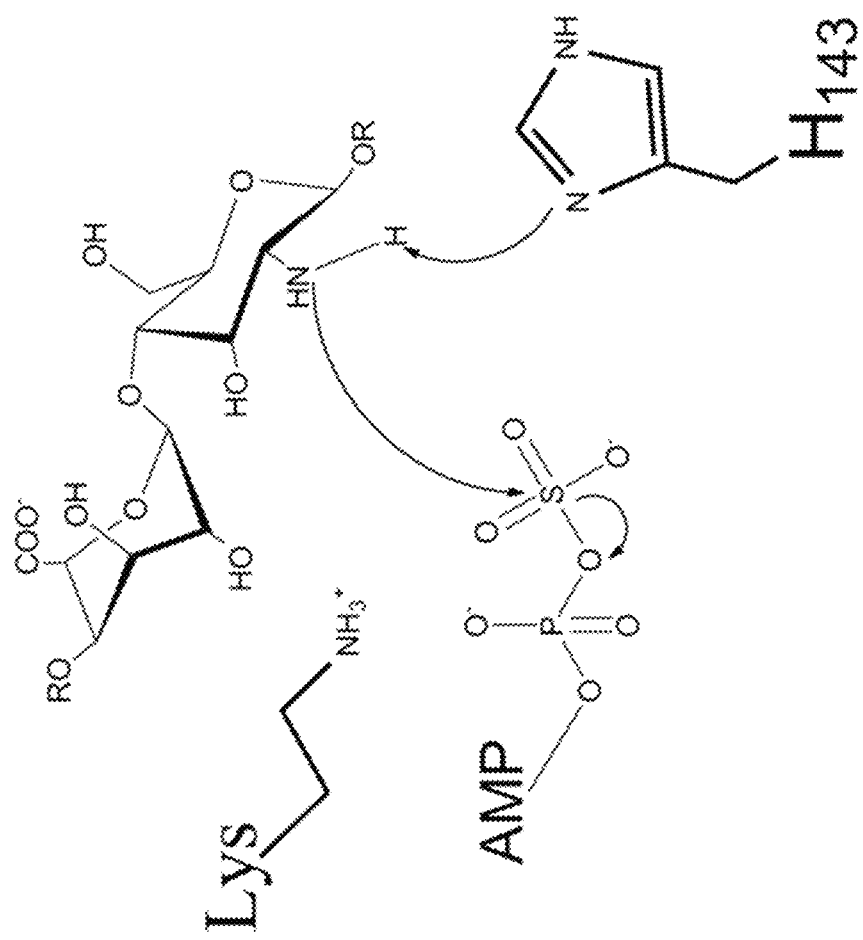
FIG. 7A, FIG. 7B, and FIG. 7C show a proposed reaction mechanism, transition state, and products formed as a result of a sulfotransfer reaction between a natural NDST enzyme, PAPS, and N-deacetylated heparosan.
Figure 7B:
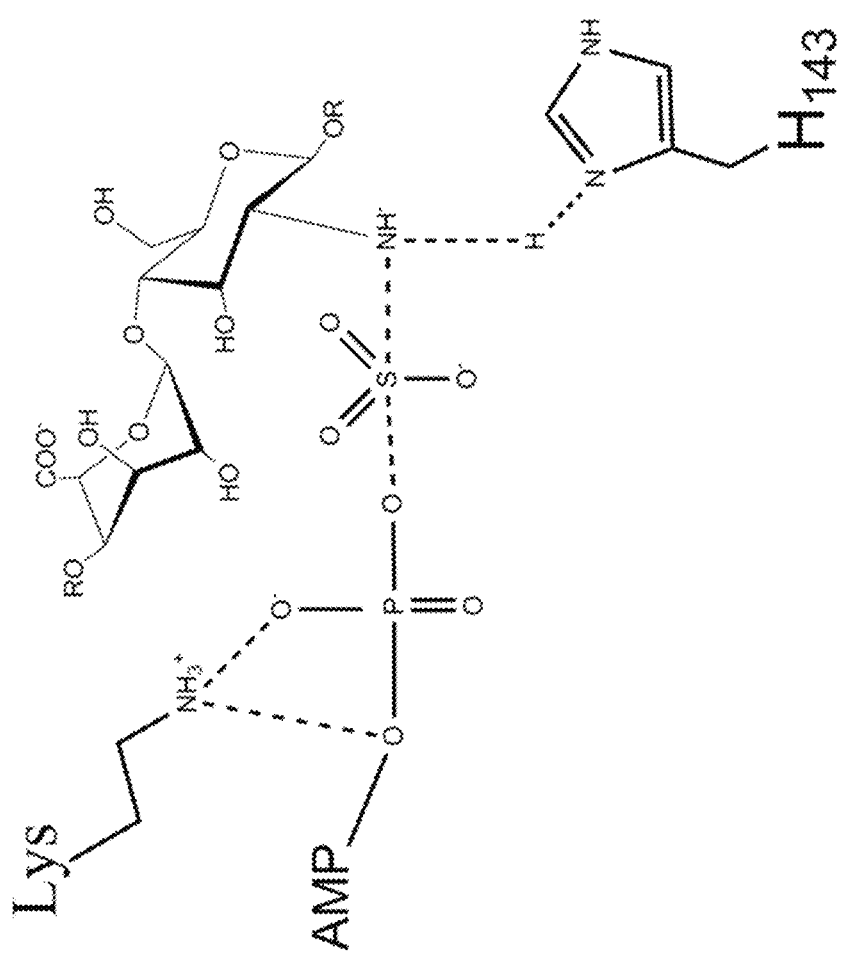
Figure 7C:
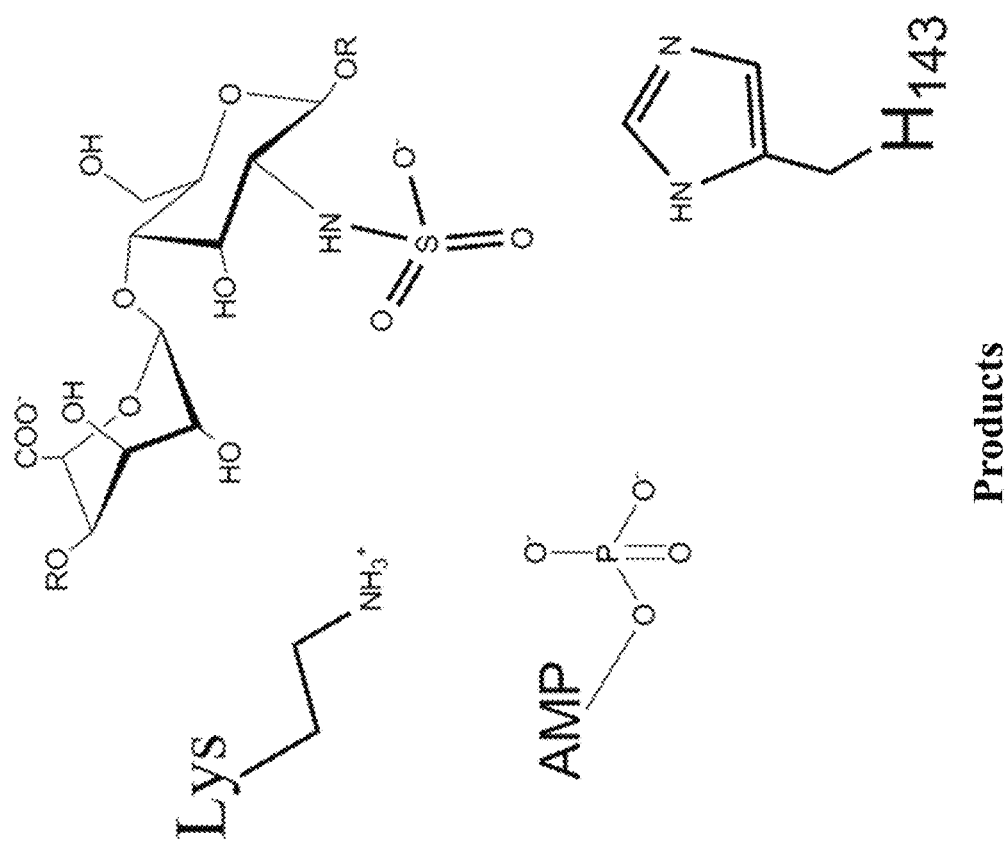

Without being limited by a particular theory, it is believed that these residues either facilitate or participate in the chemical reaction, or enable binding of PAPS or the polysaccharide within the active site. In particular and as illustrated in FIG. 7A, FIG. 7B, and FIG. 7C, the histidine residue at position 143 of the N-sulfotransferase domain (SEQ ID NO: 164) of the human NDST1 enzyme is in position to abstract one of the two protons within the amine functional group of an unsubstituted glucosaminyl residue, enabling the nitrogen atom to initiate the nucleophilic attack of PAPS and remove the sulfate functional group. Additionally, lysine residues at position 41 and 260 are also universally conserved, and are thought to coordinate with the sulfate moiety, driving binding of PAPS within the active site as well as stabilizing the transition state during the course of the reaction (see Gesteira, T. F., et al., above, as well as Sueyoshi, T., et al., (1998) *FEBS Letters* 433:211-214, the disclosure of which is incorporated by reference in its entirety).

However, as described above, natural NDST enzymes are unable to catalyze the transfer of the sulfate group from an aryl sulfate compound to the polysaccharide, because it is believed that the binding pocket for PAPS within the natural active site either does not have a high enough affinity for aryl sulfate compounds to facilitate binding and/or that the aryl sulfate compounds are sterically hindered from entering the active site altogether. Consequently, and in another embodiment, the N-sulfotransferase domain of a natural NDST enzyme can be mutated in several locations to enable binding of the aryl sulfate compound within the active site and/or to optimally position the aryl sulfate compound so transfer of the sulfate group to the polysaccharide can occur.

Accordingly, and in another embodiment, engineered NST enzymes of the present invention can comprise a single N-sulfotransferase domain that is mutated relative to the N-sulfotransferase domain of any of the natural NDST enzymes within EC 2.8.2.8, including enzymes having the amino acid sequences illustrated in FIG. 6A, FIG. 6B, and FIG. 6C. In other embodiments, engineered NST enzymes of the present invention can further comprise an N-deacetylase domain that has an identical or mutated amino acid sequence of the N-deacetylase domain of any of the natural NDST enzymes within EC 2.8.2.8.

In another embodiment, mutations engineered into the amino acid sequences of the engineered NST enzymes facilitate a biological activity in which aryl sulfate compounds can both bind and react with the enzyme as sulfo group donors. In another embodiment, although the engineered NST enzymes can bind and react with an aryl sulfate compound as a sulfo group donor, they retain the natural NDSTs' biological activity with heparosan-based polysaccharides comprising disaccharide units having the structure of Formula II, including but not limited to N-deacetylated heparosan, as a sulfo group acceptor. Without being limited by a particular theory, it is believed that because of the mutations inserted into the amino acid sequences of the engineered NST enzymes, their sulfotransferase activity may comprise the direct transfer of a sulfo group from an aryl sulfate compound to the sulfo acceptor polysaccharide, using a similar mechanism as described in FIGS. 7A-7C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by an N-unsubstituted glucosamine within N-deacetylated heparosan to form the N-sulfated product. By either mechanism, the engineered NST enzymes are able to achieve sulfo transfer from an aryl sulfate compound to a heparosan-based polysaccharide, as described in the examples, below.

In another embodiment, an engineered NST enzyme can comprise one or more mutated amino acid sequence motifs relative to the conserved amino acid sequence motifs, corresponding to SEQ ID NOs 221-225, which are found in the N-sulfotransferase domains of natural NDSTs, as described above and indicated in the multiple sequence alignment in FIG. 6A, FIG. 6B, and FIG. 6C. In another embodiment, each mutated amino acid sequence motif that is present in the amino acid sequence of the engineered NST enzyme comprises at least one amino acid mutation relative to the corresponding conserved amino acid sequence motif within the N-sulfotransferase domains of natural NDST enzymes within EC 2.8.2.8. In another embodiment, an engineered NST enzyme comprises one mutated amino acid sequence motif. In another embodiment, an engineered NST enzyme comprises two mutated amino acid sequence motifs. In another embodiment, an engineered NST enzyme comprises three mutated amino acid sequence motifs. In another embodiment, an engineered NST enzyme comprises four mutated amino acid sequence motifs. In another embodiment, an engineered NST enzyme comprises five mutated amino acid sequence motifs. In another embodiment, an engineered NST enzyme that includes at least one mutated amino acid sequence motif can have an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Figure 8:
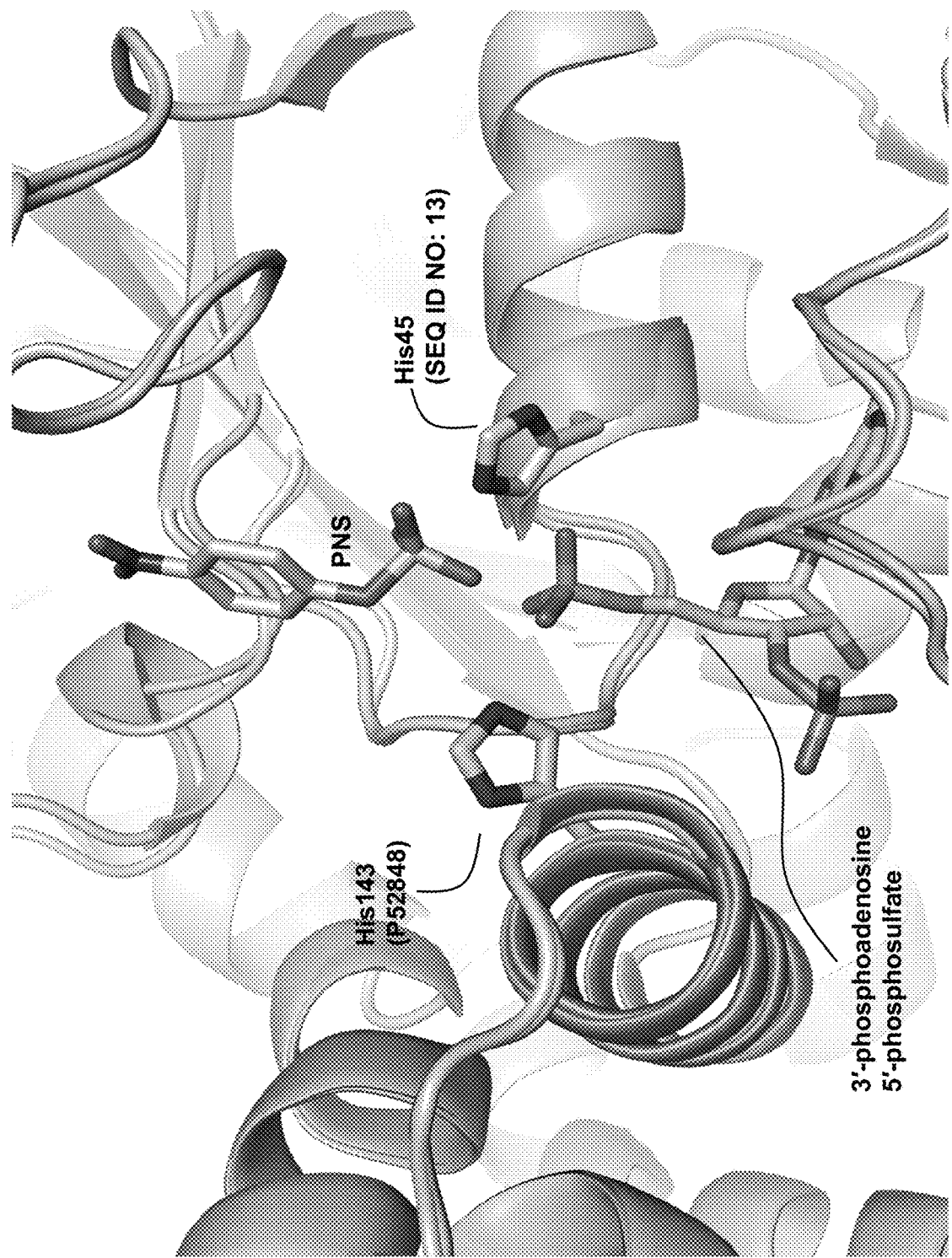
FIG. 8 shows a three-dimensional model of PNS bound within the active site of an engineered NST enzyme, superimposed over the crystal structure of the N-sulfotransferase domain of a natural enzyme from the EC. 2.8.2.8 enzyme class.

In another embodiment, upon viewing the crystal structure of the N-sulfotransferase domain of the human NDST1 (PDB code: 1NST) within a 3D molecular visualization system (including, as a non-limiting example, the open-source software, PyMOL), the structure of related sequences, such as those of engineered NST enzymes that contain one or more amino acid sequence motifs that are mutated relative to the human NDST1 N-sulfotransferase domain (SEQ ID NO: 164), can be modeled for comparison as illustrated in FIGS. 8-11. In one non-limiting example, FIG. 8 shows a magnified view of the active site of the human NDST1 N-sulfotransferase domain that is overlaid with an engineered NST enzyme comprising the amino acid sequence of SEQ ID NO: 13, in which the structure of the engineered enzyme is calculated upon making mutations relative to the human N-sulfotransferase domain amino acid sequence. Adenosine 3',5'-diphosphate, which is the product of a sulfotransfer reaction in which PAPS is the sulfo donor, and which was co-crystallized with the NDST1 N-sulfotransferase domain, is also illustrated within the active site. PNS is also modeled into the engineered enzyme active site, using the consensus solutions of molecular dynamics (MD) simulations that designed to calculate the optimized position and orientation of a ligand within an enzyme active site adjacent to the polysaccharide binding site (not shown), if such solutions are possible.

As illustrated in FIG. 8, although there are several mutations within SEQ ID NO: 13 made relative to sequence of the human NDST1 N-sulfotransferase domain (SEQ ID NO: 164, UniProtKB Accession No. P52848) indicated in FIG. 6A, FIG. 6B, and FIG. 6C, the respective protein backbones are in a nearly identical location to one another, enabling a one-to-one comparison of the active sites. Within the structure of the engineered enzyme comprising the sequence of SEQ ID NO: 13, the consensus solutions from MD simulations indicate that the sulfate moiety within PNS is favored to bind adjacent to a histidine residue, His-45, that has been mutated relative to the natural threonine residue at that position, which is universally conserved within EC 2.8.2.8. On the other hand, within the human NDST1 N-sulfotransferase domain, the adenosine 3',5'-diphosphate is located near to the conserved His-143, described above. Although the sulfo group that would be comprised within the PAPS substrate is not shown, those skilled in the art would appreciate that if PAPS were present, the sulfate group would be oriented in a position immediately adjacent to His-143 and partially overlapping with the sulfate group within PNS. Without being limited by a particular theory, it is believed that the nearly overlapping location of the sulfate groups accounts for the engineered enzyme's ability to facilitate sulfo group transfer by using His-143 as a base to remove the proton from the glucosaminyl residue within the polysaccharide.

Figure 9:
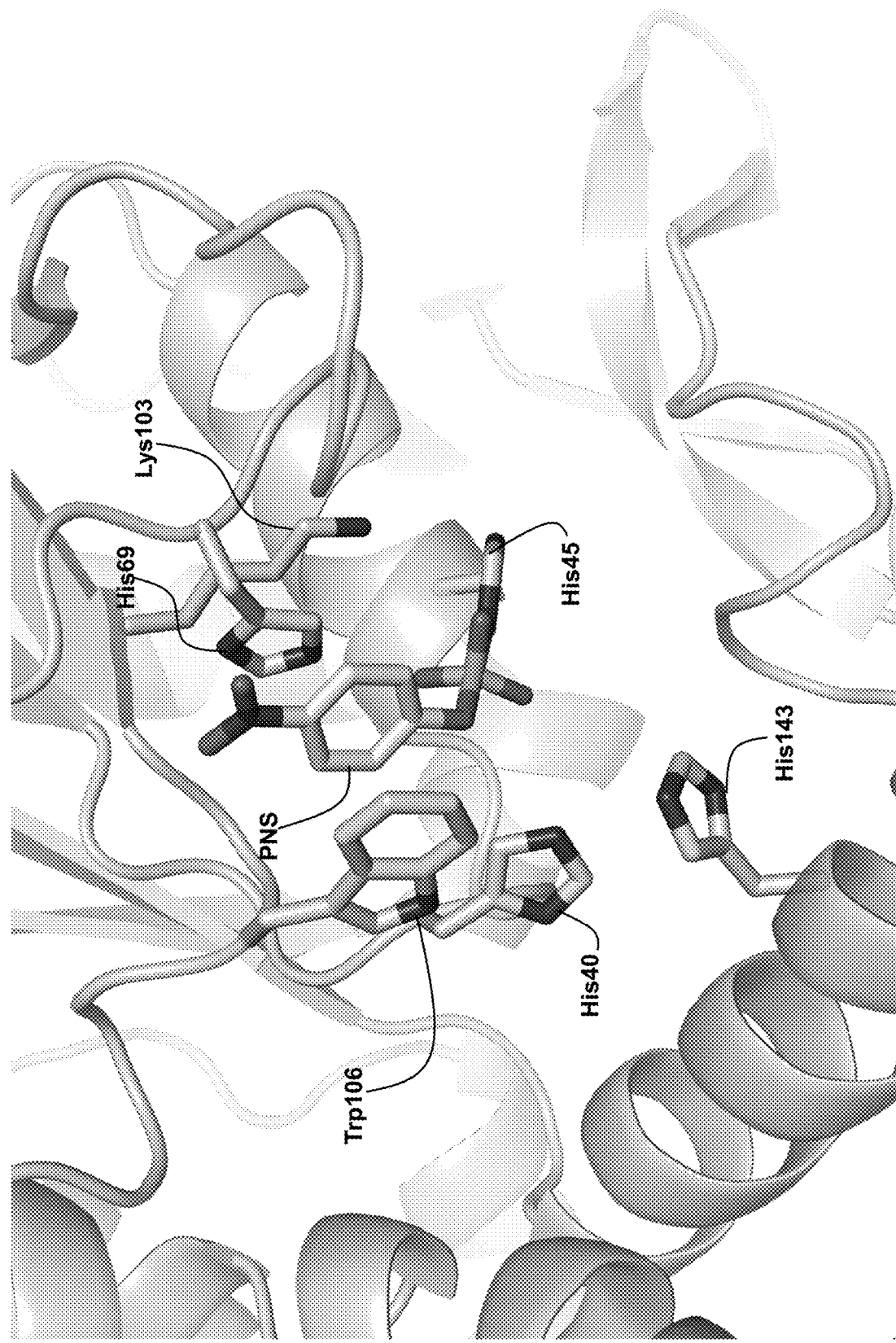
FIG. 9 shows a three-dimensional model of the engineered enzyme modeled in FIG. 8, illustrating amino acid mutations present within the active site.

However, even though the sulfate groups appear to bind in a nearly identical location within the active site, aryl sulfate compounds cannot be utilized with natural NDST enzymes to facilitate sulfo group transfer to a polysaccharide. As described above, the amino acid residues within the active site of the natural sulfotransferases are evolved to have strong binding affinity for PAPS, and without being limited by a particular theory, it is believed that the enzymes likely do not have enough affinity for aryl sulfate compounds to drive binding and sulfotransferase activity. Consequently, it is believed that other mutations can assist to drive binding of aryl sulfate compounds within the active site. FIG. 9 illustrates other mutations that surround PNS within the engineered enzyme comprising the amino acid sequence of SEQ ID NO: 13, including Trp-106, His-69, and His-40. PNS carbon atoms are positioned between Trp-106 and His-69, and appear to provide a-π stacking binding contacts with both amino acid side chains. Additionally, the E2 nitrogen atoms within His-69 and His-40 appear to coordinate with the sulfuryl group of PNS directly. Lysine residues retained from the natural enzyme sequence, Lys-41 (not shown, for clarity) and Lys-103 appear to be in position to coordinate with the sulfate group during transfer in order to stabilize the transition state. Of note, the natural amino acid residue, Lys-260, which also coordinates with the sulfate group in PAPS, is mutated to a valine residue within the engineered enzyme sequence. Without being limited by a particular theory, it is believed that His-45, which is necessary for the reaction with PNS, would exhibit charge repulsion with a lysine residue at position 260, and that the mutation to a valine residue retains some steric bulk within the binding site while eliminating the charge repulsion. Lys-103 is nonetheless positioned to coordinate with the sulfuryl group, particularly when the sulfuryl group is associated or bound to His-45, as shown in FIG. 9.

Figure 10:
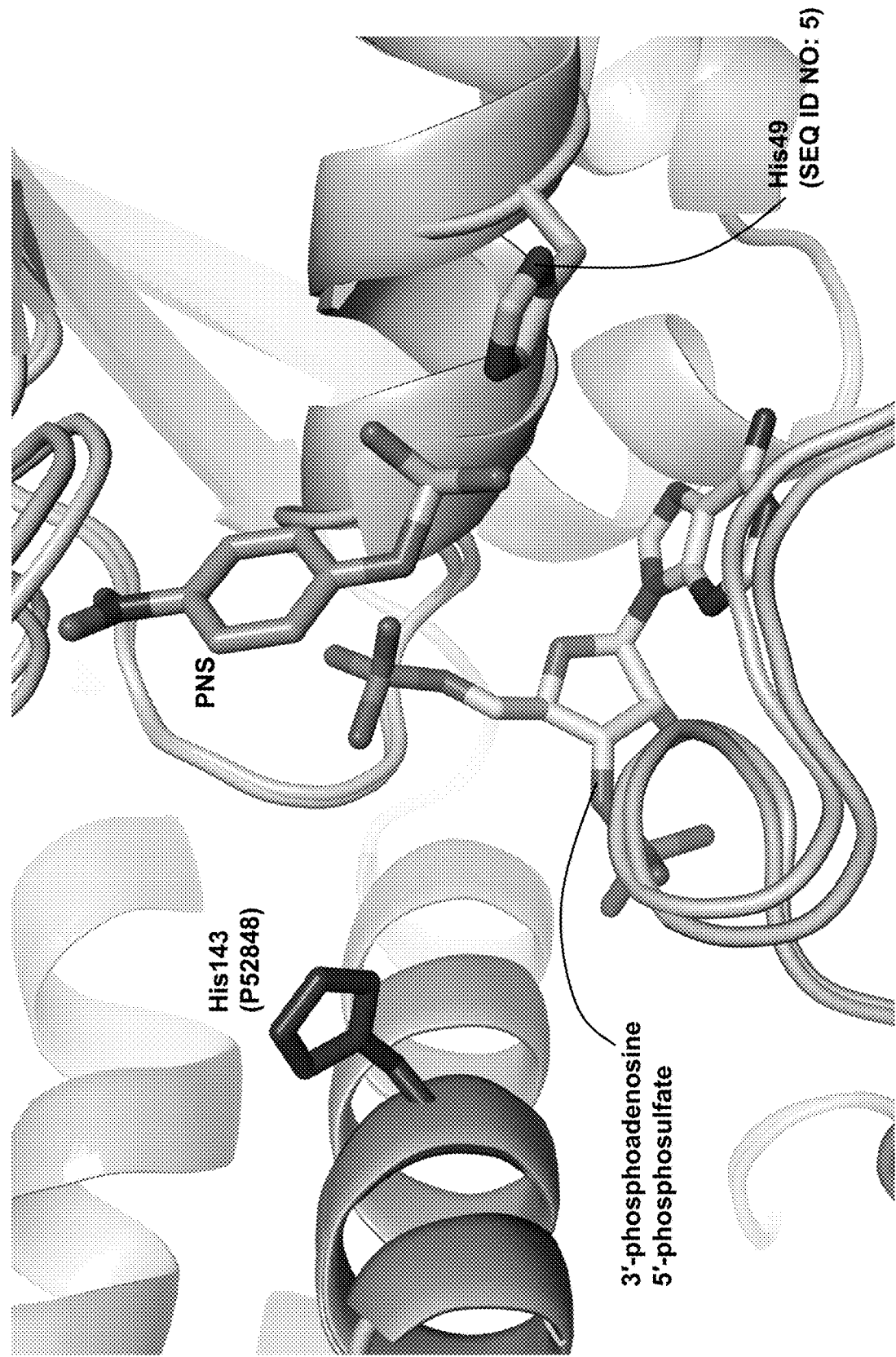
FIG. 10 shows another three-dimensional model of PNS bound within the active site of an engineered NST enzyme, superimposed over the crystal structure of the N-sulfotransferase domain of a natural enzyme from the EC. 2.8.2.8 enzyme class.
Figure 11:
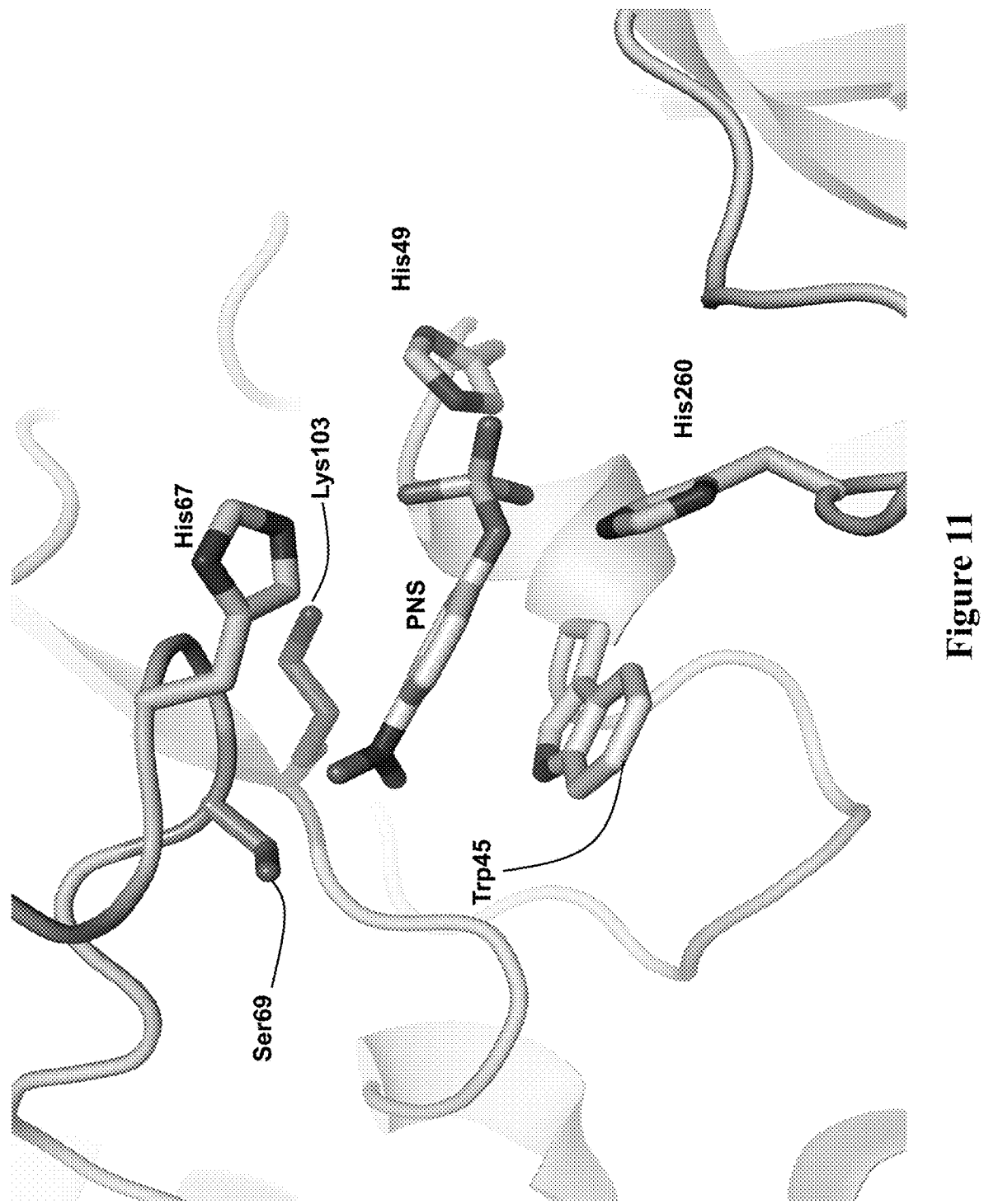
FIG. 11 shows a three-dimensional model of the engineered enzyme modeled in FIG. 10, illustrating amino acid mutations present within the active site.

In another non-limiting example, FIG. 10 shows a magnified view of the active site of the N-sulfotransferase domain of human NDST1 (SEQ ID NO: 164, UniProtKB Accession No. P52848) overlaid with a different engineered NST enzyme, comprising the amino acid sequence of SEQ ID NO: 5. PNS is modeled into the engineered enzyme active site, as described above. As with the engineered enzyme comprising the amino acid sequence SEQ ID NO: 13, the protein backbone of the engineered enzyme comprising the amino acid sequence of SEQ ID NO: 5 also has a nearly identical structure to the N-sulfotransferase domain of the human enzyme. However, the consensus solutions from MD simulations indicate that the sulfate moiety within PNS is favored to bind adjacent to a different histidine mutation (His-49), which is mutated from a leucine residue that is conserved within the active site of the natural NDST enzymes. Consequently, mutations within SEQ ID NO: 13 that formed binding contacts with PNS are not necessarily present in SEQ ID NO: 5. As illustrated in FIG. 11 and similar to SEQ ID NO: 13, there are two mutations present within SEQ ID NO: 5 that appear to form a-a stacking binding contacts surrounding the aromatic moiety of PNS, Trp-45 and His-67. Other mutations that comprise side chains that appear to coordinate with PNS include Ser-69 (coordinating with the nitro functional group of PNS) and His-260 (coordinating with the sulfate moiety). Similar to SEQ ID NO: 13, because the natural lysine residue at position 260 is mutated, the natural Lys-103 residue is utilized within SEQ ID NO: 5 to coordinate with the sulfate moiety within PNS.

Those skilled in the art would appreciate that engineered NST enzymes of any other amino acid sequence, including, but not limited to, those described by SEQ ID NO: 7, SEQ ID NO: 9, SEQ ID NO: 11, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, would likely exhibit a similar structure to the N-sulfotransferase domain of human NDST1 and engineered NST enzymes having the amino acid sequence of SEQ ID NO: 5 and SEQ ID NO: 13. Without being limited by a particular theory, it is also believed that NCS would bind in a similar position as PNS within the active site of any of the engineered NST enzymes, since the structures of the two aryl sulfate compounds are very similar, except that the sulfate group is located ortho on the aromatic ring relative to the nitro group, rather than para to the nitro group.

Further, the engineered NST enzymes of the present invention can include mutated amino acid sequence motifs that comprise one or more of the above-described mutations as well as other mutations that facilitate binding of substrates, the sulfotransfer reaction, or the stability of the enzyme during protein expression. In another embodiment, an engineered NST enzyme can include the mutated amino acid sequence motif, $X_1$-K-T-G-A-W/F-A/L-L-$X_2$-H (SEQ ID NO: 278), mutated from the conserved amino acid sequence Q-K-T-G-T-T-A-L-Y-L (SEQ ID NO: 277) within natural NDST enzymes, wherein $X_1$ is selected from the group consisting of glutamine, serine, and alanine; and $X_2$ is selected from the group consisting of tyrosine, threonine, and histidine. Engineered NST enzymes that include the mutated amino acid sequence motif $X_1$-K-T-G-A-W/F-A/L-L-$X_2$-H (SEQ ID NO: 278) include, but are not limited to SEQ ID NO: 5 (described above), as well as SEQ ID NO: 7, SEQ ID NO: 15; SEQ ID NO: 18, SEQ ID NO: 20, SEQ ID NO: 21, and SEQ ID NO: 25. In further embodiments, engineered NST enzymes can further include the mutated amino acid sequence motif, T-$X_3$-$X_4$-S, mutated from the conserved amino acid sequence T-F-E-E (SEQ ID NO: 222), wherein $X_3$ is a mutation selected from the group consisting of histidine and glycine; $X_4$ is a mutation selected from the group consisting of glycine, histidine, and serine; and wherein at least one of $X_3$ and $X_4$ is a histidine residue. In some even further embodiments, $X_1$ is glutamine and $X_2$ is tyrosine (SEQ ID NO: 280), $X_3$ is histidine and $X_4$ is glycine (SEQ ID NO: 237), and the engineered NST enzyme further comprises the mutated amino acid sequence motif, C-L-G-K/R-S-H-G-R (SEQ ID NO: 281). In other even further embodiments, $X_1$ is serine and $X_2$ is threonine (SEQ ID NO: 282), $X_3$ is glycine and $X_4$ is histidine (SEQ ID NO: 238), and the engineered NST enzyme further comprises the mutated amino acid sequence motif, C-H-G-K/R-R-W-G-R (SEQ ID NO: 283). In sill other even further embodiments, $X_1$ is alanine and $X_2$ is histidine (SEQ ID NO: 284), $X_3$ is histidine and $X_4$ is serine (SEQ ID NO: 285), and the engineered NST enzyme further comprises the mutated amino acid sequence motif, C-A-H-K/R-G-L-G-R (SEQ ID NO: 286).

In another embodiment, engineered NST enzymes can include the mutated amino acid sequence motif, H-$X_5$-T-G-$X_6$-H-A (SEQ ID NO: 226), mutated from the conserved amino acid sequence Q-K-T-G-T-T-A (SEQ ID NO: 221), wherein $X_5$ is selected from the group consisting of lysine and glycine; and $X_6$ is a mutation selected from the group consisting of glycine and valine. Engineered NST enzymes that include the mutated amino acid sequence motif H-$X_5$-T-G-$X_6$-H-A (SEQ ID NO: 226) include, but are not limited to SEQ ID NO: 13 (described above), as well as SEQ ID NO: 9, SEQ ID NO: 11; SEQ ID NO: 19, SEQ ID NO: 22, SEQ ID NO: 23, and SEQ ID NO: 24. In further embodiments, $X_5$ is glycine and $X_6$ is glycine (SEQ ID NO: 227). In some even further embodiments, the engineered NST enzyme further comprises the mutated amino acid sequence motif, C-G-G-K/R-H-L-G-R (SEQ ID NO: 287). In other even further embodiments, the engineered NST enzyme further comprises the mutated amino acid sequence motif, F-E-H-S-G (SEQ ID NO: 288).

In another embodiment, within any of the engineered NST enzymes that include the mutated amino acid sequence motif, H-$X_5$-T-G-$X_6$-H-A (SEQ ID NO: 226), $X_5$ is selected to be lysine and $X_6$ is selected to be valine (SEQ ID NO: 228), and the engineered NST enzyme further comprises the mutated amino acid sequence motif, T-G-N-H (SEQ ID NO: 289).

Figure 12:
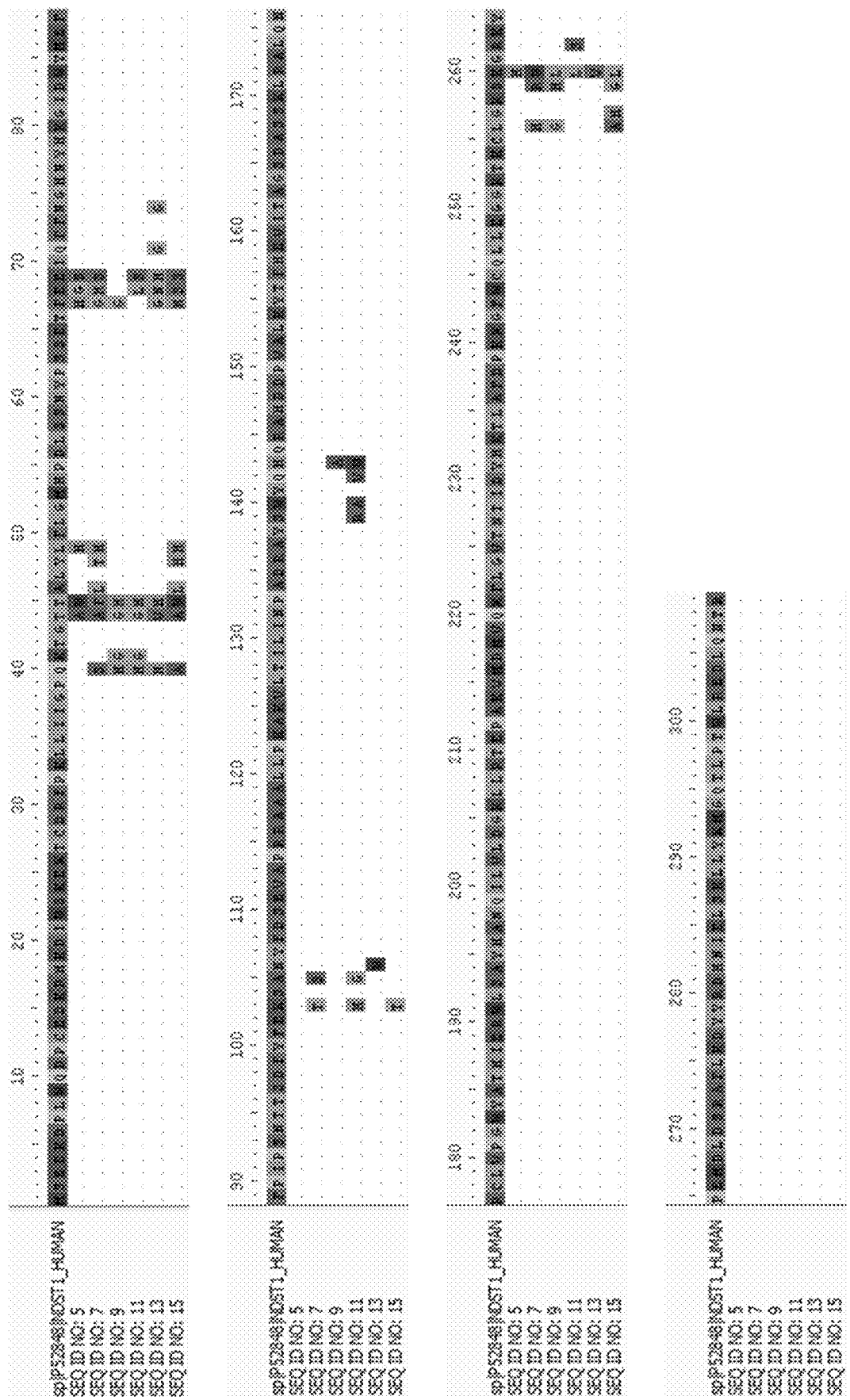
FIG. 12 shows a sequence alignment of polypeptides comprising the amino acid sequences of SEQ ID NO: 5, SEQ ID NO: 7, SEQ ID NO: 9, SEQ ID NO: 11, SEQ ID NO: 13, and SEQ ID NO: 15, respectively, depicting the position and identity of amino acid residues differences between each of the illustrated sequences.

Furthermore, the amino acid sequences (SEQ ID NO: 5, SEQ ID NO: 7 SEQ ID NO: 9, SEQ ID NO: 11, SEQ ID NO: 13, SEQ ID NO: 15) of six engineered NST enzymes, which have been experimentally determined to be active with aryl sulfate compounds as sulfo group donors (see Example 3 below) can be compared with the amino acid sequence of the N-sulfotransferase domain of the human NDST1 enzyme (SEQ ID NO: 164, entry sp|P52848|NDST1_HUMAN) in a multiple sequence alignment to determine if there are relationships between mutations among each of the enzymes. Within the multiple sequence alignment, a period within the amino acid sequence of an engineered enzyme indicates identity at a particular position with the N-sulfotransferase domain of human NDST1. As shown in FIG. 12, the sequence alignment demonstrates that while over 90% of the amino acid residues within the six sulfotransferase sequences are identical, there are several positions in which multiple amino acids can be chosen. Without being limited by a particular theory, these enzymes appear to have a similar relationship with each other as the N-sulfotransferase domains of the NDST enzymes that comprise EC 2.8.2.8. As a result, and in another embodiment, engineered NST enzymes comprising an amino acid sequence in which multiple amino acids can be chosen at defined positions are disclosed as SEQ ID NO: 18 and SEQ ID NO: 19. Positions at which the identity of an amino acid can be chosen from a selection of possible residues are denoted in terms "Xaa," "Xn," or "position n," where n refers to the residue position.

In another embodiment, within an engineered NST enzyme comprising the amino acid sequence of SEQ ID NO: 18 or SEQ ID NO: 19, the amino acid residue at position 41 is lysine, the amino acid residue at position 44 is alanine, the amino acid residue at position 45 is an aromatic amino acid residue, preferably tyrosine or phenylalanine, and the amino acid residue at position 49 is histidine. In another embodiment, when the engineered NST enzyme comprises the above residues from positions 41-49, the amino acid residue at position 67 is glycine or histidine, the amino acid residue at position 68 is selected from the group consisting of glycine, histidine, and serine, and the amino acid residue at position 69 is serine.

In another embodiment, within an engineered NST enzyme comprising the amino acid sequence of SEQ ID NO: 18 or SEQ ID NO: 19, the amino acid residue at position 40 is histidine and the amino acid residue at position 45 is histidine. In further embodiments, the amino acid residue at position 41 is glycine and the amino acid residue at position 44 is glycine. In other further embodiments, the amino acid residue at position 41 is lysine and the amino acid residue at position 44 is valine. In even further embodiments, the amino acid residue at position 67 is glycine and the amino acid residue at position 69 is histidine. In still further embodiments, the amino acid residue at position 106 is tryptophan. In even still further embodiments, the amino acid residue at position 260 is valine.

In another embodiment, within an engineered NST enzyme comprising the amino acid sequence of SEQ ID NO: 18 or SEQ ID NO: 19, the amino acid sequence can optionally include one or more mutations at residue positions not specified by an "Xn" or "X," so long as any such mutations do not eliminate the NST and/or aryl sulfate-dependent activity of the enzyme. In another embodiment, such mutations not eliminating aryl sulfate-dependent activity at positions not specified by an "Xn" or "X" can include substitutions, deletions, and/or additions.

Accordingly, in another embodiment, an engineered NST enzyme utilized in accordance with any of the methods of the present invention can comprise an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. In another embodiment, engineered NST enzymes comprising the amino acid sequence of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, or SEQ ID NO: 25 can react with any aryl sulfate compound. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

Engineered 2OSTs

In nature, 2OSTs recognize, bind, and react with N-sulfated heparosan polysaccharides as sulfo group acceptors. Within the N-sulfated heparosan, a majority of the glucosaminyl residues are generally N-sulfated, and the sulfo group is transferred to the 2-O position of a hexuronic acid residue, generally glucuronic acid or iduronic acid. As with the natural NDST enzymes described above, natural 2OSTs transfer the sulfo group to the polysaccharide upon reacting with PAPS as a sulfo group donor. However, natural 2OSTs are members of the EC 2.8.2.- enzyme class. N-sulfated heparosan that react with natural 2OST enzymes as sulfo group acceptors typically comprise at least one of two distinct structural motifs. In a first non-limiting example, natural 2OST enzymes can recognize, bind, and react with N-sulfated heparosan having the structure of Formula IV, below:

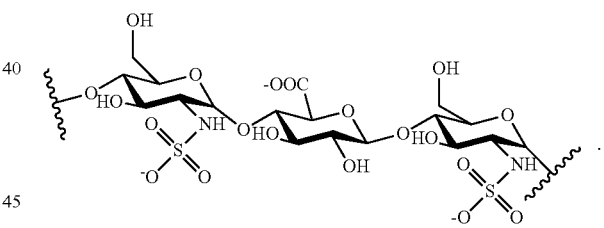

In another non-limiting example, natural 2OST enzymes can recognize, bind, and react with N-sulfated heparosan having the structure of Formula V, below:

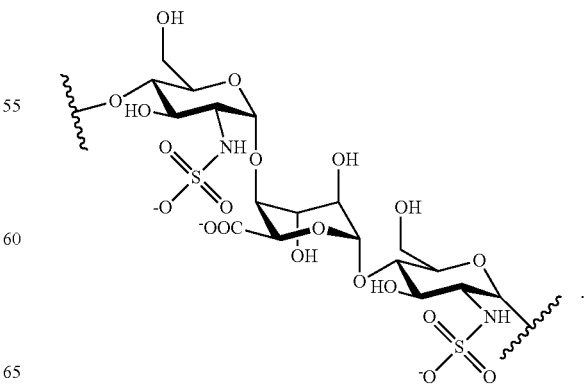

In both instances, the hexuronic acid residue (glucuronic acid in Formula IV, iduronic acid in Formula V) is flanked on either side by N-sulfated glucosamine residues that are otherwise unsubstituted at the 3-O and 6-O positions. Natural 2OST enzymes, and their biological activity with polysaccharides comprising the structures of Formula IV or Formula V, have been described by Rong, J., et al., (2001) *Biochemistry* 40 (18):5548-5555, the disclosure of which is incorporated by reference in its entirety.

As described above, although the portion of the N-sulfated heparosan comprising the structure of Formula IV or Formula V contains N-sulfated glucosamine residues, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similarly, heparosan-based polysaccharides can comprise one or more structural motifs comprising the structure of Formula IV and/or the structure of Formula V within the same polysaccharide, any of which can be 2-O sulfated by the same enzyme. Typically, N-sulfated heparosan capable of reacting with 2OST comprises at least eight monosaccharide residues. In another embodiment, the engineered 2OSTs of the present invention have identical preference as natural 2OSTs for N-sulfated heparosan as a sulfo group acceptor, particularly N-sulfated heparosan comprising the structure(s) of Formula IV and/or Formula V.

The stereochemistry of the hexuronic acid residue in N-sulfated heparosan comprising the structure of Formula IV or Formula V can be controlled by the presence of a glucuronyl $C_5$-epimerase, which reversibly inverts the stereochemistry of the $C_5$-carbon of hexuronic acid residues. However, once the hexuronyl residue within a polysaccharide comprising the structure of Formula IV or Formula V is 2-O sulfated, the hexuronic acid residue can no longer be epimerized. Generally, N-sulfated heparosan that can react with a 2OST in vivo are almost exclusively synthesized as disaccharide units of N-sulfoglucosamine and glucuronic acid. One or more of these glucuronic acid residues are often epimerized to an iduronic acid residue prior to reacting with the 2OST enzyme to form 2-O sulfated iduronic acid residues. However, and without being limited by a particular theory, it is believed that natural 2OST enzymes generally have preference for binding and reacting with N-sulfated heparosan comprising the structure of Formula V, and that most N,2O-HS polysaccharides produced in vivo generally comprise 2-O sulfated iduronic acid.

Upon successfully binding PAPS and N-sulfated heparosan comprising the structure of Formula IV, natural 2OST enzymes can catalyze transfer of the sulfo group to the 2-O position of a glucuronic acid residue, forming an N,2O-HS product comprising the structure of Formula VI, below:

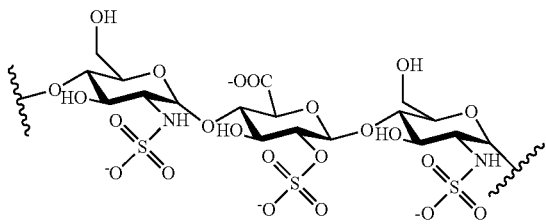

Upon successfully binding PAPS and N-sulfated heparosan comprising the structure of Formula V, natural 2OST can catalyze transfer of the sulfo group to the 2-O position of an iduronic acid residue, forming an N,2O-HS product comprising the structure of Formula VII, below:

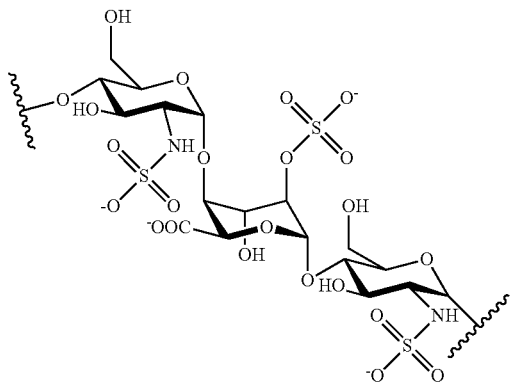

Figure 13:
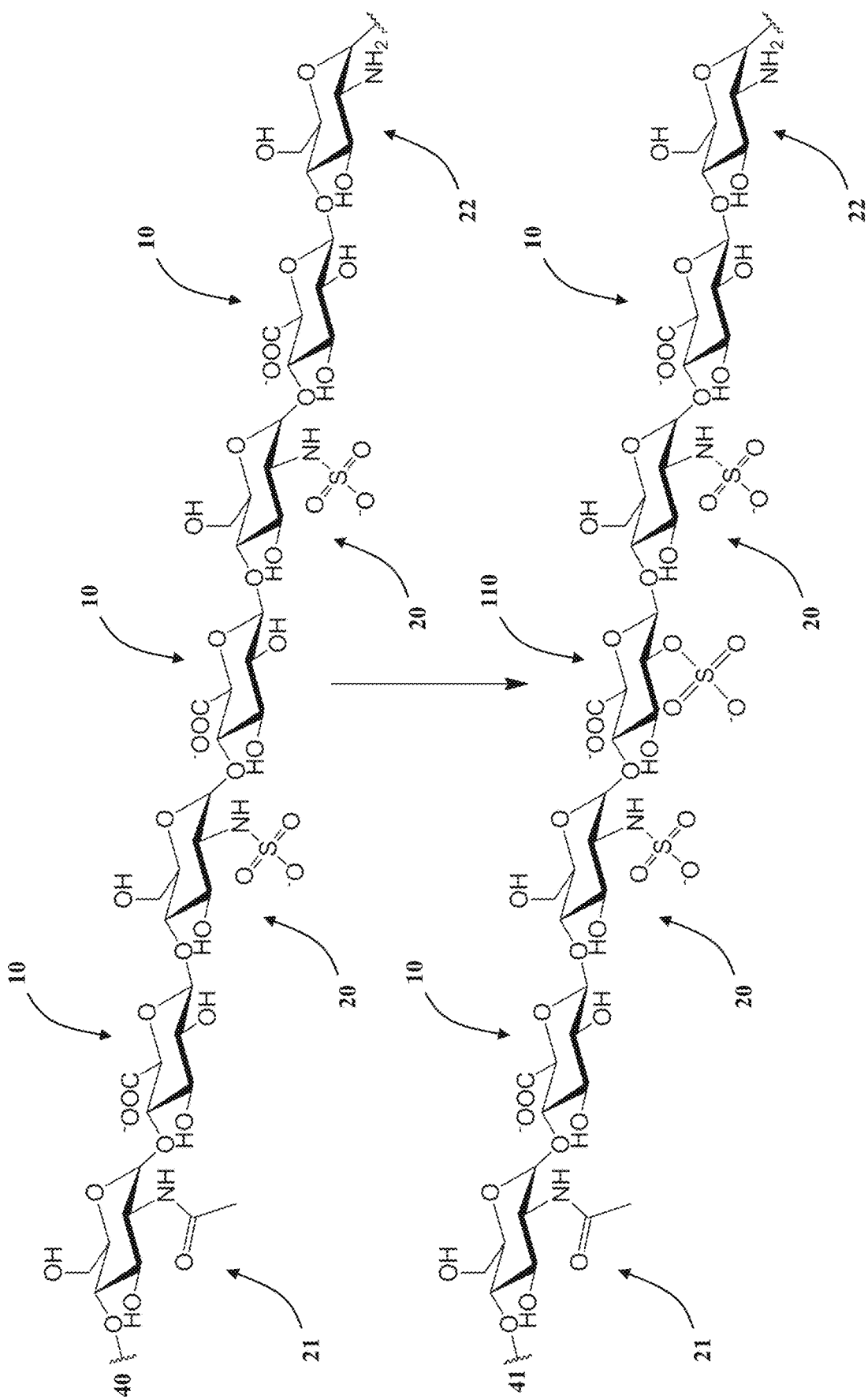
FIG. 13 shows a non-limiting example of a heparosan-based polysaccharide that can be used as a sulfo group acceptor with engineered 2OST enzymes of the present invention.

In another embodiment, in order to be 2-O sulfated, a glucuronic acid or iduronic acid residue must be adjacent to two N-sulfated glucosamine residues, as shown in Formula IV and Formula V. A non-limiting example of one such polysaccharide is illustrated in FIG. 13. In FIG. 13, hexuronyl residues 10 within polysaccharide 40 are flanked by glucosaminyl residues 20, 21, and 22, that are either N-sulfated, N-acetylated, or unsubstituted, respectively. In another embodiment, upon reacting the polysaccharide 40 with an engineered 2OST, only the hexuronyl residue 10 flanked by two N-sulfated glucosamine residues 20 can be 2-O sulfated, ultimately forming a 2-O sulfated hexuronyl residue 110 within the product polysaccharide 41.

Figure 14:
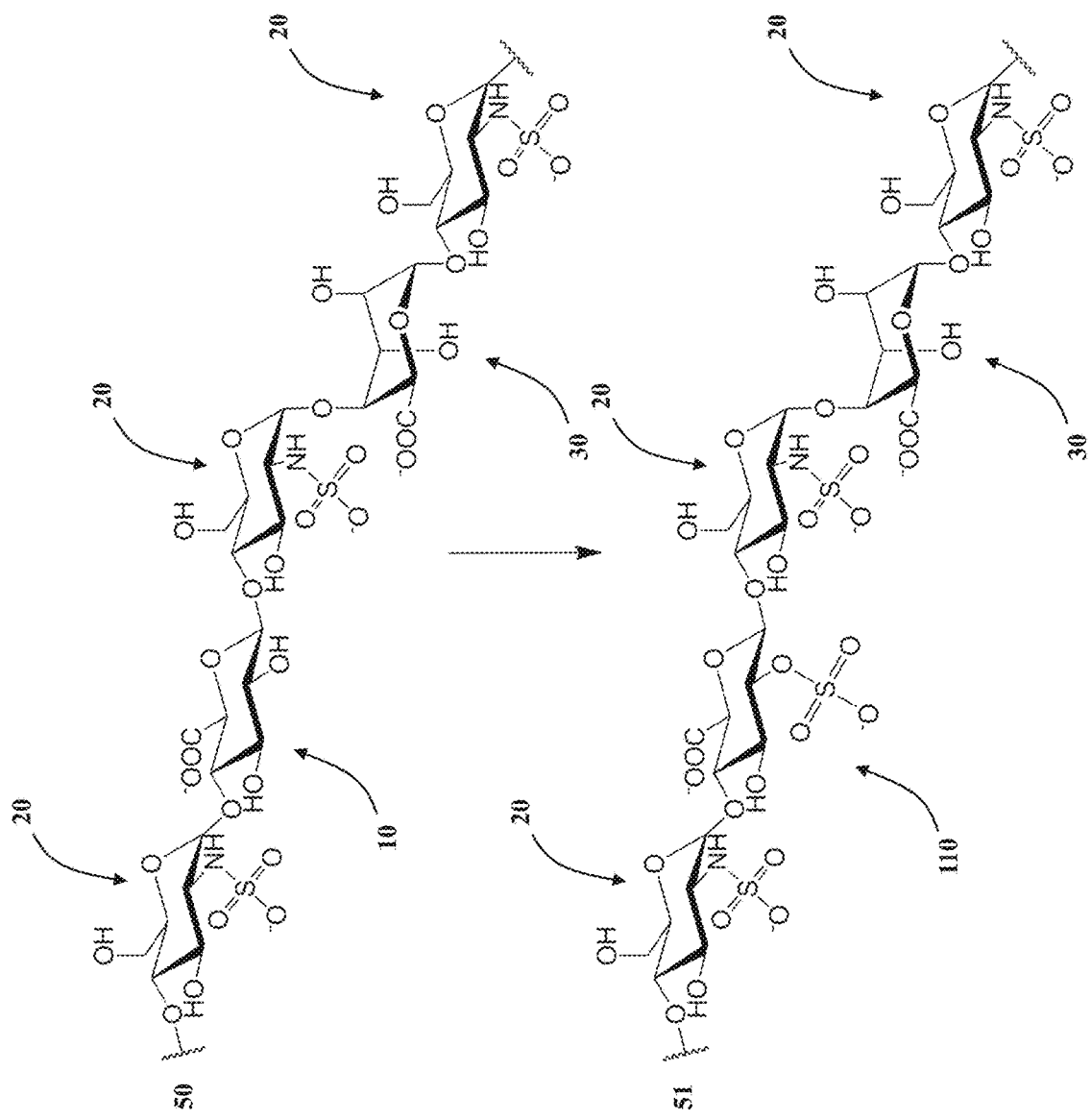
FIG. 14 shows another non-limiting example of a heparosan-based polysaccharide that can be used as a sulfo group acceptor with engineered 2OST enzymes of the present invention, where a sulfate group is transferred to the 2-O position of a glucuronic acid residue within the heparosan-based polysaccharide.
Figure 15:
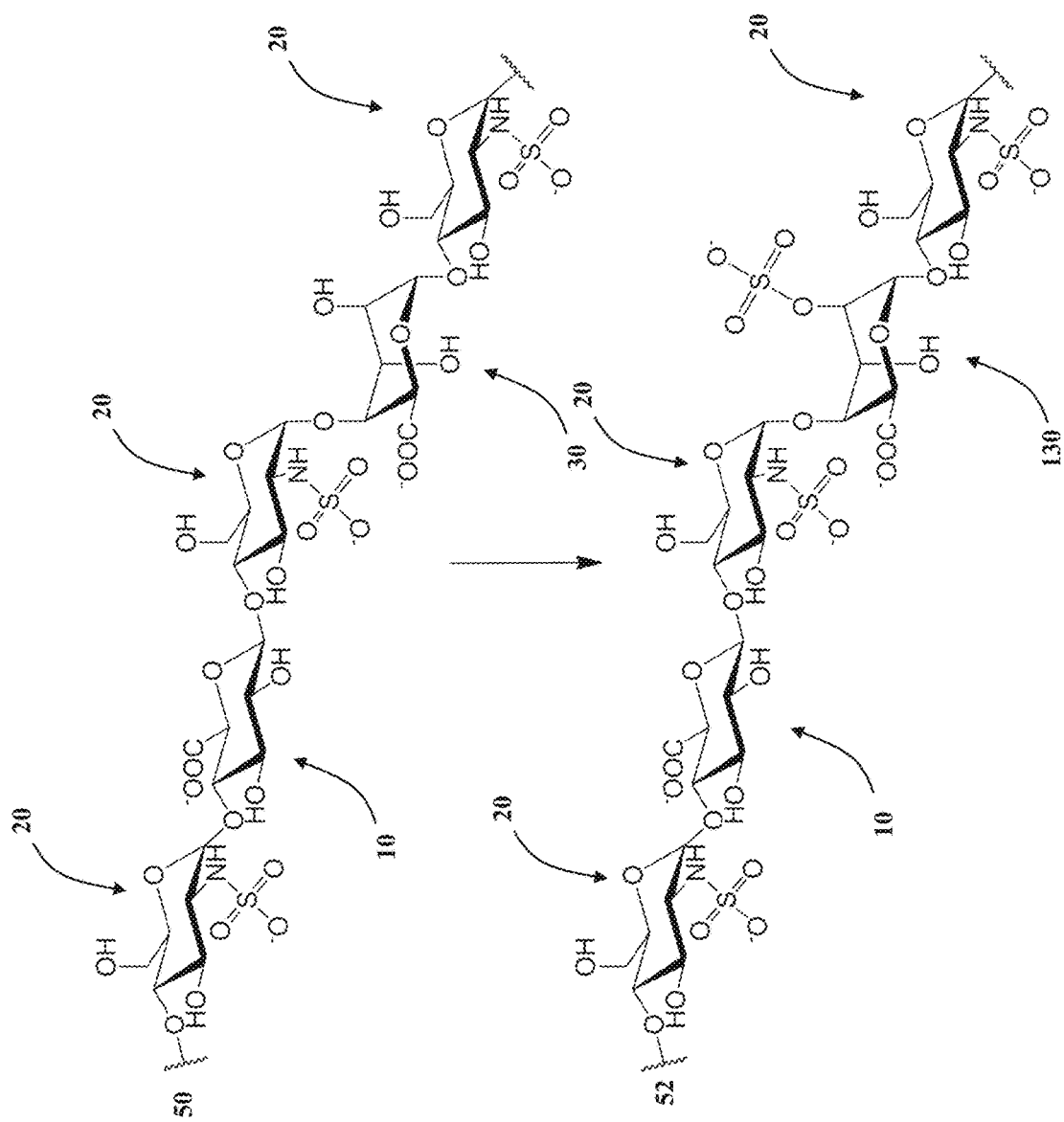
FIG. 15 shows another non-limiting example of a heparosan-based polysaccharide that can be used as a sulfo group acceptor with engineered 2OST enzymes of the present invention, where a sulfate group is transferred to the 2-O position of an iduronic acid residue within the polysaccharide.
Figure 16:
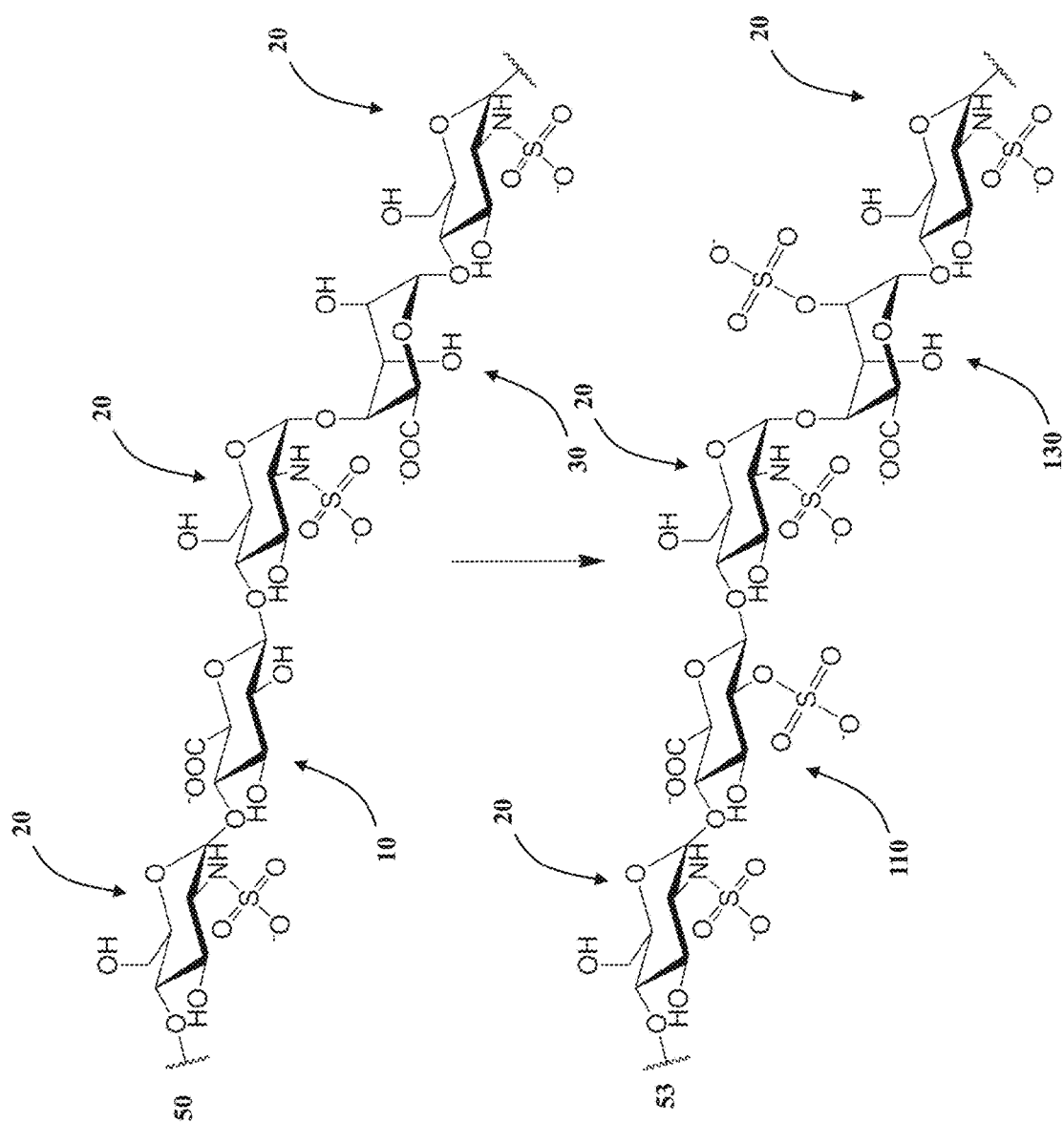
FIG. 16 shows another non-limiting example of a heparosan-based polysaccharide that can be used as a sulfo group acceptor with engineered 2OST enzymes of the present invention, where a sulfate group is transferred to both the 2-O position of a glucuronic acid residue and the 2-O position of an iduronic acid residue within the polysaccharide.
Figure 17A:
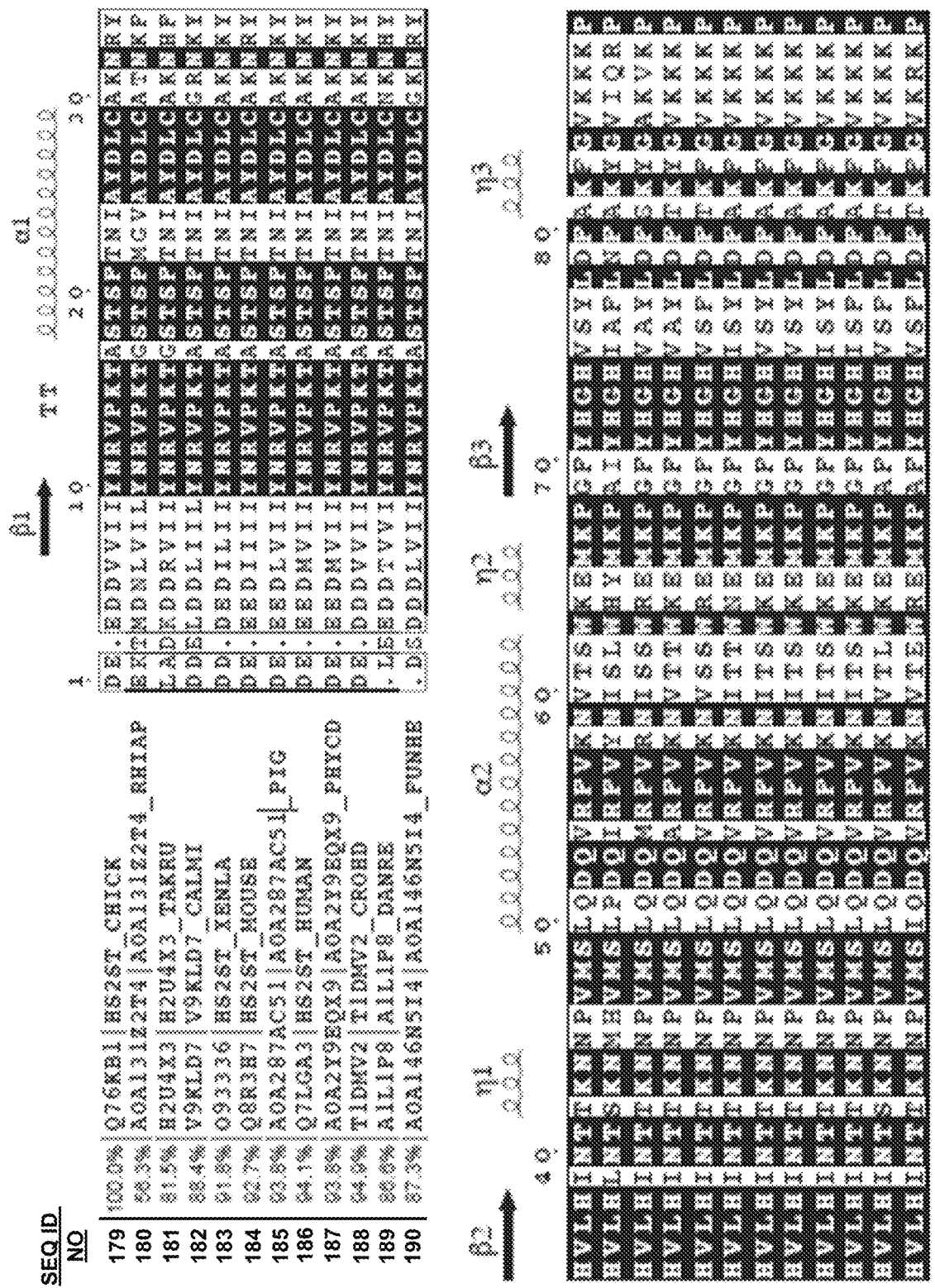
FIG. 17A, FIG. 17B, FIG. 17C, and FIG. 17D show a multiple sequence alignment for twelve wild-type 2OST enzymes within EC 2.8.2.-, illustrating conserved amino acid sequence motifs that are present regardless of overall sequence identity.
Figure 17B:
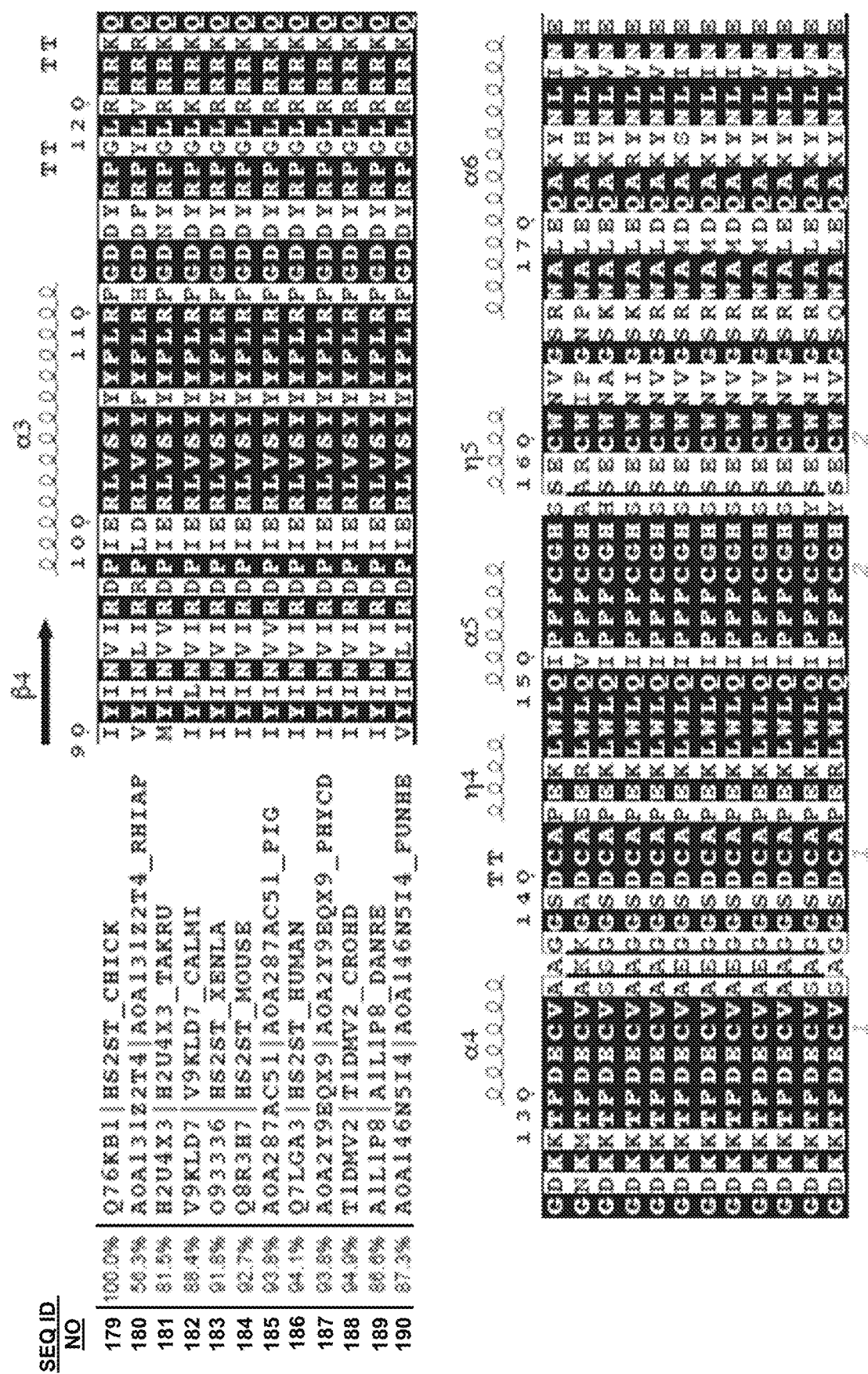
Figure 17C:
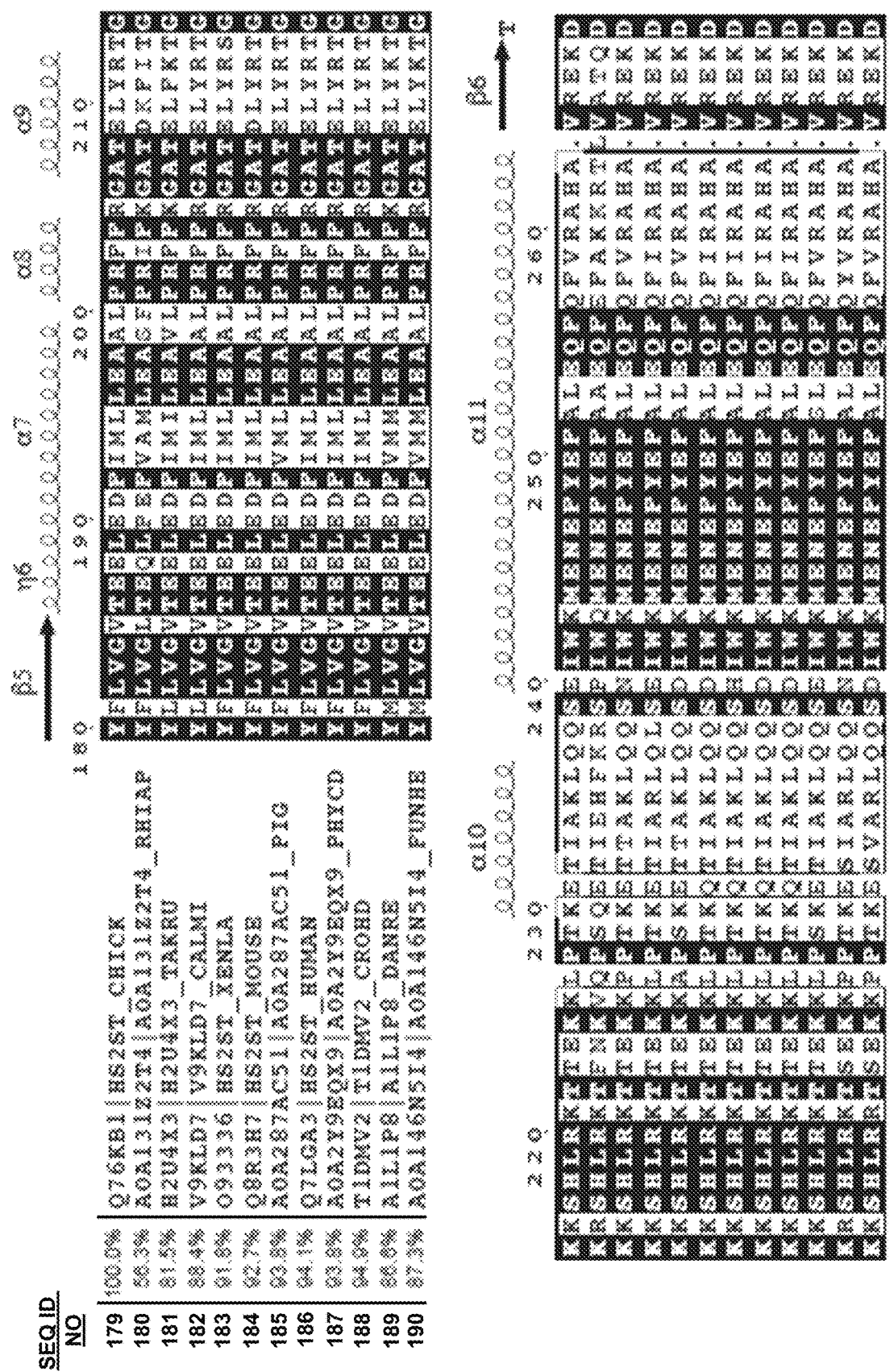
Figure 17D:
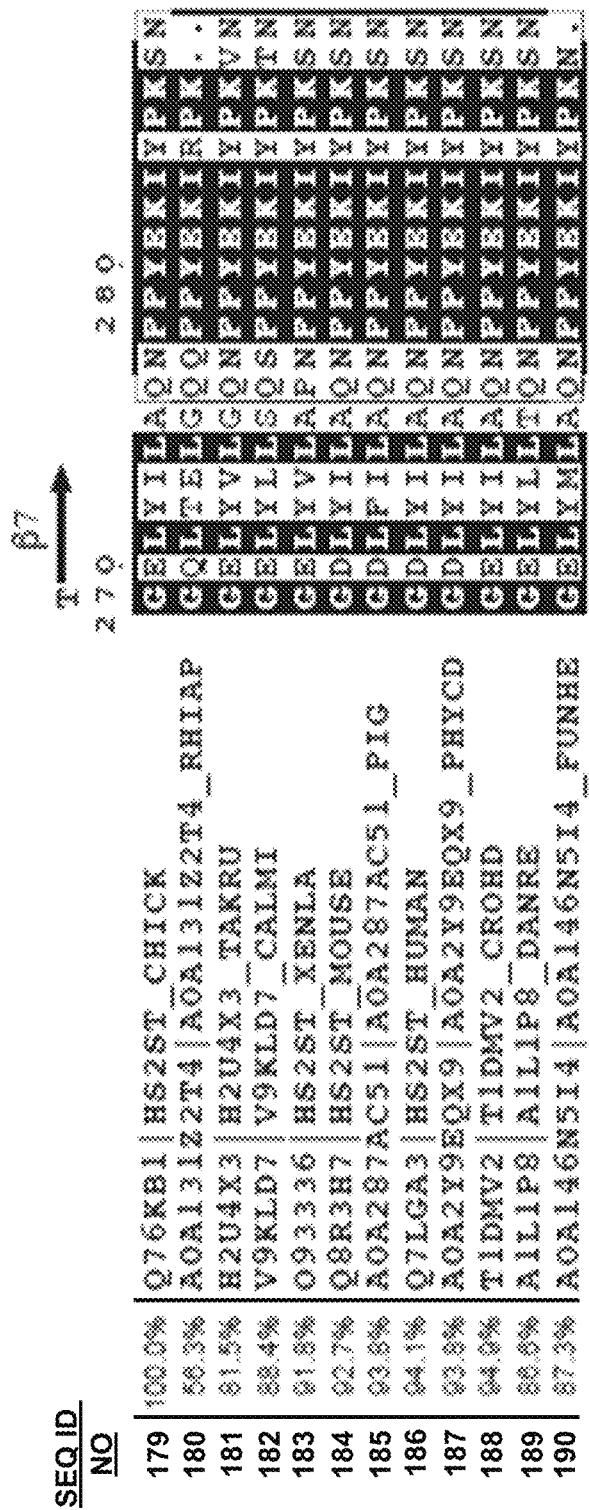

In another non-limiting example, portions of N-sulfated heparosan comprising the structures of Formula IV and Formula V are illustrated by polysaccharide 50 in each of FIG. 14, FIG. 15, and FIG. 16. In FIG. 14, FIG. 15, and FIG. 16, a hexuronyl residue 10 and an epimerized hexuronyl residue 30 are alternated between three N-sulfoglucosaminyl residues 20 within polysaccharide 50. Although hexuronyl residues 10 and 30 are represented in a chair conformation, those skilled in the art can appreciate that such monosaccharide residues within a longer oligo- or polysaccharide chain can adopt several different conformations, including chair, half-chair, boat, skew, and skew boat conformations, and that those additional conformations are omitted for clarity.

In another embodiment, upon reacting polysaccharide 50 with an engineered aryl sulfate-dependent 2OST enzyme, the enzyme can catalyze sulfo group transfer to hexuronyl residue 10 to form a sulfated hexuronyl residue 110 within product polysaccharide 51 (FIG. 14), to epimerized hexuronyl residue 30 to form a sulfated epimerized hexuronyl residue 130 within product polysaccharide 52 (FIG. 15), or to both hexuronyl residue 10 and epimerized hexuronyl residue 30 to form a sulfated hexuronyl residue 110 and a sulfated epimerized hexuronyl residue 130, respectively, within product polysaccharide 53 (FIG. 16).

Natural 2OSTs generally comprise approximately 325-375 amino acid residues that in some cases vary greatly in their sequence, yet ultimately have the exact same function, namely, to catalyze the transfer of a sulfo group from PAPS to the 2-O position of hexuronyl residues within N-sulfated heparosan. Without being limited by a particular theory, it is believed that each of the natural 2OSTs can catalyze the same chemical reaction because there are multiple amino acid sequence motifs and secondary structures, particularly in region(s) that define their active sites, that are either identical or highly conserved across all species.

Further, it is believed that several of the conserved amino acid sequence motifs are directly involved in binding of either PAPS and/or the polysaccharide, or participate in the chemical reaction itself. The identity between the natural 2OST enzymes can be demonstrated by comparing the amino acid sequence of the chicken 2OST (SEQ ID NO: 179), which has known crystal structures (PDB codes: 3F5F and 4NDZ) in which amino acid residues within the active site have been identified, alongside the amino acid sequences of other natural 2OSTs within EC 2.8.2.-. A multiple sequence alignment of twelve enzymes, including the chicken, human, and other eukaryotic 2OST enzymes (SEQ ID NOs 179-190), is shown in FIG. 17A, FIG. 17B, FIG. 17C, and FIG. 17D, along with percent identity relative to the chicken 2OST reference sequence (SEQ ID NO: 179, UniProtKB Accession No. Q76KB1). As illustrated in FIG. 17A, FIG. 17B, FIG. 17C, and FIG. 17D, sequences range from having 94.9/a sequence identity with the Q76KB1 reference sequence (SEQ ID NO: 188, entry tr|T1DMV2|TIDMV2_CROHD) for the timber rattlesnake 2OST, down to 56.3% sequence identity (SEQ ID NO: 180, entry tr|A0A131Z2T4| A0A131Z2T4_RHIAP) for the brown ear tick 2OST. The human enzyme (SEQ ID NO: 186, entry sp|Q7LGA3|HS2ST_HUMAN) has 94.1% sequence identity with the Q76KB1 reference sequence. Those skilled in the art would appreciate that the multiple sequence alignment was limited to twelve sequences for clarity, and that there are hundreds of amino acid sequences encoding for natural 2OST enzymes that have been identified and that have highly conserved active site and/or binding regions as well.

Within FIG. 17A, FIG. 17B, FIG. 17C, and FIG. 17D, amino acids that are depicted in white with a black background at a particular position, are 100% identical across all sequences. Amino acids that are highly conserved, meaning that the amino acids are either identical, or chemically or structurally similar, at a particular position are enclosed with a black outline. Within highly conserved regions, consensus amino acids that are present in a majority of the sequences are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural chicken HS 2OST enzyme as a reference. The β symbol adjacent to an arrow refers to a β-sheet, whereas a coil adjacent to an α symbol or a η symbol refers to a helix secondary structure.

Figure 18A:
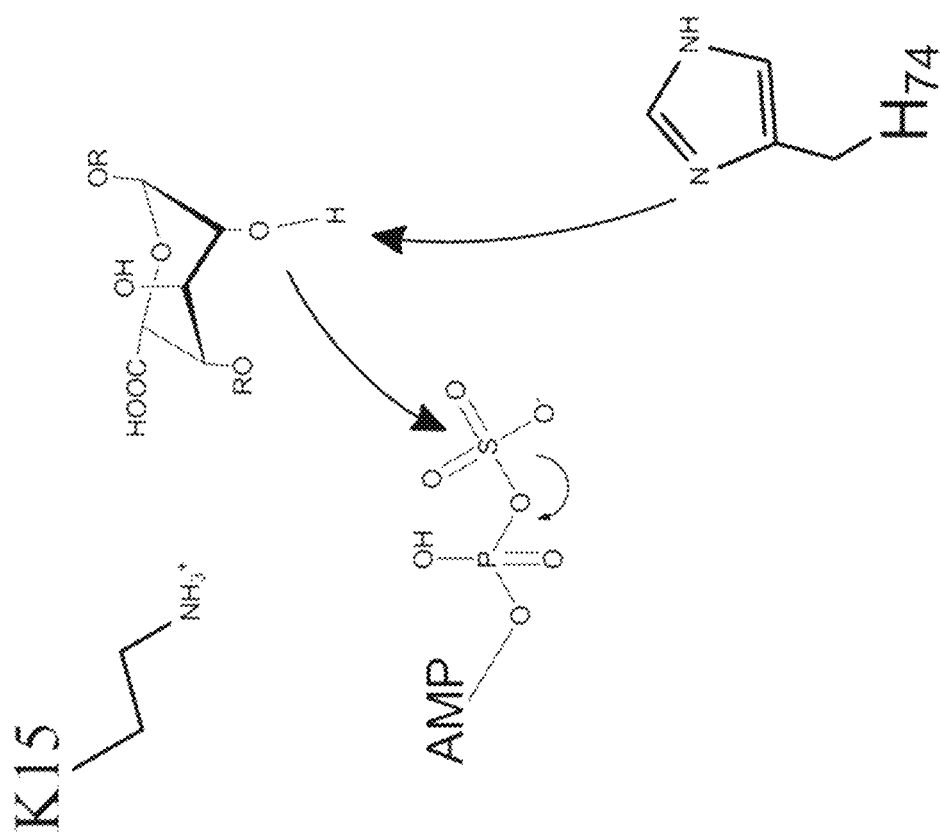
FIG. 18A, FIG. 18B, and FIG. 18C show a proposed reaction mechanism, transition state, and products formed as a result of a sulfotransfer reaction between conserved residues within natural 2OST enzymes, PAPS, and a heparosan-based polysaccharide.
Figure 18B:
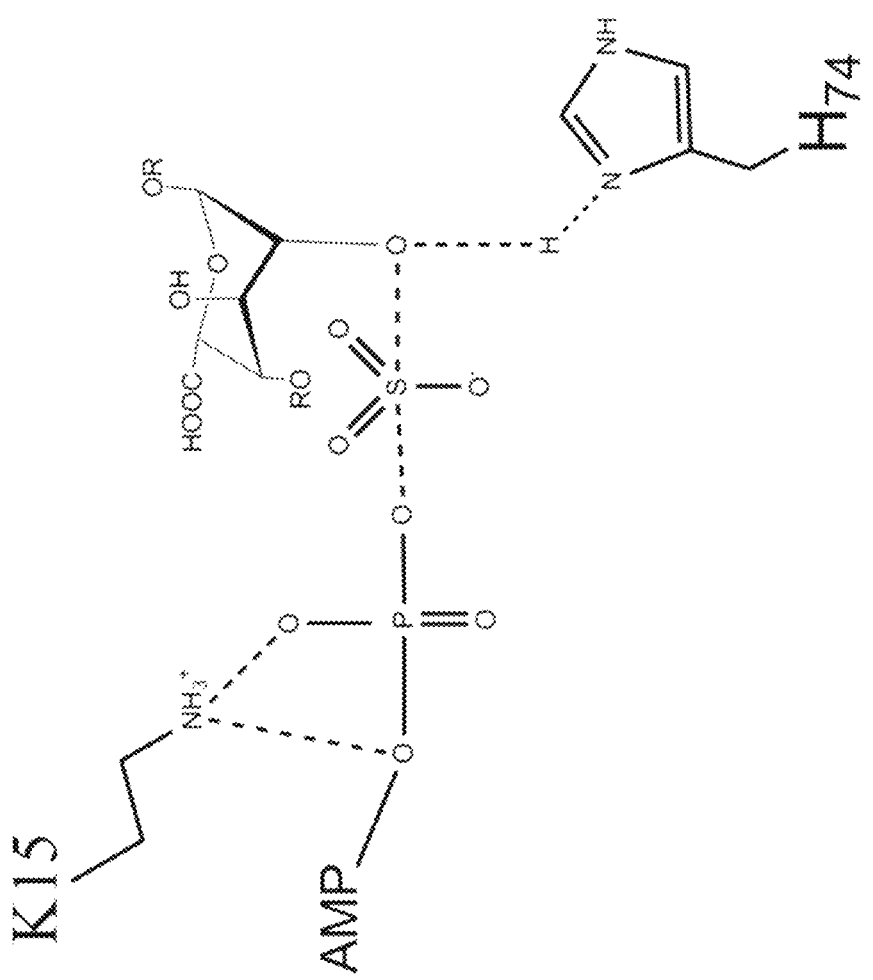
Figure 18C:
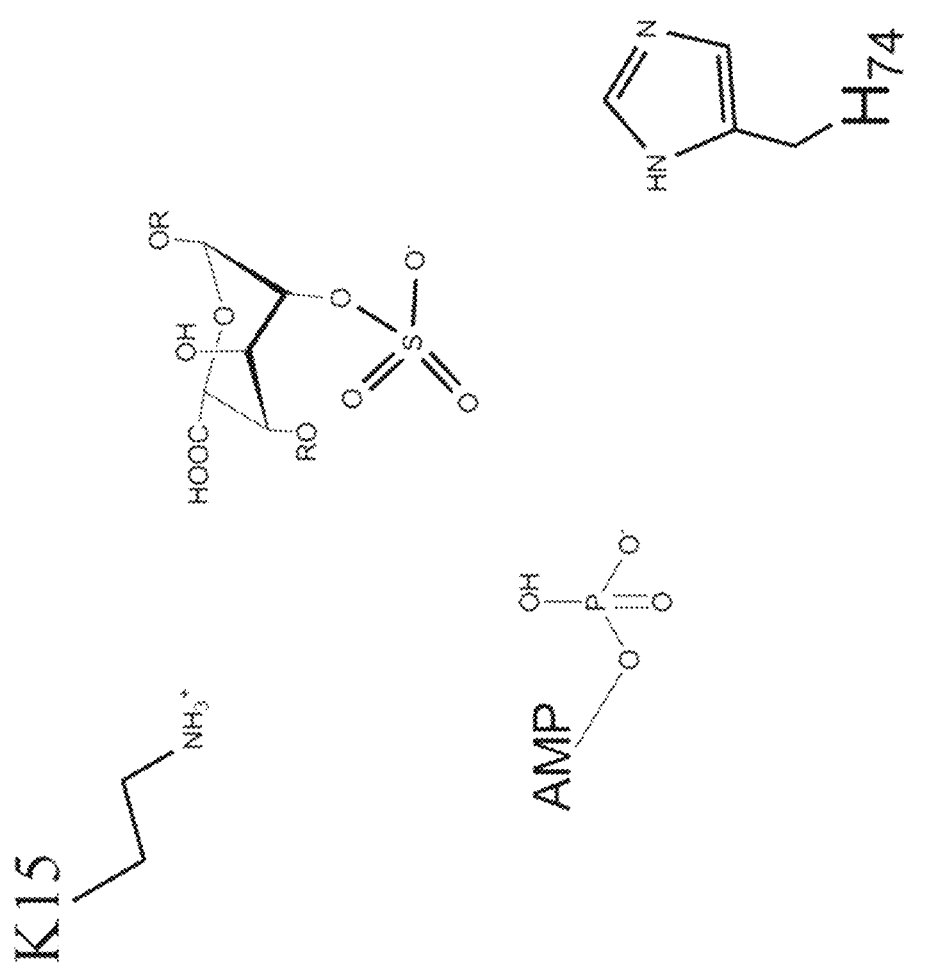

Within the twelve aligned sequences in FIG. 17A, FIG. 17B, FIG. 17C, and FIG. 17D, there are several conserved amino acid motifs that include one or more amino acids that comprise the active site, based on the crystal structures of the chicken 2OST enzyme described above. Based on the numbering of the amino acid residues within FIG. 17A, FIG. 17B, FIG. 17C, and FIG. 17D, these motifs include residues 12-19 (R-V-P-K-T-A/G-S-T), residues 40-44 (N-T-S/T-K-N), residues 71-74 (Y-H-G-H), residues 108-115 (F-L-R-F/H-G-D-D/N-F/Y), residues 121-125 (R-R-K/R-Q-G), and residues 217-222 (S-H-L-R-K/R-T), which correspond to SEQ ID NO: 244, SEQ ID NO: 273, SEQ ID NO: 274, SEQ ID NO: 245, SEQ ID NO: 246, and SEQ ID NO: 247 in the sequence listing, respectively. Without being limited by a particular theory, it is believed that these residues either facilitate or participate in the chemical reaction, or enable binding of PAPS or the polysaccharide within the active site. In particular and as illustrated in FIG. 18A, FIG. 18B, and FIG. 18C, the histidine residue at position 74 abstracts the proton from the 2-O position of the iduronic acid residue within the polysaccharide, enabling nucleophilic attack and removal of the sulfo group from PAPS, whereas the lysine residue at position 15 coordinates with the phosphate moiety of PAPS to stabilize the transition state of the enzyme before the N,2O-HS product is released from the active site.

However, as described above, the natural 2OST enzymes within EC 2.8.2.- are unable to catalyze the transfer of the sulfate group from an aryl sulfate compound to the polysaccharide. As with the natural NDST enzymes, it is believed that the binding pocket for PAPS within the active site of the natural sulfotransferase either does not have a high enough affinity for aryl sulfate compounds to facilitate binding and/or that the aryl sulfate compounds are sterically hindered from entering the active site altogether. Consequently, and in another embodiment, any natural 2OST enzyme can be selected and mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, the engineered 2OST enzymes of the present invention can be mutants of natural 2OST enzymes within EC 2.8.2.-, including enzymes having the amino acid sequences illustrated in FIG. 17A, FIG. 17B, FIG. 17C, and FIG. 17D (SEQ ID NOs 179-190). In another embodiment, mutations engineered into the amino acid sequences of the engineered 2OSTs facilitate a biological activity in which aryl sulfate compounds can both bind and react with the enzyme as sulfo group donors. In another embodiment, although the engineered 2OSTs can bind and react with an aryl sulfate compound as a sulfo group donor, they can retain the natural 2OST enzymes' biological activity with N-sulfated heparosan as a sulfo group acceptor. Without being limited by a particular theory, it is believed that because of the mutations inserted into the amino acid sequences of the engineered 2OST enzymes, their sulfotransferase activity may comprise the direct transfer of a sulfuryl group from an aryl sulfate compound to the heparosan-based polysaccharide, using a similar mechanism as described in FIGS. 18A-18C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 2-O position of a hexuronic acid residue, to form the N,2O-HS product. By either mechanism, engineered 2OST enzymes are able to achieve sulfo transfer from an aryl sulfate compound to a heparosan-based polysaccharide, as described in the examples, below.

In another embodiment, an engineered 2OST enzyme can comprise one or more mutated amino acid sequence motifs relative to the conserved amino acid sequence motifs that are found in the natural 2OST enzymes within EC 2.8.2.-, as described above and indicated in the multiple sequence alignment in FIG. 17A, FIG. 17B, FIG. 17C, and FIG. 17D. In another embodiment, each mutated amino acid sequence motif that is present in the amino acid sequence of the engineered enzyme comprises at least one amino acid mutation relative to the corresponding conserved amino acid sequence motif within the natural 2OST enzymes. In another embodiment, an engineered 2OST enzyme can comprise one mutated amino acid sequence motif. In another embodiment, an engineered 2OST enzyme can comprise two mutated amino acid sequence motifs. In another embodiment, an engineered 2OST enzyme can comprise three mutated amino acid sequence motifs. In another embodiment, an engineered 2OST enzyme can comprise four mutated amino acid sequence motifs. In another embodiment, an engineered 2OST enzyme can comprise five mutated amino acid sequence motifs. In another embodiment, an engineered 2OST enzyme can comprise six mutated amino acid sequence motifs. In another embodiment, an engineered 2OST enzyme that includes at least one mutated amino acid sequence motif relative to any of the natural enzymes within EC 2.8.2.- can have an amino acid sequence selected from the group consisting of SEQ ID NO: 63, SEQ ID NO: 65, SEQ ID NO: 68, and SEQ ID NO: 69.

Figure 19:
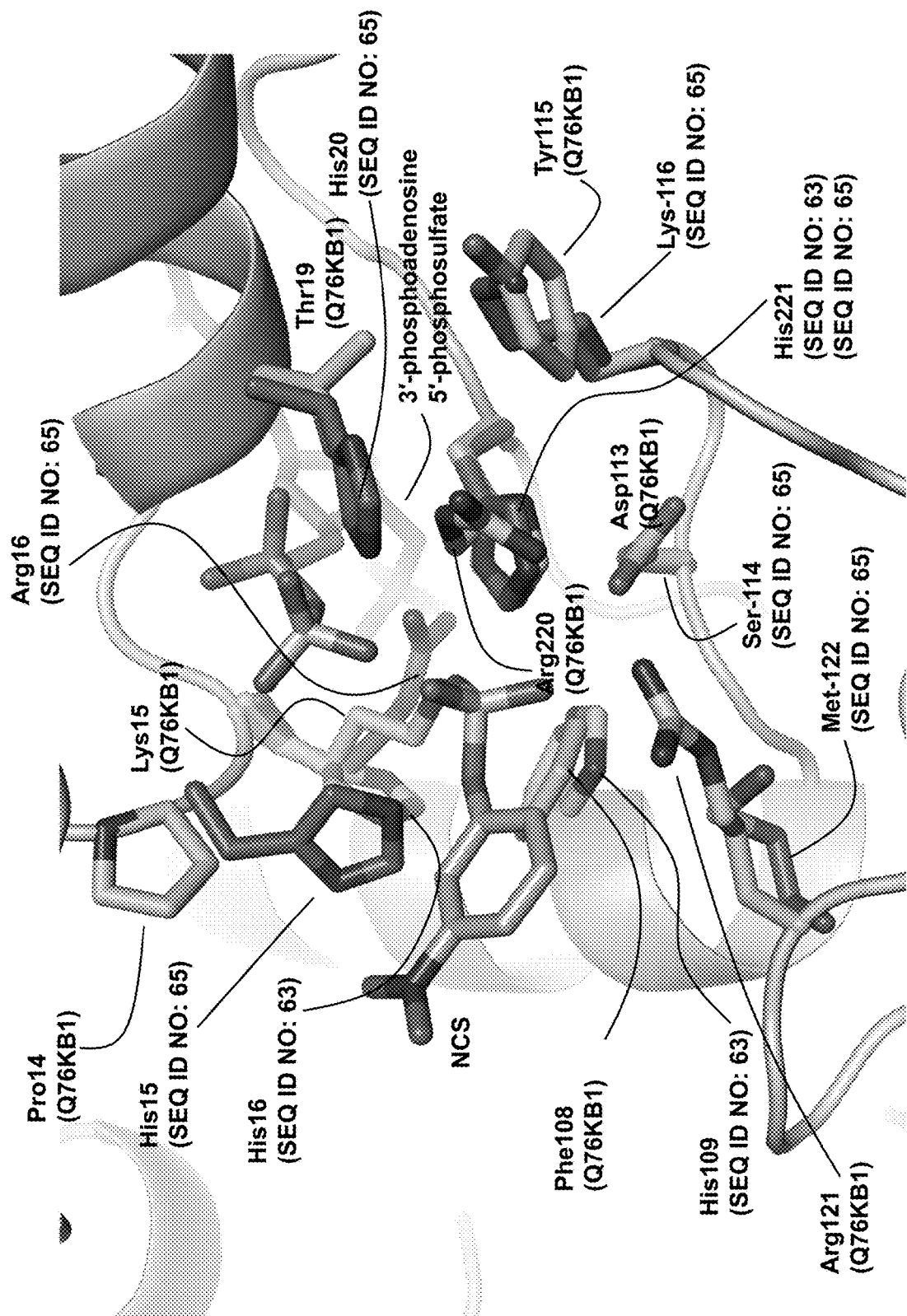
FIG. 19 shows a three-dimensional model of a mutated amino acid sequence motif enabling binding of NCS within the active site of an engineered 2OST enzyme, superimposed over the crystal structure of a natural 2-O sulfotransferase enzyme.

In another embodiment, upon viewing a crystal structure of the chicken 2OST (PDB code: 3F5F) within a 3D molecular visualization system (including, as a non-limiting example, the open-source software, PyMOL), the structure of related sequences, such as those of engineered 2OST enzymes that contain one or more mutated amino acid sequence motifs relative to the chicken 2OST amino acid sequence (SEQ ID NO: 179), can be modeled for comparison as illustrated in FIG. 19. FIG. 19 shows a magnified view of the active site of the chicken 2OST enzyme overlaid with the modeled active sites of two engineered 2OST enzymes, comprising the amino acid sequences of SEQ ID NO: 63 and SEQ ID NO: 65, in which the structure of the engineered enzyme is calculated upon making mutations relative to the chicken 2OST amino acid sequence. Adenosine 3',5'-diphosphate, which is the product of a sulfotransfer reaction in which PAPS is the sulfo donor, and which was co-crystallized with the chicken 2OST, is also illustrated within the active site. The sulfate group that would be present in the natural substrate, PAPS, is modeled onto the 5'-phosphate functional group to illustrate its approximate position within the active site prior to initiating the reaction. NCS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown.

As illustrated in FIG. 19, although there are several mutations made to SEQ ID NO: 63 and SEQ ID NO: 65, relative to the chicken 2OST, the respective protein backbones appear to be in a nearly identical location to one another, enabling a one-to-one comparison of the active sites. When comparing the models of the two active sites, PAPS is located in the background and adjacent to a lysine residue (position 15 of SEQ ID NO: 179), whereas the convergent solutions from the above MD simulations indicate that binding of NCS appears to be favored on the opposite side of the active site. However, binding of NCS would be sterically hindered in the natural 2OST enzyme in part by the lysine residue as well as the phenylalanine residue located on the nearby a-helix (position 108 of SEQ ID NO: 179). Without being limited by a particular theory, it is believed that binding of NCS in the active site of the engineered enzyme comprising the amino acid sequence of SEQ ID NO: 63 is facilitated by the mutation of the lys-15 residue to a histidine residue, which creates additional space within the active site and provides a π-π stacking partner for the aromatic ring within NCS. Also without being limited by a particular theory, it is believed that binding of NCS in the active site of the engineered enzyme comprising the amino acid sequence of SEQ ID NO: 65 is facilitated by the mutation of the lys-15 to an arginine residue in concert with the adjacent mutation of the proline residue (position 14 of SEQ ID NO: 179) to a histidine residue. The increased number of conformational degrees of freedom of the arginine side chain appears to facilitate entry of the NCS while still being in a position to provide a polar contact to stabilize the transition state during the transfer reaction, while the adjacent histidine appears to provide additional binding contacts for NCS.

Another mutation of note includes the mutation from an arginine residue (position 220 of SEQ ID NO: 179) to a histidine residue, a mutation that is found at position 221 in both SEQ ID NO: 63 and SEQ ID NO: 65. Without being limited by a particular theory, it is believed that the mutated histidine residue appears to be in a favorable position to facilitate removal of the sulfate group from NCS. Other illustrated mutations from the chicken 2OST enzyme amino acid sequence (SEQ ID NO: 179), particularly mutations present in SEQ ID NO: 65 (His-20, Ser-114, Lys-116, Met-122) may similarly drive binding of NCS within the active site, either by providing a direct binding contact with the sulfate moiety within NCS (His-20), coordinating with other mutated residues (Ser-114 coordinating with His-221), or by increasing the hydrophobic environment near NCS (Met-122).

Those skilled in the art would appreciate that engineered 2OST enzymes of any other amino acid sequence, including, but not limited to, those disclosed by SEQ ID NO: 68 and SEQ ID NO: 69, would likely exhibit a similar structure to the chicken 2OST, as well as engineered 2OSTs having the amino acid sequence of SEQ ID NO: 63 and SEQ ID NO: 65. Without being limited by a particular theory, it is believed that PNS would bind in a similar position as NCS within the active site of any of the engineered 2OST enzymes, since the structures of the two aryl sulfate compounds are very similar, except that the sulfate group is located ortho on the aromatic ring relative to the nitro group in NCS, rather than para to the nitro group in PNS.

Accordingly, in another embodiment, an engineered 2OST enzyme of the present invention can comprise an amino acid sequence selected from the group consisting of SEQ ID NO: 63, SEQ ID NO: 65, SEQ ID NO: 68, and SEQ ID NO: 69. In another embodiment, engineered 2OST enzymes comprising the amino acid sequence of SEQ ID NO: 63, SEQ ID NO: 65, SEQ ID NO: 68, or SEQ ID NO: 69 can react with any aryl sulfate compound. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

In another embodiment, within reaction mixtures that comprise any natural or engineered 2OST enzyme, particularly an engineered 2OST enzyme comprising the amino acid sequence of SEQ ID NO: 63, SEQ ID NO: 65, SEQ ID NO: 68, or SEQ ID NO: 69, the reaction mixture can further comprise a glucuronyl $C_5$-epimerase to catalyze formation of an N,2O-HS product. In some embodiments, the N,2O-HS product can comprise the structure of Formula VI. In other embodiments, the N,2O-HS product can comprise the structure of Formula VII. In another embodiment, the glucuronyl $C_5$-epimerase can comprise the amino acid sequence of SEQ ID NO: 67. In another embodiment, the glucuronyl $C_5$-epimerase can comprise residues 34-617 of SEQ ID NO: 67.

Engineered 6OSTs

In nature, 6OSTs generally recognize, bind, and react with N-, 2-O sulfated heparosan-based polysaccharides (N,2O-HS) as sulfo group acceptors. Additionally, either adjacent hexuronic acid residue can be either glucuronic acid or iduronic acid, and can optionally be 2-O sulfated. Typically, the hexuronic acid at the non-reducing end of the glucosamine residue receiving the 6-O sulfo group is 2-O sulfated iduronic acid, and in many instances, the glucosamine residue itself is also N-sulfated. Similar to the natural NDST and 2OST enzymes, natural 6OST enzymes transfer the sulfo group to the polysaccharide upon reacting with PAPS as a sulfo group donor. As with wild-type 2OSTs, natural 6OST enzymes are also members of the EC 2.8.2.- enzyme class. In a non-limiting example, natural 6OST enzymes can recognize, bind, and react with N,2O-HS polysaccharides comprising the structure of Formula VIII, below:

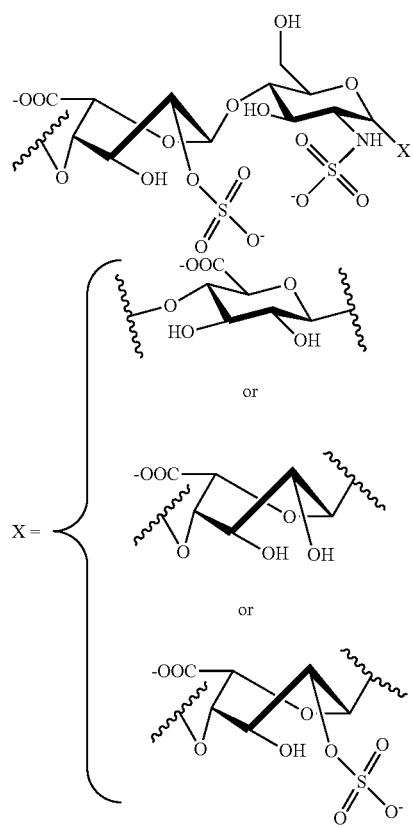

wherein the glucosamine residue receiving the 6-O sulfo group is N-sulfated and is adjacent to a 2-O sulfated iduronic acid residue at its non-reducing end, and X comprises any of the hexuronyl residues depicted in Formula VIII, above. Natural 6OST enzymes having biological activity with N,2O-HS, including but not limited to those comprising the structure of Formula VIII, have been described by Xu, Y., et al., (2017) *ACS Chem. Biol.* 12 (1):73-82 and Holmborn, K., et al., (2004) *J. Biol. Chem.* 279, (41):42355-42358, the disclosures of which are incorporated by reference in their entireties.

As described above, although the portion of the heparosan-based polysaccharide that reacts with the 6OST enzyme can comprise the structure of Formula VIII, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similar to the other engineered sulfotransferase enzymes above, engineered 6OST enzymes can transfer a sulfo group to multiple glucosamine residues within the same polysaccharide molecule, and multiple glucosamine residues within the same polysaccharide molecule can be 6-O sulfated by the same polypeptide. Typically, heparosan-based polysaccharides that can react with the engineered 6OST enzymes, including N,2O-HS polysaccharides comprising the structure of Formula VIII, can comprise at least three monosaccharide residues. In another embodiment, engineered 6OSTs of the present invention can have the same preference as natural 6OST enzymes for N,2O-HS, particularly with N,2O-HS comprising the structure of Formula VIII, as a sulfo group acceptor.

Upon successfully binding PAPS and an N,2O-HS comprising the structure of Formula VIII, natural 6OST enzymes can catalyze transfer of the sulfo group to the 6-O position of the glucosamine residue, forming an N,2O,6O-HS product comprising the structure of Formula IX, below:

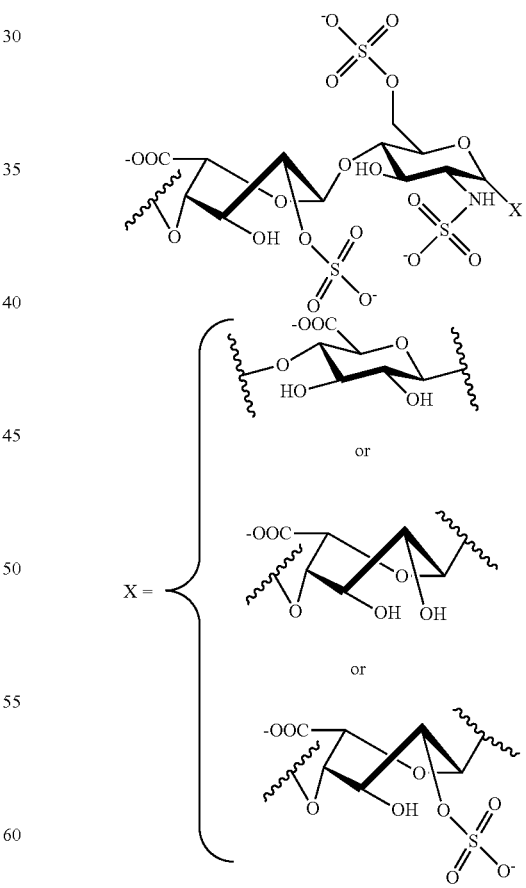

wherein X comprises any of the hexuronyl residues depicted in Formula IX, above.

Figure 20:
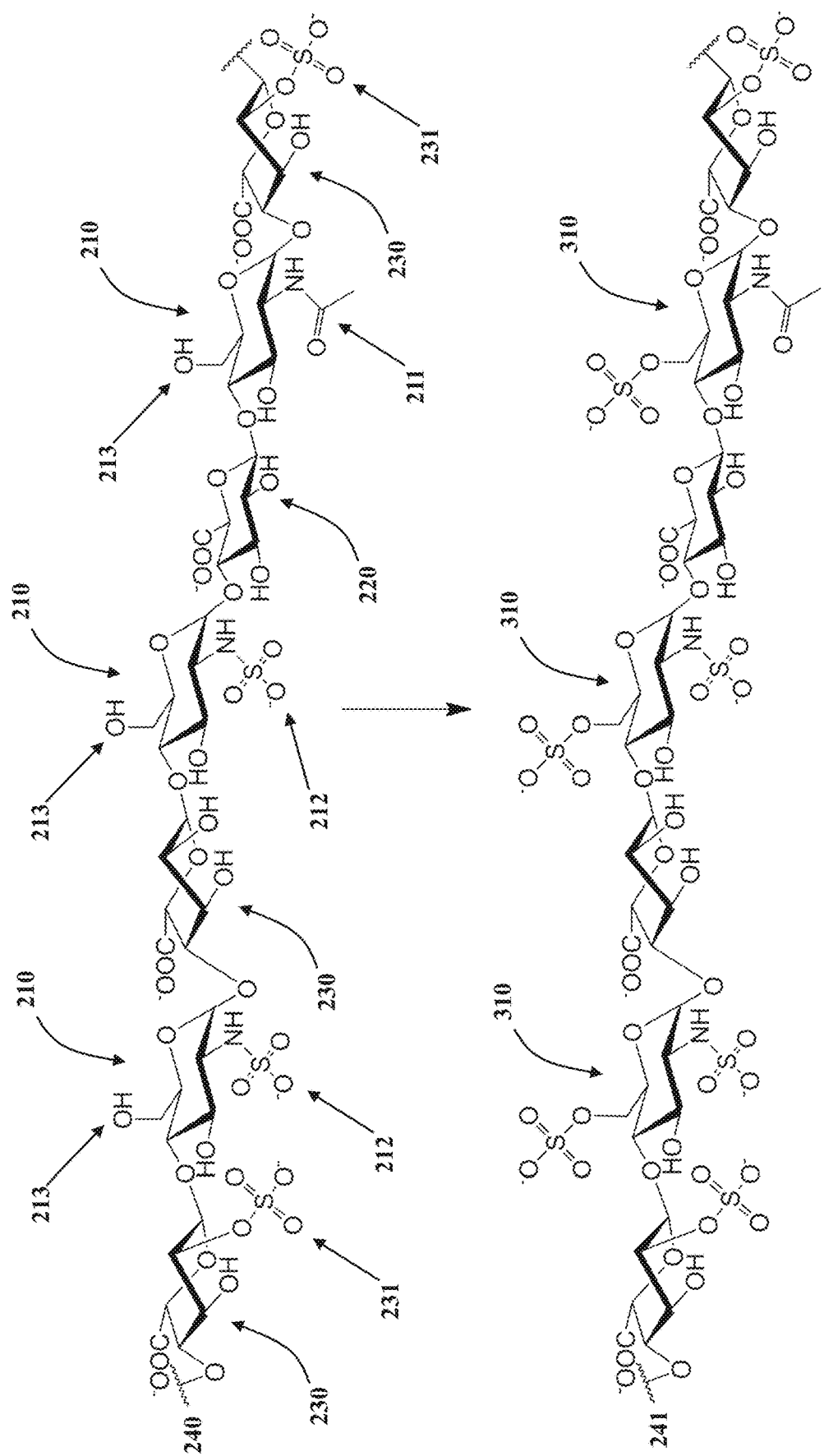
FIG. 20 shows a non-limiting example of a heparosan-based polysaccharide that can be used as a sulfo group acceptor with engineered 6OST enzymes of the present invention, in which the 6-O position of multiple glucosamine residues can receive a sulfo group.

In another embodiment, engineered 6OSTs of the present invention can bind and react with any of the heparosan-based polysaccharides described herein, including heparosan-based polysaccharides that are recognized as sulfo group acceptors by the engineered NSTs, engineered 2OSTs, and engineered 3OSTs (described in further detail below). In another embodiment, engineered 6OSTs of the present invention can bind and react with N,2O-HS comprising the structure of Formula VIII, in order to form N,2O,6O-HS products comprising the structure of Formula IX. A non-limiting example of one such heparosan-based polysaccharide that can react with an engineered 6OST enzyme as a sulfo group acceptor is illustrated in FIG. 20. FIG. 20 shows a polysaccharide 240 that includes three N-substituted glucosamine residues 210 that can be N-substituted with either an acetyl group 211 or a sulfate group 212. Within the polysaccharide 240, N-substituted glucosamine residues 210 that are capable of acting as a sulfo acceptor are flanked by two hexuronyl residues. Hexuronyl residues can include any residue represented by the functional group "X" in Formula VIII, particularly glucuronyl residue 220 and iduronyl residue 230. Either the glucuronyl residue 220 or iduronyl residue 230 can further be substituted by a sulfate group 231 at the 2-O position. Upon reacting the polysaccharide 240 with an engineered 6OST enzyme and a sulfo group donor, the 6-O position 213 of any of the glucosamine residues 210 can be sulfated, ultimately forming 6-O sulfated glucosamine residues 310 within the product polysaccharide 241.

Natural 6OST enzymes generally comprise approximately 300-700 amino acid residues that can in some cases vary greatly in their sequence, yet ultimately have the exact same function, namely, to catalyze the transfer of a sulfo group from PAPS to the 6-O position of glucosamine residues within N,2O-HS, particularly those comprising the structure of Formula VIII. Without being limited by a particular theory, it is believed that each of the natural 6OSTs can catalyze the same chemical reaction because there are multiple amino acid sequence motifs and secondary structures that are either identical or highly conserved across all species.

Figure 21A:
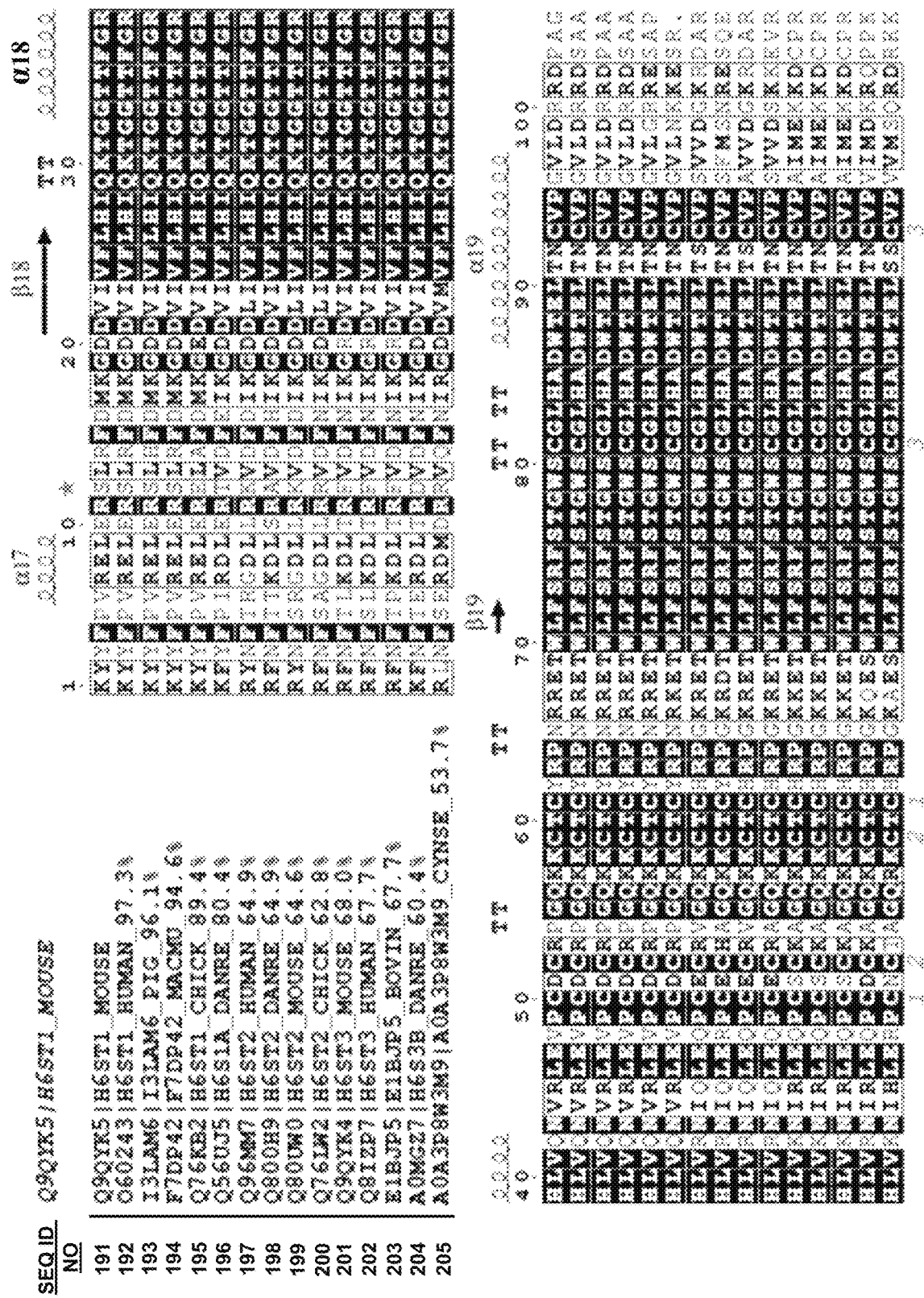
FIG. 21A, FIG. 21B, and FIG. 21C show a multiple sequence alignment for fifteen wild-type 6OST enzymes within EC 2.8.2.-, illustrating conserved amino acid sequence motifs that are present regardless of overall sequence identity.
Figure 21B:
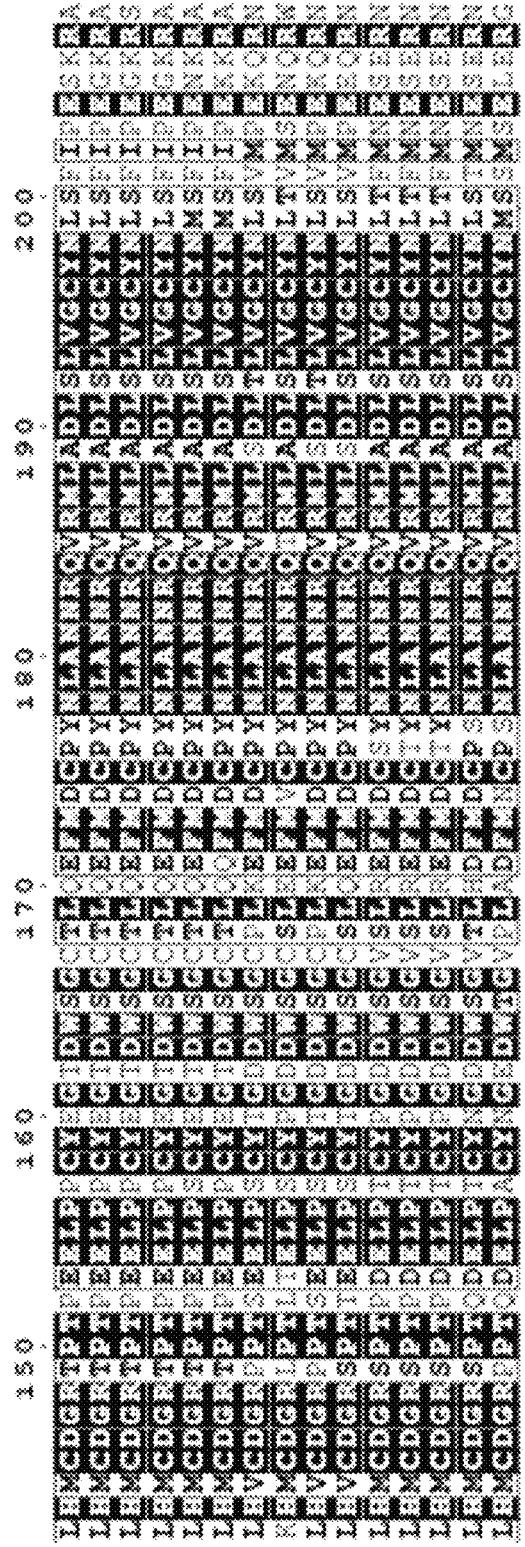
Figure 21C:
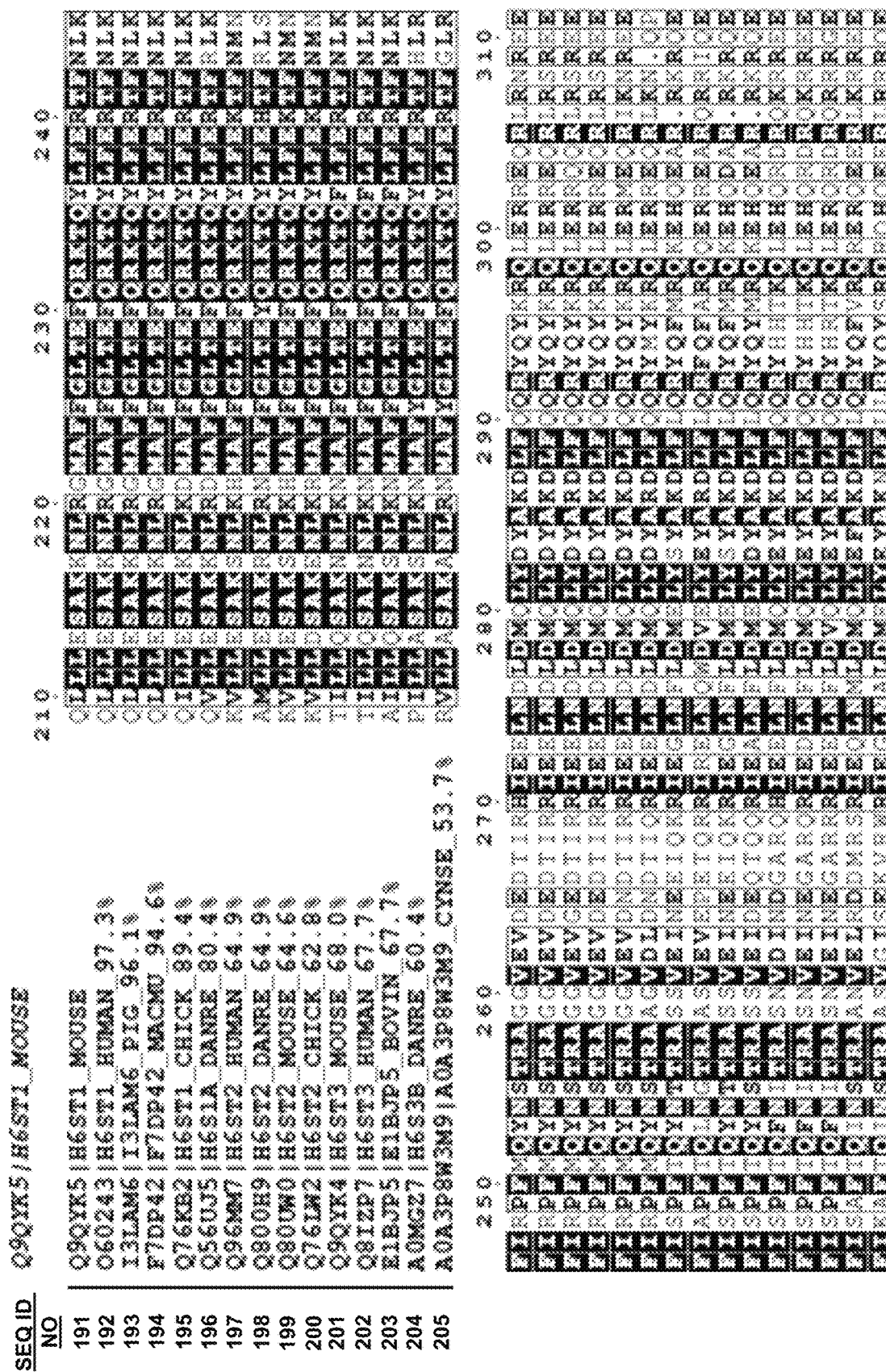

Further, it is believed that several of the conserved amino acid sequence motifs are directly involved in binding of either PAPS and/or the polysaccharide, or participate in the chemical reaction itself. The identity between the natural 6OST enzymes can be demonstrated by comparing the amino acid sequence of the zebrafish 6OST isoform 3-B enzyme (SEQ ID NO: 204), which has known crystal structures (PDB codes 5T03, 5T05 and 5T0A) in which amino acid residues within the active site have been identified, alongside the amino acid sequences of other natural 6OSTs. A multiple sequence alignment of fifteen enzymes (SEQ ID NOs 191-205) is shown in FIG. 21A, FIG. 21B, and FIG. 21C, along with the percent identity of each sequence relative to the mouse 6OST (isoform 1) reference sequence (SEQ ID NO: 191, UniProtKB Accession No. Q9QYK5). As illustrated in FIG. 21A, FIG. 21B, and FIG. 21C, sequences range from having 97.3% identity with the Q9QYK5 reference sequence (SEQ ID NO: 192, entry O60243|H6ST1_HUMAN) down to 53.7% identity (SEQ ID NO: 205, entry A0A3P8W3M9| A0A3P8W3M9_CYSNE). For comparison, the zebrafish 6OST3-B enzyme (SEQ ID NO: 204, entry A0MGZ7|H6S3B_DANRE) has 60.4% sequence identity with SEQ ID NO: 191. Those skilled in the art would appreciate that the multiple sequence alignment was limited to fifteen sequences for clarity, and that there are hundreds of amino acid sequences encoding for natural 6OST enzymes that have been identified and that have highly conserved active site and/or binding regions as well.

Within FIG. 21A, FIG. 21B, and FIG. 21C, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural zebrafish 6OST enzyme (SEQ ID NO: 204) as a reference. The β symbol adjacent to an arrow refers to a β-sheet, whereas a coil adjacent to an α symbol refers to a helix secondary structure. Each of the fifteen aligned sequences in illustrated FIG. 21A, FIG. 21B, and FIG. 21C (SEQ ID NOs 191-205) have been truncated relative to their natural full-length sequences to coincide with the engineered enzymes of the present invention, particularly those having the amino acid sequences SEQ ID NO: 104, SEQ ID NO: 106, and SEQ ID NO: 108. In particular, the residues illustrated in FIG. 21A, FIG. 21B, and FIG. 21C are aligned with residues 67-377 of SEQ ID NO: 191.

Figure 22A:
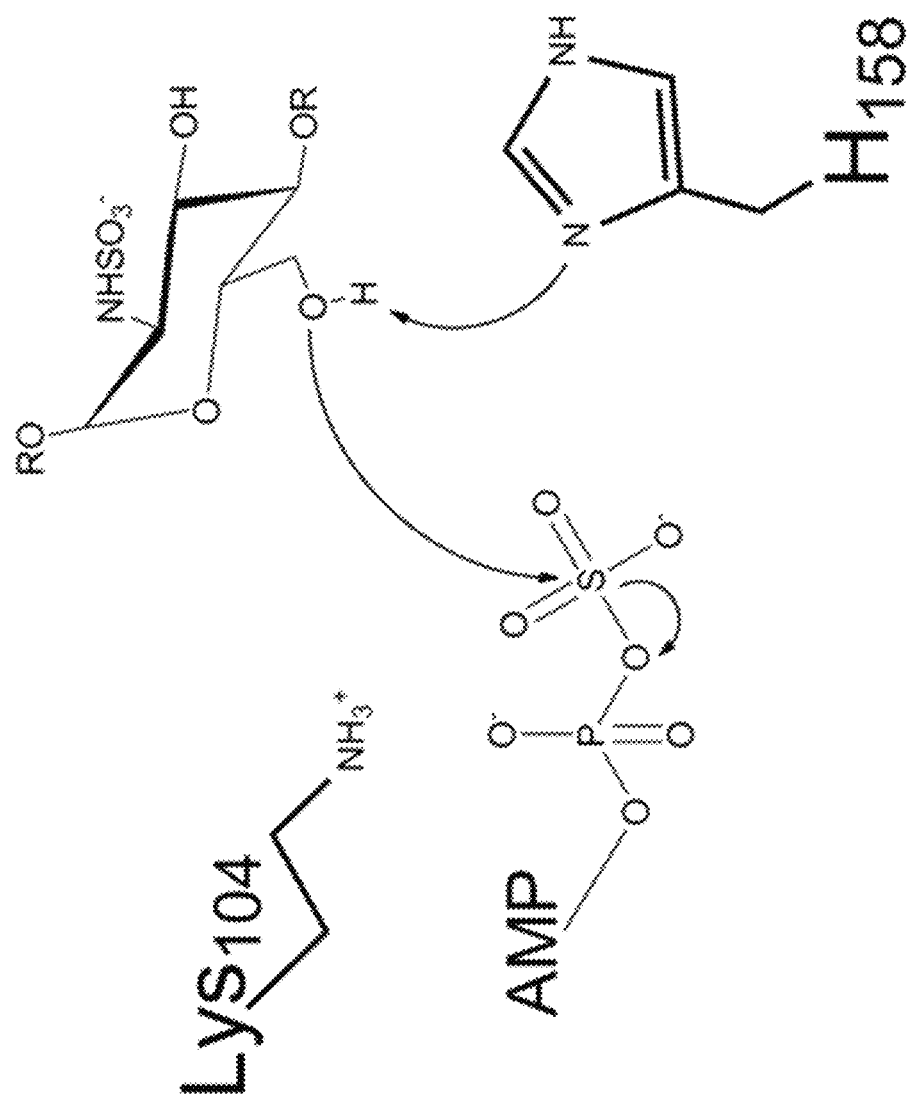
FIG. 22A, FIG. 22B, and FIG. 22C show a proposed reaction mechanism, transition state, and products formed as a result of a sulfotransfer reaction between conserved residues within natural 6OST enzymes, PAPS, and a heparosan-based polysaccharide.
Figure 22B:
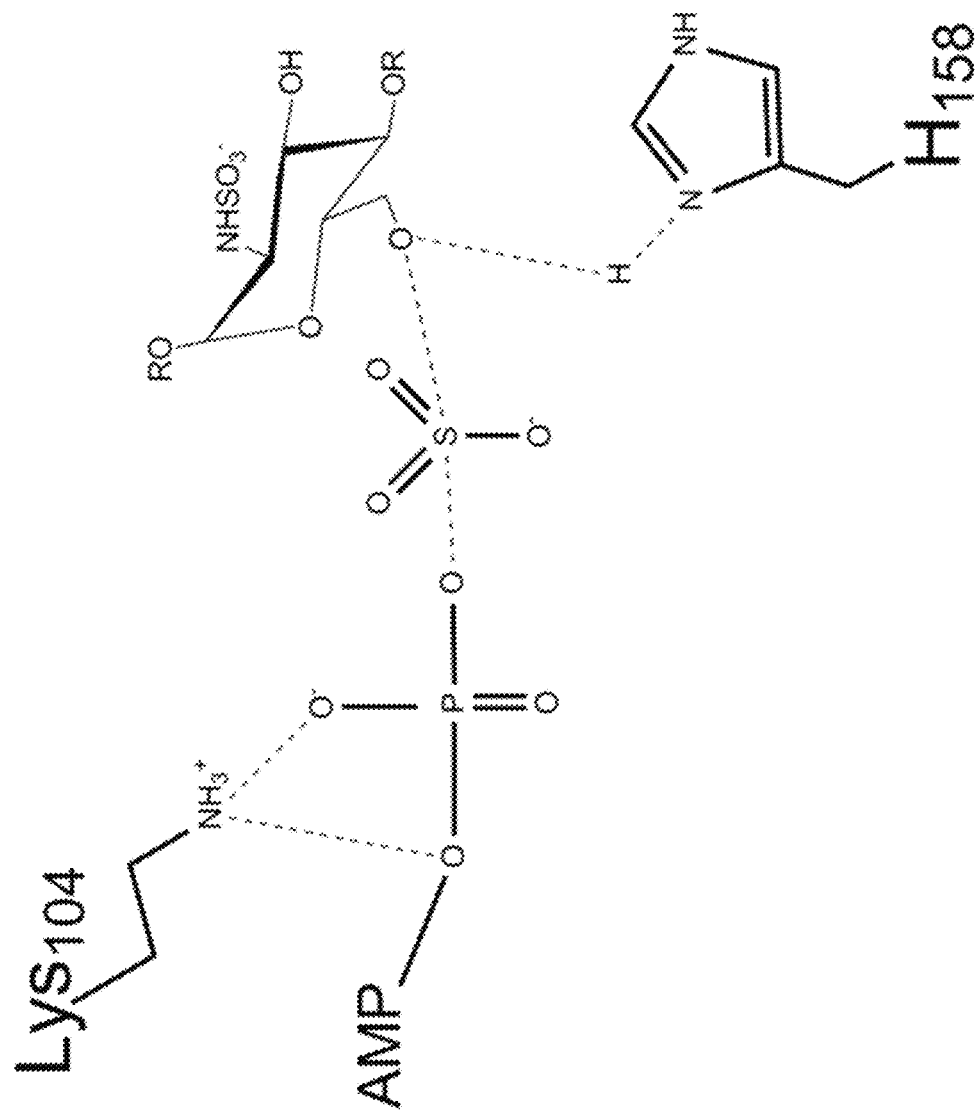
Figure 22C:
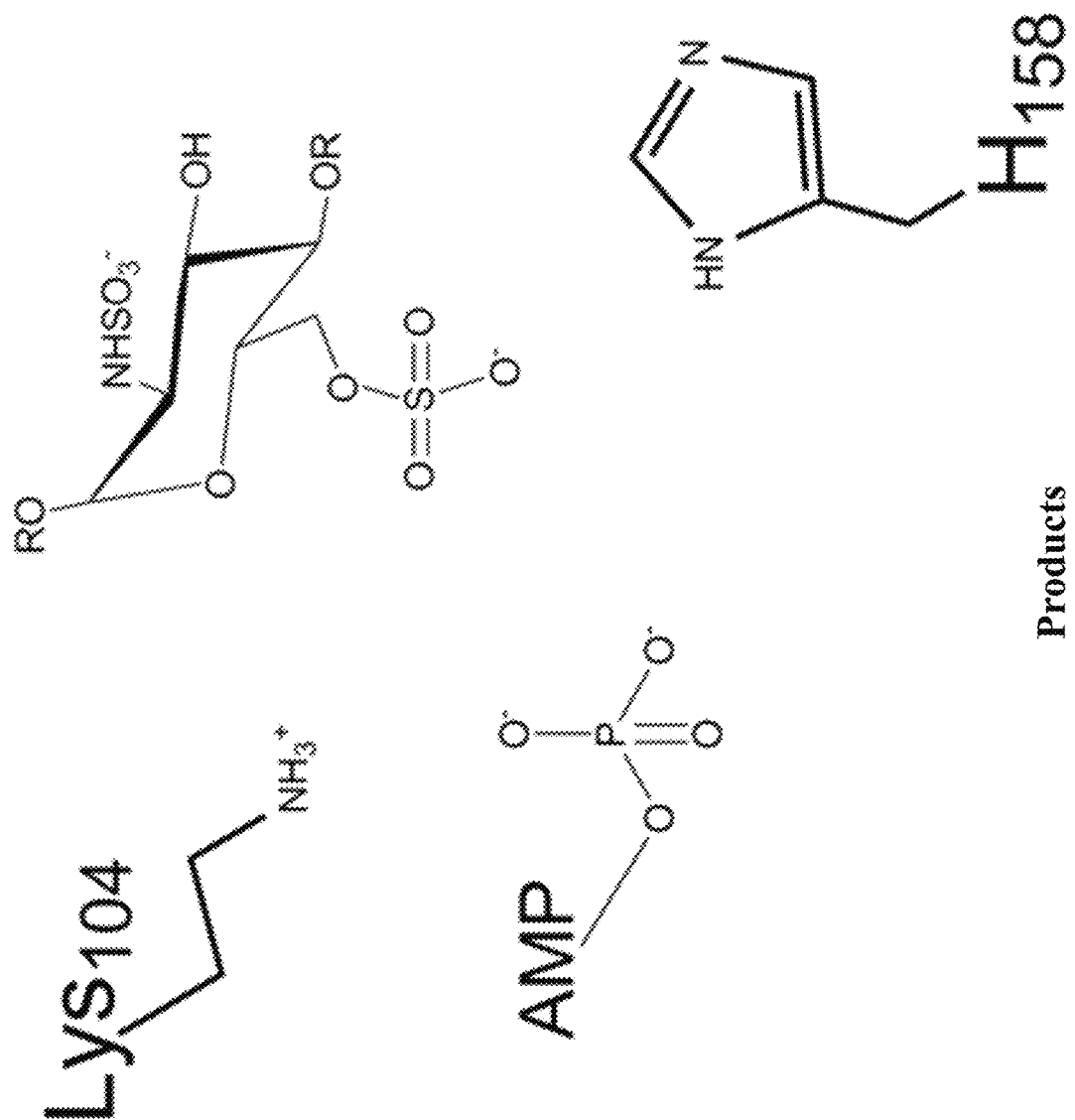

Within the fifteen aligned sequences in FIG. 21A, FIG. 21B, and FIG. 21C, there are several conserved amino acid sequence motifs that include one or more amino acids that comprise the active site, based on the crystal structure of the zebrafish 6OST3-B enzyme (SEQ ID NO: 204, entry A0MGZ7|H6S3B_DANRE) described above. Based on the numbering of the amino acid residues within FIG. 21A, FIG. 21B, and FIG. 21C, these conserved amino acid sequence motifs include amino acid residues 29 through 34 (Q-K-T-G-G-T); 81 through 86 (C-G-L-H-A-D); 127 through 139 (S-E-W-R/K-H-V-Q-R-G-A-T-W-K); 178 through 184 (N-L-A-N-N-R-Q); and 227 through 231 (L-T-E-F/Y-Q), which correspond to SEQ ID NO: 254, SEQ ID NO: 255, SEQ ID NO: 256, SEQ ID NO: 290, and SEQ ID NO: 276 in the sequence listing, respectively. In particular, and as illustrated in FIG. 22A, FIG. 22B, and FIG. 22C, the histidine residue within the C-G-L-H-A-D conserved amino acid sequence motif (SEQ ID NO: 255) appears to be in position to abstract the hydrogen atom from the 6'-hydroxyl group of an N-sulfoglucosamine residue, enabling the negatively-charged oxygen atom to then initiate the nucleophilic attack of PAPS and remove the sulfate group. Additionally, the universally conserved lysine residue within the Q-K-T-G-G-T conserved amino acid sequence motif (SEQ ID NO: 254) appears to coordinate with the 5'-phosphate in PAPS, while the universally conserved histidine and tryptophan residues at positions 131 and 138 coordinate with the N-sulfoglucosamine residue (see Xu, Y., et al., above).

However, as described above, natural 6OST enzymes are unable to catalyze the transfer of the sulfate group from an aryl sulfate compound to a polysaccharide. Without being limited by a particular theory, and as with the natural NDST and 2OST enzymes described above, it is believed that the binding pocket for PAPS within the active site of the natural 6OST either does not have a high enough affinity for aryl sulfate compounds to facilitate binding and/or that the aryl sulfate compounds are sterically hindered from entering the active site. Consequently, and in another embodiment, a natural 6OST enzyme can be mutated in several locations to enable binding of the aryl sulfate compound within the active site and/or to optimally position the aryl sulfate compound so transfer of the sulfate group to the polysaccharide can occur.

Accordingly, and in another embodiment, engineered 6OST enzymes of the present invention can be mutants of natural 6OST enzymes within EC 2.8.2.-, including enzymes having the amino acid sequences illustrated in FIG. 21A, FIG. 21B, and FIG. 21C (SEQ ID NOs 191-205). In another embodiment, mutations engineered into the amino acid sequences of the engineered 6OST enzymes facilitate a biological activity in which aryl sulfate compounds can both bind and react with the enzyme as sulfo group donors. In another embodiment, although the engineered 6OST enzymes can bind and react with an aryl sulfate compound as a sulfo group donor, they can retain the natural 6OST enzymes' biological activity with N,2O-HS polysaccharides, including but not limited to those comprising the structure of Formula VIII, as sulfo group acceptors. Without being limited by a particular theory, it is believed that because of the mutations selected for the amino acid sequences of the engineered 6OST enzymes, their sulfotransferase activity may comprise the direct transfer of a sulfuryl group from an aryl sulfate compound to the heparosan-based polysaccharide, using a similar mechanism as described in FIGS. 22A-22C, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 6-O position of a glucosamine residue, to form a 6-O sulfated HS product. In another embodiment, the 6-O sulfated HS product of either sulfotransfer mechanism is an N,2O,6O-HS product. Engineered 6OST enzymes of the present invention are able to achieve sulfo group transfer from an aryl sulfate compound to N,2O-HS, as described in the examples below.

In another embodiment, an engineered 6OST enzyme can comprise one or more mutated amino acid sequence motifs relative to the conserved amino acid sequence motifs (SEQ ID NO: 254, SEQ ID NO: 255, SEQ ID NO: 256, SEQ ID NO: 290, and SEQ ID NO: 276) found in natural 6OST enzymes, as described above and indicated in the multiple sequence alignment of SEQ ID NOs 191-205 in FIG. 21A, FIG. 21B, and FIG. 21C. In another embodiment, each mutated amino acid sequence motif that is present in the amino acid sequence of the engineered 6OST enzyme comprises at least one amino acid mutation relative to the corresponding conserved amino acid sequence motif within the natural 6OST enzymes. In another embodiment, an engineered 6OST enzyme can comprise one mutated amino acid sequence motif. In another embodiment, an engineered 6OST enzyme can comprise two mutated amino acid sequence motifs. In another embodiment, an engineered 6OST enzyme can comprise three mutated amino acid sequence motifs. In another embodiment, an engineered 6OST enzyme can comprise four mutated amino acid sequence motifs. In another embodiment, an engineered 6OST enzyme can comprise five mutated amino acid sequence motifs. In another embodiment, an engineered 6OST enzyme that includes at least one mutated amino acid sequence motif relative to any of the natural 6OST enzymes within EC 2.8.2.- can have an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

Figure 23:
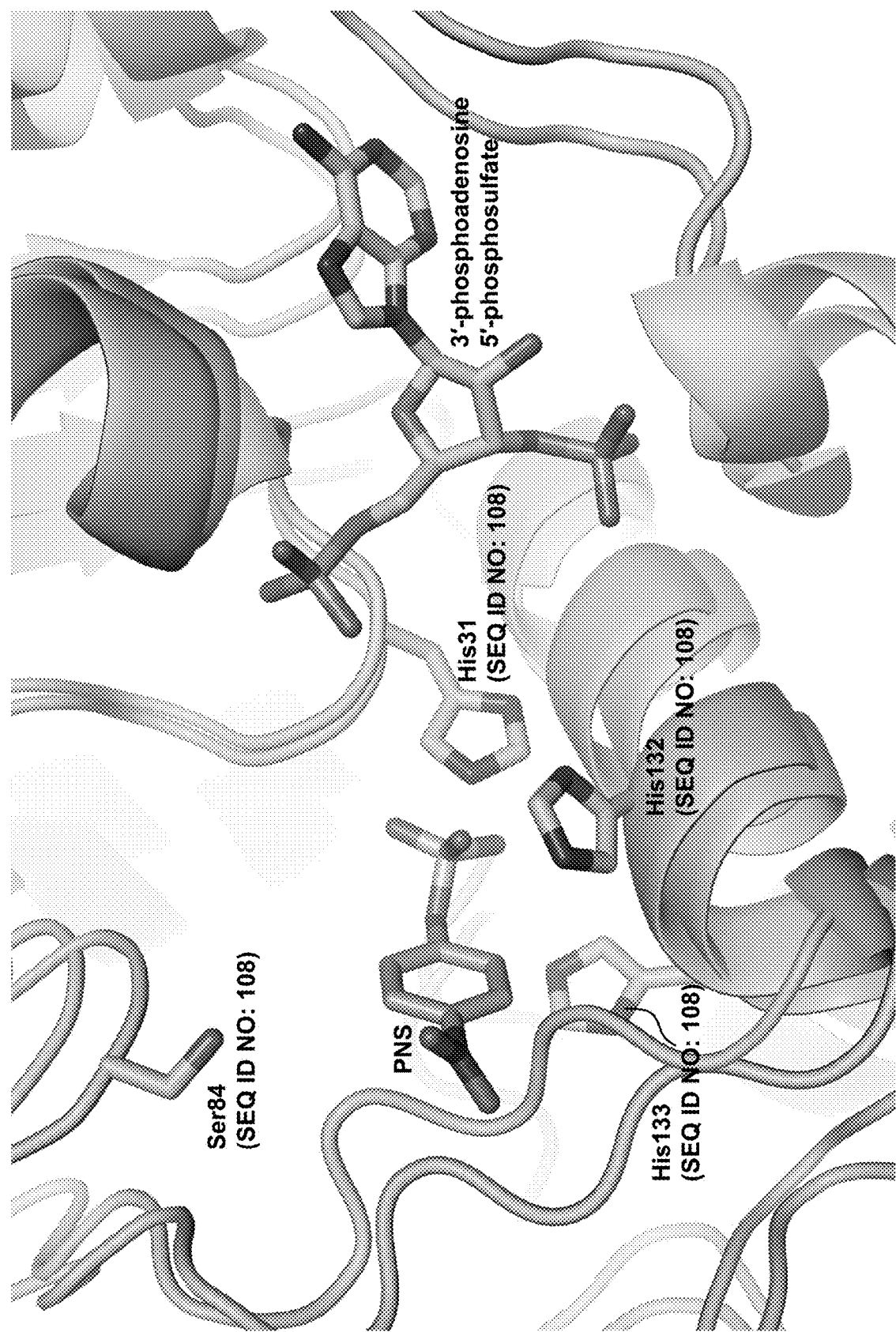
FIG. 23 shows a three-dimensional model of a mutated amino acid sequence motif enabling binding of PNS within the active site of an engineered 6OST enzyme, superimposed over the crystal structure of a natural 6OST enzyme.

In another embodiment, upon viewing any of the crystal structures of the zebrafish 6OST3-B (SEQ ID NO: 204, UniProtKB Accession No. A0MGZ7) within a 3D molecular visualization system (including, as a non-limiting example, the open-source software, PyMOL), the structure of related sequences, such as those of engineered 6OST enzymes that contain one or more mutated amino acid sequence motifs relative to any of the zebrafish 6OST structures, can be modeled for comparison as illustrated in FIG. 23. FIG. 23 shows a magnified view of the active site of the zebrafish 6OST3-B enzyme (PDB code: 5T03) overlaid with one of the engineered enzymes of the present invention, comprising the amino acid sequence of SEQ ID NO: 108, in which the structure of the engineered 6OST enzyme is calculated upon making mutations relative to the zebrafish 6OST amino acid sequence. Adenosine 3',5'-diphosphate, which is the product of a sulfotransfer reaction in which PAPS is the sulfo donor, and which was co-crystallized with the zebrafish 6OST3-B, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 23, although there are several mutations made SEQ ID NO: 108, relative to the zebrafish 6OST enzyme, the respective protein backbones appear to be in a nearly identical location to one another, enabling a one-to-one comparison of the active sites. However, when comparing the two active sites, the adenosine 3',5'-diphosphate product appears to be located on the opposite side of the central a-helix as the PNS molecule, as determined by the convergent solutions from the above MD simulations. Without being limited by a particular theory, it is believed that the convergent MD simulation solutions place PNS on the opposite side of the a-helix because there is not enough of an affinity toward PNS in the same or similar position as PAPS within the zebrafish enzyme. As described by Xu, Y., et al., above, the conserved histidine abstracts the proton from the 6' hydroxyl group of N-sulfoglucosamine, which is then subsequently able to react with PAPS to initiate sulfo group transfer. Yet, despite the apparent differences in the binding pocket for PAPS and PNS, engineered 6OST enzymes comprising the amino acid sequences of SEQ ID NO: 104, SEQ ID NO: 106, and SEQ ID NO: 108 all achieved sulfo group transfer from an aryl sulfate compound to the 6-O position of one or more glucosamine residues within a heparosan-based polysaccharide, as described in the examples below.

Figure 24:
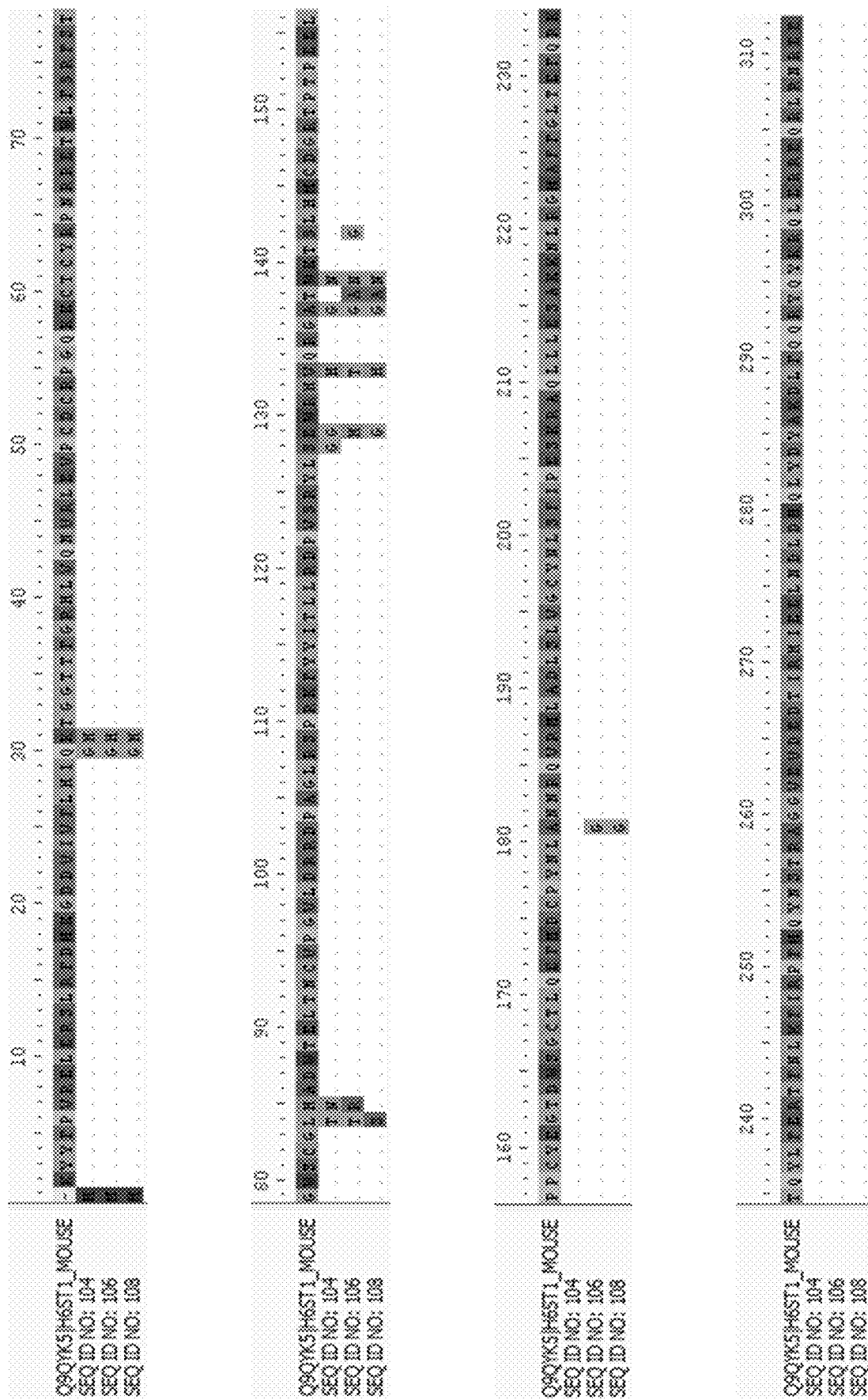
FIG. 24 shows a sequence alignment of polypeptides comprising the amino acid sequences of SEQ ID NO: 104, SEQ ID NO: 106, and SEQ ID NO: 108, respectively, depicting the position and identity of amino acid residues differences between each of the illustrated sequences.

As a result, and without being limited by a particular theory, one or more of the mutations present within the active site of engineered 6OST enzymes may assist binding of the sulfate moiety of the aryl sulfate compound in a position in which it can be transferred to the sulfo acceptor HS polysaccharide. As illustrated in FIG. 23, the engineered enzyme has the amino acid sequence SEQ ID NO: 108, and the aryl sulfate compound is PNS. However, a heparosan-based polysaccharide is not illustrated. In a non-limiting example, the histidine residue engineered into position 31 of SEQ ID NO: 108 may be in position to facilitate removal of the sulfate group from PNS using a ping-pong mechanism, similar to the mechanism described in Malojcic, et al, above. Additionally, the histidine residue engineered into position 133 of SEQ ID NO: 108 may further coordinate with the sulfate moiety along with the conserved histidine at position 132 of SEQ ID NO: 108 (corresponding to position 131 in each of SEQ ID NOs 190-205). Mutation to G-A-N at positions 137-139 of SEQ ID NO: 22 (corresponding to the conserved A-T-W motif at positions 136-138 of SEQ ID NOs 190-205) removes steric bulk that may prevent binding of PNS in a position where the sulfate can be abstracted by the engineered histidine at position 31 of SEQ ID NO: 108. The mutations to G-A-N within the loop containing A-T-W also appears to cause the loop to move away from PNS, which may further assist PNS to reach its binding pocket. Finally, a serine residue engineered into position 84 of SEQ ID NO: 108 may create an additional hydrogen-binding contact to assist the engineered enzyme in retaining the zebrafish enzyme's natural activity with the sulfo acceptor polysaccharide.

Those skilled in the art would appreciate that engineered 6OST enzymes of any other amino acid sequence, including, but not limited to, those disclosed by SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, would likely exhibit similar structural motifs, particularly within the active site. Without being limited by a particular theory, it is believed that NCS would bind in a similar position as PNS within any of the engineered enzymes, since the structures of the two aryl sulfate compounds are very similar, except that the sulfate group is located ortho on the aromatic ring relative to the nitro group, rather than para to the nitro group.

In another embodiment, engineered 6OST enzymes that can be utilized in accordance with methods of the present invention can comprise one or more mutated amino acid sequence motifs, which can be determined in-part by comparing conserved amino acid sequence motifs indicated in the multiple sequence alignment of SEQ ID NOs 191-205 in FIG. 21A, FIG. 21B, and FIG. 21C with the known structure(s) of natural enzymes and/or modeled engineered enzymes, including but not limited to, as a non-limiting example, enzymes illustrated in FIG. 23. In another embodiment, mutated amino acid sequence motifs that can be comprised within an engineered 6OST enzyme can be selected from the group consisting of (a) G-H-T-G-G-T (SEQ ID NO: 257); (b)C-G-$X_1$-$X_2$-A-D (SEQ ID NO: 291), wherein $X_1$ is selected from the group consisting of threonine and serine, and $X_2$ is selected from the group consisting of asparagine, arginine, and histidine; (c) $X_3$-$X_4$-W-R-H-$X_5$-Q-R-G-G-$X_6$-N-K (SEQ ID NO: 260), wherein $X_3$ is selected from the group consisting of serine and glycine, $X_4$ is selected from the group consisting of glycine and histidine, $X_5$ is selected from the group consisting of histidine and threonine, and $X_6$ is selected from the group consisting of alanine and threonine; and (d)N-L-$X_7$-N-N-R-Q (SEQ ID NO: 292), wherein $X_7$ is selected from the group consisting of alanine and glycine; including any combination thereof. Each of the mutated amino acid sequence motifs corresponds with a conserved amino acid motif indicated in FIG. 21A, FIG. 21B, and FIG. 21C above: SEQ ID NO: 257 corresponds to the conserved amino acid sequence motif, Q-K-T-G-G-T (SEQ ID NO: 254); mutated amino acid sequence motif SEQ ID NO: 291 corresponds to the conserved amino acid sequence motif, C-G-L-H-A-D (SEQ ID NO: 255); mutated amino acid sequence motif SEQ ID NO: 260 corresponds to the conserved amino acid sequence motif, S-E-W-(R/K)-H-V-Q-R-G-A-T-W-K (SEQ ID NO: 256); and mutated amino acid sequence motif SEQ ID NO: 292 corresponds to the conserved amino acid sequence motif, N-L-A-N-N-R-Q (SEQ ID NO: 290). In another embodiment, engineered 6OST enzymes comprising at least one mutated amino acid sequence motif described above can be selected from the group consisting of: SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

In another embodiment and in one non-limiting example, engineered 6OST enzymes can comprise the mutated amino acid sequence motifs SEQ ID NO: 291 and SEQ ID NO: 260 within the same amino acid sequence. Engineered enzymes comprising the mutated amino acid sequence motifs SEQ ID NO: 291 and SEQ ID NO: 260 include, but are not limited to, enzymes comprising the amino acid sequences of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122. In another embodiment, each of the engineered 6OST enzymes comprising the mutated amino acid sequence motifs SEQ ID NO: 291 and SEQ ID NO: 260 have a similar active site as SEQ ID NO: 108, as illustrated in FIG. 23. Without being limited to another theory, it is believed that several of the mutations comprised within mutated amino acid sequence motifs SEQ ID NO: 291 and SEQ ID NO: 260 have one or more functions during sulfotransferase activity, including not limited to: increasing the affinity of aryl sulfate compounds to the active site by reducing the size of the binding pocket, increasing the hydrophobicity of the pocket, removing or creating polar or hydrogen bonding contacts, and/or creating π-π interactions with the aromatic moieties of the aryl sulfate compounds; stabilizing the transition state of the enzyme during the chemical reaction; and/or participating in the chemical reaction itself.

In another embodiment, within engineered 6OST enzymes that comprise the mutated amino acid sequence motifs SEQ ID NO: 291 and SEQ ID NO: 260, $X_4$ is glycine and $X_5$ is histidine (as illustrated in SEQ ID NO: 263). In other embodiments, $X_4$ is histidine and $X_5$ is threonine (as illustrated in SEQ ID NO: 264).

In another embodiment, within engineered 6OST enzymes comprising the mutated amino acid sequence motifs SEQ ID NO: 291 and SEQ ID NO: 260, $X_3$ is serine and $X_6$ is alanine (as illustrated in SEQ ID NO: 262), and $X_7$ is glycine (as illustrated in SEQ ID NO: 293). In other embodiments, $X_3$ is glycine and $X_6$ is threonine (as illustrated in SEQ ID NO: 261), and $X_7$ is alanine (as illustrated in SEQ ID NO: 294).

Furthermore, the amino acid sequences (SEQ ID NO: 104, SEQ ID NO: 106, and SEQ ID NO: 108) of three engineered 6OST enzymes, which have been experimentally determined to be active sulfotransferases with aryl sulfate compounds as sulfo group donors (see Example 5 below) can be compared with the amino acid sequence of the mouse 6OST1 enzyme (SEQ ID NO: 191, entry Q9QYK5|H6ST1_MOUSE) in a multiple sequence alignment to determine if there are relationships between mutations among each of the enzymes. A period within the amino acid sequence of an engineered enzyme indicates identity at a particular position with the mouse 6OST enzyme. As shown in FIG. 24, the sequence alignment demonstrates that while over 90% of the amino acid residues within the three sulfotransferase sequences are identical, there are several positions in which multiple amino acids can be chosen. Without being limited by a particular theory, these enzymes have a similar relationship with each other as the natural 6OST enzymes within EC 2.8.2.-. As a result, and in another embodiment, engineered 6OST enzymes comprising an amino acid sequence in which multiple amino acids can be chosen at defined positions are disclosed as SEQ ID NO: 112 and SEQ ID NO: 113. Positions at which the identity of an amino acid can be chosen from a selection of possible residues are denoted in terms "Xaa," "Xn," or "position n," where n refers to the residue position.

In another embodiment, within SEQ ID NO: 112, residues having the designation, "X," illustrate known instances in which there is a lack of identity at a particular position within the amino acid sequences of SEQ ID NO: 104, SEQ ID NO: 106, and SEQ ID NO: 108. In another embodiment, the amino acid sequence, SEQ ID NO: 113, also illustrates known instances in which there is a lack of identity at a particular position within the amino acid sequences of SEQ ID NO: 104, SEQ ID NO: 106, and SEQ ID NO: 108, but SEQ ID NO: 113 further comprises N-terminal residues 1-66, and C-terminal residues 378-411, of several natural full-length 6OST enzymes within EC 2.8.2.-, including, as non-limiting examples, the mouse, human, and pig 6OST1 enzymes (SEQ ID NOs 295-297). In contrast, amino acid residues in SEQ ID NO: 104, SEQ ID NO: 106, SEQ ID NO: 108, and SEQ ID NO: 112 correspond with residues 67-377 of several full-length 6OST enzymes within EC 2.8.2.-, including, as non-limiting examples, the mouse, human, and pig 6OST enzymes (SEQ ID NOs 191-193). To facilitate protein expression, an N-terminal methionine residue was added to each of the SEQ ID NO: 104, SEQ ID NO: 106, SEQ ID NO: 108, and SEQ ID NO: 112 amino acid sequences, relative to residues 67-377 of the mouse, human, and pig 6OST1 enzymes (SEQ ID NOs 191-193).

In another embodiment, any selection can be made for an X residue, defined by the amino acid sequence SEQ ID NO: 112 or SEQ ID NO: 113, so long as the resulting enzyme maintains its 6OST activity upon reacting with an aryl sulfate compound as a sulfo group donor.

In another embodiment, within an engineered 6OST enzyme comprising the amino acid sequence of SEQ ID NO: 112, the amino acid residue at position 129 is glycine and the amino acid residue at position 133 is histidine. In another embodiment, within an engineered 6OST enzyme comprising the amino acid sequence of SEQ ID NO: 112, the amino acid residue at position 129 is histidine and the amino acid residue at position 133 is threonine. In another embodiment, within an engineered 6OST enzyme comprising the amino acid sequence of SEQ ID NO: 113, the amino acid residue at position 194 is glycine and the amino acid residue at position 198 is histidine. In another embodiment, within an engineered 6OST enzyme comprising the amino acid sequence of SEQ ID NO: 113, the amino acid residue at position 194 is histidine and the amino acid residue at position 198 is threonine.

In another embodiment, within an engineered 6OST enzyme comprising the amino acid sequence of SEQ ID NO: 112, the amino acid residue at position 128 is serine, the amino acid residue at position 138 is alanine, and the amino acid residue at position 181 is glycine. In another embodiment, within an engineered 6OST enzyme comprising the amino acid sequence of SEQ ID NO: 112, the amino acid residue at position 128 is glycine, the amino acid residue at position 138 is threonine, and the amino acid residue at position 181 is alanine. In another embodiment, within an engineered 6OST enzyme comprising the amino acid sequence of SEQ ID NO: 113, the amino acid residue at position 193 is serine, the amino acid residue at position 203 is alanine, and the amino acid residue at position 246 is glycine. In another embodiment, within an engineered 6OST enzyme comprising the amino acid sequence of SEQ ID NO: 113, the amino acid residue at position 193 is glycine, the amino acid residue at position 203 is threonine, and the amino acid residue at position 246 is alanine.

In another embodiment, within an engineered 6OST enzyme comprising the amino acid sequence of SEQ ID NO: 112 or SEQ ID NO: 113, the amino acid sequence can optionally include one or more mutations at residue positions not specified by an "Xn" or "X," so long as any such mutations do not eliminate the 6OST and/or aryl sulfate-dependent activity of the enzyme. In another embodiment, such mutations not eliminating aryl sulfate-dependent activity at positions not specified by an "Xn" or "X" can include substitutions, deletions, and/or additions.

Accordingly, in another embodiment, an engineered 6OST enzyme utilized in accordance with any of the methods of the present invention can comprise an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. In another embodiment, engineered 6OST enzymes comprising the amino acid sequence of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122 can react with any aryl sulfate compound. In further embodiments, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

Engineered 3OSTs

In nature, HS 3OSTs generally recognize, bind, and react with N,2O-HS and N,2O,6O-HS heparosan-based polysaccharides as sulfo group acceptors. Generally, the glucosamine residue that receives the sulfo group at the 3-O position is N-sulfated, and is optionally also 6-O sulfated. Additionally, either adjacent hexuronic acid residue can be glucuronic acid or iduronic acid, either of which can optionally be 2-O sulfated. Often, the glucosamine residue being 3-O sulfated is adjacent to a glucuronic acid on its non-reducing end and a 2-O sulfated iduronic acid on its reducing end. Similar to each of the natural sulfotransferases described above, naturally-occurring 3OSTs transfer a sulfo group to the heparosan-based polysaccharide upon reacting with PAPS as a sulfo group donor. Natural 3OST enzymes that utilize PAPS as the sulfo group donor are members of the EC 2.8.2.23 enzyme class. In a non-limiting example, natural 3OST enzymes can recognize, bind, and react with N,2O,6O-HS polysaccharides comprising the structure of Formula X, below:

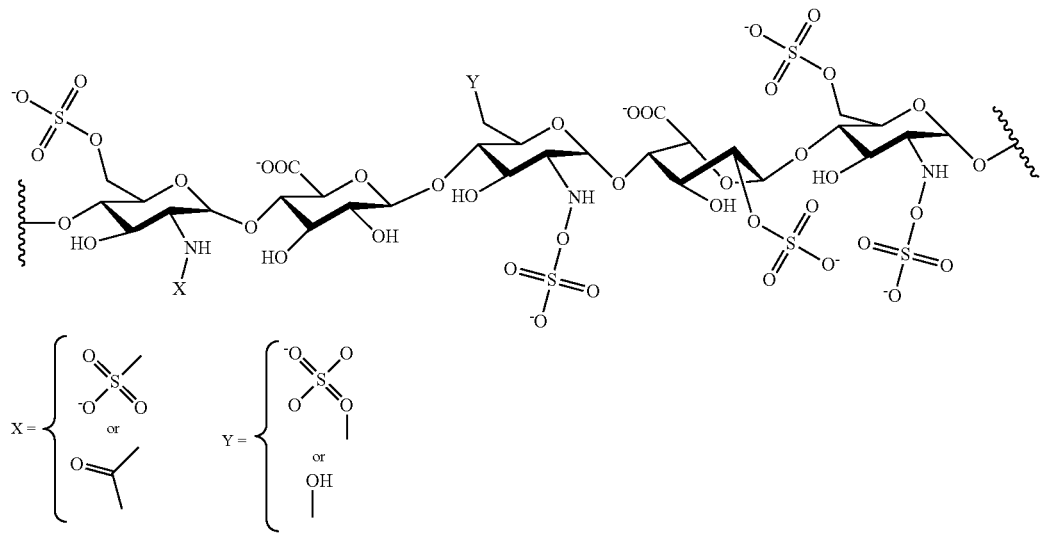

wherein the central glucosamine residue is N-sulfated and is adjacent to glucuronic acid at its non-reducing end and a 2-O sulfated iduronic acid residue at its reducing end, X can optionally be a sulfate group or an acetyl group, and Y can optionally be a sulfate group or a hydroxyl group.

As described above, although the portion of the heparosan-based polysaccharide that reacts with the 3OST enzyme can comprise the structure of Formula X, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similar to the other engineered sulfotransferase enzymes above, engineered 3OST enzymes can transfer a sulfo group to multiple glucosamine residues within the same polysaccharide molecule, and multiple glucosamine residues within a polysaccharide molecule can be 3-O sulfated by the same polypeptide. Typically, N,2O,6O-HS polysaccharides that can react with natural 3OSTs as sulfo group acceptors typically comprise at least five monosaccharide residues, as shown in Formula X. In another embodiment, N,2O,6O-HS polysaccharides comprising the structure of Formula X and can react with natural 3OSTs as sulfo group acceptors can comprise at least thirty-two monosaccharide residues. In another embodiment, engineered 3OSTs of the present invention can have the same preference as natural 3OST enzymes for N,2O, 6O-HS, particularly with N,2O,6O-HS comprising the structure of Formula X, as sulfo group acceptors.

Upon successfully binding PAPS and an N,2O,6O-HS polysaccharide comprising the structure of Formula X, natural 3OST enzymes can catalyze transfer of the sulfo group to the 3-O position of the central glucosamine residue, forming an N,2O,3O,6O-HS product comprising the structure of Formula I, below:

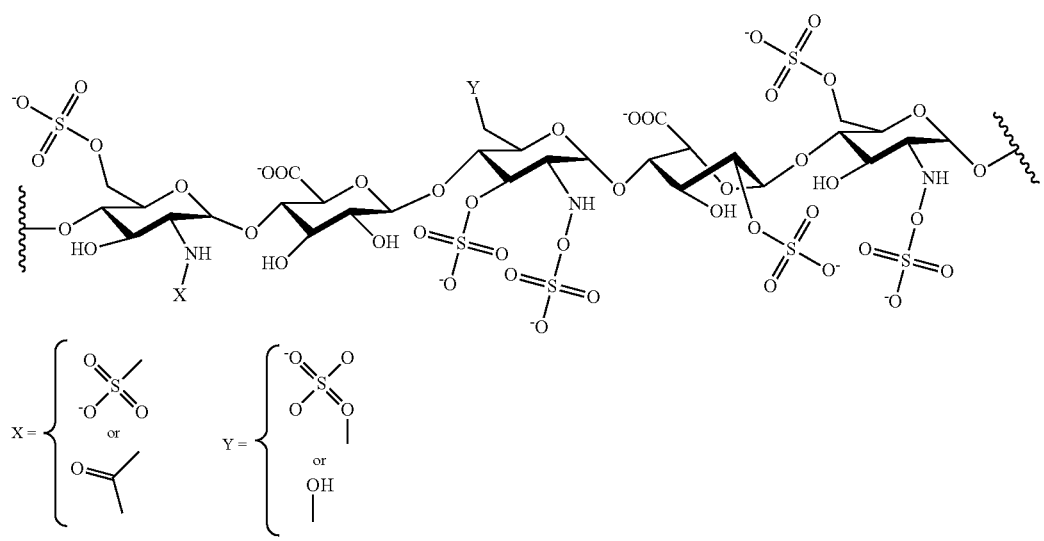

wherein X is either a sulfo group or an acetate group and Y is either a sulfo group or a hydroxyl group. Natural 3OST enzymes, which have biological activity with N,2O,6O-HS polysaccharides comprising the structure of Formula X as sulfo group acceptors and form N,2O,3O,6O-HS products comprising the structure of Formula I, have been described by Xu, D., et al., (2008) *Nat. Chem. Biol.* 4(3): 200-202 and Edavettal, S. C., et al., (2004) *J. Biol. Chem.* 24(11): 25789-25797, the disclosures of which are incorporated by reference in their entireties. Further, N,2O,3O,6O-HS products comprising the structure of Formula I can be found within unfractionated heparin (UFH), as well as low molecular weight heparins (LMWH) that are derived from UFH. Methods for forming anticoagulant N,2O,3O,6O-HS, including UFH, using engineered 3OSTs are described in further detail, below.

Figure 25:
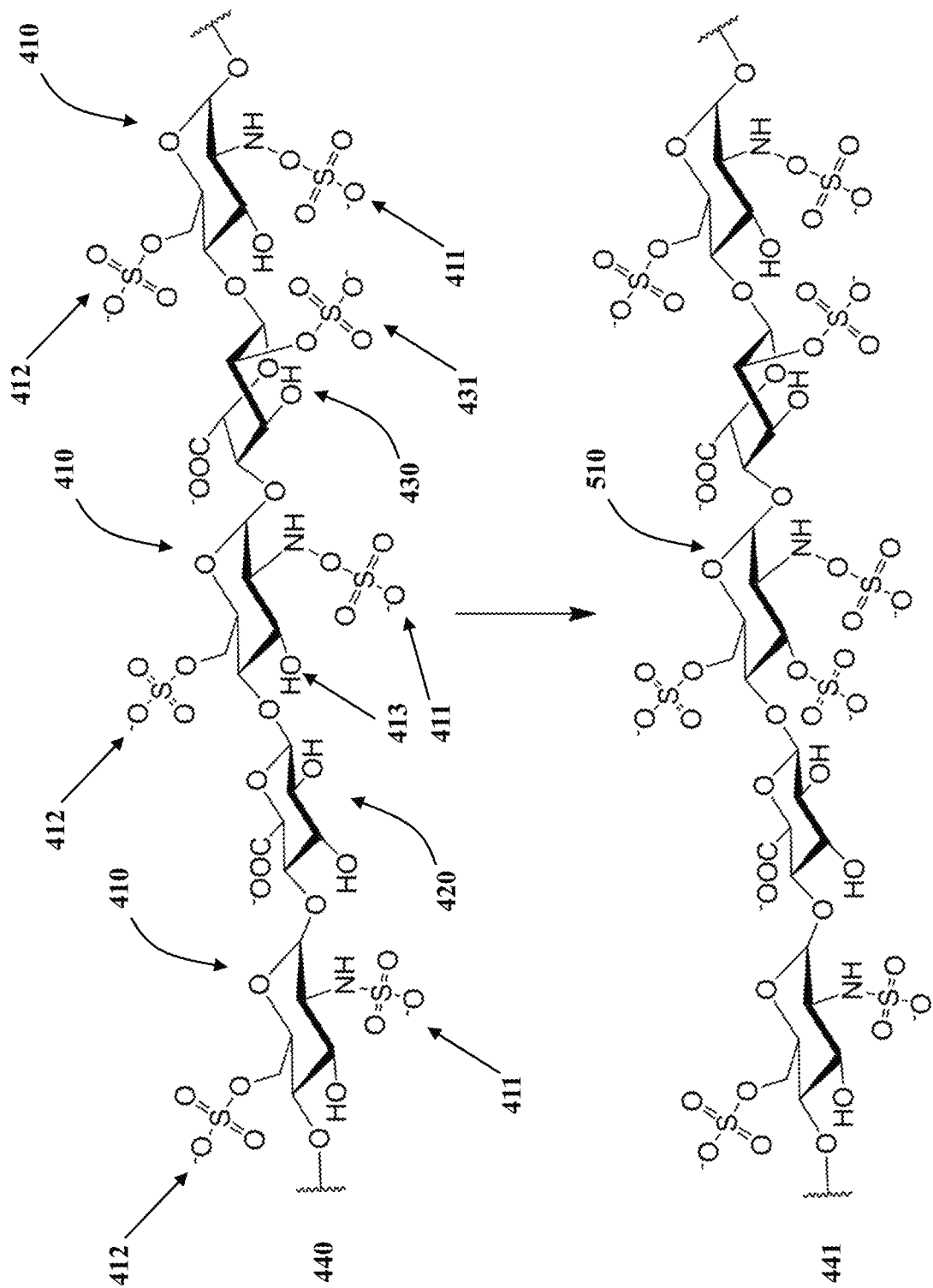
FIG. 25 shows a non-limiting example of a heparosan-based polysaccharide that can be used as a sulfo group acceptor with engineered 3OST enzymes of the present invention, to form an N,2O,3O,6O-HS product comprising a polysaccharide sequence motif having the structure of Formula I.

A non-limiting example of N,2O,6O-HS that can react as a sulfo group acceptor with engineered 3OST enzymes of the present invention is illustrated in FIG. 25. FIG. 25 shows a polysaccharide 440 that includes three glucosamine residues 410 comprising an N-sulfo group 411 at each N-position and an O-sulfo group 412 at each 6-O position. Within the polysaccharide 440, glucosamine residues 410 that are capable of acting as a sulfo acceptor must be flanked by two hexuronic acid residues. Hexuronic acid residues can include any residue represented by the functional group "X" in Formula X, and are shown in FIG. 25 as glucuronic acid residue 420 and iduronic acid residue 430. Either hexuronic acid residue can further be substituted by a sulfo group 431 at the 2-O position. Upon reacting the polysaccharide 440 with an 3OST enzyme and a sulfo group donor, the 3-O position 413 of any of the glucosaminyl residues 410 can be sulfated. As shown in FIG. 25, the central glucosamine residue 410 receives a sulfo group, ultimately forming a 3-O sulfated glucosaminyl residue 510 within the sulfated product polysaccharide 441. Also as shown, sulfated product polysaccharide 441 comprises the structure of Formula I.

Natural 3OST enzymes within EC 2.8.2.23 generally comprise approximately 300-325 amino acid residues that can in some cases vary greatly in their sequence, yet ultimately have the exact same function, namely, to catalyze the transfer of a sulfuryl group from PAPS to the 3-O position of N-sulfoglucosamine residues within N,2O-HS or N,2O,6O-HS polysaccharides, particularly those comprising the structure of Formula X. Without being limited by a particular theory, it is believed that each of the natural 3OSTs within the EC 2.8.2.23 enzyme class can catalyze the same chemical reaction because there are multiple amino acid sequence motifs and secondary structures that are either identical or highly conserved across all species.

Further, it is believed that several of the conserved amino acid sequence motifs are directly involved in binding of either PAPS and/or the polysaccharide, or participate in the chemical reaction itself. The identity between the natural 3OST enzymes can be demonstrated by comparing the amino acid sequences of the mouse or human 3OST1 enzyme (SEQ ID NO: 213 and SEQ ID NO: 206, respectively), which have known crystal structures (PDB codes 3UAN and 1ZRH, respectively) in which amino acid residues within the active site have been identified, alongside the amino acid sequences of other natural 3OSTs within EC 2.8.2.23. Further, a direct comparison of the mouse and human 3OST structures indicate that both enzymes have nearly identical active sites and overall folds, even though the two enzymes have only an 83% sequence identity with one another.

Figure 26A:
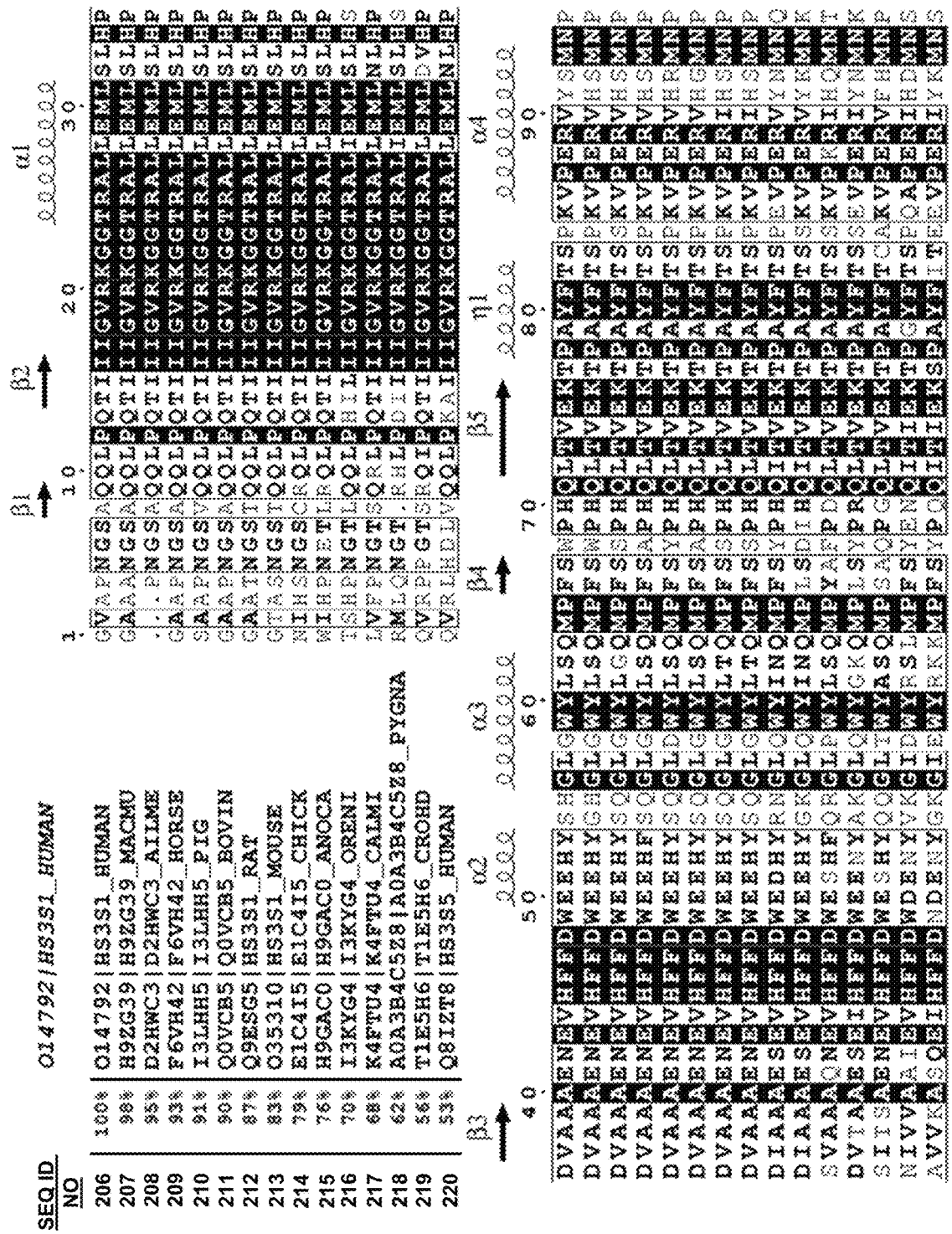
FIG. 26A, FIG. 26B, and FIG. 26C show a multiple sequence alignment for fifteen wild-type 3OST enzymes within EC 2.8.2.23, illustrating conserved amino acid sequence motifs that are present regardless of overall sequence identity.
Figure 26B:
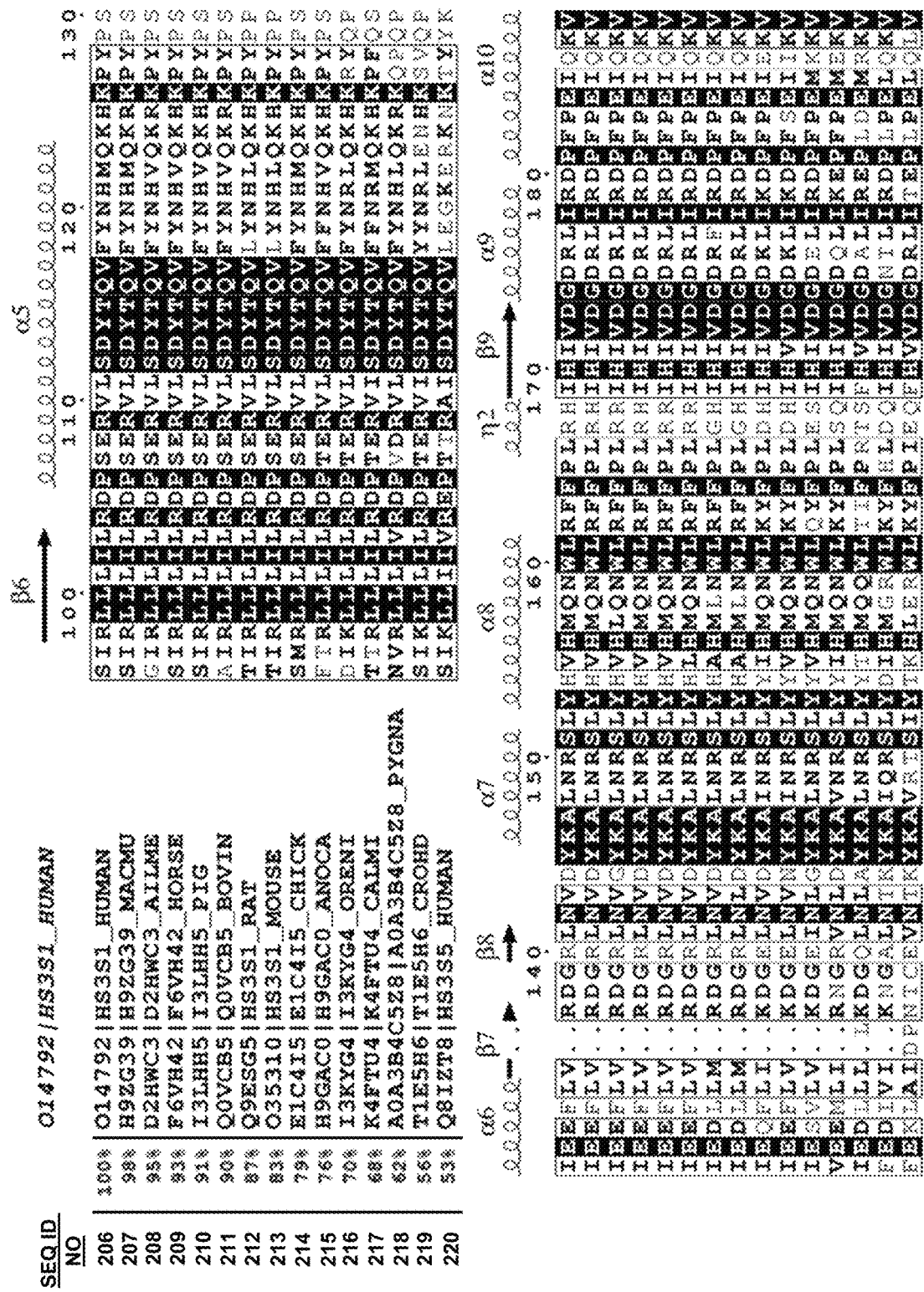
Figure 26C:
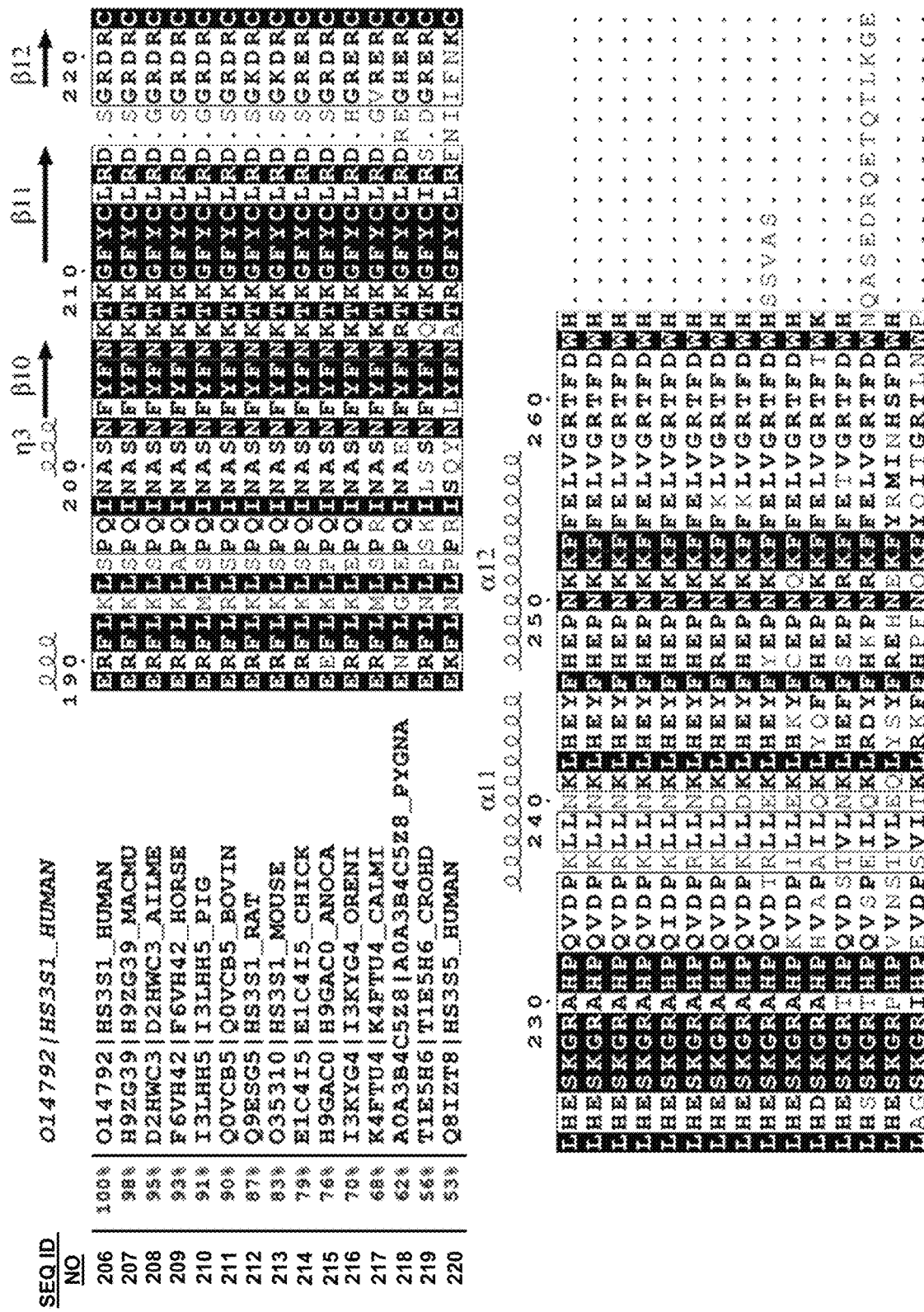

A multiple sequence alignment of the amino acid sequences of fifteen enzymes within EC 2.8.2.23 (SEQ ID NOs 206-220), including the mouse (SEQ ID NO: 213) and human 3OST1 (SEQ ID NO: 206) enzymes, is shown in FIG. 26A, FIG. 26B, and FIG. 26C, along with the percent identity of each sequence relative to the human 3OST1 reference sequence (SEQ ID NO: 206, UniProtKB Accession No. O14792). As illustrated in FIG. 26A, FIG. 26B, and FIG. 26C, sequences range from having 98% identity with SEQ ID NO: 206 (SEQ ID NO: 207, entry tr|H9ZG39|H9ZG39_MACMU) for the rhesus monkey 3OST1, down to 53% identity (SEQ ID NO: 220, entry sp|Q8IZT8|HS3S5_HUMAN) for human 3OST5. Those skilled in the art would appreciate that the multiple sequence alignment was limited to fifteen sequences for clarity, and that there are hundreds of amino acid sequences encoding for natural 3OST enzymes that have been identified and that have highly conserved active site and/or binding regions as well.

Within FIG. 26A, FIG. 26B, and FIG. 26C, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural human sulfotransferase enzyme as a reference. The β symbol adjacent to an arrow refers to a β-sheet, whereas a coil adjacent to an α symbol or a η symbol refers to a helix secondary structure.

Within the fifteen aligned sequences in FIG. 26A, FIG. 26B, and FIG. 26C (SEQ ID NOs 206-220), there are several conserved amino acid sequence motifs that include one or more amino acids that comprise the active site, based on the crystal structures of the mouse (SEQ ID NO: 213, entry sp|O35310|HS3S1_MOUSE) and human 3OST1 (SEQ ID NO: 206, entry sp|O14792|HS3S1_HUMAN) enzymes described above. Based on the numbering of the amino acid residues within FIG. 26A, FIG. 26B, and FIG. 26C, these motifs include residues 16-27 (including G-V-R-K-G-G from residues 18-23, SEQ ID NO: 265), residues 43-48 (E-V/I—H-F-F-D, SEQ ID NO: 298), residues 78-81 (P-A/G-Y-F), residues 112-117 (S-D-Y-T-Q-V, SEQ ID NO: 267), and residues 145-147 (Y-K-A). It is believed that these residues either facilitate or participate in the chemical reaction, or enable binding of PAPS or the polysaccharide within the active site. In particular, within residues 43-48, as described above and as illustrated in FIG. 4A, FIG. 4B, and FIG. 4C, the glutamic acid residue at position 43 abstracts the proton from the 3-O position of the N-sulfoglucosamine residue within the polysaccharide, enabling the nucleophilic attack and removal of the sulfo group from PAPS, whereas His-45 and Asp-48 coordinate to stabilize the transition state of the enzyme before the sulfurylated polysaccharide product is released from the active site.

However, as described above, the natural 3OST enzymes are unable to catalyze the transfer of the sulfate group from an aryl sulfate compound to a polysaccharide. Without being limited by a particular theory, and as with the natural NDST, 2OST, and 6OST enzymes described above, it is believed that the binding pocket for PAPS within the active site of the natural sulfotransferase either does not have a high enough affinity for aryl sulfate compounds to facilitate binding and/or that the aryl sulfate compounds are sterically hindered from entering the active site. Consequently, and in another embodiment, a natural 3OST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered 3OST enzymes of the present invention can be mutants of natural 3OST enzymes within EC 2.8.2.23, including enzymes having the amino acid sequences of SEQ ID NOs 206-220. In another embodiment, mutations engineered into the amino acid sequences of the engineered 3OST enzymes facilitate a biological activity in which aryl sulfate compounds can both bind and react with the enzyme as sulfo group donors. In another embodiment, although the engineered 3OST enzymes can bind and react with an aryl sulfate compound as a sulfo group donor, they can retain the natural 3OST enzymes' biological activity with N,2O,6O-HS, including but not limited to those comprising the structure of Formula X, as sulfo group acceptors. Without being limited by a particular theory, it is believed that because of the mutations inserted into the amino acid sequences of the engineered 3OST enzymes, their sulfotransferase activity may comprise the direct transfer of a sulfuryl group from an aryl sulfate compound to the heparosan-based polysaccharide, using a similar mechanism as described in FIGS. 4A-4C, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 3-O position of a glucosamine residue, to form a 3-O sulfated HS product. In another embodiment, the 3-O sulfated product of either sulfotransfer mechanism is an N,2O, 3O,6O-HS product.

In another embodiment, an engineered 3OST enzyme can comprise one or more mutated amino acid sequence motifs relative to the conserved amino acid sequence motifs (SEQ ID NO: 265, SEQ ID NO: 298, P-A/G-Y-F, and SEQ ID NO: 267) found in natural 3OST enzymes, as described above and indicated in the multiple sequence alignment in FIG. 26A, FIG. 26B, and FIG. 26C and SEQ ID NOs 206-220. In another embodiment, each mutated amino acid sequence motif that is present in the amino acid sequence of the engineered enzyme comprises at least one amino acid mutation relative to the corresponding conserved amino acid sequence motif within the natural 3OST enzymes. In another embodiment, an engineered 3OST enzyme can comprise one mutated amino acid sequence motif. In another embodiment, an engineered 3OST enzyme can comprise two mutated amino acid sequence motifs. In another embodiment, an engineered 3OST enzyme can comprise three mutated amino acid sequence motifs. In another embodiment, an engineered 3OST enzyme can comprise four mutated amino acid sequence motifs. In another embodiment, an engineered 3OST enzyme can comprise five mutated amino acid sequence motifs. In another embodiment, an engineered 3OST enzyme that includes at least one mutated amino acid sequence motif relative to any of the wild-type 3OST enzymes within EC 2.8.2.23 can have an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

Figure 27:
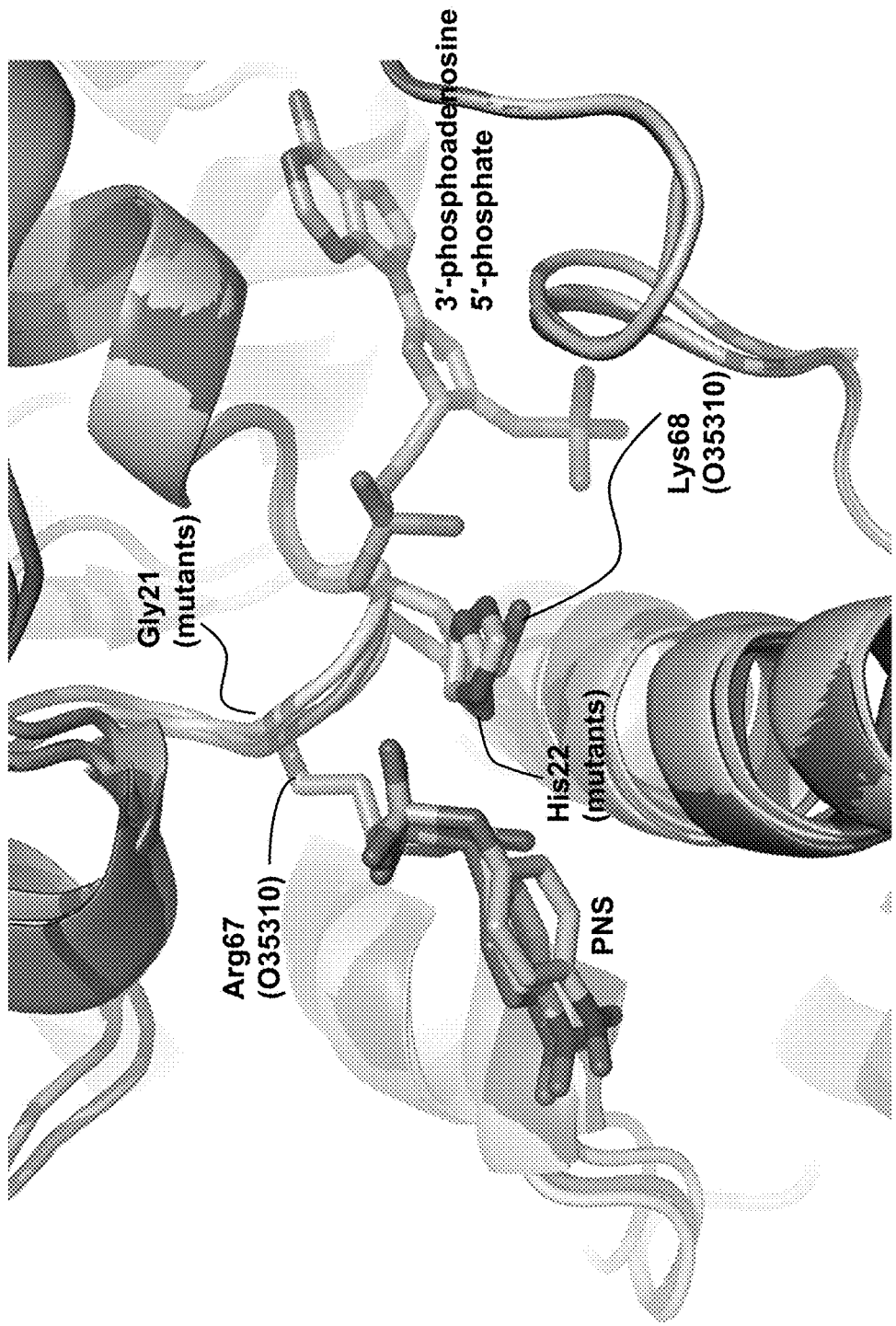
FIG. 27 shows a three-dimensional model of a mutated amino acid sequence motif enabling binding of PNS within the active site of an engineered 3OST enzyme, superimposed over the crystal structure of a natural 3OST enzyme.

In another embodiment, upon viewing the crystal structure of the mouse 3OST within a 3D molecular visualization system (including, as a non-limiting example, the open-source software, PyMOL), the structure of related sequences, such as those of engineered 3OST enzymes that contain one or more mutated amino acid sequence motifs relative to the mouse 3OST1 (SEQ ID NO: 213, UniProtKB Accession No. O35310) structure, can be modeled for comparison as illustrated in FIG. 27. FIG. 27 shows a magnified view of the active site of the mouse 3OST1 enzyme (PDB code: 3UAN) with three engineered 3OST enzymes, comprising the amino acid sequences of SEQ ID NO: 147, SEQ ID NO: 149, and SEQ ID NO: 151. Adenosine 3',5'-diphosphate, which is the product of a sulfotransfer reaction in which PAPS is the sulfo donor, and which was co-crystallized with the mouse 3OST1, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 27, although there are several mutations made to SEQ ID NO: 147, SEQ ID NO: 149, and SEQ ID NO: 151 relative to the amino acid sequence of the natural mouse 3OST1 enzyme (SEQ ID NO: 213), the respective protein backbones are in a nearly identical location to one another, enabling a one-to-one comparison of the active sites. However, when comparing the two active sites, the adenosine 3',5'-diphosphate product from the natural sulfotransfer reaction is adjacent to the lysine residue (shown in FIG. 27 as Lys68), whereas the convergent solutions from the above MD simulations indicate that PNS binding within the engineered enzymes is favored on the opposite side of the active site. Without being limited by a particular theory, it is believed that the convergent MD simulation solutions place PNS on the opposite side of the active site because there is not enough of an affinity toward PNS in the same or similar position as PAPS. Yet, despite the apparent differences in the binding pocket for PAPS and PNS, engineered 3OST enzymes comprising the amino acid sequences of SEQ ID NO: 147, SEQ ID NO: 149, and SEQ ID NO: 151 all achieved sulfo transfer from an aryl sulfate compound to the 3-O position of one or more positions within a heparosan-based polysaccharide, as described in the examples below.

Further, the arginine residue corresponding to position 20 of the mouse 3OST1 (SEQ ID NO: 213) and which is conserved in all of the other 3OST enzymes in SEQ ID NOs 206-220, would appear to block PNS from binding in the position indicated in FIG. 27. Accordingly, and in another embodiment, engineered 3OST enzymes that bind PNS can comprise a mutation of the active site arginine residue to a glycine residue, which removes all steric hindrance for PNS to bind within the binding pocket. As indicated in the amino acid sequences for SEQ ID NO: 147, SEQ ID NO: 149, SEQ ID NO: 151, SEQ ID NO: 154, SEQ ID NO: 155, SEQ ID NO: 156, and SEQ ID NO: 157, the arginine to glycine mutation is at position 21. As indicated in the amino acid sequences for SEQ ID NO: 158, SEQ ID NO: 159, and SEQ ID NO: 160, the arginine to glycine mutation is at position 99.

Similarly, the next amino acid residue in each of the engineered enzymes, corresponding to position 22 in the amino acid sequences SEQ ID NO: 147, SEQ ID NO: 149, SEQ ID NO: 151, SEQ ID NO: 154, SEQ ID NO: 155, SEQ ID NO: 156, and SEQ ID NO: 157, is mutated to a histidine residue. Without being limited by a particular theory, it is believed that the mutation to a histidine residue from the conserved lysine residue (corresponding to position 21 in each of the amino acid sequences in FIG. 26A) facilitates removal of the sulfate group from PNS, using a similar mechanism as described by Malojcic, et al., above. As indicated in the amino acid sequences for SEQ ID NO: 158, SEQ ID NO: 159, and SEQ ID NO: 160, the lysine to histidine residue is at position 100.

Those skilled in the art would appreciate that engineered 3OST enzymes of any other amino acid sequence, including, but not limited to, those disclosed by SEQ ID NO: 154, SEQ ID NO: 155, SEQ ID NO: 156, SEQ ID NO: 157, SEQ ID NO: 158, SEQ ID NO: 159, and SEQ ID NO: 160, would likely exhibit a similar structure would exhibit similar structural motifs as engineered enzymes having the amino acid sequences of SEQ ID NO: 147, SEQ ID NO: 149, and SEQ ID NO: 151, particularly within the active site. Without being limited by a particular theory, it is also believed that NCS would bind in a similar position as PNS within the active site of any of the engineered enzymes, since the structures of the two aryl sulfate compounds are very similar, except that the sulfate group is located ortho on the aromatic ring relative to the nitro group, rather than para to the nitro group.

In another embodiment, engineered 3OST enzymes of the present invention can comprise one or more mutated amino acid sequence motifs, which can be determined in-part by comparing conserved amino acid sequence motifs (SEQ ID NO: 265, SEQ ID NO: 298, P-A/G-Y-F, and SEQ ID NO: 267) indicated in the multiple sequence alignment of SEQ ID NOs 206-220 in FIG. 26A, FIG. 26B, and FIG. 26C with the known structure(s) of native 3OST enzymes and/or modeled engineered enzymes, including but not limited to the engineered 3OST enzymes illustrated in FIG. 27. In another embodiment, mutated amino acid sequence motifs that can be comprised within an engineered 3OST enzyme can be selected from the group consisting of (a) G-V-G-H-G-G (SEQ ID NO: 268); (b) H-S-Y-F (SEQ ID NO: 269); (c)S-$X_1$-$X_2$-T-H-$X_3$, wherein $X_1$ is selected from the group consisting of alanine and leucine; $X_2$ is selected from the group consisting of tyrosine and glycine, and $X_3$ is selected from the group consisting of methionine and leucine; and (d) Y-$X_4$-G, wherein $X_4$ is selected from the group consisting of valine and threonine; including any combination thereof. Each of the mutated amino acid sequence motifs corresponds with a conserved amino acid motif indicated in FIG. 26A, FIG. 26B, and FIG. 26C above: SEQ ID NO: 268 corresponds to the conserved amino acid sequence motif G-V-R-K-G-G (SEQ ID NO: 265); SEQ ID NO: 269 corresponds to the conserved amino acid sequence motif P-A/G-Y-F; S-$X_1$-$X_2$-T-H-$X_3$ corresponds to the conserved amino acid sequence motif S-D-Y-T-Q-V (SEQ ID NO: 267); and the mutated amino acid sequence motif Y-$X_4$-G corresponds to the conserved amino acid sequence motif Y-K-A. In another embodiment, an engineered 3OST enzyme comprising each of the mutated amino acid sequence motifs above can be selected from the group consisting of: SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

In another embodiment, each of the mutated amino acid sequence motifs can comprise at least one mutation that is made relative to the conserved amino acids found in the natural 3OST enzymes within EC 2.8.2.23. In another embodiment, SEQ ID NO: 268 contains an R-K to G-H mutation, relative to the conserved amino acid sequence motif, G-V-R-K-G-G (SEQ ID NO: 265). In another embodiment, SEQ ID NO: 269 contains a P-A/G to an H-S mutation relative to the conserved amino acid sequence motif, P-A/G-Y-F. In another embodiment, in addition to potential mutations made at the $X_1$, $X_2$, and $X_3$ positions, S—$X_1$-$X_2$-T-H-$X_3$ comprises a Q to H mutation, relative to the conserved amino acid sequence motif, S-D-Y-T-Q-V (SEQ ID NO: 267). In another embodiment, in addition to a mutation at the $X_4$ position, mutated amino acid sequence motif Y-$X_4$-G comprises an A to G mutation, relative to the conserved amino acid sequence motif, Y-K-A.

In another embodiment, $X_1$ is alanine, $X_2$ is tyrosine and $X_3$ is methionine (SEQ ID NO: 270), and $X_4$ is valine or threonine. In other embodiments, $X_1$ is leucine, $X_2$ is glycine, and $X_3$ is leucine (SEQ ID NO: 300), and $X_4$ is threonine. Without being limited to another theory, it is believed that one or more of the mutations comprised within mutated amino acid sequence motifs SEQ ID NO: 269, S—$X_1$-$X_2$-T-H-$X_3$, and Y-$X_4$-G play a role in stabilizing the transition state of the enzyme during the chemical reaction, or in increasing the affinity of aryl sulfate compounds to the active site, including by reducing the size of the binding pocket, increasing the hydrophobicity of the pocket, and/or creating π-π interactions with the aromatic moieties of the aryl sulfate compounds.

Figure 28:
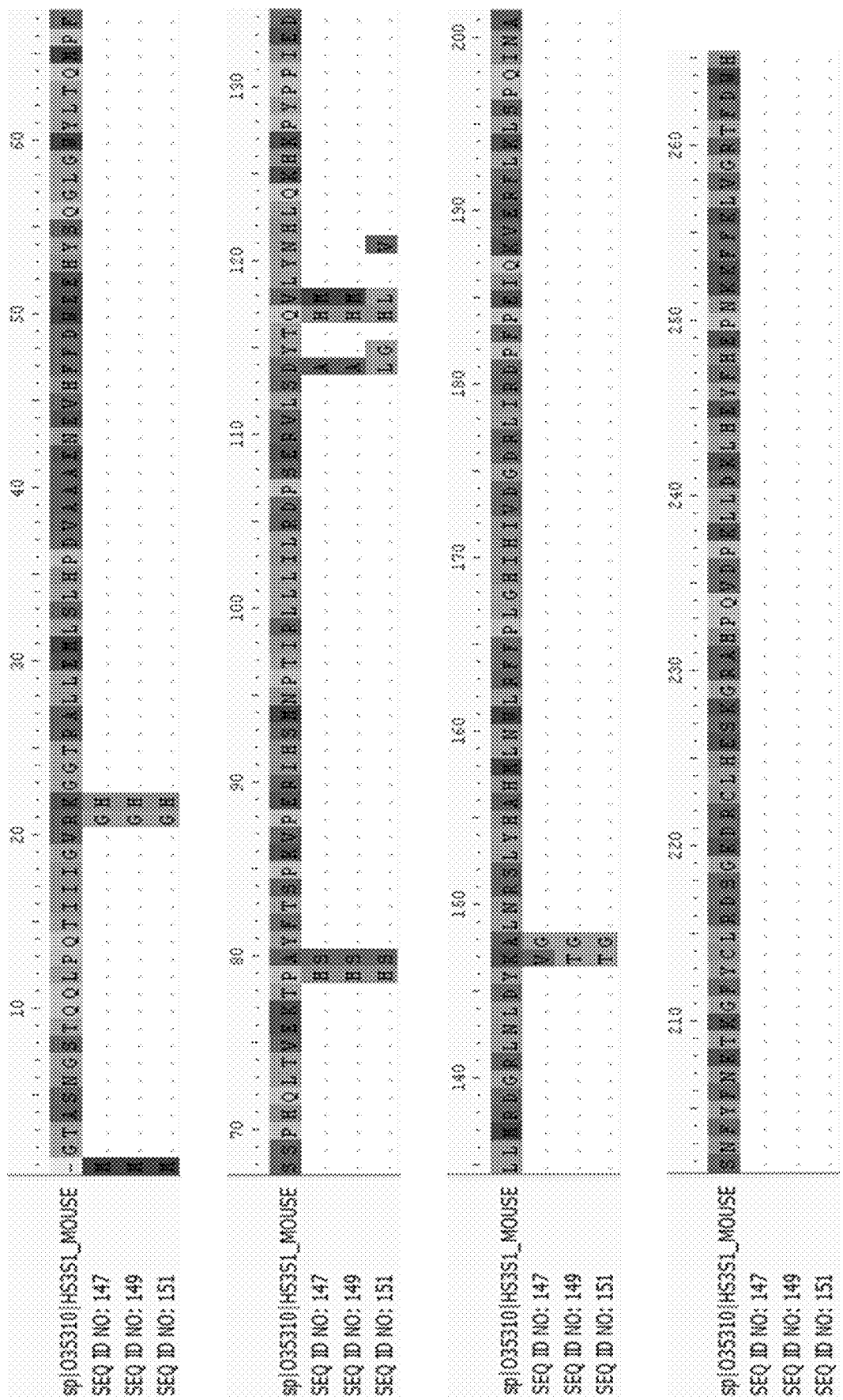
FIG. 28 shows a sequence alignment of polypeptides comprising the amino acid sequences of SEQ ID NO: 147, SEQ ID NO: 149, and SEQ ID NO: 151, respectively, depicting the position and identity of amino acid residues differences between each of the illustrated sequences.

Furthermore, the amino acid sequences (SEQ ID NO: 147, SEQ ID NO: 149, and SEQ ID NO: 151) of three engineered 3OST enzymes, which have been experimentally determined to be active with aryl sulfate compounds as sulfo group donors (see Example 6 below) can be compared with the amino acid sequence of the human 3OST1 enzyme (SEQ ID NO: 206, entry sp|O14792|HS3S1_HUMAN) in a multiple sequence alignment to determine if there are relationships between mutations among each of the enzymes. A period within the amino acid sequence of an engineered enzyme indicates identity at a particular position with the human 3OST enzyme. As shown in FIG. 28, the sequence alignment demonstrates that while over 90% of the amino acid residues within the three sulfotransferase sequences are identical, there are several positions in which multiple amino acids can be chosen. As a result, and in another embodiment, an engineered 3OST enzyme comprising an amino acid sequence in which multiple amino acids can be chosen at defined positions is disclosed as SEQ ID NO: 154. Positions at which the identity of an amino acid can be chosen from a selection of possible residues are denoted in terms "Xaa," "Xn," or "position n," where n refers to the residue position.

In another embodiment, within an engineered 3OST enzyme comprising the amino acid sequence of SEQ ID NO: 154, the amino acid residue at position 114 is alanine and the amino acid residue at position 118 is methionine. In further embodiments, the amino acid residue at position 147 is selected from the group consisting of valine and threonine.

In another embodiment, within an engineered 3OST enzyme comprising the amino acid sequence of SEQ ID NO: 154, the amino acid residue at position 114 is leucine, the amino acid residue at position 118 is leucine, and the amino acid residue at position 121 is valine. In further embodiments, the amino acid residue at position 115 is glycine. In even further embodiments, the amino acid residue at position 147 is threonine.

In another embodiment, within an engineered 3OST enzyme comprising the amino acid sequence of SEQ ID NO: 154, the amino acid sequence can optionally include one or more mutations at residue positions not specified by an "Xn" or "X," so long as any such mutations do not eliminate the 3OST and/or aryl sulfate-dependent activity of the enzyme. In another embodiment, such mutations not eliminating aryl sulfate-dependent activity at positions not specified by an "Xn" or "X" can include substitutions, deletions, and/or additions.

Accordingly, in another embodiment, an engineered 3OST enzyme utilized in accordance with any of the methods of the present invention can comprise an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. In another embodiment, engineered 3OST enzymes comprising the amino acid sequence of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160 can react with any aryl sulfate compound. In further embodiments, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

In Vitro Synthesis of Sulfated Polysaccharides

In an embodiment of the invention, any of the engineered sulfotransferase enzymes described above can be utilized to synthesize HS polysaccharide products. Generally, sulfation can be accomplished by treating a heparosan-based polysaccharide and an aryl sulfate compound with an engineered sulfotransferase enzyme to form the sulfated product. As described above and without being limited by a particular theory, it is believed that sulfotransferase enzymes that recognize heparosan-based polysaccharides as sulfo group acceptors, but also bind and react with aryl sulfate compounds as sulfo donors, have neither been observed in nature nor described previously.

HS polysaccharide compositions that are utilized for industrial, commercial, or pharmaceutical uses can be obtained in large quantities by isolating them from animal sources, particularly pigs and cattle, within which the polysaccharides are produced in vivo. (see Xu, Y., et al., (2011) *Science* 334 (6055): 498-501). A worldwide contamination crisis in 2007 and 2008 of heparin obtained from pigs shone a spotlight on the fragility of solely relying on obtaining them from animal sources. Consequently, there has been a push to develop synthetic routes to synthesizing heparin, LMWH, and other anticoagulant HS polysaccharides in vitro in large enough quantities to compliment or replace animal-sourced products. That push has only been strengthened even further by the African swine flu epidemic that decimated the worldwide pig population, especially in China, in 2019.

In order to synthesize HS polysaccharides in vitro, there have historically been two reaction schemes: total chemical synthesis and chemoenzymatic synthesis. While both types of reaction schemes have led to purified products that in some instances are homogeneous, synthetic routes as a whole have been inadequate to produce specific HS polysaccharide compositions, particularly heparin, on an industrial scale. For example, the production of such polysaccharides using total chemical synthesis has historically required as many as 60 steps and resulted in very low yields (see Balagurunathan, K., et al., (eds.) (2015) *Glycosaminoglycans: Chemistry and Biology*, Methods in Molecular Biology, vol. 1229, DOI 10.1007/978-1-4939-1714-3_2, © Springer Science+Business Media New York).

Chemoenzymatic synthesis routes, on the other hand, generally utilize far fewer steps and increase the scale of the generated anticoagulant products into multi-milligram amounts (See U.S. Pat. Nos. 8,771,995 and 9,951,149, the disclosures of which are incorporated by reference in its entirety). The improvements in the quantity of obtainable product can be attributed to the ability to combine recombinant versions of natural HS sulfotransferases with PAPS in a reaction vessel in order to catalyze the transfer of sulfo groups to heparosan-based polysaccharides. Yet, chemoenzymatic methods to this point are still not suitable to synthesize gram- or larger-scale amounts of anticoagulant HS polysaccharides because of the wild-type sulfotransferases' reliance on PAPS for their activity, as described in U.S. Pat. Nos. 5,541,095, 5,817,487, 5,834,282, 6,861,254, 8,771,995, 9,951,149, and U.S. Pat. Pubs. 2009/0035787, 2013/0296540, and 2016/0122446, the disclosures of which are incorporated by reference in their entireties. PAPS is a highly expensive and unstable molecule that has been an obstacle to the large-scale production of enzymatically sulfated products, including heparin, because the half-life of PAPS at pH 8.0 is only about 20 hours.

Furthermore, product inhibition by adenosine 3',5'-diphosphate has also been a limiting factor to large-scale synthesis of sulfated products. The highly negative impact of the product inhibition by adenosine 3',5'-diphosphate can be somewhat reduced by employing a PAPS regeneration system (see U.S. Pat. No. 6,255,088, above, and Burkhart, et al. (2000) *J. Org. Chem.* 65: 5565-5574) that converts adenosine 3',5'-diphosphate into PAPS. Despite the PAPS regeneration system, however, the absolute necessity to supply PAPS to initiate the chemical reaction with PAPS-dependent sulfotransferases nonetheless creates an insurmountably high-cost barrier to synthesize sulfated products, including heparin, on an industrial, production-grade scale.

In contrast to the known syntheses of heparin that require PAPS as sulfo donors in order to drive enzyme activity, the methods of the present invention obviate the need to use PAPS altogether, because each of the sulfotransferases of the present invention have been engineered to recognize, bind, and react with aryl sulfate compounds, which do not react with natural HS sulfotransferases, as sulfo donors. Without being limited by a particular theory, it is believed that the engineered sulfotransferases of the present invention are the only known sulfotransferases that are capable of reacting with aryl sulfate compounds as sulfo group donors, while also reacting with polysaccharides, particularly heparosan-based polysaccharides, as sulfo group acceptors.

Thus, in another embodiment, the invention provides methods and kits for synthesizing HS polysaccharides. Generally, a method for sulfating a heparosan-based polysaccharide using the engineered sulfotransferases of the present invention comprises the following steps: (a) providing an aryl sulfate compound; (b) providing any of the engineered sulfotransferase enzymes described above, wherein the engineered sulfotransferase enzyme has biological activity with an aryl sulfate compound as a sulfo group donor; (c) providing a heparosan-based polysaccharide; (d) combining the aryl sulfate compound, the sulfotransferase enzyme, and the heparosan-based polysaccharide into a reaction mixture; and (e) transferring the sulfo group from the aryl sulfate compound to the heparosan-based polysaccharide, using the sulfotransferase enzyme, thereby forming the sulfated polysaccharide product. In another embodiment, the aryl sulfate compound can be selected from the consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. According to the present invention, the aryl sulfate compound is PNS. According to the present invention, the aryl sulfate compound is NCS.

In another embodiment, when the engineered sulfotransferase enzyme is a NST enzyme, the heparosan-based polysaccharide can be an N-deacetylated heparosan polysaccharide comprising one or more disaccharide units comprising the structure of Formula II, and the engineered sulfotransferase can have an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. In another embodiment, the N-sulfated HS polysaccharide comprises one or more disaccharide units having the structure of Formula III.

In another embodiment, N-deacetylated heparosan and/or other heparosan-based polysaccharides comprising disaccharide units having the structure of Formula II can be obtained commercially. In another embodiment, heparosan can be isolated from natural sources and chemically modified to N-deacetylate glucosamine residues and also control the molecular weight of the polysaccharides within the composition. In particular, heparosan can be found within bacteria as capsules that regulate cell entry by metabolites and other exogenous materials. Such bacteria, include, but are not limited to, *Pasteurella multocida* and *Escherichia coli* (*E. coli*). In some embodiments, heparosan can be extracted and purified from *E. coli*, particularly the K5 strain of *E. coli*, as a polydisperse mixture of polysaccharide molecules having varying molecular weights. Procedures for isolating heparosan from the K5 strain of *E. coli* are discussed and provided in Wang, Z., et al., (2010) *Biotechnol. Bioeng.* 107 (6):964-973, the disclosure of which is incorporated by reference in its entirety; see also DeAngelis, P. L. (2015) *Expert Opinion on Drug Delivery* 12 (3):349-352; Ly, M., et al., (2010) *Anal. Bioanal. Chem.* 399:737-745; and Zhang, C., et al., (2012) *Metabolic Engineering* 14:521-527, the disclosures of which are also incorporated in their entireties.

In another embodiment, a portion or all of the heparosan composition can be N-deacetylated by treating it with a base, particularly lithium hydroxide or sodium hydroxide (see Wang, Z., et al., (2011) *Appl. Microbiol. Biotechnol.* 91 (1):91-99, the disclosure of which is incorporated by reference in its entirety; see also PCT publication PCT/US2012/026081, the disclosure of which is incorporated by reference in its entirety). In another embodiment, the base is sodium hydroxide. Depending on the degree of N-deacetylation desired, the concentration of the heparosan, and the concentration of the base, one skilled in the art can determine how long to incubate heparosan with the base according to the procedures described in Wang, et al., (2011), above.

In another embodiment, N-deacetylated heparosan can be obtained with molecular weight and N-acetyl glucosamine contents useful for synthesizing UFH that meets one or more of the benchmarks set forth by the United States Pharmacopeia (USP), described in further detail below. In another embodiment, heparosan can be incubated with a base, preferably sodium hydroxide, until a desired amount of N-acetylated glucosamine residues remains within the N-deacetylated product. In another embodiment, N-acetyl glucosamine residues can comprise less than 60%, including less than 30%, 20%, 18%, 16%, 14%, 12%, or 10%, down to less than 5%, and preferably in a range from 12% and up to 18%, of the glucosamine residues within the N-deacetylated heparosan. In another embodiment, the N-acetyl glucosamine can comprise about 15% of the glucosamine residues within the N-deacetylated heparosan.

Additionally, and without being limited by a particular theory, it is believed that in addition to N-deacetylating glucosamine residues, the reaction between heparosan and a base can simultaneously depolymerize the heparosan polysaccharides and reduce their molecular weight, which can in turn reduce the weight-average molecular weight ($\overline{M}_w$) of the N-deacetylated heparosan. Typically, heparosan polysaccharides isolated from bacteria, including but not limited to *E. coli*, have a molecular weight ranging from about 3,000 Da to about 150,000 Da, and compositions of isolated heparosan can have a $\overline{M}_w$ in the range of about 25,000 Da up to about 50,000 Da (see Ly, M., et al. and Wang, et al., (2011), above). In another embodiment, a heparosan composition either obtained from commercial sources or isolated from bacteria, including but not limited to *E. coli*, can be treated with a base, preferably sodium hydroxide, for a time sufficient to reduce the $\overline{M}_w$ of the N-deacetylated heparosan to a target or desired level. In another embodiment, the N-deacetylated heparosan can have an $\overline{M}_w$ of at least 1,000 Da, including at least 2,000 Da, 4,000 Da, 6,000 Da, 7,000 Da, 8,000 Da, 8,500 Da, 9,000 Da, 9,500 Da, 10,000 Da, 10,500 Da, 11,000 Da, 11,500 Da, 12,000 Da, 12,500 Da, 13,000 Da, 13,500 Da, 14,000 Da, 15,000 Da, 16,000 Da, or 18,000 Da, up to at least 20,000 Da. In another embodiment, the N-deacetylated heparosan can have an $\overline{M}_w$ of less than 20,000 Da, including less than 18,000 Da, 16,000 Da, 15,000 Da, 14,000 Da, 13,500 Da, 13,000 Da, 12,500 Da, 12,000 Da, 11,500 Da, 11,000 Da, 10,500 Da, 10,000 Da, 9,500 Da, 9,000 Da, 8,500 Da, 8,000 Da, 7,000 Da, 6,000 Da, or 4,000 Da, down to less than 2,000 Da. In another embodiment, the N-deacetylated heparosan can have an $\overline{M}_w$ in any range listed above between and inclusive of 1,000 Da and 20,000 Da, and preferably in any range listed above between and inclusive of 9,000 Da and 12,500 Da.

The preparation of N-deacetylated heparosan having such molecular weight properties and N-acetyl glucosamine content is described in detail in Wang, et al., (2011), above. In another embodiment, the time sufficient to react a heparosan with a base, preferably sodium hydroxide, to form an N-deacetylated heparosan product having an $\overline{M}_w$ in a range between 9,000 Da and 12,500 Da, as well as an N-acetyl glucosamine content in a range from 12% and up to 18%, can be at least 1 hour, including at least 2, 4, 6, 8, 10, 12, or 18 hours, and up to at least 24 hours, depending on the molecular weight properties and concentration of the heparosan starting material, and the identity and concentration of the base used to carry out the reaction.

In another embodiment, when the engineered sulfotransferase enzyme is a 2OST enzyme, the heparosan-based polysaccharide can be an N-sulfated HS polysaccharide comprising one or more structural motifs comprising the structure of Formula IV and/or Formula V, and the engineered sulfotransferase can have an amino acid sequence selected from the group consisting of SEQ ID NO: 65, SEQ ID NO: 66, SEQ ID NO: 67, and SEQ ID NO: 69. In another embodiment, the method can further comprise the step of providing a glucuronyl $C_5$-epimerase, preferably a glucuronyl $C_5$-epimerase comprising the amino acid sequence of SEQ ID NO: 67, and more preferably residues 34-617 of SEQ ID NO: 67, and combining the glucuronyl $C_5$-epimerase with the reaction mixture. In another embodiment, the N-sulfated HS can be commercially obtained. In another embodiment, the N-sulfated HS can be the sulfated product of an engineered NST or natural NDST enzyme. In another embodiment, the sulfated polysaccharide product of the engineered 2OST enzyme is an N,2O-HS polysaccharide comprising the structure of Formula VI and/or Formula VII.

In another embodiment, the N-sulfated HS can be obtained by chemically N-sulfating N-deacetylated heparosan. In another embodiment, the N-deacetylated heparosan can be chemically sulfated by adding a composition comprising sulfur trioxide and/or one or more sulfur-trioxide containing compounds or adducts. Chemical N-sulfation of glucosamine residues within polysaccharides using sulfur trioxide is commonly known in the art (see Lloyd, A. G., et al., (1971) *Biochem. Pharmacol.* 20 (3):637-648; Nadkarni, V. D., et al., (1996) *Carbohydrate Research* 290:87-96; Kuberan, B., et al., (2003) *J. Biol. Chem.* 278 (52):52613-52621; Zhang, Z., et al., (2008) *J. Am. Chem. Soc.* 130 (39):12998-13007; and Wang, et al., (2011), above; see also U.S. Pat. No. 6,991,183 and U.S. Pat. Pub. 2008/020789, the disclosures of which are incorporated by reference in their entireties). Sulfur trioxide complexes are generally mild enough bases to enable the selected N-sulfation of polysaccharides without causing depolymerization, unlike sodium hydroxide (see Gilbert, E. E., (1962) *Chem. Rev.* 62(6):549-589). Non-limiting examples of sulfur trioxide-containing complexes include sulfur dioxide-pyridine, sulfur dioxide-dioxane, sulfur dioxide-trimethylamine, sulfur dioxide-triethylamine, sulfur dioxide-dimethylaniline, sulfur dioxide-thioxane, sulfur dioxide-Bis(2-chloroethyl) ether, sulfur dioxide-2-methylpyridine, sulfur dioxide-quinoline, or sulfur dioxide-dimethylformamide.

In another embodiment, when the engineered sulfotransferase enzyme is a 6OST enzyme, the heparosan-based polysaccharide is an N,2O-HS polysaccharide comprising one or more structural motifs comprising the structure of Formula VIII. In another embodiment, the engineered 6OST enzyme can have an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. In another embodiment, the heparosan-based polysaccharide for reacting with the engineered 6OST enzyme can be commercially obtained. In another embodiment, the heparosan-based polysaccharide for the engineered 6OST enzyme can be the sulfated N,2O-HS polysaccharide product of an engineered or natural 2OST enzyme. In another embodiment, the sulfated polysaccharide product of the engineered 6OST enzyme is an N,2O,6O-HS polysaccharide comprising the structure of Formula IX.

In another embodiment, when the engineered sulfotransferase enzyme is a 3OST enzyme, the heparosan-based polysaccharide can be an N,2O,6O-HS polysaccharide comprising one or more structural motifs comprising the structure of Formula X. In another embodiment, the engineered 3OST can have an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. In another embodiment, the heparosan-based polysaccharide for reacting with the engineered 3OST enzyme can be commercially obtained. In another embodiment, the heparosan-based polysaccharide for the engineered 3OST enzyme can be the sulfated N,2O, 6O-HS polysaccharide product of an engineered or natural 6OST enzyme. In another embodiment, the sulfated polysaccharide product is an N,2O,3O,6O-HS polysaccharide comprising the structure of Formula I. In another embodiment, the N,2O,3O,6O-HS is obtained as a polydisperse composition having one or more molecular weight properties and/or anticoagulant activities as UFH.

As described above, UFH, LMWH, and other heparin compositions that have anticoagulant activity are comprised of N,2O,3O,6O-HS polysaccharides that include the structure of Formula I. (see Desai, U. R., et al., (1998) *J. Biol. Chem.* 273 (13):7478-7487). The medical use of UFH, LMWH, and other heparins has been well documented for decades. The anticoagulant activity of heparins can include, but are not limited to, inactivation of Factor IIa (thrombin) and/or Factor Xa, two proteins that are vital in the blood-clotting cascade. In particular, when a N,2O,3O,6O-HS polysaccharide binds to antithrombin (AT), it causes a conformational change in the enzyme that enables the formation of a ternary complex between the polysaccharide, AT, and either thrombin or Factor Xa (see Li, W., et al., (2004) *Nat. Struct. Mol. Biol.* 11 (9):857-862, the disclosure of which is incorporated by reference in its entirety). In order to bind with AT and induce its conformational change, an N,2O,3O,6O-HS polysaccharide comprises a specific five-residue AT-recognition sequence, which is equivalent to the structure of Formula I.

While anticoagulation can be induced by binding antithrombin with an oligosaccharide consisting only of the AT-recognition sequence, there is typically enhanced anticoagulant activity when the composition comprises N,2O, 3O,6O-HS polysaccharides having more than five sugar residues (see Grey, E., et al., (2008) *Thromb. Haemost.* 99:807-818, the disclosure of which is incorporated by reference in its entirety). As reported by Grey, et al, a secondary binding interaction can be formed between the polysaccharide and thrombin when the N,2O,3O,6O-HS polysaccharide comprises at least thirteen sugar residues on either side of the AT-recognition sequence to act as a "bridge" that allows the polysaccharide to bind to thrombin while also bound to AT. As a result, N,2O,3O,6O-HS polysaccharides typically require a minimum of eighteen sugar residues in order to potentially form the ternary complex between the N,2O,3O,6O-HS polysaccharide, AT, and thrombin. However, and without being limited by a particular theory, it is believed that because the distribution of the AT-recognition sequence within a particular polysaccharide molecule is random, some N,2O,3O,6O-HS polysaccharides between eighteen and thirty-one sugar residues can theoretically comprise an AT-recognition sequence toward the center of the molecule that does not have thirteen adjacent sugar residues on either side. Consequently, the N,2O,3O, 6O-HS polysaccharide must be at least thirty-two sugar residues long to guarantee that the thirteen residue "bridge" adjacent to the AT-recognition sequence can be formed, no matter where the AT-recognition sequence is within the molecule. As a result, in some embodiments, the N,2O,3O, 6O-HS polysaccharide product of the engineered 3OST enzyme can be at least five sugar residues, preferably at least eighteen sugar residues, and more preferably at least thirty-two sugar residues.

In another embodiment, anticoagulant N,2O,3O,6O-HS products of the engineered 3OST enzyme can satisfy benchmark requirements determined by the USP for pharmaceutical UFH compositions with regard to product purity, particularly purity from other sulfated polysaccharides, including but not limited to chondroitin sulfate. In particular, over-sulfated chondroitin sulfate (OSCS) was determined to be the source of contamination within pharmaceutical UFH compositions that caused hundreds of deaths worldwide in 2007 and 2008. In another embodiment, and without being limited by a particular theory, anticoagulant N,2O,3O,6O-HS products prepared using an engineered 3OST enzyme can be formed from to be substantially free from chondroitin sulfate, particularly OSCS, because the heparosan-based polysaccharides using as starting material can be provided and/or prepared in vitro without the same polysaccharide contaminants that are inherently present in anticoagulant N,2O,3O,6O-HS polysaccharides isolated from animal sources.

The USP has defined a reference standard (Chemical Abstracts Service (CAS) No: 9041-08-1) for UFH by which all pharmaceutical compositions are measured. The molecular weight properties of USP-compliant UFH must satisfy all of the following benchmarks: (1) the proportion of polysaccharides within the composition having a molecular weight over 24,000 Da is not more than 20%; (2) the $\overline{M}_w$ of the composition itself is between 15,000 Da and 19,000 Da; and (3) the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 (see Mulloy, B., et al., (2014) *Anal. Bioanal. Chem.* 406:4815-4823, the disclosure of which is incorporated by reference in its entirety). Further, the anticoagulant activity of USP-compliant UFH must satisfy all of the following benchmarks: an anti-IIa activity of not less than 180 International Units per milligram (IU mg$^{-1}$); an anti-Xa activity of not less than 180 IU mg$^{-1}$; and a ratio of anti-Xa to anti-IIa activity in a range of 0.9:1 up to 1.1:1. In another embodiment, anticoagulant N,2O,3O,6O-HS products prepared by an engineered 3OST enzyme can satisfy any or more of the above anticoagulant activity and molecular weight requirements determined by the United States Pharmacopeia (USP) for pharmaceutical UFH compositions.

With respect to the molecular weight properties of the N,2O,3O,6O-HS product of engineered 3OST in particular, these can be controlled in part based on the control of the molecular weight properties of the heparosan-based polysaccharide utilized as the sulfo group acceptor. The most controllable opportunity to control the molecular weight of a heparosan-based polysaccharide is by N-deacetylating and depolymerizing heparosan, as described above. Thus, in another embodiment, a series of sulfotransferase reactions can be performed in order to control the molecular weight of the anticoagulant N,2O,3O,6O-HS product. In another embodiment, a series of sulfotransferase reactions can be performed according to the following steps: (a) forming an N-sulfated heparosan product from N-deacetylated heparosan using a NST; (b) forming an N,2O-HS polysaccharide product using a 2OST and the N-sulfated heparosan product of step (a); (c) forming an N,2O,6O-HS polysaccharide product using a 6OST and the N,2O-HS polysaccharide product of step (b); and (d) forming an anticoagulant N,2O,3O,6O-HS polysaccharide product using a 3OST and the N,2O,6O-HS polysaccharide product of step (c). In another embodiment, all of the sulfotransferases are engineered sulfotransferases, and the sulfo donor in each reaction is an aryl sulfate compound, preferably PNS or NCS. In another embodiment, the N-deacetylated heparosan has an $\overline{M}_w$ in a range between 9,000 Da and 12,500 Da, as well as an N-acetyl glucosamine content in a range from 12% and up to 18%, as described in Wang, et al., (2011), above. Alternatively, and in another embodiment, the N-sulfated heparosan product utilized as the sulfo group acceptor for the 2OST can be chemically sulfated from N-deacetylated heparosan, as described above.

Thus, in another embodiment, an N,2O,3O,6O-HS product prepared by an engineered 3OST enzyme can have an $\overline{M}_w$ of at least 1,000 Da, including at least 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 16,000 Da, 17,000 Da, 18,000 Da, 19,000 Da, 20,000 Da, 21,000 Da, 22,000 Da, 23,000 Da, or 24,000 Da, up to at least 50,000 Da. In another embodiment, an N,2O,3O,6O-HS product prepared by an engineered 3OST enzyme can have an $\overline{M}_w$ of less than 50,000 Da, including less than 24,000 Da, 23,000 Da, 22,000 Da, 21,000 Da, 20,000 Da, 19,000 Da, 18,000 Da, 17,000 Da, 16,000 Da, 15,000 Da, 14,000 Da, 13,000 Da, 12,000 Da, 11,000 Da, 10,000 Da, 9,000 Da, 8,000 Da, 7,000 Da, 6,000 Da, 5,000 Da, 4,000 Da, or 3,000 Da, down to less than 2,000 Da. In another embodiment, an N,2O,3O,6O-HS product prepared by an engineered 3OST enzyme can have an $\overline{M}_w$ in any range listed above between and inclusive of 1,000 Da and 50,000 Da, and preferably in any range listed above between and inclusive of 15,000 Da and about 19,000 Da.

Similarly, in another embodiment, an N,2O,3O,6O-HS product prepared by an engineered 3OST enzyme can have a size distribution such that less than 50%, including less than 45%, 40%, 35%, 30%, 25%, 20%, 15%, 10%, 5%, 3%, or 2%, down to less than 1% of the N,2O,3O,6O-HS polysaccharides within the N,2O,3O,6O-HS product have a molecular weight greater than 24,000 Da. In another embodiment, less than or equal to 20% of the N,2O,3O,6O-HS polysaccharides within the N,2O,3O,6O-HS product have a molecular weight greater than 24,000 Da. In another embodiment, when less than or equal to 20% of the N,2O,3O,6O-HS polysaccharides within the N,2O,3O,6O-HS product have a molecular weight greater than 24,000 Da, the N,2O,3O,6O-HS product can have an $\overline{M}_w$ in any range listed above between and inclusive of 1,000 Da and 24,000 Da, and preferably in any range listed above between and inclusive of 15,000 Da and about 19,000 Da.

In another embodiment, an N,2O,3O,6O-HS product prepared by an engineered 3OST enzyme can have a size distribution such that the ratio of the number of polysaccharides within the composition having a molecular weight between 8,000 Da and 16,000 Da relative to the number of polysaccharides within the composition having a molecular weight between 16,000 Da and 24,000 Da is not less than 0.5:1, including not less than 0.75:1, 0.9:1, 1.0:1, 1.1:1, 1.3:1, or 1.5:1, up to not less than 2.0:1, and preferably not less than 1.0:1. In another embodiment, N,2O,3O,6O-HS products in which the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 can also have an $\overline{M}_w$ in any range listed above between and inclusive of 1,000 Da and 24,000 Da, and preferably in any range listed above and inclusive of 15,000 Da and about 19,000 Da, in which less than or equal to 20% of the N,2O,3O,6O-HS polysaccharides within the N,2O,3O,6O-HS product have a molecular weight greater than 24,000 Da.

In another embodiment, an anticoagulant N,2O,3O,6O-HS product prepared by an engineered 3OST enzyme can have an anti-Xa activity of at least about 1 IU mg$^{-1}$, including at least about 50 IU mg$^{-1}$, at least 75 IU mg$^{-1}$, 100 IU mg$^{-1}$, 150 IU mg$^{-1}$, 200 IU mg$^{-1}$, or 500 IU mg$^{-1}$, up to at least about 1,000 IU mg$^{-1}$. In another embodiment, an anticoagulant N,2O,3O,6O-HS product prepared by an engineered 3OST enzyme can have an anti-IIa activity of at least about 1 IU mg$^{-1}$, including at least about 50 IU mg$^{-1}$, at least 75 IU mg$^{-1}$, 100 IU mg$^{-1}$, 150 IU mg$^{-1}$, 200 IU mg$^{-1}$, or 500 IU mg$^{-1}$, up to at least about 1,000 IU mg$^{-1}$. In another embodiment, an anticoagulant N,2O,3O,6O-HS product prepared by an engineered 3OST enzyme can have a ratio of anti-Xa activity to anti-of at least 0.5:1, including at least 0.75:1, 0.9:1, 1:1, 1.1:1, 1.3:1, 1.5:1, 2.0:1, 3.0:1, 4.0:1, 5.0:1, 6.0:1, 7.0:1, 8.0:1, 9.0:1, 10.0:1, 20:1, 40:1, 60:1, or 80:1, up to at least 100:1. However, anticoagulant N,2O,3O,6O-HS polysaccharides that are thirty-two sugar residues or longer and are able to form the tertiary complex with AT and thrombin typically have a ratio of anti-Xa activity to anti-Ha activity that is usually close to 1:1, approximately between 0.9:1 to 1.1:1 (see Keire, D. A., et al., (2011) *Anal. Bioanal. Chem.* 399:581-591, the disclosure of which is incorporated by reference in its entirety).

Preparation of Engineered Aryl Sulfate-Dependent Enzymes

In general, the engineered enzymes encoded by the disclosed nucleic acid and amino acid sequences can be expressed and purified using any microbiological technique known in the art, including as described below. The aryl sulfate-dependent activity of each purified enzyme can be determined spectrophotometrically or fluorescently and/or using mass spectrometry (MS) or nuclear magnetic resonance (NMR) spectroscopy to characterize the starting materials and/or sulfated polysaccharide products. Such methods are described below in the Examples section.

The engineered gene products, proteins and polypeptides of the present invention can also include analogs that contain insertions, deletions, or mutations relative to the disclosed DNA or peptide sequences, and that also encode for enzymes that catalyze reactions in which aryl sulfate compounds are substrates. In another embodiment, each analog similarly catalyzes sulfotransfer reactions in which aryl sulfate compounds are utilized as sulfo donors. Analogs can be derived from nucleotide or amino acid sequences as disclosed herein, or they can be designed synthetically in silico or de novo using computer modeling techniques. Those skilled in the art will appreciate that other analogs, as yet undisclosed or undiscovered, can be used to design and/or construct different sulfate-dependent enzymes of the present invention. There is no need for a gene product, protein, or polypeptide to comprise all or substantially all of a nucleic acid or amino acid sequence of an engineered enzyme as disclosed herein. Such sequences are herein referred to as "segments." Further, the gene products, proteins, and polypeptides discussed and disclosed herein can also include fusion or recombinant engineered enzymes comprising full-length sequences or biologically functional segments of sequences disclosed in the present invention. Methods of preparing such proteins are known in the art.

In addition to the nucleic acid and amino acid sequences disclosed herein, any of the methods of the present invention can be practiced by engineered enzymes comprising amino acid sequences that are substantially identical to a disclosed amino acid sequence (SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160), or expressed from nucleic acids comprising a nucleotide sequence that is substantially identical to a disclosed nucleotide sequence (SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152). Those skilled in the art can determine appropriate nucleotide sequences that encode for polypeptides having the amino acid sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160 based on the nucleotide sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152.

"Substantially identical" sequences, as used in the art, refer to sequences which differ from a particular reference sequence by one or more deletions, substitutions, or additions, the net effect of which is to retain at least some of the biological activity of the engineered polypeptide encoded by the reference sequence. Namely, the biological activity of the engineered sulfotransferase enzymes comprises the transfer of a sulfo group from an aryl sulfate compound to a polysaccharide acting as a sulfo group acceptor. In another embodiment, the polysaccharide is a heparosan-based and/or HS polysaccharide. Accordingly, as used to describe the engineered enzymes of the present invention, "substantial identity" can refer either to identity with a particular gene product, polypeptide or amino acid sequence of an engineered enzyme, or a gene or nucleic acid sequence encoding for an engineered enzyme. Such sequences can include mutations of the disclosed sequences or a sequence in which the biological activity is altered, enhanced, or diminished to some degree but retains at least some of the original biological activity of a disclosed reference amino acid sequence or polypeptide encoded by a disclosed reference nucleic acid sequence.

Alternatively, DNA analog sequences are substantially identical to the specific DNA sequences disclosed herein if: (a) the DNA analog sequence is derived from coding regions of the any of the disclosed nucleic acid sequences; or (b) the DNA analog sequence is capable of hybridization of DNA sequences of (a) under stringent conditions and which encode for a biologically-active gene product; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity, namely, transferring a sulfo group from an aryl sulfate compound to polysaccharides, particularly heparosan-based or HS polysaccharides, are also considered to be substantially identical. In determining the substantial identity of nucleic acid sequences, all subject nucleic acid sequences capable of encoding substantially identical amino acid sequences are considered to be substantially identical to a reference nucleic acid sequence, regardless of differences in codon sequences or amino acid substitutions to create biologically functional equivalents.

At a biological level, identity is just that, i.e. the same amino acid at the same relative position in a given family member of a gene family. Homology and similarity are generally viewed as broader terms. For example, biochemically similar amino acids, for example leucine and isoleucine or glutamic acid/aspartic acid, can be alternatively present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

In some embodiments, the genes and gene products include within their respective sequences a sequence "essentially as that" of a gene encoding for an engineered enzyme or its corresponding protein. A sequence essentially as that of a gene encoding for an engineered enzyme refers to sequences that are substantially identical or substantially similar to a portion of a disclosed nucleic acid sequence and contains a minority of bases or amino acids (whether DNA or protein) that are not identical to those of a disclosed protein or a gene, or which are not a biologically functional equivalent. Biological functional equivalence is well understood in the art and is further discussed in detail below. Nucleotide sequences are "essentially the same" where they have between about 75% and about 85%, or particularly, between about 86% and about 90%, or more particularly greater than 90%, or even more particularly between about 91% and about 95%, or still more particularly, between about 96% and about 99%, of nucleic acid residues which are identical to the nucleotide sequence of a disclosed gene. Similarly, peptide sequences which have about 80%, or 90%, or particularly from 90-95%, or more particularly greater than 96%, or even more particularly 95-98%, or still more particularly 99% or greater amino acids which are identical or functionally equivalent or biologically functionally equivalent to the amino acids of a disclosed polypeptide sequence will be sequences which are "essentially the same."

Additionally, alternate nucleic acid sequences that include functionally equivalent codons are also encompassed by this invention. Functionally equivalent codons refer to codons that encode the same amino acid, such as the ACG and AGU codons for serine. Thus, substitution of functionally equivalent codons of Table 1, below, into the sequence examples of any of the nucleotide sequences disclosed above ultimately encode for biologically functional equivalent enzymes that are dependent on binding and reacting with aryl sulfate compounds in order to catalyze sulfo transfer. Thus, the present invention includes amino acid and nucleic acid sequences comprising such substitutions but which are not set forth herein in their entirety for convenience.

Those skilled in the art would recognize that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains its biological activity with respect to binding and reacting with aryl sulfate compounds as sulfo donors. The addition of terminal sequences particularly applies to nucleic acid sequences which can, for example, include various non-coding sequences flanking either of the 5' or 3' portions of the coding region or can include various internal sequences, or introns, which are known to occur within genes.

TABLE 1

Functionally Equivalent Codons

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic Acid | Asp | D | GAC | GAU | | |
| Glutamic Acid | Glu | E | GAA | GAG | | |
| Phenylalanine | Phe | F | UUC | UUU | | |

TABLE 1-continued

Functionally Equivalent Codons

| Amino Acids | | | Codons | | | | | |
|---|---|---|---|---|---|---|---|---|
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | LUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | ACG | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

As discussed above, modifications and changes can be made in the sequence of any of the disclosed engineered enzymes, including conservative and non-conserved mutations, deletions, and additions while still constituting a molecule having like or otherwise desirable characteristics. For example, certain amino acids can be substituted for other amino acids in a protein structure without appreciable loss of interactive capacity with particular structures or compounds, particularly aryl sulfate compounds and/or sulfo acceptor polysaccharides. This can occur because the ability of a protein to recognize, bind, and react with other structures or compounds within its environment defines that protein's biological functional activity, not the sequence itself. Consequently, certain amino acid sequence substitutions can be made in that protein's sequence to obtain a protein with the equal, enhanced, or diminished properties. One non-limiting example of such amino acid substitutions that can occur without an appreciable loss of interactive activity include substitutions in external domains or surfaces of the protein that do not affect the folding and solubility of the protein. Similarly, amino acids can potentially be added to either terminus of the protein so long as the ability of the protein to fold or to recognize and bind its substrates is not deleteriously affected. One skilled in the art can appreciate that several other methods and/or strategies can be utilized to alter an enzyme's sequence without affecting its activity.

Consequently, mutations, deletions, additions, or other alterations to a parent enzyme's structure or sequence in which the modified enzyme retains the parent enzyme's biological activity can be defined to be biologically functionally equivalent to the parent enzyme. Thus, biologically functional equivalent enzymes, with respect to the engineered aryl sulfate-dependent enzymes, can include any substitution or modification of an amino acid sequence disclosed in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, in which the resultant modified enzyme is dependent on interacting with aryl sulfate compounds, particularly PNS or NCS, to catalyze sulfo transfer to polysaccharides, particularly heparosan-based and/or HS polysaccharides. In particular, such substitutions or modifications can result from conservative mutations in the amino acid sequence in any portion of the protein, as described below, although non-conservative mutations in non-catalytically active regions of the enzyme are also contemplated. Consequently, the engineered enzymes can be expressed from any nucleic acid having a nucleotide sequence that encodes for a biologically functional equivalent enzyme, although such nucleotide sequences are not set forth herein in their entirety for convenience.

Alternatively, recombinant DNA technology can be used to create biologically functionally equivalent proteins or peptides in which changes in the protein structure can be engineered, based on considerations of the properties of the amino acids being exchanged. Rationally-designed changes can be introduced through the application of site-directed mutagenesis techniques, for example, to test whether certain mutations affect positively or negatively affect the enzyme's aryl sulfate-dependent catalytic activity and/or binding of sulfo donors or acceptors within the enzyme's active site.

Amino acid substitutions, such as those which might be employed in modifying any of the engineered enzymes described herein, are generally based on the relative similarity of the amino acid side-chain substituents, for example, their hydrophobicity, hydrophilicity, charge, size, and the like. Those skilled in the art are familiar with the similarities between certain amino acids, such as the size, shape and type of the amino acid side-chain substituents. Non-limiting examples include relationships such as that arginine, lysine and histidine are all positively charged residues; that alanine, glycine and serine are all of similar size; and that phenylalanine, tryptophan and tyrosine all have a generally similar shape. Consequently, the amino acids that comprise the following groups-arginine, lysine and histidine; alanine, glycine and serine; and phenylalanine, tryptophan and tyrosine—are defined herein as biologically functional equivalents to the other amino acids in the same group. Other biologically functionally equivalent changes will be appreciated by those of skill in the art.

One such method to evaluate biologically functional equivalents is to evaluate and consider the hydropathic index of each of the amino acids. Each of the twenty common amino acids has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6);

histidine (−3.2); glutamic acid (−3.5); glutamine (−3.5); aspartic acid (−3.5); asparagine (−3.5); lysine (−3.9); and arginine (−4.5).

The relationship between an amino acid residue's hydropathic index and the biological function of a protein is generally understood in the art. (Kyte, J., et al., (1982) *J. Mol. Biol.* 157 (1):105-132.) It is known that certain amino acids can be substituted for other amino acids having a similar hydropathic index or score and still retain a similar biological activity. In making changes based upon the hydropathic index, the substitution of amino acids whose hydropathic indices are within ±2 of the original value is the preferred measure to determine whether the substitution is biologically functionally equivalent, though those substitutions which are within ±1 of the original value are particularly preferred, and those within ±0.5 of the original value are even more particularly preferred.

Similarly, it is also understood in the art that the substitution of like amino acids can be made effectively on the basis of hydrophilicity. U.S. Pat. No. 4,554,101, the disclosure of which is incorporated by reference in its entirety, states that the greatest local average hydrophilicity of a protein, as governed by the hydrophilicity of its adjacent amino acids, correlates with its immunogenic, antigenic, and other biological properties of the protein. It is understood that an amino acid can be substituted for another having a similar hydrophilicity value and still obtain a biologically equivalent protein. As reported in U.S. Pat. No. 4,554,101, the following hydrophilicity values have been assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

As when making mutations based on the hydropathic index of an amino acid, similar changes can be made with regard to hydrophilicity. Thus, the substitution of amino acids whose hydrophilicity values are within 2 of the original value is the preferred measure to determine whether the substitution is biologically functionally equivalent, though those substitutions which are within ±1 of the original value are particularly preferred, and those within ±0.5 of the original value are even more particularly preferred.

In another embodiment, isolated nucleic acids, or functional fragments thereof, that encode for the engineered enzymes of the present invention are provided. In some embodiments, the engineered enzymes comprise an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. In other embodiments, the present invention provides isolated nucleic acids encoding functional fragments of the engineered enzymes of the present invention, or mutants thereof in which conservative substitutions have been made for particular residues in the amino acid sequences of any of the engineered enzymes listed above.

Additionally, isolated nucleic acids used to express any of the engineered enzymes of the present invention may be joined to other nucleic acid sequences for use in various applications. Thus, for example, the isolated nucleic acids may be ligated into cloning or expression vectors, as are commonly known in the art and as described in the examples below. Additionally, nucleic acids may be joined in-frame to sequences encoding another polypeptide so as to form a fusion protein, as is commonly known in the art. Fusion proteins can comprise a coding region for the engineered enzyme that is aligned within the same expression unit with other proteins or peptides having desired functions, such as for solubility, purification, or immunodetection. Thus, in another embodiment, cloning, expression and fusion vectors comprising any of the above-described nucleic acids, that encode for an engineered enzyme of the present invention are also provided.

Furthermore, nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. Those skilled in the art would recognize that a nucleic acid fragment of almost any length can be employed, with the total length typically being limited by the ease of preparation and use in the intended recombinant DNA protocol.

In particular, recombinant vectors in which the coding portion of the gene or DNA segment is positioned under the control of a promoter are especially useful. In some embodiments, the coding DNA segment can be associated with promoters isolated from bacterial, viral, eukaryotic, or mammalian cells. Promoters specific to the cell type chosen for expression are often the most effective. The use of promoter and cell type combinations for protein expression is generally known to those of skill in the art of molecular biology (See, e.g., Sambrook et al. (2012) Molecular Cloning: A Laboratory Manual, Fourth Edition, Cold Spring Harbor Laboratory Press, Cold Spring Harbor, N.Y., incorporated by reference in its entirety). The promoters employed can be constitutive or inducible and can be used under the appropriate conditions to direct high-level expression of the introduced DNA segment, such as is advantageous in the large-scale production of recombinant proteins or peptides. Appropriate promoter systems that are often effective for high-level expression include, but are not limited to, the vaccinia virus promoter, the baculovirus promoter, and the Ptac promoter.

Thus, in some embodiments, an expression vector can be utilized that comprises a nucleotide sequence encoding for a biologically-active, engineered enzyme suitable the present invention. In one example, an expression vector can comprise any nucleotide sequence that encodes for an aryl sulfate-dependent gene product. In further embodiments, an expression vector comprises a nucleic acid comprising the nucleotide sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152. In other further embodiments, the expression vector comprises a nucleic acid comprising any nucleotide sequence that encodes for a polypeptide comprising the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In even further embodiments, any nucleic acid sequence encoding for an engineered enzyme of the present invention can be codon-optimized based on the expression host used to produce the enzyme. The preparation of recombinant vectors and codon optimization are well known to those of skill in the art and described in many references, such as, for example, Sambrook et al. (2012) Molecular Cloning: A Laboratory Manual, Fourth Edition, Cold Spring Harbor Laboratory Press, Cold Spring Harbor, N.Y.

Those skilled in the art would recognize that the DNA coding sequences to be expressed, in this case those encoding the engineered gene products, are positioned in a vector adjacent to and under the control of a promoter. As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, poly-A addition sites are placed about 30 to 2000 nucleotides "downstream" of the coding sequence at a position prior to transcription termination.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

Optionally, an expression vector of the invention comprises a polynucleotide operatively linked to an enhancer-promoter. As used herein, the phrase "enhancer-promoter" means a composite unit that contains both enhancer and promoter elements. For example, an expression vector can comprise a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present invention can be any enhancer-promoter that drives expression in a cell to be transfected. By employing an enhancer-promoter with well-known properties, the level and pattern of gene product expression can be optimized.

Engineered enzymes of the present invention can be expressed within cells or cell lines, either prokaryotic or eukaryotic, into which have been introduced the nucleic acids of the present invention so as to cause clonal propagation of those nucleic acids and/or expression of the proteins or peptides encoded thereby. Such cells or cell lines are useful for propagating and producing nucleic acids, including those disclosed in sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152. Such cells or cell lines are also useful for producing the engineered enzymes themselves, including those described by sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, fragments of those sequences thereof, or fusion proteins including those sequences). Bacterial cells (e.g., *E. coli*) may be used with a variety of expression vector systems including, for example, plasmids with the T7 RNA polymerase/promoter system, bacteriophage λ regulatory sequences, or M13 Phage regulatory elements. Bacterial hosts may also be transformed with fusion protein vectors that create, for example, Protein A, lacZ, trpE, maltose-binding protein (MBP), small ubiquitin-related modifier (SUMO), poly-His tag, or glutathione-S-transferase (GST) fusion proteins. All of these, as well as many other prokaryotic expression systems, are well known in the art and widely available commercially (e.g., pGEX-27 (Amrad, USA) for GST fusions).

In some embodiments of the invention, expression vectors comprising nucleic acid sequences as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152 can also comprise genes or nucleic acid sequences encoding for fusion proteins with any engineered enzyme. In further embodiments, expression vectors can additionally include the malE gene, which encodes for the maltose binding protein. Upon inducing protein expression from such expression vectors, the expressed gene product comprises a fusion protein that includes maltose binding protein and an engineered enzyme comprising the amino acid sequence set forth in SEQ ID NO: 1, SEQ ID NO: 3, NO: 159, or SEQ ID NO: 160. As used herein, the term "transformed cell" is intended to embrace any cell, or the descendant of any cell, into which has been introduced any of the nucleic acids of the invention, whether by transformation, transfection, transduction, infection, or other means. Methods of producing appropriate vectors, transforming cells with those vectors, and identifying transformants are well known in the art. (See, e.g., Sambrook et al. (2012) Molecular Cloning: A Laboratory Manual, Fourth Edition, Cold Spring Harbor Laboratory Press, Cold Spring Harbor, N.Y.)

Prokaryotic cells useful for producing transformed cells include members of the bacterial genera *Escherichia* (e.g., *E. coli*), *Pseudomonas* (e.g., *P. aeruginosa*), and *Bacillus* (e.g., *B. subtilis, B. stearothermophilus*), as well as many others well known and frequently used in the art. Prokaryotic cells are particularly useful for the production of large quantities of the proteins or peptides (e.g., engineered enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO:

SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In other further embodiments, an expression vector that includes any of the above nucleic acids that encode for any of the above engineered enzymes can additionally include a gene encoding for a SUMO modifier, such as, in a non-limiting example, SUMO-1.

In other embodiments, expression vectors according to the present invention can additionally include a nucleic acid sequence encoding for a poly-His tag. Upon inducing protein expression from such expression vectors, the expressed gene product comprises a fusion protein that includes the poly-His tag and an engineered enzyme comprising the amino acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In a further embodiment, expression vectors can include both a nucleic acid sequence encoding for a poly-His tag and the malE gene or a SUMO gene, from which a fusion protein can be expressed that includes a poly-His tag, MBP, or SUMO, along with any engineered enzyme.

Eukaryotic cells and cell lines useful for producing transformed cells include mammalian cells (e.g., endothelial cells, mast cells, COS cells, CHO cells, fibroblasts, hybridomas, oocytes, embryonic stem cells), insect cells lines (e.g., Drosophila Schneider cells), yeast, and fungi. Non-limiting examples of such cells include, but are not limited to, COS-7 cells, CHO, cells, murine primary cardiac microvascular endothelial cells (CME), murine mast cell line C57.1, human primary endothelial cells of umbilical vein (HU-VEC), F9 embryonal carcinoma cells, rat fat pad endothelial cells (RFPEC), and L cells (e.g., murine LTA tk– cells).

Vectors may be introduced into the recipient or "host" cells by various methods well known in the art including, but not limited to, calcium phosphate transfection, strontium phosphate transfection, DEAE dextran transfection, electroporation, lipofection, microinjection, ballistic insertion on micro-beads, protoplast fusion or, for viral or phage vectors, by infection with the recombinant virus or phage.

In some embodiments, the present invention provides substantially pure preparations of engineered enzymes dependent on reacting with aryl sulfate compounds for biological activity. In further embodiments, purified engineered enzymes can comprise the amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160.

In another embodiment, the present invention provides engineered enzyme variants in which conservative or non-conservative substitutions have been made for certain residues within the amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. Conservative or non-conservative substitutions can be made at any point in the amino acid sequence, including residues that surround the active site or are involved in catalysis, provided that the enzyme retains measurable catalytic activity; namely, the transfer of a sulfo group from an aryl sulfate compound to a polysaccharide, particularly a heparosan-based and/or HS polysaccharide. In other embodiments, the aryl sulfate compound is PNS. In still other embodiments, the aryl sulfate compound is NCS.

In another embodiment, the engineered sulfotransferase enzymes have at least 50%, including at least 60%, 70%, 80%, 85%, 90% or 95% up to at least 99% amino acid sequence identity to an amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, while retaining its catalytic activity of transfer of a sulfo group from an aryl sulfate compound to a polysaccharide, particularly a heparosan-based and/or HS polysaccharide. Such sequences may be routinely produced by those of ordinary skill in the art, and sulfotransferase activity may be tested by routine methods such as those disclosed herein.

Further, and in another embodiment, the amino acid sequence(s) of any of the engineered sulfotransferases utilized in accordance with any of the methods described herein can be characterized as a percent identity relative to a natural sulfotransferase that catalyzes the same reaction using PAPS as the sulfo donor, so long as the sulfotransferase has aryl sulfate-dependent activity. For example, and in another embodiment, an engineered aryl sulfate-dependent NST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of the N-sulfotransferase domain of any of the natural NDST enzymes within EC 2.8.2.8, including biological functional fragments thereof. In a further embodiment, the engineered NST can comprise at least 50%, including at least 55%, 60%, 65%, 70%, 75%, 80%, 85%, 90%, or 95%, up to at least 97% sequence identity with the amino acid sequence of the N-sulfotransferase domain of the human NDST1 enzyme (entry sp|P52848|NDST_1_HUMAN, in FIG. 6A, FIG. 6B, and FIG. 6C, above).

In another embodiment, an engineered aryl sulfate-dependent 2OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 2OST enzymes within EC 2.8.2.-, including biological functional fragments thereof. In a further embodiment, the engineered 2OST can comprise at least 50%, including at least 55%, 60%, 65%, 70%, 75%, 80%, 85%, 90%, or 95%, up to at least 97% sequence identity with the amino acid sequence of the natural chicken 2OST enzyme (entry sp|Q76KB1|HS2ST_CHICK, in FIG. 17A, FIG. 17B, FIG. 17C, and FIG. 17D, above).

In another embodiment, an engineered aryl sulfate-dependent 6OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 6OST enzymes within EC 2.8.2.-, including biological functional fragments thereof. In a further embodiment, the engineered 6OST can comprise at least 50%, including at least 55%, 60%, 65%, 70%, 75%, 80%, 85%, 90%, or 95%, up to at least 97% sequence identity with the amino acid sequence of the mouse 6OST1 enzyme (UniProtKB Accession No. Q9QYK5). In a further embodiment, the engineered 6OST can comprise at least 50%, including at least 55%, 60%, 65%, 70%, 75%, 80%, 85%, 90%, or 95%, up to at least 97% sequence identity with residues 67-377 of the amino acid sequence of the mouse 6OST1 enzyme (entry Q9QYK5|H6ST1_MOUSE, in FIG. 21A, FIG. 21B, and FIG. 21C, above).

In another embodiment, an engineered aryl sulfate-dependent 3OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural enzymes within EC 2.8.2.23, including biological functional fragments thereof. In a further embodiment, the engineered 3OST can comprise at least 50%, including at least 55%, 60%, 65%, 70%, 75%, 80%, 85%, 90%, or 95%, up to at least 97% sequence identity with residues 48-311 of the amino acid sequence of the natural human 3OST1 enzyme (entry O14792|HS3S1_HUMAN, in FIG. 26A, FIG. 26B, and FIG. 26C, above).

Substantially pure engineered enzymes may be joined to other polypeptide sequences for use in various applications. Thus, for example, engineered enzymes may be joined to one or more additional polypeptides so as to form a fusion protein, as is commonly known in the art. The additional polypeptides may be joined to the N-terminus, C-terminus or both termini of the engineered enzyme. Such fusion proteins may be particularly useful if the additional polypeptide sequences are easily identified (e.g., by providing an antigenic determinant), are easily purified (e.g., by providing a ligand for affinity purification), or enhance the solubility of the engineered enzyme in solution.

In another embodiment, substantially pure proteins may comprise only a portion or fragment of the amino acid sequence of an engineered enzyme. In some instances, it may be preferable to employ a minimal fragment retaining aryl sulfate-dependent activity, particularly if the minimal fragment enhances the solubility or reactivity of the enzyme. Thus, in some embodiments, methods of the present invention can be practiced using substantially pure engineered sulfotransferases of any length, including full-length forms described by the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, including minimal functional fragments thereof. Additionally, these proteins may also comprise conservative or non-conservative substitution variants as described above.

The engineered enzymes may be substantially purified by any of a variety of methods selected on the basis of the properties revealed by their protein sequences. Typically, the engineered enzymes, fusion proteins, or fragments thereof, can be purified from cells transformed or transfected with expression vectors, as described above. Insect, yeast, eukaryotic, or prokaryotic expression systems can be used, and are well known in the art. In the event that the protein or fragment localizes within microsomes derived from the Golgi apparatus, endoplasmic reticulum, or other membrane-containing structures of such cells, the protein may be purified from the appropriate cell fraction. Alternatively, if the protein does not localize within these structures, or aggregates in inclusion bodies within the recombinant cells (e.g., prokaryotic cells), the protein may be purified from whole lysed cells or from solubilized inclusion bodies by standard means.

Purification can be achieved using standard protein purification procedures including, but not limited to, affinity chromatography, gel-filtration chromatography, ion-exchange chromatography, high-performance liquid chromatography (RP-HPLC, ion-exchange HPLC, size-exclusion HPLC), high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

An engineered enzyme, or a fragment thereof, may also be conveniently purified by creating a fusion protein including the desired sequence fused to another peptide such as an antigenic determinant, a poly-histidine tag (e.g., QIAexpress vectors, QIAGEN Corp., Chatsworth, Calif.), or a larger protein (e.g., GST using the pGEX-27 vector (Amrad, USA), green fluorescent protein using the Green Lantern vector (GIBCO/BRL. Gaithersburg, Md.), maltose binding protein using the pMAL vector (New England Biolabs, Ipswich, Mass.), or a SUMO protein. The fusion protein may be expressed and recovered from prokaryotic or eukaryotic cells and purified by any standard method based upon the fusion vector sequence. For example, the fusion protein may be purified by immunoaffinity or immunoprecipitation with an antibody to the non-aryl sulfate-dependent enzyme portion of the fusion or, in the case of a poly-His tag, by affinity binding to a nickel column. The desired engineered enzyme protein or fragment can then be further purified from the fusion protein by enzymatic cleavage of the fusion protein. Methods for preparing and using such fusion constructs for the purification of proteins are well known in the art and numerous kits are now commercially available for this purpose.

Furthermore, in some embodiments, isolated nucleic acids encoding for any engineered enzyme may be used to transform host cells. The resulting proteins may then be substantially purified by well-known methods including, but not limited to, those described in the examples below. Alternatively, isolated nucleic acids may be utilized in cell-free in vitro translation systems. Such systems are also well known in the art.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

EXAMPLES

The following working and prophetic examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Cloning, Expression, and Purification of the Engineered Aryl Sulfate-Dependent Enzymes A study was conducted in accordance with embodiments of the present disclosure to determine whether genes according to the present invention could be transformed into host cells capable of overexpressing engineered aryl sulfate-dependent enzymes, particularly enzymes having sulfotransferase activity. After expression, each aryl sulfate-dependent enzyme was isolated and purified from the host cell.

Generally, DNA coding for genes of any sequence can be synthesized de novo by methods commonly known in the art, including but not limited to oligonucleotide synthesis and annealing. Alternatively, DNA can be synthesized commercially and purchased from any one of several laboratories that regularly synthesize genes of a given sequence, including but not limited to ThermoFisher Scientific, GenScript, DNA 2.0, or OriGene. Persons skilled in the art would appreciate that there are several companies that provide the same services, and that the list provided above is merely a small sample of them. Genes of interest can be synthesized independently and subsequently inserted into a bacterial or other expression vector using conventional molecular biology techniques, or the genes can be synthesized concurrently with the DNA comprising the expression vector itself. Similar to genes of interest, suitable expression vectors can also be synthesized or obtained commercially. Often, bacterial expression vectors include genes that confer selective antibiotic resistance to the host cell, as well as genes that permit the cell to overproduce the protein of interest in response to the addition of isopropyl β-D-1-thiogalactopyranoside (IPTG). Bacterial production of proteins of interest using IPTG to induce protein expression is widely known in the art.

As described above, expression vectors can also include genes that enable production of fusion proteins that include the desired protein that is co-expressed with an additional, known protein to aid in protein folding and solubility. Non-limiting examples of fusion proteins that are commonly produced and are well-known in the art include fusions with MBP, SUMO, or green fluorescent protein. In particular, MBP fusion proteins facilitate easier purification because MBP possesses high affinity for amylose-based resins used in some affinity chromatography columns, while SUMO fusion proteins can include a poly-histidine tag that enables affinity purification on columns with $Ni^{2+}$-based resins as a stationary phase. Often, fusion proteins between the protein of interest and MBP and/or SUMO can optionally include an amino acid linking sequence that connects the two proteins. Non-limiting examples of commercial expression vectors that can be purchased to produce MBP fusion proteins include the pMAL-c5E™ and pMAL-c5X™ vectors, which can be obtained from New England Biolabs. Similarly, and in another non-limiting example, commercial expression vectors can also be purchased to produce SUMO fusion proteins, such as the pE-SUMOpro AMP vector, available from LifeSensors, Inc. Once the fusion proteins are produced and purified, proteases can be utilized to cleave the fused protein and any associated linker sequences from the enzyme, if cleavage is necessary for activity.

Additionally, expression vectors can also include DNA coding for a poly-histidine tag that can be synthesized at either the N- or C-terminus of the protein of interest. As with MBP fusions, proteins that include a poly-histidine tag simplify the enzyme purification because the tag has a high affinity for $Ni^{2+}$ resins that are utilized in many purification columns. Additionally, poly-histidine tags can optionally be cleaved after purification if it is necessary for optimal activity of the enzyme. A non-limiting example of an expression vector encoding for a C-terminal poly-histidine tag is the pET21b vector, available from Novagen. Another non-limiting example of an expression vector encoding for a poly-histidine tag is the pE-SUMO vector, which encodes for a poly-histidine tag at the N-terminus of the SUMO protein.

In the present example, double-stranded DNA fragments comprising the nucleotide sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO:

107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152, encoding for engineered aryl sulfate-dependent enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively, were synthesized using Integrated DNA Technologies' (IDT) gBlocks® Gene Fragments synthesis service. Polymerase chain reactions (PCR) were initiated to generate copies of each double-stranded DNA fragment, using forward and reverse primers comprising appropriate restriction enzyme recognition sequences to facilitate insertion into an expression vector. Genes comprising the nucleotide sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152, encoding for engineered enzymes comprising the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively, contained NdeI and BamHI restriction enzyme recognition sequences, and were ligated into the pMAL-c5x expression vector using quick ligation kits provided by NEB. Expression vectors were then transformed into competent DH5-a E. coli cells. Single clones were incubated in LB medium with 100 µL/mL ampicillin. Nucleotide sequences of each gene and expression vector within the transformed host cells were confirmed by commercial DNA sequencing (GeneWiz).

Protein expression of engineered enzymes comprising the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151 was achieved by transforming confirmed DNA constructs into competent SHuffle® T7 Express lysY E. coli cells, although protein expression has also been achieved by transforming confirmed DNA constructs into competent BL21 (DE3) E. coli cells. From either construct, resultant colonies were used to inoculate 250 mL cultures in LB medium, which were allowed to shake and incubate at 32° C. until an optical density at 600 nM (OD 600) of approximately 0.4 to 0.6 was observed. Expression was induced by the addition of 100 µM IPTG to each culture at 18° C.

Upon incubation at 18° C. overnight, expressed cells were harvested by centrifuging at 3,620 g and resuspending the pellet in 10 mL of resuspension buffer (25 mM Tris-HCl, pH 7.5; 0.15 M NaCl; 0.2 mg/mL lysozyme; 10 µg/ml DNase I; 5 mM $MgCl_2$; and 0.1% (w/v) Triton-X 100). Resuspended cells were lysed upon sonication on ice for three pulses of 10 seconds each, and subsequently passed through a 0.45-µm syringe filter. The resulting supernatant was loaded into a 5-mL spin column (G-biosciences) comprising Dextrin Sepharose® resin (GE Biosciences) suspended in a binding buffer comprising 25 mM Tris-HCl, pH 7.5 and 0.15 M NaCl. Enzymes of interest were eluted from the column upon adding an elution buffer comprising 25 mM Tris-HCl, pH 7.5; 0.15 M NaCl; and 40 mM maltose.

On the other hand, genes comprising the nucleotide sequences SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, or SEQ ID NO: 109, encoding for engineered enzymes comprising the amino acid sequences SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, or SEQ ID NO: 108, respectively, contained BsaI and XbaI restriction enzyme recognition sequences, and were ligated into the pE-SUMO vector (LifeSensors, Inc.). Expression vectors were then transformed into competent BL21-DE3 E. coli cells. Single clones were incubated in Terrific Broth with 100 µL/mL ampicillin. Nucleotide sequences of each gene and expression vector within the transformed host cells were confirmed by commercial DNA sequencing (GeneWiz).

Protein expression of engineered enzymes comprising the amino sequences SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, or SEQ ID NO: 108 was achieved by inoculating 500 mL cultures in Terrific Broth with ampicillin and allowing the cultures to incubate with shaking at 35° C. until an OD 600 of approximately 0.6-0.8 was reached. Protein expression was induced by the addition of 0.2 mM IPTG at 18° C. Cultures were then allowed to incubate at 18° C. overnight, and were subsequently lysed and filtered using an identical procedure as described above. The engineered enzymes were subsequently purified in a 5-mL spin column (G-biosciences) comprising HisPur Ni-NTA resin (Thermofisher) suspended in a binding buffer comprising 25 mM Tris-HCl, pH 7.5, 0.15 M NaCl, 5 mM $MgCl_2$, and 30 mM imidazole. Enzymes of interest were eluted from the column upon adding an elution buffer comprising 25 mM Tris-HCl, pH 7.5, 0.15 M NaCl, 5 mM $MgCl_2$, and 300 mM imidazole.

Example 2: Confirmation of Aryl Sulfate-Dependent Sulfatase Activity

Generally, the sulfatase activity of the aryl sulfate-dependent enzymes can be readily determined because the desulfurylated aromatic products of many aryl sulfate compounds, including but not limited to, PNS, MUS, 7-hydroxycoumarin sulfate, phenyl sulfate, 4-acetylphenyl sulfate, indoxyl sulfate, 1 naphthyl sulfate, 2NapS, and NCS each have the ability to absorb light or fluoresce in the near ultraviolet or visible spectrum. The absorbance or fluorescence by the desulfurylated aromatic product can be detected using a spectrophotometer or a fluorimeter, respectively. Those skilled in the art would readily be able to determine which instrument to use to monitor the progress of a reaction based on the spectral properties of the particular aryl sulfate compound and its desulfurylated aromatic product(s).

In one non-limiting example, reactions in which PNS is utilized as a substrate produce p-nitrophenol as a product upon hydrolysis of the sulfate ester linkage. Reaction mixtures having a pH greater than the pKa of p-nitrophenol (about 7.15) turn yellow because the negatively-charged p-nitrophenolate ion is prevalent over the neutrally-charged p-nitrophenol. Typically, the maximum absorbance of visible light by a solution containing the p-nitrophenolate ion can be observed at a wavelength of about 405 nm. Consequently, an absorbance value under reaction conditions that is greater than a negative control containing only PNS in identical buffer conditions indicates that the enzyme is active. Similarly, as more p-nitrophenolate ion is produced as a result of catalysis by a particular aryl sulfate-dependent enzyme, the absorbance of the reaction mixture as a function of time can be measured at about 405 nm to determine reaction rate and other kinetic information. As another non-limiting example, the production of the desulfurylated product of NCS, 4-nitrocatechol, upon hydrolysis of the sulfate ester linkage can be measured in reactions having a pH greater than the pKa of 4-nitrocatechol (about 7.17), by observing the absorbance of visible light at a wavelength of about 515 nm.

As another limiting example, the desulfurylated products of 2NapS can fluoresce in solution in response to being excited by radiation at a lower wavelength. Depending on the pH of the solution, the desulfurylated product is either 2-naphthol or the 2-naphtholate ion (pKa=9.5). To ensure the presence of a single 2-naphthyl species in solution, compositions with completed reactions are typically quenched with either an acid or a base in order to drive equilibrium to either the complete formation of 2-naphthol, which has an emission maximum of around 355 nM, or the 2-naphtholate ion, which has an emission maximum of about 410 nm. In either instance, the desulfurylated product can be excited at a wavelength of around 320 nm.

Thus, a study was conducted in accordance with embodiments of the present disclosure to determine the sulfatase activity of purified enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151. Non-steady state sulfatase activity with PNS, NCS, and 2NapS was monitored in 100-µL reactions containing 50 µM enzyme and 5 mM of substrate in elution buffer. In reactions containing PNS, the absorbance of the reaction mixture as a result of the production of p-nitrophenolate was measured at 401 nm. In reactions containing NCS, the absorbance of the reaction mixture as a result of the production of 4-nitrocatechol was measured at 515 nm. Reaction mixtures containing 2NapS were quenched by adding 0.1M NaOH to convert all of the 2-naphthol produced as a result of the reaction to the 2-naphtholate ion. All of the sets of activity experiments were conducted using a Spectramax M2 Microplate Reader (Molecular Dynamics). Additionally, a negative control reaction condition was set up for each experiment, which contained the aryl sulfate compound in the elution buffer (see above), but with no enzyme present. Activity experiments for the engineered enzymes were conducted in several data sets. All raw data were normalized and evaluated as a percentage of the increase in signal over a control in which all other components but enzyme was added, with results reported below in Tables 2-10. In particular, the results of enzymes that are mutants of natural NDST enzymes are reported in Table 2, Table 3, and Table 4, the results of enzymes that are mutants of natural 2OSTs are reported in Table 5 and Table 6, the results of enzymes that are mutants of natural 6OSTs are reported in Table 7 and Table 8, and the results of enzymes that are mutants of natural 3OSTs are reported in Table 9 and Table 10.

TABLE 2

|  | PNS ($Abs_{401}$) | (−) control | % increase |
|---|---|---|---|
| SEQ ID NO: 1 | 0.078 | 0.055 | 42% |
| SEQ ID NO: 3 | 0.1095 | 0.055 | 99% |
| SEQ ID NO: 5 | 0.0965 | 0.055 | 75% |
| SEQ ID NO: 7 | 0.0925 | 0.055 | 68% |
| SEQ ID NO: 9 | 0.107 | 0.079 | 35% |
| SEQ ID NO: 11 | 0.128 | 0.079 | 62% |
| SEQ ID NO: 15 | 0.083 | 0.059 | 42% |

TABLE 3

|  | NCS (Abs$_{515}$) | (−) control | % increase |
| --- | --- | --- | --- |
| SEQ ID NO: 3 | 0.0545 | 0.041 | 33% |
| SEQ ID NO: 5 | 0.0545 | 0.041 | 33% |
| SEQ ID NO: 7 | 0.057 | 0.041 | 39% |
| SEQ ID NO: 9 | 0.168 | 0.083 | 102% |
| SEQ ID NO: 11 | 0.213 | 0.083 | 157% |
| SEQ ID NO: 13 | 0.201 | 0.083 | 143% |

TABLE 4

|  | 2NapS ($\lambda_{em,410}$) | (−) control | % increase |
| --- | --- | --- | --- |
| SEQ ID NO: 3 | 2.974 × 10$^6$ | 1.804 × 10$^6$ | 65% |
| SEQ ID NO: 5 | 3.188 × 10$^6$ | 1.804 × 10$^6$ | 76% |
| SEQ ID NO: 9 | 2.972 × 10$^6$ | 1.804 × 10$^6$ | 65% |
| SEQ ID NO: 11 | 2.965 × 10$^6$ | 1.804 × 10$^6$ | 64% |

TABLE 5

|  | NCS (Abs$_{515}$) | (−) control | % increase |
| --- | --- | --- | --- |
| SEQ ID NO: 27 | 0.064 | 0.046 | 39% |
| SEQ ID NO: 29 | 0.063 | 0.046 | 37% |
| SEQ ID NO: 33 | 0.072 | 0.046 | 56% |
| SEQ ID NO: 45 | 0.085 | 0.046 | 85% |
| SEQ ID NO: 53 | 0.082 | 0.046 | 78% |
| SEQ ID NO: 63 | 0.069 | 0.046 | 50% |
| SEQ ID NO: 65 | 0.065 | 0.046 | 41% |

TABLE 6

|  | PNS (Abs$_{401}$) | (−) control | % increase |
| --- | --- | --- | --- |
| SEQ ID NO: 27 | 0.103 | 0.073 | 41% |
| SEQ ID NO: 33 | 0.077 | 0.046 | 67% |
| SEQ ID NO: 35 | 0.076 | 0.046 | 65% |
| SEQ ID NO: 37 | 0.089 | 0.046 | 93% |
| SEQ ID NO: 39 | 0.076 | 0.046 | 65% |
| SEQ ID NO: 41 | 0.084 | 0.046 | 82% |
| SEQ ID NO: 45 | 0.124 | 0.080 | 55% |
| SEQ ID NO: 47 | 0.194 | 0.095 | 105% |
| SEQ ID NO: 51 | 0.210 | 0.095 | 121% |
| SEQ ID NO: 53 | 0.120 | 0.080 | 50% |
| SEQ ID NO: 55 | 0.067 | 0.046 | 45% |
| SEQ ID NO: 57 | 0.072 | 0.046 | 57% |
| SEQ ID NO: 59 | 0.073 | 0.046 | 59% |
| SEQ ID NO: 61 | 0.068 | 0.046 | 48% |
| SEQ ID NO: 63 | 0.105 | 0.073 | 44% |
| SEQ ID NO: 65 | 0.105 | 0.080 | 31% |

TABLE 7

|  | PNS (Abs$_{401}$) | (−) control | % increase |
| --- | --- | --- | --- |
| SEQ ID NO: 70 | 0.1340 | 0.114 | 18% |
| SEQ ID NO: 72 | 0.0740 | 0.065 | 14% |
| SEQ ID NO: 74 | 0.1150 | 0.103 | 12% |
| SEQ ID NO: 76 | 0.0990 | 0.075 | 32% |
| SEQ ID NO: 78 | 0.1020 | 0.075 | 36% |
| SEQ ID NO: 80 | 0.1010 | 0.075 | 35% |
| SEQ ID NO: 82 | 0.1160 | 0.103 | 13% |
| SEQ ID NO: 86 | 0.0950 | 0.075 | 27% |
| SEQ ID NO: 88 | 0.1070 | 0.075 | 43% |
| SEQ ID NO: 90 | 0.1290 | 0.106 | 22% |
| SEQ ID NO: 92 | 0.0910 | 0.08 | 14% |
| SEQ ID NO: 94 | 0.0980 | 0.08 | 23% |
| SEQ ID NO: 106 | 0.0810 | 0.068 | 19% |
| SEQ ID NO: 108 | 0.0840 | 0.068 | 23% |

TABLE 8

|  | NCS (Abs$_{515}$) | (−) control | % increase |
| --- | --- | --- | --- |
| SEQ ID NO: 70 | 0.097 | 0.077 | 27% |
| SEQ ID NO: 74 | 0.079 | 0.072 | 9% |
| SEQ ID NO: 76 | 0.06 | 0.044 | 36% |
| SEQ ID NO: 78 | 0.056 | 0.044 | 27% |
| SEQ ID NO: 80 | 0.057 | 0.044 | 30% |
| SEQ ID NO: 82 | 0.08 | 0.072 | 10% |
| SEQ ID NO: 84 | 0.064 | 0.056 | 14% |
| SEQ ID NO: 86 | 0.06 | 0.049 | 22% |
| SEQ ID NO: 88 | 0.067 | 0.049 | 37% |
| SEQ ID NO: 90 | 0.087 | 0.072 | 20% |
| SEQ ID NO: 92 | 0.058 | 0.05 | 16% |
| SEQ ID NO: 94 | 0.061 | 0.05 | 22% |
| SEQ ID NO: 96 | 0.093 | 0.077 | 22% |
| SEQ ID NO: 98 | 0.092 | 0.077 | 20% |
| SEQ ID NO: 100 | 0.049 | 0.044 | 11% |
| SEQ ID NO: 102 | 0.053 | 0.047 | 12% |
| SEQ ID NO: 104 | 0.054 | 0.044 | 23% |
| SEQ ID NO: 106 | 0.064 | 0.056 | 15% |

TABLE 9

|  | PNS (Abs$_{401}$) | (−) control | % increase |
| --- | --- | --- | --- |
| SEQ ID NO: 123 | 0.0730 +/− .00283 | 0.0545 | 34% |
| SEQ ID NO: 127 | 0.0745 +/− .00354 | 0.0544 | 37% |
| SEQ ID NO: 129 | 0.0730 +/− .00141 | 0.0545 | 34% |
| SEQ ID NO: 133 | 0.0730 +/− 0.0 | 0.0544 | 34% |
| SEQ ID NO: 135 | 0.1000 +/− .00566 | 0.0658 | 52% |
| SEQ ID NO: 137 | 0.1060 +/− .00141 | 0.0658 | 61% |
| SEQ ID NO: 141 | 0.0860 +/− .00283 | 0.0589 | 46% |
| SEQ ID NO: 143 | 0.1030 +/− 0.0 | 0.0792 | 30% |
| SEQ ID NO: 147 | 0.0865 +/− .00071 | 0.0588 | 47% |
| SEQ ID NO: 149 | 0.0890 +/− 0.0 | 0.0589 | 51% |
| SEQ ID NO: 151 | 0.0900 +/− 0.0 | 0.0588 | 53% |

TABLE 10

|  | NCS (Abs$_{515}$) | (−) control | % increase |
| --- | --- | --- | --- |
| SEQ ID NO: 123 | 0.0505 +/− .00354 | 0.0391 | 29% |
| SEQ ID NO: 125 | 0.0505 +/− .00495 | 0.0391 | 29% |
| SEQ ID NO: 131 | 0.0560 +/− .00141 | 0.0409 | 37% |
| SEQ ID NO: 135 | 0.0735 +/− .01768 | 0.0420 | 75% |
| SEQ ID NO: 137 | 0.0560 +/− .00283 | 0.0421 | 61% |
| SEQ ID NO: 139 | 0.1550 +/− .00265 | 0.0829 | 87% |
| SEQ ID NO: 141 | 0.0560 +/− .00141 | 0.0409 | 37% |
| SEQ ID NO: 143 | 0.1520 +/− .00954 | 0.0831 | 83% |
| SEQ ID NO: 145 | 0.1850 +/− .001 | 0.0830 | 123% |
| SEQ ID NO: 149 | 0.0565 +/− .00212 | 0.0409 | 38% |
| SEQ ID NO: 151 | 0.0585 +/− .00212 | 0.0409 | 43% |

As can be observed in the Tables above, some of the enzymes are active with PNS, some are active with NCS, and many are active with both PNS and NCS. Generally, reaction mixtures containing enzymes active with either aryl sulfate compound demonstrated an absorbance that was approximately 1.1 to 2.5 times greater than the negative control.

Example 3: Mass Spectrometric Characterization of the N-Sulfated Polysaccharide Products of Engineered Aryl Sulfate-Dependent NST Enzymes A study was conducted in accordance with embodiments of the present disclosure to confirm glucosaminyl N-sulfotransferase activity of enzymes comprising the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 by detecting the presence of N-sulfated polysaccharide products formed as a result of their sulfotransfer reaction, using mass spectrometry (MS). Each engineered enzyme was purified according to the procedure of Example 1. Sulfotransferase activity was monitored in 100 µL reactions containing 50 µM of enzyme. To each purified protein solution, 20 mg of an aryl sulfate compound (either PNS or NCS) was dissolved in 2 mL of reaction buffer (50 mM MES pH 7.0, 2 mM $CaCl_2$), added to the protein solution, and incubated at 37° C. for 10 min. 2.5 mL of 2 mg/mL solution of N-deacetylated heparosan was added to protein/donor solution and incubated overnight at 37° C. The N-deacetylated heparosan was synthesized according to the protocol described in Balagurunathan, K. et al (eds.) (2015), *Glycosaminoglycans: Chemistry and Biology*, Methods in Molecular Biology, vol. 1229, DOI 10.1007/978-1-4939-1714-3_2, ©Springer Science+Business Media, New York, pp. 11-19 (section 3.1). To purify the N-sulfated product, the incubated reaction mixture was centrifuged the following day at 5,000×g for 10 min. The filter was washed once with 2 mL water, and centrifuged again. The filtrate was added to a 1K MWCO Dialysis membrane, dialyzed for 2 days in Milli-Q water, with water changes at 1 h, 2 h, 8 h, 16 h, 32 h, and then lyophilized.

The lyophilized N-sulfated products from each reaction were subsequently digested with a mixture of three carbon-oxygen lyases comprising the amino acid sequences of SEQ ID NO: 161, SEQ ID NO: 162, and SEQ ID NO: 163, which catalyze the β-eliminative cleavage of heparosan-based polysaccharides. Such lyases are available from New England Biolabs, among other chemical and biological commercial entities. 1 µL of each lyase was incubated with 50 µg of the lyophilized sulfated polysaccharide product and the provided digestion buffer, and incubated over 24 hours according to the packaged instructions provided by New England Biolabs with each lyase. After digestion, the lyase enzymes were inactivated by heating to 100° C. for 5 minutes. Samples were centrifuged at 14,000 rpm for 30 minutes before introduction to a strong anion exchange, high performance liquid chromatography (SAX) analysis. SAX analysis was performed on a Dionex Ultimate 3000 LC system interface. Separation was carried out on a 4.6×250 mm Waters Spherisorb analytical column with 5.0 µm particle size at 45° C. Mobile phase solution A was 2.5 mM sodium phosphate, pH 3.5, while mobile phase solution B was 2.5 mM sodium phosphate, pH 3.5, and 1.2 M Sodium perchlorate. After each sample was loaded onto the column, mobile phase solutions were applied to the column at a ratio of 98% mobile phase solution A and 2% mobile phase solution B for five minutes at a flow rate of 1.4 mL/min. After five minutes, a linear gradient of increasing mobile phase solution B was applied until the ratio of mobile phase solution A to mobile phase solution B was 50:50.

Using the SAX analysis, it was determined that six of the eight tested enzymes were active as sulfotransferases. However, each of the sulfotransferases were not necessarily active with both PNS and NCS. Enzymes having the amino acid sequences of SEQ ID NO: 5, SEQ ID NO: 7, and SEQ ID NO: 13 had activity with NCS only, and the enzyme having the amino acid sequence of SEQ ID NO: 15 had activity with PNS only. Enzymes having the amino acid sequences of SEQ ID NO: 9 and SEQ ID NO: 11 had activity with both aryl sulfate compounds.

Figure 29:
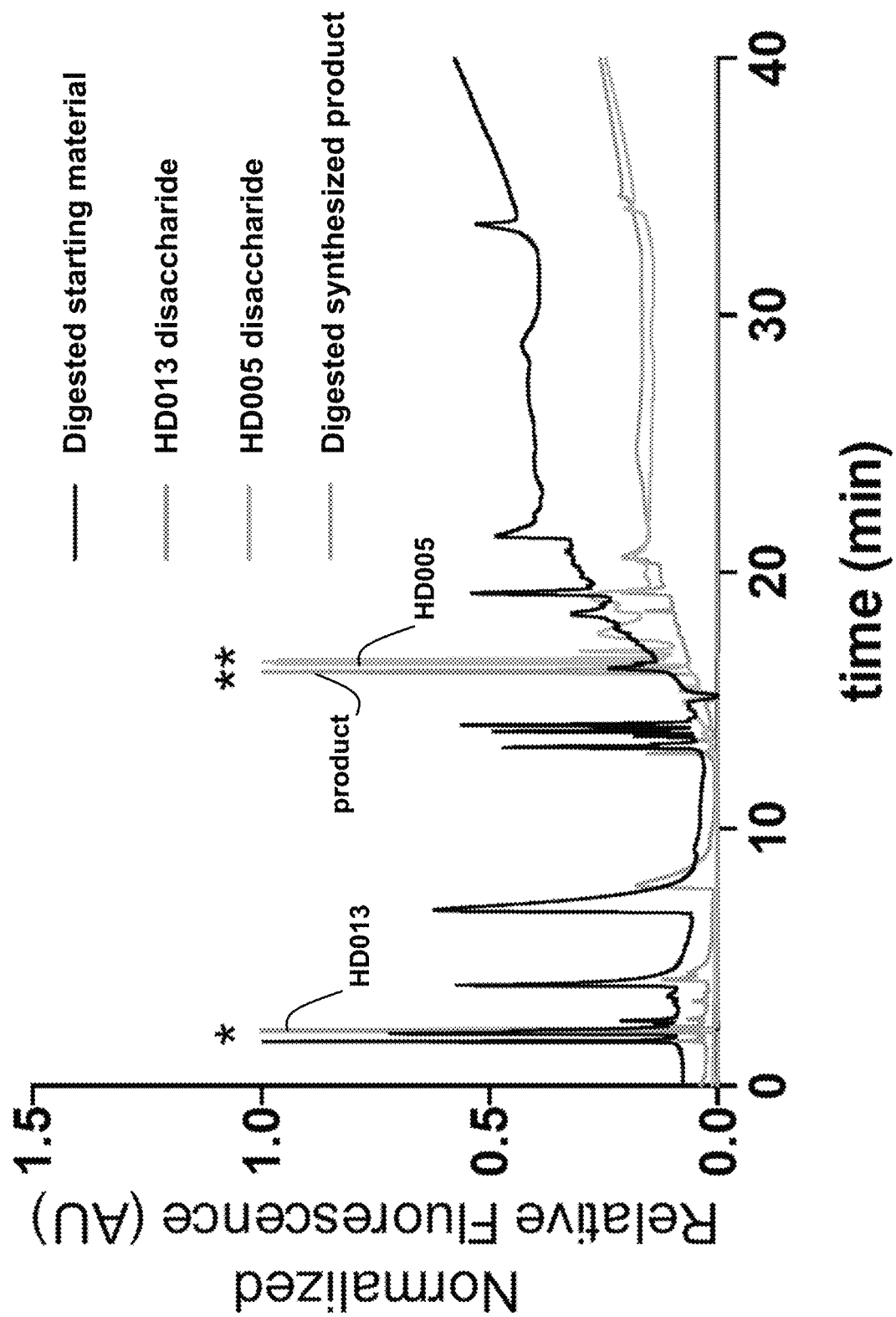
FIG. 29 shows a series of overlaid SAX-HPLC chromatograms of N-sulfated polysaccharide products synthesized using an engineered NST enzyme, compared to commercial standards.

Representative chromatograms from SAX analysis illustrating the presence of N-sulfated products produced as a result of the reaction are shown in FIG. 29. Both the N-deacetylated heparosan starting material and the N-sulfated product produced by SEQ ID NO: 13 were digested with the lyases having the amino acid sequence of SEQ ID NO: 161, SEQ ID NO: 162, and SEQ ID NO: 163 according the digestion procedure described above. Two disaccharide standards (HD005 and HD013) that are commercially available from Iduron, Ltd were also analyzed using SAX. The HD013 disaccharide comprises an unsubstituted glucosamine residue and a reduced hexuronic acid. The HD005 disaccharide is the same as HD013 except that the glucosamine residue is N-sulfated. All of the overlaid chromatograms are normalized so the most prominent peak in each chromatogram is assigned a normalized relative fluorescence value of 1.0.

As shown in FIG. 29, the most prominent peak for HD013 disaccharide (illustrated with a * symbol) elutes almost immediately, whereas the most prominent peak for the HD005 disaccharide (illustrated with a ** symbol) elutes after approximately 17 minutes. This is expected under SAX conditions because positively-charged species (like HD013) typically do not bind to the column, whereas negatively-charged species (like HD005) do bind to the column. The N-deacetylated heparosan, which is similarly non-sulfated, most prominently elutes at a nearly identical time as HD013. Similarly, the lyophilized sample produced during the reaction shows a peak at a nearly identical time as HD005, indicating that the sample contains an N-sulfated product. Other peaks within each of the chromatograms, particularly within the synthesized starting materials and products, indicate a lack of sample purity based on the use of spin-filtration columns as the sole basis of purifying the polysaccharides in each instance. Those skilled in the art would appreciate that there are several other separations techniques that can be utilized if a more purified product is desired. Additionally, the drifting upward of the baseline of the fluorescent signal in the chromatograms is a known phenomenon when increasing amounts of salt are introduced onto the column via the mobile phase.

Example 4: Mass Spectrometric Characterization of the 2-O Sulfated Polysaccharide Products of Engineered Aryl Sulfate-Dependent 2OST Enzymes A study was conducted in accordance with embodiments of the present disclosure to confirm hexuronyl 2-O sulfotransferase activity of enzymes comprising the amino acid sequence of SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 by detecting the presence of 2-O sulfated polysaccharide products formed as a result of their sulfotransfer reaction, using a similar procedure as in Example 3, except that the sulfo acceptor polysaccharide was commercial heparan sulfate in which the 2-O sulfate groups had been selectively removed by chemical means (product DSH001/2, available from Galen Laboratory Supplies) and analysis of each of the digested samples containing sulfated products was conducted using mass spectrometry, coupled with SAX-based high performance liquid chromatography (LCMS).

Disaccharides obtained by digesting the 2-O sulfated products using the carbon-oxygen lyases having the amino acid sequence of SEQ ID NO: 161, SEQ ID NO: 162, and SEQ ID NO: 163 and according to the procedure described above in Example 3 were quantified on a Shimadzu LCMS-8050 Triple Quadrupole Liquid Chromatograph Mass Spectrometer. 100 ng of each of the digested samples, diluted in 10 mM ammonium bicarbonate (pH 10). The disaccharides were separated on a Thermo Hypercarb HPLC column (100×2.1 mm, 5 μm). The mobile phase consisted of 10 mM ammonium bicarbonate (pH 10), and the disaccharides were eluted with an acetonitrile gradient of 0% to 20% for 2.5 min, held at 20% for the next 2.5 min, with 2 min of equilibration at 0% before the next injection; the flow rate was 0.2 mL/min, and the total run time was 7.1 min.

Figure 3B:
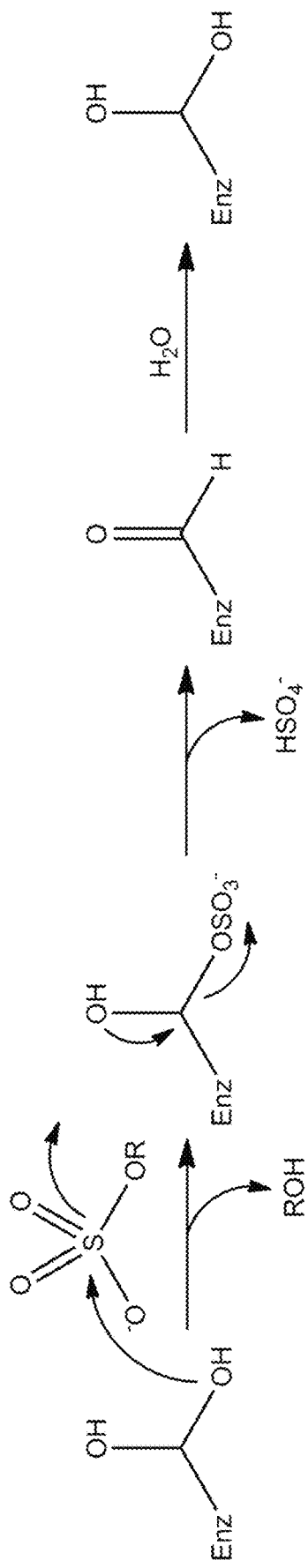
Figure 30A:
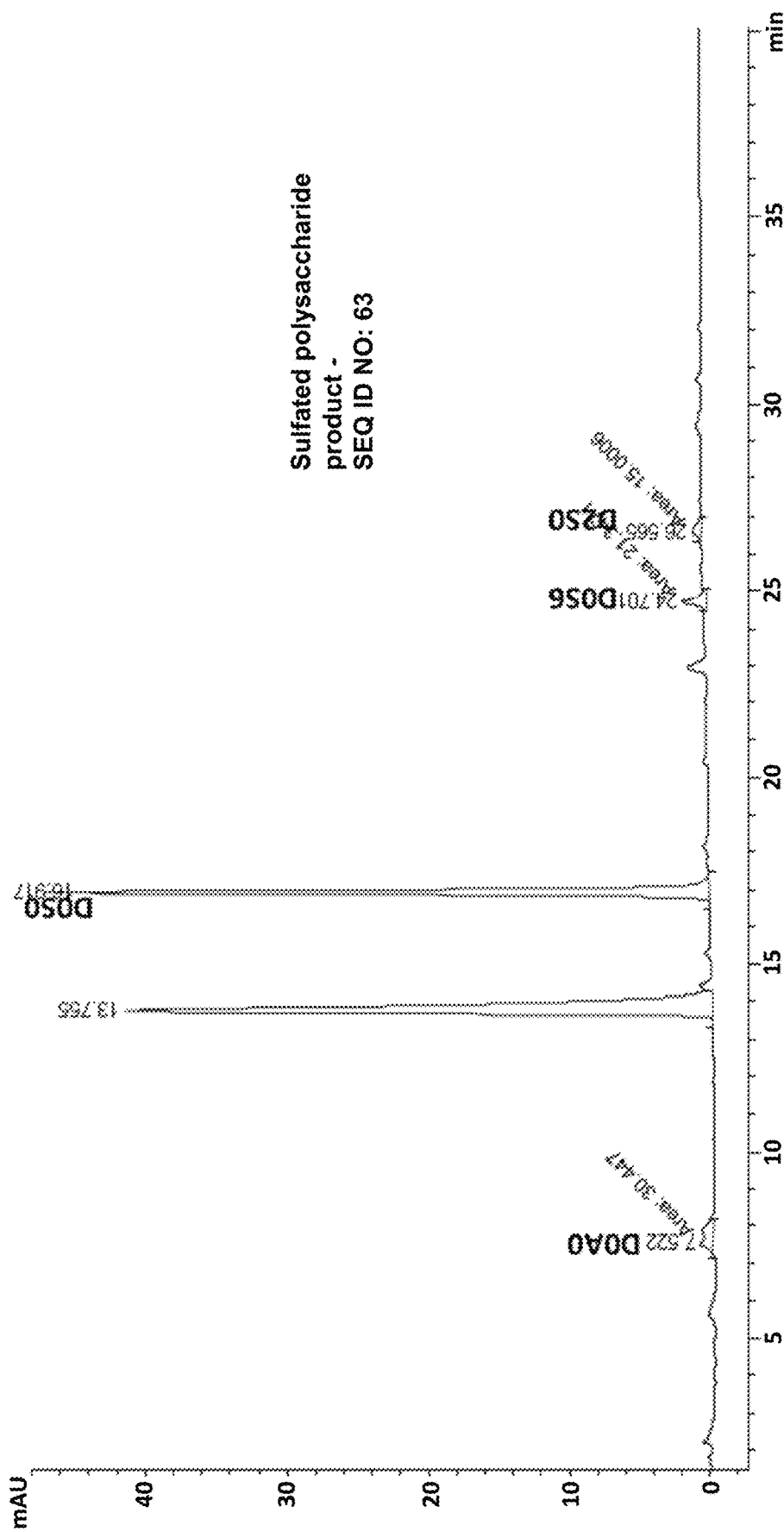
FIG. 30A and FIG. 30B show LCMS chromatograms of 2-O sulfated polysaccharide products synthesized using engineered 2OST enzymes having the amino acid sequence of SEQ ID NO: 63 and SEQ ID NO: 65, respectively.
Figure 30B:
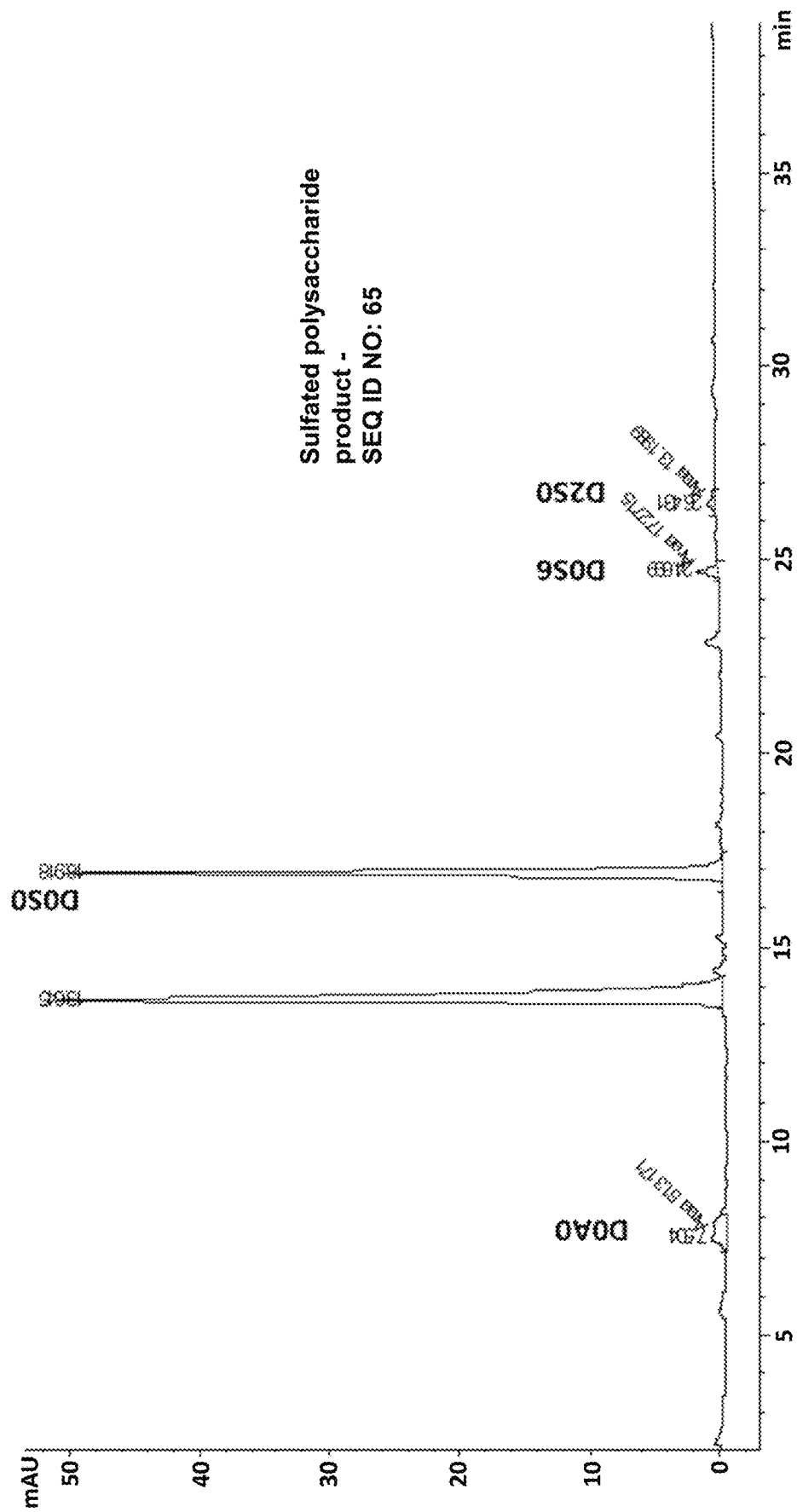

The extracted ion chromatograms from the LCMS are shown in FIG. 30A and FIG. 3B, corresponding to 2-O sulfated products obtained from reactions with engineered enzymes having the amino acid sequences of SEQ ID NO: 63 or SEQ ID NO: 65, respectively. Peaks were compared with chromatograms of a series of eight disaccharide standards, as well as a chromatogram from 100 ng of a commercial UFH polysaccharide (CAS code: 9041-08-1, available from Millipore Sigma), which was also digested using the lyase mixture. The eight reference disaccharide standards (D0A0, D0S0, D0A6, D2A0, D0S6, D2S0, D2A6, D2S6) represent disaccharides that are variably sulfated at the N-, 2-O and 6-O positions. In particular, the disaccharide D2S0 represents a disaccharide having a hexuronyl residue sulfated at the 2-O position and an N-sulfated glucosamine residue. The retention time and peak areas from the spectra from all of the disaccharide standards (not shown), the digested commercial sulfated polysaccharide (not shown), and the sulfated polysaccharide products of the engineered enzymes having the amino acid sequence of SEQ ID NO: 63 or SEQ ID NO: 65 are collected in Table 11, below. Since the ionization of each individual disaccharide is different, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 11

| Peak No. | Di saccharides | Peak Area % | | |
|---|---|---|---|---|
| | | Commercial standard | SEQ ID NO: 63 | SEQ ID NO: 65 |
| 1 | D0A0 | 3.9 | 5.9 | 9.1 |
| 2 | D0S0 | 3.9 | 87.1 | 85.5 |
| 3 | D0A6 | 3.4 | ND | ND |
| 4 | D2A0 | 1.8 | ND | ND |
| 5 | D0S6 | 11.8 | 4.1 | 3.1 |
| 6 | D2S0 | 6.6 | 2.9 | 2.3 |
| 7 | D2A6 | 1.6 | ND | ND |
| 8 | D2S6 | 67.0 | ND | ND |

Sulfotransferase activity of the engineered enzymes was confirmed by the re-sulfation at the 2-O position of hexuronic acid residues within the sulfo acceptor polysaccharide that had previously been desulfated prior to the reaction. This is illustrated by the presence of D2S0 disaccharides within the products isolated from reactions of both engineered enzymes and NCS. Without being limited by a particular theory, it is also believed that the activity of the engineered enzyme is dependent on reacting with a portion of the polysaccharide in which the hexuronic acid residue is adjacent to a glucosamine residue that is N-sulfated, but not 6-O sulfated. This is illustrated by the lack of D2S6 (2-O sulfated hexuronic acid residue and an N,6-sulfated glucosamine residue) and D2A6 (2-O sulfated hexuronic acid residue and a 6-O sulfated N-acetyl glucosamine residue) disaccharides detected within the isolated sulfated polysaccharide product. This is a similar sulfo acceptor reactivity to natural 2OST enzymes EC 2.8.2.-, which react with N-sulfated heparosan comprising either the structure of Formula IV or Formula V.

Example 5: Mass Spectrometric Characterization of the 6-O Sulfated Polysaccharide Products of Engineered Aryl Sulfate-Dependent 6OST Enzymes A study was conducted in accordance with embodiments of the present disclosure to confirm glucosaminyl 6-O sulfotransferase activity of enzymes comprising the amino acid sequence of SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO 102, SEQ ID NO: 104, SEQ ID NO: 106, or SEQ ID NO: 108 by detecting the presence of 6-O sulfated polysaccharide products as a result of their sulfotransfer reaction, using a similar LCMS procedure as in Example 4, except that the sulfo acceptor polysaccharide was prepared by chemically 6-O desulfating commercially available UFH (CAS code: 9041-08-1, available from Millipore Sigma), according to the procedure provided by Kariya, Y., et al., (2000) *J. Biol. Chem.* 275 (34):25949-25958).

Figure 31A:
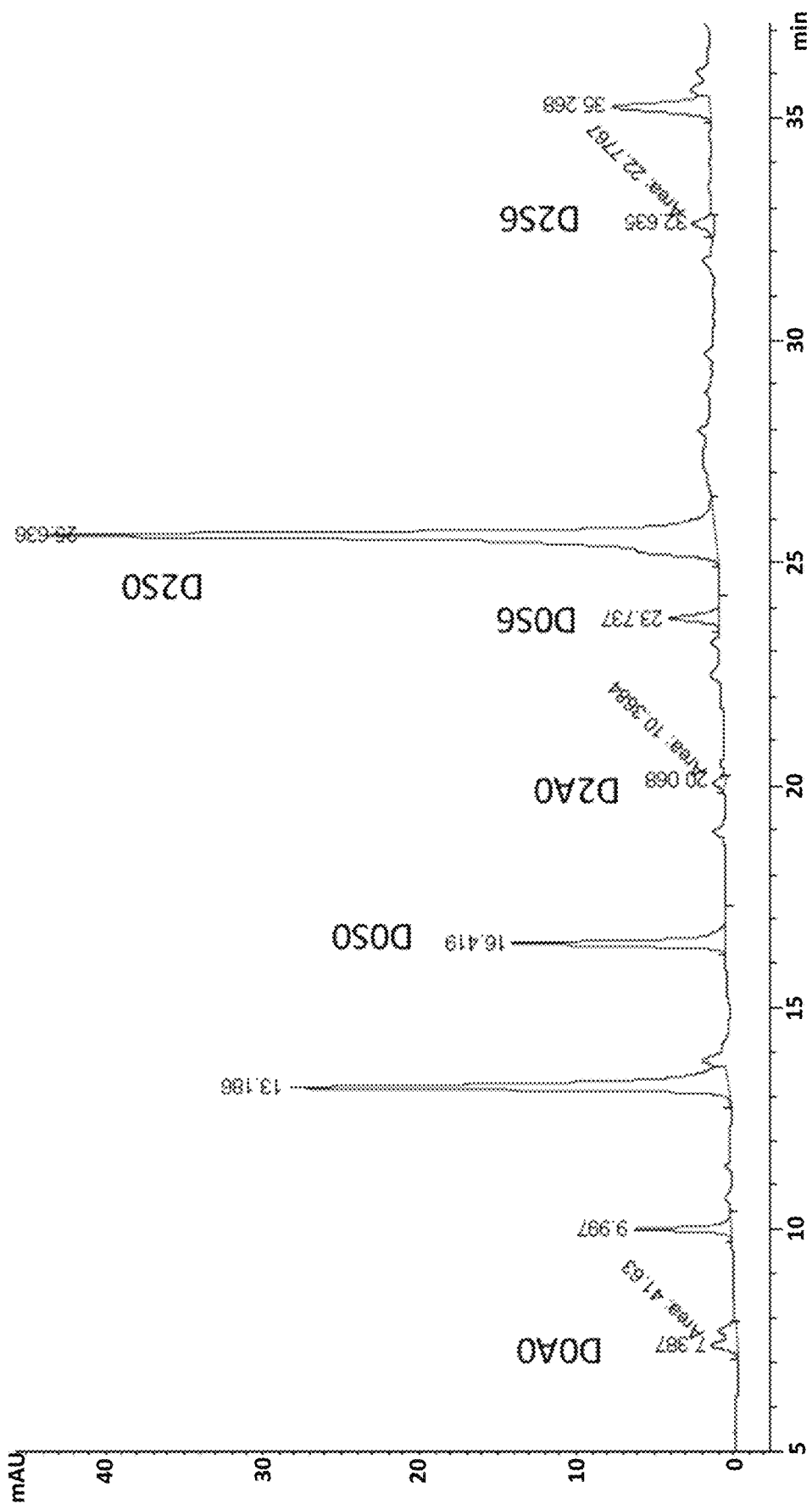
FIG. 31A, FIG. 31B, and FIG. 31C show LCMS chromatograms of a 6-O sulfated polysaccharide product synthesized using an engineered 6OST having the amino acid sequence SEQ ID NO 104, SEQ ID NO: 106, and SEQ ID NO: 108, respectively.
Figure 31B:
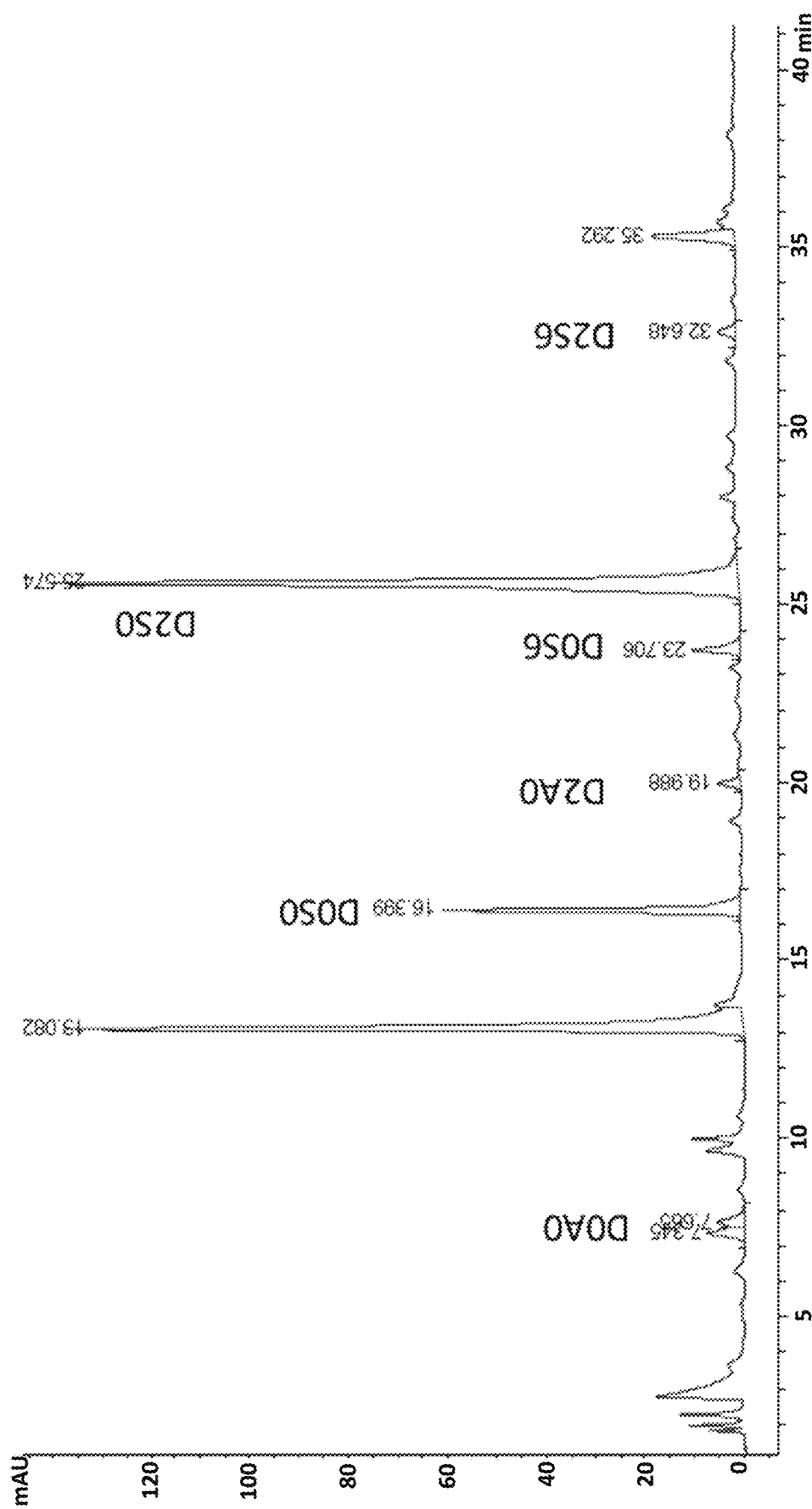
Figure 31C:
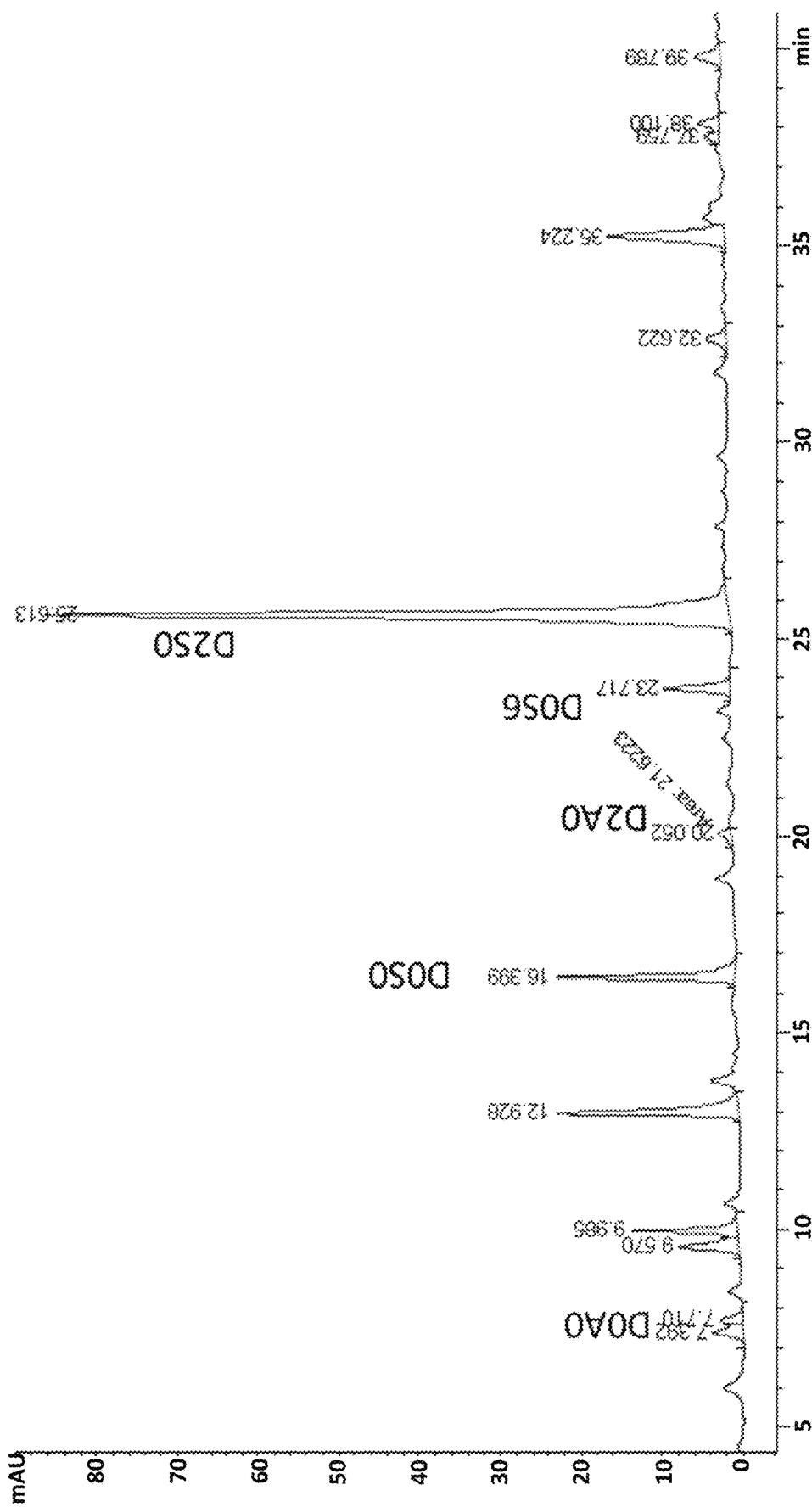

The extracted ion chromatograms corresponding to 6-O sulfated products obtained from reactions with engineered enzymes having the amino acid sequences of SEQ ID NO: 104, SEQ ID NO: 106, or SEQ ID NO: 108 are shown in FIG. 31A, FIG. 31B, and FIG. 31C, respectively. Enzymes having the sequence of SEQ ID NO: 104 and SEQ ID NO: 106 were active when NCS was the sulfo group donor, while the enzyme having the sequence of SEQ ID NO: 108 was active when PNS was the sulfo group donor. Assigned peaks were based on the determined retention times of eight reference disaccharide standards. The eight reference disaccharide standards (D0A0, D0S0, D0A6, D2A0, D0S6, D2S0, D2A6, and D2S6) represent disaccharides that are variably sulfated at the N-, 2-O, and 6-O positions. D0A6, D0S6, D2A6, and D2S6 comprise 6-O sulfated glucosamine residues. S6 indicates an N,6-sulfated glucosamine residue, while A6 indicates a 6-O sulfated N-acetyl glucosamine residue. Each chromatogram indicates two integrable peaks, D0S6 and D2S6, correlating to the synthesis of N,6-sulfated glucosamine residues, adjacent to a hexuronic acid residue that is either non sulfated or sulfated at the 2-O position, respectively. The peak area % of all the labelled disaccharides is in Table 12, below. Since the ionization of each individual disaccharide is different, especially for D0A0 and D2S6, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 12

| Peak No. | Di saccharides | RT (min) | Peak Area % | | |
|---|---|---|---|---|---|
| | | | SEQ ID NO: 104 | SEQ ID NO: 106 | SEQ ID NO: 108 |
| 1 | D0A0 | 7.7 | 4.6 | 6.0 | 5.4 |
| 2 | D0S0 | 16.4 | 14.2 | 18.4 | 13.0 |
| 3 | D0A6 | ND | ND | ND | ND |
| 4 | D2A0 | 20.0 | 1.1 | 1.8 | 1.3 |

TABLE 12-continued

| Peak No. | Di saccharides | RT (min) | Peak Area % | | |
|---|---|---|---|---|---|
| | | | SEQ ID NO: 104 | SEQ ID NO: 106 | SEQ ID NO: 108 |
| 5 | D0S6 | 23.7 | 4.0 | 3.7 | 5.6 |
| 6 | D2S0 | 25.6 | 73.5 | 68.4 | 72.4 |
| 7 | D2A6 | ND | ND | ND | ND |
| 8 | D2S6 | 32.7 | 2.5 | 1.7 | 2.3 |

Sulfotransferase activity of the engineered enzymes was confirmed by the re-sulfation at the 6-O position of glucosamine residues that had been desulfated by the procedure according to Kariya, Y., et al, above. This is illustrated by the presence of D0S6 and D2S6 disaccharides within the products isolated from the reactions with each enzyme. Among each of the engineered enzymes, it appears that the 6OST having the amino acid sequence of SEQ ID NO: 108 was the most active, based on comparing the peak area percentages of the D0S6 and D2S6 disaccharides. However, while D0A6 and D2A6 polysaccharides were not observed in any of the 6-O sulfated products produced by the engineered enzymes, without being limited by any particular theory, it is believed that these enzymes may nonetheless be able to transfer a sulfo group to N-acetyl glucosamine residues in different reaction conditions, particularly by increasing the concentration of the enzyme and/or polysaccharide where the presence of N-acetyl glucosamine residues is confirmed prior to the reaction, based on the reactivity of natural 6OST enzymes.

Example 6: Mass Spectrometric Characterization of the 3-O Sulfated Polysaccharide Products of Engineered Aryl Sulfate-Dependent 3OST Enzymes A study was conducted in accordance with embodiments of the present disclosure to confirm glucosaminyl 3-O sulfotransferase activity of enzymes comprising the amino acid sequence of SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151 by detecting the presence of 3-O sulfated polysaccharide products as a result of their sulfotransfer reaction, using a reaction, using a similar LCMS procedure as in Example 4, except that the sulfo acceptor polysaccharide was commercially-available UFH (CAS code: 9041-08-1, available from Millipore Sigma). Even though the unmodified UFH contains ~3.5% (w/w) of 3-O sulfated glucosamine residues, about ~60% of the glucosamine residues are N,6-sulfated and are adjacent to a 2-O sulfated hexuronic acid residue, as in Formula X. Consequently, these N,6-sulfated glucosamine residues can still be 3-O sulfated.

Figure 32A:
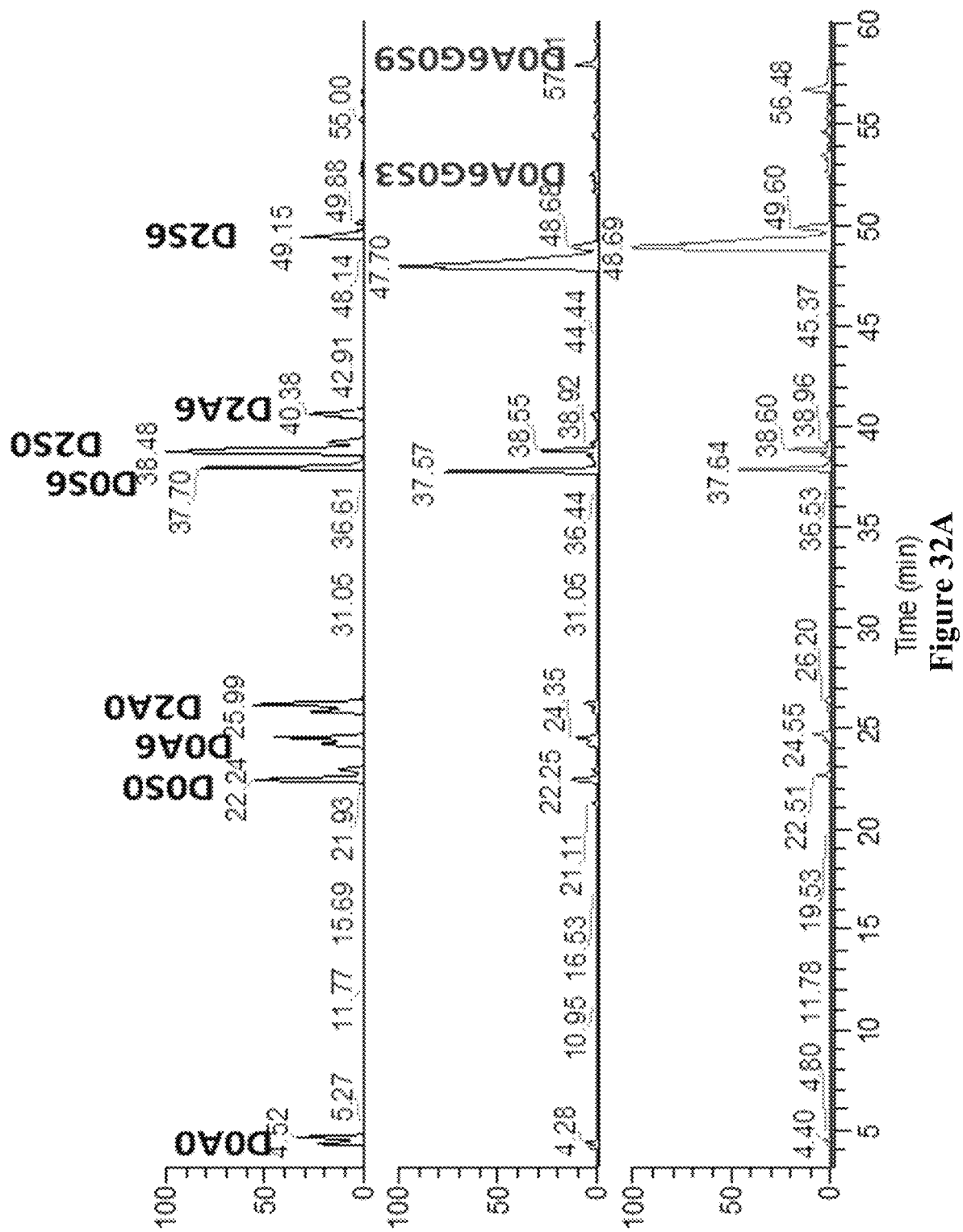
FIG. 32A and FIG. 32B show a series of six LCMS chromatograms of sulfated polysaccharide products synthesized using engineered 3OST enzymes, compared to a series of disaccharide and polysaccharide standards.
Figure 32B:
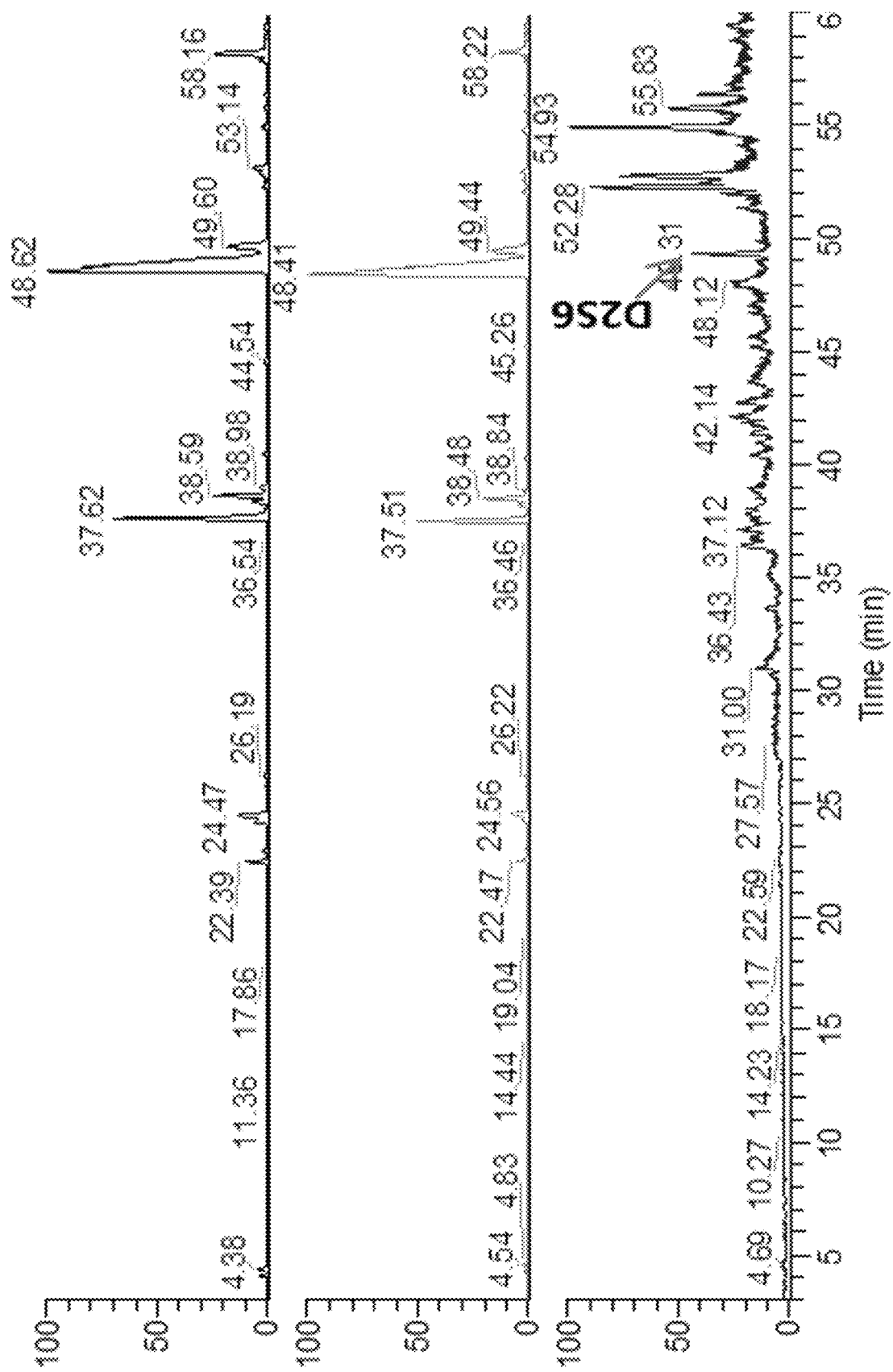

The extracted ion chromatograms are shown in FIG. 32A and FIG. 32B, along with chromatograms of a series of ten reference standards and 100 ng of the commercial polysaccharide, which was also digested using the lyase mixture. The ten reference standards (D0A0, D0S0, D0A6, D2A0, D0S6, D2S0, D2A6, D2S6, D0A6G0S3, and D0A6G0S9) represent di- or tetrasaccharides that are variably sulfated at the N-, 2-O, 3-O, and 6-O positions (FIG. 32A, top). For clarity, reference peaks that include 3-O sulfated glucosamine residues (D0A6G0S3) and (D0A6G0S9) are indicated in the digested commercial polysaccharide spectrum (FIG. 32A, center). Four mass spectra representing the digested sulfated polysaccharide products from reactions with enzymes comprising the amino acid sequence of SEQ ID NO: 147 (PNS, FIG. 32B, center), SEQ ID NO: 149 (PNS, FIG. 32B, bottom) (NCS, FIG. 32A, bottom), and SEQ ID NO: 151 (NCS, FIG. 32A, top) are shown below the digested commercial polysaccharide spectrum. The peak area % of all the labelled disaccharides and tetrasaccharides is in Table 13, below. Since the ionization of each individual disaccharide is different, especially for D0A0 and D2S6, the present percent in EIC chromatograms may not represent their actual abundance. However, the ionization efficiency is identical for each disaccharide or tetrasaccharide from sample to sample. Therefore, it is believed that comparing the peak area percent of the same saccharides from sample to sample can still be achieved.

TABLE 13

| peak No. | Disaccharides | RT (min) | Peak Area % | | | |
|---|---|---|---|---|---|---|
| | | | Commercial standard | SEQ ID NO: 147 | SEQ ID NO: 149 (NCS) | SEQ ID NO: 149 (PNS) |
| 1 | D0A0 | 4.5 | 1.9 | 0.6 | 0.8 | 1.4 | N.D. |
| 2 | D0S0 | 22.5 | 3.7 | 1.4 | 1.7 | 2.3 | N.D. |
| 3 | D0A6 | 24.6 | 4.2 | 2.8 | 3.1 | 4.5 | N.D. |
| 4 | D2A0 | 26.2 | 2.2 | 0.5 | 0.8 | 0.5 | N.D. |
| 5 | D0S6 | 37.5 | 16.0 | 10.9 | 10.6 | 13.1 | N.D. |
| 6 | D2S0 | 38.5 | 6.5 | 4.9 | 5.4 | 5.4 | N.D. |
| 7 | D2A6 | 40.3 | 1.6 | 0.8 | 0.8 | 0.9 | N.D. |
| 8 | D2S6 | 48.4 | 60.3 | 73.4 | 71.6 | 64.0 | 100.0 |
| 9 | D0A6G0S3 | 52.9 | 0.6 | 0.8 | 0.9 | 1.4 | N.D. |
| 10 | D0A6G0S9 | 58.2 | 3.0 | 4.0 | 4.1 | 6.5 | N.D. |

Sulfotransferase activity of each of the engineered enzymes was confirmed by the increase in the abundance of the D0A6G0S3 (hexuronic acid-6-O-sulfated N-acetyl glucosamine-glucuronic acid-N,3,6-sulfated glucosamine) and D0A6G0S9 (hexuronic acid-6-O-sulfated N-acetyl glucosamine-glucuronic acid-N,3-sulfated glucosamine) tetrasaccharides relative to the commercial UFH sample. However, the total abundance of disaccharides in the SEQ ID NO: 149 PNS sample was much lower than other samples. Subsequent trials included re-running the experiment with 10 times more injection volume, and a re-digestion of the sample with the lyase mixture. Nonetheless, only the D2S6 disaccharide could ever be found, indicating that the abundance of the SEQ ID NO: 149 PNS sulfated polysaccharide sample isolated initially was extremely low, and/or that the polysaccharide resists lyase digestion, causing the product to potentially elute from the column with a retention time longer than one hour.

Nonetheless, NMR studies (indicated below in Example 7) indicated 3-O sulfotransferase activity with the enzyme comprising the amino acid sequence SEQ ID NO: 149 when PNS is the aryl sulfate compound. Further, the enzyme having the amino acid sequence of SEQ ID NO: 149 was determined to be active as a sulfotransferase when NCS is the aryl sulfate compound. Therefore, it is believed that the observed results for the SEQ ID NO: 149 PNS sulfated polysaccharide sample during the LCMS experiment result from the sample produced for the purpose of the experiment, and not the activity of the enzyme itself. Otherwise, a higher abundance of 3-O sulfation was found in all of the other sulfated polysaccharide products from SEQ ID NO: 147, SEQ ID NO: 149, and SEQ ID NO: 151, relative to the commercial UFH standard.

Example 7: Confirmation of Sulfotransferase Activity of the Engineered 3OSTs Using Nuclear Magnetic Resonance A study was conducted in accordance with embodiments of the present disclosure to confirm the 3-O sulfotransferase activity of the engineered enzymes having the amino acid sequence of SEQ ID NO: 147, SEQ ID NO: 149, and SEQ ID NO: 151, particularly the activity of the enzyme having the amino acid sequence SEQ ID NO: 149 with PNS as the sulfo group donor. Each enzyme was purified according to the procedure of Example 1. To each purified protein solution, 20 mg of an aryl sulfate compound (PNS or NCS) dissolved in 2 mL of reaction buffer (50 mM MES pH 7.0, 2 mM $CaCl_2$) was added to the protein solution and incubated at 37° C. for 10 min. 2.5 mL of 2 mg/mL solution of the commercial UFH polysaccharide utilized in Example 6 was added to protein/donor solution and incubated overnight at 37° C.

Figure 33:
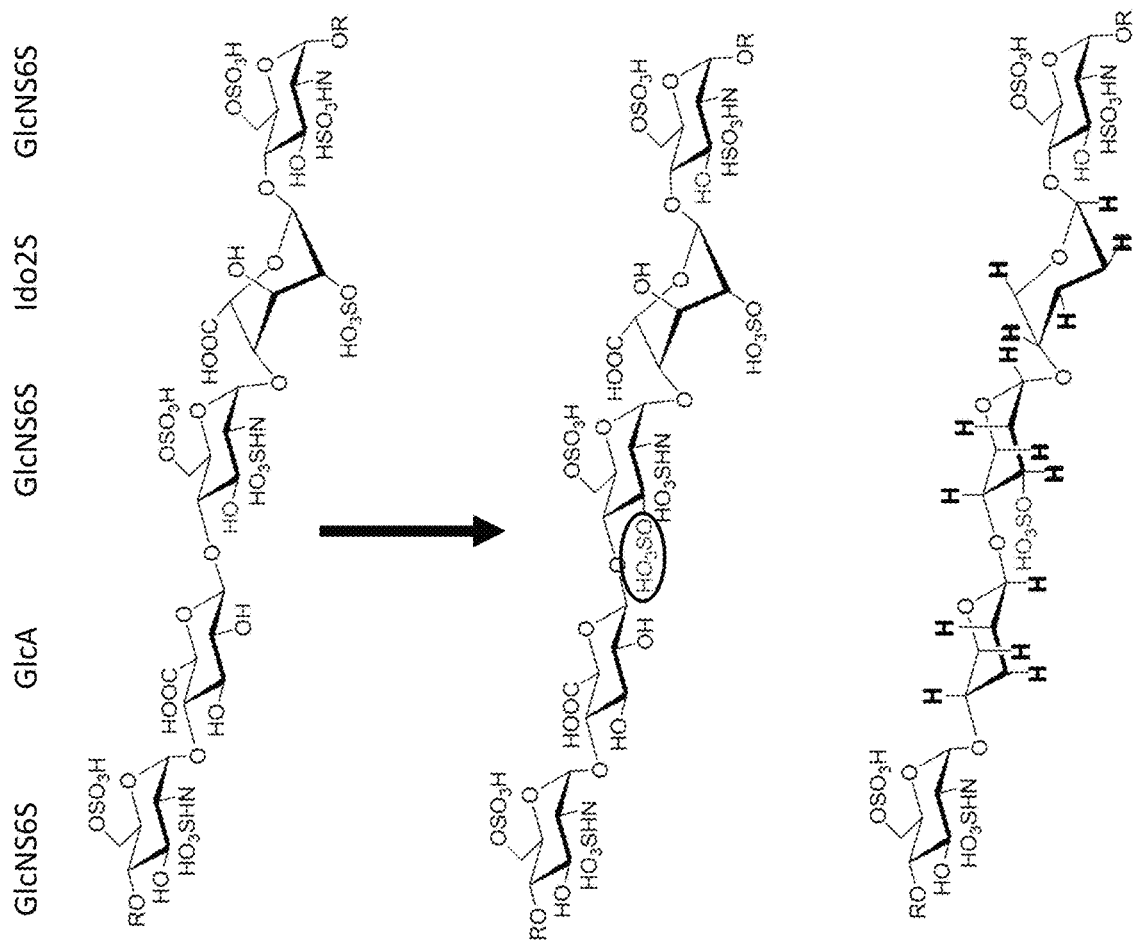
FIG. 33 shows the reaction scheme for deuterium labeling of protons of interest for nuclear magnetic resonance (NMR) studies.

Each reaction was centrifuged at 5,000×g for 10 min, applied to a pre-wetted 30K MWCO Amicon-15 filter and centrifuged at 5,000×g for 10 min. The filter was washed once with 2 mL water, and centrifuged again. The filtrate was added to a 1K MWCO Dialysis membrane, dialyzed for 2 days in Milli-Q water, with water changes at 1 h, 2 h, 8 h, 16 h, 32 h, and then lyophilized. The dry, white powder was resuspended in 400 μL $D_2O$, lyophilized to remove exchangeable protons, then resuspended in 600 μL $D_2O$ and transferred to NMR tubes (Wilmad, 0.38 mm×7"). To determine if sulfotransfer took place, $^1$H-NMR spectra were obtained on a Bruker 600 MHz NMR, 32 scans, with water suppression. The overall reaction scheme is shown in FIG. 33. Within FIG. 33, the 3-O positions of any of the glucosamine residues can be sulfated by the 3OST enzyme. The sulfated 3-O position is circled in the central polysaccharide. Exchangeable protons having the ability to exhibit resonance upon deuterium exchange are shown in bold, in the bottom polysaccharide. Crude mixture peaks were integrated to literature-referenced spectra for the sulfo acceptor polysaccharide and associated 3-O sulfated product.

Figure 34:
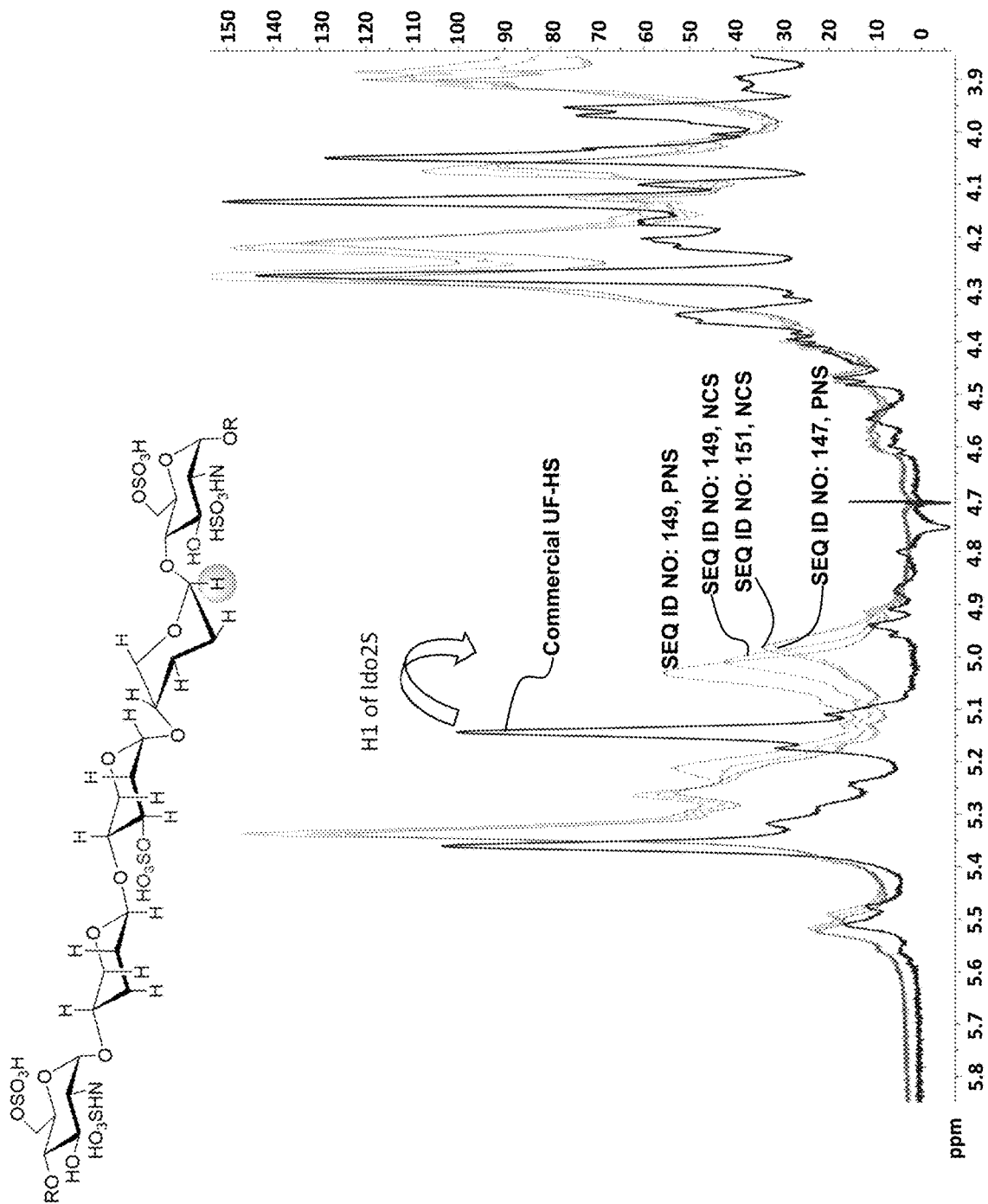
FIG. 34 shows $^1$H-NMR spectra for sulfated polysaccharide products formed by the engineered 3OST enzymes of the present invention, upon reacting with either PNS or NCS.

As shown in the overlain spectra in FIG. 34, a sharp peak at 5.15 ppm that correlates to the proton at the C2 carbon of the 2-O sulfated iduronic acid present in the commercial UFH disappears upon reacting with enzymes comprising the amino acid sequence of SEQ ID NO: 147, SEQ ID NO: 149, and SEQ ID NO: 151. The proton of interest is circled in the polysaccharide shown above the spectra. The $^1$H NMR spectra for a 3-O sulfated product synthesized by enzymes comprising the amino acid sequence of SEQ ID NO: 147, SEQ ID NO: 149, or SEQ ID NO: 151 in reaction with either PNS and/or NCS are all illustrated. In each of the product spectra, the IdoA$_{2S}$ peak shifts to between approximately 5.0 and 5.05 ppm. A similar transition is shown when incubating the natural human sulfotransferase enzyme with the same polysaccharide substrate and PAPS (data not shown).

Figure 35:
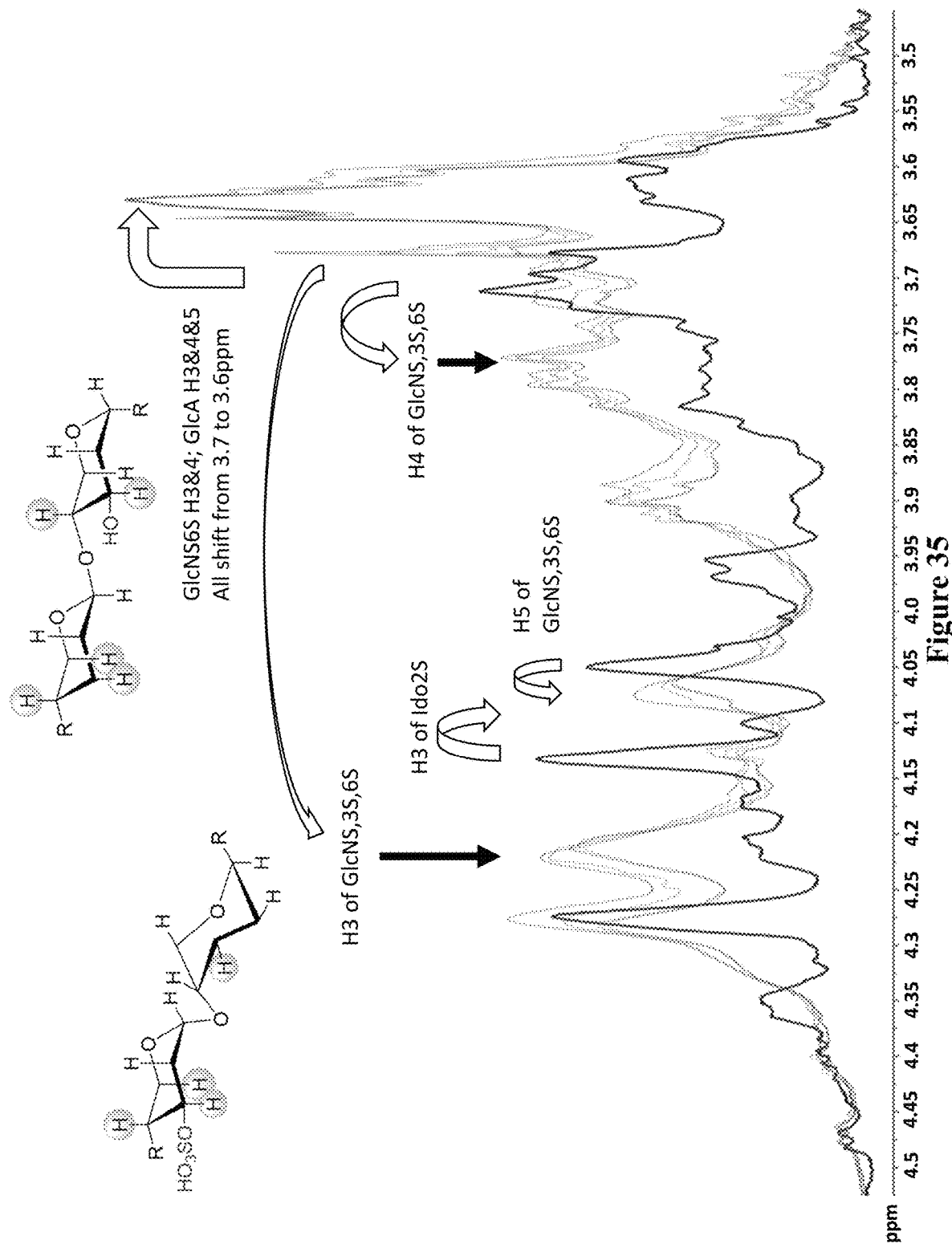
FIG. 35 shows a magnified view of the 3.5 ppm to 4.5 ppm region of the $^1$H-NMR spectra from FIG. 34.

As shown in FIG. 35, the region between 4.5 and 3.5 shows several peaks that similarly shift in response to the addition of the sulfate group to the 3-O position of a glucosamine residue, all of which correlate to the same shifts observed upon incubating the human 3OST1 enzyme with the same commercial UFH substrate and PAPS. Peaks that shift are indicated in curved arrows, and positions of the peaks from 3-O sulfated polysaccharides produced by enzymes having the amino acid sequence of SEQ ID NO: 147, SEQ ID NO: 149, or SEQ ID NO: 151, are shown with straight arrows. The largest shift occurs for H3 of Glc$_{NS3S6S}$, from 3.7 ppm to 4.2 ppm. This results from being closest to the newly added 3-O sulfate group. Additionally, the H3 proton of Ido$_{2S}$ and H5 of Glc$_{NS3S6S}$ both converge toward a peak at 4.07 ppm, which shows two overlapping peaks. H4 of Glc$_{NS3S6S}$ shifts moderately downfield from the 3.7 ppm region to the 3.8 ppm region, and according to references, many peaks such as H3 & H4 from Glc$_{NS6S}$ and H3, H4, and H5 from GlcA shift from the 3.7 ppm region to the 3.6 ppm region.

Example 8: Chemical Synthesis of N-Sulfated Heparosan for Use with Engineered Sulfotransferases of the Present Invention A study was conducted in accordance with embodiments of the present disclosure to chemically synthesize N-sulfated heparosan for use as sulfo acceptor polysaccharides with any of the engineered aryl sulfate-dependent sulfotransferases of the present invention, particularly the engineered 2OST enzymes. N-deacetylated heparosan was prepared according to the protocol described in Balagurunathan, K. et al., above. Particularly, the heparosan that eluted from the DEAE resin was precipitated overnight in ethanol saturated with sodium acetate, at −30° C., before being resuspended in water and dialyzed within a cellulose dialysis membrane having a 1,000 Da molecular weight cut-off (MWCO).

To N-deacetylate the heparosan, enough sodium hydroxide pellets (~4.0 g) were dissolved to make a 2.5 M solution in a 40 mL aliquot of the dialyzed heparosan in water. The solution was incubated at 55° C. for 16 hours, with shaking at 100 rpm. The sodium hydroxide within the sample was then neutralized with acetic acid until the solution reached a pH of ~7.0, and then dialyzed in water overnight within a 1,000 MWCO dialysis membrane.

Subsequent N-sulfation of the N-deacetylated heparosan was accomplished by adding 100 mg of sodium carbonate and 100 mg of sulfur trioxide-triethylamine complex, and allowing the composition to incubate at 48° C. until all of the solid was dissolved. The pH of the solution was then readjusted to ~9.5, using acetic acid. After incubation at 48° C. overnight with shaking at 100 rpm, an additional 100 mg of sodium carbonate and 100 mg of sulfur trioxide-triethylamine complex was added, before subsequent readjustment of the pH to ~9.5 using acetic acid. The solution was incubated at 48° C. for an additional 24 hours. The sulfated polysaccharide solution was neutralized with acetic acid to a pH of ~7.0, and dialyzed in water overnight within a 1,000 MWCO dialysis membrane. The dialyzed N-sulfated heparosan was then lyophilized prior to further use. The N-sulfated heparosan was then further purified by loading it onto a Zenix SEC-100 column and eluting it isocratically with 0.1 M ammonium acetate, pH 9.0.

Figure 36:
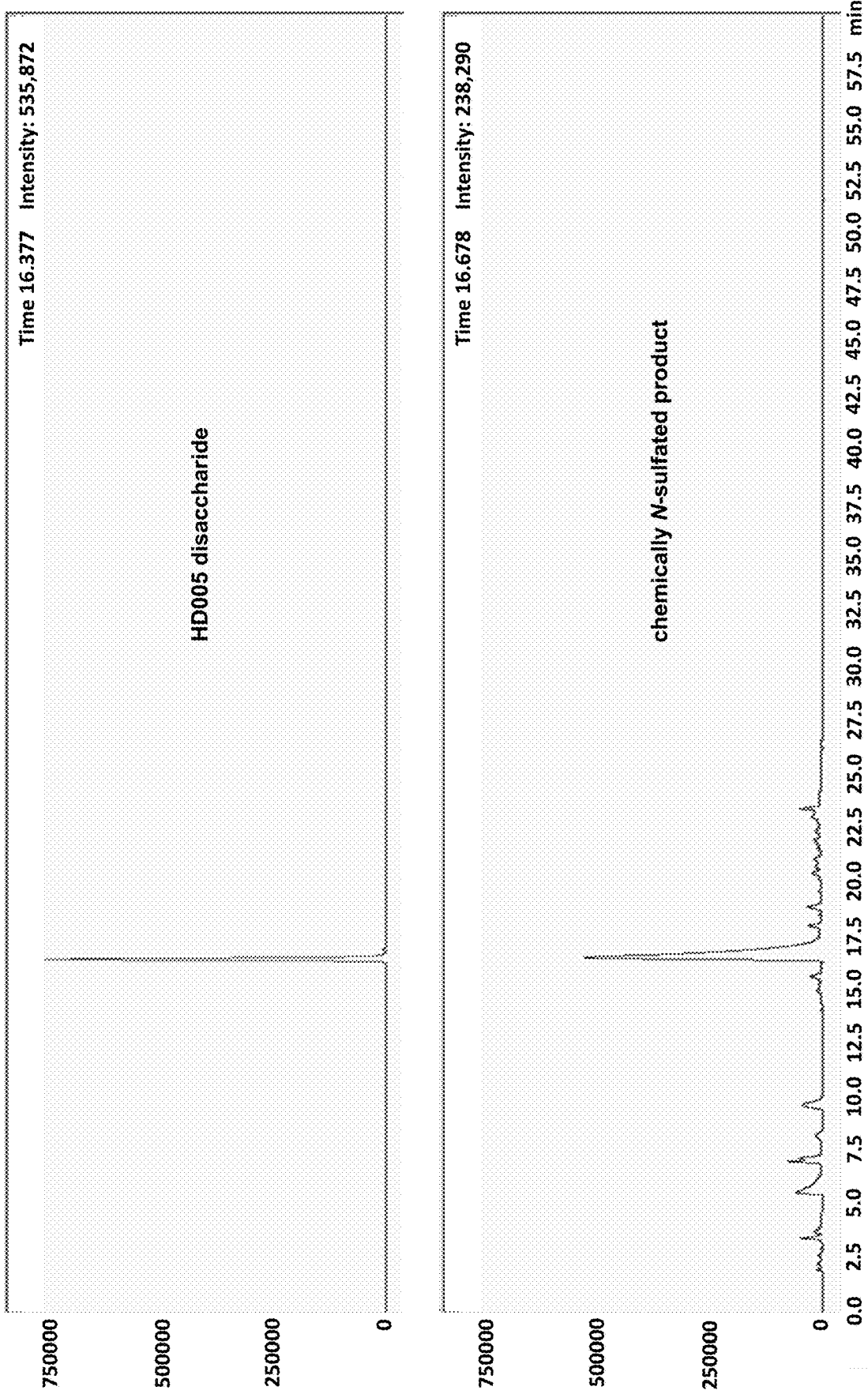
FIG. 36 shows a SAX-HPLC chromatogram of a chemically N-sulfated polysaccharide product, compared to a commercial standard.

The functionalization of the purified heparosan-based polysaccharide was characterized by digesting it with a mixture of three carbon-oxygen lyases comprising the amino acid sequences of SEQ ID NO: 161, SEQ ID NO: 162, and SEQ ID NO: 163, and analyzing the digested samples using SAX, using a similar procedure described above. As a positive control, the commercial HD005 disaccharide of Example 3, containing N-sulfated glucosamine residues, was also analyzed. Representative chromatograms of both samples are shown in FIG. 36. In both chromatograms, a strong peak is present at about 16.5 minutes, indicating that the synthesized sample contains N-sulfated glucosamine residues.

Example 9: Preparation of an N,2O-HS Polysaccharide Product

A study was conducted in accordance with embodiments of the present disclosure to synthesize an N,2O-HS polysaccharide product comprising the structure of either Formula VI or Formula VII, using an engineered 2OST and the N-sulfated heparosan synthesized in Example 8 as the sulfo acceptor. In a conical-bottom centrifuge tube, 80 mM aliquots of NCS were dissolved in 50 mM MES pH 7.0, 2 mM $CaCl_2$. To each solution, 2 mg of the enzyme having the sequence of SEQ ID NO: 63, based on the absorbance of the enzyme sample at 280 nm, was added (about 4 mL). 5 mg of the lyophilized N-sulfated heparosan synthesized in Example 8 was resuspended in 1 mL of water and added to the reaction mixture containing the enzyme and NCS. The entire reaction mixture was then incubated at 34° C. with shaking at 30 rpm, for 48 hours. A second set of reactions were prepared using the same procedure, except that 2 mg of a $C_5$-hexuronyl epimerase comprising the amino acid sequence of SEQ ID NO: 67 was also added to the reaction mixture, prior to incubation.

The polysaccharide products from both sets of reactions were purified by first precipitating out the proteins from the reaction mixtures by placing the reaction vessels in boiling water for 10 minutes and centrifuging at high speed to form a pellet. The supernatant containing the polysaccharide products was decanted from the pellet and dialyzed in water overnight within a 1,000 MWCO dialysis membrane. The dialyzed products were then lyophilized for future use.

Figure 37:
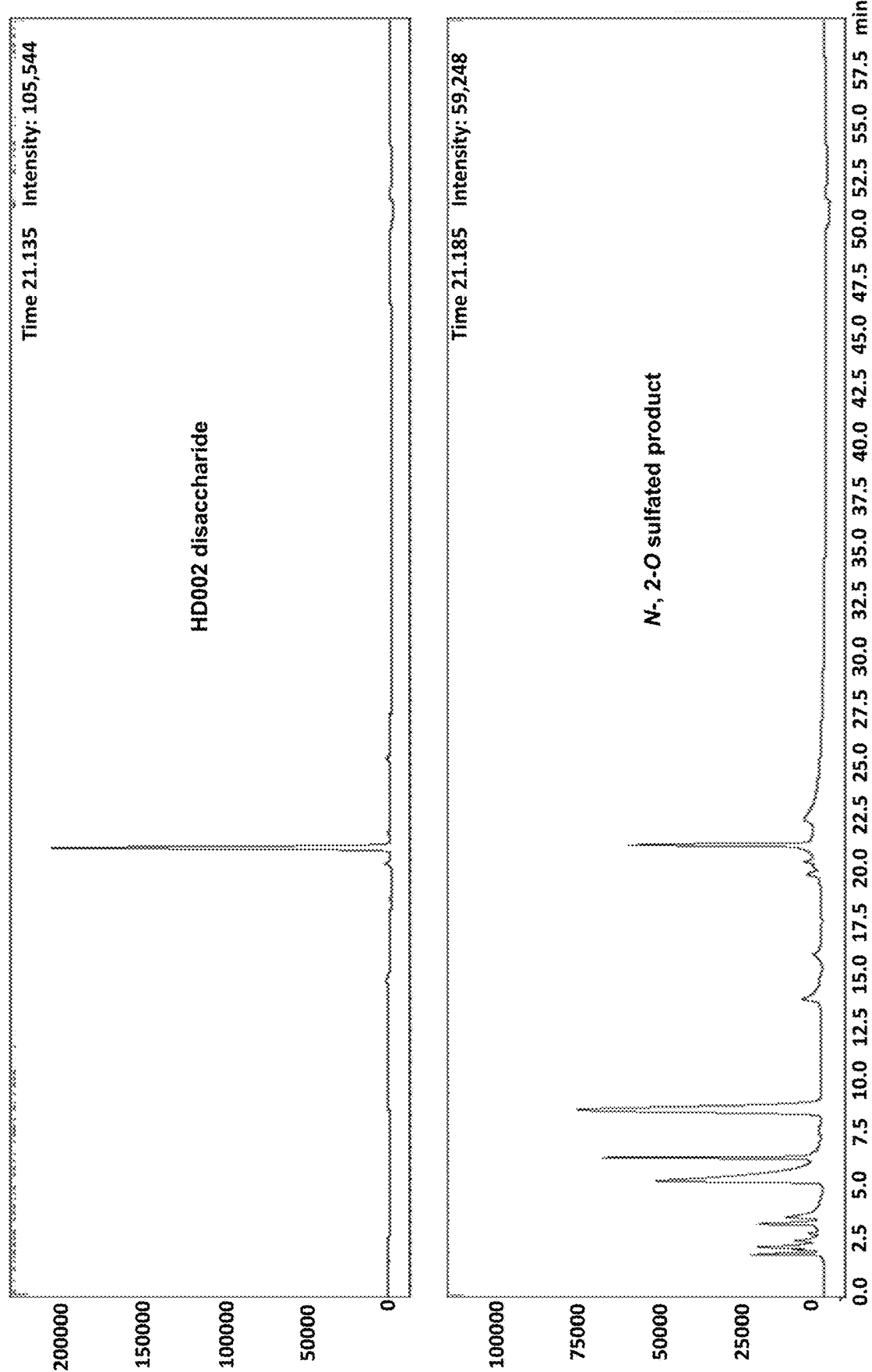
FIG. 37 shows a SAX-HPLC chromatogram of an enzymatically 2-O sulfated polysaccharide product prepared using the chemically N-sulfated polysaccharide product of Example 8 as the sulfo acceptor polysaccharide, compared to a commercial standard.
Figure 38:
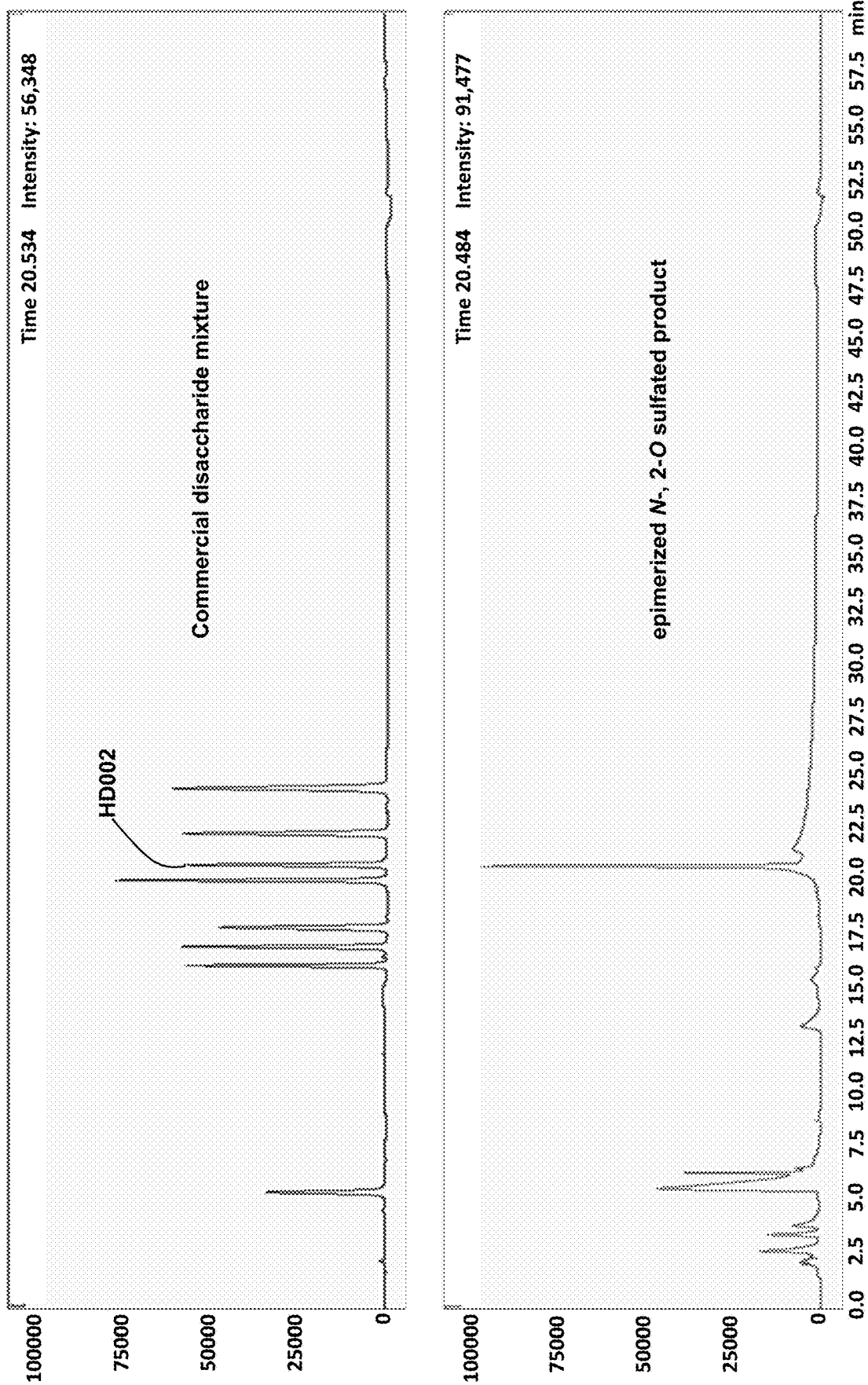
FIG. 38 shows a SAX-HPLC chromatogram of an enzymatically 2-O sulfated polysaccharide product prepared using the chemically N-sulfated polysaccharide product of Example 8 as the sulfo acceptor polysaccharide and with a $C_5$-hexuronyl epimerase included in the reaction mixture, compared to a commercial standard.

To characterize the polysaccharide products, lyophilized samples were resuspended in 400 µL of water, and purified using a Q-Sepharose Fast Flow Column (GE Biosciences). Samples were eluted from the column using a gradient ranging from 0 to 2M NaCl, in 20 mM sodium acetate buffer, pH 5.0. Purified polysaccharides were then digested and analyzed by SAX according to the procedures in Example 3 above, along with a commercial polysaccharide, HD002 (Iduron), which contains disaccharides of 2-O sulfated uronic acid and N-sulfated glucosamine. Representative chromatograms of reactions either without or including the epimerase enzyme are shown in FIG. 37 and FIG. 38, respectively. In FIG. 37, the chromatogram for the HD002 disaccharide has a single, sharp peak at about 21.1 minutes, which correlates to a sharp peak at a nearly identical time in the reaction product, indicating the time that an N,2O-HS product comprising the structure of Formula VI was formed as a result of the reaction. In FIG. 38, the HD002 disaccharide was provided within a mixture containing other disaccharide standards, with the disaccharide corresponding to HD002 eluting at 20.5 minutes, corresponding with the elution time of the HD002 standard in FIG. 37. The epimerized reaction product has a sharp peak at a nearly identical elution time to the HD002 standard, indicating that an N,2O-HS product comprising the structure of Formula VII was formed as a result of the reaction.

Example 10: Preparation of an N,2O,6O-HS Product

A study was conducted in accordance with embodiments of the present disclosure to synthesize an N,2O,6O-HS product comprising the structure of Formula IX, using the procedure of Example 9, except that the epimerized N,2O-HS product of Example 9 was used as the sulfo acceptor polysaccharide, and the engineered 6OST having the amino acid sequence of SEQ ID NO: 104 was used as the enzyme.

Figure 39:
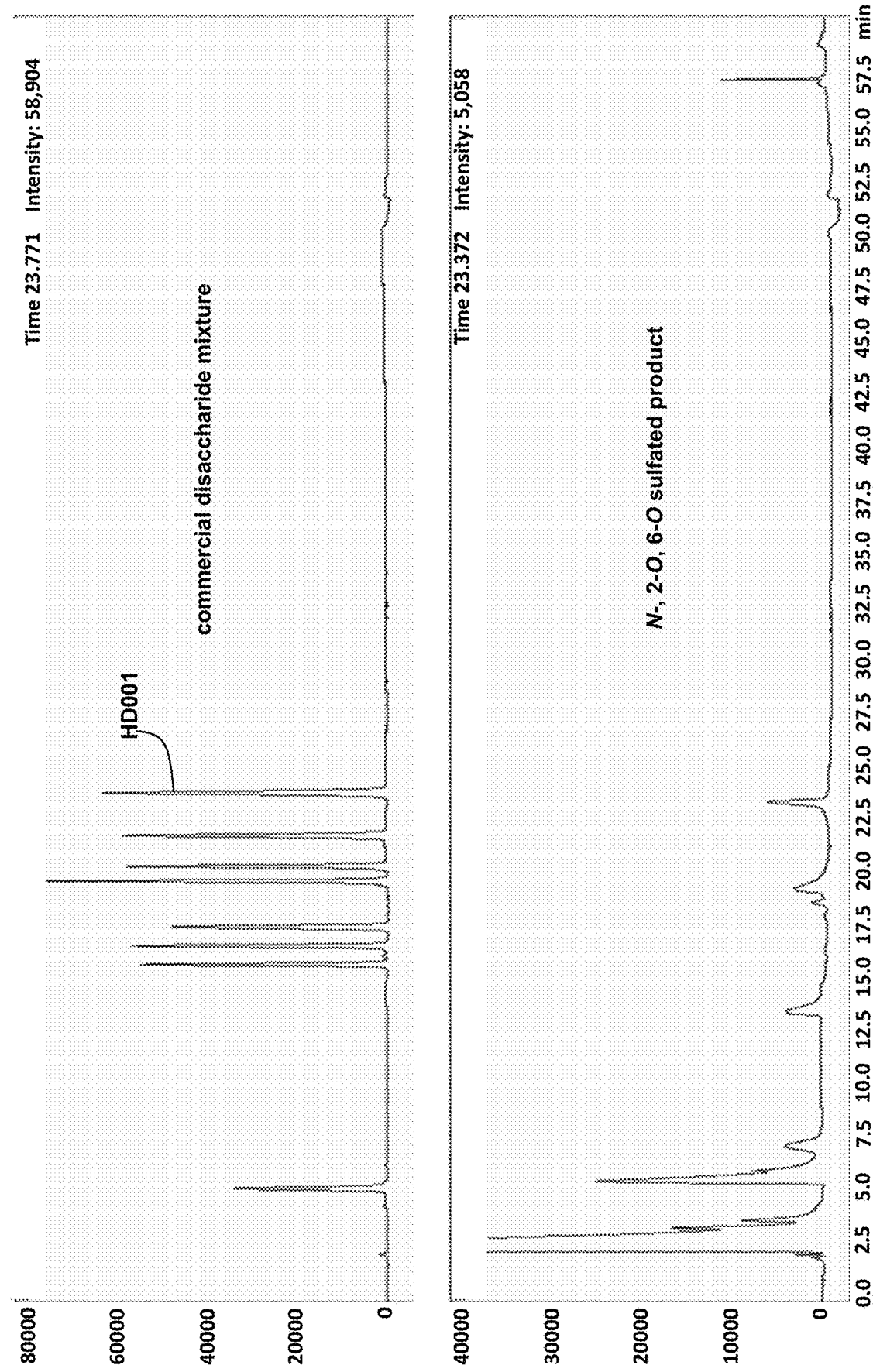
FIG. 39 shows a SAX-HPLC chromatogram of an enzymatically 6-O sulfated polysaccharide product prepared using a 2-O sulfated polysaccharide product of Example 9 as the sulfo group acceptor, compared to a commercial standard.

Representative chromatograms of the sulfated polysaccharide product and a mixture of commercial disaccharides are shown in FIG. 39. The chromatogram of the commercial mixture exhibits a peak at about 23.7 minutes, correlates to disaccharide HD001 (Iduron), which consists of disaccharides of 2-O sulfated uronic acid and N-, 6-O sulfated glucosamine, while the reaction product exhibits a similar peak at 23.4 minutes, indicating that an N,2O,6O-HS product was formed as a result of the reaction. Other peaks present within the N,2O,6O-HS product include undigested polysaccharide (2.5 min), unsubstituted uronic acid and N-acetylated glucosamine (5.5 min), and unsubstituted uronic acid and N-, 6-O sulfated glucosamine.

Example 11: Preparation of an N,2O,3O,6O-HS Product

A study is conducted in accordance with embodiments of the present disclosure to synthesize a sulfated polysaccharide product comprising the structure of Formula I and having N-, 6-O, 3-O sulfated glucosamine and 2-O sulfated hexuronic acid residues, using the procedure of Example 9 except that the chemically synthesized N-, 2-O, 6-O sulfated polysaccharide of Example 10 is used as the sulfo acceptor polysaccharide, and an engineered 3-O sulfotransferase enzyme having the amino acid sequence of SEQ ID NO: 147, SEQ ID NO: 149, or SEQ ID NO: 151 is used as the sulfotransferase. Sulfated polysaccharide products are digested and analyzed according to the procedure of Example 9, using SAX. It is expected that upon comparison to a digested commercial tetrasaccharide comprising a N-, 6-O, 3-O sulfated glucosamine residue, that it will be determined that the sulfated polysaccharide product is 3-O sulfated as a result of the reaction.

Example 12: Confirmation of Anticoagulant Activity of the N,2O,3O,6O-HS Product

A study is conducted in accordance with embodiments of the present disclosure to determine whether N,2O,3O,6O-HS products produced according to procedures of Example 6 or Example 7, using any of the 3OST enzymes described herein, which are expected to have a binding affinity to antithrombin (See Meneghetti, G., et al. (2017) *Org. Biomol. Chem.* 15:6792-6799). A control reaction containing a commercial N,2O,3O,6O-HS product known to have activity with antithrombin, such as the USP reference standard (CAS No: 9041-08-1). Human antithrombin (AT) (1 mg/mL) is incubated with different substrates in the presence of a dye, such as the SyproOrange™ dye (Invitrogen). The dye is diluted in water (1 unit Sypro:50 units water (v/v)) and 3.5 µL of the diluted dye is added to the mixture reaction in PBS buffer. The SyproOrange™ dye has an excitation wavelength of 300 nm or 470 nm and emits at 570 nm when bound to hydrophobic residues. 25 µg of a N,2O,3O,6O-HS product is included in each reaction mixture. Reactions are incubated at 31° C. for 2 min, before being subjected to a step-wise temperature gradient from 32 to 85° C. in a 0.5° C. steps. Between each temperature step, a 5-second incubation period can be taken to ensure sample equilibrations. Reactions can be developed using a real-time PCR System. It is expected that the melting curves of the control reaction with the USP reference standard, as well as the synthesized N,2O,3O,6O-HS products, will each be shifted to a higher temperature than a standard with the dye and AT alone, indicating that the AT can bind to the N,2O,3O,6O-HS products because the N,2O,3O,6O-HS products contain at least one AT-recognition sequence comprising the structure of Formula I.

Example 13: Determination of Engineered Aryl Sulfate-Dependent Mutants of Other EC 2.8.2.8 Enzymes A study is conducted in accordance with embodiments of the present disclosure to engineer additional aryl sulfate-dependent NST enzymes. As described above, the aryl sulfate-dependent NST enzymes having the amino acid sequences of SEQ ID NO: 5, SEQ ID NO: 7, SEQ ID NO: 9, SEQ ID NO: 11, SEQ ID NO: 13, or SEQ ID NO: 15 have been engineered to be mutants of the N-sulfotransferase domain of the human NDST1 enzyme (see entry sp|P52848|NDST_1_HUMAN, in FIG. 6A, FIG. 6B, and FIG. 6C above), which is a member of enzyme class EC 2.8.2.8. By generating and analyzing a multiple sequence alignment that includes the amino acid sequences of the N-sulfotransferase domain of one or more of the other NDST enzymes as well as the amino acid sequences of aryl sulfate-dependent NST enzymes having the amino acid sequences of SEQ ID NO: 5, SEQ ID NO: 7, SEQ ID NO: 9, SEQ ID NO: 11, SEQ ID NO: 13, and/or SEQ ID NO: 15, mutations in the amino acid sequences in the engineered NST enzymes can be observed relative to the amino acid sequences of the native EC 2.8.2.8 enzymes within the same alignment. Upon selecting the amino acid sequence of the N-sulfotransferase domain of a natural 2.8.2.8 enzyme that is not the human NDST1, mutations that are present within the amino acid sequences of SEQ ID NO: 5, SEQ ID NO: 7, SEQ ID NO: 9, SEQ ID NO: 11, SEQ ID NO: 13, and/or SEQ ID NO: 15 can be engineered into the native sequence in order to form additional mutants that can have aryl sulfate-dependent sulfotransferase activity.

As a non-limiting example, the amino acid sequence encoding for the N-sulfotransferase domain of the pig NDST1 (entry tr|M3V841|M3V841_PIG, as illustrated in the sequence alignment in FIG. 6A, FIG. 6B, and FIG. 6C, above), is aligned with the amino acid sequences of SEQ ID NO: 5, SEQ ID NO: 7, SEQ ID NO: 9, SEQ ID NO: 11, SEQ ID NO: 13, and SEQ ID NO: 15. Amino acid mutations that are present in SEQ ID NO: 5, SEQ ID NO: 7, SEQ ID NO: 9, SEQ ID NO: 11, SEQ ID NO: 13, and SEQ ID NO: 15 are engineered into their equivalent positions within the amino acid sequence of the N-sulfotransferase domain of the pig NDST1 enzyme, in order to generate the mutant amino acid sequences SEQ ID NO: 20, SEQ ID NO: 21, SEQ ID NO: 22, SEQ ID NO: 23, SEQ ID NO: 24, or SEQ ID NO: 25, respectively. Enzymes comprising the amino acid sequences of SEQ ID NO: 20, SEQ ID NO: 21, SEQ ID NO: 22, SEQ ID NO: 23, SEQ ID NO: 24, or SEQ ID NO: 25, respectively, will be utilized in Example 14 and Example 15, below. However, a person skilled in the art would appreciate that the same procedure can be applied to generate mutants of the N-sulfotransferase domain, or the entire enzyme, with respect to any of the other glucosaminyl natural NDST enzymes, and that those are omitted for clarity.

Example 14: Expression and Purification of Engineered Aryl Sulfate-Dependent EC 2.8.2.8 Mutants A study is conducted in accordance with embodiments of the present disclosure to determine whether genes encoding for engineered NST enzymes having the amino acid sequences SEQ ID NO: 20, SEQ ID NO: 21, SEQ ID NO: 22, SEQ ID NO: 23, SEQ ID NO: 24, or SEQ ID NO: 25, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 20, SEQ ID NO: 21, SEQ ID NO: 22, SEQ ID NO: 23, SEQ ID NO: 24, or SEQ ID NO: 25, respectively, based on the desired expression host. Upon synthesizing or inserting those genes within a suitable expression vector, it is expected that genes encoding for each of the amino acid sequences SEQ ID NO: 20, SEQ ID NO: 21, SEQ ID NO: 22, SEQ ID NO: 23, SEQ ID NO: 24, and SEQ ID NO: 25, respectively, will be transformed into host cells, and that enzymes containing those sequences will be subsequently expressed, isolated, and purified in a sufficient quantity and purity to determine aryl sulfate-dependent NST activity.

Example 15: Sulfotransferase Activity of EC 2.8.2.8 Mutants

A study is conducted in accordance with embodiments of the present disclosure to determine whether mutant enzymes comprising the sequences of SEQ ID NO: 20, SEQ ID NO: 21, SEQ ID NO: 22, SEQ ID NO: 23, SEQ ID NO: 24, or SEQ ID NO: 25, respectively, are active sulfotransferases, using the procedures of Example 3. It is expected that SAX studies will confirm the presence of N-sulfated polysaccharide products formed as a result of reacting N-deacetylated heparosan and an aryl sulfate compound with each of the engineered enzymes comprising the sequences of SEQ ID NO: 20, SEQ ID NO: 21, SEQ ID NO: 22, SEQ ID NO: 23, SEQ ID NO: 24, or SEQ ID NO: 25, respectively.

Example 16: Determination of Engineered Aryl Sulfate-Dependent Mutants of Other 2OST Enzymes within EC 2.8.2.-

A study is conducted in accordance with embodiments of the present disclosure to engineer additional aryl sulfate-dependent 2OST enzymes. As described above, the aryl sulfate-dependent 2OST enzymes having the amino acid sequences of SEQ ID NO: 63 and SEQ ID NO: 65 have been engineered to be mutants of the chicken HS 2OST enzyme (see entry sp|Q76KB1|HS2ST_CHICK, in FIG. 17A, FIG. 17B, FIG. 17C, and FIG. 17D, above), which is a member of enzyme class EC 2.8.2.-. By generating and analyzing a multiple sequence alignment that includes the amino acid sequences of one or more of the other 2OST enzymes within EC 2.8.2.-, as well as the amino acid sequences of aryl sulfate-dependent 2OST enzymes having the amino acid sequences of SEQ ID NO: 63 and/or SEQ ID NO: 65, mutations in the amino acid sequences in the engineered 2OST enzymes can be observed relative to the amino acid sequences of the wild-type 2OST enzymes within the same alignment. Upon selecting the amino acid sequence of a wild-type 2OST enzyme that is not the chicken 2OST enzyme, mutations that are present within the amino acid sequences of SEQ ID NO: 63 and/or SEQ ID NO: 65 can be engineered into the wild-type sequence in order to form additional mutants that can have aryl sulfate-dependent sulfotransferase activity.

As a non-limiting example, the amino acid sequence encoding for the human 2OST enzyme (entry sp|Q7LGA3|HS2ST_HUMAN, as illustrated in the sequence alignment in FIG. 17A, FIG. 17B, FIG. 17C, and FIG. 17D, above), is aligned with the amino acid sequences of SEQ ID NO: 63 and SEQ ID NO 65. Amino acid mutations that are present in SEQ ID NO 63 and SEQ ID NO: 65 are engineered into their equivalent positions within the amino acid sequence of the human 2OST enzyme, in order to generate the mutant amino acid sequences SEQ ID NO: 68 or SEQ ID NO: 69, respectively. Enzymes comprising the amino acid sequences of SEQ ID NO: 68 or SEQ ID NO: 69, respectively, will be utilized in Example 17 and Example 18, below. However, a person skilled in the art would appreciate that the same procedure can be applied to generate aryl sulfate-dependent mutants with respect to any of the other 2OST enzymes within the EC 2.8.2.-enzyme class, and that those are omitted for clarity.

Example 17: Expression and Purification of EC 2.8.2.- Mutants Having Hexuronyl 2-O Sulfotransferase Activity A study is conducted in accordance with embodiments of the present disclosure to determine whether genes encoding for engineered 2OST enzymes having the amino acid sequences SEQ ID NO: 68 or SEQ ID NO: 69, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 68 or SEQ ID NO: 69, respectively, based on the desired expression host. Upon synthesizing or inserting those genes within a suitable expression vector, it is expected that genes encoding for each of the amino acid sequences SEQ ID NO: 68 and SEQ ID NO: 69, respectively, will be transformed into host cells, and that enzymes containing those sequences will be subsequently expressed, isolated, and purified in a sufficient quantity and purity to determine aryl sulfate-dependent hexuronyl 2-O sulfotransferase activity.

Example 18: Hexuronyl 2-O Sulfotransferase Activity of EC 2.8.2.- Mutants

A study is conducted in accordance with embodiments of the present disclosure to determine whether mutant enzymes comprising the sequences of SEQ ID NO: 68 or SEQ ID NO: 69, respectively, are active sulfotransferases, using the procedures of Example 4. It is expected that MS studies will confirm the presence of N,2O-HS products formed as a result of reacting an N-sulfated heparosan-based polysaccharide and an aryl sulfate compound with each of the engineered enzymes comprising the sequences of SEQ ID NO: 68 and SEQ ID NO: 69, respectively. It is also expected that both enzymes will be active with heparosan-based polysaccharides comprising either or both of Formula IV or Formula V.

Example 19: Determination of Engineered Aryl Sulfate-Dependent Mutants of Other 6OST Enzymes within EC 2.8.2.-

A study is conducted in accordance with embodiments of the present disclosure to engineer additional aryl sulfate-dependent 6OST enzymes. As described above, the aryl sulfate-dependent 6OST enzymes having the amino acid sequences of SEQ ID NO: 104, SEQ ID NO: 106, or SEQ ID NO: 108 have been engineered to be mutants of the mouse 6OST1 enzyme (see entry Q9QYK5|H6ST1_MOUSE, in FIG. 21A, FIG. 21B, and FIG. 21C, above), which is a member of enzyme class EC 2.8.2.-. By generating and analyzing a multiple sequence alignment that includes both the amino acid sequences of one or more of the other 6OST enzymes within EC 2.8.2.-, as well as the amino acid sequences of aryl sulfate-dependent 6OST enzymes having the amino acid sequences of SEQ ID NO: 104, SEQ ID NO: 106, and/or SEQ ID NO: 108, mutations in the amino acid sequences in the engineered 6OST enzymes can be observed relative to the amino acid sequences of the wild-type 6OST enzymes within the same alignment. Upon selecting the amino acid sequence of a wild-type 6OST enzyme that is not the mouse 6OST1 enzyme, mutations that are present within the amino acid sequences of SEQ ID NO: 104, SEQ ID NO: 106, and/or SEQ ID NO: 108 can be engineered into the wild-type sequence in order to form additional mutants that can have aryl sulfate-dependent sulfotransferase activity.

As a non-limiting example, the amino acid sequence encoding for the pig 6OST1 enzyme (entry I3LAM6|I3LAM6_PIG, as illustrated in the sequence alignment in FIG. 21A, FIG. 21B, and FIG. 21C, above), is aligned with the amino acid sequences of SEQ ID NO: 104, SEQ ID NO: 106, and SEQ ID NO: 108. Amino acid mutations that are present in SEQ ID NO: 104, SEQ ID NO: 106, and SEQ ID NO: 108 are engineered into their equivalent positions within the amino acid sequence of the pig 6OST1 enzyme, in order to generate mutant amino acid sequences. Generated mutant amino acid sequences corresponding to residues 67-377 of the pig 6OST1 enzyme, as illustrated in FIG. 21A, FIG. 21B, and FIG. 21C, above, are disclosed as SEQ ID NO: 114, SEQ ID NO: 115, and SEQ ID NO: 116, respectively. Generated mutant amino acid sequences corresponding to the full-length amino acid sequence for the pig 6OST1 enzyme (not shown in FIG. 21A, FIG. 21B, and FIG. 21C, above) are disclosed as SEQ ID NO: 117, SEQ ID NO: 118, and SEQ ID NO: 119, respectively.

In another non-limiting example, the full-length amino acid sequence encoding for the encoding for the mouse 6OST3 enzyme (entry Q9QYK4|H6HS3_MOUSE, a truncated sequence for which is illustrated in the sequence alignment in FIG. 21A, FIG. 21B, and FIG. 21C, above) is aligned with the amino acid sequences of SEQ ID NO: 104, SEQ ID NO: 106, and SEQ ID NO: 108. Amino acid mutations that are present in SEQ ID NO: 104, SEQ ID NO: 106, and SEQ ID NO: 108 are engineered into their equivalent positions within the amino acid sequence of the mouse 6OST3 enzyme, in order to generate mutant amino acid sequences. The generated full-length amino acid sequences are disclosed as SEQ ID NO: 120, SEQ ID NO: 121, and SEQ ID NO: 122, respectively. Enzymes comprising the amino acid sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, will be utilized in Example 20 and Example 21, below. However, a person skilled in the art would appreciate that the same procedure can be applied to generate aryl sulfate-dependent mutants with respect to any of the other natural 6OST enzymes within the EC 2.8.2.-enzyme class, and that those are omitted for clarity.

Example 20: Expression and Purification of EC 2.8.2.- Mutants Having Glucosaminyl 6-O Sulfotransferase Activity A study is conducted in accordance with embodiments of the present disclosure to determine whether genes encoding for engineered 6OST enzymes having the amino acid sequences SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, based on the desired expression host. Upon synthesizing or inserting those genes within a suitable expression vector, it is expected that genes encoding for each of the amino acid sequences SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, respectively, will be transformed into host cells, and that enzymes containing those sequences will be subsequently expressed, isolated, and purified in a sufficient quantity and purity to determine aryl sulfate-dependent glucosaminyl 6-O sulfotransferase activity.

Example 21: Glucosaminyl 6-O Sulfotransferase Activity of EC 2.8.2.- Mutants

A study is conducted in accordance with embodiments of the present disclosure to determine whether mutant enzymes comprising the sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, are active sulfotransferases, using the procedures of Example 5. It is expected that MS studies will confirm the presence of N,2O,6O-HS products formed as a result of reacting an N,2O-HS polysaccharide and an aryl sulfate compound with each of the engineered enzymes comprising the sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, respectively.

Example 22: Determination of Engineered Aryl Sulfate-Dependent Mutants of Other 3OST Enzymes within EC 2.8.2.23

A study is conducted in accordance with embodiments of the present disclosure to engineer additional aryl sulfate-dependent 3OST enzymes. As described above, the aryl sulfate-dependent 3OST enzymes having the amino acid sequences of SEQ ID NO: 147, SEQ ID NO: 149, or SEQ ID NO: 151 have been engineered to be mutants of the human 3OST1 enzyme (see entry sp|O14792|HS3S1_HUMAN, in FIG. 26A, FIG. 26B, and FIG. 26C, above), which is a member of enzyme class EC 2.8.2.23. By generating and analyzing a multiple sequence alignment that includes both the amino acid sequences of one or more of the other 3OST enzymes within EC 2.8.2.23, as well as the amino acid sequences of aryl sulfate-dependent 3OST enzymes having the amino acid sequences of SEQ ID NO: 147, SEQ ID NO: 149, and/or SEQ ID NO: 151, mutations in the amino acid sequences in the engineered 3OST enzymes can be observed relative to the amino acid sequences of the wild-type 3OST enzymes within the same alignment. Upon selecting the amino acid sequence of a wild-type 3OST enzyme that is not the human 3OST1 enzyme, mutations that are present within the amino acid sequences of SEQ ID NO: 147, SEQ ID NO: 149, and/or SEQ ID NO: 151 can be engineered into the wild-type sequence in order to form additional mutants that can have aryl sulfate-dependent sulfotransferase activity.

As a non-limiting example, the amino acid sequence encoding for the pig 3OST1 enzyme (entry tr|I3LHH5| I3LHH5_PIG, as illustrated in the sequence alignment in FIG. 26A, FIG. 26B, and FIG. 26C, above), is aligned with the amino acid sequences of SEQ ID NO: 147, SEQ ID NO: 149, and SEQ ID NO: 151. Amino acid mutations that are present in SEQ ID NO: 147, SEQ ID NO: 149, or SEQ ID NO: 151 are engineered into their equivalent positions within the amino acid sequence of the pig 3OST1 enzyme, in order to the generate mutant amino acid sequences SEQ ID NO: 155, SEQ ID NO: 156, or SEQ ID NO: 157, respectively.

In another non-limiting example, the full-length amino acid sequence encoding for the encoding for the mouse 3OST5 enzyme (not shown in FIG. 26A, FIG. 26B, and FIG. 26C, above) is aligned with the amino acid sequences of SEQ ID NO: 147, SEQ ID NO: 149, and SEQ ID NO: 151. Amino acid mutations that are present in SEQ ID NO: 147, SEQ ID NO: 149, and SEQ ID NO: 151 are engineered into their equivalent positions within the amino acid sequence of the mouse 3OST5 enzyme, in order to generate mutant amino acid sequences. The generated full-length amino acid sequences are disclosed as SEQ ID NO: 158, SEQ ID NO: 159, and SEQ ID NO: 160, respectively.

Enzymes comprising the amino acid sequences of SEQ ID NO: 155, SEQ ID NO: 156, SEQ ID NO: 157, SEQ ID NO: 158, SEQ ID NO: 159, or SEQ ID NO: 160 respectively, will be utilized in Example 23 and Example 24, below. However, a person skilled in the art would appreciate that the same procedure can be applied to generate aryl sulfate-dependent mutants with respect to any of the other 3OST enzymes within the EC 2.8.2.23 enzyme class, and that those are omitted for clarity.

Example 23: Expression and Purification of EC 2.8.2.23 Mutants Having Glucosaminyl 3-0 Sulfotransferase Activity A study is conducted in accordance with embodiments of the present disclosure to determine whether genes encoding for engineered 3OST enzymes having the amino acid sequences SEQ ID NO: 155, SEQ ID NO: 156, SEQ ID NO: 157, SEQ ID NO: 158, SEQ ID NO: 159, or SEQ ID NO: 160, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 155, SEQ ID NO: 156, SEQ ID NO: 157, SEQ ID NO: 158, SEQ ID NO: 159, or SEQ ID NO: 160, respectively, based on the desired expression host. Upon synthesizing or inserting those genes within a suitable expression vector, it is expected that genes encoding for each of the amino acid sequences SEQ ID NO: 155, SEQ ID NO: 156, SEQ ID NO: 157, SEQ ID NO: 158, SEQ ID NO: 159, and SEQ ID NO: 160, respectively, will be transformed into host cells, and that enzymes containing those sequences will be subsequently expressed, isolated, and purified in a sufficient quantity and purity to determine aryl sulfate-dependent glucosaminyl 3-O sulfotransferase activity.

Example 24: Glucosaminyl 3-O Sulfotransferase Activity of EC 2.8.2.23 Mutants

A study is conducted in accordance with embodiments of the present disclosure to determine whether mutant enzymes comprising the sequences of SEQ ID NO: 155, SEQ ID NO: 156, SEQ ID NO: 157, SEQ ID NO: 158, SEQ ID NO: 159, or SEQ ID NO: 160, respectively, are active sulfotransferases, using the procedures of Example 6 and/or Example 7. It is expected that MS and/or NMR studies will confirm the presence of N,2O,3O,6O-HS products formed as a result of reacting an N,2O,6O-HS polysaccharide and an aryl sulfate compound with each of the engineered enzymes comprising the sequences of SEQ ID NO: 155, SEQ ID NO: 156, SEQ ID NO: 157, SEQ ID NO: 158, SEQ ID NO: 159, and SEQ ID NO: 160, respectively.

Because the instant application is a continuation or divisional application, to the extent any amendments, characterizations, or other assertions previously made (in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

```
                          SEQUENCE LISTING

Sequence total quantity: 300
SEQ ID NO: 1              moltype = AA   length = 309
FEATURE                   Location/Qualifiers
REGION                    1..309
                          note = Engineered glucosaminyl N-sulfotransferase
                           mutant_sulfatase 1
source                    1..309
                          mol_type = protein
                          organism = synthetic construct
SEQUENCE: 1
MSEEKDPLWQ DPCEDKRHKD IWSKEKTCDR FPKLLIIGPH KTGHTALYLF LGMHPDLSSN    60
YPSSTTGESI GFFNGHNYHK GIDWYMEFFP IPSNTTSDFY FEAHGGYFDS EVAPRRAAAL   120
LPKAKVLTIL INPADRAYSW YQHQRAHDDP VALKYTFHEV ITAGSDASSK LRALQNRCLV   180
PGWYATHIER WLSAYHANQI LVLDGKLLRT EPAKVMDMVQ KFLGVTNTID YHKTLAFDPK   240
KGFWCQLLEG GKTKCLGKSK GRKYPEMDLD SRAFLKDYYR DHNIELSKLL YKMGQTLPTW   300
LREDLQNTR                                                           309

SEQ ID NO: 2              moltype = DNA   length = 927
FEATURE                   Location/Qualifiers
misc_feature              1..927
                          note = Polynucleotide sequence encoding for engineered
                           glucosaminylN-sulfotransferase mutant_sulfatase 1
source                    1..927
                          mol_type = other DNA
                          organism = synthetic construct
SEQUENCE: 2
atgagcgaag agaaggaccc tttgtggcag gacccgtgcg aagataagcg ccacaaagac    60
atctggtcga aagaaaagac gtgcgaccgt ttccctaaac ttttaattat cggtccgcat   120
aagacagggc atacagcact ttatttattt ttggggatgc acccggattt gtcctcgaac   180
tatccctcgt ctacgaccgg ggagagcatt ggcttcttca atggacacaa ctatcataag   240
ggaattgact ggtatatgga attcttccct atccccagca atactacctc agatttctac   300
ttcgaagcgc acgggggta ttttgatagc gaggtcgccc cacgtcgcgc tgccgcattg   360
cttcccaagg caaaggtgct tactattttg attaaccctg cagaccgtgc ttactcctgg   420
tatcaacacc aacgtgcgca cgatgatcct gtggcgttga aatacacatt tcacgaagta   480
attactgcgg gatctgatgc gtctagcaaa ttgcgtgcct tacagaaccg ctgccttgtt   540
ccaggttggt acgccacgca cattgagcgt tggctgtctg cgtatcacgc taaccagatt   600
cttgtattag acgaaaatt gctgcgtaca gagcccgcta aggtgatgga tatggtgcaa   660
aagttccttg gtgtaacgaa caccattgat tatcataaaa cgttggcttt tgaccctaaa   720
aagggatttt ggtgccagtt acttgaagga gggaagacaa agtgtctggg gaagagcaaa   780
gggcgtaaat acccagaaat ggatttagat agtcgcgcat tccttaaaga ttactatcgc   840
gatcataaca tcgaattatc gaagcttttta tacaaaatgg gccagacatt gccaacgtgg   900
ctgcgtgaag acttgcagaa cacacgc                                       927

SEQ ID NO: 3              moltype = AA   length = 309
FEATURE                   Location/Qualifiers
REGION                    1..309
                          note = Engineered glucosaminyl N-sulfotransferase
                           mutant_sulfatase 2
source                    1..309
                          mol_type = protein
                          organism = synthetic construct
SEQUENCE: 3
MSEEKDPLWQ DPCEDKRHKD IWSKEKTCDR FPKLLIIGPQ KTGAWALYHF LGMHPDLSSN    60
YPSSESHARI QFFNGHNYHK GIDWYMEFFP IPSNTTSDFY FEMSANYFDS EVAPRRAAAL   120
LPKAKVLTIL INPADRAYSW YQHQRAHDDP VALKYTFHEV ITAGSDASSK LRALQNRCLV   180
PGWYATHIER WLSAYHANQI LVLDGKLLRT EPAKVMDMVQ KFLGVTNTID YHKTLAFDPK   240
KGFWCQLLEG GKTKCLHKRA GRKYPEMDLD SRAFLKDYYR DHNIELSKLL YKMGQTLPTW   300
LREDLQNTR                                                           309

SEQ ID NO: 4              moltype = DNA   length = 927
FEATURE                   Location/Qualifiers
misc_feature              1..927
                          note = Polynucleotide sequence encoding for engineered
                           glucosaminylN-sulfotransferase mutant_sulfatase 2
source                    1..927
```

```
                            mol_type = other DNA
                            organism = synthetic construct
SEQUENCE: 4
atgagcgaag agaaggaccc tttgtggcag gacccgtgcg aggacaagcg ccacaaggac  60
atttggagta aggaaaagac atgcgaccgc ttcccgaaat tattgattat tggtccgcag 120
aaaactgggg catgggcatt gtaccacttc ttaggtatgc acccagactt atcgtctaac 180
tatccatcct ccgaaagtca tgctcgcatc caattcttca acggtcataa ctatcataag 240
ggtattgact ggtacatgga gttttttccc atccccagta ataccactag tgactttttac 300
tttgagatgt cggcaaacta ctttgacagc gaggttgctc cgctcgtcgt ggcagcgctt 360
ctgccgaaag ccaaggtatt aactattttg atcaacccag cagatcgtgc gtatagttgg 420
taccagcacc aacgcgccca tgatgatcct gtcgctctta agtacacctt ccatgaagta 480
attacggcgg gcagcgatgc ttcgtctaaa cttgtgcgt tgcagaatcg ctgcctggtt 540
cccgggtggt acgcgaccca cattgagcgc tggctttccg catatcatgc caatcaaatc 600
ttggtattgg acggaaaagct tctgcgcacc gagcctgcga aagtgatgga catggtacag 660
aagttcttag gagttacaaa tacgatcgat tatcacaaga cccttgcttt tgaccctaaa 720
aaaggattct ggtgccaact tttggaggga ggtaagacta gtgccttca taaacgcgca 780
gggcgcaaat atcccgagat ggacttagat tcacgcgcgt tccttaaaga ttactatcgt 840
gatcataata tcgagttaag caaacttctg tataagatgg gacagacact gcctacatgg 900
ctgcgtgaag acttgcagaa cacacgc                                    927

SEQ ID NO: 5            moltype = AA   length = 309
FEATURE                 Location/Qualifiers
REGION                  1..309
                        note = Engineered glucosaminyl
                        N-sulfotransferasemutant_sulfotransferase 1
source                  1..309
                        mol_type = protein
                        organism = synthetic construct
SEQUENCE: 5
MSEEKDPLWQ DPCEDKRHKD IWSKEKTCDR FPKLLIIGPQ KTGAWALYHF LGMHPDLSSN  60
YPSSETHGSI QFFNGHNYHK GIDWYMEFFP IPSNTTSDFY FEKSANYFDS EVAPRRAAAL 120
LPKAKVLTIL INPADRAYSW YQHQRAHDDP VALKYTFHEV ITAGSDASSK LRALQNRCLV 180
PGWYATHIER WLSAYHANQI LVLDGKLLRT EPAKVMDMVQ KFLGVTNTID YHKTLAFDPK 240
KGFWCQLLEG GKTKCLGKSH GRKYPEMDLD SRAFLKDYYR DHNIELSKLL YKMGQTLPTW 300
LREDLQNTR                                                        309

SEQ ID NO: 6            moltype = DNA   length = 927
FEATURE                 Location/Qualifiers
misc_feature            1..927
                        note = Polynucleotide sequence encoding for engineered
                        glucosaminylN-sulfotransferase mutant_sulfotransferase 1
source                  1..927
                        mol_type = other DNA
                        organism = synthetic construct
SEQUENCE: 6
atgagcgaag agaaggaccc tttgtggcag gacccgtgcg aggacaaacg ccacaaagac  60
atttggtcga aggagaaaac ctgtgaccgc ttccctaagt tgcttattat tggtccgcaa 120
aagaccggcg cctgggcgct ttaccatttc ctgggtatgc atcccgatct tagttccaac 180
tacccgtcga gtgaaacaca tggcagtatc caattcttta atggacataa ctaccataag 240
ggcatcgact ggtatatgga attttttccc attccctcaa ataccacttc tgactttttat 300
ttcgagaaat cagcgaatta ttttgacagt gaggtagcgc ctcgccgcgc agcagcattg 360
ttgcccaaag caaagtgct gactattctt atcaatccag ctgaccgcgc atattcttgg 420
tatcagcacc agcgcgccca cgacgacccg gtggcgctga aatacacatt ccatgaagtg 480
attactgctg gaagcgatgc gtcgtctaag ttgcgtgctc tgcagaaccg ctgtttggta 540
cctggctggt atgctacgca cattgaacgt tggctgtcac catatcacgc gaaccagata 600
ctggttttag atggtaaatt acttcgcacg gagccagcta agtcatgga catggtacaa 660
aagttcctgg gggtaacgaa taccattgat tatcataaga ctttggcttt cgaccccaag 720
aagggatttt ggtgccagtt attggagggg gcaagacga gtgcttagg caaatcgcat 780
gggcgcaagt acccggagat ggatttggac tcacgcgcct tcttaagga ctactaccgc 840
gaccacaaca ttgaattgag taaattatta tacaaaatgg gcaaactct tccgacttgg 900
ttgcgtgaag acttgcagaa cacacgc                                    927

SEQ ID NO: 7            moltype = AA   length = 309
FEATURE                 Location/Qualifiers
REGION                  1..309
                        note = Engineered glucosaminyl
                        N-sulfotransferasemutant_sulfotransferase 2
source                  1..309
                        mol_type = protein
                        organism = synthetic construct
SEQUENCE: 7
MSEEKDPLWQ DPCEDKRHKD IWSKEKTCDR FPKLLIIGPS KTGAFLLTHF LGMHPDLSSN  60
YPSSETHGSI QFFNGHNYHK GIDWYMEFFP IPSNTTSDFY FETSSNYFDS EVAPRRAAAL 120
LPKAKVLTIL INPADRAYSW YQHQRAHDDP VALKYTFHEV ITAGSDASSK LRALQNRCLV 180
PGWYATHIER WLSAYHANQI LVLDGKLLRT EPAKVMDMVQ KFLGVTNTID YHKTLAFDPK 240
KGFWCQLLEG GKTKCHGKRW GRKYPEMDLD SRAFLKDYYR DHNIELSKLL YKMGQTLPTW 300
LREDLQNTR                                                        309

SEQ ID NO: 8            moltype = DNA   length = 927
```

```
FEATURE              Location/Qualifiers
misc_feature         1..927
                     note = Polynucleotide sequence encoding for engineered
                       glucosaminylN-sulfotransferase mutant_sulfotransferase 2
source               1..927
                     mol_type = other DNA
                     organism = synthetic construct
SEQUENCE: 8
atgagcgaag agaaggaccc tttgtggcag gacccgtgcg aggacaaacg ccataaggac    60
atctggtcga agagaagac  ttgtgaccgt tttccaaaat tactattat  cggtccttca   120
aagaccggcg ctttccttt  aacccacttt ttggggatgc atccagacct tagttcaaat   180
tacccttcgt ctgagactgg gcattccatt caattcttca acgggcacaa ttatcacaag   240
ggtattgact ggtacatgga attttccccg attccgagca atacaacttc gattttttac   300
tttgaaacct catccaatta ttttgattcc gaagtcgctc cacgccgcgc cgctgctttg   360
ttgccaaaag ctaaggtttt gactattctg atcaacccgg ctgaccgcgc ctattcatgg   420
taccaacacc agcgtgctca tgatgaccca gtggctttga agtatacgtt ccatgaggtc   480
attacagcgg cagcgacgc  aagctccaaa cttcgcgcat tgcaaaaccg ctgccttgtg   540
cccggttggt acgcgacaca cattgaacgc tggctgtccg cttaccacgc caaccaaatt   600
ttagttttag atgggaaatt acttcgtacc gaacctgcca aggtcatgga catggtgcag   660
aaatttttgg gagtcactaa cactatcgac taccacaaaa cattggcatt cgatccaaaa   720
aagggggttt ggtgccagct tttagaaggg gcaagacga  agtgtcacgg aagcgttgg   780
gggcgtaagt atccagagat ggatcttgat agccgcgctt tcttaaaaga ttattaccgt   840
gaccacaaca ttgagcttag caaactgctt tacaagatgg gtcagacact tccgacatgg   900
ctgcgtgaag acttgcagaa cacacgc                                       927

SEQ ID NO: 9         moltype = AA  length = 309
FEATURE              Location/Qualifiers
REGION               1..309
                     note = Engineered glucosaminyl
                       N-sulfotransferasemutant_sulfotransferase 3
source               1..309
                     mol_type = protein
                     organism = synthetic construct
SEQUENCE: 9
MSEEKDPLWQ DPCEDKRHKD IWSKEKTCDR FPKLLIIGPH GTGGHALYLF LGMHPDLSSN    60
YPSSETGEEI QFFNGHNYHK GIDWYMEFFP IPSNTTSDFY FEKSANYFDS EVAPRRAAAL   120
LPKAKVLTIL INPADRAYSW YQAQRAHDDP VALKYTFHEV ITAGSDASSK LRALQNRCLV   180
PGWYATHIER WLSAYHANQI LVLDGKLLRT EPAKVMDMVQ KFLGVTNTID YHKTLAFDPK   240
KGFWCQLLEG GKTKCGGKHL GRKYPEMDLD SRAFLKDYYR DHNIELSKLL YKMGQTLPTW   300
LREDLQNTR                                                           309

SEQ ID NO: 10        moltype = DNA  length = 927
FEATURE              Location/Qualifiers
misc_feature         1..927
                     note = Polynucleotide sequence encoding for engineered
                       glucosaminylN-sulfotransferase mutant_sulfotransferase 3
source               1..927
                     mol_type = other DNA
                     organism = synthetic construct
SEQUENCE: 10
atgagcgaag agaaggaccc tttgtggcag gacccgtgcg aagataagcg tcacaaggac    60
atctggtcaa agagaaaac  ttgcgaccgc tttccgaaat tgttaattat tggaccacat   120
ggcaccgggg gtcacgcact ttacttattc ttgggaatgc acccagatct gagctccaac   180
taccccagct ctgaaaccgg cgaagaaatc caattttca  acgggcacaa ttatcataaa   240
ggcattgatt ggtatatgga attcttcccc atcccgtcta atactaccag cgatttctat   300
tttgaaaaaa gtgcgaacta cttcgactcg gaggtggcac ccgtcgtgc  tgcggcctta   360
ctgccaaagg ccaaggtttt aaccatcttg attaatccgg ctgaccgtgc ttattcctgg   420
taccaggctc aacgcgcaca tgacgacccc gttgcgctta aatatacatt ccacgaggtc   480
attactgcgg gctctgatgc ttcttcgaaa cttcgtgcgc tgcaaaatcg ttgtttagtg   540
ccgggttggt acgccacgca catcgagcgt tggcttagtg cctaccatgc gaatcaaatc   600
cttgtcttgg atgggaagct tttgcgtact gaaccggcca aggtcatgga catggtccag   660
aagtttctgg gtgttaccaa cactattgat taccataaga ctttagcctt cgatccgaag   720
aaaggcttct ggtgtcaatt acttgagggt ggtaagacca agtgcggagg aaaacatctt   780
gggcgcaaat accccgaaat ggacttagat agccgtgcct tctgaaaaga ttactaccgc   840
gaccataata tcgagcttag caaattattg tacaaaatgg gccaaacctt gccgacgtgg   900
ctgcgtgaag acttgcagaa cacacgc                                       927

SEQ ID NO: 11        moltype = AA  length = 309
FEATURE              Location/Qualifiers
REGION               1..309
                     note = Engineered glucosaminyl
                       N-sulfotransferasemutant_sulfotransferase 4
source               1..309
                     mol_type = protein
                     organism = synthetic construct
SEQUENCE: 11
MSEEKDPLWQ DPCEDKRHKD IWSKEKTCDR FPKLLIIGPH GTGGHALYLF LGMHPDLSSN    60
YPSSETFLSI QFFNGHNYHK GIDWYMEFFP IPSNTTSDFY FEHSGNYFDS EVAPRRAAAL   120
LPKAKVLTIL INPADRAYRA YVWQRAHDDP VALKYTFHEV ITAGSDASSK LRALQNRCLV   180
```

```
PGWYATHIER WLSAYHANQI LVLDGKLLRT EPAKVMDMVQ KFLGVTNTID YHKTLAFDPK    240
KGFWCQLLEG GKTKCLGKSL GSKYPEMDLD SRAFLKDYYR DHNIELSKLL YKMGQTLPTW    300
LREDLQNTR                                                           309

SEQ ID NO: 12            moltype = DNA  length = 927
FEATURE                  Location/Qualifiers
misc_feature             1..927
                         note = Polynucleotide sequence encoding for engineered
                           glucosaminylN-sulfotransferase mutant_sulfotransferase 4
source                   1..927
                         mol_type = other DNA
                         organism = synthetic construct
SEQUENCE: 12
atgagcgaag agaaggaccc tttgtggcag gacccgtgcg aagataagcg ccacaaggac    60
atctggagca aggagaaaac ttgcgaccgc tttccaaagt tgctgattat tgggcctcac    120
ggcacgggcg gccacgcgct gtacctgttt cttggcatgc acccggacct ttccagcaat    180
tatcctagta gtgagacatt tttgagtatc aatttttta acggacataa ctatcacaaa    240
ggtatcgatt ggtacatgga attcttccca attccgtcta atacgacatc tgactttat    300
ttcgagcatt cggggaatta ctttgattcc gaggtagccc acgccgtgc cgccgctctt    360
ttgcccaagg cgaaagtctt gactattctt attaatcccg cagaccgtgc ctaccgcgcg    420
tatgtatggc aacgcgcaca cgatgaccca gtcgcattga aatatacatt ccatgaggtg    480
attaccgcgg gtagtgacgc ttctagcaag ttacgtgctc ttcagaatcg ctgccttgtc    540
ccaggttggt atgccacaca catcgaacgt tggctgtccg cctaccatgc taatcagatt    600
cttgtgctgg atggtaaatt gttgcgtaca gagcctgcca agttatggga tatggtgcaa    660
aaattttgg gtgttacgaa tactattgat taccataaga cacttgcatt tgacccgaaa    720
aaaggtttct ggtgccaatt gttggagggt ggcaagacta agtgcttagg taagagtctt    780
ggttcgaagt accccgaaat ggatttagac tcgcgcgctt tcttgaagga ctattatcgt    840
gaccacaata tcgaactttc taaactttta tataagatgg gccaaacact tccacgtgg    900
ctgcgtgaag acttgcagaa cacacgc                                       927

SEQ ID NO: 13            moltype = AA  length = 309
FEATURE                  Location/Qualifiers
REGION                   1..309
                         note = Engineered glucosaminyl
                           N-sulfotransferasemutant_sulfotransferase 5
source                   1..309
                         mol_type = protein
                         organism = synthetic construct
SEQUENCE: 13
MSEEKDPLWQ DPCEDKRHKD IWSKEKTCDR FPKLLIIGPH KTGVHALYLF LGMHPDLSSN    60
YPSSETGNHI GFFGGHNYHK GIDWYMEFFP IPSNTTSDFY FEKSAWYFDS EVAPRRAAAL    120
LPKAKVLTIL INPADRAYSW YQHQRAHDDP VALKYTFHEV ITAGSDASSK LRALQNRCLV    180
PGWYATHIER WLSAYHANQI LVLDGKLLRT EPAKVMDMVQ KFLGVTNTID YHKTLAFDPK    240
KGFWCQLLEG GKTKCLGKSV GRKYPEMDLD SRAFLKDYYR DHNIELSKLL YKMGQTLPTW    300
LREDLQNTR                                                           309

SEQ ID NO: 14            moltype = DNA  length = 927
FEATURE                  Location/Qualifiers
misc_feature             1..927
                         note = Polynucleotide sequence encoding for engineered
                           glucosaminylN-sulfotransferase mutant_sulfotransferase 5
source                   1..927
                         mol_type = other DNA
                         organism = synthetic construct
SEQUENCE: 14
atgagcgaag agaaggaccc tttgtggcag gacccgtgcg aagataagcg tcataaagac    60
atttggagta agagaagac ttgtgatcgt ttccccaagt tactgatcat cggcccacat    120
aagacaggag tacatgcatt gtacttgttt ttgggaatgc atccggacct gtcttcaaat    180
taccccagtt cagagacagg caatcacatc ggcttcttcg gaggacataa ctaccacaaa    240
ggcatcgatt ggtacatgga attctttcct atcccctca atactacctc agattttat    300
ttcgagaaaa gtgcttggta ctttgactcc gaagttgctc ctcgtcgcgc agcagcatta    360
cttccaaagg cgaaagttct gactattttg atcaacccg cggatcgcgc ctacagctgg    420
tatcaacacc agcgcgccca cgatgatcct gtcgcattga aatacacctt tcatgaagtt    480
atcaccgctg gctccgatgc gtctagcaaa ttgcgtgcat tacagaatcg ttgccttgtg    540
ccaggatggt acgctaccca tattgagcgc tggctgagtg catatcacgc gaatcagatt    600
ctggtgttag atggaaagct gctgcgtact gaaccggcca agtaatggga catggttcaa    660
aagttcctgg gggtgacgaa cacaattgat taccataaga ctcttgcatt tgatcctaag    720
aaaggctttt ggtgtcaact tttagagggg ggaagacca agtgcttagg aagagcgtg    780
ggacgcaagt accccgaaat ggactttagat tcgcgtgctt tcttgaagga ttattatcgc    840
gaccacaaca ttgaactttc taaactgtta tacaagatgg ccagacact gccgacctgg    900
ctgcgtgaag acttgcagaa cacacgc                                       927

SEQ ID NO: 15            moltype = AA  length = 309
FEATURE                  Location/Qualifiers
REGION                   1..309
                         note = Engineered glucosaminyl
                           N-sulfotransferasemutant_sulfotransferase 6
source                   1..309
                         mol_type = protein
```

```
                        organism = synthetic construct
SEQUENCE: 15
MSEEKDPLWQ  DPCEDKRHKD  IWSKEKTCDR  FPKLLIIGPA  KTGAWLLHHF  LGMHPDLSSN   60
YPSSETHSSI  QFFNGHNYHK  GIDWYMEFFP  IPSNTTSDFY  FETSANYFDS  EVAPRRAAAL  120
LPKAKVLTIL  INPADRAYSW  YQHQRAHDDP  VALKYTFHEV  ITAGSDASSK  LRALQNRCLV  180
PGWYATHIER  WLSAYHANQI  LVLDGKLLRT  EPAKVMDMVQ  KFLGVTNTID  YHKTLAFDPK  240
KGFWCQLLEG  GKTKCAHKGL  GRKYPEMDLD  SRAFLKDYYR  DHNIELSKLL  YKMGQTLPTW  300
LREDLQNTR                                                               309

SEQ ID NO: 16           moltype = DNA  length = 927
FEATURE                 Location/Qualifiers
misc_feature            1..927
                        note = Polynucleotide sequence encoding for engineered
                         glucosaminylN-sulfotransferase mutant_sulfotransferase 6
source                  1..927
                        mol_type = other DNA
                        organism = synthetic construct
SEQUENCE: 16
atgagcgaag agaaggaccc tttgtggcag gacccgtgcg aagataagcg tcacaaggat   60
atttggtcca agaaaagac ctgcgatcgc tttcccaagc tgttaatcat cggcccggcc  120
aaaacaggcg cctggctttt gcatcatttc ctgggcatgc atcccgactt gtcgagtaac  180
tatccgtcgt ccgaaactca ctcctctatt caattcttca atggcataa ttatcacaag  240
ggtatcgact ggtacatgga gttctttcca atccctagta atacaaccag tgatttttat  300
tttgagacta gcgctaacta cttttgattca gaggtggcac cgcgtcgtgc ggcggcgctg  360
ttgccgaagg cgaaagtttt aactatcttg atcaatccgg cagatcgtgc gtacagctgg  420
taccaacatc aacgtgctca cgatgacccg gtggccctga aatataccct ccacgaggtc  480
attacagccg gaagtgacgc ttccagtaaa ttgcgcgcgt tacaaaatcg ttgtctggtc  540
cctgggtggt acgcaacgca cattgaacgc tggttatcgg cataccacgc aaatcagatc  600
cttgtgcttg acgaaagtt attgcgtact gaaccggcca aggtgatgga tatggtacag  660
aaattccttg gcgtcaccaa tacgatcgac tatcacaaga cgcttgcctt cgaccccaag  720
aagggggtttt ggtgccaact tttagagggt ggtaagacaa agtgtgctca taaggggtta  780
ggccgcaagt accctgaaat ggatctggac tcgcgcgctt ttttgaaaga ctattatcgc  840
gatcacaata ttgagttgag caagttgctg tataaaatgg gacagacact gccgacctgg  900
ctgcgtgaag acttgcagaa cacacgc                                       927

SEQ ID NO: 17           moltype = AA  length = 309
FEATURE                 Location/Qualifiers
REGION                  1..309
                        note = Engineered glucosaminyl N-sulfotransferase
                         mutant_variable
SITE                    40
                        note = MISC_FEATURE - Xaa is glutamine, histidine, serine,
                         or alanine
SITE                    41
                        note = MISC_FEATURE - Xaa is lysine or glycine
SITE                    44
                        note = MISC_FEATURE - Xaa is alanine, histidine, glycine,
                         or valine
SITE                    45
                        note = MISC_FEATURE - Xaa is threonine, tryptophan,
                         histidine, or phenylalanine
SITE                    46
                        note = MISC_FEATURE - Xaa is alanine or leucine
SITE                    48
                        note = MISC_FEATURE - Xaa is tyrosine, threonine, or
                         histidine
SITE                    49
                        note = MISC_FEATURE - Xaa is leucine or histidine
SITE                    65
                        note = MISC_FEATURE - Xaa is glutamic acid or threonine
SITE                    66
                        note = MISC_FEATURE - Xaa is threonine or serine
SITE                    67
                        note = MISC_FEATURE - Xaa is phenylalanine, glycine, or
                         histidine
SITE                    68
                        note = MISC_FEATURE - Xaa is glutamic acid, histidine,
                         alanine, leucine, glycine,asparagine, or serine
SITE                    69
                        note = MISC_FEATURE - Xaa is glutamic acid, serine,
                         arginine, or histidine
SITE                    71
                        note = MISC_FEATURE - Xaa is glutamine or glycine
SITE                    74
                        note = MISC_FEATURE - Xaa is asparagine or glycine
SITE                    103
                        note = MISC_FEATURE - Xaa is lysine, alanine, methionine,
                         histidine, or threonine
SITE                    104
```

|   |   |
|---|---|
| SITE | 105 |
|   | note = MISC_FEATURE - Xaa is serine or histidine |
| SITE | 106 |
|   | note = MISC_FEATURE - Xaa is alanine, serine, or glycine |
| SITE | 139 |
|   | note = MISC_FEATURE - Xaa is asparagine, glycine, or tryptophan |
| SITE | 140 |
|   | note = MISC_FEATURE - Xaa is serine or arginine |
| SITE | 142 |
|   | note = MISC_FEATURE - Xaa is tryptophan or alanine |
| SITE | 143 |
|   | note = MISC_FEATURE - Xaa is glutamine or valine |
| SITE | 256 |
|   | note = MISC_FEATURE - Xaa is histidine, alanine, or tryptophan |
| SITE | 257 |
|   | note = MISC_FEATURE - Xaa is leucine, histidine, glycine, or alanine |
| SITE | 259 |
|   | note = MISC_FEATURE - Xaa is glycine or histidine |
| SITE | 260 |
|   | note = MISC_FEATURE - Xaa is serine, arginine, histidine, or glycine |
| SITE | 262 |
|   | note = MISC_FEATURE - Xaa is lysine, alanine, histidine, tryptophan, or leucine |
|   | note = MISC_FEATURE - Xaa is arginine or serine |
| source | 1..309 |
|   | mol_type = protein |
|   | organism = synthetic construct |

SEQUENCE: 17
```
MSEEKDPLWQ DPCEDKRHKD IWSKEKTCDR FPKLLIIGPX XTGXXXLXXF LGMHPDLSSN   60
YPSSXXXXXI XFFXGHNYHK GIDWYMEFPP IPSNTTSDFY FEXXXXYFDS EVAPRRAAAL  120
LPKAKVLTIL INPADRAYXX YXXQRAHDDP VALKYTFHEV ITAGSDASSK LRALQNRCLV  180
PGWYATHIER WLSAYHANQI LVLDGKLLRT EPAKVMDMVQ KFLGVTNTID YHKTLAFDPK  240
KGFWCQLLEG GKTKCXXKXX GXKYPEMDLD SRAFLKDYYR DHNIELSKLL YKMGQTLPTW  300
LREDLQNTR                                                        309
```

|   |   |
|---|---|
| SEQ ID NO: 18 | moltype = AA length = 309 |
| FEATURE | Location/Qualifiers |
| REGION | 1..309 |
|   | note = Engineered glucosaminyl N-sulfotransferasemutant_sulfotransferase 7 |
| SITE | 40 |
|   | note = MISC_FEATURE - Xaa is glutamine, serine, or alanine |
| SITE | 45 |
|   | note = MISC_FEATURE - Xaa is tryptophan or phenylalanine |
| SITE | 46 |
|   | note = MISC_FEATURE - Xaa is alanine or leucine |
| SITE | 48 |
|   | note = MISC_FEATURE - Xaa is tyrosine, threonine, or histidine |
| SITE | 67 |
|   | note = MISC_FEATURE - Xaa is histidine or glycine |
| SITE | 68 |
|   | note = MISC_FEATURE - Xaa is glycine, histidine, or serine |
| SITE | 103 |
|   | note = MISC_FEATURE - Xaa is lysine or threonine |
| SITE | 105 |
|   | note = MISC_FEATURE - Xaa is alanine or serine |
| SITE | 256 |
|   | note = MISC_FEATURE - Xaa is leucine, histidine, or alanine |
| SITE | 257 |
|   | note = MISC_FEATURE - Xaa is glycine or histidine |
| SITE | 259 |
|   | note = MISC_FEATURE - Xaa is serine, arginine, or glycine |
| SITE | 260 |
|   | note = MISC_FEATURE - Xaa is histidine, tryptophan, or leucine |
| source | 1..309 |
|   | mol_type = protein |
|   | organism = synthetic construct |

SEQUENCE: 18
```
MSEEKDPLWQ DPCEDKRHKD IWSKEKTCDR FPKLLIIGPX KTGAXXLXHF LGMHPDLSSN   60
YPSSETXXSI QFFNGHNYHK GIDWYMEFPP IPSNTTSDFY FEXSXNYFDS EVAPRRAAAL  120
LPKAKVLTIL INPADRAYSW YQHQRAHDDP VALKYTFHEV ITAGSDASSK LRALQNRCLV  180
PGWYATHIER WLSAYHANQI LVLDGKLLRT EPAKVMDMVQ KFLGVTNTID YHKTLAFDPK  240
KGFWCQLLEG GKTKCXXKXX GRKYPEMDLD SRAFLKDYYR DHNIELSKLL YKMGQTLPTW  300
```

```
LREDLQNTR                                                                   309

SEQ ID NO: 19           moltype = AA  length = 309
FEATURE                 Location/Qualifiers
REGION                  1..309
                        note = Engineered glucosaminyl
                        N-sulfotransferasemutant_sulfotransferase 8
SITE                    41
                        note = MISC_FEATURE - Xaa is glycine or lysine
SITE                    44
                        note = MISC_FEATURE - Xaa is glycine or valine
SITE                    67
                        note = MISC_FEATURE - Xaa is glycine or phenylalanine
SITE                    68
                        note = MISC_FEATURE - Xaa is glutamic acid, leucine, or
                         asparagine
SITE                    69
                        note = MISC_FEATURE - Xaa is glutamic acid, serine, or
                         histidine
SITE                    71
                        note = MISC_FEATURE - Xaa is glutamine or glycine
SITE                    74
                        note = MISC_FEATURE - Xaa is asparagine or glycine
SITE                    103
                        note = MISC_FEATURE - Xaa is lysine or histidine
SITE                    105
                        note = MISC_FEATURE - Xaa is alanine or glycine
SITE                    106
                        note = MISC_FEATURE - Xaa is asparagine or tryptophan
SITE                    139
                        note = MISC_FEATURE - Xaa is serine or arginine
SITE                    140
                        note = MISC_FEATURE - Xaa is tryptophan or alanine
SITE                    142
                        note = MISC_FEATURE - Xaa is glutamine or valine
SITE                    143
                        note = MISC_FEATURE - Xaa is histidine, alanine, or
                         tryptophan
SITE                    256
                        note = MISC_FEATURE - Xaa is leucine or glycine
SITE                    259
                        note = MISC_FEATURE - Xaa is serine or histidine
SITE                    260
                        note = MISC_FEATURE - Xaa is leucine or valine
SITE                    262
                        note = MISC_FEATURE - Xaa is arginine or serine
source                  1..309
                        mol_type = protein
                        organism = synthetic construct
SEQUENCE: 19
MSEEKDPLWQ DPCEDKRHKD IWSKEKTCDR FPKLLIIGPH XTGXHALYLF LGMHPDLSSN   60
YPSSETXXXI XFFXGHNYHK GIDWYMEFFP IPSNTTSDFY FEXSXXYFDS EVAPRRAAAL  120
LPKAKVLTIL INPADRAYXX YXXQRAHDDP VALKYTFHEV ITAGSDASSK LRALQNRCLV  180
PGWYATHIER WLSAYHANQI LVLDGKLLRT EPAKVMDMVQ KFLGVTNTID YHKTLAFDPK  240
KGFWCQLLEG GKTKCXGKXX GXKYPEMDLD SRAFLKDYYR DHNIELSKLL YKMGQTLPTW  300
LREDLQNTR                                                          309

SEQ ID NO: 20           moltype = AA  length = 309
FEATURE                 Location/Qualifiers
REGION                  1..309
                        note = Engineered glucosaminyl
                        N-sulfotransferasemutant_sulfotransferase 9
source                  1..309
                        mol_type = protein
                        organism = synthetic construct
SEQUENCE: 20
MSEEKDPLWQ DPCEDKRHKD IWSKEKTCDR FPKLLIIGPQ KTGAWALYHF LGLHPDLSSN   60
YPSSETHGSI QFFNGHNYHK GIDWYMDFFP IPSNTTSDFY FEKSANYFDS DVAPRRAAAL  120
LPKAKVLTIL INPADRAYSW YQHQRAHDDP AALRYTFHEV ITAGPDASLK LRALQNRCLV  180
PGWYATHLER WLGAFHANQI LVLDGKLLRT EPARVMDTVQ KFLGVTNTID YHKTLAFDPK  240
KGFWCQLLEG GKTKCLGRSH GRKYPDMDPD SRAFLRDYYR DHNIELSKLL YKMGQTLPTW  300
LREELQNTR                                                          309

SEQ ID NO: 21           moltype = AA  length = 309
FEATURE                 Location/Qualifiers
REGION                  1..309
                        note = Engineered glucosaminyl
                        N-sulfotransferasemutant_sulfotransferase 10
source                  1..309
```

```
SEQUENCE: 21
MSEEKDPLWQ DPCEDKRHKD IWSKEKTCDR FPKLLIIGPS KTGAFLLTHF LGLHPDLSSN    60
YPSSETGHSI QFFNGHNYHK GIDWYMDFFP IPSNTTSDFY FETSSNYFDS DVAPRRAAAL   120
LPKAKVLTIL INPADRAYSW YQHQRAHDDP AALRYTFHEV ITAGPDASLK LRALQNRCLV   180
PGWYATHLER WLGAFHANQI LVLDGKLLRT EPARVMDTVQ KFLGVTNTID YHKTLAFDPK   240
KGFWCQLLEG GKTKCHGRRW GRKYPDMDPD SRAFLRDYYR DHNIELSKLL YKMGQTLPTW   300
LREELQNTR                                                          309

SEQ ID NO: 22           moltype = AA  length = 309
FEATURE                 Location/Qualifiers
REGION                  1..309
                        note = Engineered glucosaminyl
                        N-sulfotransferasemutant_sulfotransferase 11
source                  1..309
                        mol_type = protein
                        organism = synthetic construct
SEQUENCE: 22
MSEEKDPLWQ DPCEDKRHKD IWSKEKTCDR FPKLLIIGPH HTGGHALYLF LGLHPDLSSN    60
YPSSETGEEI QFFNGHNYHK GIDWYMDFFP IPSNTTSDFY FEKSANYFDS DVAPRRAAAL   120
LPKAKVLTIL INPADRAYSW YQAQRAHDDP AALRYTFHEV ITAGPDASLK LRALQNRCLV   180
PGWYATHLER WLGAFHANQI LVLDGKLLRT EPARVMDTVQ KFLGVTNTID YHKTLAFDPK   240
KGFWCQLLEG GKTKCGGRHL GRKYPDMDPD SRAFLRDYYR DHNIELSKLL YKMGQTLPTW   300
LREELQNTR                                                          309

SEQ ID NO: 23           moltype = AA  length = 309
FEATURE                 Location/Qualifiers
REGION                  1..309
                        note = Engineered glucosaminyl
                        N-sulfotransferasemutant_sulfotransferase 12
source                  1..309
                        mol_type = protein
                        organism = synthetic construct
SEQUENCE: 23
MSEEKDPLWQ DPCEDKRHKD IWSKEKTCDR FPKLLIIGPH GTGGHALYLF LGLHPDLSSN    60
YPSSETFLSI QFFNGHNYHK GIDWYMDFFP IPSNTTSDFY FEHSGNYFDS DVAPRRAAAL   120
LPKAKVLTIL INPADRAYRA YVWQRAHDDP AALRYTFHEV ITAGPDASLK LRALQNRCLV   180
PGWYATHLER WLGAFHANQI LVLDGKLLRT EPARVMDTVQ KFLGVTNTID YHKTLAFDPK   240
KGFWCQLLEG GKTKCLGRSL GSKYPDMDPD SRAFLRDYYR DHNIELSKLL YKMGQTLPTW   300
LREELQNTR                                                          309

SEQ ID NO: 24           moltype = AA  length = 309
FEATURE                 Location/Qualifiers
REGION                  1..309
                        note = Engineered glucosaminyl
                        N-sulfotransferasemutant_sulfotransferase 13
source                  1..309
                        mol_type = protein
                        organism = synthetic construct
SEQUENCE: 24
MSEEKDPLWQ DPCEDKRHKD IWSKEKTCDR FPKLLIIGPH KTGVHALYLF LGLHPDLSSN    60
YPSSETGNHI GFFGGHNYHK GIDWYMDFFP IPSNTTSDFY FEKSAWYFDS DVAPRRAAAL   120
LPKAKVLTIL INPADRAYSW YQHQRAHDDP AALRYTFHEV ITAGPDASLK LRALQNRCLV   180
PGWYATHLER WLGAFHANQI LVLDGKLLRT EPARVMDTVQ KFLGVTNTID YHKTLAFDPK   240
KGFWCQLLEG GKTKCLGRSV GRKYPDMDPD SRAFLRDYYR DHNIELSKLL YKMGQTLPTW   300
LREELQNTR                                                          309

SEQ ID NO: 25           moltype = AA  length = 309
FEATURE                 Location/Qualifiers
REGION                  1..309
                        note = Engineered glucosaminyl
                        N-sulfotransferasemutant_sulfotransferase 14
source                  1..309
                        mol_type = protein
                        organism = synthetic construct
SEQUENCE: 25
MSEEKDPLWQ DPCEDKRHKD IWSKEKTCDR FPKLLIIGPA KTGAWLLHHF LGLHPDLSSN    60
YPSSETHSSI QFFNGHNYHK GIDWYMDFFP IPSNTTSDFY FETSANYFDS DVAPRRAAAL   120
LPKAKVLTIL INPADRAYSW YQHQRAHDDP AALRYTFHEV ITAGPDASLK LRALQNRCLV   180
PGWYATHLER WLGAFHANQI LVLDGKLLRT EPARVMDTVQ KFLGVTNTID YHKTLAFDPK   240
KGFWCQLLEG GKTKCAHRGL GRKYPDMDPD SRAFLRDYYR DHNIELSKLL YKMGQTLPTW   300
LREELQNTR                                                          309

SEQ ID NO: 26           moltype = DNA  length = 870
FEATURE                 Location/Qualifiers
misc_feature            1..870
                        note = Polynucleotide sequence encoding for engineered
                        hexuronyl 2-Osulfotransferase mutant_sulfatase 1
```

| | |
|---|---|
| source | 1..870<br>mol_type = other DNA<br>organism = synthetic construct |

SEQUENCE: 26

```
atggatgagg aagacgacgt cgtgattatt tataaccatg tacataagac tgccagccat    60
tcattcacga atatcgcgta cgatctttgc gctaaaaacc gttatcatgt tttacatatt   120
aataccacca aaaacaatcc ggtgatgtca ttgcaggatc aggtgcgttt cgtaaagaat   180
gtcacctcat ggaaagagat gaagccaggg ttttatcatg gcacgttag ttatttggat    240
tttgctaagt ttggtgtaaa gaagaagccc atctcacatca atgtcattcg tgatcccatt   300
gaacgcttgg tctcctatta ctacttttg cgctttggcg acgactaccg ccccggatta    360
cgccgccgca agcaggggga caagaaaact tttgacgaat cgtcgctgc cggtggtagc    420
gactgcgccc cggagaaatt atggcttcaa attcccttt tctgcggcca ttcttcggaa    480
tgctggaacg taggtagtcg ctgggctctt gaacaggcaa aatataatct tatcaacgaa   540
tactttcttg tcggagttac cgaggagttg gaggactta ttatgcttct ggaggctgcg    600
ctgccgcgtt tttttcgtgg tgcgaccgag ctgtatcgta caggtaaaaa aagtcatctt   660
cgtaaaacga cggaaaagaa gctgccaact aaggaaacaa tcgcgaaact gcaacagagt   720
gaaatctgga aaatgaaaa tgaattctat gagtttgccc tggagcaatt ccaattcgtt   780
cgcgcccatg ccgtacgtga aaggacggc gaattatata ccttgcaca aaacttcttc    840
tatgagaaga tctatcctaa gtctaactaa                                    870
```

| | |
|---|---|
| SEQ ID NO: 27 | moltype = AA  length = 289 |
| FEATURE | Location/Qualifiers |
| REGION | 1..289<br>note = Engineered hexuronyl 2-O sulfotransferase<br>mutant_sulfatase 1 |
| source | 1..289<br>mol_type = protein<br>organism = synthetic construct |

SEQUENCE: 27

```
MDEEDDVVII YNHVHKTASH SFTNIAYDLC AKNRYHVLHI NTTKNNPVMS LQDQVRFVKN    60
VTSWKEMKPG FYHGHVSYLD FAKFGVKKKP IYINVIRDPI ERLVSYYYFL RFGDDYRPGL   120
RRRKQGDKKT FDECVAAGGS DCAPEKLWLQ IPFFCGHSSE CWNVGSRWAL EQAKYNLINE   180
YFLVGVTEEL EDFIMLLEAA LPRFFRGATE LYRTGKKSHL RKTTEKKLPT KETIAKLQQS   240
EIWKMENEFY EFALEQFQFV RAHAVREKDG ELYILAQNFF YEKIYPKSN               289
```

| | |
|---|---|
| SEQ ID NO: 28 | moltype = DNA  length = 870 |
| FEATURE | Location/Qualifiers |
| misc_feature | 1..870<br>note = Polynucleotide sequence encoding for engineered<br>hexuronyl 2-Osulfotransferase mutant_sulfatase 2 |
| source | 1..870<br>mol_type = other DNA<br>organism = synthetic construct |

SEQUENCE: 28

```
atggatgagg aagacgacgt cgtgattatt tataaccgtg taccgaccac tgcccatacg    60
tcattcacga atatcgcgta cgatctttgc gctaaaaacc gttatcatgt tttacatatt   120
aataccacca aaaacaatcc ggtgatgtca ttgcaggatc aggtgcgttt cgtaaagaat   180
gtcacctcat ggaaagagat gaagccaggg ttttatcatg gcacgttag ttatttggat    240
tttgctaagt ttggtgtaaa gaagaagccc atctacatca atgtcattcg tgatcccatt   300
gaacgcttgg tctcctatta ctaccatttg cgctttggcg acgactaccg ccccggatta   360
cgccgccgca agcaggggga caagaaaact tttgacgaat cgtcgctgc cggtggtagc    420
gactgcgccc cggagaaatt atggcttcaa attcccttt tctgcggcca ttcttcggaa    480
tgctggaacg taggtagtcg ctgggctctt gaacaggcaa aatataatct tatcaacgaa   540
tactttcttg tcggagttac cgaggagttg gaggactta ttatgcttct ggaggctgcg    600
ctgccgcgtt tttttcgtgg tgcgaccgag ctgtatcgta caggtaaaaa aagtcatctt   660
cgtaaaacga cggaaaagaa gctgccaact aaggaaacaa tcgcgaaact gcaacagagt   720
gaaatctgga aaatgaaaa tgaattctat gagtttgccc tggagcaatt ccaattcgtt   780
cgcgcccatg ccgtacgtga aaggacggc gaattatata ccttgcaca aaacttcttc    840
tatgagaaga tctatcctaa gtctaactaa                                    870
```

| | |
|---|---|
| SEQ ID NO: 29 | moltype = AA  length = 289 |
| FEATURE | Location/Qualifiers |
| REGION | 1..289<br>note = Engineered hexuronyl 2-O sulfotransferase<br>mutant_sulfatase 2 |
| source | 1..289<br>mol_type = protein<br>organism = synthetic construct |

SEQUENCE: 29

```
MDEEDDVVII YNRVPTTAHT SFTNIAYDLC AKNRYHVLHI NTTKNNPVMS LQDQVRFVKN    60
VTSWKEMKPG FYHGHVSYLD FAKFGVKKKP IYINVIRDPI ERLVSYYYHL RFGDDYRPGL   120
RRRKQGDKKT FDECVAAGGS DCAPEKLWLQ IPFFCGHSSE CWNVGSRWAL EQAKYNLINE   180
YFLVGVTEEL EDFIMLLEAA LPRFFRGATE LYRTGKKSHL RKTTEKKLPT KETIAKLQQS   240
EIWKMENEFY EFALEQFQFV RAHAVREKDG ELYILAQNFF YEKIYPKSN               289
```

| | |
|---|---|
| SEQ ID NO: 30 | moltype = DNA  length = 870 |
| FEATURE | Location/Qualifiers |
| misc_feature | 1..870<br>note = Polynucleotide sequence encoding for engineered |

|   |   |   |
|---|---|---|
| | | hexuronyl 2-Osulfotransferase mutant_sulfatase 3 |
| source | 1..870 | |
| | | mol_type = other DNA |
| | | organism = synthetic construct |

SEQUENCE: 30

```
atggatgagg aagacgacgt cgtgattatt tataaccgtg tacataccac tgccagcacg   60
tcattcacga atatcgcgta cgatctttgc gctaaaaacc gttatcatgt tttacatatt  120
aataccacca aaaacaatcc ggtgatgtca ttgcaggatc aggtgcgttt cgtaaagaat  180
gtcacctcat ggaaagagat gaagccaggg ttttatcatg ggcacgttag ttatttggat  240
tttgctaagt ttggtgtaaa gaagaagccc atctacatca atgtcattcg tgatcccatt  300
gaacgcttgg tctcctatta ctactttttg cgctttggcg acgactaccg ccccggatta  360
cgccgccgca agcaggggga caagaaaact tttgacgaat gcgtcgctgc cggtggtagc  420
gactgcgccc cggagaaatt atggcttcaa attccctttt tctgcggcca ttcttcggaa  480
tgctggaacg taggtagtcg ctgggctctt gaacaggcaa aatataatct tatcaacgaa  540
tactttcttg tcggagttac cgaggagttg gaggacttta ttatgcttct ggaggctgcg  600
ctgccgcgtt ttttttcgtgg tgcgaccgag ctgtatcgta caggtaaaaa aagtcatctt  660
cgtaaaacga cggaaaagaa gctgccaact aaggaaacaa tcgcgaaact gcaacagagt  720
gaaatctgga aaatggaaaa tgaattctat gagtttgccc tggagcaatt ccaattcgtt  780
cgcgcccatg ccgtacgtga gaaggacggc gaattatata tccttgcaca aaacttcttc  840
tatgagaaga tctatcctaa gtctaactaa                                   870
```

|   |   |   |
|---|---|---|
| SEQ ID NO: 31 | moltype = AA length = 289 | |
| FEATURE | Location/Qualifiers | |
| REGION | 1..289 | |
| | | note = Engineered hexuronyl 2-O sulfotransferase mutant_sulfatase 3 |
| source | 1..289 | |
| | | mol_type = protein |
| | | organism = synthetic construct |

SEQUENCE: 31

```
MDEEDDVVII YNRVHTTAST SFTNIAYDLC AKNRYHVLHI NTTKNNPVMS LQDQVRFVKN   60
VTSWKEMKPG FYHGHVSYLD FAKFGVKKKP IYINVIRDPI ERLVSYYYFL RFGDDYRPGL  120
RRRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL RKTTEKKLPT KETIAKLQQS  240
EIWKMENEFY EFALEQFQFV RAHAVREKDG ELYILAQNFF YEKIYPKSN              289
```

|   |   |   |
|---|---|---|
| SEQ ID NO: 32 | moltype = DNA length = 870 | |
| FEATURE | Location/Qualifiers | |
| misc_feature | 1..870 | |
| | | note = Polynucleotide sequence encoding for engineered hexuronyl 2-Osulfotransferase mutant_sulfatase 4 |
| source | 1..870 | |
| | | mol_type = other DNA |
| | | organism = synthetic construct |

SEQUENCE: 32

```
atggatgagg aagacgacgt cgtgattatt tataaccgtg taccgaccac tgcccataac   60
tcattcacga atatcgcgta cgatctttgc gctaaaaacc gttatcatgt tttacatatt  120
aataccacca aaaacaatcc ggtgatgtca ttgcaggatc aggtgcgttt cgtaaagaat  180
gtcacctcat ggaaagagat gaagccaggg ttttatcatg ggcacgttag ttatttggat  240
tttgctaagt ttggtgtaaa gaagaagccc atctacatca atgtcattcg tgatcccatt  300
gaacgcttgg tctcctatta ctaccatttg cgctttggcg acgactaccg ccccggatta  360
cgccgccgca agcaggggga caagaaaact tttgacgaat gcgtcgctgc cggtggtagc  420
gactgcgccc cggagaaatt atggcttcaa attccctttt tctgcggcca ttcttcggaa  480
tgctggaacg taggtagtcg ctgggctctt gaacaggcaa aatataatct tatcaacgaa  540
tactttcttg tcggagttac cgaggagttg gaggacttta ttatgcttct ggaggctgcg  600
ctgccgcgtt ttttttcgtgg tgcgaccgag ctgtatcgta caggtaaaaa aagtcatctt  660
cgtaaaacga cggaaaagaa gctgccaact aaggaaacaa tcgcgaaact gcaacagagt  720
gaaatctgga aaatggaaaa tgaattctat gagtttgccc tggagcaatt ccaattcgtt  780
cgcgcccatg ccgtacgtga gaaggacggc gaattatata tccttgcaca aaacttcttc  840
tatgagaaga tctatcctaa gtctaactaa                                   870
```

|   |   |   |
|---|---|---|
| SEQ ID NO: 33 | moltype = AA length = 289 | |
| FEATURE | Location/Qualifiers | |
| REGION | 1..289 | |
| | | note = Engineered hexuronyl 2-O sulfotransferase mutant_sulfatase 4 |
| source | 1..289 | |
| | | mol_type = protein |
| | | organism = synthetic construct |

SEQUENCE: 33

```
MDEEDDVVII YNRVPTTAHN SFTNIAYDLC AKNRYHVLHI NTTKNNPVMS LQDQVRFVKN   60
VTSWKEMKPG FYHGHVSYLD FAKFGVKKKP IYINVIRDPI ERLVSYYYHL RFGDDYRPGL  120
RRRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL RKTTEKKLPT KETIAKLQQS  240
EIWKMENEFY EFALEQFQFV RAHAVREKDG ELYILAQNFF YEKIYPKSN              289
```

|   |   |
|---|---|
| SEQ ID NO: 34 | moltype = DNA length = 870 |
| FEATURE | Location/Qualifiers |
| misc_feature | 1..870 |

|  |  |  |
|---|---|---|
| | note = Polynucleotide sequence encoding for engineered<br>hexuronyl 2-Osulfotransferase mutant_sulfatase 5 | |
| source | 1..870<br>mol_type = other DNA<br>organism = synthetic construct | |

SEQUENCE: 34

```
atggatgagg aagacgacgt cgtgattatt tataaccgtg taccgaacac tgccagcacg   60
tcattcacga atatcgcgta cgatctttgc gctaaaaacc gttatcatgt tttacatatt  120
aataccacca aaaacaatcc ggtgatgtca ttgcaggatc aggtgcgttt cgtaaagaat  180
gtcacctcat ggaaagagat gaagccaggg ttttatcatg ggcacgttag ttatttggat  240
tttgctaagt ttggtgtaaa gaagaagccc atctacatca atgtcattcg tgatcccatt  300
gaacgcttgg tccattatta ctaccatttg cgctttggcg acgactaccg ccccggatta  360
cgccgccgca agcaggggga caagaaaact tttgacgaat gcgtcgctgc cggtggtagc  420
gactgcgccc cggagaaatt atggcttcaa attccttttt tctgcggcca ttcttcggaa  480
tgctggaacg taggtagtcg ctgggctctt gaacaggcaa aatataatct tatcaacgaa  540
tactttcttg tcggagttac cgaggagttg gaggacttta ttatgcttct ggaggctgcg  600
ctgccgcgtt tttttcgtgg tgcgaccgag ctgtatcgta caggtaaaaa aagtcatctt  660
cgtaaaacga cggaaaagaa gctgccaact aaggaaacaa tcgcgaaact gcaacagagt  720
gaaatctgga aaatggaaaa tgaattctat gagtttgccc tggagcaatt ccaattcgtt  780
cgcgcccatg ccgtacgtga aaggacggc gaattatata ccttgcaca aaacttcttc  840
tatgagaaga tctatcctaa gtctaactaa                                    870
```

| SEQ ID NO: 35 | moltype = AA length = 289 | |
|---|---|---|
| FEATURE | Location/Qualifiers | |
| REGION | 1..289<br>note = Engineered hexuronyl 2-O sulfotransferase<br>mutant_sulfatase 5 | |
| source | 1..289<br>mol_type = protein<br>organism = synthetic construct | |

SEQUENCE: 35

```
MDEEDDVVII YNRVPNTAST SFTNIAYDLC AKNRYHVLHI NTTKNNPVMS LQDQVRFVKN   60
VTSWKEMKPG FYHGHVSYLD FAKFGVKKKP IYINVIRDPI ERLVHYYYHL RFGDDYRPGL  120
RRRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL RKTTEKKLPT KETIAKLQQS  240
EIWKMENEFY EFALEQFQFV RAHAVREKDG ELYILAQNFF YEKIYPKSN              289
```

| SEQ ID NO: 36 | moltype = DNA length = 870 | |
|---|---|---|
| FEATURE | Location/Qualifiers | |
| misc_feature | 1..870<br>note = Polynucleotide sequence encoding for engineered<br>hexuronyl 2-Osulfotransferase mutant_sulfatase 6 | |
| source | 1..870<br>mol_type = other DNA<br>organism = synthetic construct | |

SEQUENCE: 36

```
atggatgagg aagacgacgt cgtaatcatc tacaaccgcg tcccgcacac agccagccac   60
tccttcacca atattgcgta tgatctgtgc gctaagaacc gttaccatgt gttgcacatt  120
accactacga agcgtaaccc cgtaatgtca cttcaagatc aagttcgctt cgttaagaac  180
gtgacatctt ggaaggagat gaagccagga ttctatcatg gggaagttag ctacttggac  240
tttgccaagt tcggtgtaaa gaaaaaacca atctacatca atgttattcg tgatcccatt  300
gaacgcttag tgtcttacta ttatgccctt cgctttggag cgaccgtcg cccggggctt  360
cgtatgcgca agcaagggga caagaagacc ttcgacgagt gtgtagccgc gggtgggtct  420
gactgtgcgc cggaaaagtt atggttacaa attccatttt tctgtggtca ctcgtcagag  480
tgctggaata ttggttcgcg ctgggcgctg gagcaagcga aatataactt gattaatgaa  540
tacttttag taggggtgac agaggagttg gaggacttta ttatgcttct tgaggctgcg  600
ttacctcgct tttttcgcgg tgcgactgag ttgtatcgta ccggtaaaaa atctcatctg  660
cataaaacaa ctgaaaagaa gctgccaacg aaagagacga ttgctaaact tcagcagagt  720
gagatctgga aaatggaaaa tgagttctac gagtttgcct tggagcaatt ccaattcgtg  780
cgtgcccatg ccgttcgtga aaaggatggt gaattataca tcttggcaca gaatttcttc  840
tatgagaaaa tttatcctaa gtctaactaa                                    870
```

| SEQ ID NO: 37 | moltype = AA length = 289 | |
|---|---|---|
| FEATURE | Location/Qualifiers | |
| REGION | 1..289<br>note = Engineered hexuronyl 2-O sulfotransferase<br>mutant_sulfatase 6 | |
| source | 1..289<br>mol_type = protein<br>organism = synthetic construct | |

SEQUENCE: 37

```
MDEEDDVVII YNRVPHTASH SFTNIAYDLC AKNRYHVLHI TTTKRNPVMS LQDQVRFVKN   60
VTSWKEMKPG FYHGEVSYLD FAKFGVKKKP IYINVIRDPI ERLVSYYYAL RFGGDRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289
```

| SEQ ID NO: 38 | moltype = DNA length = 870 | |
|---|---|---|
| FEATURE | Location/Qualifiers | |

```
misc_feature            1..870
                        note = Polynucleotide sequence encoding for engineered
                        hexuronyl 2-Osulfotransferase mutant_sulfatase 7
source                  1..870
                        mol_type = other DNA
                        organism = synthetic construct
SEQUENCE: 38
atggatgagg aagacgacgt cgtaatcatc tacaaccgcg tcccgcacac agccgagcac   60
tccttcacca atattgcgta tgatctgtgc gctaagaacc gttaccatgt gttgcacatt  120
accactacga agcgtaaccc cgtaatgtca cttcaagatc aagttcgctt cgttaagaac  180
gtgacatctt ggaaggagat gaagccagga ttctatcatg gggaagttag ctacttggac  240
tttgccaagt tcggtgtaaa gaaaaaacca atctacatca tgttattcg tgatcccatc   300
gaacgcttag tgtcttacta ttatgccctt cgctttggag cgaccgtcg cccggggctt   360
cgtatgcgca agcaagggga caagaagacc ttcgacgagt gtgtagccgc gggtgggtct  420
gactgtgcgc cggaaaagtt atggttacaa attccatttt tctgtggtca ctcgtcagag  480
tgctggaatg ttggttcgcg ctgggcgctg agcaagcga aatataactt gattaatgaa   540
tacttttag taggggtgac agaggagttg gaggacttta ttatgcttct tgaggctgcg   600
ttacctcgct ttttccgcgg tgcgactgag ttgtatcgta ccggtaaaaa atctcatctg  660
cataaaacaa ctgaaaagaa gctgccaacg aaagagacga ttgctaaact tcagcagagt  720
gagatctgga aatggaaaa tgagttctac gagtttgcct tggagcaatt ccaattcgtg   780
cgtgcccatg ccgttcgtga aaaggatggt gaattataca tcttggcaca gaatttcttc  840
tatgagaaaa tttatcctaa gtctaactaa                                   870

SEQ ID NO: 39           moltype = AA   length = 289
FEATURE                 Location/Qualifiers
REGION                  1..289
                        note = Engineered hexuronyl 2-O sulfotransferase
                        mutant_sulfatase 7
source                  1..289
                        mol_type = protein
                        organism = synthetic construct
SEQUENCE: 39
MDEEDDVVII YNRVPHTAEH SFTNIAYDLC AKNRYHVLHI TTTKRNPVMS LQDQVRFVKN   60
VTSWKEMKPG FYHGEVSYLD FAKFGVKKKP IYINVIRDPI ERLVSYYYAL RFGGDRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289

SEQ ID NO: 40           moltype = DNA   length = 870
FEATURE                 Location/Qualifiers
misc_feature            1..870
                        note = Polynucleotide sequence encoding for engineered
                        hexuronyl 2-Osulfotransferase mutant_sulfatase 8
source                  1..870
                        mol_type = other DNA
                        organism = synthetic construct
SEQUENCE: 40
atggatgagg aagacgacgt cgtgatcatc tacaaccgtg ttcctcacac ggcttcgcac   60
tctttcacga atatcgctta cgacttatgt gccaagaatc gttatcatgt gttacacatc  120
actaccacca aaaacaaccc cgtcatgtcg ttacaggacc aagtgcgttt cgtgaaaaac  180
gttacatcct ggaaggagat gaaacccggt ttctatcatg gaatggtctc ttacctggat  240
tttgctaaat ttggtgtgaa aaaaaaaccc atttatatta acgtcatccg cgatccaatc  300
gagcgtttgg ttctcttatta ttatgcctta cgtttcggga gtgatcgccg tcccggattg  360
cgtatgcgta aacagggaga caagaaaact ttcgatgaat gtgttgccgc cggaggttcc  420
gactgtgcac cggaaaaact gtggcttcag atccctttct tttgtgggtca cagttcagaa  480
tgttgaaacg tcgggtcacg ttgggcgctt gaacaggcca agtacaatct tatcaacgag  540
tattttctgg tagggatgac tgaagagctg gaggacttta ttatgcttct tgaagcggca  600
ttgccacgct ttttcgtgg cgcgactgaa ttatatcgta caggaaagaa atcgcacttg  660
cacaagacta cagaaaaaaa actgcctact aaggagacga ttgctaagtt gcaacaatca  720
gaaatttgga agatgaaaaa cgaattctac gagttcgcat tagaacagtt tcaattcgta  780
cgcgctcacg ctgtgcgtga aaagacgggg gaactgtaca ttttggccca aaattttttc  840
tatgagaaaa tttatcctaa gtctaactaa                                   870

SEQ ID NO: 41           moltype = AA   length = 289
FEATURE                 Location/Qualifiers
REGION                  1..289
                        note = Engineered hexuronyl 2-O sulfotransferase
                        mutant_sulfatase 8
source                  1..289
                        mol_type = protein
                        organism = synthetic construct
SEQUENCE: 41
MDEEDDVVII YNRVPHTASH SFTNIAYDLC AKNRYHVLHI TTTKNNPVMS LQDQVRFVKN   60
VTSWKEMKPG FYHGMVSYLD FAKFGVKKKP IYINVIRDPI ERLVSYYYAL RFGSDRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289

SEQ ID NO: 42           moltype = DNA   length = 870
```

```
FEATURE                 Location/Qualifiers
misc_feature            1..870
                        note = Polynucleotide sequence encoding for engineered
                          hexuronyl 2-Osulfotransferase mutant_sulfatase 9
source                  1..870
                        mol_type = other DNA
                        organism = synthetic construct
SEQUENCE: 42
atggatgagg aagacgacgt cgtaattatc tacaatcgcg tgccacacac ggcatcccat   60
tcattcacca acattgcgta cgatttgtgt gcaaaaaacc gttatcatgt cttacacatc  120
aacactacaa aaaacaatcc cgtaatgagt ctgcaagatc aggtccgttt tgtcaaaaat  180
gtaacctcgt ggaaggagat gaagccgggc ttctatcacg ggatggtcag ctaccttgac  240
tttgctaaat ttggggtaaa gaaaaaacct atctatatca atgtgattcg tgatcctatc  300
gaacgccttg taagttatta ctacgctctt cgtttcgggg cagatcgccg tcccggactt  360
cgcatgcgca agcaggggga taagaagaca tttgacgagt gcgtcgcggc gggtggatct  420
gattgtgccc ctgagaaact gtggttgcaa attccattct tttgtgggca cagcagtgag  480
tgctggaatg tgggatctcg ttgggctctg aacaggcca agtacaacct tattaatgag  540
tacttcttag taggagtcac ggaagagctt gaagacttca ttatgttact ggaagcagcc  600
ttgcctcgtt ttttccgcgg tgcaacggag ctgtaccgca cagggaaaaa atcccatctt  660
cataagacca cagagaaaaa actgccgacg aaggagacga ttcgaaaact gcaacaaagt  720
gaaatctgga agatggagaa tgaattttat gagtttgctt tggagcaatt tcaattcgtc  780
cgtgcgcatg cggtccgtga aaaggacggt gaattgtata tcttggctca aaactttttc  840
tatgagaaaa tttatcctaa gtctaactaa                                   870

SEQ ID NO: 43           moltype = AA  length = 289
FEATURE                 Location/Qualifiers
REGION                  1..289
                        note = Engineered hexuronyl 2-O sulfotransferase
                          mutant_sulfatase 9
source                  1..289
                        mol_type = protein
                        organism = synthetic construct
SEQUENCE: 43
MDEEDDVVII YNRVPHTASH SFTNIAYDLC AKNRYHVLHI NTTKNNPVMS LQDQVRFVKN   60
VTSWKEMKPG FYHGMVSYLD FAKFGVKKKP IYINVIRDPI ERLVSYYYAL RFGADRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289

SEQ ID NO: 44           moltype = DNA  length = 870
FEATURE                 Location/Qualifiers
misc_feature            1..870
                        note = Polynucleotide sequence encoding for engineered
                          hexuronyl 2-Osulfotransferase mutant_sulfatase 10
source                  1..870
                        mol_type = other DNA
                        organism = synthetic construct
SEQUENCE: 44
atggatgagg aagacgacgt cgtaatcatc tacaaccgcg tcccgcacac agccagccac   60
tccttcacca atattgcgta tgatctgtgc gctaagaacc gttaccatgt gttgcacatt  120
accactacga agcgtaaccc cgtaatgtca cttcaagatc aagttcgctt cgttaagaac  180
gtgacatctt ggaaggagat gaagccagga ttctatcatg gggaagttag ctacttggac  240
tttgccaagt tcggtgtaaa gaaaaaacca atctacatca atgttattcg tgatcccatc  300
gaacgcttag tgtcttacta ttatgccctt cgctttggag ccgaccgtcg cccggggctt  360
cgtatgcgca agcaagggga caagaagacc ttcgacgagt gtgtagccgc gggtgggtct  420
gactgtgcgc ggaaaagtt atggttacaa attccatttt tctgtggtca ctcgtcagag  480
tgctggaatg ttggttcgcg ctgggcgctg agcaagcga aatataactt gattaatgaa  540
tacttttag taggggtgac agaggagttg gaggacttta ttatgcttct tgaggctgcg  600
ttacctcgct ttttccgcgg tgcgactgag ttgtatcgta caggtaaaaa atctcatctg  660
cataaaacaa ctgaaaagaa gctgccaacg aaagagacga ttgctaaact tcagcagagt  720
gagatctgga aaatggaaaa tgagttctac gagtttgcct tggagcaatt ccaattcgtg  780
cgtgcccatg ccgttcgtga aaaggatggt gaattataca tcttggcaca gaatttcttc  840
tatgagaaaa tttatcctaa gtctaactaa                                   870

SEQ ID NO: 45           moltype = AA  length = 289
FEATURE                 Location/Qualifiers
REGION                  1..289
                        note = Engineered hexuronyl 2-O sulfotransferase
                          mutant_sulfatase 10
source                  1..289
                        mol_type = protein
                        organism = synthetic construct
SEQUENCE: 45
MDEEDDVVII YNRVPHTASH SFTNIAYDLC AKNRYHVLHI TTTKRNPVMS LQDQVRFVKN   60
VTSWKEMKPG FYHGEVSYLD FAKFGVKKKP IYINVIRDPI ERLVSYYYAL RFGADRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289
```

```
SEQ ID NO: 46           moltype = DNA   length = 870
FEATURE                 Location/Qualifiers
misc_feature            1..870
                        note = Polynucleotide sequence encoding for engineered
                        hexuronyl 2-Osulfotransferase mutant_sulfatase 11
source                  1..870
                        mol_type = other DNA
                        organism = synthetic construct
SEQUENCE: 46
atggatgagg aagacgacgt cgtaattatc tacaatcgcg taccgcatac tgcaagccac   60
agctttacta acatcgccta tgatttgtgt gcgaagaacc gctatcatgt actgcatatt  120
acgacgacca agaataatcc tgtaatgtcc ttacaggacc aagttcgctt cgttaaaaac  180
gtaacttcgt ggaaagagat gaagccaggg ttttaccacg gaatggtcag ctacttagat  240
ttcgcaaagt tcggtgtgaa gaaaaagccc atctatatca atgtcatccg cgaccctatc  300
gaacgtctgg tatcttacta ttatgcgctt cgcttcggcg gtgatcgccg tcctggttta  360
cgtatgcgta agcaaggaga taagaaaacc ttcgacgaat gtgtcgcggc cggggggcagt  420
gactgtgccc cggagaagtt atggttacag atcccatttt tttgtggaca cagttccgaa  480
tgttggaacg tgggtagtcg ttgggcatta gagcaagcca agtacaactt aatcaatgaa  540
tatttcttgg taggtgtaac tgaggagctg gaagactta ttatgttact tgaagctgcg  600
ctgccccgtt tctttcgtgg tgcgacggag ttataccgta cagggaagaa gagccactta  660
cataagacaa ctgagaaaaa gttacccacg aagaaacaa tcgctaaatt acaacaaagt  720
gagatttgga agatggaaaa cgaatttat gagttcgcat tagaacagtt tcaattcgtg  780
cgtgcgcatg cggtccgcga gaaggacggt gaactttaca ttcttgcaca gaacttcttc  840
tatgagaaaa tttatcctaa gtctaactaa                                    870

SEQ ID NO: 47           moltype = AA    length = 289
FEATURE                 Location/Qualifiers
REGION                  1..289
                        note = Engineered hexuronyl 2-O sulfotransferase
                        mutant_sulfatase 11
source                  1..289
                        mol_type = protein
                        organism = synthetic construct
SEQUENCE: 47
MDEEDDVVII YNRVPHTASH SFTNIAYDLC AKNRYHVLHI TTTKNNPVMS LQDQVRFVKN    60
VTSWKEMKPG FYHGMVSYLD FAKFGVKKKP IYINVIRDPI ERLVSYYYAL RFGGDRRPGL  120
RMRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289

SEQ ID NO: 48           moltype = DNA   length = 870
FEATURE                 Location/Qualifiers
misc_feature            1..870
                        note = Polynucleotide sequence encoding for engineered
                        hexuronyl 2-Osulfotransferase mutant_sulfatase 12
source                  1..870
                        mol_type = other DNA
                        organism = synthetic construct
SEQUENCE: 48
atggatgagg aagacgacgt cgtaattatc tacaaccgcg tccatcgtac tgcgtctcac   60
agctttacta acattgccta cgacttatgc gcaaagaatc gttaccacgt tttgcatatt  120
aacacgacca agggtaatcc ggtaatgtca ttgcaagatc aggtgcgttt cgtaaaaaac  180
gtcacgagct ggaaagaaat gaagccggga ttttaccacg ggacagtcag ctaccttgat  240
tttgcaaaat tcggagtcaa aaaaaaaccc atttacatta acgtgatccg cgatccaatt  300
gaacgtcttg tctcgtacta ttatttctta cgtttcggga cgacctgcg tccgggtttg  360
cgtcgtcgca aacaaggaga caagaagaca tttgacgaat gtgtagcagc aggggggctct  420
gactgcgccc ggaaaaaatt gtggttacag atcccgttct tttgtggaca tagttccgag  480
tgctggaatg taggctcccg ttgggcgtta gaacaggcaa aatacaatct gattaacgag  540
tactttttag taggcgttga cgaggagtta gaagatttta ttatgctgtt agaggcggcg  600
ctgccgcgtt ttttccgtgg agccacggaa ttgtatcgta ccgaaaagaa atctcacctt  660
cacaagacta cagaaaaaaa attaccaact aagagacaa tcgcaaagtt gcagcagtcg  720
gagatctgga agatggaaaa tgagttttat gaattcgcat tagaacagtt ccaattcgtt  780
cgtgcgcacg cagtacgcga aaaggacggg gagctttaca tcctggctca gaattttttc  840
tatgagaaaa tttatcctaa gtctaactaa                                    870

SEQ ID NO: 49           moltype = AA    length = 289
FEATURE                 Location/Qualifiers
REGION                  1..289
                        note = Engineered hexuronyl 2-O sulfotransferase
                        mutant_sulfatase 12
source                  1..289
                        mol_type = protein
                        organism = synthetic construct
SEQUENCE: 49
MDEEDDVVII YNRVHRTASH SFTNIAYDLC AKNRYHVLHI NTTKGNPVMS LQDQVRFVKN    60
VTSWKEMKPG FYHGTVSYLD FAKFGVKKKP IYINVIRDPI ERLVSYYYFL RPGNDLRPGL  120
RRRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289
```

```
SEQ ID NO: 50            moltype = DNA  length = 870
FEATURE                  Location/Qualifiers
misc_feature             1..870
                         note = Polynucleotide sequence encoding for engineered
                          hexuronyl 2-Osulfotransferase mutant_sulfatase 13
source                   1..870
                         mol_type = other DNA
                         organism = synthetic construct
SEQUENCE: 50
atggatgagg aagacgacgt cgtaattatc tacaaccgcg tccatcgtac tgcgtctcac   60
agctttacta acattgccta cgacttatgc gcaaagaatc gttaccacgt tttgcatatc  120
aacacgacca agggtaatcc ggtaatgtca ttgcaagatc aggtgcgttt cgtaaaaaac  180
gtcacgagct ggaaagaaat gaagccggga ttttaccacg ggccagtcag ctaccttgat  240
tttgcaaaat tcggagtcaa aaaaaaaccc atttacatta acgtgatccg cgatccaatt  300
gaacgtcttg tctcgtacta ttatttctta cgtttcggga gcgacctgcg tccgggtttg  360
cgtcagcgca acaaggaga caagaagaca tttgacgaat gtgtagcagc aggggggctct  420
gactgcgccc cggaaaaatt gtggttacag atcccgttct tttgtggaca tagttccgag  480
tgctggaatg taggctcccg ttgggcgtta gaacaggcaa aatacaatct gattaacgag  540
tacttttag taggcgtgac cgaggagtta gaagatttta ttatgctgtt agaggcggcg  600
ctgccgcgtt ttttccgtgg agccacgaa ttgtatcgta ccggaaagaa atctcacctt  660
cacaagacta cagaaaaaaa attaccaact aaagagacaa tcgcaaagtt gcagcagtcg  720
gagatctgga agatggaaaa tgagttttat gaattcgcat tagaacagtt ccaattcgtt  780
cgtgcgcacg cagtacgcga aaaggacggg gagctttaca tcctggctca gaattttttc  840
tatgagaaaa tttatcctaa gtctaactaa                                   870

SEQ ID NO: 51            moltype = AA  length = 289
FEATURE                  Location/Qualifiers
REGION                   1..289
                         note = Engineered hexuronyl 2-O sulfotransferase
                          mutant_sulfatase 13
source                   1..289
                         mol_type = protein
                         organism = synthetic construct
SEQUENCE: 51
MDEEDDVVII YNRVHRTASH SFTNIAYDLC AKNRYHVLHI NTTKGNPVMS LQDQVRFVKN   60
VTSWKEMKPG FYHGPVSYLD FAKFGVKKKP IYINVIRDPI ERLVSYYYFL RFGSDLRPGL  120
RQRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
EIWKMENEFY EFALEQFQFV RAHAVREKDG ELYILAQNFF YEKIYPKSN              289

SEQ ID NO: 52            moltype = DNA  length = 870
FEATURE                  Location/Qualifiers
misc_feature             1..870
                         note = Polynucleotide sequence encoding for engineered
                          hexuronyl 2-Osulfotransferase mutant_sulfatase 14
source                   1..870
                         mol_type = other DNA
                         organism = synthetic construct
SEQUENCE: 52
atggatgagg aagacgacgt cgtgattatc tataaccgcg tgcatcgtac ggcttcacat   60
tcgttcacaa atattgcgta cgacctttgt gctaagaatc gctatcacgt cttacacatc  120
aacaccacca aaggcaatcc tgtcatgtct cttcaagatc aagtacgttt cgtgaagaac  180
gtgacatcat ggaaggagat gaagccgggg ttctaccatg gccgtaag ttacttggat  240
ttcgctaaat ttggggttaa aaaaaagcct atctacatta atgttattcg tgaccctatc  300
gaacgtttgg tttcctatta ttacttcctt cgctttggaa atgatcgccg tcctggtttg  360
cgtcaacgca agcagggcga taaaaaaaca tttgacgaat gcgtagctgc cggcggctcc  420
gactgtgcgc cagaaaagct gtggttacag atcccatttt tctgtggaca ctcctcggag  480
tgttggaacg tggggtcgcg ttgggcatta gaacaggcca aatacaattt aatcaacgaa  540
tatttcctgg ttggcgtcac ggaggaactg gaagatttca ttatgctttt agaagctgcg  600
ttaccacgct tctttcgcgg cgctaccgag ttataccgta ccggaaagaa gtctcatctg  660
cacaagacga cggaaaagaa gcttccact aaagaaacta ttgctaaatt acagcagagt  720
gaaatctgga aaatggaaaa tgagttctac gagttcgcgt tggaacagtt tcaattcgtt  780
cgtgcccatg ccgttcgcga aaaggatggc gaattgtata tccttgccca gaacttcttc  840
tatgagaaaa tttatcctaa gtctaactaa                                   870

SEQ ID NO: 53            moltype = AA  length = 289
FEATURE                  Location/Qualifiers
REGION                   1..289
                         note = Engineered hexuronyl 2-O sulfotransferase
                          mutant_sulfatase 14
source                   1..289
                         mol_type = protein
                         organism = synthetic construct
SEQUENCE: 53
MDEEDDVVII YNRVHRTASH SFTNIAYDLC AKNRYHVLHI NTTKGNPVMS LQDQVRFVKN   60
VTSWKEMKPG FYHGPVSYLD FAKFGVKKKP IYINVIRDPI ERLVSYYYFL RFGNDRRPGL  120
RQRKQGDKKT FDECVAAGGS DCAPEKLWLQ IPFFCGHSSE CWNVGSRWAL EQAKYNLINE  180
YFLVGVTEEL EDFIMLLEAA LPRFFRGATE LYRTGKKSHL HKTTEKKLPT KETIAKLQQS  240
```

EIWKMENEFY EFALEQFQFV RAHAVREKDG ELYILAQNFF YEKIYPKSN                289

SEQ ID NO: 54           moltype = DNA   length = 870
FEATURE                 Location/Qualifiers
misc_feature            1..870
                        note = Polynucleotide sequence encoding for engineered
                        hexuronyl 2-Osulfotransferase mutant_sulfatase 15
source                  1..870
                        mol_type = other DNA
                        organism = synthetic construct
SEQUENCE: 54
atggatgagg aagacgacgt cgtgattatt tataaccgtg tgcctcacac tgcttcgacc    60
tcatttacaa acattgctta cgatctttgt gctaagaatc gttaccacgt cctgcatatt   120
aacacgacaa aaaataaccc tgtaatgtct cttcaagatc aagtccgctt cgtgaaaaat   180
gtgacgagtt ggaaagaaat gaagccggga tttatcacg ggcccgtgtc ataccttgac    240
ttcgctaaat ttggggttaa gaaaaaacct atctatatca atgtgatccg tgatcccatc   300
gaacgccttg tttcatatta ttatgcatta cgttttggtt cagattatcg cccaggcctt   360
cgcatgcgta agcaagggga caagaagaca ttcgatgagt gcgttgcggc ggggggatca   420
gattgtgcac cagagaagct gtggttgcaa atcccgttct tctgcggaca cagctccgaa   480
tgttggaatg tcgggtcacg ttgggcgctt aacaggcta agtacaatct gattaacgag    540
tacttttttag tcggtgttac ggaggagttg gaagacttca ttatgctgct ggaggctgcg  600
ctgccccgct tcttccgcgg cgccaccgag ttgtaccgta caggaaagaa gtcccattta   660
cacaagcata ctgagaaaaa gttgcccact aaggaaacca ttgctaagtt gcaacagtcg   720
gaaatttgga aatggagaa cgagttctac gaatttgcat tagaacagtt ccaatttgtt    780
cgtgcccatg ccgtacgtga aaggacggc gaattatata tccttgcaca aaacttcttc    840
tatgagaaga tctatcctaa gtctaactaa                                    870

SEQ ID NO: 55           moltype = AA   length = 289
FEATURE                 Location/Qualifiers
REGION                  1..289
                        note = Engineered hexuronyl 2-O sulfotransferase
                        mutant_sulfatase 15
source                  1..289
                        mol_type = protein
                        organism = synthetic construct
SEQUENCE: 55
MDEEDDVVII YNRVPHTAST SFTNIAYDLC AKNRYHVLHI NTTKNNPVMS LQDQVRFVKN     60
VTSWKEMKPG FYHGPVSYLD FAKFGVKKKP IYINVIRDPI ERLVSYYYAL RFGSDYRPGL    120
RMRKQGDKKT FDECVAAGGS DCAPEKLWLQ IPFFCGHSSE CWNVGSRWAL EQAKYNLINE    180
YFLVGVTEEL EDFIMLLEAA LPRFFRGATE LYRTGKKSHL HKHTEKKLPT KETIAKLQQS    240
EIWKMENEFY EFALEQFQFV RAHAVREKDG ELYILAQNFF YEKIYPKSN                289

SEQ ID NO: 56           moltype = DNA   length = 870
FEATURE                 Location/Qualifiers
misc_feature            1..870
                        note = Polynucleotide sequence encoding for engineered
                        hexuronyl 2-Osulfotransferase mutant_sulfatase 16
source                  1..870
                        mol_type = other DNA
                        organism = synthetic construct
SEQUENCE: 56
atggatgagg aagacgacgt cgtgattatt tataaccgtg tgcctcacac tgcttcgacc    60
tcatttacaa acattgctta cgatctttgt gctaagaatc gttaccacgt cctgcatatt   120
aacacgacaa aaaataaccc tgtaatgtct cttcaagatc aagtccgctt cgtgaaaaat   180
gtgacgagtt ggaaagaaat gaagccggga tttatcacg ggaacgtgtc ataccttgac    240
ttcgctaaat ttggggttaa gaaaaaacct atctatatca atgtgatccg tgatcccatc   300
gaacgccttg tttcatatta ttatgcatta cgttttggtt cagattatcg cccaggcctt   360
cgcatgcgta agcaagggga caagaagaca ttcgatgagt gcgttgcggc ggggggatca   420
gattgtgcac cagagaagct gtggttgcaa atcccgttct tctgcggaca cagctccgaa   480
tgttggaatg tcgggtcacg ttgggcgctt aacaggcta agtacaatct gattaacgag    540
tacttttttag tcggtgttac ggaggagttg gaagacttca ttatgctgct ggaggctgcg  600
ctgccccgct tcttccgcgg cgccaccgag ttgtaccgta caggaaagaa gtcccattta   660
cacaagcata ctgagaaaaa gttgcccact aaggaaacca ttgctaagtt gcaacagtcg   720
gaaatttgga aatggagaa cgagttctac gaatttgcat tagaacagtt ccaatttgtt    780
cgtgcccatg ccgtacgtga aaggacggc gaattatata tccttgcaca aaacttcttc    840
tatgagaaga tctatcctaa gtctaactaa                                    870

SEQ ID NO: 57           moltype = AA   length = 289
FEATURE                 Location/Qualifiers
REGION                  1..289
                        note = Engineered hexuronyl 2-O sulfotransferase
                        mutant_sulfatase 16
source                  1..289
                        mol_type = protein
                        organism = synthetic construct
SEQUENCE: 57
MDEEDDVVII YNRVPHTAST SFTNIAYDLC AKNRYHVLHI NTTKNNPVMS LQDQVRFVKN     60
VTSWKEMKPG FYHGNVSYLD FAKFGVKKKP IYINVIRDPI ERLVSYYYAL RFGSDYRPGL    120
RMRKQGDKKT FDECVAAGGS DCAPEKLWLQ IPFFCGHSSE CWNVGSRWAL EQAKYNLINE    180

```
YFLVGVTEEL EDFIMLLEAA LPRFFRGATE LYRTGKKSHL HKHTEKKLPT KETIAKLQQS   240
EIWKMENEFY EFALEQFQFV RAHAVREKDG ELYILAQNFF YEKIYPKSN               289

SEQ ID NO: 58              moltype = DNA  length = 870
FEATURE                    Location/Qualifiers
misc_feature               1..870
                           note = Polynucleotide sequence encoding for engineered
                             hexuronyl 2-Osulfotransferase mutant_sulfatase 17
source                     1..870
                           mol_type = other DNA
                           organism = synthetic construct
SEQUENCE: 58
atggatgagg aagacgacgt cgtgattatt tataaccatg ttcataagac tgcttcgcat    60
tcattcacta acatcgctta tgatttatgt gcaaagaacc gttatcacgt tcttcacatc   120
accacgacaa agggtaatcc ggtaatgtca ctgcaggacc aggttcgttt cgtcaaaaat   180
gtaacttcgt ggaaagagat gaagccgggg ttctaccacg gccccgtgtc ttatcttgac   240
ttcgcgaaat tcggagttaa aaaaaaacca atctacatca acgtgatccg cgatcctatc   300
gaacgtcttg tatcttatta ctatttttta cgcttcgggg atgactaccg ccctgggctt   360
cgtcgtcgca agcagggcga caagaaaacg ttcgacgagt gcgtcgccgc cggaggctcg   420
gactgtgctc cggagaaatt gtggttgcag attcccttt tctgtggaca ctcgtctgag   480
tgctggaacg taggatcacg ctgggcatta gaacaagcga agtataactt gattaacgag   540
tatttcctgg tcggcgtaac tgaagaactg gaggatttca ttatgcttct ggaagccgcg   600
ctgccccgtt ttttccgtgg ggccactgag ctttaccgca caggaaagaa gtctcacctt   660
cgtaaaacga ctgagaaaaa gcttcccacc aaggagacta tcgcaaaact tcaacaatca   720
gaaatttgga agatgaaaa tgagttctac gagttcgcct tggaacagtt ccagttcgtc   780
cgtgcccatg ccgtacgtga aaggacggc gaattatata tccttgcaca aaacttcttc   840
tatgagaaga tctatcctaa gtctaactaa                                   870

SEQ ID NO: 59              moltype = AA  length = 289
FEATURE                    Location/Qualifiers
REGION                     1..289
                           note = Engineered hexuronyl 2-O sulfotransferase
                             mutant_sulfatase 17
source                     1..289
                           mol_type = protein
                           organism = synthetic construct
SEQUENCE: 59
MDEEDDVVII YNHVHKTASH SFTNIAYDLC AKNRYHVLHI TTTKGNPVMS LQDQVRFVKN    60
VTSWKEMKPG FYHGPVSYLD FAKFGVKKKP IYINVIRDPI ERLVSYYYFL RFGDDYRPGL   120
RRRKQGDKKT FDECVAAGGS DCAPEKLWLQ IPFFCGHSSE CWNVGSRWAL EQAKYNLINE   180
YFLVGVTEEL EDFIMLLEAA LPRFFRGATE LYRTGKKSHL RKTTEKKLPT KETIAKLQQS   240
EIWKMENEFY EFALEQFQFV RAHAVREKDG ELYILAQNFF YEKIYPKSN               289

SEQ ID NO: 60              moltype = DNA  length = 870
FEATURE                    Location/Qualifiers
misc_feature               1..870
                           note = Polynucleotide sequence encoding for engineered
                             hexuronyl 2-Osulfotransferase mutant_sulfatase 18
source                     1..870
                           mol_type = other DNA
                           organism = synthetic construct
SEQUENCE: 60
atggatgagg aagacgacgt cgtgattatt tataaccatg ttcataagac tgcttcgcat    60
tcattcacta acatcgctta tgatttatgt gcaaagaacc gttatcacgt tcttcacatc   120
accacgacaa agaataatcc ggtaatgtca ctgcaggacc aggttcgttt cgtcaaaaat   180
gtaacttcgt ggaaagagat gaagccgggg ttctaccacg gccccgtgtc ttatcttgac   240
ttcgcgaaat tcggagttaa aaaaaaacca atctacatca acgtgatccg cgatcctatc   300
gaacgtcttg tatcttatta ctatttttta cgcttcgggg atgactaccg ccctgggctt   360
cgtcgtcgca agcagggcga caagaaaacg ttcgacgagt gcgtcgccgc cggaggctcg   420
gactgtgctc cggagaaatt gtggttgcag attcccttt tctgtggaca ctcgtctgag   480
tgctggaacg taggatcacg ctgggcatta gaacaagcga agtataactt gattaacgag   540
tatttcctgg tcggcgtaac tgaagaactg gaggatttca ttatgcttct ggaagccgcg   600
ctgccccgtt ttttccgtgg ggccactgag ctttaccgca caggaaagaa gtctcacctt   660
cgtaaaacga ctgagaaaaa gcttcccacc aaggagacta tcgcaaaact tcaacaatca   720
gaaatttgga agatgaaaa tgagttctac gagttcgcct tggaacagtt ccagttcgtc   780
cgtgcccatg ccgtacgtga aaggacggc gaattatata tccttgcaca aaacttcttc   840
tatgagaaga tctatcctaa gtctaactaa                                   870

SEQ ID NO: 61              moltype = AA  length = 289
FEATURE                    Location/Qualifiers
REGION                     1..289
                           note = Engineered hexuronyl 2-O sulfotransferase
                             mutant_sulfatase 18
source                     1..289
                           mol_type = protein
                           organism = synthetic construct
SEQUENCE: 61
MDEEDDVVII YNHVHKTASH SFTNIAYDLC AKNRYHVLHI TTTKNNPVMS LQDQVRFVKN    60
VTSWKEMKPG FYHGPVSYLD FAKFGVKKKP IYINVIRDPI ERLVSYYYFL RFGDDYRPGL   120
```

```
RRRKQGDKKT FDECVAAGGS DCAPEKLWLQ IPFFCGHSSE CWNVGSRWAL EQAKYNLINE    180
YFLVGVTEEL EDFIMLLEAA LPRFFRGATE LYRTGKKSHL RKTTEKKLPT KETIAKLQQS    240
EIWKMENEFY EFALEQFQFV RAHAVREKDG ELYILAQNFF YEKIYPKSN                289

SEQ ID NO: 62           moltype = DNA   length = 870
FEATURE                 Location/Qualifiers
misc_feature            1..870
                        note = Polynucleotide sequence encoding for engineered
                         hexuronyl 2-Osulfotransferase mutant_ sulfotransferase 1
source                  1..870
                        mol_type = other DNA
                        organism = synthetic construct
SEQUENCE: 62
atggatgagg aagacgacgt cgtgattatt tataaccgtg taccgcatac tgccagcacg    60
tcattcacga atatcgcgta cgatctttgc gctaaaaacc gttatcatgt tttacatatt    120
aataccacca aaaacaatcc ggtgatgtca ttgcaggatc aggtgcgttt cgtaaagaat    180
gtcacctcat ggaaagagat gaagccaggg ttttatcatg gcacgttag ttatttggat     240
tttgctaagt ttggtgtaaa gaagaagccc atctacatca atgtcattcg tgatcccatt    300
gaacgcttgg tctcctatta ctaccatttg cgctttggcg acgactaccg ccccggatta    360
cgccgccgca agcaggggga caagaaaact tttgacgaat gcgtcgctgc cggtggtagc    420
gactgcgccc cggagaaatt atggcttcaa attcccttt tctgcggcca ttcttcgaa      480
tgctggaacg taggtagtcg ctgggctctt gaacaggcaa aatataatct tatcaacgaa    540
tactttcttg tcggagttac cgaggagttg gaggacttta ttatgcttct ggaggctgcg    600
ctgccgcgtt tttttcgtgg tgcgaccgag ctgtatcgta caggtaaaaa aagtcatctt    660
cataaaacga cggaaaagaa gctgccaact aaggaaacaa tcgcgaaact gcaacagagt    720
gaaatctgga aaatggaaaa tgaattctat gagtttgccc tggagcaatt ccaattcgtt    780
cgcgcccatg ccgtacgcga gaaggacggc gaattatata tccttgcaca aaacttcttc    840
tatgagaaga tctatcctaa gtctaactaa                                     870

SEQ ID NO: 63           moltype = AA   length = 289
FEATURE                 Location/Qualifiers
REGION                  1..289
                        note = Engineered hexuronyl 2-O sulfotransferase
                         mutant_sulfotransferase1
source                  1..289
                        mol_type = protein
                        organism = synthetic construct
SEQUENCE: 63
MDEEDDVVII YNRVPHTAST SFTNIAYDLC AKNRYHVLHI NTTKNNPVMS LQDQVRFVKN    60
VTSWKEMKPG FYHGHVSYLD FAKFGVKKKP IYINVIRDPI ERLVSYYYHL RFGDDYRPGL    120
RRRKQGDKKT FDECVAAGGS DCAPEKLWLQ IPFFCGHSSE CWNVGSRWAL EQAKYNLINE    180
YFLVGVTEEL EDFIMLLEAA LPRFFRGATE LYRTGKKSHL HKTTEKKLPT KETIAKLQQS    240
EIWKMENEFY EFALEQFQFV RAHAVREKDG ELYILAQNFF YEKIYPKSN                289

SEQ ID NO: 64           moltype = DNA   length = 870
FEATURE                 Location/Qualifiers
misc_feature            1..870
                        note = Polynucleotide sequence encoding for engineered
                         hexuronyl 2-Osulfotransferase mutant_ sulfotransferase 2
source                  1..870
                        mol_type = other DNA
                        organism = synthetic construct
SEQUENCE: 64
atggatgagg aagacgacgt cgtaattatt tacaatcgtg tacaccgtac agcctcgcat    60
tcttttacta acattgctta tgatctgtgc gcaaaaaacc gttaccacgt gttgcacatc    120
aatactacta agggtaatcc cgttatgagc ctgcaagacc aggtgcgctt tgttaagaat    180
gttacctcct ggaaagagat gaaacctggc ttctatcacg gacctgtatc ctacttggac    240
ttcgctaaat ttggcgtaaa gaaaaaacct atttacatca atgtgatccg tgaccctatc    300
gaacgtctgg tatcgtatta ttatttcctg cgcttcggat cggataagcg tccaggtttg    360
cgcatgcgta agcaggggga taaaaaaacg tttgacgaat gcgtggcggc tggtgggagc    420
gactgtgcgc cggaaaagtt atggttgcaa atcccgtttt tctgtgggca tagctctgaa    480
tgttggaatg ttggctcgcg ctgggcgctt agcaagcta aatacaacct gatcaatgag    540
tacttcttag tcggagtaac tgaggaatta gaggacttca ttatgttgct tgaggctgct    600
ttaccacgct tcttccgcgg tgcgacagaa ttgtaccgca ccggaaaaaa gagccactta    660
cacaagacca cagaaaagaa attaccgacc aaagaaacta tcgccaagtt acaacaaagt    720
gagatttgga aaatggaaaa cgaattctat gaattcgcgt ggaacaatt tcaattcgtg    780
cgtgctcacg cagtacgcga aggacggg gagctttata ttttgcccca aaacttttc     840
tatgagaaaa tttatcctaa gtctaactaa                                     870

SEQ ID NO: 65           moltype = AA   length = 289
FEATURE                 Location/Qualifiers
REGION                  1..289
                        note = Engineered hexuronyl 2-O sulfotransferase
                         mutant_sulfotransferase2
source                  1..289
                        mol_type = protein
                        organism = synthetic construct
SEQUENCE: 65
MDEEDDVVII YNRVHRTASH SFTNIAYDLC AKNRYHVLHI NTTKGNPVMS LQDQVRFVKN    60
```

```
VTSWKEMKPG FYHGPVSYLD FAKFGVKKKP IYINVIRDPI ERLVSYYYFL RFGSDKRPGL   120
RMRKQGDKKT FDECVAAGGS DCAPEKLWLQ IPFFCGHSSE CWNVGSRWAL EQAKYNLINE   180
YFLVGVTEEL EDFIMLLEAA LPRFFRGATE LYRTGKKSHL HKTTEKKLPT KETIAKLQQS   240
EIWKMENEFY EFALEQFQFV RAHAVREKDG ELYILAQNFF YEKIYPKSN               289

SEQ ID NO: 66              moltype = AA  length = 289
FEATURE                    Location/Qualifiers
REGION                     1..289
                           note = Engineered hexuronyl 2-O sulfotransferase
                             mutant_variable
SITE                       13
                           note = MISC_FEATURE - Xaa is arginine or histidine
SITE                       15
                           note = MISC_FEATURE - Xaa is histidine or proline
SITE                       16
                           note = MISC_FEATURE - Xaa is lysine, histidine, threonine,
                             arginine, or asparagine
SITE                       19
                           note = MISC_FEATURE - Xaa is histidine, glutamic acid, or
                             serine
SITE                       20
                           note = MISC_FEATURE - Xaa is histidine, threonine, or
                             asparagine
SITE                       41
                           note = MISC_FEATURE - Xaa is threonine or asparagine
SITE                       45
                           note = MISC_FEATURE - Xaa is arginine, glycine, or
                             asparagine
SITE                       75
                           note = MISC_FEATURE - Xaa is histidine, glutamic acid,
                             methionine, proline, threonine,or asparagine
SITE                       105
                           note = MISC_FEATURE - Xaa is histidine or serine
SITE                       109
                           note = MISC_FEATURE - Xaa is histidine, alanine, or
                             phenylalanine
SITE                       114
                           note = MISC_FEATURE - Xaa is aspartic acid, glycine,
                             serine, alanine, or asparagine
SITE                       116
                           note = MISC_FEATURE - Xaa is tyrosine, arginine, or leucine
SITE                       122
                           note = MISC_FEATURE - Xaa is methionine, arginine, or
                             glutamine
SITE                       221
                           note = MISC_FEATURE - Xaa is arginine or histidine
SITE                       223
                           note = MISC_FEATURE - Xaa is threonine or histidine
source                     1..289
                           mol_type = protein
                           organism = synthetic construct
SEQUENCE: 66
MDEEDDVVII YNXVXXTAXX SFTNIAYDLC AKNRYHVLHI XTTKXNPVMS LQDQVRFVKN    60
VTSWKEMKPG FYHGXVSYLD FAKFGVKKKP IYINVIRDPI ERLVXYYYXL RFGXDXRPGL   120
RXRKQGDKKT FDECVAAGGS DCAPEKLWLQ IPFFCGHSSE CWNVGSRWAL EQAKYNLINE   180
YFLVGVTEEL EDFIMLLEAA LPRFFRGATE LYRTGKKSHL XKXTEKKLPT KETIAKLQQS   240
EIWKMENEFY EFALEQFQFV RAHAVREKDG ELYILAQNFF YEKIYPKSN               289

SEQ ID NO: 67              moltype = AA  length = 617
FEATURE                    Location/Qualifiers
source                     1..617
                           mol_type = protein
                           organism = Homo sapiens
SEQUENCE: 67
MRCLAARVNY KTLIIICALF TLVTVLLWNK CSSDKAIQFP RRSSSGFRVD GFEKRAAASE    60
SNNYMNHVAK QQSEEAFPQE QQKAPPVVGG FNSNVGSKVL GLKYEEIDCL INDEHTIKGR   120
REGNEVFLPF TWVEKYFDVY GKVVQYDGYD RFEFSHSYSK VYAQRAPYHP DGVFMSFEGY   180
NVEVRDRVKC ISGVEGVPLS TQWGPQGYFY PIQIAQYGLS HYSKNLTEKP PHIEVYETAE   240
DRDKNKPNDW TVPKGCFMAN VADKSRFTNV KQFIAPETSE GVSLQLGNTK DFIISFDLKF   300
LTNGSVSVVL ETTEKNQLFT IHYVSNAQLI AFKERDIYYG IGPRTSWSTV TRDLVTDLRK   360
GVGLSNTKAV KPTKIMPKKV VRLIAKGKGF LDNITISTTA HMAAFFAASD WLVRNQDEKG   420
GWPIMVTRKL GEGFKSLEPG WYSAMAQGQA ISTLVRAYLL TKDHIFLNSA LRATAPYKFL   480
SEQHGVKAVF MNKHDWYEEY PTTPSSFVLN GFMYSLIGLY DLKETAGEKL GKEARSLYER   540
GMESLKAMLP LYDTGSGTIY DLRHFMLGIA PNLARWDYHT THINQLQLLS TIDESPVFKE   600
FVKRWKSYLK GSRAKHN                                                  617

SEQ ID NO: 68              moltype = AA  length = 289
FEATURE                    Location/Qualifiers
REGION                     1..289
```

```
                        note = Engineered hexuronyl 2-O sulfotransferase
                        mutant_sulfotransferase3
source                  1..289
                        mol_type = protein
                        organism = synthetic construct
SEQUENCE: 68
MDEEEDMVII YNRVPHTAST SFTNIAYDLC AKNKYHVLHI NTTKNNPVMS LQDQVRFVKN   60
ITSWKEMKPG FYHGHVSYLD FAKFGVKKKP IYINVIRDPI ERLVSYYYHL RFGDDYRPGL  120
RRRKQGDKKT FDECVAEGGS DCAPEKLWLQ IPFFCGHSSE CWNVGSRWAM DQAKYNLINE  180
YFLVGVTEEL EDFIMLLEAA LPRFFRGATE LYRTGKKSHL HKTTEKKLPT KQTIAKLQQS  240
DIWKMENEFY EFALEQFQFI RAHAVREKDG DLYILAQNFF YEKIYPKSN              289

SEQ ID NO: 69           moltype = AA  length = 289
FEATURE                 Location/Qualifiers
REGION                  1..289
                        note = Engineered hexuronyl 2-O sulfotransferase
                        mutant_sulfotransferase4
source                  1..289
                        mol_type = protein
                        organism = synthetic construct
SEQUENCE: 69
MDEEEDMVII YNRVHRTASH SFTNIAYDLC AKNKYHVLHI NTTKGNPVMS LQDQVRFVKN   60
ITSWKEMKPG FYHGPVSYLD FAKFGVKKKP IYINVIRDPI ERLVSYYYFL RFGSDKRPGL  120
RMRKQGDKKT FDECVAEGGS DCAPEKLWLQ IPFFCGHSSE CWNVGSRWAM DQAKYNLINE  180
YFLVGVTEEL EDFIMLLEAA LPRFFRGATE LYRTGKKSHL HKTTEKKLPT KQTIAKLQQS  240
DIWKMENEFY EFALEQFQFI RAHAVREKDG DLYILAQNFF YEKIYPKSN              289

SEQ ID NO: 70           moltype = AA  length = 312
FEATURE                 Location/Qualifiers
REGION                  1..312
                        note = Engineered glucosaminyl 6-O sulfotransferase
                        mutant_sulfatase 1
source                  1..312
                        mol_type = protein
                        organism = synthetic construct
SEQUENCE: 70
MKYYFPVREL ERSLRFDMKG DDVIVFLHIQ KTHGTTFGRH LVQNVRLEVP CDCRPGQKKC   60
TCYRPNRRET WLFSRFSTGW SCGLHADWTE LTNCVPGVLD RRDPAGLRSP RKFYYITLLH  120
LPVHRYLSEW RHVQRGATWK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLAW FGRKTQYLFE  240
RTFNLKFIRP FMQVKSSRAS GVEVDEDTIR HIEELNDLDM QLYDYAKDLF QQRYQYKRQL  300
ERREQRLRNR EE                                                     312

SEQ ID NO: 71           moltype = DNA  length = 939
FEATURE                 Location/Qualifiers
misc_feature            1..939
                        note = Polynucleotide sequence encoding for engineered
                        glucosaminyl 6-Osulfotransferase mutant_sulfatase 1
source                  1..939
                        mol_type = other DNA
                        organism = synthetic construct
SEQUENCE: 71
atgaagtact attttccggt ccgcgaattg gagcgctctc tgcgtttcga catgaaaggg   60
gatgacgtta tttgtatttt gcatatccag aagacgcacg gaacaacatt tggacgccat  120
ttagtgcaga acgtccgctt ggaagtacca tgcgattgtc gcccaggtca gaaaaaatgc  180
acatgttatc gcccaaaccg tcgtgaaact tggctgttca gccgcttttc taccggatgt  240
tcatgcggcc ttcatgcaga ctggacggaa ttgaccaatt gtgtcccagg agtcttggac  300
cgtcgtgacc cggcgggctt gcgtagccct cgtaaattct attatattac tttgttacac  360
ttacctgttc accgctactt gtccgagtgg cgtcatgtcc agcgcggtgc aacatggaaa  420
acctccctgc acatgtgtga cggtcgtacc ccgacaccgg aggaattacc tccgtgctac  480
gagggaaccg attggagtgg ttgcacccct caagagttca tggactgtcc gtacaattta  540
gctaacaacc gccaagtccg tatgcttgct gacttaagtc tggtcggttg ttacaacctg  600
agctttattc ccgaatcgaa acgtgctcaa ctgcttctgg agtctgccaa aaagaatctg  660
cgtggaatgg ccttcttcgg cttggcttgg ttcggtcgca agacgcaata tttatttgaa  720
cgcaccttta acttgaaatt tatccgcccc ttcatgcagg taaagagtag tcgtgctagt  780
ggcgttgagg ttgacgagga tacgattcgt catatcgaag aattgaatga cttagacatg  840
cagctgtatg actacgccaa agacctgttc cagcagcgct accagtacaa acgtcagttg  900
gagcgccgcg agcagcgttt acgcaatcgt gaggaataa                         939

SEQ ID NO: 72           moltype = AA  length = 295
FEATURE                 Location/Qualifiers
REGION                  1..295
                        note = Engineered glucosaminyl 6-O sulfotransferase
                        mutant_sulfatase 2
source                  1..295
                        mol_type = protein
                        organism = synthetic construct
SEQUENCE: 72
MKGDDVIVFL HIGHTGGTTF GRHLVQNVRL EVPCDCRPGQ KKCTCYRPNR RETWLFSRFS   60
```

```
TGWSCGTNAD WTELTNCVPG VLDRRDPAGL RSPRKFYYIT LLRDPVSRYL SAWRHHQRGG   120
SNKTSLHMCD GRTPTPEELP PCYEGTDWSG CTLQEFMDCP YNLGNNRQVR MLADLSLVGC   180
YNLSFIPESK RAQLLLESAK KNLRGMAFFG LTEFQRKTQY LFERTFNLKF IRPFMQYNST   240
RAGGVEVDED TIRHIEELND LDMQLYDYAK DLFQQRYQYK RQLERREQRL RNREE        295

SEQ ID NO: 73            moltype = DNA   length = 888
FEATURE                  Location/Qualifiers
misc_feature             1..888
                         note = Polynucleotide sequence encoding for engineered
                          glucosaminyl 6-Osulfotransferase mutant_sulfatase 2
source                   1..888
                         mol_type = other DNA
                         organism = synthetic construct
SEQUENCE: 73
atgaaaggcg acgacgtcat tgtattcctg catattggtc atacaggcgg aactacgttc    60
ggacgtcact tagttcaaaa tgtgcgtctg gaggtaccct gtgattgtcg tccaggacag   120
aaaaagtgca cttgttaccg ccctaatcgc cgtgagacgt ggctgttttc tcgttttagc   180
acaggctgga gttcgggcac gaacgccgac tggaccgagc ttacgaattg cgtaccaggt   240
gttttagatc gtcgtgatcc tgccggactt cgctccccgc gtaagtttta ctacatcacg   300
ttgcttcgcg acccagttag ccgctatttg agcgcttggc gtcaccatca acgcggggc    360
tccaacaaga cttctttgca catgtgcgac gggcgcacgc cgacaccaga gaacttccg    420
ccgtgttatg aagggacgga ctggtctggt tgtacccttc aagagttcat ggattgcccg   480
tacaatctgg gcaataatcg tcaagtacgc atgttagcag accttagcct tgtaggtgc    540
tacaatttga gctttatccc tgagagtaaa cgtgctcagc ttttattaga gtccgccaaa   600
aagaattttac gtggtatggc attttttcgga ttgaccgagt tccagcgcaa acccaatac   660
ttattcgaac gcacgtttaa cttgaaattc attcgtcctt tcatgcaata taattctacc   720
cgcgcggggg gcgtagaggt ggatgaggat acgatccgcc atatcgagga gcttaacgat   780
ttggacatgc agttatacga ctacgcgaaa gactatttttc aacaacgcta tcagtacaag   840
cgtcagcttg aacgccgcga gcagcgttta cgcaatcgtg aggaataa                888

SEQ ID NO: 74            moltype = AA    length = 312
FEATURE                  Location/Qualifiers
REGION                   1..312
                         note = Engineered glucosaminyl 6-O sulfotransferase
                          mutant_sulfatase 3
source                   1..312
                         mol_type = protein
                         organism = synthetic construct
SEQUENCE: 74
MKYYFPVREL ERSLRFDMKG DDVIVFLHIS HTGGTTFGRH LVQNVRLEVP CDCRPGQKKC    60
TCYRPNRRET WLFSRFSTGW SCGTRADWTE LTNCVPGVLD RRDPAGLRSP RKFYYITLLR   120
DPVSRYLSAW RHHQRGGTNK TSLHMCDGRT PTPEELPPCY EGTDWSGCTL QEFMDCPYNL   180
ANNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                       312

SEQ ID NO: 75            moltype = DNA   length = 939
FEATURE                  Location/Qualifiers
misc_feature             1..939
                         note = Polynucleotide sequence encoding for engineered
                          glucosaminyl 6-Osulfotransferase mutant_sulfatase 3
source                   1..939
                         mol_type = other DNA
                         organism = synthetic construct
SEQUENCE: 75
atgaagtact attttccggt ccgcgaattg gagcgcagcc ttcgcttcga catgaaaggt    60
gatgatgtca tcgtattcct tcacatttca cacacaggcg gtactacttt cgggcgtcat   120
cttgtccaga atgttcgctt agaggtacca tgcgattgtc gtcccggaca aaagaaatgt   180
acttgctatc gtccgaaccg ccgtgaaaca tggcttttca gccgtttctc caccggatgg   240
tcatgtggca ctcgcgcaga ttggacgaaa ctgacaaatt gcgttccagg cgttttggac   300
cgtcgtgacc cggccggtct tcgttcgcct cgtaagtttt attatatcac cctttttgcgc   360
gatcccgtgt cgcgttatct gagtgcttgg cgccaccacc aacgtggtgg taccaacaag   420
acatcactgc acatgtgtga tggtcgtact ccaacgcccg aagagctgcc cccttgctat   480
gaaggtacag attggtcggg tgtgtactctt caggagttca tggactgtcc ctataatctg   540
gctaataatc gccaggtgcg tatgctggca gaccttagtc tggtcggttg ttacaacctg   600
agtttcatcc ccgaaagtaa gcgtgcacaa ctgcttttgg aaagcgccaa aaagaacctt   660
cgcggaatgg ctttttttcgg tttgaccgaa tttcagcgca agactcagta cctgtttgag   720
cgtacattca acttaaagtt tattcgtcct tttatgcaat acaattccac acgcgcagga   780
ggtgtagagg ttgacgaaga cacaatccgt cacattgag aattaaatga cttagatatg   840
cagctttacg attatgctaa agacctgttc cagcaacgtt atcagtacaa acgtcaactt   900
gaacgccgcg agcagcgttt acgcaatcgt gaggaataa                          939

SEQ ID NO: 76            moltype = AA    length = 312
FEATURE                  Location/Qualifiers
REGION                   1..312
                         note = Engineered glucosaminyl 6-O sulfotransferase
                          mutant_sulfatase 4
source                   1..312
                         mol_type = protein
```

```
                        organism = synthetic construct
SEQUENCE: 76
MKYYFPVREL ERSLRFDMKG DDDIVFLHIA HTGGTTFGRH LVQNVRLEVP CDCRPGQKKC    60
TCYRPNRRET WLFSRFSTGW SCGTRADWTE LTNCVPGVLD RRDPAGLRSP RKFYYITLLR   120
DPVSRYLSHW RHMQRGANNS TGLHMCDGRT PTPEELPPCY EGTDWSGCTL QEFMDCPYNL   180
GNNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                      312

SEQ ID NO: 77           moltype = DNA  length = 939
FEATURE                 Location/Qualifiers
misc_feature            1..939
                        note = Polynucleotide sequence encoding for engineered
                         glucosaminyl 6-Osulfotransferase mutant_sulfatase 4
source                  1..939
                        mol_type = other DNA
                        organism = synthetic construct
SEQUENCE: 77
atgaagtact attttccggt ccgcgaattg gagcgctcct tacgtttcga tatgaaaggc    60
gacgacgtca ttgtttttct tcacattgct catacgggag gtacgacctt ggacgccat   120
ttagtgcaaa atgtccgttt agaggtaccc tgtgattgcc gtccaggtca aaagaaatgt   180
acgtgctatc gtcctaatcg tcgtgagact tggcttttta gccgttttct cactggatgg   240
tcctgcggaa ctcgtgcgga ttggactgag ttaactaatt gtgtaccggg ggtgttggac   300
cgtcgtgacc ctgccggcct gcgtagtccg cgcaaatttt attacattac gttgcttcgc   360
gaccctgtga gccgctacct gtcccattgg cgtcacatgc aacgtggcgc aaacaactct   420
acaggcttgc acatgtgcga cggtcgtact ccaacgcctg aagaattgcc accatgttac   480
gagggcactg actggagtgg ctgcactttt a caggaattta tggattgccc ctataatctg   540
ggtaataatc gtcaggtgcg tatgctggcg gatctgtcgt tggtaggatg ttacaacctt   600
tcgtttatcc ctgaatcaaa acgcgcgcag cttttacttg agtcggcgaa aaagaattta   660
cgcggtatgg ccttttttgg gcttaccgag ttccagcgca agacacagta tttgtttgag   720
cgcacgttca acttaaaatt tattcgcccc tttatgcaat acaattctac acgcgccggt   780
ggagtggagg ttgatgagga tacgatccgc cacatcgagg aactgaatga cctgacatg   840
caattatacg attatgcgaa agatcttttt cagcaacgct accaatacaa acgccaactt   900
gaacgccgcg agcagcgttt acgcaatcgt gaggaataa                         939

SEQ ID NO: 78           moltype = AA  length = 312
FEATURE                 Location/Qualifiers
REGION                  1..312
                        note = Engineered glucosaminyl 6-O sulfotransferase
                         mutant_sulfatase 5
source                  1..312
                        mol_type = protein
                        organism = synthetic construct
SEQUENCE: 78
MKYYFPVREL ERSLRFDMKG DDDIVFLHIG HTGGTTFGRH LVQNVRLEVP CDCRPGQKKC    60
TCYRPNRRET WLFSRFSTGW SCGTQADWTE LTNCVPGVLD RRDPAGLRSP RKFYYITLLR   120
DPVSRYLSAW RHHQRGGTNK TSLHMCDGRT PTPEELPPCY EGTDWSGCTL QEFMDCPYNL   180
ANNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                      312

SEQ ID NO: 79           moltype = DNA  length = 939
FEATURE                 Location/Qualifiers
misc_feature            1..939
                        note = Polynucleotide sequence encoding for engineered
                         glucosaminyl 6-Osulfotransferase mutant_sulfatase 5
source                  1..939
                        mol_type = other DNA
                        organism = synthetic construct
SEQUENCE: 79
atgaagtact attttccggt ccgcgaattg gagcgctcct tacgtttcga catgaaaggc    60
gacgatgtaa tcgtgttcct tcatattggg cacaccgggg gcaccacatt tggccgccat   120
ctggtccaaa acgtccgttt agaggttccg tgtgactgcc gtcccggtca gaaaaaatgc   180
acctgctatc gccctaaccg ccgtgaaacc tggttgttct ctcgcttttc tactggctgg   240
tcgtgcggga cccaggctga ctggaccgag ttgacaaatt gcgtgcccgg tgttcttgat   300
cgtcgcgacc ctgcaggctt acgttcacca cgtaagtttt actacatcac gcttcttcgt   360
gatcccgtca gccgctatct tagtgcatgg cgtcatcacc aacgtggggg tactaacaaa   420
acttcattgc acatgtgcga cggcgcacc cctacgccag aagaacttcc cccatgttat   480
gaagggacag attggagtgg ctgcacccct taggagttta tggactgtcc gtataattta   540
gcaaataacc gtcaagtgcg tatgttagcg gatcttagtc tggtggggtg ttacaatttg   600
tcctttatcc ctgagagtaa gcgtgcccag ttgttgttgg agagtgcgaa gaaaacttg    660
cgtgggatgg cgttcttcgg tctgactgaa tttcaacgta aaacgcagta tttgttcgaa   720
cgcacttca atttaaagtt tatccgtccc tttatgcagt acaatagcac gcgtgcaggc   780
ggcgtagaaa tggatgagga caccattcgc catatcgaag aattaaacga tctggacatg   840
cagttatacg actatgcgaa ggacttgttt cagcagcgct accaatataa acgccaactt   900
gaacgccgcg agcagcgttt acgcaatcgt gaggaataa                         939

SEQ ID NO: 80           moltype = AA  length = 312
FEATURE                 Location/Qualifiers
```

| REGION | 1..312 |
| --- | --- |
| | note = Engineered glucosaminyl 6-O sulfotransferase mutant_sulfatase 6 |
| source | 1..312 |
| | mol_type = protein |
| | organism = synthetic construct |

SEQUENCE: 80

```
MKYYFPVREL ERSLRFDMKG DDVIVFLHIG HTGGTTFGRH LVQNVRLEVP CDCRPGQKKC    60
TCYRPNRRET WLFSRFSTGW SCGSHADWTE LTNCVPGVLD RRDPAGLRSP RKFYYITLLR   120
DPVSRYLSAW RHHQRGPANT TGLHMCDGRT PTPEELPPCY EGTDWSGCTL QEFMDCPYNL   180
ANNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                       312
```

| SEQ ID NO: 81 | moltype = DNA   length = 939 |
| --- | --- |
| FEATURE | Location/Qualifiers |
| misc_feature | 1..939 |
| | note = Polynucleotide sequence encoding for engineered glucosaminyl 6-Osulfotransferase mutant_sulfatase 6 |
| source | 1..939 |
| | mol_type = other DNA |
| | organism = synthetic construct |

SEQUENCE: 81

```
atgaagtact attttccggt ccgcgaattg gagcgctcac ttcgcttcga catgaaggga    60
gacgatgtaa tcgtcttcct tcacatcggg catacaggcg ggacgacttt cgggcgtcat   120
ttggtacaaa acgtacgttt agaggttccc tgtgattgcc gccctggaca aaagaaatgt   180
acctgctacc gcccgaaccg tcgtgaaaca tggttgttta gtcgcttctc gactggatgg   240
tcgtgcggct cccatgctga ttggacggag cttaccaatt gtgtgccagg tgtattagac   300
cgtcgtgacc cagcagggct gcgtagccca cgcaaattct attatattac attgcttcgc   360
gacccgtgt cacgttatct gagcgcctgg cgtcaccatc aacgtggtcc tgcaaacacg   420
actgacttc acatgtgtga tggccgtacc cccacacccg aagagctgcc accgtgttac   480
gagggcacgg actggtctgg ctgtactctg caagaattta tggactgccc ctataattta   540
gctaacaacc gccaagtccg tatgctggct gacctgagct ggttggttg ctataatctt   600
agttttatcc cagaaagtaa acgcgcacaa ctgttattaa aatctgcaaa gaaaaactta   660
cgcgggatgg cattttttgg cttgaccgaa ttcaacgca agacacaata ccttttcgaa   720
cgcacccttta atcttaaatt catccgtccc ttcatgcagt acaatagtac tcgtgcgggg   780
ggtgtcgaag tcgacgaaga tacgattcgc cacatcgaag aactgaacga cctggacatg   840
caattatacg attatgctaa agacttattt caacaacgtt accaatacaa gcgtcaactt   900
gaacgccgcg agcagcgttt acgcaatcgt gaggaataa                          939
```

| SEQ ID NO: 82 | moltype = AA   length = 312 |
| --- | --- |
| FEATURE | Location/Qualifiers |
| REGION | 1..312 |
| | note = Engineered glucosaminyl 6-O sulfotransferase mutant_sulfatase 7 |
| source | 1..312 |
| | mol_type = protein |
| | organism = synthetic construct |

SEQUENCE: 82

```
MKYYFPVREL ERSLRFDMKG DDVIVFLHIG HTGGTTFGRH LVQNVRLEVP CDCRPGQKKC    60
TCYRPNRRET WLFSRFSTGW SCGTRADWTE LTNCVPGVLD RRDPAGLRSP RKFYYITLLR   120
DPVSRYLSAW RHHQRGGTNK TSLHMCDGRT PTPEELPPCY EGTDWSGCTL QEFMDCPYNL   180
ANNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                       312
```

| SEQ ID NO: 83 | moltype = DNA   length = 939 |
| --- | --- |
| FEATURE | Location/Qualifiers |
| misc_feature | 1..939 |
| | note = Polynucleotide sequence encoding for engineered glucosaminyl 6-Osulfotransferase mutant_sulfatase 7 |
| source | 1..939 |
| | mol_type = other DNA |
| | organism = synthetic construct |

SEQUENCE: 83

```
atgaagtact attttccggt ccgcgaattg gagcgtagct tacgcttcga catgaaaggt    60
gacgatgtga ttgtcttcct gcacatcggt cataccgggg gtacaacgtt cggtcgccac   120
ttagtccaaa atgttcgctt ggaggttcct tgcgattgtc gtcagggca gaagaaatgt   180
acatgttacc gtcccaaccg tcgtgagact tggttattta gtcgcttttc gactggctga   240
tcctgcggca cgcgcgcaga ttggactgaa ctgacaaatt gtgtaccagg agtgttggat   300
cgtcgtgatc cgccggatt acgctctccg cgtaagttct attacattac tttgctcgc   360
gatccagtgt cacgctattt gtcggcatgg cgtcatcacc agcgtggcgg tacgaacaag   420
acgtccttgc acatgtgtga tggacgcact cccaccccgg aggagctgcc ccatgctac   480
gaaggaactg attggagtgg gtgtacatta caggagttta tggactgccc gtacaacctt   540
gccaataacc gccaagtacg catgctggca gatttgagcc tggtcggttg ctataacctt   600
tctttttatcc cagaatctaa gcgtgctcaa ctttattgg agagtgcgaa gaagaattta   660
cgcggaatgg ccttttttgg cctgacgaa ttccaacgca aaacccaata tttattcgag   720
cgcacgtttta acttgaagtt cattcgtcct ttcatgcaat ataatagcac acgtgccggg   780
ggagtcgagg tcgacgaaga tactattcgt catattgaag agctgaatga tcttgacatg   840
```

```
caactttacg attacgccaa ggatttgttt caacagcgct accaatacaa gcgtcaactt  900
gaacgccgcg agcagcgttt acgcaatcgt gaggaataa                         939
```

| SEQ ID NO: 84 | moltype = AA  length = 312 |
|---|---|
| FEATURE | Location/Qualifiers |
| REGION | 1..312 |
| | note = Engineered glucosaminyl 6-O sulfotransferase mutant_sulfatase 8 |
| source | 1..312 |
| | mol_type = protein |
| | organism = synthetic construct |

SEQUENCE: 84
```
MKYYFPVREL ERSLRFDMKG DDDIVFLHIS HTGGTTFGRH LVQNVRLEVP CDCRPGQKKC   60
TCYRPNRRET WLFSRFSTGW SCGTNADWTE LTNCVPGVLD RRDPAGLRSP RKFYYITLLR  120
DPVSRYLSAW RHHQRGGGNK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLTE FQRKTQYLFE  240
RTFNLKFIRP FMQYNSTRAG GVEVDEDTIR HIEELNDLDM QLYDYAKDLF QQRYQYKRQL  300
ERREQRLRNR EE                                                     312
```

| SEQ ID NO: 85 | moltype = DNA  length = 939 |
|---|---|
| FEATURE | Location/Qualifiers |
| misc_feature | 1..939 |
| | note = Polynucleotide sequence encoding for engineered glucosaminyl 6-Osulfotransferase mutant_sulfatase 8 |
| source | 1..939 |
| | mol_type = other DNA |
| | organism = synthetic construct |

SEQUENCE: 85
```
atgaagtact attttccggt ccgcgaattg gagcgctcat tgcgtttcga tatgaagggc   60
gacgacgtga tcgtgttttt acacatctcc cacactgttg gcaccacttt tggccgtcat  120
ttggttcaga atgtacgtct ggaggtacca tgtgactgtc gtcctggaca aaaaaaatgc  180
acttgttatc gcccgaaccg tcgtgaaact tggctgttct ctcgcttttc aaccggatgg  240
tcgtgtggga caaatgcgga ctggacagag cttacaaatt gtgttccgg cgtgttggac  300
cgtcgcgatc ctgcgggatt gcgttcgccg cgcaagttct actacattac cttactgcgc  360
gatccggtat cccgttacct gtcagcctgg cgccatcacc agcgtggcgg cggaaataaa  420
acgtcgttac acatgtgcga tggtcgtacg ccaacacccg aggaattgcc tccatgttat  480
gagggcacgg actggtccgg ctgcacactt caagagttta tggactgccc atataattta  540
gcaaataatc gccaagttcg catgttggct gacttgagcc ttgtcggctg ttacaattta  600
tcattcattc ccgaatcgaa gcgtgctcag ctgctgcttg aaagtgcaaa gaaaaatttg  660
cgttggcatgg cgttttttgg tttaacgaa tttcaacgta aaacacaata tttgttcgag  720
cgtacgttta accttaaatt catccgcccc ttcatgcagt ataattcaac acgcgctggt  780
ggagtggagg ttgatgaaga cacaattcgt catattgagg agcttaacga cttagatatg  840
cagttgtatg attacgcaaa ggatttattc caacagcgtt atcagtacaa gcgtcagctt  900
gaacgccgcg agcagcgttt acgcaatcgt gaggaataa                         939
```

| SEQ ID NO: 86 | moltype = AA  length = 312 |
|---|---|
| FEATURE | Location/Qualifiers |
| REGION | 1..312 |
| | note = Engineered glucosaminyl 6-O sulfotransferase mutant_sulfatase 9 |
| source | 1..312 |
| | mol_type = protein |
| | organism = synthetic construct |

SEQUENCE: 86
```
MKYYFPVREL ERSLRFDMKG DDDIVFLGIA HTGGATFGRH LVQNVRLEVP CDCRPGQKKC   60
TCYRPNRRET WLFSRFSTGG SCGANADWTE LTNCVPGVLD RRDPAGLRSP RKFYYITLLR  120
DPVSRYLSMW RHHQRGATHK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLTE FQRKTQYLFE  240
RTFNLKFIRP FMQYNSTRAG GVEVDEDTIR HIEELNDLDM QLYDYAKDLF QQRYQYKRQL  300
ERREQRLRNR EE                                                     312
```

| SEQ ID NO: 87 | moltype = DNA  length = 939 |
|---|---|
| FEATURE | Location/Qualifiers |
| misc_feature | 1..939 |
| | note = Polynucleotide sequence encoding for engineered glucosaminyl 6-Osulfotransferase mutant_sulfatase 9 |
| source | 1..939 |
| | mol_type = other DNA |
| | organism = synthetic construct |

SEQUENCE: 87
```
atgaagtact attttccggt ccgcgaattg gagcgctcat tgcgttttga tatgaaagga   60
gacgacgtca tcgtattttt gggcattgcc catacgggag gcgcgacatt cggacgccac  120
ctggtccaaa acgttcgcct ggaagttccc tgtgactgtc gcccaggtca agaagtgt    180
acgtgctatc gccccaaccg tcgtgagacg tggctttttc cgcgttttct cactggtggg  240
tcctgtgggg caaatgccga ctggactgag ttgacaaatt gcgtgccagg tgttctggat  300
cgccgcgacc ccgccggact cgctcaccga cgtaagtttt attacatcac tttgttcgc   360
gacccagtgt cccgttacct gtctatgtgg cgtcaccatc agcgtggtgc gacacataaa  420
acgtcgctgc acatgtgcga tggacgcacg ccgactccag aggagttgcc tccatgctac  480
gagggcacgg attggagcgg ctgcactttg caagagttta tggattgccc ttataatttg  540
```

```
gcgaacaacc gtcaagtgcg tatgttagct gatttgagtt tagttggctg ctacaatctt  600
tcctttattc ccgaatcaaa acgcgctcag ctgctgttgg agagtgcgaa gaagaacctt  660
cgcgggatgg catttttggg ccttacagag tttcaacgca agactcagta tttgtttgag  720
cgtacgttca atttgaaatt catccgtcct tttatgcagt ataatagcac ccgcgccggc  780
ggcgttgaag tagatgagga cactattcgt cacattgaag agcttaatga tctggacatg  840
cagttatatg actatgcaaa agatttattt caacagcgct atcagtacaa acgtcaactt  900
gaacgccgcg agcagcgttt acgcaatcgt gaggaataa                          939
```

```
SEQ ID NO: 88              moltype = AA   length = 312
FEATURE                    Location/Qualifiers
REGION                     1..312
                           note = Engineered glucosaminyl 6-O sulfotransferase
                           mutant_sulfatase 10
source                     1..312
                           mol_type = protein
                           organism = synthetic construct
SEQUENCE: 88
MKYYFPVREL ERSLRFDMKG DDVIVFLHIG HTGGTTFGRH LVQNVRLEVP CDCRPGQKKC   60
TCYRPNRRET WLFSRFSTGW SCGTRADWTE LTNCVPGVLD RRDPAGLRSP RKFYYITLLR  120
DPVSRYLSAW RHHQRGASNS TSLHMCDGRT PTPEELPPCY EGTDWSGCTL QEFMDCPYNL  180
GNNRQVRMLA DLSLVGCYNL SFIPESKRAQ LLLESAKKNL RGMAFFGLTE FQRKTQYLFE  240
RTFNLKFIRP FMQYNSTRAG GVEVDEDTIR HIEELNDLDM QLYDYAKDLF QQRYQYKRQL  300
ERREQRLRNR EE                                                      312
```

```
SEQ ID NO: 89              moltype = DNA  length = 939
FEATURE                    Location/Qualifiers
misc_feature               1..939
                           note = Polynucleotide sequence encoding for engineered
                           glucosaminyl 6-Osulfotransferase mutant_sulfatase 10
source                     1..939
                           mol_type = other DNA
                           organism = synthetic construct
SEQUENCE: 89
atgaagtact attttccggt ccgcgaatta gagcgctcat tgcgttttga catgaagggg   60
gatgacgtta ttgtgttcct tcatatcggc cacacaggcg ggactacgtt cggtcgccat  120
cttgtgcaga atgtccgttt ggaggtaccc tgtgactgcc gtccggggca gaaaaaatgt  180
acctgctatc gcccaaatcg ccgtgaaacg tggttattct ctcgttttag tactggatgg  240
tcgtgtggaa cccgcgctga ctggacagag cttacaaact gcgtaccagg cgtgctggac  300
cgccgtgacc ctgcgggtct tcgtagtccc cgcaagttct attatattac tcttcttcgt  360
gatccagtaa gccgttatct gagtgcttgg cgccatcacc aacgcggtgc ttcaaattcc  420
acaagccttc acatgtgcga tgggcgtact ccgaccccgg aagagcttcc gccctgttac  480
gaaggtacag attggtccgg ttgtacgctg caggaattta tggactgtcc atacaactta  540
ggcaacaatc gccaggtacg catgcttgcg gatctgagtc tggtcggttg ctacaacttg  600
tctttatcc cagaatctaa acgcgcccaa ttactgttag aaagtgcgaa gaagaacctt  660
cgtggcatgg ccttctttgg acttacggag ttccagcgta agactcaata cctgttcgag  720
cgtacattta atcttaaatt cattcgtcca ttcatgcaat ataattctac gcgcgcaggc  780
ggcgtggagg tcgatgaaga tacgatccgt catatcgagg aactgaatga tctggacatg  840
cagttatatg actacgcgaa agaccttttc caacagcgct accaatacaa gcgtcaatta  900
gagcgccgtg agcagcgttt acgcaatcgt gaggaataa                          939
```

```
SEQ ID NO: 90              moltype = AA   length = 312
FEATURE                    Location/Qualifiers
REGION                     1..312
                           note = Engineered glucosaminyl 6-O sulfotransferase
                           mutant_sulfatase 11
source                     1..312
                           mol_type = protein
                           organism = synthetic construct
SEQUENCE: 90
MKYYFPVREL ERSLRFDMKG DDVIVFLHIQ KTHGTTFGRH LVQNVRLEVP CDCRPGQKKC   60
TCYRPNRRET WLFSRFSTGW SCGLHADWTE LTNCVPGVLD RRDPAGLRSP RKFYYITLLH  120
HPVHRYLSEW RHVQRGATWK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLAW FGRKTQYLFE  240
RTFNLKFIRP FMQVKSSRAS GVEVDEDTIR HIEELNDLDM QLYDYAKDLF QQRYQYKRQL  300
ERREQRLRNR EE                                                      312
```

```
SEQ ID NO: 91              moltype = DNA  length = 939
FEATURE                    Location/Qualifiers
misc_feature               1..939
                           note = Polynucleotide sequence encoding for engineered
                           glucosaminyl 6-Osulfotransferase mutant_sulfatase 11
source                     1..939
                           mol_type = other DNA
                           organism = synthetic construct
SEQUENCE: 91
atgaagtact attttccggt ccgcgaattg gagcgctcat tgcgttttga tatgaaaggt   60
gacgacgtaa ttgtgtttct tcatattcag aagacccatg gcacaacatt tggtcgccat  120
cttgtgcaaa atgtgcgttt agaggtgccg tgtgactgcc gtccaggtca aagaaaatgc  180
acctgctatc gtccaaatcg tcgcgaaacg tggctttttct cccgtttcag cacgggttgg  240
```

```
tcctgcggct tacatgcgga ctggactgaa ctgacaaact gtgtgccagg agtgcttgat    300
cgccgcgatc cagcggggct tcgctcgccg cgcaagtttt actatatcac ccttctgcac    360
catccggtac accgctattt gagcgagtgg cgtcacgtcc agcgcggggc aacgtggaag    420
accagtttac acatgtgcga cggacgtacc cctacacccg aagagcttcc gccatgctat    480
gaaggggacgg attggagtgg ctgtacgtta caggagttca tggattgtcc ctataatctg    540
gccaataatc gtcaagtgcg tatgttagcc gacctttcac tggttggttg ctataactta    600
tcattcattc cggagtctaa acgcgctcag cttttgcttg aatctgccaa aaagaatctt    660
cgtgggatgg ctttctttgg tttagcctgg tttgggcgca aaactcaata cttattcgag    720
cgtacttttta atttgaaatt tattcgtccc ttatgcaag ttaagagtag ccgtgcatct    780
ggagtagagg tagacgaaga cactattcgt cacatcgagg agcttaatga tttggatatg    840
cagctgtacg attatgctaa agacttgttc caacagcgtt atcagtataa gcgtcagctt    900
gaacgccgcg agcagcgttt acgcaatcgt gaggaataa                           939

SEQ ID NO: 92          moltype = AA  length = 312
FEATURE                Location/Qualifiers
REGION                 1..312
                       note = Engineered glucosaminyl 6-O sulfotransferase
                       mutant_sulfatase 12
source                 1..312
                       mol_type = protein
                       organism = synthetic construct
SEQUENCE: 92
MKYYFPVREL ERSLRFDMKG DDIVFLHIQ KTHGTTFGRH LVQNVRLEVP CDCRPGQKKC     60
TCYRPNRRET WLFSRFSTGW SCGLHADWTE LTNCVPGVLD RRDPAGLRSP RKFYYITLLH    120
HPVHRYLSEW RHVQRGATWK TSLHMCDGRT PTPEELPPCY EGTDWSGCTL QEFMDCPYNL    180
ANNRQVRMLA DLSLVGCYNL SFIPESKRAQ LLLESAKKNL RGMAFFGLGW FGRKTQYLFE    240
RTFNLKFIRP FMQVKSNRAS GVEVDEDTIR HIEELNDLDM QLYDYAKDLF QQRYQYKRQL    300
ERREQRLRNR EE                                                       312

SEQ ID NO: 93          moltype = DNA  length = 939
FEATURE                Location/Qualifiers
misc_feature           1..939
                       note = Polynucleotide sequence encoding for engineered
                       glucosaminyl 6-Osulfotransferase mutant_sulfatase 12
source                 1..939
                       mol_type = other DNA
                       organism = synthetic construct
SEQUENCE: 93
atgaagtact attttccggt ccgcgaattg gagcgctcat tgcgtttcga catgaaaggt     60
gatgacgtaa tcgtatttct gcatatccaa aagacacatg gcacaacttt tggacgccat    120
ctggtccaga acgtccgtct ggaggttccg tgtgactgtc gtcccggtca aaagaaatgc    180
acatgctacc gtccaaatcg ccgtgagaca tggcttttttt cccgctttag cacgggctgg    240
agctgcggct tacatgctga ctggaccgag cttactaact gtgtcccggg ggtccttgac    300
cgccgtgatc ctgctgggtt gcgctcacct cgcaaatttt attatatcac cttattgcac    360
catccagttc accgttactt gtcggaatgg cgtcacgtcc agcgtggagc gacttggaaa    420
acgtctcttc acatgtgtga tggccgtaca cccacgcccg aagagcttcc gccatgctat    480
gaaggcactg attggtcagg gtgcaccctt caagaattca tggattgccc atacaactta    540
gccaacaatc gccaggttcg tatgttagcc gatttgtcgt tagtaggttg ctacaatctg    600
tcttttattc ccgaatcgaa gcgcgctcaa ctgttgttag agtccgcgaa gaaaaatttg    660
cgtggtatgg cgttttttgg cttgggatgg tttgggcgta agactcagta tcttttcgaa    720
cgtactttta atcttaagtt tattcgcccc ttcatgcaag ttaagtcaaa ccgcgcctca    780
ggcgtagagg tagatgaaga cacgattcgt cacatcgaag agcttaatga cttagatatg    840
caactttatg actatgccaa agatttattt cagcagcgtt accaatacaa acgtcagctt    900
gaacgccgcg agcagcgttt acgcaatcgt gaggaataa                           939

SEQ ID NO: 94          moltype = AA  length = 312
FEATURE                Location/Qualifiers
REGION                 1..312
                       note = Engineered glucosaminyl 6-O sulfotransferase
                       mutant_sulfatase 13
source                 1..312
                       mol_type = protein
                       organism = synthetic construct
SEQUENCE: 94
MKYYFPVREL ERSLRFDMKG DDIVFLHIQ KTHGTTFGRH LVQNVRLEVP CDCRPGQKKC     60
TCYRPNRRET WLFSRFSTGW SCGLHADWTE LTNCVPGVLD RRDPAGLRSP RKFYYITLLH    120
KPVHRYLSEW RHVQRGATWK TSLHMCDGRT PTPEELPPCY EGTDWSGCTL QEFMDCPYNL    180
ANNRQVRMLA DLSLVGCYNL SFIPESKRAQ LLLESAKKNL RGMAFFGLGW FGRKTQYLFE    240
RTFNLKFIRP FMQVKSSRAS GVEVDEDTIR HIEELNDLDM QLYDYAKDLF QQRYQYKRQL    300
ERREQRLRNR EE                                                       312

SEQ ID NO: 95          moltype = DNA  length = 939
FEATURE                Location/Qualifiers
misc_feature           1..939
                       note = Polynucleotide sequence encoding for engineered
                       glucosaminyl 6-Osulfotransferase mutant_sulfatase 13
source                 1..939
                       mol_type = other DNA
                       organism = synthetic construct
```

```
SEQUENCE: 95
atgaagtact attttccggt ccgcgaattg gagcgctcat tgcgttttga tatgaagggt   60
gatgatgtta ttgttttct  gcacatccaa aagacacacg ggacaacctt cggacgccac  120
ttggtgcaga acgttcgcct ggaagtacca tgcgattgtc gtcccgggca aaagaaatgc  180
acctgttacc gtcccaatcg tcgtgagacg tggttattta gccgttttc  caccgggtgg  240
agctgtggac ttcacgcaga ctggacagag ttaaccaact gtgtaccgg  tgttttggac  300
cgccgcgacc cagcggggct gcgttctcca cgtaaattct actatattac acttctgcat  360
aagcccgtac accgttatct gagtgaatgg cgtcacgtcc agcgcgggc  gacctggaag  420
acgagcctgc acatgtgcga tggtcgtacg cccactcctg aagaattacc tccctgttat  480
gagggaactg actggtcagg gtgtacatta caggagttta tggactgtcc ctataatctt  540
gctaataatc gtcaagttcg catgcttgct gacttatcat tggtggggtg ctataattta  600
tcgttcattc ctgaaagcaa acgcgcccaa ttgcttcttg agtcggctaa gaagaactta  660
cgcggtatgg ctttctttgg tttgggctgg tttggacgta aaactcaata tttgttcgag  720
cgtaccttta acttaaagtt tatccgccct tttatgcagg ttaaatccag ccgcgcatcg  780
ggagtagaag tcgatgagga tacgattcgc catatcgaag aattgaacga tctgacatg   840
caactttatg actacgctaa agatttattc caacaacgct atcagtataa acgccagctt  900
gaacgccgcg agcagcgttt acgcaatcgt gaggaataa                         939

SEQ ID NO: 96            moltype = AA  length = 312
FEATURE                  Location/Qualifiers
REGION                   1..312
                         note = Engineered glucosaminyl 6-O sulfotransferase
                          mutant_sulfatase 14
source                   1..312
                         mol_type = protein
                         organism = synthetic construct
SEQUENCE: 96
MKYYFPVREL ERSLRFDMKG DDDVIVFLHIQ KTHGTTFGRH LVQNVRLEVP CDCRPGQKKC   60
TCYRPNRRET WLFSRFSTGW SCGLHADWTE LTNCVPGVLD RRDPAGLRSP RKFYYITLLH  120
DPVHRYLSEW RHVQRGATWK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLGR FQRKTQYLFE  240
RTFNLKFIRP FMVTNSSRAS GVEVDEDTIR HIEELNDLDM QLYDYAKDLF QQRYQYKRQL  300
ERREQRLRNR EE                                                      312

SEQ ID NO: 97            moltype = DNA  length = 939
FEATURE                  Location/Qualifiers
misc_feature             1..939
                         note = Polynucleotide sequence encoding for engineered
                          glucosaminyl 6-Osulfotransferase mutant_sulfatase 14
source                   1..939
                         mol_type = other DNA
                         organism = synthetic construct
SEQUENCE: 97
atgaagtact attttccggt ccgcgaattg gagcgctcat tgcgtttcga tatgaaaggg   60
gatgatgtta ttgtgttcct gcatattcaa aaaacgcatg gcactacatt tggtcgtcat  120
ttagttcaga atgtgcgttt agaagtgccg tgtgactgtc gccctgggca gaaaaagtgc  180
acctgttacc gccctaatcg ccgtgagacg tggttgttca gtcgcttct  tactggctgg  240
tcgtgcggcc ttcatgccga ctggactgag cttacaaatt gcgttccagg tgtattagat  300
cgccgcgatc ccgctgggct gcgctcccca cgcaagtttt attatatcac tcttttacac  360
gatccagttc atcgttatct ttcagaatgg cgccacgtgc aacgcgggc  gacgtggaaa  420
acgtctcttc acatgtgcga cggtcgcact cccacgtctg aagaattgcc gccctgttac  480
gaaggaacag attggagcgg ttgcacgtta caagaattca tggattgccc ctataactta  540
gctaacaacc gtcaagtacg tatgcttgcc gacctgtccc ttgtagggtg ctacaatttg  600
tcctttattc ccgagtcaaa gcgcgctcaa cttttgttgg aaagtgcaaa aaaaaacctg  660
cgtggaatgg ctttccttcg gactgggtcg ttcaacgta  agacgcagta tttattcgag  720
cgcacgttca atttgaaatt catccgccct tttatggtca ctaattcatc ccgcgcgagc  780
ggggtcgagg tggacgagga tactatccgc catatcgaag agcttaacga cttggatatg  840
cagttgtacg attatgccaa agatcttttt caacagcgct accaatacaa gcgtcagctt  900
gaacgccgcg agcagcgttt acgcaatcgt gaggaataa                         939

SEQ ID NO: 98            moltype = AA  length = 312
FEATURE                  Location/Qualifiers
REGION                   1..312
                         note = Engineered glucosaminyl 6-O sulfotransferase
                          mutant_sulfatase 15
source                   1..312
                         mol_type = protein
                         organism = synthetic construct
SEQUENCE: 98
MKYYFPVREL ERSLRFDMKG DDDVIVFLHIA HTGGTTFGRH LVQNVRLEVP CDCRPGQKKC   60
TCYRPNRRET WLFSRFSTGG SCGAAADWTE LTNCVPGVLD RRDPAGLRSP RKFYYITLLR  120
DPVSRYLSMW RHHQRGATHK TSLHMCDGRT PTPEELPPCY EGTDWSGCTL QEFMDCPYNL  180
ANNRQVRMLA DLSLVGCYNL SFIPESKRAQ LLLESAKKNL RGMAFFGLTE FQRKTQYLFE  240
RTFNLKFIRP FMQYNSTRAG GVEVDEDTIR HIEELNDLDM QLYDYAKDLF QQRYQYKRQL  300
ERREQRLRNR EE                                                      312

SEQ ID NO: 99            moltype = DNA  length = 939
FEATURE                  Location/Qualifiers
misc_feature             1..939
```

```
                        note = Polynucleotide sequence encoding for engineered
                          glucosaminyl 6-Osulfotransferase mutant_sulfatase 15
source                  1..939
                        mol_type = other DNA
                        organism = synthetic construct
SEQUENCE: 99
atgaagtact attttccggt ccgcgaattg gagcgctcat tgcgttttga tatgaagggg      60
gatgacgtga tcgttttttct tcatattgct catactggtg gcacgacatt cggtcgccat    120
ttggtccaga acgtccgtct tgaggtgcca tgcgattgcc gtcctggcca gaagaagtgc    180
acgtgttatc gtccgaaccg ccgtgagact tggttgttta gtcgcttttc aactggcggt    240
tcgtgcggcg ccgcagcgga ttggacagaa ttaaccaatt gtgtaccggg tgttttagat    300
cgtcgcgatc cagcgggatt acgttcgccc cgtaagttct attatattac tctgttacgc    360
gatccagtct cacgctatct gtcgatgtgg cgccatcatc aacgtgggc tactcataca    420
acttcgttac acatgtgtga cggccgtact ccgacccgg agaacttcc accctgctac    480
gaaggcaccg actggtctgg atgtacgctg caggaattta tggattgtcc gtacaacttg    540
gctaacaacc gtcaagtgcg tatgttggct gatctttcat tagtcggatg ctacaacttg    600
tcgttcatcc cagaaagcaa acgtgcacag cttctgcttg agtccgccaa gaaaaatttg    660
cgtggtatgg ccttctttgg attgacagag ttccagcgca aaacgcagta tctttttcgag    720
cgtaccttca acctgaaatt tatccgcccg ttcatgcaat acaattccac tcgcgcaggg    780
ggtgttgaag tagacgagga tacgattcgt catatcgagg aattgaatga cctggatatg    840
cagctgtatg actacgcgaa agatttgttc cagcagcgct accagtacaa acgtcagctt    900
gaacgccgcg agcagcgttt acgcaatcgt gaggaataa                           939

SEQ ID NO: 100         moltype = AA  length = 295
FEATURE                Location/Qualifiers
REGION                 1..295
                        note = Engineered glucosaminyl 6-O sulfotransferase
                          mutant_sulfatase 16
source                 1..295
                        mol_type = protein
                        organism = synthetic construct
SEQUENCE: 100
MKGDDVIVFL HIGHTGGTTF GRHLVQNVRL EVPCDCRPGQ KKCTCYRPNR RETWLFSRFS      60
TGWSCGTRAD WTELTNCVPG VLDRRDPAGL RSPRKFYYIT LLRDPVSRYL SAWRHHQRGA    120
TGKTSLHMCD GRTPTPEELP PCYEGTDWSG CTLQEFMDCP YNLANNRQVR MLADLSLVGC    180
YNLSFIPESK RAQLLLESAK KNLRGMAFFG LTEFQRKTQY LFERTFNLKF IRPFMQYNST    240
RAGGVEVDED TIRHIEELND LDMQLYDYAK DLFQQRYQYK RQLERREQRL RNREE         295

SEQ ID NO: 101         moltype = DNA  length = 888
FEATURE                Location/Qualifiers
misc_feature           1..888
                        note = Polynucleotide sequence encoding for engineered
                          glucosaminyl 6-Osulfotransferase mutant_sulfatase 16
source                 1..888
                        mol_type = other DNA
                        organism = synthetic construct
SEQUENCE: 101
atgaaaggtg atgatgtgat cgttttttg catatcgggc acacaggggg gactaccttc        60
gggcgtcatc tggtgcagaa cgtacgcctt gaggtaccat gtgattgtcg ccccgggcaa    120
aaaaagtgca cttgttatcg ccctaaccgt cgtgaaactt ggttattttc cgcttttcg    180
acagggtgga gttgtggtac acgcgctgac tggacagagt tgaccaactg cgtcccaggg    240
gtacttgacc gtcgtgaccc tgctggactg cgcagcccac gtaagttcta ctacattacg    300
ttactgcgtg atcctgtatc acgttacctg tctgcctggc gccatcacca gcgcggagcg    360
acagggaaga catctctgca catgtgtgac ggacgtactc cgacgccaga agagttaccc    420
ccgtgctatg aaggtactga ttggtcgggg tgcaccctgc aagaattcat ggactgcccg    480
tacaacctgg ctaacaaccg tcaagtgcgt atgttagcgg acctgagttt ggtgggatgc    540
tacaatctga gctttatccc tgagtctaag gcgcacagt tactgcttga tcggcgaaa    600
aagaatctgc gtggcatggc gttcttcggg ctgacggaat tcagcgtaa acacaaatac    660
cttttgagc gcacgtttaa cttgaagttt attcgccgt ttatgcagta caactccacc    720
cgcgcagggg gcgtcgaggt cgatgaagat acaattgcc atattgagga gttgaacgat    780
cttgatatgc aattatacga ttacgctaaa gacttgtttc aacagcgcta tcaatacaaa    840
cgtcagttga aacgccgcga gcagcgttta cgcaatcgtg aggaataa                888

SEQ ID NO: 102         moltype = AA  length = 312
FEATURE                Location/Qualifiers
REGION                 1..312
                        note = Engineered glucosaminyl 6-O sulfotransferase
                          mutant_sulfatase 17
source                 1..312
                        mol_type = protein
                        organism = synthetic construct
SEQUENCE: 102
MRYNFSRGDL LRKVDFDIKG DDLIVFLHIQ KTHGTQFGRH LVRNIQLEQP CECRVGQKKC      60
TCHRPGKRET WLFSRFSTGW SCGLHADWTE LTSCVPAVVD GKRDARLRPS RNFHYITILR    120
DPVHRYLHEW RHVQRGATWK ASLHVCDGRP PTSEELPSCY TGDDWSGCPL KEFMDCPYNL    180
ANNRQVRMLS DLTLVGCYNL SVMPEKQRNK VLLESAKSNL KHMAFFGLGE FQRKTQYLFE    240
KTFNMNFISP FTQTNTSRAS SVEINEEIQK RIEGLNFLDM ELYSYAKDLF LQRYQFMRQK    300
EHQDARRKRQ EQ                                                       312
```

```
SEQ ID NO: 103          moltype = DNA   length = 939
FEATURE                 Location/Qualifiers
misc_feature            1..939
                        note = Polynucleotide sequence encoding for engineered
                          glucosaminyl 6-Osulfotransferase mutant_sulfatase 17
source                  1..939
                        mol_type = other DNA
                        organism = synthetic construct
SEQUENCE: 103
atgcgctata acttcagtcg tggggacctt ttacgtaaag tggatttcga tatcaaagga     60
gacgatctta ttgtgttctt acatattcaa aaaacacatg gcacgcagtt cgggcgtcac    120
ttagtccgta acatccagct tgaacagccg tgtgagtgcc gtgtgggaca aaaaaaatgc    180
acttgccacc gcccaggaaa acgcgagacc tggctgtttt cgcgcttttc tactggttgg    240
tcttgcggat tacatgctga ttggacagag ttgacgtcat ggttccggc agttgtagat    300
ggaaaacgcg atgctcgcct cgcccgtcg cgtaatttcc attacattac gatcctgcgt    360
gatccagttc accgttacct tcatgagtgg cgccatgtac agcgcggtgc tacgtggaag    420
gcatcgttgc acgtatgtga tggccgtccc ccaaatcgg aggagctgcc ctcatgttat    480
actggcgatg actggtctgg ctgccccctg aaggagttta tggattgtcc ctacaacctg    540
gccaataacc gtcaggttcg tatgttgtca gatttaacat tagtaggttg ttacaatctg    600
tcagtaatgc cagaaaagca acgtaataag gtgctgctgg aaagtgctaa gtcaaactta    660
aagcacatgg ccttctttgg ccttggagaa tttcagcgta aaacacaata cttgtttgag    720
aagacgttta atatgaactt tatctccccc tttacgcacg ctaacacctc ccgtgcttca    780
tctgtagaaa tcaatgagga aattcaaaag cgcattgagg gattgaactt tttagatatg    840
gagttatatt cttacgcaaa ggatttgttc ttgcagcgtt atcaatttat gcgtcaaaaa    900
gaacatcaag acgcacgtcg taagcgtcag gagcagtaa                           939

SEQ ID NO: 104          moltype = AA    length = 312
FEATURE                 Location/Qualifiers
REGION                  1..312
                        note = Engineered glucosaminyl 6-O
                          sulfotransferasemutant_sulfotransferase 1
source                  1..312
                        mol_type = protein
                        organism = synthetic construct
SEQUENCE: 104
MKYYFPVREL ERSLRFDMKG DDVIVFLHIG HTGGTTFGRH LVQNVRLEVP CDCRPGQKKC     60
TCYRPNRRET WLFSRFSTGW SCGTNADWTE LTNCVPGVLD RRDPAGLRSP RKFYYITLLR    120
DPVSRYLGGW RHHQRGGTNK TSLHMCDGRT PTPEELPPCY EGTDWSGCTL QEFMDCPYNL    180
ANNRQVRMLA DLSLVGCYNL SFIPESKRAQ LLLESAKKNL RGMAFFGLTE FQRKTQYLFE    240
RTFNLKFIRP FMQYNSTRAG GVEVDEDTIR HIEELNDLDM QLYDYAKDLF QQRYQYKRQL    300
ERREQRLRNR EE                                                        312

SEQ ID NO: 105          moltype = DNA   length = 939
FEATURE                 Location/Qualifiers
misc_feature            1..939
                        note = Polynucleotide sequence encoding for engineered
                          glucosaminyl 6-Osulfotransferase mutant_sulfotransferase 1
source                  1..939
                        mol_type = other DNA
                        organism = synthetic construct
SEQUENCE: 105
atgaagtact attttccggt ccgcgaattg gagcgctcac tgcgttttga tatgaagggt     60
gacgatgtga ttgtattcct tcatattggg catacaggcg ggacgacttt ggacgtcat    120
ttagtccaga acgttcgtct ggaggtaccc tgtgattgcc gcccgggtca aaaaaaatgc    180
acgtgttacc gcccaaatcg ccgtgagacc tggttgttct ctcgcttttc cacaggctgg    240
tcttgcggaa ctaacgccga ctggacagag cttaccaact gtgtcccagg ggtattggac    300
cgccgtgatc cagctgggtt gcgctcgcca cgtaaatttt actatattac cctgctgcgc    360
gatcctgtct cccgctacct gggggggctgg cgccaccatc agcgtggcgg cacaaataaa    420
acatcgttgc acatgtgtga tgggcgcacg ccaacacccg aagagcttcc cccgtgctat    480
gagggaacgg actggagtgg atgtacttta caggaattta tggactgtcc ctacaatttg    540
gcaaacaatc gtcaagtccg catgcttgcg gatcttagtt tggtcggctg ttacaacttg    600
agctttattc ccgaaagtaa gcgcgcacaa ctttttattag agagtgccaa gaagaacttg    660
cgtggaatgg cattctttgg attgaccgaa tttcagcgta aaacgcagta tttgtttgaa    720
cgtacattca acctgaaatt tatccgcccg tttatgcagt ataacagtac gcgcgcaggga    780
ggcgtggaag tggacgagga cacgattcgc cacattgagg aattgaatga ccttgatatg    840
caattgtacg actacgccaa agatctttttc cagcaacgtt atcaatacaa gcgccagctt    900
gaacgccgcg agcagcgttt acgcaatcgt gaggaataa                            939

SEQ ID NO: 106          moltype = AA    length = 312
FEATURE                 Location/Qualifiers
REGION                  1..312
                        note = Engineered glucosaminyl 6-O
                          sulfotransferasemutant_sulfotransferase 2
source                  1..312
                        mol_type = protein
                        organism = synthetic construct
SEQUENCE: 106
MKYYFPVREL ERSLRFDMKG DDVIVFLHIG HTGGTTFGRH LVQNVRLEVP CDCRPGQKKC     60
TCYRPNRRET WLFSRFSTGW SCGTRADWTE LTNCVPGVLD RRDPAGLRSP RKFYYITLLR    120
```

```
DPVSRYLSHW RHTQRGGANK TGLHMCDGRT PTPEELPPCY EGTDWSGCTL QEFMDCPYNL   180
GNNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                      312

SEQ ID NO: 107          moltype = DNA   length = 939
FEATURE                 Location/Qualifiers
misc_feature            1..939
                        note = Polynucleotide sequence encoding for engineered
                         glucosaminyl 6-Osulfotransferase mutant_sulfotransferase 2
source                  1..939
                        mol_type = other DNA
                        organism = synthetic construct
SEQUENCE: 107
atgaagtact attttccggt ccgcgaattg gagcgctcat tgcgtttcga catgaagggt    60
gatgatgtca tcgtcttcct tcacattggt cacactggtg aaccacctt tggacgtcat   120
cttgtgcaaa acgtacgttt agaggtccct tgcgattgtc gtccgggtca aaaaaaatgt   180
acttgctatc gtcctaatcg tcgtgaaacg tggcttttca cgtgttttag tacggggtgg   240
tcatgcggta cccgcgcaga ctggacgag ttaaccaact gcgtacctgg ggtgttggat    300
cgccgcgatc cggcaggttt acgctcccca cgtaaattct attatattac cctgttacgt   360
gacccagtca gtcgctattt gtctcactgg cgtcacacac aacgtggcgg cgcgaacaag   420
accggactgc acatgtgtga cgggcgtact cctacacgag aggaattacc cccatgctat   480
gagggaactg actggtcggg atgtacactg caggagttca tggactgcc atacaatctg    540
gggaataatc gccaagtccg tatgttggcg gatttaagcc ttgtcggatg ctataatttg   600
tcattcattc agaatcaaa acgcgcgcaa cttcttcttg agtcagccaa gaaaaatttg    660
cgcggaatgg cattttttcgg gttgacagaa tttcagcgca aaacacaata tcttcgcga   720
cgcacattca atttaaaatt tattcgtcct ttcatgcaat acaactctac acgtgcagga   780
ggagtcgaag tggacgagga cacaattcgc cacatcgagg aattaaatga tctggatatg   840
cagttgtatg actatgcaaa agatctgttt cagcaacgct atcaatacaa gcgtcagttg   900
gaacgccgcg agcagcgttt acgcaatcgt gaggaataa                         939

SEQ ID NO: 108          moltype = AA   length = 312
FEATURE                 Location/Qualifiers
REGION                  1..312
                        note = Engineered glucosaminyl 6-O
                         sulfotransferasemutant_sulfotransferase 3
source                  1..312
                        mol_type = protein
                        organism = synthetic construct
SEQUENCE: 108
MKYYFPVREL ERSLRFDMKG DDDIVFLHIG HTGGTTFGRH LVQNVRLEVP CDCRPGQKKC    60
TCYRPNRRET WLFSRFSTGW SCGSHADWTE LTNCVPGVLD RRDPAGLRSP RKFYYITLLR   120
DPVSRYLSGW RHHQRGGANK TSLHMCDGRT PTPEELPPCY EGTDWSGCTL QEFMDCPYNL   180
GNNRQVRMLA DLSLVGCYNL SFIPESKRAQ LLLESAKKNL RGMAFFGLTE FQRKTQYLFE   240
RTFNLKFIRP FMQYNSTRAG GVEVDEDTIR HIEELNDLDM QLYDYAKDLF QQRYQYKRQL   300
ERREQRLRNR EE                                                      312

SEQ ID NO: 109          moltype = DNA   length = 939
FEATURE                 Location/Qualifiers
misc_feature            1..939
                        note = Polynucleotide sequence encoding for engineered
                         glucosaminyl 6-Osulfotransferase mutant_sulfotransferase 3
source                  1..939
                        mol_type = other DNA
                        organism = synthetic construct
SEQUENCE: 109
atgaagtact attttccggt ccgcgaattg gagcgctcat tgcgtttcga catgaaagga    60
gacgacgtca ttgtatttt acatattggc cacaccggtg gcacgacttt ggccgtcac    120
ttagtccaaa acgtacgctt agaggtgcct tgcgactgtc gtccagggca aaagaaatgc   180
acctgctatc gccccaaccg ccgtgaaaca tggttgttta gtcgctttag taccggttgg   240
agctgtggct ctcatgctga ttggactgaa ctgacgaatt gtgtccccgg agtattggat   300
cgccgtgatc ctgctggttt acgctcacct cgcaaattct attatattac gttacttcgt   360
gatcccgtta gccgttatct tagtgggtgg cgtcaccatc aacgcggagg ggctaataag   420
acgagcctgc acatgtgtga cggacgtacg ccaaccccgg aggaactgcc gccctgttac   480
gaggggacgg actggtctgg ctgtacatta caagagttta tggattgccc atataacctg   540
ggtaacaatc gccaagtccg tatgttggcg gatctttcgc tggtgggatg ttataatta    600
agttttatcc cggagagcaa gcgtgcacag ttgctgcttg aatcagcgaa gaagaacctt   660
cgcggaatgg cattttttcgg tttaacgtga agactcagta ccttttcgag              720
cgtaccttca acttgaaatt tatccgtcct ttcatgcagt acaactccac ccgcgctggt   780
ggagttgaag tcgacgagga taccatccgc cacattgaag aacttaatga cttagatatg   840
caattgtacg actatgctaa ggactattac cagcaacgtt atcagtacaa acgccaattg   900
gaacgccgcg agcagcgttt acgcaatcgt gaggaataa                         939

SEQ ID NO: 110          moltype = AA   length = 295
FEATURE                 Location/Qualifiers
REGION                  1..295
                        note = Engineered glucosaminyl 6-O sulfotransferase
                         mutant_variable 1
SITE                    11
```

-continued

```
                        note = MISC_FEATURE - Xaa is glycine or histidine
SITE                    13
                        note = MISC_FEATURE - Xaa is glycine, alanine, serine, or
                         glutamine
SITE                    14
                        note = MISC_FEATURE - Xaa is histidine or lysine
SITE                    16
                        note = MISC_FEATURE - Xaa is histidine or glycine
SITE                    18
                        note = MISC_FEATURE - Xaa is alanine or threonine
SITE                    63
                        note = MISC_FEATURE - Xaa is glycine or tryptophan
SITE                    67
                        note = MISC_FEATURE - Xaa is threonine, serine, leucine, or
                         alanine
SITE                    68
                        note = MISC_FEATURE - Xaa is asparagine, arginine,
                         glutamine, histidine, or alanine
SITE                    103
                        note = MISC_FEATURE - Xaa is histidine or arginine
SITE                    104
                        note = MISC_FEATURE - Xaa is histidine, lysine, leucine, or
                         aspartic acid
SITE                    107
                        note = MISC_FEATURE - Xaa is histidine or serine
SITE                    111
                        note = MISC_FEATURE - Xaa is glycine or serine
SITE                    112
                        note = MISC_FEATURE - Xaa is alanine, histidine, glutamic
                         acid, methionine, or glycine
SITE                    116
                        note = MISC_FEATURE - Xaa is histidine, methionine, valine,
                         or threonine
SITE                    120
                        note = MISC_FEATURE - Xaa is glycine, alanine, or proline
SITE                    121
                        note = MISC_FEATURE - Xaa is serine, threonine, asparagine,
                         or alanine
SITE                    122
                        note = MISC_FEATURE - Xaa is asparagine, tryptophan,
                         histidine, or glycine
SITE                    123
                        note = MISC_FEATURE - Xaa is serine, lysine, or threonine
SITE                    125
                        note = MISC_FEATURE - Xaa is glycine or serine
SITE                    164
                        note = MISC_FEATURE - Xaa is glycine or alanine
SITE                    212
                        note = MISC_FEATURE - Xaa is alanine, glycine, or threonine
SITE                    213
                        note = MISC_FEATURE - Xaa is valine, arginine, or glutamic
                         acid
SITE                    215
                        note = MISC_FEATURE - Xaa is glycine or glutamine
SITE                    236
                        note = MISC_FEATURE - Xaa is valine or glutamine
SITE                    237
                        note = MISC_FEATURE - Xaa is valine, threonine, or tyrosine
SITE                    238
                        note = MISC_FEATURE - Xaa is lysine or asparagine
SITE                    240
                        note = MISC_FEATURE - Xaa is serine, asparagine, or
                         threonine
SITE                    243
                        note = MISC_FEATURE - Xaa is serine or glycine
source                  1..295
                        mol_type = protein
                        organism = synthetic construct
SEQUENCE: 110
MKGDDVIVFL XIXXTXGXTF GRHLVQNVRL EVPCDCRPGQ KKCTCYRPNR RETWLFSRFS  60
TGXSCGXXAD WTELTNCVPG VLDRRDPAGL RSPRKFYYIT LLXXPVXRYL XXWRHXQRGX  120
XXXTXLHMCD GRTPTPEELP PCYEGTDWSG CTLQEFMDCP YNLXNNRQVR MLADLSLVGC  180
YNLSFIPESK RAQLLLESAK KNLRGMAFFG LXXFXRKTQY LFERTFNLKF IRPFMXXXSX  240
RAXGVEVDED TIRHIEELND LDMQLYDYAK DLFQQRYQYK RQLERREQRL RNREE       295

SEQ ID NO: 111          moltype = AA  length = 411
FEATURE                 Location/Qualifiers
REGION                  1..411
                        note = Engineered glucosaminyl 6-O sulfotransferase
```

```
                         mutant_variable 2
SITE                     93
                         note = MISC_FEATURE - Xaa is glycine or histidine
SITE                     95
                         note = MISC_FEATURE - Xaa is glycine, serine, alanine, or
                         glutamine
SITE                     96
                         note = MISC_FEATURE - Xaa is histidine or lysine
SITE                     98
                         note = MISC_FEATURE - Xaa is histidine or glycine
SITE                     100
                         note = MISC_FEATURE - Xaa is alanine or threonine
SITE                     145
                         note = MISC_FEATURE - Xaa is glycine or tryptophan
SITE                     149
                         note = MISC_FEATURE - Xaa is threonine, serine, leucine, or
                         alanine
SITE                     150
                         note = MISC_FEATURE - Xaa is asparagine, arginine,
                         glutamine, histidine, or alanine
SITE                     185
                         note = MISC_FEATURE - Xaa is histidine or arginine
SITE                     186
                         note = MISC_FEATURE - Xaa is histidine, lysine, leucine, or
                         aspartic acid
SITE                     189
                         note = MISC_FEATURE - Xaa is histidine or serine
SITE                     193
                         note = MISC_FEATURE - Xaa is glycine or serine
SITE                     194
                         note = MISC_FEATURE - Xaa is alanine, histidine, glutamic
                         acid, methionine, or glycine
SITE                     198
                         note = MISC_FEATURE - Xaa is histidine, methionine, valine,
                         or threonine
SITE                     202
                         note = MISC_FEATURE - Xaa is glycine, alanine, pr proline
SITE                     203
                         note = MISC_FEATURE - Xaa is serine, threonine, asparagine,
                         or alanine
SITE                     204
                         note = MISC_FEATURE - Xaa is asparagine, tryptophan,
                         histidine, or glycine
SITE                     205
                         note = MISC_FEATURE - Xaa is serine, lysine, or threonine
SITE                     207
                         note = MISC_FEATURE - Xaa is glycine or serine
SITE                     246
                         note = MISC_FEATURE - Xaa is glycine or alanine
SITE                     294
                         note = MISC_FEATURE - Xaa is alanine, glycine, or threonine
SITE                     295
                         note = MISC_FEATURE - Xaa is tryptophan, arginine, or
                         glutamic acid
SITE                     297
                         note = MISC_FEATURE - Xaa is glycine or glutamine
SITE                     318
                         note = MISC_FEATURE - Xaa is valine or glutamine
SITE                     319
                         note = MISC_FEATURE - Xaa is valine, threonine, or tyrosine
SITE                     320
                         note = MISC_FEATURE - Xaa is lysine or asparagine
SITE                     322
                         note = MISC_FEATURE - Xaa is serine, asparagine, or
                         threonine
SITE                     325
                         note = MISC_FEATURE - Xaa is serine or glycine
source                   1..411
                         mol_type = protein
                         organism = synthetic construct
SEQUENCE: 111
MRRRRAGGRT MVERASKFVL VVAGSACFML ILYQYAGPGL SLGAPGGRVP PDDLDLFPTP    60
DPHYEKKYYF PVRELERSLR FDMKGDDVIV FLXIXXTXGX TFGRHLVQNV RLEVPCDCRP   120
GQKKCTCYRP NRRETWLFSR FSTGXSCGXX ADWTELTNCV PGVLDRRDPA GLRSPRKFYY   180
ITLLXXPVXR YLXXWRHXQR GXXXXTXLHM CDGRTPTPEE LPPCYEGTDW SGCTLQEFMD   240
CPYNLXNNRQ VRMLADLSLV GCYNLSFIPE SKRAQLLLES AKKNLRGMAF FGLXXFXRKT   300
QYLFERTFNL KFIRPFMXXX SXRAXGVEVD EDTIRHIEEL NDLDMQLYDY AKDLFQQRYQ   360
YKRQLERREQ RLRNREERLL HRSKEALPRE DPEEPGRVPT EDYMSHIIEK W            411
```

| SEQ ID NO: 112 | moltype = AA   length = 312 |
| --- | --- |
| FEATURE | Location/Qualifiers |
| REGION | 1..312 |
| | note = Engineered glucosaminyl 6-O sulfotransferasemutant_sulfotransferase 4 |
| SITE | 84 |
| | note = MISC_FEATURE - Xaa is threonine or serine |
| SITE | 85 |
| | note = MISC_FEATURE - Xaa is asparagine, arginine, or histidine |
| SITE | 128 |
| | note = MISC_FEATURE - Xaa is glycine or serine |
| SITE | 129 |
| | note = MISC_FEATURE - Xaa is glycine or histidine |
| SITE | 133 |
| | note = MISC_FEATURE - Xaa is histidine or threonine |
| SITE | 138 |
| | note = MISC_FEATURE - Xaa is alanine or threonine |
| SITE | 142 |
| | note = MISC_FEATURE - Xaa is glycine or serine |
| SITE | 181 |
| | note = MISC_FEATURE - Xaa is glycine or alanine |
| source | 1..312 |
| | mol_type = protein |
| | organism = synthetic construct |

SEQUENCE: 112
```
MKYYFPVREL ERSLRFDMKG DDVIVFLHIG HTGGTTFGRH LVQNVRLEVP CDCRPGQKKC   60
TCYRPNRRET WLFSRFSTGW SCGXXADWTE LTNCVPGVLD RRDPAGLRSP RKFYYITLLR  120
DPVSRYLXXW RHXQRGGXNK TXLHMCDGRT PTPEELPPCY EGTDWSGCTL QEFMDCPYNL  180
XNNRQVRMLA DLSLVGCYNL SFIPESKRAQ LLLESAKKNL RGMAFFGLTE FQRKTQYLFE  240
RTFNLKFIRP FMQYNSTRAG GVEVDEDTIR HIEELNDLDM QLYDYAKDLF QQRYQYKRQL  300
ERREQRLRNR EE                                                    312
```

| SEQ ID NO: 113 | moltype = AA   length = 411 |
| --- | --- |
| FEATURE | Location/Qualifiers |
| REGION | 1..411 |
| | note = Engineered glucosaminyl 6-O sulfotransferasemutant_sulfotransferase 5 |
| SITE | 149 |
| | note = MISC_FEATURE - Xaa is threonine or serine |
| SITE | 150 |
| | note = MISC_FEATURE - Xaa is asparagine, arginine, or histidine |
| SITE | 193 |
| | note = MISC_FEATURE - Xaa is glycine or serine |
| SITE | 194 |
| | note = MISC_FEATURE - Xaa is glycine or histidine |
| SITE | 198 |
| | note = MISC_FEATURE - Xaa is histidine or threonine |
| SITE | 203 |
| | note = MISC_FEATURE - Xaa is alanine or threonine |
| SITE | 207 |
| | note = MISC_FEATURE - Xaa is glycine or serine |
| SITE | 246 |
| | note = MISC_FEATURE - Xaa is glycine or alanine |
| source | 1..411 |
| | mol_type = protein |
| | organism = synthetic construct |

SEQUENCE: 113
```
MRRRRAGGRT MVERASKFVL VVAGSACFML ILYQYAGPGL SLGAPGGRVP PDDLDLFPTP   60
DPHYEKKYYF PVRELERSLR FDMKGDDVIV FLHIGHTGGT TFGRHLVQNV RLEVPCDCRP  120
GQKKCTCYRP NRRETWLFSR FSTGWSCGXX ADWTELTNCV PGVLDRRDPA GLRSPRKFYY  180
ITLLRDPVSR YLXXWRHXQR GGXNKTXLHM CDGRTPTPEE LPPCYEGTDW SGCTLQEFMD  240
CPYNLXNNRQ VRMLADLSLV GCYNLSFIPE SKRAQLLLES AKKNLRGMAF FGLTEFQRKT  300
QYLFERTFNL KFIRPFMQYN STRAGGVEVD EDTIRHIEEL NDLDMQLYDY AKDLFQQRYQ  360
YKRQLERREQ RLRNREERLL HRSKEALPRE DPEEPGRVPT EDYMSHIIEK W          411
```

| SEQ ID NO: 114 | moltype = AA   length = 312 |
| --- | --- |
| FEATURE | Location/Qualifiers |
| REGION | 1..312 |
| | note = Engineered glucosaminyl 6-O sulfotransferasemutant_sulfotransferase 6 |
| source | 1..312 |
| | mol_type = protein |
| | organism = synthetic construct |

SEQUENCE: 114
```
MKYYFPVREL ERSLHFDMKG DDVIVFLHIG HTGGTTFGRH LVQNVRLEVP CDCRPGQKKC   60
TCYRPNRRET WLFSRFSTGW SCGTNADWTE LTNCVPGVLD RRDPAALRTP RKFYYITLLR  120
DPVSRYLGGW RHHQRGGTNK TSLHMCDGRT PTPEELPPCY EGTDWSGCTL QEFMDCPYNL  180
```

```
ANNRQVRMLA DLSLVGCYNL SFIPEGKRSQ LLLESAKKNL RGMAFFGLTE FQRKTQYLFE     240
RTFNLKFIRP FMQYNSTRAG GVEVGEDTIR RIEELNDLDM QLYDYARDLF QQRYQYKRQL     300
ERRQQRLRSR EE                                                         312

SEQ ID NO: 115          moltype = AA  length = 312
FEATURE                 Location/Qualifiers
REGION                  1..312
                        note = Engineered glucosaminyl 6-O
                        sulfotransferasemutant_sulfotransferase 7
source                  1..312
                        mol_type = protein
                        organism = synthetic construct
SEQUENCE: 115
MKYYFPVREL ERSLHFDMKG DDVIVFLHIG HTGGTTFGRH LVQNVRLEVP CDCRPGQKKC      60
TCYRPNRRET WLFSRFSTGW SCGTRADWTE LTNCVPGVLD RRDPAALRTP RKFYYITLLR     120
DPVSRYLSHW RHTQRGGANK TGLHMCDGRT PTPEELPPCY EGTDWSGCTL QEFMDCPYNL     180
GNNRQVRMLA DLSLVGCYNL SFIPEGKRSQ LLLESAKKNL RGMAFFGLTE FQRKTQYLFE     240
RTFNLKFIRP FMQYNSTRAG GVEVGEDTIR RIEELNDLDM QLYDYARDLF QQRYQYKRQL     300
ERRQQRLRSR EE                                                         312

SEQ ID NO: 116          moltype = AA  length = 312
FEATURE                 Location/Qualifiers
REGION                  1..312
                        note = Engineered glucosaminyl 6-O
                        sulfotransferasemutant_sulfotransferase 8
source                  1..312
                        mol_type = protein
                        organism = synthetic construct
SEQUENCE: 116
MKYYFPVREL ERSLHFDMKG DDVIVFLHIG HTGGTTFGRH LVQNVRLEVP CDCRPGQKKC      60
TCYRPNRRET WLFSRFSTGW SCGSHADWTE LTNCVPGVLD RRDPAALRTP RKFYYITLLR     120
DPVSRYLSGW RHHQRGGANK TSLHMCDGRT PTPEELPPCY EGTDWSGCTL QEFMDCPYNL     180
GNNRQVRMLA DLSLVGCYNL SFIPEGKRSQ LLLESAKKNL RGMAFFGLTE FQRKTQYLFE     240
RTFNLKFIRP FMQYNSTRAG GVEVGEDTIR RIEELNDLDM QLYDYARDLF QQRYQYKRQL     300
ERRQQRLRSR EE                                                         312

SEQ ID NO: 117          moltype = AA  length = 411
FEATURE                 Location/Qualifiers
REGION                  1..411
                        note = Engineered glucosaminyl 6-O
                        sulfotransferasemutant_sulfotransferase 9
source                  1..411
                        mol_type = protein
                        organism = synthetic construct
SEQUENCE: 117
MRRRRAGSRT MVERASKFVL VVAGSACFML ILYQYAGPGL SLGAPGGRAP PDDLDLFPTP      60
DPHYEKKYYF PVRELERSLH FDMKGDDVIV FLHIGHTGGT TFGRHLVQNV RLEVPCDCRP     120
GQKKCTCYRP NRRETWLFSR FSTGWSCGTR ADWTELTNCV PGVLDRRDPA ALRTPRKFYY     180
ITLLRDPVSR YLGGWRHHQR GGTNKTSLHM CDGRTPTPEE LPPCYEGTDW SGCTLQEFMD     240
CPYNLANNRQ VRMLADLSLV GCYNLSFIPE GKRSQLLLES AKKNLRGMAF FGLTEFQRKT     300
QYLFERTFNL KFIRPFMQYN STRAGGVEVG EDTIRRIEEL NDLDMQLYDY ARDLFQQRYQ     360
YKRQLERRQQ RLRSREERLL HRAKEAPPRG DTEEPGRVPT EDYMSHIIEK W              411

SEQ ID NO: 118          moltype = AA  length = 411
FEATURE                 Location/Qualifiers
REGION                  1..411
                        note = Engineered glucosaminyl 6-O
                        sulfotransferasemutant_sulfotransferase 10
source                  1..411
                        mol_type = protein
                        organism = synthetic construct
SEQUENCE: 118
MRRRRAGSRT MVERASKFVL VVAGSACFML ILYQYAGPGL SLGAPGGRAP PDDLDLFPTP      60
DPHYEKKYYF PVRELERSLH FDMKGDDVIV FLHIGHTGGT TFGRHLVQNV RLEVPCDCRP     120
GQKKCTCYRP NRRETWLFSR FSTGWSCGTR ADWTELTNCV PGVLDRRDPA ALRTPRKFYY     180
ITLLRDPVSR YLSHWRHTQR GGANKTGLHM CDGRTPTPEE LPPCYEGTDW SGCTLQEFMD     240
CPYNLGNNRQ VRMLADLSLV GCYNLSFIPE GKRSQLLLES AKKNLRGMAF FGLTEFQRKT     300
QYLFERTFNL KFIRPFMQYN STRAGGVEVG EDTIRRIEEL NDLDMQLYDY ARDLFQQRYQ     360
YKRQLERRQQ RLRSREERLL HRAKEAPPRG DTEEPGRVPT EDYMSHIIEK W              411

SEQ ID NO: 119          moltype = AA  length = 411
FEATURE                 Location/Qualifiers
REGION                  1..411
                        note = Engineered glucosaminyl 6-O
                        sulfotransferasemutant_sulfotransferase 11
source                  1..411
                        mol_type = protein
                        organism = synthetic construct
SEQUENCE: 119
```

```
MRRRRAGSRT MVERASKFVL VVAGSACFML ILYQYAGPGL SLGAPGGRAP PDDLDLFPTP  60
DPHYEKKYYF PVRELERSLH FDMKGDDVIV FLHIGHTGGT TFGRHLVQNV RLEVPCDCRP 120
GQKKCTCYRP NRRETWLFSR FSTGWSCGSH ADWTELTNCV PGVLDRRDPA ALRTPRKFYY 180
ITLLRDPVSR YLSGWRHHQR GGANKTSLHM CDGRTPTPEE LPPCYEGTDW SGCTLQEFMD 240
CPYNLGNNRQ VRMLADLSLV GCYNLSFIPE GKRSQLLLES AKKNLRGMAF FGLTEFQRKT 300
QYLFERTFNL KFIRPFMQYN STRAGGVEVG EDTIRRIEEL NDLDMQLYDY ARDLFQQRYQ 360
YKRQLERRQQ RLRSREERLL HRAKEAPPRG DTEEPGRVPT EDYMSHIIEK W         411

SEQ ID NO: 120            moltype = AA   length = 470
FEATURE                   Location/Qualifiers
REGION                    1..470
                          note = Engineered glucosaminyl 6-O
                           sulfotransferasemutant_sulfotransferase 12
source                    1..470
                          mol_type = protein
                          organism = synthetic construct
SEQUENCE: 120
MDERFNKWLL TPVLTLLFVV IMYQYVSPSC TSSCTNFGEQ LRSGEARPPA VPSPARRAQA  60
PLDEWERRPQ LPPPPRGPPE GSRGVAAPED EDEDPGDPEE EEEEEEEEPD PEAPENGSLP 120
RFVPRFNFTL KDLTRFVDFN IKGRDVIVFL HIGHTGGTTF GRHLVKNIRL EQPCSCKAGQ 180
KKCTCHRPGK KETWLFSRFS TGWSCGTNAD WTELTNCVPA IMEKKDCPRN HSHTRNFYYI 240
TMLRDPVSRY LGGWKHHQRG GTNKTSLHMC DGRSPTPDEL PTCYPGDDWS GVSLREFMDC 300
SYNLANNRQV RMLADLSLVG CYNLTFMNES ERNTILLQSA KNNLKNMAFF GLTEFQRKTQ 360
FLFERTFNLK FISPFTQVNI TRASNVDIND GARQHIEELN FLDMQLYEYA KDLFQQRYHH 420
TKQLEHQRDR QKRREERRLQ REHRAHRWPK EDRAMEGTVT EDYNSQVVRW           470

SEQ ID NO: 121            moltype = AA   length = 470
FEATURE                   Location/Qualifiers
REGION                    1..470
                          note = Engineered glucosaminyl 6-O
                           sulfotransferasemutant_sulfotransferase 13
source                    1..470
                          mol_type = protein
                          organism = synthetic construct
SEQUENCE: 121
MDERFNKWLL TPVLTLLFVV IMYQYVSPSC TSSCTNFGEQ LRSGEARPPA VPSPARRAQA  60
PLDEWERRPQ LPPPPRGPPE GSRGVAAPED EDEDPGDPEE EEEEEEEEPD PEAPENGSLP 120
RFVPRFNFTL KDLTRFVDFN IKGRDVIVFL HIGHTGGTTF GRHLVKNIRL EQPCSCKAGQ 180
KKCTCHRPGK KETWLFSRFS TGWSCGTRAD WTELTNCVPA IMEKKDCPRN HSHTRNFYYI 240
TMLRDPVSRY LSHWKHTQRG GANKTGLHMC DGRSPTPDEL PTCYPGDDWS GVSLREFMDC 300
SYNLGNNRQV RMLADLSLVG CYNLTFMNES ERNTILLQSA KNNLKNMAFF GLTEFQRKTQ 360
FLFERTFNLK FISPFTQFNI TRASNVDIND GARQHIEELN FLDMQLYEYA KDLFQQRYHH 420
TKQLEHQRDR QKRREERRLQ REHRAHRWPK EDRAMEGTVT EDYNSQVVRW           470

SEQ ID NO: 122            moltype = AA   length = 470
FEATURE                   Location/Qualifiers
REGION                    1..470
                          note = Engineered glucosaminyl 6-O
                           sulfotransferasemutant_sulfotransferase 14
source                    1..470
                          mol_type = protein
                          organism = synthetic construct
SEQUENCE: 122
MDERFNKWLL TPVLTLLFVV IMYQYVSPSC TSSCTNFGEQ LRSGEARPPA VPSPARRAQA  60
PLDEWERRPQ LPPPPRGPPE GSRGVAAPED EDEDPGDPEE EEEEEEEEPD PEAPENGSLP 120
RFVPRFNFTL KDLTRFVDFN IKGRDVIVFL HIGHTGGTTF GRHLVKNIRL EQPCSCKAGQ 180
KKCTCHRPGK KETWLFSRFS TGWSCGSHAD WTELTNCVPA IMEKKDCPRN HSHTRNFYYI 240
TMLRDPVSRY LSGWKHHQRG GANKTSLHMC DGRSPTPDEL PTCYPGDDWS GVSLREFMDC 300
SYNLGNNRQV RMLADLSLVG CYNLTFMNES ERNTILLQSA KNNLKNMAFF GLTEFQRKTQ 360
FLFERTFNLK FISPFTQFNI TRASNVDIND GARQHIEELN FLDMQLYEYA KDLFQQRYHH 420
TKQLEHQRDR QKRREERRLQ REHRAHRWPK EDRAMEGTVT EDYNSQVVRW           470

SEQ ID NO: 123            moltype = AA   length = 265
FEATURE                   Location/Qualifiers
REGION                    1..265
                          note = Engineered glucosaminyl 3-O sulfotransferase
                           mutant_sulfatase 1
source                    1..265
                          mol_type = protein
                          organism = synthetic construct
SEQUENCE: 123
MGTASNGSTQ QLPQTIIIGV GHGGTRALLE MLSLHPDVAA AENEVHFFDW EEHYSQGLGW  60
YLTQMPFSSP HQLTVEKTHA YFTSPKVPER IHSMNPTIRL LLILRDPSER VLSAYTHMLY 120
NHLQKHKPYP PIEDLLMRDG RLNLDMVMLN RSLYHAHMLN WLRFFPLGHI HIVDGDRLIR 180
DPFPEIQKVE RFLKLSPQIN ASNFYFNKTK GFYCLRDSGK DRCLHESKGR AHPQVDPKLL 240
DKLHEYFHEP NKKFFKLVGR TFDWH                                     265

SEQ ID NO: 124            moltype = DNA   length = 795
FEATURE                   Location/Qualifiers
```

| misc_feature | 1..795 |
| | note = Polynucleotide sequence encoding for engineered |
| | glucosaminyl 3-Osulfotransferase mutant_sulfatase 1 |
| source | 1..795 |
| | mol_type = other DNA |
| | organism = synthetic construct |

SEQUENCE: 124

```
atgggaactg cgtcgaacgg cagtacgcaa cagttaccgc aaaccatcat tattggcgtg   60
ggtcacgggg ggacccgtgc acttctggaa atgttgagtc tgcaccctga cgtggccgct  120
gcagagaacg aagtccactt cttcgattgg gaggagcatt atagtcaagg cttggggtgg  180
tatcttaccc agatgccttt cagctccccc catcagctta ccgttgaaaa gactcatgcc  240
tattttacat cgcccaaagt tcctgaacgt attcatagca tgaaccccac aattcgttta  300
cttttgatcc tgcgtgatcc aagcgagcgc gttttatcgg catacacgca catgttatat  360
aatcatttgc agaagcacaa accttaccca ccaattgagg acttattgat gcgtgatggt  420
cgcttaaatt tagatatggt aatgctgaat cgttcccttt atcacgcaca catgttaaac  480
tggctgcgct tcttcccgtt gggtcatatc catattgtcg atggggatcg cttaattcgc  540
gacccatttc cggagatcca aaaggttgag cgtttcttaa aactgtcgcc tcaaatcaac  600
gcgtcaaact tttacttcaa caagacgaaa ggtttctatt gcctgcgtga tagcggtaag  660
gaccgctgct tgcatgaatc taaagggcgt gctcatccac aagttgatcc taaattactt  720
gataagctgc atgaatactt ccatgaacct aacaaaaagt tcttcaaact tgtcggccgc  780
acatttgatt ggcat                                                   795
```

| SEQ ID NO: 125 | moltype = AA length = 265 |
| FEATURE | Location/Qualifiers |
| REGION | 1..265 |
| | note = Engineered glucosaminyl 3-O sulfotransferase |
| | mutant_sulfatase 2 |
| source | 1..265 |
| | mol_type = protein |
| | organism = synthetic construct |

SEQUENCE: 125

```
MGTASNGSTQ QLPQTIIIGV GHGGTRALLE MLSLHPDVAA AENEVHFFDW EEHYSQGLGW   60
YLTQMPFSSP HQLTVEKTHA YFTSPKVPER IHSMNPTIRL LLILRDPSER VLSAYTHLLY  120
NHLQKHKPYP PIEDLLMRDG RLNLDYRGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265
```

| SEQ ID NO: 126 | moltype = DNA length = 795 |
| FEATURE | Location/Qualifiers |
| misc_feature | 1..795 |
| | note = Polynucleotide sequence encoding for engineered |
| | glucosaminyl 3-Osulfotransferase mutant_sulfatase 2 |
| source | 1..795 |
| | mol_type = other DNA |
| | organism = synthetic construct |

SEQUENCE: 126

```
atgggaactg cgtcgaacgg cagtacgcaa cagttacccc agacaattat tattggcgta   60
gggcacggag gtactcgcgc cttattggaa atgctgtcct acatccaga cgtggcagcg  120
gctgaaaacg aggtacattt cttttgactgg gaagaacact actcacaggg actgggatgg  180
tacctgaccc aaatgccctt cagttcaccg catcagttga cagtagagaa gacacatgca  240
tattttacgt cgccaaaagt cccggaacgt attcattcga tgaatcccac gattcgtctg  300
ttgttaatct tgcgtgaccc tagtgagcgt gttcttttctg cgtacactca cttgctgtat  360
aaccatttac agaaacacaa gccatatccg ccgattgaag atctgttgat gcgtgacggg  420
cgtcttaacc tggactatcg tggcctgaac cgctctttat accacgcgca catgttgaat  480
tggcttcgct tcttccccctt gggacatatt catattgtgg atggagatcg cttaatccgt  540
gatccattcc cggaaattca gaaggttgag cgtttcctga agttgtctcc acaaattaat  600
gcaagcaact tttactttaa taaaaccaag ggcttctact gtttgcgcga tagcggaaaa  660
gaccgctgcc tgcatgagtc caaaggacgt gcacatcccc aagtcgatcc aaagttgctt  720
gacaaattac acgagtattt ccatgaaccg aataaaaagt ttttaagtt ggtcggccgc  780
acatttgatt ggcat                                                   795
```

| SEQ ID NO: 127 | moltype = AA length = 265 |
| FEATURE | Location/Qualifiers |
| REGION | 1..265 |
| | note = Engineered glucosaminyl 3-O sulfotransferase |
| | mutant_sulfatase 3 |
| source | 1..265 |
| | mol_type = protein |
| | organism = synthetic construct |

SEQUENCE: 127

```
MGTASNGSTQ QLPQTIIIGV GHGGTRALLE MLSLHPDVAA AENEVHFFDW EEHYSQGLGW   60
YLTQMPFSSP HQLTVEKTHA YFTSPKVPER IHSMNPTIRL LLILRDPSER VLSAYTHLLY  120
NHLQKHKPYP PIEDLLMRDG RLNLDYVGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265
```

| SEQ ID NO: 128 | moltype = DNA length = 795 |
| FEATURE | Location/Qualifiers |
| misc_feature | 1..795 |

```
                    note = Polynucleotide sequence encoding for engineered
                      glucosaminyl 3-Osulfotransferase mutant_sulfatase 3
source              1..795
                    mol_type = other DNA
                    organism = synthetic construct
SEQUENCE: 128
atgggaactg cgtcgaacgg cagtacgcaa caattgccac agacaattat cattggcgtt   60
ggtcatgggg ggacgcgcgc tctgctggaa atgttgtccc ttcacccaga tgtggccgct  120
gcggagaacg aagttcactt cttcgactgg gaagaacact atagccaagg gttgggtgg   180
tacctgaccc aaatgccgtt cagtagtcct catcaattga ccgttgagaa aactcacgct  240
tactttacct cgcccaaggt accccgagcgc atccacagca tgaacccac tatccgcctg   300
ctgcttattt tgcgtgaccc ttcagagcgc gttttaagcg cgtatactca tcttctttat  360
aaccaccttc agaagcacaa gccttatcct ccgattgaag atttgttgat gcgcgatggc  420
cgcttgaact tagactatgt cgggcttaac cgttctcttt accatgccca catgcttaac  480
tggctgcgct ttttttccgct tggacacatc cacatcgtcg acggggaccg cttgattcgt  540
gacccctttc ccgagattca aaaggttgaa cgttctctaa agctttcacc tcaaatcaat  600
gcgtccaact tttattttaa caagactaaa ggcttctact gcttacgcga ctcaggaaaa  660
gatcgctgct tacatgaatc gaaggggcgt gcccatccac aagttgatcc taaattattg  720
gataagctgc acgaatactt ccatgagcca aataagaaat tctttaagtt agtcggccgc  780
acatttgatt ggcat                                                   795

SEQ ID NO: 129       moltype = AA  length = 265
FEATURE              Location/Qualifiers
REGION              1..265
                    note = Engineered glucosaminyl 3-O sulfotransferase
                      mutant_sulfatase 4
source              1..265
                    mol_type = protein
                    organism = synthetic construct
SEQUENCE: 129
MGTASNGSTQ QLPQTIIIGV GHGGTRALLE MLSLHPDVAA AENEVHFFDW EEHYSQGLGW   60
YLTQMPFSSP HQLTVEKTHL YFTSPKVPER IHSMNPTIRL LLILRDPSER VLSWYTHALY  120
AHLQKHKPYP PIEDLLMRDG RLNLDYTGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 130       moltype = DNA  length = 795
FEATURE              Location/Qualifiers
misc_feature        1..795
                    note = Polynucleotide sequence encoding for engineered
                      glucosaminyl 3-Osulfotransferase mutant_sulfatase 4
source              1..795
                    mol_type = other DNA
                    organism = synthetic construct
SEQUENCE: 130
atgggaactg cgtcgaacgg cagtacgcaa caattgcctc agactatcat cattggggta   60
ggacacggag gtacacgtgc attgcttgag atgttaagtc ttcatcccga tgttgctgca  120
gctgaaaatg aagtacactt tttcgactgg gaagagcact acagtcaggg actgggttgg  180
tatctgacgc agatgccttt ttcaagcccc atcagttga ccgtagaaaa gactcatctt   240
tacttcacct ccccgaaggt ccccgaacgt attcattcca tgaacccaac catccgttta  300
cttttgatcc ttcgtgatcc cagtgagcgc gtccttagtt ggtacactca tgccctgtac  360
gctcatttac agaaacacaa accatacccg ccgattgagg accttttaat gcgcgatggc  420
cgtcttaatc ttgattatac aggcctgaat cgttctcttt accacgcaca catgttaaat  480
tggctgcgtt tctttccact tggacacatc catatcgtgg atggtgaccg cttaatccgc  540
gatccttttcc cggagattca gaaagttgaa cgcttcctta actgtcacc gcagatcaat  600
gcctcgaatt tctacttcaa taagactaag gcttctact gcttgcgcga ctctggcaag  660
gatcgttgct acacgaatca taaggggcgt gctcatccac aggtcgaccc aaagttgctt  720
gacaaattgc acgaatattt tcacgagcca aataaaaagt tctttaagct ggtcggccgc  780
acatttgatt ggcat                                                   795

SEQ ID NO: 131       moltype = AA  length = 265
FEATURE              Location/Qualifiers
REGION              1..265
                    note = Engineered glucosaminyl 3-O sulfotransferase
                      mutant_sulfatase 5
source              1..265
                    mol_type = protein
                    organism = synthetic construct
SEQUENCE: 131
MGTASNGSTQ QLPQTIIIGV GHGGTRALLE MLSLHPDVAA AENEVHFFDW EEHYSQGLGW   60
YLTQMPFSSP HQLTVEKTHL YFTSPKVPER IHSMNPTIRL LLILRDPSER VLSLYTHALY  120
NHLQKHKPYP PIEDLLMRDG RLNLDYTGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 132       moltype = DNA  length = 795
FEATURE              Location/Qualifiers
misc_feature        1..795
                    note = Polynucleotide sequence encoding for engineered
```

```
                          glucosaminyl 3-Osulfotransferase mutant_sulfatase 5
source                    1..795
                          mol_type = other DNA
                          organism = synthetic construct
SEQUENCE: 132
atgggaactg cgtcgaacgg cagtacgcaa caattaccac aaacaatcat catcggggta    60
gggcatggtg gaactcgtgc tttgcttgag atgctttcac tgcatcccga cgtggctgca   120
gcggagaatg aagtgcattt cttcgattgg gaagaacatt atagccaggg ccttgggtgg   180
tatctgaccc agatgccatt cagttctccc catcagctga ccgtcgaaaa gacccatttg   240
tattttactt cgcctaaagt tcccgaacgt atccacagca tgaacccgac gattcgttta   300
ctgctgattc tgcgtgaccc gtcagagcgt gtccttagtt tatatacgca cgctttgtat   360
aaccacttac aaaaacataa accataccca cccattgaag acttattaat gcgcgacgga   420
cgtctgaact tagactacac ggggctgaat cgttcattgt atcatgccca catgcttaac   480
tggttgcgtt tttttccatt gggacacatc catattgtta acggagatcg tctgatccgc   540
gaccctttc ccgagattca aaaagtcgaa cgtttttga aattatcgcc acaaattaac   600
gcctctaatt tttacttcaa caagactaaa ggttttatt gttacgtga tagtggtaag    660
gaccgctgtc ttcatgaatc aaagggacgc gcacatcccc aagtagatcc aaaacttctg   720
gataagttac acgagtattt ccatgagcct aacaagaaat tttttaagct tgtcggccgc   780
acatttgatt ggcat                                                    795

SEQ ID NO: 133            moltype = AA  length = 265
FEATURE                   Location/Qualifiers
REGION                    1..265
                          note = Engineered glucosaminyl 3-O sulfotransferase
                          mutant_sulfatase 6
source                    1..265
                          mol_type = protein
                          organism = synthetic construct
SEQUENCE: 133
MGTASNGSTQ QLPQTIIIGV GHGGTRALLE MLSLHPDVAA AENEVHFFDW EEHYSQGLGW    60
YLTQMPFSSP HQLTVEKTHT YFTSPKVPER IHSMNPTIRL LLILRDPSER VLSLYTHALY   120
MHLQKHKPYP PIEDLLMRDG RLNLDYAGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                        265

SEQ ID NO: 134            moltype = DNA  length = 795
FEATURE                   Location/Qualifiers
misc_feature              1..795
                          note = Polynucleotide sequence encoding for engineered
                          glucosaminyl 3-Osulfotransferase mutant_sulfatase 6
source                    1..795
                          mol_type = other DNA
                          organism = synthetic construct
SEQUENCE: 134
atgggaactg cgtcgaacgg cagtacgcaa caattacctc agaccattat tattggtgtc    60
ggccatggag gaacgcgtgc tctgctggag atgctttcgc ttcaccccga cgtggcggct   120
gccgagaatg aggtacactt ttttgattgg gaagagcatt actcacaagg tttgggctgg   180
taccttactc agatgccctt ttcgtcaccg catcaactga cggtggagaa gacccacact   240
tacttcacca gtccaaaagt ccctgaacgc atccatagca tgaatcctac aattcgtctt   300
cttttgatcc ttcgcgatcc atctgagcgt gtgttatcct tatatacccca cgcgctttac   360
atgcaccttc agaagcacaa gccctatccc ccaattgagg acttgctgat gcgcgatggc   420
cgtcttaatt tggattatgc aggactgaat cgttccctgt accacgccca catgctgaac   480
tggttgcgct tctttccact tggccacatc catattgtcg acggggatcg tctgattcgt   540
gatccgttcc cagaaatcca gaaggtgaaa cgcttcctga aattgagccc acagattaac   600
gcgtcgaatt tttactttaa caaaaccaaa ggattctatt gtcttcgtga cagtggaaaa   660
gatcgctgct tacacgaatc gaaaggccgc gctcatcccc aagttgatcc gaagcttctt   720
gataagttgc acgagtactt ccacgaaccg aacaagaagt ttttcaagct ggtcggccgc   780
acatttgatt ggcat                                                    795

SEQ ID NO: 135            moltype = AA  length = 265
FEATURE                   Location/Qualifiers
REGION                    1..265
                          note = Engineered glucosaminyl 3-O sulfotransferase
                          mutant_sulfatase 7
source                    1..265
                          mol_type = protein
                          organism = synthetic construct
SEQUENCE: 135
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSVYTHALY   120
MHLQKHKPYP PIEDLLMRDG RLNLDYMGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                        265

SEQ ID NO: 136            moltype = DNA  length = 795
FEATURE                   Location/Qualifiers
misc_feature              1..795
                          note = Polynucleotide sequence encoding for engineered
                          glucosaminyl 3-Osulfotransferase mutant_sulfatase 7
```

```
source              1..795
                    mol_type = other DNA
                    organism = synthetic construct
SEQUENCE: 136
atgggaactg cgtcgaacgg cagtacgcaa cagcttcccc agacgatcat tatcggagtc   60
ggtcatggtg ggacccgcgc attactggag atgttgtcgc ttcaccctga cgtggcggcg  120
gctgaaaatg aggtgcattt ttttgactgg gaagagcatt acagtcaggg tttaggttgg  180
tacttaacgc agatgccatt ctcgtctccc catcagttga ctgtcgagaa gactcactcc  240
tattttacaa gcccgaaggt tccagaacgc atccattcta tgaacccaac cattcgttta  300
cttcttattt tgcgtgaccc ctctgagcgt gtccttagtg tttacactca cgcgctgtat  360
atgcaccttc agaaacacaa gccttatccg ccaattgaag atcgttgat gcgcgatggc   420
cgtcttaatt tggactacat gggtttaaat cgtagcttat atcatgcgca catgttgaat  480
tggttgcgct tcttccctct tggtcatatt cacattgtag acggtgatcg tttaattcgc  540
gatccgttcc ccgaaatcca aaaggtagaa cgtttcttcc acagatcaac  600
gcgtcgaatt tttacttcaa caagacaaag gcttctact gcttgcgcga ctcaggaaaa  660
gaccgttgtt tacacgagtc taaaggccgt gctcaccctc aagtagaccc taagcttttg  720
gacaaacttc acgagtactt tcatgaacca aataaaaagt tcttcaaatt ggtcggccgc  780
acatttgatt ggcat                                                   795

SEQ ID NO: 137      moltype = AA  length = 265
FEATURE             Location/Qualifiers
REGION              1..265
                    note = Engineered glucosaminyl 3-O sulfotransferase
                     mutant_sulfatase 8
source              1..265
                    mol_type = protein
                    organism = synthetic construct
SEQUENCE: 137
MGTASNGSTQ QLPQTIIIGV GHGGTRALLE MLSLHPDVAA AENEVHFFDW EEHYSQGLGW   60
YLTQMPFSSP HQLTVEKTHT YFTSPKVPER IHSMNPTIRL LLILRDPSER VLSVYTHALY  120
MHLQKHKPYP PIEDLLMRDG RLNLDYMGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 138      moltype = DNA  length = 795
FEATURE             Location/Qualifiers
misc_feature        1..795
                    note = Polynucleotide sequence encoding for engineered
                     glucosaminyl 3-Osulfotransferase mutant_sulfatase 8
source              1..795
                    mol_type = other DNA
                    organism = synthetic construct
SEQUENCE: 138
atgggaactg cgtcgaacgg cagtacgcaa cagttgcccc aaactatcat cattggagtc   60
gggcatggtg gaacacgcgc tctgttggaa atgctgtcct tgcacccga cgttgccgct  120
gcagaaaatg aagtgcactt tttcgattgg gaggaacact actcccaggg tttgggctgg  180
tatcttacac agatgccgtt cagctctcca catcagttga cagtggagaa aacgcacaca  240
tattttacat caccaaaggt cccggagcgt attcattcga tgaatccaac catccgtctt  300
ctgctgatcc ttcgcgatcc cagtgagcgc gtactgtccg tttacaccca tgccttgtat  360
atgcacttac agaaacacaa accctatcct ccaatcgaag accttctgat gcgcgatggt  420
cgccttaatc ttgactatat ggggctgaat cgttctctgt accatgcaca catgttgaac  480
tggcttcgct ttttccgtt gggccatatt catattgtgg atggcgaccg tttgattcgt  540
gacccgttcc cagagatcca aaaggttgaa cgcttttttaa aattatcgcc acaaattaat  600
gcatcgaact tctactttaa taagacgaag ggatttact gtttacgtga ttctggcaaa  660
gatcgttgtc tgcatgaatc taaagggcgt gctcatccgc aggtggaccc aaaactgtta  720
gataagttac acgagtattt tcatgagcct aacaagaaat tctttaagtt ggtcggccgc  780
acatttgatt ggcat                                                   795

SEQ ID NO: 139      moltype = AA  length = 265
FEATURE             Location/Qualifiers
REGION              1..265
                    note = Engineered glucosaminyl 3-O sulfotransferase
                     mutant_sulfatase 9
source              1..265
                    mol_type = protein
                    organism = synthetic construct
SEQUENCE: 139
MGTASNGSTQ QLPQTIIIGV GHGGTRALLE MLSLHPDVAA AENEVHFFDW EEHYSQGLGW   60
YLTQMPFSSP HQLTVEKTHT YFTSPKVPER IHSMNPTIRL LLILRDPSER VLSFYTHALY  120
MHLQKHKPYP PIEDLLMRDG RLNLDYKGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 140      moltype = DNA  length = 795
FEATURE             Location/Qualifiers
misc_feature        1..795
                    note = Polynucleotide sequence encoding for engineered
                     glucosaminyl 3-Osulfotransferase mutant_sulfatase 9
source              1..795
```

```
                        mol_type = other DNA
                        organism = synthetic construct
SEQUENCE: 140
atggaactg cgtcgaacgg cagtacgcaa caactgccgc aaactatcat catcggggtg    60
ggtcatggag gtactcgtgc attattagaa atgcttagct tgcatcctga cgtggctgcg   120
gcggaaaacg aggtgcattt tttcgattgg gaggaacatt attctcaggg cttgggatgg   180
taccttactc aaatgccatt tagtagtccg caccagctga cagtagaaaa gacacatacg   240
tacttcacca gtccgaaagt ccccgagcgt attcattcaa tgaacccgac tatccgctta   300
ctgttgattc tgcgcgaccc gtcagaacgt gtattatcat tttatactca cgcgttatat   360
atgcatcttc aaaagcacaa accgtaccca cctatcgagg acctgctgat gcgtgatgga   420
cgcctgaatc tggactataa gggcttaaat cgctctttat atcatgcgca catgctgaat   480
tggcttcgtt tctttccgtt gggacatatt cacatcgtcg acggcgaccg cttgattcgt   540
gacccgttcc ccgaaatcca gaaagttgag cgtttcttga agctgtcacc tcagattaat   600
gccagcaatt tttactttaa taagaccaag ggttctattg cccttcgcga ctccggtaaa   660
gaccgctgct tacacgagtc gaaagggcgt gcccatccac aggtcgaccc taagctgctt   720
gacaagttac acgaatactt ccatgagcca aacaaaaagt tcttcaaact tgtcggccgc   780
acatttgatt ggcat                                                    795

SEQ ID NO: 141         moltype = AA  length = 265
FEATURE                Location/Qualifiers
REGION                 1..265
                        note = Engineered glucosaminyl 3-O sulfotransferase
                         mutant_sulfatase 10
source                 1..265
                        mol_type = protein
                        organism = synthetic construct
SEQUENCE: 141
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSLATHLLY   120
VHLQKHKPYP PIEDLLMRDG RLNLDYTGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 142         moltype = DNA  length = 795
FEATURE                Location/Qualifiers
misc_feature           1..795
                        note = Polynucleotide sequence encoding for engineered
                         glucosaminyl 3-Osulfotransferase mutant_sulfatase 10
source                 1..795
                        mol_type = other DNA
                        organism = synthetic construct
SEQUENCE: 142
atgggaactg cgtcgaacgg cagtacgcaa caattaccgc aaactattat cattggtgta    60
ggacatggtg gaacgcgcgc gcttcttgaa atgttatcgc tgcaccctga tgtcgctgcc   120
gctgagaatg aagtacactt tttcgattgg gaggaacatt attcccaggg gttagggtgg   180
tatcttacac aaatgccttt tagctccccg caccaactga ccgtggaaaa aacccacagt   240
tatttttactt cgccaaaagt acccgaacgt atccactcta tgaatccgac tatccgtttg   300
ttgttaatcc tgcgtgaccc ctcggaacgt gtactttcat tagctacaca tttgttatat   360
gttcatctgc agaagcacaa accgtatccc cctatcgaag atcttcttat gcgtgatggg   420
cgcttgaatc tggactacac tggacttaac cgtagcttgt atcatgccca catgttaaac   480
tggcttcgct ttttttcttt aggccatatt catatcgttg atggcgaccg tcttattcgt   540
gatccatttc cggaaattca aaaagtggag cgtttcctga aactgagtcc acaaatcaat   600
gcctcaaact tctactttaa taaaccaaag ggtttttatt gtcttcgcga cagcggcaaa   660
gatcgctgtc ttcacgagtc aaaaggtcgc gcgcacccgc aagtcgaccc taaattactt   720
gacaagctgc acgagtattt tcacgaaccc aacaagaaat ctttaaaatt agtcggccgc   780
acatttgatt ggcat                                                    795

SEQ ID NO: 143         moltype = AA  length = 265
FEATURE                Location/Qualifiers
REGION                 1..265
                        note = Engineered glucosaminyl 3-O sulfotransferase
                         mutant_sulfatase 11
source                 1..265
                        mol_type = protein
                        organism = synthetic construct
SEQUENCE: 143
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSLGTHMLY   120
VHLQKHKPYP PIEDLLMRDG RLNLDYVGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 144         moltype = DNA  length = 795
FEATURE                Location/Qualifiers
misc_feature           1..795
                        note = Polynucleotide sequence encoding for engineered
                         glucosaminyl 3-Osulfotransferase mutant_sulfatase 11
source                 1..795
                        mol_type = other DNA
```

```
                        organism = synthetic construct
SEQUENCE: 144
atgggaactg cgtcgaacgg cagtacgcaa caattaccac agaccattat catcggggtc    60
gggcatgggg gtacacgtgc tttattagaa atgttgtcac ttcacccgga cgtagcagct   120
gcggagaatg aggtccactt tttcgactgg gaggagcatt actctcaagg cttggggtgg   180
tacttgactc aaatgccctt ctcttcgccc catcaattaa cagtcgaaaa gacccactcg   240
tacttcactt cccccaaggt tcccgaacgt attcattcca tgaacccgac cattcgcctt   300
ttgttaatcc tgcgcgatcc gtcggaacgt gtgctttcgt tgggcacaca catgctttac   360
gtccatttac agaagcacaa gccatacccg ccgatcgaag acttgctgat gcgcgacggg   420
cgtctgaatt tggactatgt aggcttgaac cgctcattat atcatgccca catgctgaac   480
tggttgcgtt tctttccatt gggtcacatc catatcgtgg atggtgaccg tttgatccgc   540
gatccattcc ctgagatcca gaaagtcgaa cgctttttaa aattgtcccc tcaaattaat   600
gctagtaact tctacttcaa caaaacaaag gggttttatt gtctgcgtga cagcggtaag   660
gatcgttgtt tgcacgaatc gaagggtcgc gcgcaccctc aagtcgatcc taaattgttg   720
gataaactgc acgaatactt ccacgaaccg aacaaaaaat ttttcaaact tgtcggccgc   780
acatttgatt ggcat                                                    795

SEQ ID NO: 145          moltype = AA   length = 265
FEATURE                 Location/Qualifiers
REGION                  1..265
                        note = Engineered glucosaminyl 3-O sulfotransferase
                         mutant_sulfatase 12
source                  1..265
                        mol_type = protein
                        organism = synthetic construct
SEQUENCE: 145
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSLYTHALY   120
VHLQKHKPYP PIEDLLMRDG RLNLDYTGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 146          moltype = DNA   length = 795
FEATURE                 Location/Qualifiers
misc_feature            1..795
                        note = Polynucleotide sequence encoding for engineered
                         glucosaminyl 3-Osulfotransferase mutant_sulfatase 12
source                  1..795
                        mol_type = other DNA
                        organism = synthetic construct
SEQUENCE: 146
atgggaactg cgtcgaacgg cagtacgcaa caactgcccc aaacgattat tattggcgtt    60
ggtcatgggg ggaccgtgc tttactgaa atgttatcac ttcaccccga tgtggctgct   120
gccgaaaacg aggtgcattt ctttgactgg gaagaacatt acagccaggg attgggatgg   180
tatcttacac aaatgccatt cagcagccct catcagttga cggtggagaa gacgcactct   240
tactttactt ctccgaaggt tccagagcgc attcactcga tgaaccctac gatccgtttg   300
ttacttattt tgcgcgaccc ctctgagcgc gttctgtcat tttatacaca tgcgttatat   360
gtgcatttac aaaagcataa gcctaccca ccaatcgagg atttactgat gcgcgatggt   420
cgcttgaatt tggactatac cggttttaaat cgctcgttgt accatgccca catgttgaac   480
tggcttcgtt ttttcccttt aggtcacatt cacattgtag atggggatcg cttgatccgt   540
gatcctttcc ctgagattca gaaagtagaa cgtttcttaa aattatcacc ccaaattaat   600
gcttctaatt tttacttcaa caagactaaa gggttctact gtcttcgcga tagtggtaaa   660
gatcgttgct tgcacgaatc caaaggacgc gcacatccac aggtagatcc aaaattgctt   720
gataagttgc acgaatactt ccacgaaccc aacaaaaaat tctttaagtt agtcggccgc   780
acatttgatt ggcat                                                    795

SEQ ID NO: 147          moltype = AA   length = 265
FEATURE                 Location/Qualifiers
REGION                  1..265
                        note = Engineered glucosaminyl 3-O
                         sulfotransferasemutant_sulfotransferase 1
source                  1..265
                        mol_type = protein
                        organism = synthetic construct
SEQUENCE: 147
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSAYTHMLY   120
NHLQKHKPYP PIEDLLMRDG RLNLDYVGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 148          moltype = DNA   length = 795
FEATURE                 Location/Qualifiers
misc_feature            1..795
                        note = Polynucleotide sequence encoding for engineered
                         glucosaminyl 3-Osulfotransferase mutant_sulfotransferase 1
source                  1..795
                        mol_type = other DNA
                        organism = synthetic construct
```

```
SEQUENCE: 148
atgggaactg cgtcgaacgg cagtacgcaa caacttccgc agactatcat cattggcgta    60
ggacatggtg gaactcgtgc tctgttggag atgttatcac ttcaccccga cgtcgcagcg   120
gctgagaatg aagttcactt tttcgattgg gaagagcatt attcgcaggg gttaggttgg   180
tatcttaccc aaatgccttt ttcgagtccc catcagttaa cagtagagaa gacccattct   240
tactttacat caccaaaagt gcctgagcgc atccattcga tgaatccgac tatccgcctt   300
ttactgatct tacgcgatcc atcagaacgc gttctttcgg catataccca catgctttat   360
aaccatttgc agaaacacaa gccatatccc cctattgagg atttattaat gcgcgatgga   420
cgcttgaacc tggattattgt aggattaaat cgctctcttt atcacgctca tatgttaaac   480
tggcttcgct tttttccgct tgggcatatc cacatcgttg atggagaccg tttaattcgt   540
gacccgtttc ctgagatcca aaggtcgaa cgcttcctga aattaagtcc tcagattaat   600
gcgagcaatt tctatttcaa caagacgaaa ggattctact gcctgcgcga ctccggtaag   660
gatcgctgcc tgcacgagtc aaaagggcgc gcgcaccctc aggtcgaccc aaagctgtta   720
gataaattgc atgagtattt ccacgaacct aataagaagt tcttcaaact tgtcggccgc   780
acatttgatt ggcat                                                    795

SEQ ID NO: 149           moltype = AA   length = 265
FEATURE                  Location/Qualifiers
REGION                   1..265
                         note = Engineered glucosaminyl 3-O
                         sulfotransferasemutant_sulfotransferase 2
source                   1..265
                         mol_type = protein
                         organism = synthetic construct
SEQUENCE: 149
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSAYTHMLY   120
NHLQKHKPYP PIEDLLMRDG RLNLDYTGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 150           moltype = DNA   length = 795
FEATURE                  Location/Qualifiers
misc_feature             1..795
                         note = Polynucleotide sequence encoding for engineered
                         glucosaminyl 3-Osulfotransferase mutant_sulfotransferase 2
source                   1..795
                         mol_type = other DNA
                         organism = synthetic construct
SEQUENCE: 150
atgggaactg cgtcgaacgg cagtacgcaa cagttgccgc agacaatcat tattggcgtc    60
ggacatggcg gaacccgtgc tcttttggaa atgctgagtc tgcaccctga cgtggcagcg   120
gcggagaatg aggttcactt ctttgattgg gaggaacatt attcgcaggg gttgggatgg   180
tatctgacgc aaatgccgtt ctccagtcca caccagttga ccgttgaaaa gacgcatagt   240
tatttttacga gtcccaaagt acctgagcgt attcatagta tgaacccgac catccgtctg   300
ttgttgatcc ttcgcgatcc cagcgaacgc gtcttatcag cgtatactca catgctgtac   360
aaccaccttc aaaaacataa gccgtaccct cccatcgaag atcttttaat gcgtgatggt   420
cgtcttaacc ttgattacac aggtttgaac cgcagtttgt atcacgctca catgttgaat   480
tggttgcgct tctttcccct tggtcatatc catattgttg acggggaccg tctgatccgc   540
gacccgttcc cagagattca gaaagtgaaa cgttttcctga aattatcccc acagatcaac   600
gcgagtaact tctatttaa caagacgaaa ggttttctatt gcttacgtga tagtgggaag   660
gaccgctgcc tgcacgagag caaaggacgt gctcatcctc aagttgaccc caagttattg   720
gataaactgc acgagtattt tcacgagcct aataaaaagt tctttaagtt agtcggccgc   780
acatttgatt ggcat                                                    795

SEQ ID NO: 151           moltype = AA   length = 265
FEATURE                  Location/Qualifiers
REGION                   1..265
                         note = Engineered glucosaminyl 3-O
                         sulfotransferasemutant_sulfotransferase 3
source                   1..265
                         mol_type = protein
                         organism = synthetic construct
SEQUENCE: 151
MGTASNGSTQ QLPQTIIIGV GHGGTRALLE MLSLHPDVAA AENEVHFFDW EEHYSQGLGW    60
YLTQMPFSSP HQLTVEKTHS YFTSPKVPER IHSMNPTIRL LLILRDPSER VLSLGTHLLY   120
VHLQKHKPYP PIEDLLMRDG RLNLDYTGLN RSLYHAHMLN WLRFFPLGHI HIVDGDRLIR   180
DPFPEIQKVE RFLKLSPQIN ASNFYFNKTK GFYCLRDSGK DRCLHESKGR AHPQVDPKLL   240
DKLHEYFHEP NKKFFKLVGR TFDWH                                         265

SEQ ID NO: 152           moltype = DNA   length = 795
FEATURE                  Location/Qualifiers
misc_feature             1..795
                         note = Polynucleotide sequence encoding for engineered
                         glucosaminyl 3-Osulfotransferase mutant_sulfotransferase 3
source                   1..795
                         mol_type = other DNA
                         organism = synthetic construct
SEQUENCE: 152
```

```
atgggaactg cgtcgaacgg cagtacgcaa caacttccac aaactatcat tattggcgtg   60
ggtcacggtg ggactcgcgc tttacttgaa atgttgagct acatccgga tgttgccgca  120
gctgaaaacg aggtccattt cttttgactgg gaggaacact attcccaggg tttggggtgg  180
tatctgacgc agatgccttt ctcgtctcct caccaactta cggttgagaa aactcattca  240
tatttcacgt cccctaaagt accagaacgt atccactcac tgaacccaac aattcgttta  300
ttgttgattt tgcgcgaccc gtcggaacgt gtgttgtcgt taggtacgca cttgctttac  360
gttcatttgc aaaagcataa accgtatcca ccgattgagg accttttgat gcgtgacgga  420
cgtttgaatt tggactatac gggcctgaat cgctcgctgt atcacgccca catgttgaac  480
tggctgcgct tcttccccct tggtcatatc cacatcgtga tggggaccg tctgatccgt  540
gacccttcc cggaaatcca gaaagtggag cgtttcctga agttatctcc acaaatcaac  600
gcgagcaatt tttactttaa caagactaaa gggttctact gtttacgtga ttctggcaaa  660
gaccgttgcc ttcatgaaag taaaggccgc gctcaccctc aagtcgaccc caaattatta  720
gataagttgc acgagtactt ccatgaacct aataagaagt tcttcaaact tgtcggccgc  780
acatttgatt ggcat                                                   795

SEQ ID NO: 153          moltype = AA  length = 265
FEATURE                 Location/Qualifiers
REGION                  1..265
                        note = Engineered glucosaminyl 3-O sulfotransferase
                         mutant_variable
SITE                    80
                        note = MISC_FEATURE - Xaa is alanine, leucine, threonine,
                         or serine
SITE                    114
                        note = MISC_FEATURE - Xaa is alanine, tryptophan, leucine,
                         valine, or phenylalanine
SITE                    115
                        note = MISC_FEATURE - Xaa is tyrosine, alanine, or glycine
SITE                    118
                        note = MISC_FEATURE - Xaa is methionine, leucine, or alanine
SITE                    121
                        note = MISC_FEATURE - Xaa is asparagine, alanine,
                         methionine, or valine
SITE                    146
                        note = MISC_FEATURE - Xaa is tyrosine or methionine
SITE                    147
                        note = MISC_FEATURE - Xaa is lysine, valine, arginine,
                         threonine, alanine, ormethionine
SITE                    148
                        note = MISC_FEATURE - Xaa is methionine or glycine
source                  1..265
                        mol_type = protein
                        organism = synthetic construct
SEQUENCE: 153
MGTASNGSTQ QLPQTIIIGV GHGGTRALLE MLSLHPDVAA AENEVHFFDW EEHYSQGLGW   60
YLTQMPFSSP HQLTVEKTHX YFTSPKVPER IHSMNPTIRL LLILRDPSER VLSXXTHXLY  120
XHLQKHKPYP PIEDLLMRDG RLNLDXXXLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 154          moltype = AA  length = 265
FEATURE                 Location/Qualifiers
REGION                  1..265
                        note = Engineered glucosaminyl 3-O
                         sulfotransferasemutant_sulfotransferase 4
SITE                    114
                        note = MISC_FEATURE - Xaa is alanine or leucine
SITE                    115
                        note = MISC_FEATURE - Xaa is tyrosine or glycine
SITE                    118
                        note = MISC_FEATURE - Xaa is methionine or leucine
SITE                    121
                        note = MISC_FEATURE - Xaa is asparagine or valine
SITE                    147
                        note = MISC_FEATURE - Xaa is valine or threonine
source                  1..265
                        mol_type = protein
                        organism = synthetic construct
SEQUENCE: 154
MGTASNGSTQ QLPQTIIIGV GHGGTRALLE MLSLHPDVAA AENEVHFFDW EEHYSQGLGW   60
YLTQMPFSSP HQLTVEKTHS YFTSPKVPER IHSMNPTIRL LLILRDPSER VLSXXTHXLY  120
XHLQKHKPYP PIEDLLMRDG RLNLDYXGLN RSLYHAHMLN WLRFFPLGHI HIVDGDRLIR  180
DPFPEIQKVE RFLKLSPQIN ASNFYFNKTK GFYCLRDSGK DRCLHESKGR AHPQVDPKLL  240
DKLHEYFHEP NKKFFKLVGR TFDWH                                        265

SEQ ID NO: 155          moltype = AA  length = 265
FEATURE                 Location/Qualifiers
REGION                  1..265
                        note = Engineered glucosaminyl 3-O
```

```
                            sulfotransferasemutant_sulfotransferase 5
source                      1..265
                            mol_type = protein
                            organism = synthetic construct
SEQUENCE: 155
MGVAPNGSAQ QLPQTIIIGV GHGGTRALLE MLSLHPDVAA AENEVHFFDW EEHYSHGLGW    60
YLSQMPFSWP HQLTVEKTHS YFTSPKVPER VYSMNPSIRL LLILRDPSER VLSLGTHLFY   120
VHMQKHKPYP SIEEFLVRDG RLNVDYTGLN RSLYHVHMQN WLRFFPLRHI HIVDGDRLIR   180
DPFPEIQKVE RFLKLSPQIN ASNFYFNKTK GFYCLRDSGR DRCLHESKGR AHPQVDPKLL   240
NKLHEYFHEP NKKFFELVGR TFDWH                                        265

SEQ ID NO: 156              moltype = AA   length = 265
FEATURE                     Location/Qualifiers
REGION                      1..265
                            note = Engineered glucosaminyl 3-O
                            sulfotransferasemutant_sulfotransferase 6
source                      1..265
                            mol_type = protein
                            organism = synthetic construct
SEQUENCE: 156
MGVAPNGSAQ QLPQTIIIGV GHGGTRALLE MLSLHPDVAA AENEVHFFDW EEHYSHGLGW    60
YLSQMPFSWP HQLTVEKTHS YFTSPKVPER VYSMNPSIRL LLILRDPSER VLSAYTHMFY   120
NHMQKHKPYP SIEEFLVRDG RLNVDYTGLN RSLYHVHMQN WLRFFPLRHI HIVDGDRLIR   180
DPFPEIQKVE RFLKLSPQIN ASNFYFNKTK GFYCLRDSGR DRCLHESKGR AHPQVDPKLL   240
NKLHEYFHEP NKKFFELVGR TFDWH                                        265

SEQ ID NO: 157              moltype = AA   length = 265
FEATURE                     Location/Qualifiers
REGION                      1..265
                            note = Engineered glucosaminyl 3-O
                            sulfotransferasemutant_sulfotransferase 7
source                      1..265
                            mol_type = protein
                            organism = synthetic construct
SEQUENCE: 157
MGVAPNGSAQ QLPQTIIIGV RKGGTRALLE MLSLHPDVAA AENEVHFFDW EEHYSHGLGW    60
YLSQMPFSWP HQLTVEKTPA YFTSPKVPER VYSMNPSIRL LLILRDPSER VLSDYTQVFY   120
NHMQKHKPYP SIEEFLVRDG RLNVDYKALN RSLYHVHMQN WLRFFPLRHI HIVDGDRLIR   180
DPFPEIQKVE RFLKLSPQIN ASNFYFNKTK GFYCLRDSGR DRCLHESKGR AHPQVDPKLL   240
NKLHEYFHEP NKKFFELVGR TFDWH                                        265

SEQ ID NO: 158              moltype = AA   length = 346
FEATURE                     Location/Qualifiers
REGION                      1..346
                            note = Engineered glucosaminyl 3-O
                            sulfotransferasemutant_sulfotransferase 8
source                      1..346
                            mol_type = protein
                            organism = synthetic construct
SEQUENCE: 158
MLFKQQVWLR QKLLVLGSLA VGSLLYLVAR VGSLDRLQPI CPVESRFGGA HNQAELPLRA    60
LQFKRGLLHE FRKGNSSKEQ VHLHDLVQQL PKAIIIGVGH GGTRALLEML NLHPAVVKAS   120
QEIHFFDNDE NYAKGIEWYR KKMPFSYPQQ ITIEKSHSYF ITEEVPERIY KMNSSIKLLI   180
IVREPTTRAI SAYTHMLEGK ERKNKTYYKF EKLAIDPNTC EVNTKYVGVR TSIYTKHLER   240
WLKYFFPIEQF HIVDGDRLIT EPLPELQLVE KFLNLPPRIS QYNLYFNATR GFYCLRFNII   300
FNKCLAGSKG RIHPEVDPSV ITKLRKFFHP FNQKFYQITR RTLNWP                  346

SEQ ID NO: 159              moltype = AA   length = 346
FEATURE                     Location/Qualifiers
REGION                      1..346
                            note = Engineered glucosaminyl 3-O
                            sulfotransferasemutant_sulfotransferase 9
source                      1..346
                            mol_type = protein
                            organism = synthetic construct
SEQUENCE: 159
MLFKQQVWLR QKLLVLGSLA VGSLLYLVAR VGSLDRLQPI CPVESRFGGA HNQAELPLRA    60
LQFKRGLLHE FRKGNSSKEQ VHLHDLVQQL PKAIIIGVGH GGTRALLEML NLHPAVVKAS   120
QEIHFFDNDE NYAKGIEWYR KKMPFSYPQQ ITIEKSHSYF ITEEVPERIY KMNSSIKLLI   180
IVREPTTRAI SAYTHMLEGK ERKNKTYYKF EKLAIDPNTC EVNTKYTGVR TSIYTKHLER   240
WLKYFFPIEQF HIVDGDRLIT EPLPELQLVE KFLNLPPRIS QYNLYFNATR GFYCLRFNII   300
FNKCLAGSKG RIHPEVDPSV ITKLRKFFHP FNQKFYQITG RTLNWP                  346

SEQ ID NO: 160              moltype = AA   length = 346
FEATURE                     Location/Qualifiers
REGION                      1..346
                            note = Engineered glucosaminyl 3-O
                            sulfotransferasemutant_sulfotransferase 10
source                      1..346
```

```
                            mol_type = protein
                            organism = synthetic construct
SEQUENCE: 160
MLFKQQVWLR QKLLVLGSLA VGSLLYLVAR VGSLDRLQPI CPVESRFGGA HNQAELPLRA   60
LQFKRGLLHE FRKGNSSKEQ VHLHDLVQQL PKAIIGVGH  GGTRALLEML NLHPAVVKAS  120
QEIHFFDNDE NYAKGIEWYR KKMPFSYPQQ ITIEKSHSYF ITEEVPERIY KMNSSIKLLI  180
IVREPTTRAI SLGTHLLEVK ERKNKTYYKF EKLAIDPNTC EVNTKYTGVR TSIYTKHLER  240
WLKYFPIEQF HIVDGDRLIT EPLPELQLVE KFLNLPPRIS QYNLYFNATR GFYCLRFNII  300
FNKCLAGSKG RIHPEVDPSV ITKLRKFFHP FNQKFYQITG RTLNWP                 346

SEQ ID NO: 161              moltype = AA  length = 394
FEATURE                     Location/Qualifiers
SIGNAL                      1..22
                            note = Signal Sequence
source                      1..394
                            mol_type = protein
                            organism = Bacteroides eggerthii
SEQUENCE: 161
MKKNIFIICM AMAAGCITTL TAQVKNAETL VPLTKRVNVQ ADTARLDQII DGCWVAVGTN   60
KKHAIQRDFT RLFAGKPSYR FELRKEDNTL EGYGKGETKG RAEFSYCYAT SADFKGLPAD  120
AYRKAQITKT VYHHGKGICP QGVSRDYEFS VYIPSALDSN VSTIFAQWHG MPDRTLVQTP  180
EGEVKKLTVD EFLELDKTTI FKKNTGHEKV AKLDKQGNPV KDKKGNPVYK AGKKNGWLVE  240
QGGYPPLAFG FSGGWFYIKA NSDRRWLTDK TDRCNASPEK TPVMKPVTSK YKSSTIAYKM  300
PFADFPKDCW VTFRVHIDWT TYGKEAENIV KPGKLDVQME YTDKKKTVKE HIVNNEVIQI  360
GRNDDDGYYF KFGIYRVGNS TVPVCYNLAG YKEE                             394

SEQ ID NO: 162              moltype = AA  length = 773
FEATURE                     Location/Qualifiers
SIGNAL                      1..22
                            note = Signal Sequence
source                      1..773
                            mol_type = protein
                            organism = Bacteroides eggerthii
SEQUENCE: 162
MKKSILFITS LFLCIFCLKS NAQQSRTEVT WEKMEDVTVP IPPQVHPRLY VRSADLPDLK   60
KRMNHPHVKE VLATLNKLGK DRTPEEEAKV KDRGFRYYFE MRGVTSRVQV QALEYLVYGD  120
KKQARRAITA MLDTLQNVNY GTQGDLSRAS GVMLTCGAMV YDWCYDQMKE SEKKAYVESF  180
IRIAKTMECG YPPRNNEPIA GHSSEWMILR DMLSAGIAIY DEYPDMYNYV IKMMFKDYLP  240
VRNYIYSGHN YHQGTSYVNV RFSNDLFSLW ILQRMGAGAI YNPAQQVFLY DFLYRRRPDG  300
QVMPAGDTNP IRKNTPSYSL PAMLASSFYK DSYLAYEYER KPNIERHCLI FDILWRDLDL  360
KAKAPDDLPL TRYSGSPFGW MIARTAWDEN SVIAEMKINE QFVGNHQHLD GGSFQLYYKG  420
PLAIDAGAYQ GSSGGYNSPH NKNFFKRTIA HNSLLVYNPD EKFACWNYGG GGKTEFAAND  480
GGQRMPGDRW ETCRSFKQLM SKDYTTGKAL AHGFGPDACK PDYSYLKGDI TQAYTDKVKE  540
AKRSFVFLNL HSTEVPGALI VFDKVVSSDP QFKKFWLLHS IEEPVIEGDR FIIRRTKNGD  600
TGMLQNQVLL PEAGNAQIEK VGGKGKEFWV FGTNYPNDAL PNRPDDANER GAWRVEVSPA  660
VPAAENYFLN VIQVADNTCK RMNDVKRIDA GKVVGVQIAD RIVTFSKNSL PLSGKIDMKV  720
DGNTSMKFVI TDLIPGTWQI KKDGKVYIPA MEVRSDDGIL SFEGTAGHYE FLR         773

SEQ ID NO: 163              moltype = AA  length = 666
FEATURE                     Location/Qualifiers
SIGNAL                      1..21
                            note = Signal Sequence
source                      1..666
                            mol_type = protein
                            organism = Bacteroides eggerthii
SEQUENCE: 163
MKIMKFILSV FLLTIAIIAD AQQLRKEAFD LLNLDYPGLE KVKTACSRQQ WEEAAQELLA   60
YYRNRTDIAH PDIDLKNLAI SKEEQKWADD AMDHTFFVHK GYQPSYNYGK DINWEYWPVK  120
DNELRWQLHR HKWFTPMGKA YRISGDEKYA KEWAFQYIRP IKKNPLVKME KENFELVSAG  180
EVKEDADNVH FAWRQLEVSN RLQDQTCQFL LFCPAEAFTP EFLTEFLVNY HRHGAYLFKN  240
YSAEGNHLLF EAQRMVYAGV FFPEFKDAAT WRESGINILN REIKKQVYDD GGQYELDPHY  300
HLAAINIFCK ALRMADCNGF RNEFPAEYLD TVKKMIEFYT NICFPDYTNP CFSDAKLGDY  360
KSELANYRDW VTLFPDSEWI RYYATEGREG APLYLSHGS  LASGFFTFRS GWKKDAAVVV  420
VKAGPKGEWH CQPDNGTFEF WFNGKNLFPD SGAYVYAGSD EVMKLRNWFR QTRVHNTLTL  480
DGRNFETTQS VTKLWQPEGR EQILVTENPS YQGLKHRRTV FFVEQTYYVI VDEAVGDAKG  540
TVNLNYHFCE GTVNVDVKKN MATTAYAGPS NVKLQCFPEK KASLKKEEGW RSIAYRQRVP  600
RTSLSFDIHK DDAEAVRYIT VIYPVKDAAS YPVLKAKFLN KDFDEKGVKV EVSVNGVARQ  660
LMSQLK                                                             666

SEQ ID NO: 164              moltype = AA  length = 309
FEATURE                     Location/Qualifiers
source                      1..309
                            mol_type = protein
                            organism = Homo sapiens
SEQUENCE: 164
MSEEKDPLWQ DPCEDKRHKD IWSKEKTCDR FPKLLIIGPQ KTGTTALYLF LGMHPDLSSN   60
YPSSETFEEI QFFNGHNYHK GIDWYMEFFP IPSNTTSDFY FEKSANYFDS EVAPRRAAAL  120
LPKAKVLTIL INPADRAYSW YQHRAHDDP  VALKYTFHEV ITAGSDASSK LRALQNRCLV  180
PGWYATHIER WLSAYHANQI LVLDGKLLRT EPAKVMDMVQ KFLGVTNTID YHKTLAFDPK  240
```

```
KGFWCQLLEG GKTKCLGKSK GRKYPEMDLD SRAFLKDYYR DHNIELSKLL YKMGQTLPTW    300
LREDLQNTR                                                           309

SEQ ID NO: 165          moltype = AA  length = 309
FEATURE                 Location/Qualifiers
source                  1..309
                        mol_type = protein
                        organism = Rattus norvegicus
SEQUENCE: 165
MSEEKDPLWQ DPCEDKRHKD IWSKEKTCDR FPKLLIIGPQ KTGTTALYLF LGMHPDLSSN    60
YPSSETFEEI QFFNGHNYHK GIDWYMEFFP IPSNTTSDFY FEKSANYFDS EVAPRRAAAL    120
LPKAKVLTIL INPADRAYSW YQHQRAHDDP VALKYTFHEV ITAGPDASSK LRALQNRCLV    180
PGWYATHIER WLSAFHANQI LVLDGKLLRT EPAKVMDTVQ KFLGVTSTVD YHKTLAFDPK    240
KGFWCQLLEG GKTKCLGKSK GRKYPEMDLD SRAFLKDYYR DHNIELSKLL YKMGQTLPTW    300
LREDLQNTR                                                           309

SEQ ID NO: 166          moltype = AA  length = 309
FEATURE                 Location/Qualifiers
source                  1..309
                        mol_type = protein
                        organism = Mus musculus
SEQUENCE: 166
MSEEKDPLWQ DPCEDKRHKD IWSKEKTCDR FPKLLIIGPQ KTGTTALYLF LGMHPDLSSN    60
YPSSETFEEI QFFNGHNYHK GIDWYMEFFP IPSNTTSDFY FEKSANYFDS EVAPRRAAAL    120
LPKAKILSIL INPADRAYSW YQHQRAHDDP VALKYTFHEV ITAGPDASSK LRALQNRCLV    180
PGWYATHIER WLSAFHANQI LVLDGKLLRT EPAKVMDTVQ KFLGVTSTVD YHKTLAFDPK    240
KGFWCQLLEG GKTKCLGKSK GRKYPEMDLD SRAFLKDYFR DHNIELSKLL YKMGQTLPTW    300
LREDLQNTR                                                           309

SEQ ID NO: 167          moltype = AA  length = 309
FEATURE                 Location/Qualifiers
source                  1..309
                        mol_type = protein
                        organism = Bos taurus
SEQUENCE: 167
MSEEKDPLWQ DPCEDKRHKD IWSKEKTCDR FPKLLIIGPQ KTGTTALYLF LGMHPDLSSN    60
YPSSETFEEI QFFNGHNYHK GIDWYMEFFP IPSNTTSDFY FEKSANYFDS EVAPRRAAAL    120
LPKAKVLTIL INPADRAYSW YQHQRAHDDP VALKYTFHEV ITAGPDASLK LRTLQNRCLV    180
PGWYATHIER WLSAFHTNQI LVLDGKLLRT EPAKVMDTVQ KFLGVTNTID YHKTLAFDPK    240
KGFWCQLLEG GKTKCLGKSK GRKYPEMDLD SRAFLKDYYR DHNVELSKLL YKMGQTLPTW    300
LREELQNTR                                                           309

SEQ ID NO: 168          moltype = AA  length = 309
FEATURE                 Location/Qualifiers
source                  1..309
                        mol_type = protein
                        organism = Sus scrofa
SEQUENCE: 168
MSEEKDPLWQ DPCEDKRHKD IWSKEKTCDR FPKLLIIGPQ KTGTTALYLF LGLHPDLSSN    60
YPSSETFEEI QFFNGHNYHK GIDWYMDFFP IPSNTTSDFY FEKSANYFDS DVAPRRAAAL    120
LPKAKVLTIL INPADRAYSW YQHQRAHDDP AALRYTFHEV ITAGPDASLK LRALQNRCLV    180
PGWYATHLER WLGAFHANQI LVLDGKLLRT EPARVMDTVQ KFLGVTNTID YHKTLAFDPK    240
KGFWCQLLEG GKTKCLGRSK GRKYPDMDPD SRAFLRDYYR DHNIELSKLL YKMGQTLPTW    300
LREELQNTR                                                           309

SEQ ID NO: 169          moltype = AA  length = 309
FEATURE                 Location/Qualifiers
source                  1..309
                        mol_type = protein
                        organism = Pelodiscus sinensis
SEQUENCE: 169
MEPPLTPVLQ DPCEDKRHKD IWSKEKTCDR FPKLLIIGPQ KTGTTALYLF LGMHPDLSSN    60
YPSSETFEEI QFFNGHNYHK GIDWYMEFFP IPSNTTSDLY FEKSANYFDS EVAPRRAAAL    120
LSKAKVITIL INPADRAYSW YQHQRAHDDP VALKYTFHEV ITARPEAPQK LRMLQNRCLV    180
PGWYATHIER WLASVAVSQI LVLDGKLLRT EPAKVMETVQ KFLGVTNFID YHKTLAFDPK    240
KGFWCQLLEG GKTKCLGKSK GRKYPEMDSD SRAFLRDYYR DHNIELSKLL YKMGQTLPTW    300
LREELQNAR                                                           309

SEQ ID NO: 170          moltype = AA  length = 309
FEATURE                 Location/Qualifiers
source                  1..309
                        mol_type = protein
                        organism = Xenopus laevis
SEQUENCE: 170
MPEEKDPLWQ DPCEDKRHKD IWSKEKTCDR FPKLLIIGPQ KTGTTALYLF LGMHSDLSSN    60
YPSSETFEEI QFYNGQNYHK GIDWYMEFFP IPSNTTSDFY FEKSANYFDS ELAPRRVAAL    120
LPKAKIITIL INPADRAYSW YQHQRAHDDP VAIKYTFQEV IKAGPEAPQR LRALQNRCLV    180
PGWYSTHIER WMNHFHANQI LVLDGKLLRT EPANVMETVQ KFLGVTNAMD YHKTLAFDPK    240
KGFWCQLLDG GKTKCLGKSK GRKYPDMDSD SRSFLMDYYR DHNIELSKLL YKMGQTLPTW    300
```

```
LREELQNTR                                                                      309

SEQ ID NO: 171            moltype = AA  length = 309
FEATURE                   Location/Qualifiers
source                    1..309
                          mol_type = protein
                          organism = Lepisosteus oculatus
SEQUENCE: 171
MPEEKDPVWQ DPCEDKRHKD IWSKEKTCDR FPKLLIIGPQ KTGTTALYLF LGMHPDLTSN    60
YPSKETFEEI QFFNGHNYHK GIDWYMEYFP LPSNTSSDFY FEKSANYFDS EMAPKRAAAL   120
LPKAKIITIL INPADRAYSW YQHQRAHDDP VALKYTFHEV ITAGHDAPLK LRILQNRCLV   180
PGWYSIHLER WLNYYHSNQI LVLDGQMLRT EPALVMEKIQ KFLGLVNIIN YHKILAFDPK   240
KGFWCQLLEG GKTKCLGKSK GRKYPEMDTD SRDFLRNYYQ EHNVELSKLL YKMGQSLPSW   300
LREELVNTR                                                          309

SEQ ID NO: 172            moltype = AA  length = 309
FEATURE                   Location/Qualifiers
source                    1..309
                          mol_type = protein
                          organism = Danio rerio
SEQUENCE: 172
MPEERDPIWQ DPCEDKRHKD IWSKEKTCDR FPKLLIIGPQ KTGTTALYLF LSMHSDLTSN    60
YPSKETFEEI QFFNGRNYHK GIDWYMEHFP LPSNTSSDFY FEKSANYFDS EVAARRAAAL   120
LPKAKIITIL INPADRAYSW YQHQRAHDDP VAQKYTFHDV ITAGRDAPIK LRVLQSRCLV   180
PGLYATHLQR WLTHYHPSQI LVLDGQMLRT EPASVMDKIQ KFLGLINTLN YHKILAFDPK   240
KGFWCQLLDG GKTKCLGKSK GRRYPDMDVD SRTFLREYYH EHNIELSKLL YKMGQPLPSW   300
LREELLHSR                                                          309

SEQ ID NO: 173            moltype = AA  length = 309
FEATURE                   Location/Qualifiers
source                    1..309
                          mol_type = protein
                          organism = Homo sapiens
SEQUENCE: 173
MPEQKDPLWQ NPCDDKRHKD IWSREKTCDH LPKFLVIGPQ KTGTTALYLF LLMHPSIISN    60
LPSPKTFEEV QFFNGNNYHK GIDWYMDFFP TPSNTTSDFL FEKSANYFHS EEAPRRAASL   120
VPKAKIITIL IDPSDRAYSW YQHQRSHEDP AALRFNFYEV ISTGHWAPSD LKTLQRRCLV   180
PGWYAVHIER WLTYFATSQL LIIDGQQLRS DPATVMDEVQ KFLGVTPRYN YSEALTFDPQ   240
KGFWCQLLEG GKTKCLGKSK GRKYPPMDPE SRTFLSNYYR DHNVELSKLL HRLGQPLPSW   300
LRQELQKVR                                                          309

SEQ ID NO: 174            moltype = AA  length = 309
FEATURE                   Location/Qualifiers
source                    1..309
                          mol_type = protein
                          organism = Homo sapiens
SEQUENCE: 174
MPDQKDPLWQ NPCDDKRHRD IWSKEKTCDR LPKFLVIGPQ KTGTTALYLF LVMHPSILSN    60
SPSPKTFEEV QFFNRNNYHR GIDWYMDFFP VPSNVTTDFL FEKSANYFHS EEAPKRAASL   120
VPKAKIITIL IDPSDRAYSW YQHQRSHEDP AALKFSFYEV ISAGPRAPSE LRALQRRCLV   180
PGWYASHIER WLVYFPPFQL LIIDGQQLRT DPATVMDEVQ KFLGVLPHYN YSEALTFDSH   240
KGFWCQLLEE GKTKCLGKSK GRKYPPMDSD SRTFLSSYYR DHNVELSKLL HKLGQPLPSW   300
LRQELQKVR                                                          309

SEQ ID NO: 175            moltype = AA  length = 311
FEATURE                   Location/Qualifiers
source                    1..311
                          mol_type = protein
                          organism = Bos taurus
SEQUENCE: 175
MPQERSPLWQ NPCDDKRHKD IWSKEKTCDR LPKFLIVGPQ KTGTTAIHFF LSLHPAVTSS    60
FPSPSTFEEI QFFNGPNYHK GIDWYMDFFP VPSNASTDFL FEKSATYFDS EVVPRRGAAL   120
LPRAKIITVL TNPADRAYSW YQHQRAHGDP VALNYTFYQV ITASSQDPPA LRSLQNRCLV   180
PGYYSTHLQR WLTYYPSGQL LIVDGQELRT NPAASMEIIQ KFLGITPPFLN YTRTLRFDED   240
KGFWCQGLEG GKTRCLGKSK GRKYPDMDAE SRLFLTDFFR NHNLELSKLL SRLGQPVPSW   300
LREELQHSSS G                                                       311

SEQ ID NO: 176            moltype = AA  length = 311
FEATURE                   Location/Qualifiers
source                    1..311
                          mol_type = protein
                          organism = Mus musculus
SEQUENCE: 176
MPQERSPLWQ NPCDDKRHKD IWSKEKTCDR LPKFLIVGPQ KTGTTAIHFF LSLHPAVTSS    60
FPSPSTFEEI QFFNGPNYHK GIDWYMDFFP VPSNASTDFL FEKSATYFDS EVVPRRGAAL   120
LPRAKIITVL INPADRAYSW YQHQRAHGDP IALNYTFYQV ISASSQAPLL LRSLQNRCLV   180
PGYYSTHLQR WLTYYPSGQL LIMDGQELRV NPAASMEIIQ KFLGITPFLN YTRTLRFDED   240
KGFWCQGLEG GKTRCLGRSK GRRYPDMDME SRLFLTDFFR NHNLELSKLL SRLGQPAPLW   300
LREELQHSSV G                                                       311
```

```
SEQ ID NO: 177         moltype = AA  length = 311
FEATURE                Location/Qualifiers
source                 1..311
                       mol_type = protein
                       organism = Homo sapiens
SEQUENCE: 177
MPQERSPLWQ NPCDDKRHKD IWSKEKTCDR LPKFLIVGPQ KTGTTAIHFF LSLHPAVTSS   60
FPSPSTFEEI QFFNSPNYHK GIDWYMDFFP VPSNASTDFL FEKSATYFDS EVVPRRGAAL  120
LPRAKIITVL TNPADRAYSW YQHQRAHGDP VALNYTFYQV ISASSQTPLA LRSLQNRCLV  180
PGYYSTHLQR WLTYYPSGQL LIVDGQELRT NPAASMESIQ KFLGITPFLN YTRTLRFDDD  240
KGFWCQGLEG GKTRCLGRSK GRRYPDMDTE SRLFLTDFFR NHNLELSKLL SRLGQPVPSW  300
LREELQHSSL G                                                      311

SEQ ID NO: 178         moltype = AA  length = 321
FEATURE                Location/Qualifiers
source                 1..321
                       mol_type = protein
                       organism = Drosophila melanogaster
SEQUENCE: 178
MPEEVDPVWG NPCDDVRHKK IWSKTKNCDS LPKFLVIGPQ KTGTTALYTF LSMHGSIASN   60
IASPETFEEV QFFNGNNYYR GLDWYMDFFP SESLPNTSSP MPTQLGSPRF MFEKSATYFD  120
GEAVPKRSHA LLPHAKIVTI LISPAKRAYS WYQHQRSHGD VIANNYSFYQ VITASDSAPR  180
ALKDLRNRCL NPGKYAQHLE HWLAYYPAQQ LHIIDGEQLR LNPIDVMNEL QRFLKIQPLL  240
DYSNHLRYDV KKGFYCQAVS EKRNKCLGKS KGRQYPAMDE RSAKLLQRYY LNHNTALVKL  300
LKKLGSRPIP QWLKDDLSTG T                                           321

SEQ ID NO: 179         moltype = AA  length = 356
FEATURE                Location/Qualifiers
source                 1..356
                       mol_type = protein
                       organism = Gallus gallus
SEQUENCE: 179
MGLLRIMLPP KLQLLAVLVF GVAVLFLENQ IQKLEESRGK LERAIARHEV REIEQRHTAD   60
GPRQEVALDE EDDVVIIYNR VPKTASTSFT NIAYDLCAKN RYHVLHINTT KNNPVMSLQD  120
QVRFVKNVTS WKEMKPGFYH GHVSYLDFAK FGVKKKPIYI NVIRDPIERL VSYYYFLRFG  180
DDYRPGLRRR KQGDKKTFDE CVAAGGSDCA PEKLWLQIPF FCGHSSECWN VGSRWALEQA  240
KYNLINEYFL VGVTEELEDF IMLLEAALPR FFRGATELYR TGKKSHLRKT TEKKLPTKET  300
IAKLQQSEIW KMENEFYEFA LEQFQFVRAH AVREKDGELY ILAQNFFYEK IYPKSN      356

SEQ ID NO: 180         moltype = AA  length = 366
FEATURE                Location/Qualifiers
source                 1..366
                       mol_type = protein
                       organism = Rhipicephalus appendiculatus
SEQUENCE: 180
MIGRILQWKV ILCFCVAISF VSVYLRFENK LALLESSRLK LTETVGRLQL FYLNERLHDF   60
PPVQESRTDA PLDDFGLPEK TMDNLVILYN RVPKTGSTSF MGVAYDLCAT NKFHVLHLNT  120
SKNMHVMSLP DQIRFVYNIS LWHYMKPAIY HGHIAFLNFA KYGVIQRPVY INLIRRPLDR  180
LVSYFYFLRH GDDFRPYLVR RRQGNKMTFD ECVAKKGADC AEERLWLQVP FFCGHAARCW  240
IPGNPWALEQ AKHNLVNHYF LVGLTEQLPE FVAMLEASFP RIFKGATDKF ITGKRSHLRK  300
TFNKVQPSQE TIEHFKRSPI WQMENEFYEF AAEQFEFAKK RTLVATQDGQ LTELGQQFFY  360
EKIRPK                                                            366

SEQ ID NO: 181         moltype = AA  length = 354
FEATURE                Location/Qualifiers
source                 1..354
                       mol_type = protein
                       organism = Takifugu rubripes
SEQUENCE: 181
MGISRIMMSH KFQLMAVLTF GVAMLFIENQ IQKLEDSRAR LERTVTIHDI ADLRHTEDGG   60
RELPLLADKD DRVIIYNRVP KTGSTSFTNI AYDLCAKNHF HVLHINTTKN NPVMSLQDQM  120
RFVRNISSWR EMKPGFYHGH VAYLDFSKYG AKVKPMYINV VRDPIERLVS YYYFLRFGDN  180
YRPGLRRRKQ GDKKTFDECV SSGGGSDCAPE KLWLQIPFFC GHHSECWNAG SKWALEQAKY  240
NLVNEYLLVG VTEELEDFIM ILEAVLPRFF KGATELFKTG KKSHLRKTTE KKPPTKETTA  300
KLQQSNIWKM ENEFYEFALE QFQFVRAHAV REKDGELYVL GQNFFYEKIY PKVN        354

SEQ ID NO: 182         moltype = AA  length = 357
FEATURE                Location/Qualifiers
source                 1..357
                       mol_type = protein
                       organism = Callorhinchus milii
SEQUENCE: 182
MGLLRIIMPP KLQLLAVVAF MITMLFLENQ IQKLEESRGK LERAIARHEV REIEQRHTMD   60
SPRQDRGGDD ELDDLIILYN RVPKTASTSF TNIAYDLCGR NKYHVLHINT TKNNPVMSLQ  120
DQARFVKNVT TWKEMKPGFY HGHVAYLDFT KYGVKKKPIY LNVIRDPIER LVSYYYFLRF  180
GDDYRPGLKR RKQGDKKTFD ECVAAGGSDC APEKLWLQIP FFCGHSSECW NIGSKWALEQ  240
ARYNLVNEYL LVGVTEELED FIMLLEAALP RFFRGATELY RTGKKSHLRK TTEKKLPTKE  300
TIARLQLSEI WKMENEFYEF ALEQFQFIRA HAVREKDGEL YLLSQSFFYE KIYPKTN     357
```

```
SEQ ID NO: 183          moltype = AA  length = 356
FEATURE                 Location/Qualifiers
source                  1..356
                        mol_type = protein
                        organism = Xenopus laevis
SEQUENCE: 183
MGLLRIMMPP KLQLLAVLTF GVLMLFLENQ IQNLEESREK LERAIARHEV REIEQRHSMD   60
GSRQEIALDD DEDILIIYNR VPKTASTSFT NIAYDLCAKN KYHVLHINTT KNNPVMSLQD  120
QVRFVKNVSS WREMKPGFYH GHVSFLDFTK FGVKKKPIYI NVIRDPIERL VSYYYFLRFG  180
DDYRPGLRRR KQGDKKTFDE CVAAGGSDCA PEKLWLQIPF FCGHSSECWN VGSRWALDQA  240
KYNLVNEYFL VGVTEELEDF IMLLEAALPR FFRGATELYR SGKKSHLRKT TEKKAPSKET  300
TAKLQQSDIW KMENEFYEFA LEQFQFVRAH AVREKDGELY VLAPNFFYEK IYPKSN      356

SEQ ID NO: 184          moltype = AA  length = 356
FEATURE                 Location/Qualifiers
source                  1..356
                        mol_type = protein
                        organism = Mus musculus
SEQUENCE: 184
MGLLRIMMPP KLQLLAVVAF AVAMLFLENQ IQKLEESRAK LERAIARHEV REIEQRHTMD   60
GPRQDATLDE EEDIIIIYNR VPKTASTSFT NIAYDLCAKN KYHVLHINTT KNNPVMSLQD  120
QVRFVKNITT WNEMKPGFYH GHISYLDFAK FGVKKKPIYI NVIRDPIERL VSYYYFLRFG  180
DDYRPGLRRR KQGDKKTFDE CVAEGGSDCA PEKLWLQIPF FCGHSSECWN VGSRWAMDQA  240
KSNLINEYFL VGVTEELEDF IMLLEAALPR FFRGATDLYR TGKKSHLRKT TEKKLPTKQT  300
IAKLQQSDIW KMENEFYEFA LEQFQFIRAH AVREKDGDLY ILAQNFFYEK IYPKSN      356

SEQ ID NO: 185          moltype = AA  length = 356
FEATURE                 Location/Qualifiers
source                  1..356
                        mol_type = protein
                        organism = Sus scrofa
SEQUENCE: 185
MGLLRIMMPP KLQLLAVVAF AVAMLFLENQ IQKLEESRSK LERAIARHEV REIEQRHTMD   60
GPRQEAALDE EEDLVIIYNR VPKTASTSFT NIAYDLCAKN KYHVLHINTT KNNPVMSLQD  120
QVRFVKNITS WKEMKPGFYH GHVSYLDFAK FGVKKKPIYI NVVRDPIERL VSYYYFLRFG  180
DDYRPGLRRR KQGDKKTFDE CVAEGGSDCA PEKLWLQIPF FCGHSSECWN VGSRWAMDQA  240
KYNLINEYFL VGVTEELEDF VMLLEAALPR FFRGATELYR TGKKSHLRKT TEKKLPTKQT  300
IAKLQQSHIW KMENEFYEFA LEQFQFIRAH AVREKDGDLF ILAQNFFYEK IYPKSN      356

SEQ ID NO: 186          moltype = AA  length = 356
FEATURE                 Location/Qualifiers
source                  1..356
                        mol_type = protein
                        organism = Homo sapiens
SEQUENCE: 186
MGLLRIMMPP KLQLLAVVAF AVAMLFLENQ IQKLEESRSK LERAIARHEV REIEQRHTMD   60
GPRQDATLDE EEDMVIIYNR VPKTASTSFT NIAYDLCAKN KYHVLHINTT KNNPVMSLQD  120
QVRFVKNITS WKEMKPGFYH GHVSYLDFAK FGVKKKPIYI NVIRDPIERL VSYYYFLRFG  180
DDYRPGLRRR KQGDKKTFDE CVAEGGSDCA PEKLWLQIPF FCGHSSECWN VGSRWAMDQA  240
KYNLINEYFL VGVTEELEDF IMLLEAALPR FFRGATELYR TGKKSHLRKT TEKKLPTKQT  300
IAKLQQSDIW KMENEFYEFA LEQFQFIRAH AVREKDGDLY ILAQNFFYEK IYPKSN      356

SEQ ID NO: 187          moltype = AA  length = 356
FEATURE                 Location/Qualifiers
source                  1..356
                        mol_type = protein
                        organism = Physeter catodon
SEQUENCE: 187
MGLLRIMMPP KLQLLAVVAF AVAMLFLENQ IQKLEESRSK LERAIARHEV REIEQRHTMD   60
GPRQDAALDE EEDMVIIYNR VPKTASTSFT NIAYDLCAKN KYHVLHINTT KNNPVMSLQD  120
QVRFVKNITS WKEMKPGFYH GHISYLDFAK FGVKKKPIYI NVIRDPIERL VSYYYFLRFG  180
DDYRPGLRRR KQGDKKTFDE CVAEGGSDCA PEKLWLQIPF FCGHSSECWN VGSRWAMDQA  240
KYNLVNEYFL VGVTEELEDF IMLLEAALPR FFRGATELYR TGKKSHLRKT TEKKLPTKQT  300
IAKLQQSDIW KMENEFYEFA LEQFQFIRAH AVREKDGDLY ILAQNFFYEK IYPKSN      356

SEQ ID NO: 188          moltype = AA  length = 356
FEATURE                 Location/Qualifiers
source                  1..356
                        mol_type = protein
                        organism = Crotalus horridus
SEQUENCE: 188
MGLLRIMLPP KLQLLAVMAF GVSVLFLENQ IQKLEESRGK LERAIAKHEV REIEQRHTVD   60
GSRSDLIPDE DDDVVIIYNR VPKTASTSFT NIAYDLCAKN KYHVLHINTT KNNPVMSLQD  120
QVRFVKNITS WKEMKPGFYH GHISFLDFAK FGVKKKPIYI NVIRDPIERL VSYYYFLRFG  180
DDYRPGLRRR KQGDKKTFDE CVAAGGSDCA PEKLWLQIPF FCGHSSECWN VGSRWALEQA  240
KYNLINEYFL VGVTEELEDF IMLLEAALPR FFRGATELYR TGKKSHLRKT TEKKLPSKET  300
IAKLQQSEIW KMENEFYEFS LEQFQFVRAH AVREKDGELY ILAQNFFYEK IYPKSN      356
```

```
SEQ ID NO: 189          moltype = AA  length = 354
FEATURE                 Location/Qualifiers
source                  1..354
                        mol_type = protein
                        organism = Danio rerio
SEQUENCE: 189
MGLLRLMMPP KFQLLALLAF AIAMIFLENQ IQKLEESRGK LEQAIARHEV REIERRHSQV    60
GVKEVQLEED DTVVIYNRVP KTASTSFTNI AYDLCNKNHY HVLHINTSKN NPVMSLQDQV   120
RFVKNVTLWK EMKPAYHGH VSFLDFTKFG VKKKPIYINV IRDPIERLVS YYYFLRFGDD   180
YRPGLRRRKQ GDKKTFDECV SAGGSDCAPE KLWLQIPFFC GHYSECWNIG SRWALEQAKY   240
NLVNEYMLVG VTEELEDFVM MLEAALPRFF KGATELYKTG KRSHLRKTSE KKPPTKESIA   300
RLQQSNIWKM ENEFYEFALE QFQYVRAHAV REKDGELYLL TQNFFYEKIY PKSN         354

SEQ ID NO: 190          moltype = AA  length = 368
FEATURE                 Location/Qualifiers
source                  1..368
                        mol_type = protein
                        organism = Fundulus heteroclitus
SEQUENCE: 190
MGLLRVMMPP KLQLLALLAF AALLAFAVAM FFLENQIQKL EESRGKLERA IARHEVREIE    60
QRHTQDGQRE RETAETAATL SDSDDDLVII YNRVPKTAST SFTNIAYDLC GKNRYHVLHI   120
NTTKNNPVMS IQDQVRFVKN VTEWREMKPA FYHGHVSFLD FTKFGVKRKP VYINLIRDPI   180
ERLVSYYYFL RFGDDYRPGL RRRKQGDKKT FDECVSAGGS DCAPERLWLQ IPFFCGHYSE   240
CWNVGSQWAL EQAKYNLVNE YMLVGVTEEL EDFVMMLEAA LPRFFRGATE LYKTGKKSHL   300
RRTSEKKPPT KESVARLQQS DIWKMENEFY EFALEQFQFV RAHAVREKDG ELYMLAQNFF   360
YEKIYPKN                                                            368

SEQ ID NO: 191          moltype = AA  length = 311
FEATURE                 Location/Qualifiers
source                  1..311
                        mol_type = protein
                        organism = Mus musculus
SEQUENCE: 191
KYYFPVRELE RSLRFDMKGD DVIVFLHIQK TGGTTFGRHL VQNVRLEVPC DCRPGQKKCT    60
CYRPNRRETW LFSRFSTGWS CGLHADWTEL TNCVPGVLDR RDPAGLRSPR KFYYITLLRD   120
PVSRYLSEWR HVQRGATWKT SLHMCDGRTP TPEELPPCYE GTDWSGCTLQ EFMDCPYNLA   180
NNRQVRMLAD LSLVGCYNLS FIPESKRAQL LLESAKKNLR GMAFFGLTEF QRKTQYLFER   240
TFNLKFIRPF MQYNSTRAGG VEVDEDTIRH IEELNDLDMQ LYDYAKDLFQ QRYQYKRQLE   300
RREQRLRNRE E                                                        311

SEQ ID NO: 192          moltype = AA  length = 311
FEATURE                 Location/Qualifiers
source                  1..311
                        mol_type = protein
                        organism = Homo sapiens
SEQUENCE: 192
KYYFPVRELE RSLRFDMKGD DVIVFLHIQK TGGTTFGRHL VQNVRLEVPC DCRPGQKKCT    60
CYRPNRRETW LFSRFSTGWS CGLHADWTEL TNCVPGVLDR RDSAALRTPR KFYYITLLRD   120
PVSRYLSEWR HVQRGATWKT SLHMCDGRTP TPEELPPCYE GTDWSGCTLQ EFMDCPYNLA   180
NNRQVRMLAD LSLVGCYNLS FIPEGKRAQL LLESAKKNLR GMAFFGLTEF QRKTQYLFER   240
TFNLKFIRPF MQYNSTRAGG VEVDEDTIRR IEELNDLDMQ LYDYAKDLFQ QRYQYKRQLE   300
RREQRLRSRE E                                                        311

SEQ ID NO: 193          moltype = AA  length = 311
FEATURE                 Location/Qualifiers
source                  1..311
                        mol_type = protein
                        organism = Sus scrofa
SEQUENCE: 193
KYYFPVRELE RSLHFDMKGD DVIVFLHIQK TGGTTFGRHL VQNVRLEVPC DCRPGQKKCT    60
CYRPNRRETW LFSRFSTGWS CGLHADWTEL TNCVPGVLDR RDPAALRTPR KFYYITLLRD   120
PVSRYLSEWR HVQRGATWKT SLHMCDGRTP TPEELPPCYE GTDWSGCTLQ EFMDCPYNLA   180
NNRQVRMLAD LSLVGCYNLS FIPEGKRSQL LLESAKKNLR GMAFFGLTEF QRKTQYLFER   240
TFNLKFIRPF MQYNSTRAGG VEVGEDTIRR IEELNDLDMQ LYDYARDLFQ QRYQYKRQLE   300
RRQQRLRSRE E                                                        311

SEQ ID NO: 194          moltype = AA  length = 311
FEATURE                 Location/Qualifiers
source                  1..311
                        mol_type = protein
                        organism = Macaca mulatta
SEQUENCE: 194
KYYFPVRELE RSLRFDMKGD DVIVFLHIQK TGGTTFGRHL VQNVRLEVPC DCRPGQKKCT    60
CYRPNRRETW LFSRFSTGWS CGLHADWTEL TNCVPGVLDR RDSAALRTPR KFYYITLLRD   120
PVSRYLSEWR HVQRGATWKT SLHMCDGRTP TPEELPPCYE GTDWSGCTLQ EFMDCPYNLA   180
NNRQVRMLAD LSLVGCYNLS FIPEGKRAQL LLESAKKNLR GMAFFGLTEF QRKTQYLFER   240
TFNLKFIRPF MQYNSTRAGG VEVDEDTIRR IEELNDLDMQ LYDYAKDLFQ QRYQYKRQLE   300
RREQRLRSRE E                                                        311
```

```
SEQ ID NO: 195          moltype = AA   length = 311
FEATURE                 Location/Qualifiers
source                  1..311
                        mol_type = protein
                        organism = Gallus gallus
SEQUENCE: 195
KYYFPVRELE RELAFDMKGE DVIVFLHIQK TGGTTFGRHL VQNVRLEVPC DCRPGQKKCT    60
CYRPNRRETW LFSRFSTGWS CGLHADWTEL TNCVPGVLGR RESAPNRTPR KFYYITLLRD   120
PVSRYLSEWR HVQRGATWKT SLHMCDGRTP TPEELPSCYE GTDWSGCTLQ EFMDCPYNLA   180
NNRQVRMLAD LSLVGCYNMS FIPENKRAQI LLESAKKNLK DMAFFGLTEF QRKTQYLFER   240
TFNLKFIRPF MQYNSTRAGG VEVDNDTIRR IEELNDLDMQ LYDYAKDLFQ QRYQYKRQLE   300
RMEQRIKNRE E                                                        311

SEQ ID NO: 196          moltype = AA   length = 309
FEATURE                 Location/Qualifiers
source                  1..309
                        mol_type = protein
                        organism = Danio rerio
SEQUENCE: 196
KFYFPIRDLE RTVDFEIKGD DVIVFLHIQK TGGTTFGRHL VQNVRLEVPC DCRPGQKKCT    60
CYRPNRKETW LFSRFSTGWS CGLHADWTEL TNCVPGVLNK KESRMKNQRK FYYITLLRDP   120
VSRYLSEWRH VQRGATWKTS LHMCDGRTPT PEELPPCYEG TDWSGCTLQQ FMDCPYNLAN   180
NRQVRMLADL SLVGCYNMSF IPEKKRAQVL LESAKKNLRD MAFFGLTEFQ RKTQYLFERT   240
FRLKFIRPFM QYNSTRAAGV DLDNDTIQRI EELNDLDMQL YDYARDLFQQ RYMYKRQLER   300
REQRLKNQP                                                           309

SEQ ID NO: 197          moltype = AA   length = 310
FEATURE                 Location/Qualifiers
source                  1..310
                        mol_type = protein
                        organism = Homo sapiens
SEQUENCE: 197
RYNFTRGDLL RKVDFDIKGD DLIVFLHIQK TGGTTFGRHL VRNIQLEQPC ECRVGQKKCT    60
CHRPGKRETW LFSRFSTGWS CGLHADWTEL TSCVPSVVDG KRDARLRPSR NFHYITILRD   120
PVSRYLSEWR HVQRGATWKA SLHVCDGRPP TSEELPSCYT GDDWSGCPLK EFMDCPYNLA   180
NNRQVRMLSD LTLVGCYNLS VMPEKQRNKV LLESAKSNLK HMAFFGLTEF QRKTQYLFEK   240
TFNMNFISPF TQYNTTRASS VEINEEIQKR IEGLNFLDME LYSYAKDLFL QRYQFMRQKE   300
HQEARRKRQE                                                          310

SEQ ID NO: 198          moltype = AA   length = 313
FEATURE                 Location/Qualifiers
source                  1..313
                        mol_type = protein
                        organism = Danio rerio
SEQUENCE: 198
RFNFTTKDLS RAVDFHIKGD DVIVFLHIQK TGGTTFGRHL VRNIQLERPC ECHAGQKKCT    60
CYRPGKRDTW LFSRFSTGWS CGLHADWTEL TNCVPSFMSN RESQERRMTP SRNYYYITIL   120
RDPVWRYLSE WRHVQRGATW KASKHMCDGR LPTLTELPSC YPGDDWSGCS LEEFMVCPYN   180
LANNRQTRML ADLSLVGCYN LTVMSENQRW AMLLESAKRN LRNMAFFGLT EYQRKTQYLF   240
EHTFRLSFIA PFTQLNGTRA ASVEVEPETQ RRIRELNQWD VELYEYARDL FLQRFQFARQ   300
QERREARQRR IQE                                                      313

SEQ ID NO: 199          moltype = AA   length = 310
FEATURE                 Location/Qualifiers
source                  1..310
                        mol_type = protein
                        organism = Mus musculus
SEQUENCE: 199
RYNFSRGDLL RKVDFDIKGD DLIVFLHIQK TGGTTFGRHL VRNIQLEQPC ECRVGQKKCT    60
CHRPGKRETW LFSRFSTGWS CGLHADWTEL TSCVPAVVDG KRDARLRPSR NFHYITILRD   120
PVSRYLSEWR HVQRGATWKA SLHVCDGRPP TSEELPSCYT GDDWSGCPLK EFMDCPYNLA   180
NNRQVRMLSD LTLVGCYNLS VMPEKQRNKV LLESAKSNLK HMAFFGLTEF QRKTQYLFEK   240
TFNMNFISPF TQYNTTRASS VEINEEIQKR IEGLNFLDME LYSYAKDLFL QRYQFMRQKE   300
HQDARRKRQE                                                          310

SEQ ID NO: 200          moltype = AA   length = 310
FEATURE                 Location/Qualifiers
source                  1..310
                        mol_type = protein
                        organism = Gallus gallus
SEQUENCE: 200
RFNFSAGDLL RRVDFNIKGD DLIVFLHIQK TGGTTFGRHL VRNIQLEQPC ECRAGQKKCT    60
CHRPGKRETW LFSRFSTGWS CGLHADWTEL TNCVPSVVDS KKEVRLRPSR NFYYITILRD   120
PVSRYLSEWR HVQRGATWKA SLHVCDGRSP TTEELPSCYT GDDWSGCSLQ EFMDCPYNLA   180
NNRQVRMLSD LSLVGCYNLS VMPEEQRNKV LLDSAKENLK RMAFFGLTEF QRKTQYLFEK   240
TFNMNFISPF TQYNSTRASS VEIDEQTQQR IEALNFLDME LYDYAKDLFL QRYQYMRQKE   300
HQEARRKRQE                                                          310

SEQ ID NO: 201          moltype = AA   length = 312
```

```
FEATURE                 Location/Qualifiers
source                  1..312
                        mol_type = protein
                        organism = Mus musculus
SEQUENCE: 201
RFNFTLKDLT RFVDFNIKGR DVIVFLHIQK TGGTTFGRHL VKNIRLEQPC SCKAGQKKCT   60
CHRPGKKETW LFSRFSTGWS CGLHADWTEL TNCVPAIMEK KDCPRNHSHT RNFYYITMLR  120
DPVSRYLSEW KHVQRGATWK TSLHMCDGRS PTPDELPTCY PGDDWSGVSL REFMDCSYNL  180
ANNRQVRMLA DLSLVGCYNL TFMNESERNT ILLQSAKNNL KNMAFFGLTE FQRKTQFLFE  240
RTFNLKFISP FTQFNITRAS NVDINDGARQ HIEELNFLDM QLYEYAKDLF QQRYHHTKQL  300
EHQRDRQKRR EE                                                     312

SEQ ID NO: 202          moltype = AA  length = 312
FEATURE                 Location/Qualifiers
source                  1..312
                        mol_type = protein
                        organism = Homo sapiens
SEQUENCE: 202
RFNFSLKDLT RFVDFNIKGR DVIVFLHIQK TGGTTFGRHL VKNIRLEQPC SCKAGQKKCT   60
CHRPGKKETW LFSRFSTGWS CGLHADWTEL TNCVPAIMEK KDCPRNHSHT RNFYYITMLR  120
DPVSRYLSEW KHVQRGATWK TSLHMCDGRS PTPDELPTCY PGDDWSGVSL REFMDCTYNL  180
ANNRQVRMLA DLSLVGCYNL TFMNESERNT ILLQSAKNNL KNMAFFGLTE FQRKTQFLFE  240
RTFNLKFISP FTQFNITRAS NVEINEGARQ RIEDLNFLDM QLYEYAKDLF QQRYHHTKQL  300
EHQRDRQKRR EE                                                     312

SEQ ID NO: 203          moltype = AA  length = 312
FEATURE                 Location/Qualifiers
source                  1..312
                        mol_type = protein
                        organism = Bos taurus
SEQUENCE: 203
RFNFTPKDLT RFVDFNIKGR DVIVFLHIQK TGGTTFGRHL VKNIRLEQPC SCKAGQKKCT   60
CHRPGKKETW LFSRFSTGWS CGLHADWTEL TNCVPAIMEK KDCPRNHSHT RNFYYITMLR  120
DPVSRYLSEW KHVQRGATWK TSLHMCDGRS PTPDELPTCY PGDDWSGVSL REFMDCTYNL  180
ANNRQVRMLA DLSLVGCYNL TFMNESERNA ILLQSAKSNL KNMAFFGLTE FQRKTQFLFE  240
RTFNLKFISP FTQFNITRAS NVEINEGARR RIEELNFLDV QLYEYAKDLF QQRYHRTKQL  300
ERQRDRQRRR GE                                                     312

SEQ ID NO: 204          moltype = AA  length = 309
FEATURE                 Location/Qualifiers
source                  1..309
                        mol_type = protein
                        organism = Danio rerio
SEQUENCE: 204
KFNFTERDLT RDVDFNIKGD DVIVFLHIQK TGGTTFGRHL VRNIRLEQPC DCKAGQKKCT   60
CHRPGKQESW LFSRFSTGWS CGLHADWTEL TNCVPVIMDK RQPPKRKRNF YYITMLRDPV  120
SRYLSEWKHV QRGATWKTSL HMCDGRSPTQ DELPTCYNGD DWSGVTLHDF MDCPSNLANN  180
RQVRMLADLS LVGCYNLSTM NESERNPILL ASAKSNLKNM AFYGLTEFQR KTQYLFERTF  240
HLRFISAFTQ INSTRAANVE LRDDMRSRIE QLNMLDMQLY EFAKDLFLQR YQFVRQRERQ  300
EERLKRREE                                                         309

SEQ ID NO: 205          moltype = AA  length = 313
FEATURE                 Location/Qualifiers
source                  1..313
                        mol_type = protein
                        organism = Cynoglossus semilaevis
SEQUENCE: 205
RLNFSERDMD RRVQFNIRGD DVMVFLHIQK TGGTTFGRHL VKNIHLERPC NCTAGQRKCT   60
CHRPGKAESW LFSRFSTGWS CGLHADWTEL SSCVPVVMSQ RDRKKVQKKK KRSFYYITML  120
RDPVSRYLSE WKHVQRGATW KTALHMCDGR PPTQDELPAC YNGEDWTGVP LADFMNCPSN  180
LANNRQVRML ADLSLVGCYN MSSMSELERG RVLLASAKAN LRNMAFYGLT EFQRKTQYLF  240
ERTFGLRFIK AFTQINSTRA ASVGISEKVR WRIEGLNALD MELYEYAKNL FLLRYQYSRQ  300
RQHQEERLRR RQE                                                    313

SEQ ID NO: 206          moltype = AA  length = 307
FEATURE                 Location/Qualifiers
source                  1..307
                        mol_type = protein
                        organism = Homo sapiens
SEQUENCE: 206
MAALLLGAVL LVAQPQLVPS RPAELGQQEL LRKAGTLQDD VRDGVAPNGS AQQLPQTIII   60
GVRKGGTRAL LEMLSLHPDV AAAENEVHFF DWEEHYSHGL GWYLSQMPFS WPHQLTVEKT  120
PAYFTSPKVP ERVYSMNPSI RLLLILRDPS ERVLSDYTQV FYNHMQKHKP YPSIEEFLVR  180
DGRLNVDYKA LNRSLYHVHM QNWLRFFPLR HIHIVDGDRL IRDPFPEIQK VERFLKLSPQ  240
INASNFYFNK TKGFYCLRDS GRDRCLHESK GRAHPQVDPK LLNKLHEYFH EPNKKFFELV  300
GRTFDWH                                                           307

SEQ ID NO: 207          moltype = AA  length = 307
FEATURE                 Location/Qualifiers
```

```
source                          1..307
                                mol_type = protein
                                organism = Macaca mulatta
SEQUENCE: 207
MAALLLGAVL LVAQPQLVPS RPAELGQQEL LRKAGTLQDD VRYGAAANGS AQQLPQTIII      60
GVRKGGTRAL LEMLSLHPDV AAAENEVHFF DWEEHYGHGL GWYLSQMPFS WPHQLTVEKT     120
PAYFTSPKVP ERVHSMNPSI RLLLILRDPS ERVLSDYTQV FYNHMQKRKP YPSIEEFLVR     180
DGRLNVDYKA LNRSLYHVHM QNWLRFFPLR HIHIVDGDRL IRDPFPEIQK VERFLKLSPQ     240
INASNFYFNK TKGFYCLRDS GRDRCLHESK GRAHPQVDPK LLNKLHEYFH EPNKKFFELV     300
GRTFDWH                                                               307

SEQ ID NO: 208                  moltype = AA   length = 261
FEATURE                         Location/Qualifiers
source                          1..261
                                mol_type = protein
                                organism = Ailuropoda melanoleuca
SEQUENCE: 208
PNGSAQQLPQ TIIIGVRKGG TRALLEMLSL HPDVAAAENE VHFFDWEEHY SQGLGWYLGQ      60
MPFSSPHQLT VEKTPAYFTS SKVPERVHSM NPGIRLLLIL RDPSERVLSD YTQVFYNHVQ     120
KRKPYPSIEE FLVRDGRLNV GYKALNRSLY HVHLQNWLRF FPLRRIHIVD GDRLIRDPFP     180
EIQKVERFLK LSPQINASNF YFNKTKGFYC LRDGGRDRCL HESKGRAHPQ VDPRLLNKLH     240
EYFHEPNKKF FELVGRTFDW H                                               261

SEQ ID NO: 209                  moltype = AA   length = 311
FEATURE                         Location/Qualifiers
source                          1..311
                                mol_type = protein
                                organism = Equus caballus
SEQUENCE: 209
MAALLLGAVL LVAQLQLMPC RPAAPGAEPG QQELVGKAAT LQNEVRAGAA PNGSAQQLPQ      60
TIIIGVRKGG TRALLEMLSL HPDVAAAENE VHFFDWEEHF SQGLGWYLSQ MPFSAPHQLT     120
VEKTPAYFTS PKVPERVHSM NPSIRLLLIL RDPSERVLSD YTQVFYNHVQ KHKPYPSIEE     180
FLVRDGRLNV DYKALNRSLY HVHMQNWLRF FPLRHIHIVD GDRLIRDPFP EIQKVERFLK     240
LAPQINASNF YFNKTKGFYC LRDSGRDRCL HESKGRAHPQ VDPKLLNKLH EYFHEPNKKF     300
FELVGRTFDW H                                                          311

SEQ ID NO: 210                  moltype = AA   length = 311
FEATURE                         Location/Qualifiers
source                          1..311
                                mol_type = protein
                                organism = Sus scrofa
SEQUENCE: 210
MAALLLGAVM LVLQLQLVPC RPAMPGAGPS QQELVRKAAT LQDEVRDSAA PNGSVQQLPQ      60
TIIIGVRKGG TRALLEMLSL HPDVAAAENE VHFFDWEEHY SQGLDWYLSQ MPFSYPHQLT     120
VEKTPAYFTS PKVPERVHRM NPSIRLLLIL RDPSERVLSD YTQVFYNHVQ KHKPYPSIEE     180
FLVRDGRLNV DYKALNRSLY HVHMQNWLRF FPLRRIHIVD GDRLIRDPFP EIQKVERFLM     240
LSPQINASNF YFNKTKGFYC LRDGGRDRCL HESKGRAHPQ IDPKLLNKLH EYFHEPNKKF     300
FELVGRTFDW H                                                          311

SEQ ID NO: 211                  moltype = AA   length = 312
FEATURE                         Location/Qualifiers
source                          1..312
                                mol_type = protein
                                organism = Bos taurus
SEQUENCE: 211
MAPLLLGAVM LVAQLQLVPS RPAVVPGDEP GLPELVRKAA ALQEEISDGA APNGSAQQLP      60
QTIIIGVRKG GTRALLEMLS LHPDVAAAEN EVHFFDWEEH YSQGLGWYLS QMPFSAPHQL     120
TVEKTPAYFT SPKVPERVHG MNPAIRLLLI LRDPSERVLS DYTQVFYNHV QKRKPYPSIE     180
EFLVRDGRLN VDYKALNRSL YHLHMQNWLR FFPLRRIHIV DGDRLIRDPF PEIQKVERFL     240
RLSPQINASN FYFNKTKGFY CLRDSGRDRC LHESKGRAHP QVDPRLLNKL HEYFHEPNKK     300
FFELVGRTFD WH                                                         312

SEQ ID NO: 212                  moltype = AA   length = 311
FEATURE                         Location/Qualifiers
source                          1..311
                                mol_type = protein
                                organism = Rattus norvegicus
SEQUENCE: 212
MTLLLLGAVL LVAQPQLVPS HPAAPGPGLK QQGLLRKVII LPEDTGEGAA TNGSTQQLPQ      60
TIIIGVRKGG TRALLEMLSL HPDVAAAENE VHFFDWEEHY SQGLGWYLTQ MPFSSPHQLT     120
VEKTPAYFTS PKVPERIHSM NPTIRLLLIL RDPSERVLSD YTQVLYNHLQ KHKPYPPIED     180
LLMRDGRLNV DYKALNRSLY HAHMNWLRF FPLGHIHIVD GDRFIRDPFP EIQKVERFLK     240
LSPQINASNF YFNKTKGFYC LRDSGKDRCL HESKGRAHPQ VDPKLLDKLH EYFREPNKKF     300
FKLVGRTFDW H                                                          311

SEQ ID NO: 213                  moltype = AA   length = 311
FEATURE                         Location/Qualifiers
source                          1..311
                                mol_type = protein
```

```
                          organism = Mus musculus
SEQUENCE: 213
MTLLLLGAVL LVAQPQLVHS HPAAPGPGLK QQELLRKVII LPEDTGEGTA SNGSTQQLPQ       60
TIIIGVRKGG TRALLEMLSL HPDVAAAENE VHFFDWEEHY SQGLGWYLTQ MPFSSPHQLT      120
VEKTPAYFTS PKVPERIHSM NPTIRLLLIL RDPSERVLSD YTQVLYNHLQ KHKPYPPIED      180
LLMRDGRLNL DYKALNRSLY HAHMLNWLRF FPLGHIHIVD GDRLIRDPFP EIQKVERFLK      240
LSPQINASNF YFNKTKGFYC LRDSGKDRCL HESKGRAHPQ VDPKLLDKLH EYFHEPNKKF      300
FKLVGRTFDW H                                                         311

SEQ ID NO: 214           moltype = AA  length = 320
FEATURE                  Location/Qualifiers
source                   1..320
                         mol_type = protein
                         organism = Gallus gallus
SEQUENCE: 214
MAAFLLGAVL LIVQPQIVPS RPAINSKAET SAQSAQRELL KKTSQKNDFK ENIHSNGSCR       60
QLPQTIIIGV RKGGTRALLE MLSLHPDIAA AESEVHFFDW EDHYRNGLQW YINQMPFSYP      120
HQITVEKTPA YFTSPEVPER VYNMNQSMRL LLILRDPSER VLSDYTQVFY NHMQKHKPYP      180
SIEQFLIKDG ELNVDYKAIN RSLYYIHMQN WLKYFPLDHI HIVDGDKLIK DPFPEIEKVE      240
RFLKLSPQIN ASNFYFNKTK GFYCLRDSGR ERCLHESKGR AHPQVDTRLL EKLHEYFYEP      300
NKKFFELVGR TFDWHSSVAS                                                 320

SEQ ID NO: 215           moltype = AA  length = 308
FEATURE                  Location/Qualifiers
source                   1..308
                         mol_type = protein
                         organism = Anolis carolinensis
SEQUENCE: 215
MAVFLLGAAL LIVQPQVVPS RPTASSKVDS TTPKESFRKR DFKDWIHPNE TLRQLPQTII       60
IGVRKGGTRA LLEMLSLHPD IAAAESEVHF FDWEEHYGKG LQWYINQMPL SDIHQITVEK      120
TPAYFTSSKV PERVYKMNKF TRLLLILRDP TERVLSDYTQ VFFNHVQKHK PYPSIEEFLV      180
KDGELNVNYK AINRSLYYVH MQNWLKYFPL DHIVVDGDK LIKDPFSEII KVEEFLKLPP       240
QINASNFYFN KTKGFYCLRD SGRDRCLHES KGRAHPKVDP ILLEKLHKYF CEPNQKFFEL      300
VGRTFDWH                                                             308

SEQ ID NO: 216           moltype = AA  length = 307
FEATURE                  Location/Qualifiers
source                   1..307
                         mol_type = protein
                         organism = Oreochromis niloticus
SEQUENCE: 216
MAALLLGLLL FAMQSPPIPS RPVADGDEGP PLPPTSSPAD NGTTSHPNGT LQQLPHILII       60
GVRKGGTRAL IEMLSLHSSV AAAQNEVHFF DWESHFQRGL PWYLSQMPYA FPDQLTVEKT      120
PAYFTSSKVP KRIHQMNTDI KLLLILRDPT ERVLSDYTQV FYNRLQKHKR YQPIESVLVK      180
DGEINLGYKA LNRSLYYVHM QNWLQYFPLE SIHIVDGDEL IRDPFPEMKK VERFLKLEPQ      240
INASNFYFNK TKGFYCLRDH GRERCLHDSK GRAHPHVAPA ILQKLYQFFH EPNKKFFELV      300
GRTFTWK                                                              307

SEQ ID NO: 217           moltype = AA  length = 315
FEATURE                  Location/Qualifiers
source                   1..315
                         mol_type = protein
                         organism = Callorhinchus milii
SEQUENCE: 217
MATFFLGLLL FLVHPVVVPS RPRFDLKYRI PPHAMRYTLP NNYSSQKIYQ PLVFPNGTSQ       60
RLPQTIIIGV RKGGTRALLE MLNLHPDVTA AESEIHFFDW EENYAKGLQW YGKQMPLSYP      120
RQLTVEKTPA YFTSSEVPER IYNMNKTTRL LLILRDPTER VISDYTQVFF NRMQKHKPFQ      180
SVEEMLIRNG RVNLDYKAVN RSLYYIHMQN WLKYFPLSQI HIVDGDQLIK EPFPEMKVE       240
RFLMLSPRIN ASNFYFNKTK GFYCLRDGVR ERCLHESKGR THPQVDSTVL NKLHEFFSEP      300
NRKFFETVGR TFDWH                                                     315

SEQ ID NO: 218           moltype = AA  length = 312
FEATURE                  Location/Qualifiers
source                   1..312
                         mol_type = protein
                         organism = Pygocentrus nattereri
SEQUENCE: 218
MAATLPAFLL FLSWSPPVPS RPTVYPGPPS PSRMLQNGTR HLPDIIIIGV RKGGTRALIE       60
MLSLHSSITS AENEVHFFDW ESHYQQGLTW YASQMPSAQP GQLTVEKTPA YFTCAKVPER      120
VFHMNPNVRL LLIVRDPVDR VLSDYTQVFY NHLQKRKPQ PIEDLLLLKD GQLNLAYKAL       180
NRSLYYTHMQ QWLTIFPRTS FHVVDGDALI REPLDEMRKV ENFLGLEPQI NAENFYFNRT      240
KGFYCLRDRE GHERCLHSSK GRTHPQVSPE ILQKLRDYFH KPNRKFFELV GRTFDWNQAS      300
EDRQETQTLK GE                                                        312

SEQ ID NO: 219           moltype = AA  length = 308
FEATURE                  Location/Qualifiers
source                   1..308
                         mol_type = protein
                         organism = Crotalus horridus
```

```
SEQUENCE: 219
MAFLLVSAYL LLTPAQAAPV ENGALVEMLM PQVLLSNKSE HYLAQVRPPG TSRQIPQTII    60
IGVRKGGTRA LLEMLDVHPN IVVAAIEVHF FDWDENYVKG IDWYRSLMPF SYENQITIEK   120
TPGYFTSPQA PERIHDMNSS IKLLLILRDP TERVISDYTQ VYYNRLENHK SVQPFEDIVI   180
KNGALNTKYK AIQRSLYDIH MGRWLKYFHL DQIHIVDGNT LIRDPLPELQ KVERFLNLPS   240
KILSSNFYFN QTKGFYCIRS DGRERCLHES KGRPHPVVNS TVLEQLYSYF REHNEKFYRM   300
INHSFDWH                                                           308

SEQ ID NO: 220          moltype = AA   length = 346
FEATURE                 Location/Qualifiers
source                  1..346
                        mol_type = protein
                        organism = Homo sapiens
SEQUENCE: 220
MLFKQQAWLR QKLLVLGSLA VGSLLYLVAR VGSLDRLQPI CPIEGRLGGA RTQAEFPLRA    60
LQFKRGLLHE FRKGNASKEQ VRLHDLVQQL PKAIIIGVRK GGTRALLEML NLHPAVVKAS   120
QEIHFFDNDE NYGKGIEWYR KKMPFSYPQQ ITIEKSPAYF ITEEVPERIY KMNSSIKLLI   180
IVREPTTRAI SDYTQVLEGK ERKNKTYYKF EKLAIDPNTC EVNTKYKAVR TSIYTKHLER   240
WLKYFPIEQF HVVDGDRLIT EPLPELQVLE KFLNLPPRIS QYNLYFNATR GFYCLRFNII   300
FNKCLAGSKG RIHPEVDPSV ITKLRKFFHP FNQKFYQITG RTLNWP                  346

SEQ ID NO: 221          moltype = AA   length = 10
FEATURE                 Location/Qualifiers
REGION                  1..10
                        note = NST conserved amino acid sequence motif 1
source                  1..10
                        mol_type = protein
                        organism = synthetic construct
SEQUENCE: 221
QKTGTTALYL                                                          10

SEQ ID NO: 222          moltype = AA   length = 4
FEATURE                 Location/Qualifiers
REGION                  1..4
                        note = NST conserved amino acid sequence motif 2
source                  1..4
                        mol_type = protein
                        organism = synthetic construct
SEQUENCE: 222
TFEE                                                                 4

SEQ ID NO: 223          moltype = AA   length = 5
FEATURE                 Location/Qualifiers
REGION                  1..5
                        note = NST conserved amino acid sequence motif 3
source                  1..5
                        mol_type = protein
                        organism = synthetic construct
SEQUENCE: 223
FEKSA                                                                5

SEQ ID NO: 224          moltype = AA   length = 5
FEATURE                 Location/Qualifiers
REGION                  1..5
                        note = NST conserved amino acid sequence motif 4
source                  1..5
                        mol_type = protein
                        organism = synthetic construct
SEQUENCE: 224
SWYQH                                                                5

SEQ ID NO: 225          moltype = AA   length = 8
FEATURE                 Location/Qualifiers
REGION                  1..8
                        note = NST conserved amino acid sequence motif 5
SITE                    4
                        note = MISC_FEATURE - Xaa is either lysine or arginine
source                  1..8
                        mol_type = protein
                        organism = synthetic construct
SEQUENCE: 225
CLGXSKGR                                                             8

SEQ ID NO: 226          moltype = AA   length = 7
FEATURE                 Location/Qualifiers
REGION                  1..7
                        note = NST engineered amino acid sequence motif 1
SITE                    2
                        note = MISC_FEATURE - Xaa is either glycine or lysine
```

```
SITE                    5
                        note = MISC_FEATURE - Xaa is either glycine or valine
source                  1..7
                        mol_type = protein
                        organism = synthetic construct
SEQUENCE: 226
HXTGXHA                                                                      7

SEQ ID NO: 227          moltype = AA  length = 7
FEATURE                 Location/Qualifiers
REGION                  1..7
                        note = NST engineered amino acid sequence motif 2
source                  1..7
                        mol_type = protein
                        organism = synthetic construct
SEQUENCE: 227
HGTGGHA                                                                      7

SEQ ID NO: 228          moltype = AA  length = 7
FEATURE                 Location/Qualifiers
REGION                  1..7
                        note = NST engineered amino acid sequence motif 3
source                  1..7
                        mol_type = protein
                        organism = synthetic construct
SEQUENCE: 228
HKTGVHA                                                                      7

SEQ ID NO: 229          moltype = AA  length = 8
FEATURE                 Location/Qualifiers
REGION                  1..8
                        note = NST engineered amino acid sequence motif 4
SITE                    4
                        note = MISC_FEATURE - Xaa is either lysine or arginine
source                  1..8
                        mol_type = protein
                        organism = synthetic construct
SEQUENCE: 229
CLGXSLGR                                                                     8

SEQ ID NO: 230          moltype = AA  length = 8
FEATURE                 Location/Qualifiers
REGION                  1..8
                        note = NST engineered amino acid sequence motif 5
SITE                    4
                        note = MISC_FEATURE - Xaa is either lysine or arginine
source                  1..8
                        mol_type = protein
                        organism = synthetic construct
SEQUENCE: 230
CLGXSVGR                                                                     8

SEQ ID NO: 231          moltype = AA  length = 4
FEATURE                 Location/Qualifiers
REGION                  1..4
                        note = NST engineered amino acid sequence motif 6
source                  1..4
                        mol_type = protein
                        organism = synthetic construct
SEQUENCE: 231
TFEH                                                                         4

SEQ ID NO: 232          moltype = AA  length = 5
FEATURE                 Location/Qualifiers
REGION                  1..5
                        note = NST engineered amino acid sequence motif 7
source                  1..5
                        mol_type = protein
                        organism = synthetic construct
SEQUENCE: 232
FEHSA                                                                        5

SEQ ID NO: 233          moltype = AA  length = 8
FEATURE                 Location/Qualifiers
REGION                  1..8
                        note = NST engineered amino acid sequence motif 8
SITE                    4
                        note = MISC_FEATURE - Xaa is either lysine or arginine
source                  1..8
```

```
                                 mol_type = protein
                                 organism = synthetic construct
SEQUENCE: 233
CLGXHKGR                                                                 8

SEQ ID NO: 234          moltype = AA   length = 7
FEATURE                 Location/Qualifiers
REGION                  1..7
                        note = NST engineered amino acid sequence motif 9
SITE                    1
                        note = MISC_FEATURE - Xaa is either serine or alanine
SITE                    6
                        note = MISC_FEATURE - Xaa is either tryptophan or
                         phenylalanine
SITE                    7
                        note = MISC_FEATURE - Xaa is either alanine or leucine
source                  1..7
                        mol_type = protein
                        organism = synthetic construct
SEQUENCE: 234
XKTGAXX                                                                  7

SEQ ID NO: 235          moltype = AA   length = 7
FEATURE                 Location/Qualifiers
REGION                  1..7
                        note = NST engineered amino acid sequence motif 10
SITE                    6
                        note = MISC_FEATURE - Xaa is either tryptophan or
                         phenylalanine
SITE                    7
                        note = MISC_FEATURE - Xaa is either alanine or leucine
source                  1..7
                        mol_type = protein
                        organism = synthetic construct
SEQUENCE: 235
SKTGAXX                                                                  7

SEQ ID NO: 236          moltype = AA   length = 7
FEATURE                 Location/Qualifiers
REGION                  1..7
                        note = NST engineered amino acid sequence motif 11
SITE                    6
                        note = MISC_FEATURE - Xaa is either tryptophan or
                         phenylalanine
SITE                    7
                        note = MISC_FEATURE - Xaa is either alanine or leucine
source                  1..7
                        mol_type = protein
                        organism = synthetic construct
SEQUENCE: 236
AKTGAXX                                                                  7

SEQ ID NO: 237          moltype = AA   length = 4
FEATURE                 Location/Qualifiers
REGION                  1..4
                        note = NST engineered amino acid sequence motif 12
source                  1..4
                        mol_type = protein
                        organism = synthetic construct
SEQUENCE: 237
THGS                                                                     4

SEQ ID NO: 238          moltype = AA   length = 4
FEATURE                 Location/Qualifiers
REGION                  1..4
                        note = NST engineered amino acid sequence motif 13
source                  1..4
                        mol_type = protein
                        organism = synthetic construct
SEQUENCE: 238
TGHS                                                                     4

SEQ ID NO: 239          moltype = AA   length = 8
FEATURE                 Location/Qualifiers
REGION                  1..8
                        note = NST engineered amino acid sequence motif 14
SITE                    4
                        note = MISC_FEATURE - Xaa is either lysine or arginine
source                  1..8
```

```
                              mol_type = protein
                              organism = synthetic construct
SEQUENCE: 239
CHGXSLGR                                                                          8

SEQ ID NO: 240                moltype = AA   length = 8
FEATURE                       Location/Qualifiers
REGION                        1..8
                              note = NST engineered amino acid sequence motif 15
SITE                          4
                              note = MISC_FEATURE - Xaa is either lysine or arginine
source                        1..8
                              mol_type = protein
                              organism = synthetic construct
SEQUENCE: 240
CLGXHLGR                                                                          8

SEQ ID NO: 241                moltype = AA   length = 8
FEATURE                       Location/Qualifiers
REGION                        1..8
                              note = NST engineered amino acid sequence motif 16
SITE                          4
                              note = MISC_FEATURE - Xaa is either lysine or arginine
source                        1..8
                              mol_type = protein
                              organism = synthetic construct
SEQUENCE: 241
CHGXSWGR                                                                          8

SEQ ID NO: 242                moltype = AA   length = 8
FEATURE                       Location/Qualifiers
REGION                        1..8
                              note = NST engineered amino acid sequence motif 17
SITE                          4
                              note = MISC_FEATURE - Xaa is either lysine or arginine
source                        1..8
                              mol_type = protein
                              organism = synthetic construct
SEQUENCE: 242
CLGXHWGR                                                                          8

SEQ ID NO: 243                moltype = AA   length = 8
FEATURE                       Location/Qualifiers
REGION                        1..8
                              note = NST engineered amino acid sequence motif 18
SITE                          4
                              note = MISC_FEATURE - Xaa is either lysine or arginine
source                        1..8
                              mol_type = protein
                              organism = synthetic construct
SEQUENCE: 243
CLGXSHGR                                                                          8

SEQ ID NO: 244                moltype = AA   length = 8
FEATURE                       Location/Qualifiers
REGION                        1..8
                              note = 2OST conserved amino acid sequence motif 1
SITE                          6
                              note = MISC_FEATURE - Xaa is either alanine or glycine
source                        1..8
                              mol_type = protein
                              organism = synthetic construct
SEQUENCE: 244
RVPKTXST                                                                          8

SEQ ID NO: 245                moltype = AA   length = 8
FEATURE                       Location/Qualifiers
REGION                        1..8
                              note = 2OST conserved amino acid sequence motif 2
SITE                          4
                              note = MISC_FEATURE - Xaa is either phenylalanine or
                                histidine
SITE                          7
                              note = MISC_FEATURE - Xaa is either aspartic acid or
                                asparagine
SITE                          8
                              note = MISC_FEATURE - Xaa is either phenylalanine or
                                tyrosine
source                        1..8
```

```
                            mol_type = protein
                            organism = synthetic construct
SEQUENCE: 245
FLRXGDXX                                                                        8

SEQ ID NO: 246              moltype = AA  length = 5
FEATURE                     Location/Qualifiers
REGION                      1..5
                            note = 2OST conserved amino acid sequence motif 3
SITE                        3
                            note = MISC_FEATURE - Xaa is either lysine or arginine
source                      1..5
                            mol_type = protein
                            organism = synthetic construct
SEQUENCE: 246
RRXQG                                                                           5

SEQ ID NO: 247              moltype = AA  length = 6
FEATURE                     Location/Qualifiers
REGION                      1..6
                            note = 2OST conserved amino acid sequence motif 4
SITE                        5
                            note = MISC_FEATURE - Xaa is either lysine or arginine
source                      1..6
                            mol_type = protein
                            organism = synthetic construct
SEQUENCE: 247
SHLRXT                                                                          6

SEQ ID NO: 248              moltype = AA  length = 8
FEATURE                     Location/Qualifiers
REGION                      1..8
                            note = 2OST engineered amino acid sequence motif 1
source                      1..8
                            mol_type = protein
                            organism = synthetic construct
SEQUENCE: 248
RVPHTAST                                                                        8

SEQ ID NO: 249              moltype = AA  length = 8
FEATURE                     Location/Qualifiers
REGION                      1..8
                            note = 2OST engineered amino acid sequence motif 2
source                      1..8
                            mol_type = protein
                            organism = synthetic construct
SEQUENCE: 249
RVHRTASH                                                                        8

SEQ ID NO: 250              moltype = AA  length = 6
FEATURE                     Location/Qualifiers
REGION                      1..6
                            note = 2OST engineered amino acid sequence motif 3
source                      1..6
                            mol_type = protein
                            organism = synthetic construct
SEQUENCE: 250
SHLHKT                                                                          6

SEQ ID NO: 251              moltype = AA  length = 8
FEATURE                     Location/Qualifiers
REGION                      1..8
                            note = 2OST engineered amino acid sequence motif 4
source                      1..8
                            mol_type = protein
                            organism = synthetic construct
SEQUENCE: 251
HLRFGDDY                                                                        8

SEQ ID NO: 252              moltype = AA  length = 8
FEATURE                     Location/Qualifiers
REGION                      1..8
                            note = 2OST engineered amino acid sequence motif 5
source                      1..8
                            mol_type = protein
                            organism = synthetic construct
SEQUENCE: 252
FLRFGSDK                                                                        8
```

```
SEQ ID NO: 253        moltype = AA  length = 5
FEATURE               Location/Qualifiers
REGION                1..5
                      note = 2OST engineered amino acid sequence motif 6
source                1..5
                      mol_type = protein
                      organism = synthetic construct
SEQUENCE: 253
MRKQG                                                                     5

SEQ ID NO: 254        moltype = AA  length = 6
FEATURE               Location/Qualifiers
REGION                1..6
                      note = 6OST conserved amino acid sequence motif 1
source                1..6
                      mol_type = protein
                      organism = synthetic construct
SEQUENCE: 254
QKTGGT                                                                    6

SEQ ID NO: 255        moltype = AA  length = 6
FEATURE               Location/Qualifiers
REGION                1..6
                      note = 6OST conserved amino acid sequence motif 2
source                1..6
                      mol_type = protein
                      organism = synthetic construct
SEQUENCE: 255
CGLHAD                                                                    6

SEQ ID NO: 256        moltype = AA  length = 13
FEATURE               Location/Qualifiers
REGION                1..13
                      note = 6OST conserved amino acid sequence motif 3
SITE                  4
                      note = MISC_FEATURE - Xaa is either lysine or arginine
source                1..13
                      mol_type = protein
                      organism = synthetic construct
SEQUENCE: 256
SEWXHVQRGA TWK                                                           13

SEQ ID NO: 257        moltype = AA  length = 6
FEATURE               Location/Qualifiers
REGION                1..6
                      note = 6OST engineered amino acid sequence motif 1
source                1..6
                      mol_type = protein
                      organism = synthetic construct
SEQUENCE: 257
GHTGGT                                                                    6

SEQ ID NO: 258        moltype = AA  length = 6
FEATURE               Location/Qualifiers
REGION                1..6
                      note = 6OST engineered amino acid sequence motif 2
SITE                  4
                      note = MISC_FEATURE - Xaa is asparagine, arginine, or
                       histidine
source                1..6
                      mol_type = protein
                      organism = synthetic construct
SEQUENCE: 258
CGTXAD                                                                    6

SEQ ID NO: 259        moltype = AA  length = 6
FEATURE               Location/Qualifiers
REGION                1..6
                      note = 6OST engineered amino acid sequence motif 3
SITE                  4
                      note = MISC_FEATURE - Xaa is asparagine, arginine, or
                       histidine
source                1..6
                      mol_type = protein
                      organism = synthetic construct
SEQUENCE: 259
CGSXAD                                                                    6

SEQ ID NO: 260        moltype = AA  length = 13
```

```
                                      -continued
FEATURE                 Location/Qualifiers
REGION                  1..13
                        note = 6OST engineered amino acid sequence motif 4
SITE                    1
                        note = MISC_FEATURE - Xaa is either serine or glycine
SITE                    2
                        note = MISC_FEATURE - Xaa is either glycine or histidine
SITE                    6
                        note = MISC_FEATURE - Xaa is either threonine or histidine
SITE                    11
                        note = MISC_FEATURE - Xaa is either threonine or alanine
source                  1..13
                        mol_type = protein
                        organism = synthetic construct
SEQUENCE: 260
XXWRHXQRGG XNK                                                              13

SEQ ID NO: 261          moltype = AA  length = 13
FEATURE                 Location/Qualifiers
REGION                  1..13
                        note = 6OST engineered amino acid sequence motif 5
SITE                    2
                        note = MISC_FEATURE - Xaa is either glycine or histidine
SITE                    6
                        note = MISC_FEATURE - Xaa is either threonine or histidine
source                  1..13
                        mol_type = protein
                        organism = synthetic construct
SEQUENCE: 261
GXWRHXQRGG TNK                                                              13

SEQ ID NO: 262          moltype = AA  length = 13
FEATURE                 Location/Qualifiers
REGION                  1..13
                        note = 6OST engineered amino acid sequence motif 6
SITE                    2
                        note = MISC_FEATURE - Xaa is either glycine or histidine
SITE                    6
                        note = MISC_FEATURE - Xaa is either threonine or histidine
source                  1..13
                        mol_type = protein
                        organism = synthetic construct
SEQUENCE: 262
SXWRHXQRGG ANK                                                              13

SEQ ID NO: 263          moltype = AA  length = 13
FEATURE                 Location/Qualifiers
REGION                  1..13
                        note = 6OST engineered amino acid sequence motif 7
SITE                    1
                        note = MISC_FEATURE - Xaa is either serine or glycine
SITE                    11
                        note = MISC_FEATURE - Xaa is either threonine or alanine
source                  1..13
                        mol_type = protein
                        organism = synthetic construct
SEQUENCE: 263
XGWRHHQRGG XNK                                                              13

SEQ ID NO: 264          moltype = AA  length = 13
FEATURE                 Location/Qualifiers
REGION                  1..13
                        note = 6OST engineered amino acid sequence motif 8
SITE                    1
                        note = MISC_FEATURE - Xaa is either serine or glycine
SITE                    11
                        note = MISC_FEATURE - Xaa is either threonine or alanine
source                  1..13
                        mol_type = protein
                        organism = synthetic construct
SEQUENCE: 264
XHWRHTQRGG XNK                                                              13

SEQ ID NO: 265          moltype = AA  length = 6
FEATURE                 Location/Qualifiers
REGION                  1..6
                        note = 3OST conserved amino acid sequence motif 1
source                  1..6
                        mol_type = protein
```

```
                        organism = synthetic construct
SEQUENCE: 265
GVRKGG                                                                          6

SEQ ID NO: 266          moltype =    length =
SEQUENCE: 266
000

SEQ ID NO: 267          moltype = AA   length = 6
FEATURE                 Location/Qualifiers
REGION                  1..6
                        note = 3OST conserved amino acid sequence motif 3
source                  1..6
                        mol_type = protein
                        organism = synthetic construct
SEQUENCE: 267
SDYTQV                                                                          6

SEQ ID NO: 268          moltype = AA   length = 6
FEATURE                 Location/Qualifiers
REGION                  1..6
                        note = 3OST engineered amino acid sequence motif 1
source                  1..6
                        mol_type = protein
                        organism = synthetic construct
SEQUENCE: 268
GVGHGG                                                                          6

SEQ ID NO: 269          moltype = AA   length = 4
FEATURE                 Location/Qualifiers
REGION                  1..4
                        note = 3OST engineered amino acid sequence motif 2
source                  1..4
                        mol_type = protein
                        organism = synthetic construct
SEQUENCE: 269
HSYF                                                                            4

SEQ ID NO: 270          moltype = AA   length = 6
FEATURE                 Location/Qualifiers
REGION                  1..6
                        note = 3OST engineered amino acid sequence motif 3
source                  1..6
                        mol_type = protein
                        organism = synthetic construct
SEQUENCE: 270
SAYTHM                                                                          6

SEQ ID NO: 271          moltype =    length =
SEQUENCE: 271
000

SEQ ID NO: 272          moltype = AA   length = 12
FEATURE                 Location/Qualifiers
REGION                  1..12
                        note = Conserved sulfatase signature seqeuence II
SITE                    2
                        note = MISC_FEATURE - Xaa can be either tyrosine or valine
SITE                    3
                        note = MISC_FEATURE - Xaa can be any amino acid
SITE                    4
                        note = MISC_FEATURE - Xaa can be either serine or threonine
SITE                    5
                        note = MISC_FEATURE - Xaa can be any amino acid
SITE                    6
                        note = MISC_FEATURE - Xaa can be any amino acid
SITE                    7
                        note = MISC_FEATURE - Xaa can be any amino acid
SITE                    10
                        note = MISC_FEATURE - Xaa can be any amino acid
SITE                    11
                        note = MISC_FEATURE - Xaa can be any amino acid
source                  1..12
                        mol_type = protein
                        organism = synthetic construct
SEQUENCE: 272
GXXXXXXGKX XH                                                                  12

SEQ ID NO: 273          moltype = AA   length = 5
```

```
FEATURE              Location/Qualifiers
REGION               1..5
                     note = 2OST conserved amino acid sequence motif 5
SITE                 3
                     note = misc_feature - Xaa can be any naturally occurring
                      amino acid
SITE                 4
                     note = MISC_FEATURE - Xaa is either serine or threonine
source               1..5
                     mol_type = protein
                     organism = synthetic construct
SEQUENCE: 273
NTXKN                                                                        5

SEQ ID NO: 274       moltype = AA  length = 4
FEATURE              Location/Qualifiers
REGION               1..4
                     note = 2OST conserved amino acid sequence motif 6
source               1..4
                     mol_type = protein
                     organism = synthetic construct
SEQUENCE: 274
YHGH                                                                         4

SEQ ID NO: 275       moltype = AA  length = 6
FEATURE              Location/Qualifiers
REGION               1..6
                     note = 6OST conserved amino acid sequence motif 4
source               1..6
                     mol_type = protein
                     organism = synthetic construct
SEQUENCE: 275
LRDVPS                                                                       6

SEQ ID NO: 276       moltype = AA  length = 5
FEATURE              Location/Qualifiers
REGION               1..5
                     note = 6OST conserved amino acid sequence motif 5
SITE                 4
                     note = MISC_FEATURE - Xaa can be either phenylalanine or
                      tyrosine
source               1..5
                     mol_type = protein
                     organism = synthetic construct
SEQUENCE: 276
LTEXQ                                                                        5

SEQ ID NO: 277       moltype = AA  length = 10
FEATURE              Location/Qualifiers
REGION               1..10
                     note = NST conserved amino acid sequence motif 6
source               1..10
                     mol_type = protein
                     organism = synthetic construct
SEQUENCE: 277
QKTGTTALYL                                                                  10

SEQ ID NO: 278       moltype = AA  length = 10
FEATURE              Location/Qualifiers
REGION               1..10
                     note = NST engineered aminoacid sequence motif 19
SITE                 1
                     note = MISC_FEATURE - Xaa is either glutamine, serine, or
                      alanine
SITE                 6
                     note = MISC_FEATURE - Xaa is either tryptophan or
                      phenylalanine
SITE                 7
                     note = MISC_FEATURE - Xaa is either alanine or leucine
SITE                 9
                     note = MISC_FEATURE - Xaa is either tyrosine, threonine, or
                      histidine
source               1..10
                     mol_type = protein
                     organism = synthetic construct
SEQUENCE: 278
XKTGAXXLXH                                                                  10

SEQ ID NO: 279       moltype =    length =
```

```
SEQUENCE: 279
000

SEQ ID NO: 280          moltype = AA  length = 10
FEATURE                 Location/Qualifiers
REGION                  1..10
                        note = NST engineered amino acid sequence motif 21
SITE                    6
                        note = MISC_FEATURE - Xaa is either tryptophan or
                         phenylalanine
SITE                    7
                        note = MISC_FEATURE - Xaa is either alanine or leucine
source                  1..10
                        mol_type = protein
                        organism = synthetic construct
SEQUENCE: 280
NKTGAXXLYH                                                                10

SEQ ID NO: 281          moltype = AA  length = 8
FEATURE                 Location/Qualifiers
REGION                  1..8
                        note = NST engineered amino acid sequence motif 22
SITE                    4
                        note = MISC_FEATURE - Xaa is either lysine or arginine
source                  1..8
                        mol_type = protein
                        organism = synthetic construct
SEQUENCE: 281
CLGXSHGR                                                                  8

SEQ ID NO: 282          moltype = AA  length = 10
FEATURE                 Location/Qualifiers
REGION                  1..10
                        note = NST engineered amino acid sequence motif 23
SITE                    6
                        note = MISC_FEATURE - Xaa is either tryptophan or
                         phenylalanine
SITE                    7
                        note = MISC_FEATURE - Xaa is either alanine or leucine
source                  1..10
                        mol_type = protein
                        organism = synthetic construct
SEQUENCE: 282
SKTGAXXLTH                                                                10

SEQ ID NO: 283          moltype = AA  length = 8
FEATURE                 Location/Qualifiers
REGION                  1..8
                        note = NST engineered amino acid sequence motif 24
SITE                    4
                        note = MISC_FEATURE - Xaa is either lysine or arginine
source                  1..8
                        mol_type = protein
                        organism = synthetic construct
SEQUENCE: 283
CHGXRWGR                                                                  8

SEQ ID NO: 284          moltype = AA  length = 10
FEATURE                 Location/Qualifiers
REGION                  1..10
                        note = NST engineered amino acid sequence motif 25
SITE                    6
                        note = MISC_FEATURE - Xaa is either tryptophan or
                         phenylalanine
SITE                    7
                        note = MISC_FEATURE - Xaa is either alanine or leucine
source                  1..10
                        mol_type = protein
                        organism = synthetic construct
SEQUENCE: 284
AKTGAXXLHH                                                                10

SEQ ID NO: 285          moltype = AA  length = 4
FEATURE                 Location/Qualifiers
REGION                  1..4
                        note = NST conserved amino acid sequence motif 26
source                  1..4
                        mol_type = protein
                        organism = synthetic construct
```

```
SEQUENCE: 285
THSS                                                                              4

SEQ ID NO: 286          moltype = AA  length = 8
FEATURE                 Location/Qualifiers
REGION                  1..8
                        note = NST engineered amino acid sequence motif 27
SITE                    4
                        note = MISC_FEATURE - Xaa is either lysine or arginine
source                  1..8
                        mol_type = protein
                        organism = synthetic construct
SEQUENCE: 286
CAHXGLGR                                                                          8

SEQ ID NO: 287          moltype = AA  length = 8
FEATURE                 Location/Qualifiers
REGION                  1..8
                        note = NST engineered amino acid sequence motif 28
SITE                    4
                        note = MISC_FEATURE - Xaa is either lysine or arginine
source                  1..8
                        mol_type = protein
                        organism = synthetic construct
SEQUENCE: 287
CGGXHLGR                                                                          8

SEQ ID NO: 288          moltype = AA  length = 5
FEATURE                 Location/Qualifiers
REGION                  1..5
                        note = NST engineered amino acid sequence motif 29
source                  1..5
                        mol_type = protein
                        organism = synthetic construct
SEQUENCE: 288
FEHSG                                                                             5

SEQ ID NO: 289          moltype = AA  length = 4
FEATURE                 Location/Qualifiers
REGION                  1..4
                        note = NST engineered amino acid sequence motif 30
source                  1..4
                        mol_type = protein
                        organism = synthetic construct
SEQUENCE: 289
TGNH                                                                              4

SEQ ID NO: 290          moltype = AA  length = 7
FEATURE                 Location/Qualifiers
REGION                  1..7
                        note = 6OST conserved amino acid sequence motif 6
source                  1..7
                        mol_type = protein
                        organism = synthetic construct
SEQUENCE: 290
NLANNRQ                                                                           7

SEQ ID NO: 291          moltype = AA  length = 6
FEATURE                 Location/Qualifiers
REGION                  1..6
                        note = 6OST engineered amino acid sequence motif 9
SITE                    3
                        note = MISC_FEATURE - Xaa is either threonine or serine
SITE                    4
                        note = MISC_FEATURE - Xaa is either asparagine, arginine,
                         or histidine
source                  1..6
                        mol_type = protein
                        organism = synthetic construct
SEQUENCE: 291
CGXXAD                                                                            6

SEQ ID NO: 292          moltype = AA  length = 7
FEATURE                 Location/Qualifiers
REGION                  1..7
                        note = 6OST engineered amino acid sequence motif 10
SITE                    3
                        note = MISC_FEATURE - Xaa is either alanine or glycine
source                  1..7
```

```
                         mol_type = protein
                         organism = synthetic construct
SEQUENCE: 292
NLXNNRQ                                                                 7

SEQ ID NO: 293           moltype = AA  length = 7
FEATURE                  Location/Qualifiers
REGION                   1..7
                         note = 6OST engineered amino acid sequence motif 11
source                   1..7
                         mol_type = protein
                         organism = synthetic construct
SEQUENCE: 293
NLGNNRQ                                                                 7

SEQ ID NO: 294           moltype = AA  length = 7
FEATURE                  Location/Qualifiers
REGION                   1..7
                         note = 6OST engineered amino acid sequence motif 12
source                   1..7
                         mol_type = protein
                         organism = synthetic construct
SEQUENCE: 294
NLANNRQ                                                                 7

SEQ ID NO: 295           moltype = AA  length = 411
FEATURE                  Location/Qualifiers
source                   1..411
                         mol_type = protein
                         organism = Mus musculus
SEQUENCE: 295
MRRRRAGGRT MVERASKFVL VVAGSACFML ILYQYAGPGL SLGAPGGRVP PDDLDLFPTP        60
DPHYEKKYYF PVRELERSLR FDMKGDDVIV FLHIQKTGGT TFGRHLVQNV RLEVPCDCRP       120
GQKKCTCYRP NRRETWLFSR FSTGWSCGLH ADWTELTNCV PGVLDRRDPA GLRSPRKFYY       180
ITLLRDPVSR YLSEWRHVQR GATWKTSLHM CDGRTPTPEE LPPCYEGTDW SGCTLQEFMD       240
CPYNLANNRQ VRMLADLSLV GCYNLSFIPE SKRAQLLLES AKKNLRGMAF FGLTEFQRKT       300
QYLFERTFNL KFIRPFMQYN STRAGGVEVD EDTIRHIEEL NDLDMQLYDY AKDLFQQRYQ       360
YKRQLERREQ RLRNEERLL HRSKEALPRE DPEEPGRVPT EDYMSHIIEK W                411

SEQ ID NO: 296           moltype = AA  length = 411
FEATURE                  Location/Qualifiers
source                   1..411
                         mol_type = protein
                         organism = Homo sapiens
SEQUENCE: 296
MRRRRAGGRT MVERASKFVL VVAGSVCFML ILYQYAGPGL SLGAPGGRAP PDDLDLFPTP        60
DPHYEKKYYF PVRELERSLR FDMKGDDVIV FLHIQKTGGT TFGRHLVQNV RLEVPCDCRP       120
GQKKCTCYRP NRRETWLFSR FSTGWSCGLH ADWTELTNCV PGVLDRRDSA ALRTPRKFYY       180
ITLLRDPVSR YLSEWRHVQR GATWKTSLHM CDGRTPTPEE LPPCYEGTDW SGCTLQEFMD       240
CPYNLANNRQ VRMLADLSLV GCYNLSFIPE GKRAQLLLES AKKNLRGMAF FGLTEFQRKT       300
QYLFERTFNL KFIRPFMQYN STRAGGVEVD EDTIRRIEEL NDLDMQLYDY AKDLFQQRYQ       360
YKRQLERREQ RLRSREERLL HRAKEALPRE DADEPGRVPT EDYMSHIIEK W                411

SEQ ID NO: 297           moltype = AA  length = 411
FEATURE                  Location/Qualifiers
source                   1..411
                         mol_type = protein
                         organism = Sus scrofa
SEQUENCE: 297
MRRRRAGSRT MVERASKFVL VVAGSACFML ILYQYAGPGL SLGAPGGRAP PDDLDLFPTP        60
DPHYEKKYYF PVRELERSLH FDMKGDDVIV FLHIQKTGGT TFGRHLVQNV RLEVPCDCRP       120
GQKKCTCYRP NRRETWLFSR FSTGWSCGLH ADWTELTNCV PGVLDRRDPA ALRTPRKFYY       180
ITLLRDPVSR YLSEWRHVQR GATWKTSLHM CDGRTPTPEE LPPCYEGTDW SGCTLQEFMD       240
CPYNLANNRQ VRMLADLSLV GCYNLSFIPE GKRSQLLLES AKKNLRGMAF FGLTEFQRKT       300
QYLFERTFNL KFIRPFMQYN STRAGGVEVG EDTIRRIEEL NDLDMQLYDY ARDLFQQRYQ       360
YKRQLERRQQ RLRSREERLL HRAKEAPPRG DTEEPGRVPT EDYMSHIIEK W                411

SEQ ID NO: 298           moltype = AA  length = 6
FEATURE                  Location/Qualifiers
REGION                   1..6
                         note = 3OST conserved amino acid sequence motif 4
SITE                     2
                         note = MISC_FEATURE - Xaa is either valine or isoleucine
source                   1..6
                         mol_type = protein
                         organism = synthetic construct
SEQUENCE: 298
EXHFFD                                                                  6
```

-continued

```
SEQ ID NO: 299        moltype =    length =
SEQUENCE: 299
000

SEQ ID NO: 300        moltype = AA   length = 6
FEATURE               Location/Qualifiers
REGION                1..6
                      note = 3OST engineered amino acid sequence motif 5
source                1..6
                      mol_type = protein
                      organism = synthetic construct
SEQUENCE: 300
SLGTHL                                                                  6
```

I claim:

1. A non-natural glucosaminyl 3-O sulfotransferase (3OST) enzyme having an amino acid sequence comprising multiple mutations relative to conserved amino acid residues and sequence motifs found in natural 3OST enzymes within enzyme class EC 2.8.2.23, wherein:
   (a) the natural 3OST enzymes comprise the following conserved amino acid sequence motifs:
      (i) a conserved amino acid sequence motif having the amino acid sequence of SEQ ID NO: 265; and
      (ii) a conserved amino acid sequence motif having the amino acid sequence of SEQ ID NO: 267; and
   (b) within the amino acid sequence of the non-natural 3OST enzyme,
      (i) the conserved amino acid sequence motif having the amino acid sequence gf SEQ ID NO: 265 is mutated to SEQ ID NO: 268, and
      (ii) the amino acid sequence of the non-natural 3OST enzyme comprises a mutated amino acid sequence motif having the amino acid sequence of SEQ ID NO: 269, and
   (c) the non-natural 3OST enzyme has sulfotransferase activity in the absence of 3'-phosphoadenosine 5'-phosphosulfate, wherein the sulfotransferase activity comprises a transfer of a sulfo group from an aryl sulfate compound to N-,2-O,6-O-sulfated heparan sulfate to form an N-,2-O,3-O,6-O-sulfated heparan sulfate product.

2. The non-natural 3OST enzyme of claim 1, wherein within the amino acid sequence of the non-natural 3OST enzyme, amino acid sequence SEQ ID NO: 267 is mutated to SEQ ID NO: 270.

3. The non-natural 3OST enzyme of claim 1, wherein the non-natural 3OST enzyme comprises an amino acid sequence selected from the group consisting of SEQ ID NO: 154, SEQ ID NO: 155, SEQ ID NO: 156, SEQ ID NO: 157, SEQ ID NO: 158, SEQ ID NO: 159, and SEQ ID NO: 160.

4. The non-natural 3OST enzyme of claim 3, wherein variable amino acid residues within SEQ ID NO: 154, defined as "X" are selected such that the non-natural 3OST enzyme has an amino acid sequence selected from the group consisting of SEQ ID NO: 147, SEQ ID NO: 149, and SEQ ID NO: 151.

5. The non-natural 3OST enzyme of claim 1, wherein amino acid sequence of the non-natural 3OST enzyme has at least 80% sequence identity with the amino acid sequence of a natural 3OST enzyme, the natural 3OST enzyme having an amino acid sequence selected from the group consisting of SEQ ID NO: 206 and SEQ ID NO: 220.

6. The non-natural 3OST enzyme of claim 1, wherein the aryl sulfate compound is selected from the group consisting of p-nitrophenyl sulfate and 4-nitrocatechol sulfate.

7. A non-natural glucosaminyl 3-O sulfotransferase (3OST) enzyme engineered to have sulfotransferase activity in the absence of 3'-phosphoadenosine 5'-phosphosulfate (PAPS), the sulfotransferase activity comprising a transfer of a sulfo group from an aryl sulfate compound to heparan sulfate to form a 3-O-sulfated heparan sulfate product, wherein the heparan sulfate comprises N-,2-O,6-O-sulfated heparan sulfate, and the 3-O-sulfated heparan sulfate product comprises N-,2-O,3-O,6-O-sulfated heparan sulfate,
   wherein the amino acid sequence of the non-natural 3OST enzyme comprises at east one amino acid sequence motif selected from the group consisting of SEQ ID NO: 268, SEQ ID NO: 269 and SEQ ID NO: 270.

8. The non-natural 3OST enzyme of claim 7, wherein the non-natural 3OST enzyme has an amino acid sequence comprising multiple mutations relative to conserved amino acid residues found in natural 3OST enzymes within enzyme class EC 2.8.2.23, wherein:
   natural 3OST enzymes have sulfotransferase activity with heparan sulfate and a sulfo group donor, the sulfo group donor consisting of PAPS, to form a 3-O-sulfated heparan sulfate product; and
   the amino acid sequence of the non-natural 3OST enzyme has at least 80% sequence identity with the amino acid sequence of a natural 3OST enzyme, the natural 3OST enzyme amino acid sequence selected from the group consisting of SEQ ID NO: 206 and SEQ ID NO: 220.

9. The non-natural 3OST enzyme of claim 8, wherein the amino acid sequence of the non-natural 3OST enzyme comprises the amino acid sequence motif having the amino acid sequence of SEQ ID NO: 268.

10. The non-natural 3OST enzyme of claim 8, wherein the amino acid sequence of the non-natural 3OST enzyme comprises the amino acid sequence motif having the amino acid sequence of SEQ ID NO: 269.

11. The non-natural 3OST enzyme of claim 8, wherein the aryl sulfate compound is selected from the group consisting of p-nitrophenyl sulfate and 4-nitrocatechol sulfate.

12. The non-natural 3OST enzyme of claim 7, wherein the amino acid sequence of the non-natural 3OST enzyme comprises the amino acid sequence motif having the amino acid sequence of SEQ ID NO: 268.

13. The non-natural 3OST enzyme of claim 12, wherein the amino acid sequence of the non-natural 3OST enzyme comprises the amino acid sequence motif having the amino acid sequence of SEQ ID NO: 269.

14. The non-natural 3OST enzyme of claim 13, wherein the amino acid sequence of the non-natural 3OST enzyme comprises the amino acid sequence motif having the amino acid sequence of SEQ ID NO: 270.

15. The non-natural 3OST enzyme of claim 7, wherein the amino acid sequence of the non-natural 3OST enzyme comprises the amino acid sequence motif having the amino acid sequence of SEQ ID NO: 269.

16. The non-natural 3OST enzyme of claim 7, wherein the aryl sulfate compound is selected from the group consisting of p-nitrophenyl sulfate and 4-nitrocatechol sulfate.

* * * * *